(12) United States Patent
Arimori et al.

(10) Patent No.: US 9,828,389 B2
(45) Date of Patent: Nov. 28, 2017

(54) TETRAZOLINONE COMPOUNDS AND THEIR USE AS PESTICIDES

(71) Applicant: SUMITOMO CHEMICAL COMPANY, LIMITED, Tokyo (JP)

(72) Inventors: Sadayuki Arimori, Takarazuka (JP); Takayuki Shioda, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/424,411

(22) PCT Filed: Sep. 27, 2013

(86) PCT No.: PCT/JP2013/077014
§ 371 (c)(1),
(2) Date: Feb. 26, 2015

(87) PCT Pub. No.: WO2014/051165
PCT Pub. Date: Apr. 3, 2014

(65) Prior Publication Data
US 2015/0203511 A1    Jul. 23, 2015

(30) Foreign Application Priority Data

Sep. 28, 2012  (JP) ................................. 2012-216038
Dec. 25, 2012  (JP) ................................. 2012-280707
(Continued)

(51) Int. Cl.
*C07D 231/12*    (2006.01)
*C07D 231/14*    (2006.01)
(Continued)

(52) U.S. Cl.
CPC ......... *C07D 498/04* (2013.01); *A01N 43/713* (2013.01); *A01N 43/90* (2013.01);
(Continued)

(58) Field of Classification Search
None
See application file for complete search history.

(56) References Cited

U.S. PATENT DOCUMENTS

| 5,605,920 A | 2/1997 | Goto et al. |
| 6,583,090 B1 | 6/2003 | Gewehr et al. |

(Continued)

FOREIGN PATENT DOCUMENTS

| CN | 1138574 A | 12/1996 |
| CN | 1798738 A | 7/2006 |

(Continued)

OTHER PUBLICATIONS

The Second Office Action (including an English translation thereof) issued in the corresponding Chinese Patent Application No. 201380050379.0 dated Apr. 8, 2016.

International Preliminary Report on Patentability and Written Opinion of the International Searching Authority (Forms PCT/IB/373 and PCT/ISA/237) for International Application No. PCT/JP2013/077014, dated Mar. 31, 2015.
International Search Report (Form PCT/ISA/210) for International Application No. PCT/JP2013/077014, dated Dec. 9, 2013.
First Office Action with Search Report (including an English translation thereof) issued in the corresponding Chinese Patent Application No. 201380050379.0 dated Oct. 20, 2015.
European Patent Office Communication issued in the corresponding European Patent Application No. 13779398.0 dated May 17, 2016.
Australian Office Action for Australian Application No. 2013320868, dated Feb. 9, 2017.
(Continued)

*Primary Examiner* — Alicia L Otton
(74) *Attorney, Agent, or Firm* — Birch, Stewart, Kolasch & Birch, LLP

(57) ABSTRACT

The present invention provides a compound having an excellent efficacy for controlling pests. A tetrazolinone compound of a formula (1) [wherein Q represents a group selected from the following group: Q1, Q2, Q3 or Q4: $R^1$, $R^2$, $R^3$ and $R^{11}$ represent independently of each other a halogen atom, an C1-C6 alkyl group, etc.; $R^4$ and $R^5$ represent independently of each other a hydrogen atom, a halogen atom or an C1-C3 alkyl group, etc.; $R^6$ represents a halogen atom, an C1-C4 alkyl group, etc.; $R^7$, $R^8$ and $R^9$ represent independently of each other a hydrogen atom, a halogen atom, etc.; and $R^{10}$ represents an C1-C3 alkyl group, etc.] shows an excellent controlling efficacy on pests.

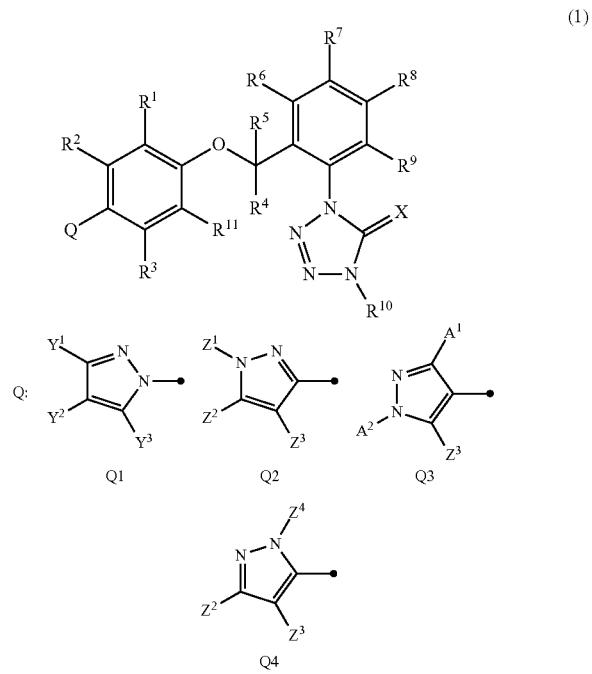

18 Claims, No Drawings

(30) Foreign Application Priority Data

May 31, 2013 (JP) .................................. 2013-115179
Jul. 4, 2013 (JP) .................................. 2013-140423

(51) Int. Cl.

| | |
|---|---|
| C07D 231/16 | (2006.01) |
| C07D 257/04 | (2006.01) |
| C07D 403/12 | (2006.01) |
| C07D 498/04 | (2006.01) |
| A01N 43/90 | (2006.01) |
| A01N 43/713 | (2006.01) |
| C07D 231/20 | (2006.01) |

(52) U.S. Cl.

CPC ......... *C07D 231/12* (2013.01); *C07D 231/14* (2013.01); *C07D 231/16* (2013.01); *C07D 231/20* (2013.01); *C07D 257/04* (2013.01); *C07D 403/12* (2013.01)

(56) References Cited

U.S. PATENT DOCUMENTS

| | | |
|---|---|---|
| 2012/0015980 A1 | 1/2012 | Fischer et al. |
| 2014/0323305 A1 | 10/2014 | Rheinheimer et al. |
| 2015/0031733 A1 | 1/2015 | Yoshimoto et al. |
| 2015/0051171 A1 | 2/2015 | Yoshimoto et al. |
| 2016/0205935 A1* | 7/2016 | Akioka ................ A01N 43/713 |

FOREIGN PATENT DOCUMENTS

| | | | |
|---|---|---|---|
| DE | 19900571 A1 | 7/1999 | |
| WO | WO 99/46246 A1 | 9/1999 | |
| WO | WO 2004/092140 A1 | 10/2004 | |
| WO | WO 2011/157654 A1 | 12/2011 | |
| WO | WO 2013/092224 A1 | 6/2013 | |
| WO | WO 2014/051161 A1 | 4/2014 | |
| WO | WO 2014/084223 A1 | 6/2014 | |
| WO | WO 2014/104268 A1 | 7/2014 | |
| WO | WO 2014/104382 A1 | 7/2014 | |
| WO | WO 2014/104384 A1 | 7/2014 | |
| WO | WO 2014/175465 A1 | 10/2014 | |
| WO | WO 15/030217 | * 3/2015 | ........... C07D 257/04 |

OTHER PUBLICATIONS

Office Action (including an English translation thereof) issued in the corresponding Israeli Patent Application No. 237579 dated Jun. 25, 2017.

Examination Report (including an English translation thereof) issued in the corresponding Taiwanese Patent Application No. 102134989 dated Apr. 25, 2017.

* cited by examiner

TETRAZOLINONE COMPOUNDS AND THEIR USE AS PESTICIDES

This application claims priority to and the benefit of Japanese Patent Application Nos. 2012-216038 filed Sep. 28, 2012, 2012-280707 filed Dec. 25, 2012, 2013-115179 filed May 31, 2013 and 2013-140423 filed Jul. 4, 2013, the entire contents of which are incorporated herein by reference.

TECHNICAL FIELD

The present invention relates to tetrazolinone compounds and its use.

BACKGROUND ART

Heretofore, various drugs for controlling pests have been widely developed and provides in practice use, but in some cases, these drugs may not exert enough efficacy.

Also, as compounds having tetrazolinone ring, 1-{2-{2-chloro-4-(3,5-dimethyl-pyrazole-1-yl)-phenoxymethyl}-phenyl}-4-methyl-1,4-dihydrotetrazole-5-one represented by the following formula (A):

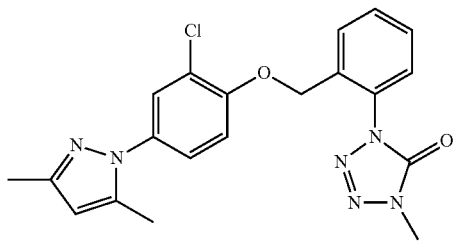

(A)

have been known (see Patent Document 1).

CITATION LIST

Patent Document

Patent Document 1: WO 1999/46246 pamphlet

SUMMARY OF THE INVENTION

An object of the present invention is to provide a compound having an excellent efficacy for controlling pests.

The present inventors have intensively studied to find that compounds having an excellent efficacy for controlling pests and as a result, found that a tetrazolinone compound of the following formula (I) has an excellent efficacy for controlling pests, which thus have completed the present invention.

Specifically, the present invention includes the following [1] to [23].

[1] A tetrazolinone compound of a formula (1):

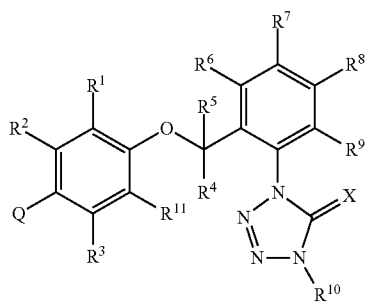

(1)

[wherein
Q represents a group selected from the following group: Q1, Q2, Q3 or Q4:

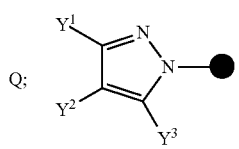

Q1

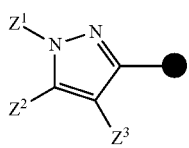

Q2

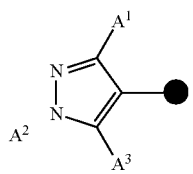

Q3

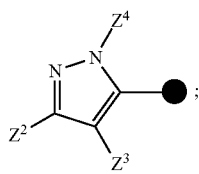

Q4

$R^1$, $R^2$, $R^3$ and $R^{11}$ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group $P^1$ or an C3-C6 cycloalkyl group optionally having one or more groups selected from Group $P^1$;

$R^4$ and $R^5$ represent independently of each other a hydrogen atom, a halogen atom or an C1-C3 alkyl group;

$R^6$ represents an C1-C4 alkyl group, a halogen atom, an C1-C4 alkoxy group, a cyano group, a nitro group, a C1-C4 haloalkyl group, an C2-C4 alkenyl group or a C2-C4 haloalkenyl group;

$R^7$, $R^8$ and $R^9$ represent independently of each other a hydrogen atom, a halogen atom, an C1-C3 alkyl group, a C1-C3 haloalkyl group, an C2-C3 alkenyl group, a C2-C3 haloalkenyl group or an C1-C3 alkoxy group;

$R^{10}$ represents an C1-C3 alkyl group, a C1-C3 haloalkyl group, an C2-C3 alkenyl group, a C2-C3 haloalkenyl group, an C2-C3 alkynyl group, a C2-C3 haloalkynyl group, a C3-C5 cycloalkyl group or a C3-C5 halocycloalkyl group;

X represents an oxygen atom or a sulfur atom;

$A^1$ and $A^3$ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group $P^1$, or a C3-C6 cycloalkyl group optionally having one or more groups selected from Group $P^1$;

$A^2$, $Z^1$ and $Z^4$ represent independently of each other a hydrogen atom, an amino group, an C3-C6 alkenyl group, C3-C6 haloalkenyl group, an C3-C6 alkynyl group, a C3-C6 haloalkynyl group, an C1-C6 alkylsulfinyl group, a C1-C6 haloalkylsulfinyl group, an C1-C6 alkylsulfonyl group, a C1-C6 haloalkylsulfonyl group, a C3-C6 cycloalkylsulfonyl group, a C3-C6 halocycloalkylsulfonyl group, an C2-C8 alkylaminosulfonyl group, a C2-C8 haloalkylaminosulfonyl group, a C3-C9 trialkylsilyl group, an C2-C6 alkylcarbonyl group, an C2-C6 alkoxycarbonyl group, an C2-C8 alkylaminocarbonyl group, a C4-C7 cycloalkylmethyl group, an C1-C6 alkyl group optionally having one or more groups selected from Group $R^1$ or a C3-C6 cycloalkyl group optionally having one or more groups selected from Group $P^1$;

$Y^1$, $Y^2$, $Y^3$, $Z^2$ and $Z^3$ represent independently of each other a hydrogen atom, a halogen atom, a cyano group, a nitro group, an amino group, a hydroxy group, a thiol group, an aldehyde group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C3-C6 alkenyloxy group, a C3-C6 haloalkenyloxy group, an C3-C6 alkynyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, C1-C6 haloakylsulfonyl group, an C1-C8 alkylaminosulfonyl group, a pentaflurosulfanyl group, a C3-C9 trialkylsilyl group, an C2-C6 alkylcarbonyl group, an C2-C6 alkoxycarbonyl group, an C2-C8 alkylaminocarbonyl group, an aminocarbonyl group, an C1-C6 alkyl group optionally having one or more groups selected from Group $P^1$ or a C3-C6 cyclolakyl group optionally having one or more groups selected from Group $P^1$; or $Y^1$ and $Y^2$ may combine each other together with the carbon atom to which they are attached to form a five-, six- or seven-membered saturated ring (with the proviso that the saturated ring may optionally contain one or more oxygen atoms or sulfur atoms as the ring-constituent atom, and the saturated ring may optionally have one or more substituents selected from Group $P^1$); or $Y^2$ and $Y^3$ may combine each other together with the carbon atom to which they are attached to form a five-, six- or seven-membered saturated ring (with the proviso that the saturated ring may optionally contain one or more oxygen atoms or sulfur atoms as the ring-constituent atom, and the saturated ring may optionally have one or more substituents selected from Group $P^1$); or $Z^1$ and $Z^2$ may combine each other together with the carbon atom or nitrogen atom to which they are attached to form a five-, six- or seven-membered saturated ring (with the proviso that the saturated ring may optionally contain one or more oxygen atoms, nitrogen atoms or sulfur atoms as the ring-constituent atom, and the saturated ring may optionally have one or more substituents selected from Group $P^1$); or $Z^2$ and $Z^3$ may combine each other together with the carbon atom to which they are attached to form a five-, six- or seven-membered saturated ring (with the proviso that the saturated ring may optionally contain one or more oxygen atoms, nitrogen atoms or sulfur atoms as the ring-constituent atom, and the saturated ring may optionally have one or more substituents selected from Group $P^1$); and Group $P^1$: a group consisting of a halogen atom, a cyano group, a C3-C6 cycloalkyl group, a C3-C6 halocycloalkyl group, an C1-C4 alkoxy group, a C1-C4 haloalkoxy group, an C1-C4 alkylthio group or a C1-C4 haloalkylthio group].

[2] The tetrazolinone compound according to [1] wherein Q represents Q1.

[3] The tetrazolinone compound according to [1] wherein Q represents Q2.

[4] The tetrazolinone compound according to [1] wherein Q represents Q3.

[5] The tetrazolinone compound according to [1] wherein Q represents Q4.

[6] The tetrazolinone compound according to any one of [1] to [5],
wherein
$R^1$ represents an C1-C3 alkyl group, a halogen atom, a C1-C3 haloalkyl group, an C2-C3 alkynyl group, a C2-C3 haloalkynyl group, a C3-C5 cycloalkyl group, a C3-C5 halocycloalkyl group, an C1-C3 alkoxy group or a C1-C3 haloalkoxy group;

$R^2$, $R^4$, $R^5$, $R^7$, $R^8$, $R^9$ and $R^{11}$ represent a hydrogen atom;

$R^3$ represents a hydrogen atom, a halogen atom, an C1-C3 alkyl group or a C1-C3 haloalkyl group;

$R^6$ represents an C1-C4 alkyl group, a halogen atom, an C1-C4 alkoxy group, a C1-C4 haloalkyl group, an C2-C4 alkenyl group or a C2-C4 haloalkenyl group;

$R^{10}$ represents a methyl group; and

X represents an oxygen atom.

[7] The tetrazolinone compound according to any one of [1], [2] or [6],
wherein
$Y^1$ and $Y^2$ may combine each other together with the carbon atom to which they are attached to form a five- or six-membered saturated ring;

$Y^2$ and $Y^3$ may combine each other together with the carbon atom to which they are attached to form a five- or six-membered saturated ring;

when each of $Y^1$, $Y^2$ and $Y^3$ does not form the five- or six-membered saturated ring, $Y^1$ represents a hydrogen atom, an C1-C6 alkyl group, a C1-C6 haloalkyl group, a C3-C6 cycloalkyl group or a C3-C6 halocycloalkyl group;

$Y^2$ represents a hydrogen atom, a halogen atom, an C1-C6 alkyl group, a C1-C6 haloalkyl group, an C2-C6 alkynyl group, an C1-C6 alkoxy group, a C1-C6 haloalkoxy group, C3-C6 cycloalkyl group or a C3-C6 halocycloalkyl group;

$Y^3$ represents a hydrogen atom, an C1-C4 alkyl group or a C1-C4 haloalkyl group.

[8] The tetrazolinone compound according to any one of [1], [3] or [6],
wherein
$Z^1$ represents an C1-C6 alkyl group, a C1-C6 haloalkyl group, an C3-C6 alkynyl group, a C3-C6 haloalkynyl group, a C3-C6 cycloalkyl group, a C3-C6 halocycloalkyl group or a C4-C7 cycloalkylmethyl group;

$Z^2$ represents a hydrogen atom, a halogen atom, an C1-C6 alkyl group, a C1-C6 haloalkyl group, an C1-C6 alkoxy group, a C1-C6 haloalkoxy group, a C3-C6 cycloalkyl group or a C3-C6 halocycloalkyl group; alternatively, $Z^1$ and $Z^2$ may combine each other together with the carbon atom or the nitrogen atom to which they are attached to form a five- or six-membered saturated ring; and $Z^3$ represents a hydrogen atom, a halogen atom, an C1-C4 alkyl group or a C1-C4 haloalkyl group.

[9] The tetrazolinone compound according to any one of [1], [2], [6] or [7],
wherein
$Y^1$ and $Y^2$ connect to each other to represent —$CH_2$—$CH_2$—$CH_2$— or —$CH_2$—$CH_2$—$CH_2$—$CH_2$—, which combines together with the carbon atoms to which $Y^1$ and $Y^2$ are attached to form a five-membered or six-membered ring;

$Y^2$ and $Y^3$ connect to each other to represent —$CH_2$—$CH_2$—$CH_2$— or —$CH_2$—$CH_2$—$CH_2$—$CH_2$—, which combines together with the carbon atoms to which $Y^2$ and $Y^3$ are attached to form a five-membered or six-membered ring;

when each of $Y^1$, $Y^2$ and $Y^3$ does not form the five- or six-membered saturated ring, $Y^1$ represents a hydrogen atom, an C1-C3 alkyl group, a C1-C3 haloalkyl group or a cyclopropyl group;

$Y^2$ represents a hydrogen atom, an C1-C3 alkyl group, a C1-C3 haloalkyl group or an C1-C3 alkoxy group; and $Y^3$ represents a hydrogen atom or a methyl group.

[10] The tetrazolinone compound according to any one of [1], [3] or [6],
wherein
$Z^1$ represents an C1-C6 alkyl group, a C1-C6 haloalkyl group, an C3-C6 alkynyl group or a C4-C7 cycloalkylmethyl group;

$Z^2$ represents a hydrogen atom, a halogen atom, a cyano group, an C1-C6 alkyl group, a C1-C6 haloalkyl group, an C1-C6 alkoxy group, an C3-C6 alkynyloxy group, an C1-C6 alkylthio group or a C1-C6 haloalkoxy group; and $Z^3$ represents a hydrogen atom, a halogen atom, a cyano group, an C1-C4 alkyl group or a C1-C4 haloalkyl group.

[11] The tetrazolinone compound according to any one of [1], [3] or [6],
wherein
$Z^1$ represents an C1-C6 alkyl group or a C1-C6 haloalkyl group;

$Z^2$ represents a hydrogen atom, a halogen atom, a cyano group, a methoxy group, an ethoxy group, a 2-propynyloxy group, a methylthio group, a difluoromethyl group, a trifluoromethyl group or an C1-C3 alkyl group; and $Z^3$ represents a hydrogen atom, a halogen atom, a cyano group or a methyl group.

[12] The tetrazolinone compound according to any one of [1], [3], [6] or [8],
wherein
$Z^1$ represents an C1-C6 alkyl group or a C1-C6 haloalkyl group;

$Z^2$ represents a hydrogen atom, a chlorine atom, a trifluoromethyl group or an C1-C3 alkyl group; and $Z^3$ represents a hydrogen atom, a halogen atom or a methyl group.

[13] The tetrazolinone compound according to any one of [1], [2], [6] or [7],
wherein
$Y^1$ and $Y^2$ connect to each other to represent —$CH_2$—$CH_2$—$CH_2$—$CH_2$—, which combines together with the carbon atoms to which they are attached to form a six-membered ring;

$Y^2$ and $Y^3$ connect to each other to represent —$CH_2$—$CH_2$—$CH_2$—$CH_2$—, which combines together with the carbon atoms to which they are attached to form a six-membered ring;

when each of $Y^1$, $Y^2$ and $Y^3$ does not form the six-membered saturated ring, $Y^1$ represents a hydrogen atom or an C1-C3 alkyl group;

$Y^2$ represents a hydrogen atom, a halogen atom, a cyano group, an C1-C3 alkyl group, a C1-C3 haloalkyl group or an C1-C3 alkoxy group; and $Y^3$ represents a hydrogen atom or a methyl group.

[14] The tetrazolinone compound according to any one of [1] to [13],
wherein
$R^1$ represents a methyl group, an ethyl group, a chlorine atom, a bromine atom or a trifluoromethyl group;

$R^3$ represents a hydrogen atom or a methyl group; and $R^6$ represents a methyl group, an ethyl group, chlorine atom, a bromine atom, a methoxy group or an ethoxy group.

[15] A tetrazolinone compound of a formula (2):

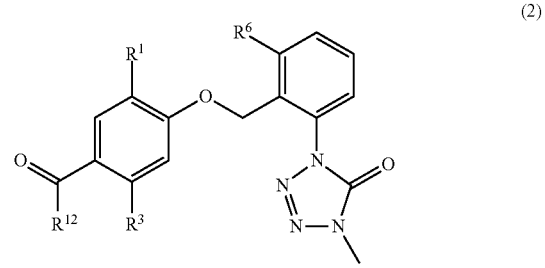

[wherein
$R^1$ represents a methyl group, an ethyl group, chlorine atom, a bromine atom, a trifluoromethyl group or a cyclopropyl group;

$R^3$ represents a hydrogen atom or a methyl group;

$R^6$ represents a methyl group, an ethyl group, chlorine atom, a bromine atom, a methoxy group or an ethoxy group; and $R^{12}$ represents an C1-C6 alkyl group, a C1-C6 haloalkyl group, a C3-C6 cycloalkyl group or a C1-C6 halocycoalkyl group].

[16] The tetrazolinone compound according to [15],
wherein
$R^1$ represents a methyl group, an ethyl group, chlorine atom or a bromine atom;

$R^3$ represents a hydrogen atom or a methyl group;

$R^6$ represents a methyl group, an ethyl group, a chlorine atom, a bromine atom or a methoxy group; and $R^{12}$ represents a methyl group, an ethyl group or a cyclopropyl group.

[17] An agent for controlling pests comprising the tetrazolinone compound according to any one of [1] to [16].

[18] A method for controlling pests comprising applying an effective amount of the tetrazolinone compound according to any one of [1] to [16] to plant or soil.

[19] Use of the tetrazolinone compound according to any one of [1] to [16] for controlling pests.

[20] A tetrazolinone compound represented by a formula (3):

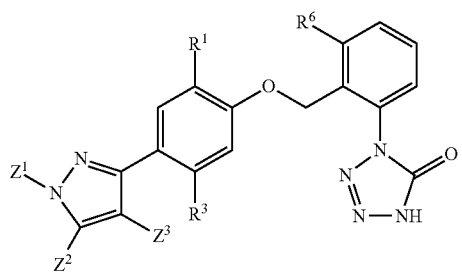
(3)

[wherein $R^1$ represents a methyl group, an ethyl group, a chlorine atom, a bromine atom or a trifluoromethyl group;

$R^3$ represents a hydrogen atom or a methyl group;

$R^6$ represents an C1-C3 alkyl group, a halogen atom or an C1-C2 alkoxy group;

$Z^1$ represents an C1-C3 alkyl group;

$Z^2$ represents a hydrogen atom, an C1-C2 alkoxy group, an C1-C3 alkyl group, an C1-C2 alkylthio group, a halogen atom or a cyano group; and $Z^3$ represents a hydrogen atom, an C1-C3 alkyl group, a halogen atom or a cyano group].

[21] The tetrazolinone compound according to [20], wherein $R^1$ represents a methyl group;

$R^3$ represents a hydrogen atom;

$R^6$ represents an C1-C2 alkyl group;

$Z^1$ represents an C1-C3 alkyl group;

$Z^2$ represents a C1-C2 alkoxy group or a halogen atom;

$Z^3$ represents an C1-C3 alkyl group.

[22] A pyrazole compound represented by a formula (4):

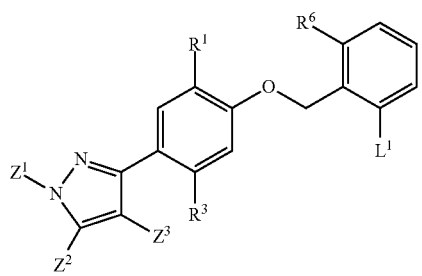
(4)

[wherein $R^1$ represents a methyl group, an ethyl group, a chlorine atom, a bromine atom or a trifluoromethyl group;

$R^3$ represents a hydrogen atom or a methyl group;

$R^6$ represents an C1-C3 alkyl group, a halogen atom or an C1-C2 alkoxy group;

$Z^1$ represents an C1-C3 alkyl group;

$Z^2$ represents a hydrogen atom, an C1-C2 alkoxy group, an C1-C3 alkyl group, an C1-C2 alkylthio group, a halogen atom or a cyano group;

$Z^3$ represents a hydrogen atom, an C1-C3 alkyl group, a halogen atom or a cyano group; and $L^1$ represents a nitro group, an amino group, an isocyanate group, a carboxyl group, an C2-C6 alkoxycarbonyl group, a halogen atom, a halocarbonyl group, NSO, $C(O)N_3$, $C(O)NH_2$, $C(O)NHCl$, $C(O)NHBr$ or $C(O)NHOH$].

[23] The pyrazole compound according to [22], wherein $R^1$ represents a methyl group;

$R^3$ represents a hydrogen atom;

$R^6$ represents an C1-C2 alkyl group;

$Z^1$ represents an C1-C3 alkyl group;

$Z^2$ represents an C1-C2 alkoxy group or a halogen atom;

$Z^3$ represents an C1-C3 alkyl group; and $L^1$ represents a nitro group, an amino group or an isocyanate group.

The present invention can control pests.

DESCRIPTION OF EMBODIMENTS

The compound of the present invention (hereinafter, sometimes referred to as "the present compound") is a tetrazolinone compound of a formula (1):

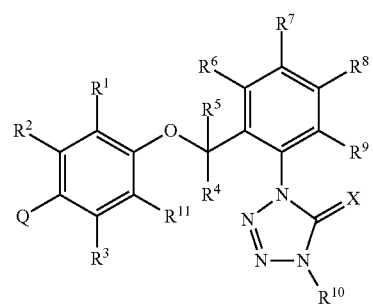
(1)

[wherein

Q represents a group selected from the following group: Q1, Q2, Q3 or Q4:

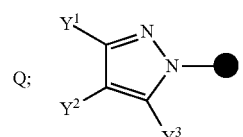
Q1

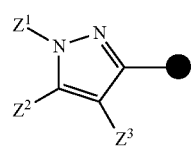
Q2

-continued

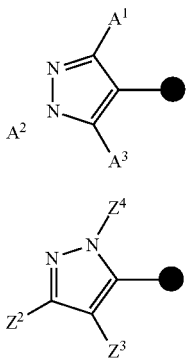

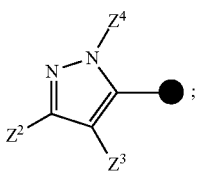

$R^1$, $R^2$, $R^3$ and $R^{11}$ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group $P^1$ or an C3-C6 cycloalkyl group optionally having one or more groups selected from Group $P^1$;

$R^4$ and $R^5$ represent independently of each other a hydrogen atom, a halogen atom or an C1-C3 alkyl group;

$R^6$ represents an C1-C4 alkyl group, a halogen atom, an C1-C4 alkoxy group, a cyano group, a nitro group, a C1-C4 haloalkyl group, an C2-C4 alkenyl group or a C2-C4 haloalkenyl group;

$R^7$, $R^8$ and $R^9$ represent independently of each other a hydrogen atom, a halogen atom, an C1-C3 alkyl group, a C1-C3 haloalkyl group, an C2-C3 alkenyl group, a C2-C3 haloalkenyl group or an C1-C3 alkoxy group;

$R^{10}$ represents an C1-C3 alkyl group, a C1-C3 haloalkyl group, an C2-C3 alkenyl group, a C2-C3 haloalkenyl group, an C2-C3 alkynyl group, a C2-C3 haloalkynyl group, a C3-C5 cycloalkyl group or a C3-C5 halocycloalkyl group;

X represents an oxygen atom or a sulfur atom;

$A^1$ and $A^3$ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group $P^1$, or a C3-C6 cycloalkyl group optionally having one or more groups selected from Group $P^1$;

$A^2$, $Z^1$ and $Z^4$ represent independently of each other a hydrogen atom, an amino group, an C3-C6 alkenyl group, a C3-C6 haloalkenyl group, an C3-C6 alkynyl group, a C3-C6 haloalkynyl group, an C1-C6 alkylsulfinyl group, a C1-C6 haloalkylsulfinyl group, an C1-C6 alkylsulfonyl group, a C1-C6 haloalkylsulfonyl group, a C3-C6 cycloalkylsulfonyl group, a C3-C6 halocycloalkylsulfonyl group, an C2-C8 alkylaminosulfonyl group, a C2-C8 haloalkylaminosulfonyl group, a C3-C9 trialkylsilyl group, an C2-C6 alkylcarbonyl group, an C2-C6 alkoxycarbonyl group, an C2-C8 alkylaminocarbonyl group, a C4-C7 cycloalkylmethyl group, an C1-C6 alkyl group optionally having one or more groups selected from Group $P^1$ or a C3-C6 cycloalkyl group optionally having one or more groups selected from Group $P^1$;

$Y^1$, $Y^2$, $Y^3$, $Z^2$ and $Z^3$ represent independently of each other a hydrogen atom, a halogen atom, a cyano group, a nitro group, an amino group, a hydroxy group, a thiol group, an aldehyde group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C3-C6 alkenyloxy group, a C3-C6 haloalkenyloxy group, an C3-C6 alkynyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloakylsulfonyl group, an C1-C8 alkylaminosulfonyl group, a pentaflurosulfanyl group, a C3-C9 trialkylsilyl group, an C2-C6 alkylcarbonyl group, an C2-C6 alkoxycarbonyl group, an C2-C8 alkylaminocarbonyl group, an aminocarbonyl group, an C1-C6 alkyl group optionally having one or more groups selected from Group $P^1$ or a C3-C6 cyclolakyl group optionally having one or more groups selected from Group $P^1$; or $Y^1$ and $Y^2$ may combine each other together with the carbon atom to which they are attached to form a five-, six- or seven-membered saturated ring (with the proviso that the saturated ring may optionally contain one or more oxygen atoms or sulfur atoms as the ring-constituent atom, and the saturated ring may optionally have one or more substituents selected from Group $P^1$); or $Y^2$ and $Y^3$ may combine each other together with the carbon atom to which they are attached to form a five-, six- or seven-membered saturated ring (with the proviso that the saturated ring may optionally contain one or more oxygen atoms or sulfur atoms as the ring-constituent atom, and the saturated ring may optionally have one or more substituents selected from Group $P^1$); or $Z^1$ and $Z^2$ may combine each other together with the carbon atom or nitrogen atom to which they are attached to form a five-, six- or seven-membered saturated ring (with the proviso that the saturated ring may optionally contain one or more oxygen atoms, nitrogen atoms or sulfur atoms as the ring-constituent atom, and the saturated ring may optionally have one or more substituents selected from Group $P^1$); or $Z^2$ and $Z^3$ may combine each other together with the carbon atom to which they are attached to form a five-, six- or seven-membered saturated ring (with the proviso that the saturated ring may optionally contain one or more oxygen atoms, nitrogen atoms or sulfur atoms as the ring-constituent atom, and the saturated ring may optionally have one or more substituents selected from Group $P^1$); and Group $P^1$: a group consisting of a halogen atom, a cyano group, a C3-C6 cycloalkyl group, a C3-C6 halocycloalkyl group, an C1-C4 alkoxy group, a C1-C4 haloalkoxy group, an C1-C4 alkylthio group or a C1-C4 haloalkylthio group].

Also, in the present invention a tetrazolinone compound represented by a formula (2):

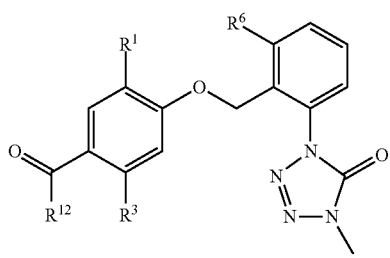

(2)

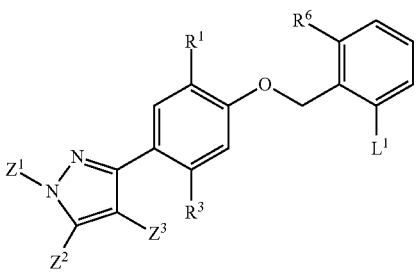

(4)

[wherein

R¹ represents a methyl group, an ethyl group, chlorine atom, a bromine atom, a trifluoromethyl group or a cyclopropyl group;

R³ represents a hydrogen atom or a methyl group;

R⁶ represents a methyl group, an ethyl group, a chlorine atom, a bromine atom, a methoxy group or an ethoxy group; and R¹² represents an C1-C6 alkyl group, a C1-C6 haloalkyl group, a C3-C6 cycloalkyl group or a C1-C6 halocycloalkyl group]

is also included, which is used in a preparation of the present compound and has an excellent efficacy for controlling pests.

Also, in the present invention a tetrazolinone compound represented by a formula (3):

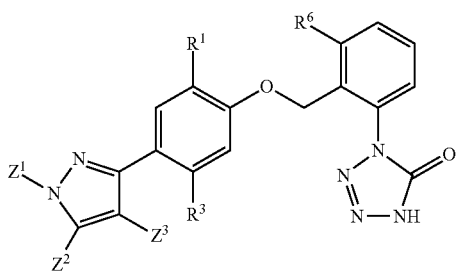

(3)

[wherein

R¹ represents a methyl group, an ethyl group, a chlorine atom, a bromine atom or a trifluoromethyl group;

R³ represents a hydrogen atom or a methyl group;

R⁶ represents an C1-C3 alkyl group, a halogen atom or an C1-C2 alkoxy group;

Z¹ represents an C1-C3 alkyl group;

Z² represents a hydrogen atom, an C1-C2 alkoxy group, an C1-C3 alkyl group, an C1-C2 alkylthio group, a halogen atom or a cyano group; and Z³ represents a hydrogen atom, an C1-C3 alkyl group, a halogen atom or a cyano group]

is also included, which is used in a preparation of the present compound.

Also, in the present invention a pyrazole compound represented by a formula (4):

[wherein

R¹ represents a methyl group, an ethyl group, a chlorine atom, a bromine atom or a trifluoromethyl group;

R³ represents a hydrogen atom or a methyl group;

R⁶ represents an C1-C3 alkyl group, a halogen atom or an C1-C2 alkoxy group;

Z¹ represents an C1-C3 alkyl group;

Z² represents a hydrogen atom, an C1-C2 alkoxy group, an C1-C1 alkyl group, an C1-C2 alkylthio group, a halogen atom or a cyano group;

Z³ represents a hydrogen atom, an C1-C3 alkyl group, a halogen atom or a cyano group; and L¹ represents a nitro group, an amino group, an isocyanate group, a carboxyl group, an C2-C6 alkoxycarbonyl group, a halogen atom, a halocarbonyl group, NSO, C(O)N₃, C(O)NH₂, C(O)NHCl, C(O)NHBr or C(O)NHOH] (hereinafter, referred to as "the present pyrazole compound").
is also included.

Hereinafter, the present invention is explained in detail.

The substituent to be used herein is specifically described below.

The term "halogen atom" includes, for example, a fluorine atom, a chlorine atom, a bromine atom and an iodine atom.

The term "C1-C6 alkyl group" represents a straight or branched alkyl group of one to six carbon atoms, and includes, for example, a methyl group, an ethyl group, a propyl group, an isopropyl group, a butyl group, an isobutyl group, a sec-butyl group, a tert-butyl group, a pentyl group and a hexyl group.

The term "C1-C5 alkyl group" represents a straight or branched alkyl group of one to five carbon atoms, and includes, for example, a methyl group, an ethyl group, a propyl group, an isopropyl group, a butyl group, an isobutyl group, a sec-butyl group, a tert-butyl group and a pentyl group.

The term "C1-C4 alkyl group" represents a straight or branched alkyl group of one to four carbon atoms, and includes, for example, a methyl group, an ethyl group, a propyl group, an isopropyl group, a butyl group, an isobutyl group, a sec-butyl group and a tert-butyl group.

The term "C1-C3 alkyl group" includes, for example, a methyl group, an ethyl group, a propyl group and an isopropyl group.

The term "C1-C2 alkyl group" includes, for example, a methyl group and an ethyl group.

The term "C1-C6 haloalkyl group" represents a group wherein at least one hydrogen atom of the straight or branched C1-C6 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, a 4-fluorobutyl group, and a 2,2-difluorohexyl group. The halogen atom that can be substituted for a hydrogen atom includes a fluorine atom, a chlorine atom, a bromine atom and an iodine atom.

The term "C1-C4 haloalkyl group" represents a group wherein at least one hydrogen atom of the straight or branched C1-C4 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, and a 4-fluorobutyl group. The halogen atom that can be substituted for a hydrogen atom includes a fluorine atom, a chlorine atom, a bromine atom and an iodine atom.

The term "C1-C3 haloalkyl group" includes, for example, a chloromethyl group, a dichloromethyl group, a fluoromethyl group, a difluoromethyl group, chlorofluoromethyl group, a dichlorofluoromethyl group, a chlorodifluoromethyl group, a trifluoromethyl group, trichloromethyl group, a tribromomethyl group, a 2-fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, a heptafluoropropyl group and a 1-(fluoromethyl)-2-fluoroethyl group.

The term "C1-C6 perfluoroalkyl group" represents a group wherein all hydrogen atoms of the straight or branched C1-C6 alkyl group is substituted with a fluorine atom, and includes, for example, a trifluoromethyl group, a pentafluoroethyl group, a heptafluoropropyl group, heptafluoroisopropyl group, a nonafluorobutyl group, a nonafluoro-tert-butyl group, an undecafluoropentyl group and a dodecafluorohexyl group.

The term "C3-C6 cycloalkyl group" represents cyclic alkyl group of three to six carbon atoms, and encompasses a cycloalkyl group having an alkyl group, and includes, for example, a cyclopropyl group, a cyclobutyl group, a cyclopentyl group, a cyclohexyl group, a 1-methylcyclopropyl group, a 2-methylcyclopropyl group, a 2,2-dimethylcyclopropyl group and a 2,3-dimethylcyclopropyl group.

The term "C3-C5 cycloalkyl group" represents a cyclic alkyl group of three to five carbon atoms, and encompasses a cycloalkyl group having an alkyl group, and includes, for example, a cyclopropyl group, a cyclobutyl group, a cyclopentyl group, a 1-methylcyclopropyl group, a 2-methylcyclopropyl group, a 2,2-dimethylcyclopropyl group and a 2,3-dimethylcyclopropyl group.

The term "C3-C4 cycloalkyl group" represents a cyclic alkyl group of three to four carbon atoms, and encompasses a cycloalkyl group having an alkyl group, and includes, for example, a cyclopropyl group, a cyclobutyl group and a 1-methylcyclopropyl group.

The term "C4-C7 cycloalkylmethyl group" represents a methyl group having a cyclic alkyl of three to six carbon atoms, and the cyclic alkyl group may further optionally contain alkyl group(s), and the number of carbon atom of the cycloalkylmethyl group is four to seven. The C4-C7 cycloalkyl group includes, for example, a cyclopropylmethyl group, a cyclobutylmethyl group, a cyclopentylmethyl group, a cyclohexylmethyl group, a 1-methylcyclopropylmethyl group, a 2-methylcyclopropylmethyl group and a 2,2-dimethylcyclopropylmethyl group.

The term "C3-C6 halocycloalkyl group" represents a group wherein at least one hydrogen atom of the C3-C6 cycloalkyl group is substituted with a halogen atom, and includes, for example a 1-fluorocyclopropyl group, a 2-fluorocyclopropyl group, a 2,2-difluorocyclopropyl group, a 1-chlorocyclopropyl group, a 2-chloro-2-fluorocyclopropyl group, 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, 2,2,3,3-tetrafluorocyclobutyl group, a 1-fluorocyclobutyl group, a 1-chlorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group and a 4,4-difluorocyclohexyl group. The halogen atom that can be substituted for a hydrogen atom includes a fluorine atom, a chlorine atom, a bromine atom and an iodine atom.

The term "C3-C5 halocycloalkyl group" represents a group wherein at least one hydrogen atom of the C3-C5 cycloalkyl group is substituted with a halogen atom, and includes, for example a 1-fluorocyclopropyl group, a 2-fluorocyclopropyl group, a 2,2-difluorocyclopropyl group, 1-chlorocyclopropyl group, a 2-chloro-2-fluorocyclopropyl group, 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2-chlorocyclopentyl group and a 3-chlorocyclopentyl group. The halogen atom that can be substituted for a hydrogen atom includes a fluorine atom, a chlorine atom, a bromine atom and an iodine atom.

The term "C2-C6 alkenyl group" represents a straight or branched alkenyl group of two to six carbon atoms, and includes, for example, a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, an 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group and a 5-hexenyl group.

A term "C2-C6 haloalkenyl group" represents a group wherein at least one hydrogen atom of the straight or branched C2-C6 alkenyl group is substituted with a halogen atom, and includes, for example, a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a 3,4-dibromo-1-pentenyl group, a 4,4-difluoro-3-methyl-3-butenyl group, a 3,3,4,4,5,5,5-heptafluoro-1-pentenyl group, a 5,5-difluoro-4-pentenyl group, a 4,5,5-trifluoro-4-pentenyl group, 3,4,4,4-tetrafluoro-3-trifluoromethyl-1-butenyl group, 4,4,4-trifluoro-3-methyl-2-butenyl group, a 3,5,5-trifluoro-2,4-pentadienyl group, a 4,4,5,5,6,6,6-heptafluoro-2-hexenyl group, a 3,4,4,5,5,5-hexafluoro-3-trifluoromethyl-1-pentenyl group, a 4,5,5,5-tetrafluoro-4-trifluoromethyl-2-pentenyl group and a 5-bromo-4,5,5-trifluoro-4-trifluoromethyl-2-pentenyl group. The halogen atom that can be substituted for a hydrogen atom includes a fluorine atom, a chlorine atom, a bromine atom and an iodine atom.

The term "C3-C6 alkenyl group" represents a straight or branched alkenyl group of three to six carbon atoms, and includes, for example, a 2-propenyl group, a 2-butenyl group, a 1-methyl-2-propenyl group, a 3-butenyl group, a 2-methyl-2 propenyl group, an 1-ethyl-2-propenyl group, a 2-pentenyl group, a 3-pentenyl group, a 1-methyl-2-butenyl group, a 4-pentenyl group, a 1-methyl-3-butenyl group, a 1,2-dimethyl-2-propenyl group, a 1,1-dimethyl-2-propenyl group, a 2-methyl-2-butenyl group, a 3-methyl-2-butenyl group, a 2-methyl-3-butenyl group, a 3-methyl-3-butenyl group, a 1-vinyl-2-propenyl group, a 2-hexenyl group, a 3-hexenyl group, a 4-hexenyl group and a 5-hexenyl group.

A term "C3-C6 haloalkenyl group" represents a group wherein at least one hydrogen atom of the straight or branched C3-C6 alkenyl group is substituted with a halogen atom, and includes, for example, a 3-chloro-2-propenyl group, a 3-bromo-2-propenyl group, a 2-chloro-2-propenyl group, a 3,3-difluoro-2-propenyl group, a 2,3,3-trichloro-2-propenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3-chloro-4,4,4-trifluoro-2-butenyl group, a 3,4-dibromo-1-pentenyl group, a 4,4-difluoro-3-methyl-3-butenyl group, a 5,5-difluoro-4-pentenyl group, a 4,5,5-trifluoro-4-pentenyl group, a 4,4,4-trifluoro-3-methyl-2-butenyl group, a 3,5,5-trifluoro-2,4-pentadienyl group, a 4,4,5,5,6,6,6-heptafluoro-2-hexenyl group, a 4,5,5,5-tetrafluoro-4-trifluoromethyl-2-pentenyl group and a 5-bromo-4,5,5-trifluoro-4-trifluoromethyl-2-pentenyl group. The halogen atom that can be substituted for a hydrogen atom includes a fluorine atom, a chlorine atom, a bromine atom and an iodine atom.

The term "C2-C4 alkenyl group" includes, for example, a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group and a 2-methyl-2-propenyl group.

The term "C2-C3 alkenyl group" includes, for example, a vinyl group, a 1-propenyl group, an isopropenyl group and a 2-propenyl group.

A term "C2-C4 haloalkenyl group" represents a group wherein at least one hydrogen atom of the straight or branched C2-C4 alkenyl group is substituted with a halogen atom, and includes, for example, a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group and a 3,4,4-trifluoro-1,3-butadienyl group. The halogen atom that can be substituted for a hydrogen atom includes a fluorine atom, a chlorine atom, a bromine atom and an iodine atom.

A term "C2-C3 haloalkenyl group" includes, for example, a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group and a 2,3,3-trichloro-2-propenyl group.

The term "C2-C6 alkynyl group" represents an alkynyl group of two to six carbon atoms which may be straight or branched and includes, for example, an ethynyl group, a propargyl group, a 1-butyne-3-yl group, a 3-methyl-1-butyne-3-yl group, a 2-butynyl group, a 3-butynyl group, a 2-pentynyl group, a 3-pentynyl group, a 4-pentynyl group, a 1-hexynyl group and a 5-hexynyl group.

The term "C2-C6 haloalkynyl group" represents a group wherein at least one hydrogen atom of the straight or branched C2-C6 alkynyl group is substituted with a halogen atom, and includes, for example, a fluoroethynyl group, a 3-fluoro-2-propynyl group, a 3-chloro-2-propynyl group, a 3-bromo-2-propynyl group, an 3-iodo-2-propynyl group, chloro-1-propynyl group, a 5-chloro-4-pentynyl group, a 3,3,3-trifluoro-1-propynyl group, a 3,3-difluoro-1-propynyl group, a 4,4,4-trifluoro-2-butynyl group, a perfluoro-2-butynyl group, a perfluoro-2-pentynyl group, a perfluoro-3-pentynyl group and a perfluoro-1-hexynyl group. The halogen atom that can be substituted for a hydrogen atom includes a fluorine atom, a chlorine atom, a bromine atom and an iodine atom.

The term "C3-C6 alkynyl group" represents an alkynyl group of three to six carbon atoms which may be straight or branched, and includes, for example, a 2-propynyl group, a 1-butyne-3-yl group, a 3-methyl-1-butyne-3-yl group, a butynyl group, a 3-butynyl group, a 2-pentynyl group, a 3-pentynyl group, a 4-pentynyl group, a 1-hexynyl group and a 5-hexynyl group.

The term "C3-C6 haloalkynyl group" represents a group wherein at least one hydrogen atom of the straight or branched C3-C6 alkynyl group is substituted with a halogen atom, and includes, for example, a 3-chloro-2-propynyl group, a 3-bromo-2-propynyl group, an 3-iodo-2-propynyl group, a 5-chloro-4-pentynyl group, a 4,4,4-trifluoro-2-butynyl group, a perfluoro-2-butynyl group, a perfluoro-2-pentynyl group and a perfluoro-3-pentynyl group. The halogen atom that can be substituted for a hydrogen atom includes a fluorine atom, a chlorine atom, a bromine atom and an iodine atom.

The term "C2-C3 alkynyl group" includes, for example, an ethynyl group, a 1-propynyl group and a 2-propynyl group.

The term "C3-C4 alkynyl group" includes, for example, a 2-propynyl group, a 2-butynyl group and a 3-butynyl group.

The term "C2-C3 haloalkynyl group" includes, for example, a fluoroethynyl group, a 3-fluoro-2-propynyl group, a 3-chloro-2-propynyl group, a 3-bromo-2-propynyl group, an 3-iodo-2-propynyl group, a 3-chloro-1-propynyl group, a 3,3,3-trifluoro-1-propynyl group and a 3,3-difluoro-1-propynyl group.

The term "C1-C6 alkoxy group" represents an alkoxy group of one to six carbon atoms which may be straight or branched, and includes, for example, a methoxy group, an ethoxy group, a propyloxy group, an isopropyloxy group, butyloxy group, an isobutyloxy group, a sec-butyloxy group, a tert-butyloxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group and a 4-methylpentyloxy group.

The term "C1-C4 alkoxy group" represents an alkoxy group of one to four carbon atoms which may be straight or branched, and includes, for example, a methoxy group, an ethoxy group, a propyloxy group, an isopropyloxy group, a butyloxy group, an isobutyloxy group, a sec-butyloxy group and a tert-butyloxy group.

The term "C1-C3 alkoxy group" includes, for example, a methoxy group, an ethoxy group, a propyloxy group and an isopropyloxy group.

The term "C1-C2 alkoxy group" includes, for example, a methoxy group and an ethoxy group.

The term "C1-C6 haloalkoxy group" represents a group wherein at least one hydrogen atom of the straight or branched C1-C6 alkoxy group is substituted with a halogen atom, and includes, for example, a trifluoromethoxy group, a trichloromethoxy group, a chloromethoxy group, a dichloromethoxy group, a fluoromethoxy group, difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy propoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a nonabromobutoxy group, a nonaiodobutoxy group, a perfluoropentyloxy group, a perchloropentyloxy group, a perbromopentyloxy group, a perfluorohexyloxy group, a perchlorohexyloxy group, a perbromohexyloxy group and a periodohexyloxy group. The halogen atom that can be substituted for a hydrogen atom includes a fluorine atom, a chlorine atom, a bromine atom and an iodine atom.

The term "C1-C4 haloalkoxy group" represents a group wherein at least one hydrogen atom of the straight or branched C1-C4 alkoxy group is substituted with a halogen atom, and includes, for example, a trifluoromethoxy group, a trichloromethoxy group, a chloromethoxy group, a dichloromethoxy group, a fluoromethoxy group, difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 2,3,3-trifluoropropoxy group, a nonafluorobutoxy group, a nonachlorobutoxy group, a nonabromobutoxy group and a nonaiodobutoxy group. The halogen atom that can be substituted for a hydrogen atom includes a fluorine atom, a chlorine atom, a bromine atom and an iodine atom.

The term "C1-C3 haloalkoxy group" represents a group wherein at least one hydrogen atom of the straight or branched C1-C3 alkoxy group is substituted with a halogen atom, and includes, for example, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group and a 3,3,3-trifluoropropoxy group. The halogen atom that can be substituted for a hydrogen atom includes a fluorine atom, a chlorine atom, a bromine atom and an iodine atom.

The term "C1-C6 alkylthio group" represents an alkylthio group of one to six carbon atoms which may be straight or branched, and includes, for example, a methylthio group, an ethylthio group, a n-propylthio group, an isopropylthio group, a butylthio group, a sec-butylthio group, a tert-butylthio group, a pentylthio group, an isopentylthio group, a neopentylthio group, a n-hexylthio group, an isohexylthio group and a sec-hexylthio group.

The term "C1-C6 haloalkylthio group" represents a group wherein at least one hydrogen atom of the straight or branched C1-C6 alkylthio group is substituted with halogen atom, and includes, for example, monofluoromethylthio group, a difluoromethylthio group, trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, a 2,3,3-trifluoropropylthio group, a nonafluorobutylthio group, a nonachlorobutylthio group, a nonabromobutylthio group, a nonaiodobutylthio group, a perfluoropentylthio group, a perchloropentylthio group, a perbromopentylthio group, a perfluorohexylthio group, a perchlorohexylthio group, a perbromohexylthio group and a periodohexylthio group. The halogen atom that can be substituted for a hydrogen atom includes a fluorine atom, a chlorine atom, a bromine atom and an iodine atom.

The term "C1-C4 alkylthio group" includes, for example, methylthio group, an ethylthio group, propylthio group, an isopropylthio group, a butylthio group, an isobutylthio group and a tert-butylthio group.

The term "C1-C2 alkylthio group" includes, for example, a methylthio group and an ethylthio group.

The term "C1-C4 haloalkylthio group" represents a group wherein at least one hydrogen atom of the straight or branched C1-C4 alkylthio group is substituted with a halogen atom, and includes, for example, a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group and a 2,2-difluoroethylthio group. The halogen atom that can be substituted for a hydrogen atom includes a fluorine atom, a chlorine atom, a bromine atom and an iodine atom.

The term "C3-C6 alkenyloxy group" represents a straight or branched alkenyloxy group of three to six carbon atoms, and includes, for example, a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, 2-methyl-3-butenyloxy group, a 3-methyl-3-butenyloxy group, a 1-vinyl-2-propenyloxy group and a 5-hexenyloxy group.

The term "C3-C6 haloalkenyloxy group" represents a group wherein at least one hydrogen atom of the straight or branched C3-C6 alkenyloxy group is substituted with a halogen atom, and includes, for example, a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 3-chloro-2-butenyloxy group, a 4,4,4-trifluoro-2-butenyloxy group, a 4-bromo-4,4-difluoro-2-butenyloxy group, a 3-bromo-3-butenyloxy group, a 3,4,4-trifluoro-3-butenyloxy group, a 3,4,4-tribromo-3-butenyloxy group, a 3-bromo-2-methyl-2-propenyloxy group, a 3,3-difluoro-2-methyl-2-propenyloxy group, a 3-chloro-4,4,4-trifluoro-2-butenyloxy group, 4,4-difluoro-3-methyl-3-butenyloxy group, a 5,5-difluoro-4-pentenyloxy group, a 4,5,5-trifluoro-4-pentenyloxy group, a 4,4,4-trifluoro-3-methyl-2-butenyloxy group, a 3,5,5-trifluoro-2,4-pentadienyloxy group, a 4,4,5,5,6,6,6-heptafluoro-2-hexenyloxy group, a 4,5,5,5-tetrafluoro-4-trifluoromethyl-2-pentenyloxy group and a 5-bromo-4,5,5-trifluoro-4-trifluoromethyl-2-pentenyloxy group. The halogen atom that can be substituted for a hydrogen atom includes a fluorine atom, a chlorine atom, a bromine atom and an iodine atom.

The term "C3-C6 alkynyloxy group" represents a straight or branched alkynyloxy group of three to six carbon atoms, and includes, for example, a 2-propynyloxy group, a 1-butyne-3-yloxy group, a 3-methyl-1-butyne-3-yloxy group, a 2-butynyloxy group, a 3-butynyloxy group, a 2-penthynyloxy group, a 3-penthynyloxy group, a 4-penthynyloxy group and a 5-hexynyloxy group.

The term "C3-C4 alkynyloxy group" represents a straight or branched alkynyloxy group of three to four carbon atoms, and includes, for example, a 2-propynyloxy group, a 1-butyne-3-yloxy group and a 2-butynyloxy group.

The term "C3-C6 haloalkynyloxy group" represents a group wherein at least one hydrogen atom of the straight or branched C3-C6 alkynyloxy group is substituted with a halogen atom, and includes, for example, a 3-chloro-2-propynyloxy group, a 3-bromo-2-propynyloxy group, an 3-iodo-2-propynyloxy group, a 5-chloro-4-pentynyloxy group, a 4,4,4-trifluoro-2-butynyloxy group, perfluoro-2-butynyloxy group, a perfluoro-3-butynyloxy group, perfluoro-2-pentynyloxy group, a perfluoro-3-pentynyloxy group, a perfluoro-4-pentynyloxy group and a perfluoro-5-hexynyloxy group. The halogen atom that can be substituted for a hydrogen atom includes a fluorine atom, a chlorine atom, a bromine atom and an iodine atom.

The term "C3-C6 alkenylthio group" represents a straight or branched alkenylthio group of three to six carbon atoms, and includes, for example, a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group and a 5-hexenylthio group.

The term "C3-C6 haloalkenythio group" represents a group wherein at least one hydrogen atom of the straight or branched C3-C6 alkynythio group is substituted with a halogen atom, and includes, for example, a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo-2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 4-bromo-4,4-difluoro-2-butenylthio group, a 3-bromo-3-butenylthio group, a 3,4,4-trifluoro-3-butenylthio group, a 3,4,4-tribromo-3-butenylthio group, a 3-bromo-2-methyl-2-propenylthio group, a 3,3-difluoro-2-methyl-2-propenylthio group, a 3-chloro-4,4,4-trifluoro-2-butenylthio group, a 4,4-difluoro-3-methyl-3-butenylthio group, a 5,5-difluoro-4-pentenylthio group, a 4,5,5-trifluoro-4-pentenylthio group, a 4,4,4-trifluoromethyl-3-methyl-2-butenylthio group, a 3,5,5-trifluoro-2,4-pentadienylthio group, a 4,4,5,5,6,6,6-heptafluoro-2-hexenylthio group, a 4,5,5,5-tetrafluoro-4-trifluoromethyl-2-pentenylthio group and a 5-bromo-4,5,5-trifluoro-4-trifluoromethyl-2-pentenylthio group. The halogen atom that can be substituted for a hydrogen atom includes a fluorine atom, a chlorine atom, a bromine atom and an iodine atom.

The term "C3-C6 alkynythio group" represents a straight or branched alkynylthio group of three to six carbon atoms, and includes, for example, a propargylthio group, a 1-butyne-3-ylthio group, a 3-methyl-1-butyne-3-ylthio group, a 2-butynylthio group, a 3-butynylthio group, a 2-pentynylthio group, a 3-pentynylthio group, a 4-pentynylthio group and a 5-hexynylthio group.

The term of "C3-C6 haloalkynythio group" represents a group wherein at least one hydrogen atom of the straight or branched C3-C6 alkynythio group is substituted with a halogen atom, and includes, for example, a 3-chloro-2-propynylthio group, a 3-bromo-2-propynylthio group, an 3-iodo-2-propynylthio group, a 5-chloro-4-pentynylthio group, a 4,4,4-trifluoro-2-butynylthio group, a perfluoro-2-butynylthio group, perfluoro-3-butynylthio group, a perfluoro-2-pentynylthio group, a perfluoro-3-pentynylthio group, a perfluoro-4-pentynylthio group and a perfluoro-5-hexynylthio group. The halogen atom that can be substituted for a hydrogen atom includes a fluorine atom, a chlorine atom, a bromine atom and an iodine atom.

The term "C1-C8 alkylamino group" represents an amino group wherein one or two hydrogen atom(s) on the nitrogen atom is substituted with the straight and/or branched alkyl group which may be same or different from each other, and the total number of carbon atom of the alkyl group on the nitrogen atom is one to eight. Examples of the C1-C8 alkylamino group include a methylamino group, an ethylamino group, a propylamino group, an isopropylamino group, a N,N-dimethylamino group, a N,N-diethylamino group, an N-ethyl-N-methylamino group, a butylamino group, a pentylamino group, a hexylamino group, a N,N-dibutylamino group and a N-sec-butyl-N-methylamino group.

The term "C1-C8 haloalkylamino group" represents a group wherein at least one hydrogen atom of the C1-C8 alkylamino group is substituted with a halogen atom, and includes, for example, a 2,2,2-trifluoroethylamino group, a N,N-(2,2-di-trifluoroethyl)amino group, a N,N-(2,2-di-trichloroethyl)amino group and a pentafluoropropylamino group. The halogen atom that can be substituted for a hydrogen atom includes a fluorine atom, a chlorine atom, a bromine atom and an iodine atom.

The term "C2-C6 alkylcarbonyl group" represents an an alkylcarbonyl group of two to six carbon atoms having a straight or branched C1-C5 alkyl group, and includes, for example, a methylcarbonyl group, an ethylcarbonyl group, a propylcarbonyl group, an isopropylcarbonyl group, a pivaloyl group, a butylcarbonyl group and a pentylcarbonyl group.

The term "C2-C6 alkoxycarbonyl group" represents an an alkoxycarbonyl group of two to six carbon atoms having a straight or branched C1-C5 alkyl group, and includes, for example, a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isoamyloxycarbonyl group, neopentyloxycarbonyl group, a 2-pentyloxycarbonyl group, 3-pentyloxycarbonyl group and a 2-methylbutyloxycarbonyl group.

The term "C2-C8 alkylaminocarbonyl group" represents an aminocarbonyl group wherein one or two hydrogen atom(s) on the nitrogen atom is substituted with the straight and/or branched alkyl group which may be same or different from each other, and the total number of carbon atom of the alkyl group on the nitrogen atom is one to seven. Examples of the C2-C8 alkylaminocarbonyl group include a methylaminocarbonyl group, an ethylaminocarbonyl group, a propylaminocarbonyl group, an isopropylaminocarbonyl group, a butylaminocarbonyl group, a N,N-dimethylaminocarbonyl group, a N,N-diethylaminocarbonyl group, a N,N-dipropylaminocarbonyl group and a N,N-diisopropylaminocarbonyl group.

The term "C3-C9 trialkylsilyl group" represents a trialkylsily group of three to nine carbon atoms having a straight or branched C3-C9 trialkyl group, and includes, for example, a trimethylsilyl group, a tert-butyldimethylsilyl group, a triethylsilyl group, an isopropyldimethylsilyl group and a triisopropylsilyl group.

The term "halocarbonyl group" includes groups: C(O)F, C(O)Cl, C(O)Br and C(O)I.

The term "C1-C6 alkylsulfonyl group" represents an alkylsulfonyl group having a straight or branched C1-C6 alkyl group, and includes, for example, a methylsulfonyl group, an ethylsulfonyl group, a propylsulfonyl group, an isopropylsulfonyl group, a butylsulfonyl group, an isobutylsulfonyl group, a sec-butylsulfonyl group, pentylsulfonyl group, an isoamylsulfonyl group, neopentylsulfonyl group, a 2-pentylsulfonyl group, a 3-pentylsulfonyl group, a 2-methylbutylsulfonyl group, a hexylsulfonyl group, an isohexylsulfonyl group, a 3-methylpentylsulfonyl group and a 4-methylpentylsulfonyl group.

The term "C1-C6 haloalkylsulfonyl group" represents a group wherein at least one hydrogen atom of the straight or branched C1-C6 alkylsulfonyl group is substituted with a halogen atom, and includes, for example, a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, pentabromoethylsulfonyl group, a pentaiodoethylsulfonyl group, a 2,2,2-trichloroethylsulfonyl group, a 2,2,2-trifluoroethylsulfonyl group, a 2,2,2-tribromoethylsulfonyl group, a 2,2,2-triiodoethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a nonafluorobutylsulfonyl group, nonachlorobutylsulfonyl group, a nonabromobutylsulfonyl group, a nonaiodobutylsulfonyl group, a perfluoropentylsulfonyl group, a perchloropentylsulfonyl group, a perbromopentylsulfonyl group, a perfluorohexylsulfonyl group, a perchlorohexylsulfonyl group, a perbromohexylsulfonyl group and a periodohexylsulfonyl group. The halogen atom that can be substituted for a hydrogen atom includes a fluorine atom, a chlorine atom, a bromine atom and an iodine atom.

The term "C3-C6 cycloalkylsulfonyl group" represents a cyclic alkylsulfonyl group of three to six carbon atoms, and includes, for example, a cyclopropylsulfonyl group, a cyclobutylsulfonyl group, a cyclopentylsulfonyl group, a cyclohexylsulfonyl group, a 1-methylcyclopropylsulfonyl group and a 2,2-dimethylcyclopropylsulfonyl group.

The term "C3-C6 halocycloalkylsulfonyl group" represents a group wherein at least one hydrogen atom of the C3-C6 cyclic alkylsulfonyl group is substituted with a halogen atom, and includes, for example, a 2-fluorocyclopropylsulfonyl group, a 2,2-difluorocyclopropylsulfonyl group, a 2-chloro-2-fluorocyclopropylsulfonyl group, a 2,2-dichlorocyclopropylsulfonyl group, a 2,2-dibromocyclopropylsulfonyl group, a 2,2-difluoro-1-methylcyclopropylsulfonyl group, a 2,2-dichloro-1-methylcyclopropylsulfonyl group, a 2,2-dibromo-1-methylcyclopropylsulfonyl group, a 1-(trifluoromethyl)cyclopropylsulfonyl group, a 2,2,3,3-tetraflurocyclobutylsulfonyl group, a 2-chlorocyclohexylsulfonyl group, a 4,4-difluorocyclohexylsulfonyl group and a 4-chlorocycohexylsulfonyl group. The halogen atom that can be substituted for a hydrogen atom includes a fluorine atom, a chlorine atom, a bromine atom and an iodine atom.

The term "C1-C8 alkylaminosulfonyl group" represents an aminosulfonyl group wherein one or two hydrogen atom(s) on the nitrogen atom is substituted with the straight and/or branched alkyl group which may be same or different from each other, and the total number of carbon atom of the alkyl group on the nitrogen atom is one to eight. Examples of the C1-C8 alkylaminosulfonyl group include a methylaminosulfonyl group, an ethylaminosulfonyl group, a propylaminosulfonyl group, an isopropylaminosulfonyl group, a butylaminosulfonyl group, a N,N-dimethylaminosulfonyl group, a N,N-diethylaminosulfonyl group, a N,N-dipropylaminosulfonyl group, a N,N-diisopropylaminosulfonyl group, a pentylaminosulfonyl group and a hexylaminosulfonyl group.

The term "C2-C8 alkylaminosulfonyl group" represents an aminosulfonyl group wherein one or two hydrogen atom(s) on the nitrogen atom is substituted with the straight and/or branched alkyl group which may be same or different from each other, and the total number of carbon atom of the alkyl group on the nitrogen atom is two to eight. Examples of the C2-C8 alkylaminosulfonyl group include an ethylaminosulfonyl group, a propylaminosulfonyl group, an isopropylaminosulfonyl group, a butylaminosulfonyl group, a N,N-dimethylaminosulfonyl group, a N,N-diethylaminosulfonyl group, a N,N-dipropylaminosulfonyl group, a N,N-diisopropylaminosulfonyl group, a pentylaminosulfonyl group and a hexylaminosulfonyl group.

The term "C1-C8 haloalkylaminosulfonyl group" represents a group wherein at least one hydrogen atom of the C1-C8 alkylaminosulfonyl group is substituted with halogen atom, and includes, for example, a trifluoromethylaminosulfonyl group, a 2,2,2-trifluoroethylaminosulfonyl group, a N,N-di-(2,2,2-trifluoroethyl)aminosulfonyl group, a N,N-di-(2,2,2-trichloroethyl)aminosulfonyl group and a pentafluoropropylaminosulfonyl group. The halogen atom that can be substituted for a hydrogen atom includes a fluorine atom, a chlorine atom, a bromine atom and an iodine atom.

The term "C2-C8 haloalkylaminosulfonyl group" represents a group wherein at least one hydrogen atom of the C2-C8 alkylaminosulfonyl group is substituted with a halogen atom, and includes, for example, a 2,2,2-trifluoroethylaminosulfonyl group, a N,N-di-(2,2,2-trifluoroethyl)aminosulfonyl group, a N,N-di-(2,2,2-trichloroethyl) aminosulfonyl group and a pentafluoropropylaminosulfonyl group. The halogen atom that can be substituted for a hydrogen atom includes a fluorine atom, a chlorine atom, a bromine atom and an iodine atom.

The term "C1-C6 alkylsulfinyl group" represents a straight or branched alkylsulfinyl group of one to six carbon atoms, and includes, for example, a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, an isoamylsulfinyl group, neopentylsulfinyl group, a 2-pentylsulfinyl group, a 3-pentylsulfinyl group, a 2-methylbutylsulfinyl group, a hexylsulfinyl group, an isohexylsulfinyl group, a 3-methylpentylsulfinyl group and a 4-methylpentylsulfinyl group.

The term "C1-C6 haloalkylsulfinyl group" represents a group wherein at least one hydrogen atom of the straight or branched C1-C6 alkylsulfinyl group is substituted with a halogen atom, and includes, for example, a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-tribromoethylsulfinyl group, a 2,2,2-triiodoethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a nonafluorobutylsulfinyl group, a nonachlorobutylsulfinyl group, a nonabromobutylsulfinyl group, a nonaiodobutylsulfinyl group, a perfluoropentylsulfinyl group, a perchloropentylsulfinyl group, a perbromopentylsulfinyl group, a perfluorohexylsulfinyl group, a perchlorohexylsulfinyl group, a perbromohexylsulfinyl group and a periodohexylsulfinyl group. The halogen atom that can be substituted for a hydrogen atom includes a fluorine atom, a chlorine atom, a bromine atom and an iodine atom.

The terms "aldehyde group" and "formyl group" represent the same meanings.

The term "C1-C6 alkyl group optionally having one or more groups selected from Group $P^1$" represents an C1-C6 alkyl group wherein a hydrogen atom being attached to the carbon atom may be optionally substituted with one or more atom or group selected from Group $P^1$, and when said C1-C6 alkyl group has two or more atoms or groups selected from Group $P^1$, the atoms or groups selected from Group $P^1$ may be same or different from each other.

Examples of the C1-C6 alkyl group optionally having one or more groups selected from Group $P^1$ include a trifluoromethyl group, a trichloromethyl group, a tribromomethyl group, a 2,2,2-trifluoroethyl group, a 2,2,2-trichloroethyl group, a 3,3,3-trifluoropropyl group, a difluoromethyl group, a 2,2-difluoroethyl group, a 1,1-difluoroethyl group, a pentafluoroethyl group, a heptafluoroisopropyl group, a 1,1,2,2-tetrafluoroethyl group, a 2,2,3,3,3-pentafluoropropyl group, a 2,2,3,3,3-pentafluorobutyl group, a cyclopropylmethyl group, a cyclopropylethyl group, a cyclopropylpropyl group, a cyclopropylbutyl group, a cyclopropylpentyl group, a cyclopropylhexyl group, a cyclobutylmethyl group, a cyclobutylethyl group, a cyclobutylpropyl group, a cyclobutylbutyl group, a cyclopentylmethyl group, a cyclopentylethyl group, a cyclopentylpropyl group, a cyclohexylethyl group, a cyclohexylpropyl group, a 1-fluorocyclopropylmethyl group, a 1-fluorocyclopropylethyl group, a 1-fluorocyclopropylpropyl group, a 2,2-difluorocyclopropylmethyl group, a 2,2-difluorocyclopropylethyl group, a 2,2-difluorocyclopropylpropyl group, a pentafluorocyclopropylmethyl group, a pentafluorocyclopropylethyl group, a pentafluorocyclopropylpropyl group, a 1-chlorocyclopropylmethyl group, a 1-chlorocyclopropylethyl group, a 1-chlorocyclopropylpropyl group, a 2,2-dichlorocyclopropylmethyl group, a 2,2-dichlorocyclopropylethyl group, a 2,2-dichlorocyclopropylpropyl group, a pentachlorocyclopropylmethyl group, a pentachlorocyclopropylethyl group, a pentachlorocyclopropylpropyl group, a 1-fluorocyclobutylmethyl group, a 1-fluorocyclobutylethyl group, a 1-fluorocyclobutylpropyl group, a 2,2-difluorocyclobutylmethyl group, a 2,2-difluorocyclobutylethyl group, a 2,2-difluorocyclobutylpropyl group, a 1-chlorocyclobutylmethyl group, a 1-chlorocyclobutylethyl group, a 1-chlorocyclobutylpropyl group, a 2,2-dichlorocyclobutylmethyl group, a 2,2-dichlorocyclobutylethyl group, a 2,2-dichlorocyclobutylpropyl group, a 1-fluorocyclopentylmethyl group, a 1-fluorocyclopentylethyl group, a 1-fluorocyclopentylpropyl group, a 2,2-difluorocyclopentylmethyl group, a 2,2-difluorocyclopentylethyl group, 2,2-difluorocyclopentylpropyl group, a 3,3-difluorocyclopentylmethyl group, a 3,3-difluorocyclopentylethyl group, a 3,3-difluorocyclopentylpropyl group, a 1-chlorocyclopentylmethyl group, a 1-chlorocyclopentylethyl group, a 1-chlorocyclopentylpropyl group, a 2,2-dichlorocyclopentylmethyl group, a 2,2-dichlorocyclopentylethyl group, a 2,2-dichlorocyclopentylpropyl group, a 3,3-dichlorocyclopentylmethyl group, a 3,3-dichlorocyclopentylethyl group, a 3,3-dichlorocyclopentylpropyl group, a 1-fluorocyclohexylmethyl group, a 1-fluorocyclohexylethyl group, a 1-fluorocyclohexylpropyl group, a 2,2-difluorocyclohexylmethyl group, a 2,2-difluorocyclohexylethyl group, a 2,2-difluorocyclohexylpropyl group, a 3,3-difluorocyclohexylmethyl group, a 3,3-difluorocyclohexylethyl group, a 3,3-difluorocyclohexylpropyl group, a 4,4-difluorocyclohexylmethyl group, a 4,4-difluorocyclohexylethyl group, a 4,4-difluorocyclohexylpropyl group, a 1-chlorocyclohexylmethyl group, a 1-chlorocyclohexylethyl group, a 1-chlorocyclohexylpropyl group, a 2,2-dichlorocyclohexylmethyl group, a 2,2-dichlorocyclohexylethyl group, a 2,2-dichlorocyclohexylpropyl group, a 3,3-dichlorocyclohexylmethyl group, a 3,3-dichlorocyclohexylethyl group, a 3,3-dichlorocyclohexylpropyl group, a methoxymethyl group, an ethoxymethyl group, an isopropoxymethyl group, a tert-butoxymethyl group, a 2-methoxyethyl group, an 2-ethoxyethyl group, a 2-tert-butoxyethyl group, a 3-methoxypropyl group, an 3-ethoxypropyl group, a trifluoromethoxymethyl group, a 2-trifluoromethoxyethyl group, a 3-trifluoromethoxypropyl group, a 4-trifluoromethoxybutyl group, a difluoromethoxymethyl group, a 2-difluoromethoxyethyl group, a 2-pentafluoroethoxyethyl group, a 3-pentafluoroethoxypropyl group, a 1,1,2,2-tetrafluoroethoxymethyl group, a 2-(1,1,2,2-tetrafluoroethoxy)-ethyl group, a methylthiomethyl group, a 2-methylthioethyl group, a 3-methylthiopropyl group, an ethylthiomethyl group, an 2-ethylthioethyl group, an 3-ethylthiopropyl group, a tert-butylthiomethyl group, a 2-(tert-butylthio)-ethyl group, a 3-(tert-butylthio)-propyl group, a trifluoromethylthiomethyl group, a 2-trifluoromethylthioethyl group, a trifluoromethylthiopropyl group, a cyanomethyl group, a 2-cyanoethyl group, a 3-cyanopropyl group, a 1-cyanoethyl group, a 2-cyano-2-methylethyl group and a 2-cyano-2-methylpropyl group and the others.

The term "C3-C6 cycloalkyl group optionally having one or more groups selected from Group $P^1$" represents an C3-C6 cycloalkyl group wherein a hydrogen atom being attached to the carbon atom may be optionally substituted with one or more atom or group selected from Group $P^1$, and when said C3-C6 alkyl group has two or more atoms or groups selected from Group $P^1$, the atoms or groups selected from Group $P^1$ may be same or different from each other.

Examples of the C3-C6 cycloalkyl group optionally having one or more groups selected from Group $P^1$ include a 1-fluorocyclopropyl group, a 2,2-difluorocyclopropyl group, a 1-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 2,2,3,3-tetrafluorocyclobutyl group, a 2,2,3,3-tetrafluorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group, a 4,4-difluorocyclohexyl group, a 1-cyclopropylcyclopropyl group, a 2-cyclopropylcyclopropyl group, a 2,2-bis-cyclopropylcyclopropyl group, a 2,3-bis-cyclopropylcyclopropyl group, a 1-cyclopropylcyclobutyl group, a 1-cyclobutylcyclobutyl group, a 2-cyclopropylcyclobutyl group, a 1-cyclopropylcyclopentyl group, a 2-cyclopropylcyclopentyl group, a 1-(1-fluorocyclopropyl)-cyclopropyl group, a 1-(2,2-difluorocyclopropyl)-cyclopropyl group, a 1-(1-chlorocyclopropyl)-cyclopropyl group, a 1-(2,2-dichlorocyclopropyl)-cyclopropyl group, a 1-methoxycyclopropyl group, a 1-methoxycyclobutyl group, a 1-methoxycyclopentyl group, a 1-methoxycyclohexyl group, a 2-methoxycyclopropyl group, a 2-methoxycyclobutyl group, a 2-methoxycyclopentyl group, a 2-methoxycyclohexyl group, an 2-ethoxycyclopropyl group, an 2-ethoxycyclobutyl group, an 2-ethoxycyclopentyl group, an 2-ethoxycyclohexyl group, an 1-ethoxycyclopropyl group, an 1-ethoxycyclobutyl group, an 1-ethoxycyclopentyl group, an 1-ethoxycyclohexyl group, an 1-isopropoxycyclopropyl group, an 1-isopropoxycyclobutyl group, an 1-isopropoxycyclopentyl group, an 1-isopropoxycyclohexyl group, a 1-trifluoromethoxycyclopropyl group, a 2-trifluoromethoxycyclopropyl group, a 1-difluoromethoxycyclopropyl group, a 2-difluoromethoxycyclopropyl group, a 1-(2,2-difluoroethoxy)-cyclopropyl group, a 2-(2,2-difluoroethoxy)-cyclopropyl group, a 1-methylthiocyclopropyl group, an 1-ethylthiocyclopropyl group, a 2-methylthiocyclopropyl group, an 2-ethylthiocyclopropyl group, a 1-trifluoromethylthiocyclopropyl group, a 2-trifluoromethylthiocyclopropyl group, a 1-cyanocyclopropyl group, a 2-cyanocyclopropyl group and a 2,2-dicyanocyclopropyl group and the others.

$Y^1$ and $Y^2$ may combine each other together with the carbon atom to which they are attached to form a five-, six- or seven-membered saturated ring, and the saturated ring may optionally contain one or more oxygen atoms or sulfur atoms as the ring-constituent atom, and the saturated ring may optionally have one or more groups selected from Group $P^1$ as substituent. Examples of Q1 include the following structures:

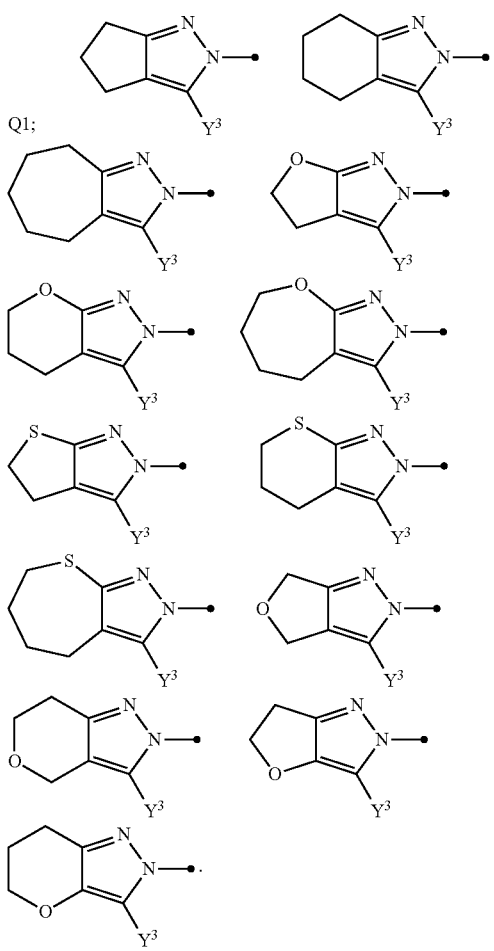

In terms of a convenience of production, preferred Q1 includes the following structures:

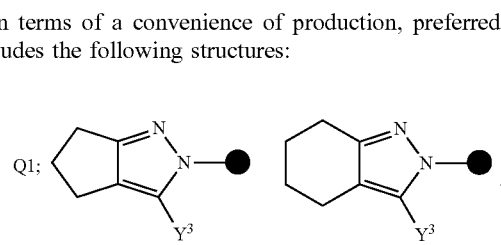

More preferred Q1 includes the following structure:

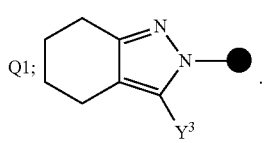

$Y^2$ and $Y^3$ may combine each other together with the carbon atom to which they are attached to form a five-, six- or seven-membered saturated ring, and the saturated ring may optionally contain one or more oxygen atoms or sulfur atoms as the ring-constituent atom, and the saturated ring may optionally have one or more groups selected from Group $P^1$ as substituent. Examples of Q1 include the following structures:

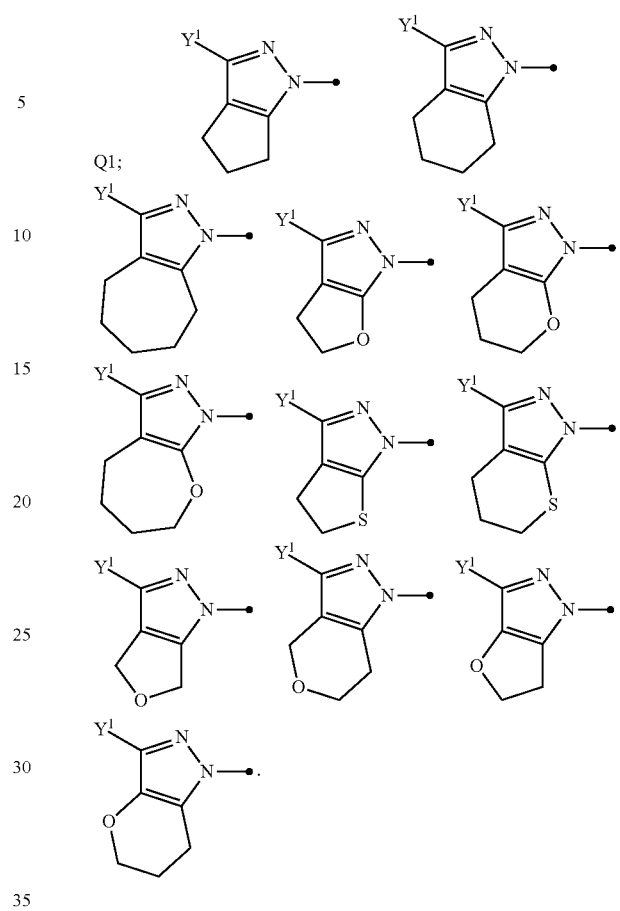

In terms of a convenience of production, preferred Q1 includes the following structures:

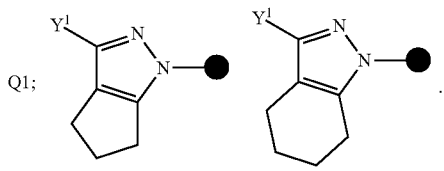

More preferred Q1 includes the following structure:

$Z^1$ and $Z^2$ may combine each other together with the carbon atom or nitrogen atom to which they are attached to form a five-, six- or seven-membered saturated ring, and the saturated ring may optionally contain one or more oxygen atoms, nitrogen atoms or sulfur atoms as the ring-constituent atom, and the saturated ring may optionally have one or more groups selected from Group $P^1$ as substituent. Examples of Q2 include the following structures:

Q2;
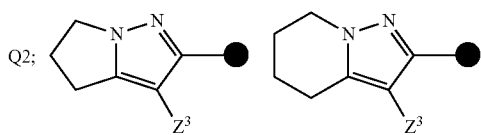
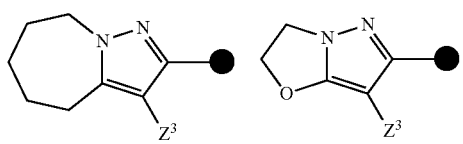
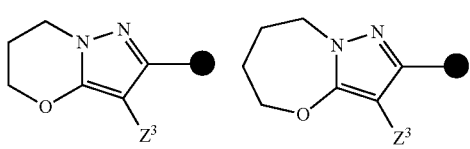
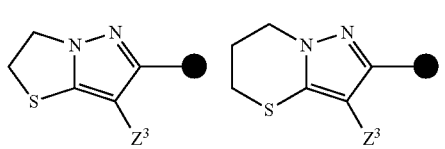
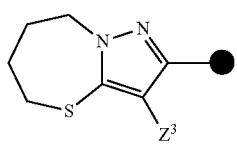

In terms of a convenience of production, preferred Q2 includes the following structures:

Q2;
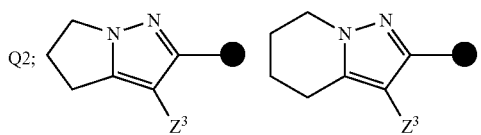

More preferred Q2 includes the following structures:

Q2;
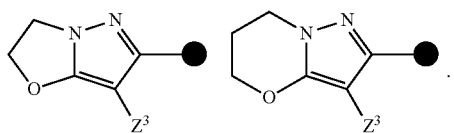

$Z^2$ and $Z^3$ may combine each other together with the carbon atom to which they are attached to form a five-, six- or seven-membered saturated ring, and the saturated ring may optionally contain one or more oxygen atoms or sulfur atoms as the ring-constituent atom, and the saturated ring may optionally have one or more substituents selected from Group $P^1$ as substituent. Examples of Q2 include the following structures:

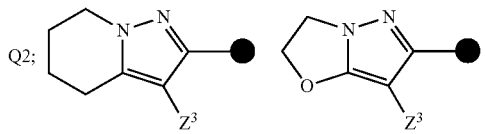

Q2; $Z^1$
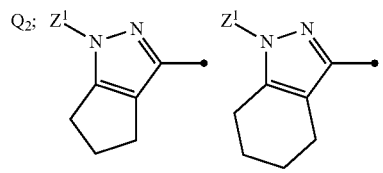
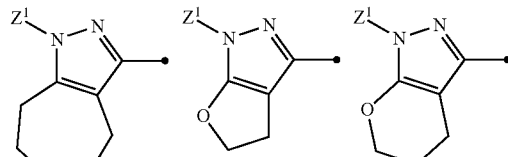
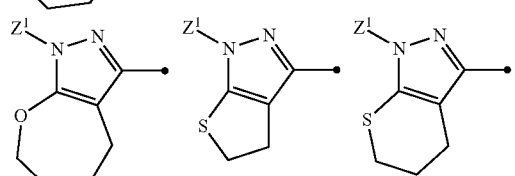
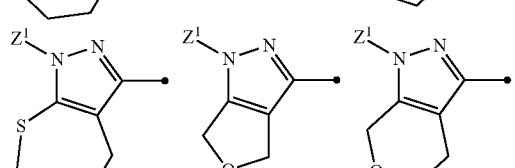
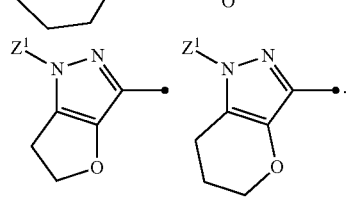

Examples of an embodiment of the present compound include the compounds of the formula (1) wherein the substituents represent the following ones.

a compound of the formula (1) wherein $A^2$, $Z^1$ and $Z^4$ represents independently of each other a hydrogen atom, an amino group, an C3-C6 alkenyl group, a C3-C6 haloalkenyl group, an C3-C6 alkynyl group, a C3-C6 haloalkynyl group, an C1-C6 alkylsulfinyl group, a C1-C6 haloalkylsulfinyl group, an C1-C6 alkylsulfonyl group, a C1-C6 haloalkylsulfonyl group, a C3-C6 cycloalkylsulfonyl group, a C3-C6 halocycloalkylsulfonyl group, an C2-C8 alkylaminosulfonyl group, a C2-C8 haloalkylaminosulfonyl group, a C3-C9 trialkylsilyl group, an C2-C6 alkylcarbonyl group, an C2-C6 alkoxycarbonyl group, an C2-C8 alkylaminocarbonyl group, a C4-C7 cycloalkylmethyl group, an C1-C6 alkyl group optionally having one or more groups selected from Group $P^1$ or a C3-C6 cycloakyl group optionally having one or more groups selected from Group $P^1$;

a compound of the formula (1) wherein $R^1$ represents a methyl group, an ethyl group, a propyl group or a butyl group;

a compound of the formula (1) wherein $R^1$ represents an ethynyl group, a 1-propynyl group, a 2-propynyl group, a 1-butynyl group or a 2-butynyl group;

a compound of the formula (1) wherein $R^1$ represents a cyclopropyl group;

a compound of the formula (1) wherein $R^1$ represents a trifluoromethyl group;

a compound of the formula (1) wherein $R^1$ represents a fluorine atom, a chlorine atom, a bromine atom or an iodine atom;

a compound of the formula (1) wherein $R^2$ represents a hydrogen atom or a fluorine atom;

a compound of the formula (1) wherein $R^4$ represents a hydrogen atom or a fluorine atom;

a compound of the formula (1) wherein $R^5$ represents a hydrogen atom or a fluorine atom;

a compound of the formula (1) wherein $R^7$ represents a hydrogen atom or a fluorine atom;

a compound of the formula (1) wherein $R^8$ represents a hydrogen atom or a fluorine atom;

a compound of the formula (1) wherein $R^9$ represents a hydrogen atom or a fluorine atom;

a compound of the formula (1) wherein $R^{11}$ represents a hydrogen atom or a fluorine atom;

a compound of the formula (1) wherein $R^2$ represents a hydrogen atom;

a compound of the formula (1) wherein $R^4$ represents a hydrogen atom;

a compound of the formula (1) wherein $R^5$ represents a hydrogen atom;

a compound of the formula (1) wherein $R^7$ represents a hydrogen atom;

a compound of the formula (1) wherein $R^8$ represents a hydrogen atom;

a compound of the formula (1) wherein $R^9$ represents a hydrogen atom;

a compound of the formula (1) wherein $R^{11}$ represents a hydrogen atom;

a compound of the formula (1) wherein $R^6$ represents a methyl group, an ethyl group, a propyl group, a butyl group or an isobutyl group;

a compound of the formula (1) wherein $R^6$ represents a vinyl group, a 1-propenyl group or a 2-propenyl group;

a compound of the formula (1) wherein $R^6$ represents a methoxy group, an ethoxy group or a propyloxy group;

a compound of the formula (1) wherein $R^6$ represents a trifluoromethyl group, a difluoromethyl group, a pentafluoroethyl group, a 3,3,3-trifluoroethyl group or a 2,2-difluoroethyl group;

a compound of the formula (1) wherein $R^6$ represents a fluorine atom, a chlorine atom, a bromine atom or an iodine atom;

a compound of the formula (1) wherein $R^6$ represents a cyano group;

a compound of the formula (1) wherein $R^3$ represents a methyl group, an ethyl group, a fluorine atom, a chlorine atom, a bromine atom or an iodine atom;

a compound of the formula (1) wherein $R^{10}$ represents a methyl group, an ethyl group, a difluoromethyl group or a 2,2-difluoroethyl group;

a compound of the formula (1) wherein $R^{10}$ represents a methyl group;

a compound of the formula (1) wherein X represents an oxygen atom;

a compound of the formula (1) wherein X represents a sulfur atom;

a compound of the formula (1) wherein $A^1$ and $A^3$ may be same or different from each other, and represent independently of each other a hydrogen atom, a halogen atom or a cyano group;

a compound of the formula (1) wherein $A^1$ and $A^3$ may be same or different from each other, and represent independently of each other an C1-C6 alkyl group;

a compound of the formula (1) wherein $A^1$ and $A^3$ may be same or different from each other, and represent independently of each other a C1-C6 haloalkyl group;

a compound of the formula (1) wherein $A^2$ and $Z^4$ may be same or different from each Other, and represent independently of each other an C1-C6 alkyl group;

a compound of the formula (1) wherein $A^2$ and $Z^4$ may be same or different from each other, and represent independently of each other a C1-C6 haloalkyl group;

a compound of the formula (1) wherein $A^2$ and $Z^4$ may be same or different from each other, and represent independently of each other an C1-C6 alkynyl group;

a compound of the formula (1) wherein $A^2$ and $Z^4$ may be same or different from each other, and represent independently of each other a C1-C6 haloalkynyl group;

a compound of the formula (1) wherein $Z^1$ represents an C1-C6 alkyl group which may be optionally substituted with a group selected from Group $P^1$;

a compound of the formula (1) wherein $Z^2$ represents an C1-C6 alkyl group which may be optionally substituted with a group selected from Group $P^1$;

a compound of the formula (1) wherein $R^2$, $R^4$, $R^5$, $R^7$, $R^8$, $R^9$ and $R^{11}$ represent a hydrogen atom;

a compound of the formula (1) wherein $R^2$, $R^4$, $R^5$, $R^7$, $R^8$, $R^9$ and $R^{11}$ represent a hydrogen atom and X represents an oxygen atom;

a compound of the formula (1) wherein $R^2$, $R^4$, $R^5$, $R^7$, $R^8$, $R^9$ and $R^{11}$ represent a hydrogen atom and $R^{10}$ represents a methyl group;

a compound of the formula (1) wherein $R^2$, $R^4$, $R^5$, $R^7$, $R^8$, $R^9$ and $R^{11}$ represent a hydrogen atom, $R^{10}$ represents a methyl group, and X represents an oxygen atom;

a compound of the formula (1) wherein $R^2$, $R^4$, $R^5$, $R^8$, $R^9$ and $R^{11}$ represent a hydrogen atom, $R^{10}$ represents a methyl group, X represents an oxygen atom and Q represents Q1 or Q2;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q1, Q2 or Q4;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q1;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q2;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q3;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q4;

a compound of the formula (1) wherein $R^1$ represents a halogen atom;

a compound of the formula (1) wherein $R^1$ represents an C1-C3 alkyl group;

a compound of the formula (1) wherein $R^1$ represents a C1-C3 haloalkyl group;

a compound of the formula (1) wherein $R^1$ represents an C2-C3 alkynyl group;

a compound of the formula (1) wherein $R^1$ represents a C2-C3 haloalkynyl group;

a compound of the formula (1) wherein $R^1$ represents a C3-C5 cycloalkyl group;

a compound of the formula (1) wherein $R^1$ represents a C3-C5 halocycloalkyl group;

a compound of the formula (1) wherein $R^1$ represents an C1-C3 alkoxy group;

a compound of the formula (1) wherein $R^1$ represents a C1-C3 haloalkoxy group;

a compound of the formula (1) wherein $R^1$ represents a halogen atom, an C1-C3 alkyl group, a C1-C3 haloalkyl group or a C3-C5 cycloalkyl group;

a compound of the formula (1) wherein $R^1$ represents a halogen atom, an C1-C3 alkyl group or a C1-C3 haloalkyl group;

a compound of the formula (1) wherein $R^1$ represents a chlorine atom, a bromine atom, a methyl group, an ethyl group or a trifluoromethyl group;

a compound of the formula (1) wherein $R^3$ represents a hydrogen atom;

a compound of the formula (1) wherein $R^3$ represents a halogen atom;

a compound of the formula (1) wherein $R^3$ represents an C1-C3 alkyl group;

a compound of the formula (1) wherein $R^3$ represents a C1-C3 haloalkyl group;

a compound of the formula (1) wherein $R^3$ represents a hydrogen atom, a halogen atom or an C1-C3 alkyl group;

a compound of the formula (1) wherein $R^3$ represents a hydrogen atom, a chlorine atom or a methyl group;

a compound of the formula (1) wherein $R^3$ represents a hydrogen atom or a methyl group;

a compound of the formula (1) wherein $R^6$ represents a halogen atom;

a compound of the formula (1) wherein $R^6$ represents an C1-C4 alkyl group;

a compound of the formula (1) wherein $R^6$ represents a C1-C4 haloalkyl group;

a compound of the formula (1) wherein $R^6$ represents an C2-C4 alkenyl group;

a compound of the formula (1) wherein $R^6$ represents a C2-C4 haloalkenyl group;

a compound of the formula (1) wherein $R^6$ represents an C1-C4 alkoxy group;

a compound of the formula (1) wherein $R^6$ represents a halogen atom, an C1-C4 alkyl group, a C1-C4 haloalkyl group or an C1-C4 alkoxy group;

a compound of the formula (1) wherein $R^6$ represents a halogen atom, an C1-C3 alkyl group, a C1-C3 haloalkyl group or an C1-C2 alkoxy group;

a compound of the formula (1) wherein $R^6$ represents a halogen atom, a methyl group, an ethyl group, difluoromethyl group, a trifluoromethyl group, a methoxy group or an ethoxy group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q1, represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q1, represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, an C1-C4 haloalkyl group or an C1-C4 alkoxy group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, an C1-C3 haloalkyl group or an C1-C2 alkoxy group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q1, represents a chlorine atom, a bromine atom, a methyl group, an ethyl group, or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and represent a hydrogen atom, $R^3$ represents a hydrogen atom or a methyl group, $R^6$ represents a halogen atom, an C1-C4 alkyl group, a C1-C4 haloalkyl group or an C1-C2 alkoxy group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{10}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{18}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2$, $R^4$, $R^9$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, $R^1$ represents a halogen atom, an C1-C3 alkyl group or a 01-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C3 alkoxy group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{10}$ represent a hydrogen atom, $R^3$ represents a hydrogen atom, a chlorine atom or a methyl group, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C4 alkyl group, a C1-C4 haloalkyl group or an C1-C4 alkoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, an C1-C3 alkyl group, a C1-C3 haloalkyl group or an C1-C2 alkoxy group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, and X represents an oxygen atom;

a compound of the formula (1) wherein $Y^1$ represents a hydrogen atom;

a compound of the formula (1) wherein $Y^1$ represents an C1-C6 alkyl group;

a compound of the formula (1) wherein $Y^1$ represents a C1-C6 haloalkyl group;

a compound of the formula (1) wherein $Y^1$ represents a C3-C6 cycloalkyl group;

a compound of the formula (1) wherein $Y^1$ represents a C3-C6 halocycloalkyl group;

a compound of the formula (1) wherein $Y^1$ represents a hydrogen atom, an C1-C6 alkyl group, a C1-C6 haloalkyl group or a C3-C6 cycloalkyl group;

a compound of the formula (1) wherein $Y^1$ represents a hydrogen atom, an C1-C6 alkyl group or a C1-C6 haloalkyl group;

a compound of the formula (1) wherein $Y^1$ represents a hydrogen atom, an C1-C3 alkyl group or a C1-C3 haloalkyl group;

a compound of the formula (1) wherein Y represents a hydrogen atom, a methyl group, an ethyl group or a trifluoromethyl group;

a compound of the formula (1) wherein $Y^2$ represents a hydrogen atom;

a compound of the formula (1) wherein $Y^2$ represents a halogen atom;

a compound of the formula (1) wherein $Y^2$ represents an C1-C6 alkyl group;

a compound of the formula (1) wherein $Y^2$ represents a C1-C6 haloalkyl group;

a compound of the formula (1) wherein $Y^2$ represents an C2-C3 alkynyl group;

a compound of the formula (1) wherein $Y^2$ represents an C1-C6 alkoxy group;

a compound of the formula (1) wherein $Y^2$ represents a C1-C6 haloalkoxy group;

a compound of the formula (1) wherein $Y^2$ represents a C3-C6 cycloalkyl group;

a compound of the formula (1) wherein $Y^2$ represents a C3-C6 halocycloalkyl group;

a compound of the formula (1) wherein $Y^1$ and $Y^2$ connect via a divalent straight saturated carbon chain to form a five-membered or six-membered ring;

a compound of the formula (1) wherein $Y^1$ and $Y^2$ connect to each other to represent —CH$_2$—CH$_2$—CH$_2$— or —CH$_2$—CH$_2$—CH$_2$—CH$_2$—, which combines together with the carbon atoms to which $Y^1$ and $Y^2$ are attached to form a five-membered or six-membered ring;

a compound of the formula (1) wherein $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group;

a compound of the formula (1) wherein $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group;

a compound of the formula (1) wherein $Y^2$ represents a hydrogen atom, a fluorine atom, a chlorine atom, a bromine atom, a methyl group, an ethyl group, a propyl group, an isobutyl group, an ethynyl group, a 1-propynyl group, a trifluoromethyl group, a difluoromethyl group, a methoxy group, an ethoxy group or a cyclopropyl group;

a compound of the formula (1) wherein $Y^3$ represents a hydrogen atom;

a compound of the formula (1) wherein $Y^3$ represents an C1-C4 alkyl group;

a compound of the formula (1) wherein $Y^3$ represents a C1-C4 haloalkyl group;

a compound of the formula (1) wherein $Y^3$ represents a hydrogen atom, an C1-C3 alkyl group or a C1-C3 haloalkyl group;

a compound of the formula (1) wherein $Y^3$ represents a hydrogen atom, a methyl group or an ethyl group;

a compound of the formula (1) wherein $Y^2$ and $Y^3$ connect via a divalent straight saturated carbon chain to form a five-membered or six-membered ring;

a compound of the formula (1) wherein $Y^2$ and $Y^3$ connect to each other to represent —CH$_2$—CH$_2$—CH$_2$— or —CH$_2$—CH$_2$—CH$_2$—CH$_2$—, which combines together with the carbon atoms to which $Y^1$ and $Y^2$ are attached to form a five-membered or six-membered ring;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, alternatively $Y^1$ and $Y^2$ connect via a divalent straight saturated carbon chain to form a five-membered or six-membered ring, and $Y^3$ represents a hydrogen atom, an C1-C3 alkyl group or a C1-C3 haloalkyl group, alternatively $Y^2$ and $Y^3$ connect via a divalent straight saturated carbon chain to form a five-membered or six-membered ring;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents an C2-C3 alkynyl group, an C1-C6 alkoxy group or a C3-C6 cycloalkyl group, $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or an C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or an C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, 1-propynyl group, a trifluoromethyl group, a difluoromethyl group, a methoxy group, an ethoxy group or は cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, 1-propynyl group, a trifluoromethyl group, a difluoromethyl group, a methoxy group, an ethoxy group or cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Y^1$ represents a hydrogen atom, an C1-C6 alkyl group or a C1-C6 haloalkyl, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, $R^{10}$ represents a methyl group, X represents an oxygen atom, $Y^1$ represents a hydrogen atom, an C1-C6 alkyl group or a C1-C6 haloalkyl, $Y^2$ represents a hydrogen atom, a fluorine atom, a chlorine atom, a bromine atom, a methyl group, an ethyl group, a propyl group, an isopropyl group, an ethynyl group, 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, an C1-C6 alkyl group or a C1-C6 haloalkyl, $Y^2$ represents a hydrogen atom, a fluorine atom, a chlorine atom, a bromine atom, a methyl group, an ethyl group, a propyl group, an isopropyl group, an ethynyl group, 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, Y represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, Y represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a an C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group, or an C1-C4 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group, or an C1-C2 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6-haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group, or an C1-C2 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group, a C3-C6 cycloalkyl group, alternatively $Y^1$ and $Y^2$ connect via a divalent straight saturated carbon chain to form a five-membered or six-membered ring, and $Y^3$ represents a hydrogen atom, an C1-C3 alkyl group or a C1-C3 haloalkyl group, alternatively $Y^2$ and $Y^3$ connect via a divalent straight saturated carbon chain to form a five-membered or six-membered ring;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group, or an C1-C2 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^{17}$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, an C1-C3 alkyl group or an C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or an C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or cyclopropyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{10}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group, alternatively $Y^1$ and $Y^2$ connect to each other to represent —CH$_2$—CH$_2$—CH$_2$— or —CH$_2$—CH$_2$—CH$_2$—CH$_2$—, which combines together with the carbon atoms to which $Y^1$ and $Y^2$ are attached to form a five-membered or six-membered ring, or $Y^2$ and $Y^3$ connect to each other to represent —CH$_2$—CH$_2$—CH$_2$— or —CH$_2$—CH$_2$—CH$_2$—CH$_2$—, which combines together with the carbon atoms to which $Y^2$ and $Y^3$ are attached to form a five-membered or six-membered ring;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein $Z^1$ represents an C1-C6 alkyl group;

a compound of the formula (1) wherein $Z^1$ represents a C1-C6 haloalkyl group;

a compound of the formula (1) wherein $Z^1$ represents an C3-C6 alkynyl group;

a compound of the formula (1) wherein $Z^1$ represents a C3-C6 haloalkynyl group;

a compound of the formula (1) wherein $Z^1$ represents a C3-C6 cycloalkyl group;

a compound of the formula (1) wherein $Z^1$ represents a C4-C7 cycloalkylmethyl group;

a compound of the formula (1) wherein $Z^1$ represents an C1-C6 alkyl group, a C1-C6 haloalkyl group, an C3-C6 alkynyl group or a C4-C7 cycloalkylmethyl group;

a compound of the formula (1) wherein $Z^1$ represents an C1-C4 alkyl group, a C1-C3 haloalkyl group, an C3-C4 alkynyl group or a cyclopropylmethyl group;

a compound of the formula (1) wherein $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group;

a compound of the formula (1) wherein $Z^2$ represents a hydrogen atom;

a compound of the formula (1) wherein $Z^2$ represents a halogen atom;

a compound of the formula (1) wherein $Z^2$ represents an C1-C6 alkyl group;

a compound of the formula (1) wherein $Z^2$ represents a C1-C6 haloalkyl group;

a compound of the formula (1) wherein $Z^2$ represents a C3-C6 cycloalkyl group;

a compound of the formula (1) wherein $Z^2$ represents an C1-C6 alkoxy group;

a compound of the formula (1) wherein $Z^2$ represents a C1-C6 haloalkoxy group;

a compound of the formula (1) wherein $Z^2$ represents an C2-C6 alkynyl group;

a compound of the formula (1) wherein $Z^2$ represents a C2-C6 haloalkynyl group;

a compound of the formula (1) wherein $Z^2$ represents a hydrogen atom, an C1-C6 alkyl group, a C1-C6 haloalkyl group or a C3-C6 cycloalkyl group;

a compound of the formula (1) wherein $Z^2$ represents a hydrogen atom, an C1-C3 alkyl group, a C1-C3 haloalkyl group or a cyclopropyl group;

a compound of the formula (1) wherein $Z^2$ represents a hydrogen atom, a methyl group, an ethyl group, an isopropyl group or a cyclopropyl group;

a compound of the formula (1) wherein $Z^3$ represents a hydrogen atom;

a compound of the formula (1) wherein $Z^3$ represents an C1-C6 alkyl group;

a compound of the formula (1) wherein $Z^3$ represents a C1-C6 haloalkyl group;

a compound of the formula (1) wherein $Z^3$ represents a C3-C6 cycloalkyl group;

a compound of the formula (1) wherein $Z^3$ represents an C1-C6 alkoxy group;

a compound of the formula (1) wherein $Z^3$ represents a C1-C6 haloalkoxy group;

a compound of the formula (1) wherein $Z^3$ represents an C2-C6 alkynyl group;

a compound of the formula (1) wherein $Z^3$ represents a C2-C6 haloalkynyl group;

a compound of the formula (1) wherein $Z^3$ represents a hydrogen atom, a C1-C3 alkyl group, a C1-C3 haloalkyl group or a cyclopropyl group;

a compound of the formula (1) wherein $Z^3$ represents a hydrogen atom, a methyl group or an ethyl group;

a compound of the formula (1) wherein Q-represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents hydrogen atom, an C1-C6 alkyl group, a C1-C6 haloalkyl group or C3-C6 cycloalkyl group, $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents, a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents a halogen atom, an C1-C4 alkyl group, a C1-C4 haloalkyl group or an C1-C4 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, a C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{19}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a. C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents a halogen atom, an C1-C3 alkyl group, a C1-C3 haloalkyl group or an C1-C2 alkoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a halogen atom, a methyl group, an ethyl group, a difluoromethyl group, a trifluoromethyl group, a methoxy group or an ethoxy group, $R^{10}$ represents a methyl group, X represents an oxygen atom, $Z^1$ represents a methyl group, an ethyl group, a propyl group, an isopropyl group, a 2,2-difluoroethyl group, a 2,2,2-trifluoroethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q1, $R^1$ represents a hydrogen atom, a halogen atom or an C1-C6 alkyl group, $R^2$ represents a hydrogen atom, a halogen atom or an C1-C6 alkyl group, $R^3$ represents a hydrogen atom or an C1-C6 alkyl group, $R^4$, $R^5$, $R^7$, $R^8$ and $R^9$ represent a hydrogen atom, $R^{10}$ represents a methyl group, $R^{11}$ represents a hydrogen atom or an C1-C6 alkyl group, $R^6$ represents a halogen atom, an C1-C4 alkyl group, a C1-C4 haloalkyl group or an C1-C4 alkoxy group, X represents an oxygen atom, $Y^1$ represents an C1-C6 alkyl group optionally having halogen atom or a hydrogen atom, $Y^2$ represents an C1-C6 alkyl group optionally having halogen atom, a hydrogen atom, a halogen atom, an C1-C6 alkoxy group or an aldehyde group, $Y^3$ represents an C1-C6 alkyl group optionally having halogen atom or a hydrogen atom, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q1, $R^1$ represents a hydrogen atom, a halogen atom or an C1-C6 alkyl group, $R^2$ represents a hydrogen atom, a halogen atom or an C1-C6 alkyl group, $R^3$ represents a hydrogen atom or an C1-C6 alkyl group, $R^4$, $R^5$, $R^7$, $R^8$ and $R^9$ represent a hydrogen atom, $R^{10}$ represents a methyl group, $R^{11}$ represents a hydrogen atom or an C1-C6 alkyl group, $R^6$ represents a halogen atom, an C1-C4 alkyl group, a C1-C4 haloalkyl group or an C1-C4 alkoxy group, X represents an oxygen atom, $Y^1$ represents an C1-C6 alkyl group optionally having halogen atom or a hydrogen atom, $Y^2$ represents an C1-C6 alkyl group optionally having halogen atom, a hydrogen atom, a halogen atom, an C1-C6 alkoxy group, an aldehyde group or a C3-C6 cycloalkyl group, $Y^3$ represents an C1-C6 alkyl group optionally having halogen atom or a hydrogen atom, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a halogen atom, an C1-C6 alkyl group or a C3-C6 cycloalkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkyl group or an C1-C4 alkoxy group, X represents an oxygen atom, $Z^1$ represents an C1-C6 alkyl group optionally having one or more atoms or groups selected from the group consisting of halogen atom and C3-C6 cycloalkyl group, a hydrogen atom, an C3-C6 alkynyl group, an C2-C8 alkylaminosulfonyl group, an C1-C6 alkylsulfonyl group or a C3-C6 cycloalkylsulfonyl group, $Z^2$ represents a hydrogen atom or an C1-C6 alkyl group, and $Z^3$ represents a hydrogen atom;

a compound of the formula (1) wherein Q represents Q2, $R^1$ represents a halogen atom, an C1-C6 alkyl group or a C3-C6 cycloalkyl group, $R^2$, $R^4$, $R^5$, $R^7$, $R^8$, $R^9$ and $R^{11}$ represent a hydrogen atom, $R^3$ represents a hydrogen atom or an C1-C6 alkyl group, $R^{10}$ represents a methyl group, $R^6$ represents an C1-C4 alkyl group, an C1-C4 alkoxy group or a halogen atom, X represents an oxygen atom, $Z^1$ represents an C1-C6 alkyl group optionally having one or more atoms or groups selected from the group consisting of halogen atom, cyano group and C3-C6 cycloalkyl group, a hydrogen atom, an C3-C6 alkynyl group, an C2-C8 alkylaminosulfonyl group, an C1-C6 alkylsulfonyl group or a C3-C6 cycloalkylsulfonyl group, $Z^2$ represents a hydrogen atom, an C1-C6 alkyl group optionally having halogen atom or a halogen atom, and $Z^3$ represents a hydrogen atom, a halogen atom or an C1-C6 alkyl group;

a compound of the formula (1) wherein Q represents Q2, $R^1$ represents a halogen atom or an C1-C6 alkyl group, $R^2$, $R^3$, $R^4$, $R^5$, $R^7$, $R^8$, $R^9$ and $R^{11}$ represent a hydrogen atom, $R^{10}$ represents an C1-C3 alkyl group, $R^6$ represents an C1-C4 alkyl group, an C1-C4 alkoxy group or a halogen atom, X represents an oxygen atom, $Z^1$ represents an C1-C6 alkyl group, $Z^2$ represents a hydrogen atom, an C1-C6 alkyl group optionally having halogen atom or a halogen atom, and $Z^3$ represents a hydrogen atom, an C1-C6 alkyl group or a halogen atom;

a compound of the formula (1) wherein Q represents Q2, $R^1$ represents a halogen atom, an C1-C6 alkyl group or a C3-C6 cycloalkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkyl group or an C1-C4 alkoxy group, X represents an oxygen atom, $Z^1$ represents an C1-C6 alkyl group optionally having one or more atoms or groups selected from the group consisting of halogen atom and C3-C6 cycloalkyl group, a hydrogen atom, an C3-C6 alkynyl group, an C2-C8 alkylaminosulfonyl group, an C1-C6 alkylsulfonyl group or a C3-C6 cycloalkylsulfonyl group, $Z^2$ represents a hydrogen atom, an C1-C6 alkyl group, a C1-C3 haloalkyl group or a halogen atom, and $Z^3$ represents a hydrogen atom or an C1-C3 alkyl group;

a compound of the formula (1) wherein Q represents Q2, $R^1$ represents a halogen atom, an C1-C6 alkyl group or a C3-C6 cycloalkyl group, $R^2$, $R^4$, $R^5$, $R^7$, $R^8$, $R^9$ and $R^{11}$ represent a hydrogen atom, $R^3$ represents an C1-C6 alkyl group, $R^{10}$ represents a methyl group, $R^6$ represents a halogen atom, an C1-C4 alkyl group, a C1-C4 haloalkyl group or an C1-C4 alkoxy group, $Z^1$ represents an C1-C6 alkyl group optionally having one or more atoms or groups selected from the group consisting of halogen atom, cyano group and C3-C6 cycloalkyl group, a hydrogen atom, an C3-C6 alkynyl group, an C2-C8 alkylaminosulfonyl group, an C1-C6 alkylsulfonyl group or a C3-C6 cycloalkylsulfonyl group, $Z^2$ represents a hydrogen atom, an C1-C6 alkyl group, an C1-C6 alkoxy group, a C1-C6 haloalkyl group or a halogen atom, $Z^3$ represents a hydrogen atom, an C1-C6 alkyl group, a halogen atom, an aldehyde group or a cyano group, alternatively $Z^1$ and $Z^2$ combines together with the carbon atoms or the nitrogen atoms to which $Z^1$ and $Z^2$ are attached to form a five-membered or six-membered saturated ring, said saturated ring may optionally contain oxygen atom(s) as ring-constituent atom;

a compound of the formula (1) wherein Q represents Q3, $R^1$ represents a halogen atom or an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkyl group or an C1-C4 alkoxy group, X represents an oxygen atom, $A^1$ represents a hydrogen atom or an C1-C6 alkyl group, $A^2$ represents a hydrogen atom or an C1-C6 alkyl group, and $A^3$ represents a hydrogen atom or an C1-C6 alkyl group;

a compound of the formula (1) wherein Q represents Q4, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkyl group, X represents an oxygen atom, $Z^4$ represents an C1-C6 alkyl group, and $Z^2$ and $Z^3$ represent a hydrogen atom;

a compound of the formula (1) wherein Q represents Q4, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkoxy group, X represents an oxygen atom, $Z^2$ represents a hydrogen atom or an C1-C6 alkyl group, Z represents a hydrogen atom, and $Z^4$ represents an C1-C6 alkyl group optionally having C3-C6 cycloalkyl group;

a compound of the formula (1) wherein Q represents Q4, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkyl group or an C1-C4 alkoxy group, X represents an oxygen atom, $Z^2$ represents an C1-C6 alkyl group optionally having halogen atom or a halogen atom, $Z^3$ represents a hydrogen atom, and $Z^4$ represents an C1-C6 alkyl group optionally having C3-C6 cycloalkyl group;

a compound of the formula (1) wherein Q represents Q1, $R^1$ represents a hydrogen atom, a fluorine atom, a chlorine atom, a bromine atom, a trifluoromethyl group, a methyl group, an ethyl group or a cyclopropyl group, $R^2$ represents a hydrogen atom, a chlorine atom or a methyl group, $R^3$ represents a hydrogen atom, a chlorine atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents a halogen atom, a methyl group, an ethyl group, a difluoromethyl group, a trifluoromethyl group, a methoxy group or an ethoxy group, X represents an oxygen atom, $Y^1$ represents a hydrogen atom, a methyl group, an ethyl group, an isopropyl group, a cyclopropyl group, a tert-butyl group or a trifluoromethyl group, $Y^2$ represents a hydrogen atom, a chlorine atom, a bromine atom, a methyl group, an ethyl group, a difluoromethyl group, cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a fluorine atom, a chlorine atom, a bromine atom, a methyl group, an ethyl group, a difluoromethyl group, a trifluoromethyl group, a methoxy group or an ethoxy group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group, or a cyclopropylmethyl group, $Z^2$ represents a hydrogen atom, a methyl group or an ethyl group, and $Z^3$ represents a hydrogen atom, a chlorine atom, a bromine atom or a methyl group;

a compound of the formula (1) wherein Q represents Q2, $R^1$ represents a chlorine atom, a bromine atom, a methyl group, an ethyl group, a propyl group, a butyl group or a cyclopropyl group, $R^1$, $R^3$, $R^4$, $R^5$, $R^7$, $R^8$, $R^9$ and $R^{11}$ represent a hydrogen atom, $R^{10}$ represents a methyl group, $R^6$ represents a fluorine atom, a chlorine atom, a bromine atom, a methyl group, an ethyl group, a difluoromethyl group, a trifluoromethyl group, a methoxy group or an ethoxy group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group, or a cyclopropylmethyl group, $Z^2$ represents a hydrogen atom, a methyl group, a trifluoromethyl group or an ethyl group, and $Z^3$ represents a hydrogen atom, a chlorine atom, a bromine atom or a methyl group;

a compound of the formula (1) wherein Q represents Q1, $R^1$ represents a hydrogen atom, a fluorine atom, a chlorine atom, a trifluoromethyl group or a methyl group, $R^2$ represents a hydrogen atom, a chlorine atom or a methyl group, $R^3$ represents a hydrogen atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents a halogen atom, a methyl group, an ethyl group, a trifluoromethyl group, a methoxy group or an ethoxy group, X represents an oxygen atom, $Y^1$ represents a hydrogen atom, a methyl group, an ethyl group, an isopropyl group, a tert-butyl group or a trifluoromethyl group, $Y^2$ represents a hydrogen atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methyl group, an ethyl group, a methoxy group or an ethoxy group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom or a methyl group, and $Z^3$ represents a hydrogen atom, a methyl group or a bromine atom;

a compound of the formula (1) wherein Q represents Q2, $R^1$ represents a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methyl group, an ethyl group, a methoxy group or an ethoxy group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, and $Z^3$ represents a hydrogen atom, a methyl group or a bromine atom;

a compound of the formula (1) wherein Q represents Q3, $R^1$ represents a chlorine atom or a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methyl group or a methoxy group, X represents an oxygen atom, $A^1$ represents a hydrogen atom or a methyl group, $A^2$ represents a hydrogen atom, a methyl group, an ethyl group, a propyl group, an isopropyl group, a butyl group or an isobutyl group, and $A^3$ represents a hydrogen atom or a methyl group;

a compound of the formula (1) wherein Q represents Q4, $R^1$ represents a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methoxy group, X represents an oxygen atom, $Z^4$ represents an isobutyl group, an isopentyl group, a pentyl group or a cyclopropylmethyl group, and $Z^2$ and $Z^3$ represent a hydrogen atom;

a compound of the formula (1) wherein Q represents Q1, $R^1$ represents a hydrogen atom, a halogen atom or an C1-C6 alkyl group, $R^2$ represents a hydrogen atom, a halogen atom or an C1-C6 alkyl group, $R^3$ represents a hydrogen atom or an C1-C6 alkyl group, $R^4$, $R^5$, $R^7$, $R^8$ and $R^9$ represent a hydrogen atom, $R^{10}$ represents a methyl group, $R^{11}$ represents a hydrogen atom or an C1-C6 alkyl group, $R^6$ represents an C1-C4 alkyl group, X represents an oxygen atom, $Y^1$ represents an C1-C6 alkyl group optionally having halogen atom or a hydrogen atom, $Y^2$ represents an C1-C6 alkyl group optionally having halogen atom, a hydrogen atom, a halogen atom, an C1-C6 alkoxy group or an aldehyde group, $Y^3$ represents an C1-C6 alkyl group optionally having halogen atom, a hydrogen atom, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a halogen atom, an C1-C6 alkyl group or a C3-C6 cycloalkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkyl group, X represents an oxygen atom, $Z^1$ represents an C1-C6 alkyl group optionally having one or more atoms or groups selected from the group consisting of halogen atom and C3-C6 cycloalkyl group, a hydrogen atom, a C3-C6 alkynyl group, an C2-C8 alkylaminosulfonyl group, an C1-C6 alkylsulfonyl group or a C3-C6 cycloalkylsulfonyl group, $Z^2$ represents a hydrogen atom, an C1-C6 alkyl group, a C1-C3 haloalkyl group or a halogen atom, and $Z^3$ represents a hydrogen atom;

a compound of the formula (1) wherein Q represents Q1, $R^1$ represents a hydrogen atom, a fluorine atom, a chlorine atom, a bromine atom, a trifluoromethyl group, a methyl group, an ethyl group or a cyclopropyl group, $R^2$ represents a hydrogen atom, a chlorine atom or a methyl group, $R^3$ represents a hydrogen atom, a chlorine atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents an C1-C4 alkyl group, X represents an oxygen atom, $Y^1$ represents a hydrogen atom, a methyl group, an ethyl group, an isopropyl group, a cyclopropyl group, a tert-butyl group or a trifluoromethyl group, $Y^2$ represents a hydrogen atom, a chlorine atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkyl group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, and $Z^3$ represents a hydrogen atom, a chlorine atom, a bromine atom or a methyl group;

a compound of the formula (1) wherein Q represents Q1, $R^1$ represents a hydrogen atom, a fluorine atom, a chlorine atom, a trifluoromethyl group or a methyl group, $R^2$ represents a hydrogen atom, a chlorine atom or a methyl group, $R^3$ represents a hydrogen atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents an C1-C4 alkyl group, X represents an oxygen atom, $Y^1$ represents a hydrogen atom, a methyl group, an ethyl group, an isopropyl group, a tert-butyl group or a trifluoromethyl group, $Y^2$ represents a hydrogen atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkyl group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, $Z^3$ represents a hydrogen atom, a methyl group or a bromine atom;

a compound of the formula (1) wherein Q represents Q1, $R^1$ represents a hydrogen atom, a halogen atom or a C1-C6 alkyl group, $R^2$ represents a hydrogen atom, a halogen atom or an C1-C6 alkyl group, $R^3$ represents a hydrogen atom or an C1-C6 alkyl group, $R^4$, $R^5$, $R^7$, $R^8$ and $R^9$ represent a hydrogen atom, $R^{10}$ represents a methyl group, $R^{11}$ represents a hydrogen atom or an C1-C6 alkyl group, $R^6$ represents a methyl group or an ethyl group, X represents an oxygen atom, $Y^1$ represents an C1-C6 alkyl group optionally having halogen atom or a hydrogen atom, $Y^2$ represents an C1-C6 alkyl group optionally having halogen atom, a hydrogen atom, a halogen atom, an C1-C6 alkoxy group or an aldehyde group, $Y^3$ represents an C1-C6 alkyl group optionally having halogen atom or a halogen atom, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a hydrogen atom, a C1-C6 alkyl group or a C3-C6 cycloalkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methyl group or an ethyl group, X represents an oxygen atom, $Z^1$ represents an C1-C6 alkyl group optionally having one or more atoms or groups selected from the group consisting of halogen atom and C3-C6 cycloalkyl group, a hydrogen atom, an C3-C6 alkynyl group, an C2-C8 alkylaminosulfonyl group, an C1-C6 alkylsulfonyl group or an C3-C6 cycloalkylsulfonyl group, $Z^2$ represents a hydrogen atom, an C1-C6 alkyl group, a C1-C3 haloalkyl group or a halogen atom, and $Z^3$ represents a hydrogen atom;

a compound of the formula (1) wherein Q represents Q1, $R^1$ represents a hydrogen atom, a fluorine atom, a chlorine atom, a bromine atom, a trifluoromethyl group, a methyl group, an ethyl group or a cyclopropyl group, $R^2$ represents a hydrogen atom, a chlorine atom or a methyl group, $R^3$ represents a hydrogen atom, a chlorine atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents a methyl group or an ethyl group, X represents an oxygen atom, $Y^1$ represents a hydrogen atom, a methyl group, an ethyl group, an isopropyl group, a cyclopropyl group, a tert-butyl group or a trifluoromethyl group, $Y^2$ represents a hydrogen atom, a chlorine atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q1, $R^1$ represents a hydrogen atom, a halogen atom or an C1-C3 alkyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents an C1-C3 alkyl group, X represents an oxygen atom, $Y^1$ represents a hydrogen atom, a methyl group, an ethyl group or an isopropyl group, $Y^2$ represents a hydrogen atom, a halogen atom, a cyano group, an C1-C3 alkyl group, a difluoromethyl group or a methoxy group, $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q1, $R^1$ represents a hydrogen atom, a halogen atom or an C1-C3 alkyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group or an ethyl group, X represents an oxygen atom, $Y^1$ represents a hydrogen atom, a methyl group, an ethyl group or an isopropyl group, $Y^2$ represents a hydrogen atom, a halogen atom, a cyano group, a methyl group, an ethyl group, a difluoromethyl group or a methoxy group, $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q1, $R^1$ represents a hydrogen atom, a chlorine atom or a methyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group, X represents an oxygen atom, $Y^1$ represents a hydrogen atom, a methyl group, an ethyl group or an isopropyl group, $Y^2$ represents a hydrogen atom, a halogen atom, a cyano group, a methyl group, an ethyl group, a difluoromethyl group or a methoxy group, $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methyl group or an ethyl group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, $Z^3$ represents a hydrogen atom, a chlorine atom, a bromine atom or a methyl group;

a compound of the formula (1) wherein Q represents Q1, $R^1$ represents a hydrogen atom, a fluorine atom, a chlorine atom, a trifluoromethyl group or a methyl group, $R^2$ represents a hydrogen atom, a chlorine atom or a methyl group, $R^3$ represents a hydrogen atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents a methyl group or an ethyl group, X represents an oxygen atom, $Y^1$ represents a hydrogen atom, a methyl group, an ethyl group, an isopropyl group, a tert-butyl group or a trifluoromethyl group, $Y^2$ represents a hydrogen atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methyl group or an ethyl group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, and $Z^3$ represents a hydrogen atom, a methyl group or a bromine atom;

a compound of the formula (1) wherein Q represents Q1, $R^1$ represents a hydrogen atom, a halogen atom or an C1-C6 alkyl group, $R^2$ represents a hydrogen atom, a halogen atom or an C1-C6 alkyl group, $R^3$ represents a hydrogen atom or an C1-C6 alkyl group, $R^4$, $R^5$, $R^7$, $R^8$ and $R^9$ represent a hydrogen atom, $R^{10}$ represents a methyl group, $R^{11}$ represents a hydrogen atom or an C1-C6 alkyl group, $R^6$ represents an C1-C4 alkoxy group, X represents an oxygen atom, $Y^1$ represents an C1-C6 alkyl group optionally having halogen atom or a hydrogen atom, $Y^2$ represents an C1-C6 alkyl group optionally having halogen atom, a hydrogen atom, a halogen atom, an C1-C6 alkoxy group or an aldehyde group, $Y^3$ represents an C1-C6 alkyl group optionally having halogen atom or a hydrogen atom, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a halogen atom, an C1-C6 alkyl group or a C3-C6 cycloalkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkoxy group, X represents an oxygen atom, $Z^1$ represents an C1-C6 alkyl group optionally having one or more atoms or groups selected from the group consisting of halogen atom and C3-C6 cycloalkyl group, a hydrogen atom, an C3-C6 alkynyl group, an C2-C8 alkylaminosulfonyl group, an C1-C6 alkylsulfonyl group or a C3-C6 cycloalkylsulfonyl group, $Z^2$ represents a hydrogen atom, an C1-C6 alkyl group, a C1-C3 haloalkyl group or a halogen atom, and $Z^3$ represents a hydrogen atom;

a compound of the formula (1) wherein Q represents Q1, $R^1$ represents a hydrogen atom, a fluorine atom, a chlorine atom, a bromine atom, a trifluoromethyl group, a methyl group, an ethyl group or a cyclopropyl group, $R^2$ represents a hydrogen atom, a chlorine atom or a methyl group, $R^3$ represents a hydrogen atom, a chlorine atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents an C1-C4 alkoxy group, X represents an oxygen atom, $Y^1$ represents a hydrogen atom, a methyl group, an ethyl group, an isopropyl group, a cyclopropyl group, a tert-butyl group or a trifluoromethyl group, $Y^2$ represents a hydrogen atom, a chlorine atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkoxy group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, and $Z^3$ represents a hydrogen atom, a chlorine atom, a bromine atom or a methyl group;

a compound of the formula (1) wherein Q represents Q1, $R^1$ represents a hydrogen atom, a fluorine atom, a chlorine atom, a trifluoromethyl group or a methyl group, $R^2$ represents a hydrogen atom, a chlorine atom or a methyl group, $R^3$ represents a hydrogen atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents an C1-C4 alkoxy group, X represents an oxygen atom, Y represents a hydrogen atom, a methyl group, an ethyl group, an isopropyl group, a tert-butyl group or a trifluoromethyl group, $Y^2$ represents a hydrogen atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 alkoxy group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, and $Z^3$ represents a hydrogen atom, a methyl group or a bromine atom;

a compound of the formula (1) wherein Q represents Q1, $R^1$ represents a hydrogen atom, a halogen atom or an C1-C6 alkyl group, $R^2$ represents a hydrogen atom, a halogen atom or an C1-C6 alkyl group, $R^3$ represents a hydrogen atom or an C1-C6 alkyl group, $R^4$, $R^5$, $R^7$, $R^8$ and $R^9$ represent a hydrogen atom, $R^{10}$ represents a methyl group, $R^{11}$ represents a hydrogen atom or an C1-C6 alkyl group, $R^6$ represents a methoxy group or an ethoxy group, X represents an oxygen atom, $Y^1$ represents an C1-C6 alkyl group optionally having halogen atom or a hydrogen atom, $Y^2$ represents an C1-C6 alkyl group optionally having halogen atom, a hydrogen atom, a halogen atom, an C1-C6 alkoxy group or an aldehyde group, $Y^3$ represents an C1-C6 alkyl group optionally having halogen atom or a hydrogen atom, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a halogen atom, an C1-C6 alkyl group or a C3-C6 cycloalkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methoxy group or an ethoxy group, X represents an oxygen atom, $Z^1$ represents an C1-C6 alkyl group optionally having one or more atoms or groups selected from the group consisting of halogen atom and C3-C6 cycloalkyl group, a hydrogen atom, an C3-C6 alkynyl group, an C2-C8 alkylaminosulfonyl group, an C2-C6 alkylsulfonyl group, or a C3-C6 cycloalkylsulfonyl group, $Z^2$ represents a hydrogen atom, an C1-C6 alkyl group, a C1-C3 haloalkyl group or a halogen atom, and $Z^3$ represents a hydrogen atom;

a compound of the formula (1) wherein Q represents Q1, $R^1$ represents a hydrogen atom, a fluorine atom, a chlorine atom, a bromine atom, a trifluoromethyl group, a methyl group, an ethyl group or a cyclopropyl group, $R^2$ represents a hydrogen atom, a chlorine atom or a methyl group, $R^3$ represents a hydrogen atom, a chlorine atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents a methoxy group or an ethoxy group, X represents an oxygen atom, $Y^1$ represents a hydrogen atom, a methyl group, an ethyl group, an isopropyl group, a cyclopropyl group, a tert-butyl group or a trifluoromethyl group, $Y^2$ represents a hydrogen atom, a chlorine atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methoxy group or an ethoxy group, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, $Z^3$ represents a hydrogen atom, a chlorine atom, a bromine atom or a methyl group;

a compound of the formula (1) wherein Q represents Q1, $R^1$ represents a hydrogen atom, a fluorine atom, a chlorine atom, a trifluoromethyl group or a methyl group, $R^2$ represents a hydrogen atom, a chlorine atom or a methyl group, $R^3$ represents a hydrogen atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents a methoxy group or an ethoxy group, X represents an oxygen atom, $Y^1$ represents a hydrogen atom, a methyl group, an ethyl group, an isopropyl group, a tert-butyl group or a trifluoromethyl group, $Y^2$ represents a hydrogen atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, X represents an oxygen atom, $R^6$ represents a methoxy group or an ethoxy group, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, and $Z^3$ represents a hydrogen atom, a methyl group or a bromine atom;

a compound of the formula (1) wherein Q represents Q1, $R^1$ represents a hydrogen atom, a halogen atom or an C1-C6 alkyl group, $R^2$ represents a hydrogen atom, a halogen atom or an C1-C6 alkyl group, $R^3$ represents a hydrogen atom or an C1-C6 alkyl group, $R^4$, $R^5$, $R^7$, $R^8$ and $R^9$ represent a hydrogen atom, $R^{10}$ represents a methyl group, $R^{11}$ represents a hydrogen atom or an C1-C6 alkyl group, $R^6$ represents a halogen atom, X represents an oxygen atom, $Y^1$ represents an C1-C6 alkyl group optionally having halogen atom or a hydrogen atom, $Y^2$ represents an C1-C6 alkyl group optionally having halogen atom, a hydrogen atom, a halogen atom, an C1-C6 alkoxy group or an aldehyde group, $Y^3$ represents an C1-C6 alkyl group optionally having halogen atom or a hydrogen atom, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a halogen atom, an C1-C6 alkyl group or a C3-C6 cycloalkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a halogen atom, X represents an oxygen atom, $Z^1$ represents an C1-C6 alkyl group optionally having one or more atoms or groups selected from the groups consisting of halogen atom and C3-C6 cycloalkyl group, a hydrogen atom, an C3-C6 alkynyl group, an C2-C8 alkylaminosulfonyl group, an C1-C6 alkylsulfonyl group or a C3-C6 cycloalkylsulfonyl group, $Z^2$ represents a hydrogen atom, an C1-C6 alkyl group, a C1-C3 haloalkyl group or a halogen atom, and $Z^3$ represents a hydrogen atom;

a compound of the formula (1) wherein Q represents Q1, $R^1$ represents a hydrogen atom, a fluorine atom, a chlorine atom, a bromine atom, a trifluoromethyl group, a methyl group, an ethyl group or a cyclopropyl group, $R^2$ represents a hydrogen atom, a chlorine atom or a methyl group, $R^3$ represents a hydrogen atom, a chlorine atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents a halogen atom, X represents an oxygen atom, $Y^1$ represents a hydrogen atom, a methyl group, an ethyl group, an isopropyl group, a cyclopropyl group, a tert-butyl group or a trifluoromethyl group, $Y^2$ represents a hydrogen atom, a chlorine atom, a bromine atom, a methyl group, an ethyl group, a difluoromethyl group, a cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a halogen atom, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, $Z^3$ represents a hydrogen atom, a chlorine atom, a bromine atom or a methyl group;

a compound of the formula (1) wherein Q represents Q1, $R^1$ represents a hydrogen atom, a fluorine atom, a chlorine atom, a trifluoromethyl group or a methyl group, $R^2$ represents a hydrogen atom, a chlorine atom or a methyl group, $R^3$ represents a hydrogen atom or a methyl group, $R^4$, $R^5$, $R^7$, $R^8$ and $R^9$ represent a hydrogen atom, $R^{10}$ represents a methyl group, $R^{11}$ represents a hydrogen atom or a methyl group, $R^6$ represents a halogen atom, X represents an oxygen atom, $Y^1$ represents a hydrogen atom, a methyl group, an ethyl group, an isopropyl group, a tert-butyl group or a trifluoromethyl group, $Y^2$ represents a hydrogen atom, a bromine atom, a methyl group, an ethyl group, a difluoromethyl group, cyclopropyl group, a methoxy group or an aldehyde group, $Y^3$ represents a hydrogen atom, a methyl group, an ethyl group, an isopropyl group, a difluoromethyl group or a trifluoromethyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a bromine atom, a methyl group, an ethyl group, a propyl group, a butyl group or a cyclopropyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a halogen atom, X represents an oxygen atom, $Z^1$ represents a hydrogen atom, a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a trifluoromethyl group or a chlorine atom, and $Z^3$ represents a hydrogen atom, a methyl group or a bromine atom;

a compound of the formula (1) wherein Q represents Q2, $R^1$ represents a halogen atom, an C1-C4 alkyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents an C1-C4 alkyl group, a C1-C4 haloalkyl group, an C1-C4 alkoxy group or a halogen atom, $Z^1$ represents an C1-C6 alkyl group, a C1-C6 haloalkyl group, a C3-C6 alkynyl group or a C4-C7 cycloalkylmethyl group, $Z^2$ represents a hydrogen atom, a halogen atom, a cyano group, an C1-C6 alkyl group, a C1-C6 haloalkyl group, an C1-C6 alkoxy group, a C3-C6 alkynyloxy group, an C1-C6 alkylthio group or a C1-C6 haloalkoxy group, $Z^3$ represents a hydrogen atom, a halogen atom, a cyano group, a C1-C4 alkyl group or a C1-C4 haloalkyl group;

a compound of the formula (1) wherein Q represents Q2, $R^1$ represents a halogen atom, an C1-C4 alkyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents an C1-C4 alkyl group, a C1-C4 haloalkyl group, an C1-C4 alkoxy group or a halogen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a halogen atom, an C1-C6 alkyl group, a C1-C6 haloalkyl group, an C1-C6 alkoxy group, an C3-C6 alkynyloxy group, an C1-C6 alkylthio group or a C1-C6 haloalkoxy group, $Z^3$ represents a hydrogen atom, a halogen atom, a cyano group, an C1-C4 alkyl group or a C1-C4 haloalkyl group;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl, an ethyl group, a methoxy group, an ethoxy group, a trifluoromethyl group or a halogen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a halogen atom, a cyano group, an C1-C6 alkyl group, a C1-C6 haloalkyl group, an C1-C6 alkoxy group, an C3-C6 alkynyloxy group, an C1-C6 alkylthio group or a C1-C6 haloalkoxy group, and $Z^3$ represents a hydrogen atom, a halogen atom, a cyano group, an C1-C4 alkyl group or a C1-C4 haloalkyl group;

a compound of the formula (1) wherein Q represents Q2, $R^1$ represents a halogen atom or an C1-C4 alkyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group or an ethyl group, X represents an oxygen atom, $Z^1$ represents an C1-C6 alkyl group, $Z^2$ represents a hydrogen atom, a halogen atom, a cyano group, an C1-C6 alkyl group, a C1-C6 haloalkyl group, an C1-C6 alkoxy group, an C3-C6 alkynyloxy group, an C1-C6 alkylthio group or a C1-C6 haloalkoxy group, $Z^3$ represents a hydrogen atom, a halogen atom, a cyano group, an C1-C4 alkyl group or a C1-C4 haloalkyl group;

a compound of the formula (1) wherein Q represents Q2, $R^1$ represents a halogen atom or an C1-C4 alkyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group or an ethyl group, X represents an oxygen atom, $Z^1$ represents an C1-C6 alkyl group, $Z^2$ represents a hydrogen atom, a halogen atom, an C1-C6 alkyl group, a C1-C6 haloalkyl group, an C1-C6 alkoxy group, an C3-C6 alkynyloxy group, an C1-C6 alkylthio group or a C1-C6 haloalkoxy group, and $Z^3$ represents a hydrogen atom, a halogen atom, a cyano group, an C1-C4 alkyl group or a CL-C4 haloalkyl group;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents an C1-C4 alkoxy group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a halogen atom, an C1-C6 alkyl group, a C1-C6 haloalkyl group, an C1-C6 alkoxy group or an C1-C6 alkylthio group, and $Z^3$ represents a hydrogen atom, a halogen atom or an C1-C4 alkyl group;

a compound of the formula (1) wherein Q represents Q2, $R^1$ represents a chlorine atom or a methyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a halogen atom, X represents an oxygen atom, $Z^1$ represents an C1-C6 alkyl group, $Z^2$ represents a hydrogen atom, a halogen atom, an C1-C6 alkyl group, a C1-C6 haloalkyl group, an C1-C6 alkoxy group or an C1-C6 alkylthio group, and $Z^3$ represents a hydrogen atom, a halogen atom or an C1-C4 alkyl group;

a compound of the formula (1) wherein Q represents Q2, $R^1$ represents a halogen atom or a methyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group, X represents an oxygen atom or a sulfur atom, $Z^1$ represents an C1-C6 alkyl group, $Z^2$ represents a hydrogen atom, a halogen atom, a cyano group, an C1-C6 alkyl group, a C1-C6 haloalkyl group, an C1-C6 alkoxy group, an C3-C6 alkynyloxy group, an C1-C6 alkylthio group or a C1-C6 haloalkoxy group, and $Z^3$ represents a hydrogen atom, a halogen atom, a cyano group, an C1-C4 alkyl group or a C1-C4 haloalkyl group;

a compound of the formula (1) wherein Q represents Q2, $R^1$ represents a halogen atom or a methyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group, X represents an oxygen atom, $Z^1$ represents an C1-C6 alkyl group, $Z^2$ represents a hydrogen atom, a halogen atom, a cyano group, an C1-C6 alkyl group, a C1-C6 haloalkyl group, an C1-C6 alkoxy group, an C3-C6 alkynyloxy group, an C1-C6 alkylthio group or a C1-C6 haloalkoxy group, and $Z^3$ represents a hydrogen atom, a halogen atom, a cyano group, an C1-C4 alkyl group or a C1-C4 haloalkyl group;

a compound of the formula (1) wherein Q represents Q2, $R^1$ represents a halogen atom, an C1-C4 alkyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents an C1-C4 alkyl group, an C1-C4 alkoxy group or a halogen atom, X represents an oxygen atom, $Z^1$ represents an C1-C6 alkyl group or a C1-C6 haloalkyl group, $Z^2$ represents a hydrogen atom, a chlorine atom, a cyano group, a methoxy group, an ethoxy group, a 2-propynyloxy group, a methylthio group, a difluoromethoxy group, a 2,2-difluoroethoxy group, a difluoromethyl group, a trifluoromethyl group or an C1-C3 alkyl group, and $Z^3$ represents a hydrogen atom, a halogen atom, a cyano group or a methyl group;

a compound of the formula (1) wherein Q represents Q2, $R^1$ represents a halogen atom, an C1-C4 alkyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents an C1-C4 alkyl group, an C1-C4 alkoxy group or a halogen atom, X represents an oxygen atom, $Z^1$ represents an C1-C6 alkyl group or a C1-C6 haloalkyl group, $Z^2$ represents a hydrogen atom, a chlorine atom, a methoxy group, an ethoxy group, a 2-propynyloxy group, a methylthio group, a difluoromethoxy group, a 2,2-difluoroethoxy group, a difluoromethyl group, a trifluoromethyl group or an C1-C3 alkyl group, and $Z^3$ represents a hydrogen atom, a halogen atom, a cyano group or a methyl group;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group, an ethyl group, a methoxy group, an ethoxy group or a halogen atom, $Z^1$ represents an C1-C6 alkyl group or a C1-C6 haloalkyl group, $Z^2$ represents a hydrogen atom, a chlorine atom, a cyano group, a methoxy group, an ethoxy group, a 2-propynyloxy group, a methylthio group, a difluoromethoxy group, a 2,2-difluoroethoxy group, a difluoromethyl group, a trifluoromethyl group or an C1-C3 alkyl group, and $Z^3$ represents a hydrogen atom, a halogen atom, a cyano group or a methyl group;

a compound of the formula (1) wherein Q represents Q2, $R^1$ represents a chlorine atom or a methyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group or an ethyl group, X represents an oxygen atom or a sulfur atom, $Z^1$ represents an C1-C6 alkyl group, $Z^2$ represents a hydrogen atom, a chlorine atom, a cyano group, a methoxy group, an ethoxy group, a difluoromethyl group, a trifluoromethyl group, a 2-propynyloxy group, a methylthio group, a difluoromethoxy group, a 2,2-difluoroethoxy group or an C1-C3 alkyl group, and $Z^3$ represents a hydrogen atom, a halogen atom, a cyano group or a methyl group;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methoxy group or an ethoxy group, X represents an oxygen atom, $Z^1$ represents an C1-C6 alkyl group or a C1-C6 haloalkyl group, $Z^2$ represents a hydrogen atom, a chlorine atom, a methoxy group, an ethoxy group, a methylthio group, a trifluoromethyl group or an C1-C3 alkyl group, and $Z^3$ represents a hydrogen atom, a halogen atom or a methyl group;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methoxy group, X represents an oxygen atom, $Z^1$ represents an C1-C6 alkyl group or a C1-C6 haloalkyl group, $Z^2$ represents a hydrogen atom, a chlorine atom, a methoxy group, an ethoxy group, a methylthio group, a trifluoromethyl group or an C1-C3 alkyl group, and $Z^3$ represents a hydrogen atom, a halogen atom or a methyl group;

a compound of the formula (1) wherein Q represents Q2, $R^1$ represents a chlorine atom or a methyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a halogen atom, X represents an oxygen atom, $Z^1$ represents an C1-C6 alkyl group, $Z^2$ represents a hydrogen atom, a chlorine atom, a methoxy group, an ethoxy group, a methylthio group, a trifluoromethyl group or an C1-C3 alkyl group, and $Z^3$ represents a hydrogen atom, a halogen atom or a methyl group;

a compound of the formula (1) wherein Q represents Q2, $R^1$ represents a chlorine atom or a methyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group, X represents an oxygen atom or a sulfur atom, $Z^1$ represents an C1-C6 alkyl group, $Z^2$ represents a hydrogen atom, a chlorine atom, a cyano group, a methoxy group, an ethoxy group, a 2-propynyloxy group, a difluoromethoxy group, a 2,2-difluoroethoxy group, a methylthio group, a difluoromethyl group, a trifluoromethyl group or an C1-C3 alkyl group, and $Z^3$ represents a hydrogen atom, a halogen atom, a cyano group or a methyl group;

a compound of the formula (1) wherein Q represents Q2, $R^1$ represents a chlorine atom or a methyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a methyl group, X represents an oxygen atom, $Z^1$ represents an C1-C6 alkyl group, $Z^2$ represents a hydrogen atom, a chlorine atom, a cyano group, a methoxy group, an ethoxy group, a 2-propynyloxy group, a difluoromethoxy group, a 2,2-difluoroethoxy group, a methylthio group, a difluoromethyl group, a trifluoromethyl group or an C1-C3 alkyl group, and $Z^3$ represents a hydrogen atom, a halogen atom, a cyano group or a methyl group;

a compound of the formula (1) wherein Q represents Q2, $R^1$ represents a chlorine atom, a bromine atom, a methyl group, an ethyl group, a propyl group, a butyl group or a cyclopropyl group, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group, an ethyl group, a trifluoromethyl group, a methoxy group, an ethoxy group, a fluorine atom, a chlorine atom or a bromine atom, X represents an oxygen atom or a sulfur atom, $Z^1$ represents a methyl group, an ethyl group, a propyl group, an isopropyl group, a butyl group, an isobutyl group, an isopentyl group, a pentyl group, an isohexyl group, a 2,2,2-trifluoroethyl group, a 2,2-difluoroethyl group, a 2-propynyl group, a 2-butynyl group, a N,N-dimethylaminosulfonyl group, a methylsulfonyl group, an ethylsulfonyl group, a cyclopropylsulfonyl group or a cyclopropylmethyl group, $Z^2$ represents a hydrogen atom, a methyl group, a methoxy group, an ethoxy group, a 2-propynyloxy group, a difluoromethoxy group, a 2,2-difluoroethoxy group, a methylthio group, a difluoromethyl group, a trifluoromethyl group, a chlorine atom or a cyano group, and $Z^3$ represents a hydrogen atom, a methyl group, a difluoromethyl group, a fluorine atom, a chlorine atom, a bromine atom, an iodine atom or a cyano group;

a compound of the formula (1) wherein Q represents Q2, $R^1$ represents a methyl group or a chlorine atom, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group or an ethyl group, X represents an oxygen atom or a sulfur atom, $Z^1$ represents a methyl group, an ethyl group or an isopropyl group, $Z^2$ represents a hydrogen atom, a methyl group, a methoxy group, an ethoxy group, a methylthio group, a 2-propynyloxy group, a difluoromethoxy group, a 2,2-difluoroethoxy group, a difluoromethyl group, a trifluoromethyl group, a chlorine atom or a cyano group, and $Z^3$ represents a hydrogen atom, a methyl group, a halogen atom or a cyano group;

a compound of the formula (1) wherein Q represents Q2, $R^1$ represents a methyl group or a chlorine atom, $R^2$, $R^4$, $R^5$, $R^7$, $R^8$, $R^9$ and $R^{11}$ represent a hydrogen atom, $R^3$ represents a hydrogen atom or a methyl group, $R^{10}$ represents a methyl group, $R^6$ represents a methyl group, X represents an oxygen atom or a sulfur atom, $Z^1$ represents a methyl group, an ethyl group or an isopropyl group, $Z^2$ represents a hydrogen atom, a methyl group, a methoxy group, an ethoxy group, a methylthio group, a 2-propynyloxy group, a difluoromethoxy group, a 2,2-difluoroethoxy group, a difluoromethyl group, a trifluoromethyl group, a chlorine atom or a cyano group, and $Z^3$ represents a hydrogen atom, a methyl group, a halogen atom または a cyano group;

a compound of the formula (1) wherein Q represents Q2, $R^1$ represents a methyl group, an ethyl group, a chlorine atom, a bromine atom or a trifluoromethyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents an C1-C3 alkyl group, a halogen atom or an C1-C2 alkoxy group, $Z^1$ represents an C1-C3 alkyl group, $Z^2$ represents an C1-C2 alkoxy group, a C1-C2 haloalkoxy group, an C3-C4 alkynyloxy group, an C1-C3 alkyl group, an C1-C2 alkylthio group, a halogen atom or a cyano group, and $Z^2$ represents an C1-C3 alkyl group, a halogen atom or a cyano group;

a compound of the formula (1) wherein Q represents Q2, $R^1$ represents a methyl group, $R^2$, $R^4$, $R^5$, $R^7$, $R^8$, $R^9$ and $R^{11}$ represent a hydrogen atom, $R^{10}$ represents a methyl group, $R^6$ represents an C1-C3 alkyl group, a halogen atom or an C1-C3 alkoxy group, $Z^1$ represents an C1-C6 alkyl group, $Z^2$ represents a hydrogen atom, an C1-C3 alkoxy group, an C1-C3 alkyl group, a C1-C3 haloalkyl group or a halogen atom, and $Z^3$ represents a hydrogen atom, an C1-C3 alkyl group, a halogen atom or an aldehyde group.

Examples of an embodiment of the present compound include the compounds of the formula (2) wherein the substituents represent the following ones.

a compound of the formula (2) wherein $R^1$ represents a methyl group, an ethyl group, a chlorine atom or a bromine atom, $R^3$ represents a hydrogen atom or a methyl group, $R^6$ represents a methyl group or an ethyl group, and $R^{12}$ represents an C1-C6 alkyl group;

a compound of the formula (2) wherein $R^1$ represents a methyl group, an ethyl group, a chlorine atom or a bromine atom, $R^3$ represents a hydrogen atom or a methyl group, $R^6$ represents a methyl group or an ethyl group, and $R^{12}$ represents a methyl group or an ethyl group;

a compound of the formula (2) wherein $R^1$ represents a methyl group, an ethyl group, a chlorine atom or a bromine atom, $R^3$ represents a hydrogen atom or a methyl group, $R^6$ represents a methoxy group or an ethoxy group, and $R^{12}$ represents an C1-C6 alkyl group;

a compound of the formula (2) wherein $R^1$ represents a methyl group, an ethyl group, a chlorine atom or a bromine atom, $R^3$ represents a hydrogen atom or a methyl group, $R^6$ represents a methoxy group or an ethoxy group, and $R^{12}$ represents a methyl group or an ethyl group;

a compound of the formula (2) wherein $R^1$ represents a methyl group, an ethyl group, a chlorine atom or a bromine atom, $R^3$ represents a hydrogen atom or a methyl group, $R^6$ represents a chlorine atom or a bromine atom, and $R^{12}$ represents an C1-C6 alkyl group;

a compound of the formula (2) wherein $R^1$ represents a methyl group, an ethyl group, a chlorine atom or a bromine atom, $R^3$ represents a hydrogen atom or a methyl group, $R^6$ represents a chlorine atom or a bromine atom, and $R^{12}$ represents a methyl group or an ethyl group;

Examples of an embodiment of the present compound include the compounds of the formula (3) wherein the substituents represent the following ones.

a compound of the formula (3) wherein $R^1$ represents a methyl group, an ethyl group, a chlorine atom or a bromine atom, $R^3$ represents a hydrogen atom or a methyl group, $R^6$ represents a methyl group, an ethyl group or a chlorine atom, $Z^1$ represents an C1-C3 alkyl group, $Z^2$ represents an C1-C2 alkoxy group or a halogen atom, and $Z^3$ represents an C1-C3 alkyl group;

a compound of the formula (3) wherein $R^1$ represents a methyl group, $R^3$ represents a hydrogen atom, $R^6$ represents a methyl group, Z represents an C1-C3 alkyl group, $Z^2$ represents an C1-C2 alkoxy group or a halogen atom, and $Z^3$ represents an C1-C3 alkyl group;

a compound of the formula (3) wherein $R^1$ represents a methyl group, $R^3$ represents a hydrogen atom, $R^6$ represents a methyl group, $Z^1$ represents an C1-C3 alkyl group, $Z^2$ represents an C1-C2 alkoxy group, and $Z^3$ represents an C1-C3 alkyl group;

a compound of the formula (3) wherein $R^1$ represents a methyl group, $R^3$ represents a hydrogen atom, $R^6$ represents a methyl group, $Z^1$ represents a methyl group, $Z^2$ represents a methoxy group, an ethoxy group or a chlorine atom, and $Z^3$ represents a methyl group;

a compound of the formula (3) wherein $R^1$ represents a methyl group, $R^3$ represents a hydrogen atom, $R^6$ represents a methyl group, $Z^1$ represents a methyl group, $Z^2$ represents a methoxy group or an ethoxy group, and $Z^3$ represents a methyl group;

Examples of an embodiment of the present compound include the compounds of the formula (4) wherein the substituents represent the following ones.

a compound of the formula (4) wherein $L^1$ represents a nitro group, an amino group or an isocyanate group, $R^1$ represents a methyl group, $R^3$ represents a hydrogen atom, $R^6$ represents a methyl group, $Z^1$ represents an C1-C3 alkyl group, $Z^2$ represents an C1-C2 alkyl group or a halogen atom, and $Z^3$ represents an C1-C3 alkyl group;

a compound of the formula (4) wherein $L^1$ represents a nitro group, an amino group or an isocyanate group, $R^1$ represents a methyl group, $R^3$ represents a hydrogen atom, $R^6$ represents a methyl group, $Z^1$ represents an C1-C3 alkyl group, $Z^2$ represents an C1-C2 alkoxy group, and $Z^3$ represents an C1-C3 alkyl group;

a compound of the formula (4) wherein $L^1$ represents a nitro group, an amino group or an isocyanate group, $R^1$ represents a methyl group, $R^3$ represents a hydrogen atom, $R^6$ represents a methyl group, $Z^1$ represents a methyl group, $Z^2$ represents a methoxy group, an ethoxy group or a chlorine atom, and $Z^3$ represents a methyl group;

a compound of the formula (4) wherein $L^1$ represents a nitro group, an amino group or an isocyanate group, $R^1$ represents a methyl group, $R^3$ represents a hydrogen atom, $R^6$ represents a methyl group, $Z^1$ represents a methyl group, $Z^2$ represents a methoxy group or an ethoxy group, and $Z^3$ represents a methyl group;

a compound of the formula (4) wherein $L^1$ represents a nitro group, an amino group or an isocyanate group, $R^1$ represents a methyl group, $R^3$ represents a hydrogen atom, $R^6$ represents a methyl group, $Z^1$ represents a methyl group or a ethyl group, $Z^2$ represents a methoxy group or an ethoxy group or a chlorine atom or a cyano group, and $Z^3$ represents a methyl group, a chlorine atom or a bromine atom;

a compound of the formula (4) wherein $L^1$ represents a nitro group, an amino group or an isocyanate group, $R^1$ represents a methyl group, $R^3$ represents a hydrogen atom, $R^6$ represents a methyl group, $Z^1$ represents a methyl group or a ethyl group, $Z^2$ represents a methoxy group or an ethoxy group or a chlorine atom or a cyano group, and $Z^3$ represents a methyl group, a chlorine atom, a bromine atom or a cyano group;

Herein, when in a formula (I), $R^4$ and $R^5$ are different from each other, the present compound of the formula (1) may have an asymmetric carbon atom therein, and may thus include optically active substances and racemates, without being limited thereto.

Next, a process for preparing the present compound is explained.

The present compound can be prepared, for example, according to the below-mentioned process.

(Process A)

The present compound of the formula (1) can be prepared by reacting a compound of a formula (A-1) (hereinafter, described as Compound (A-1)) with a compound of a formula (A-2) (hereinafter, described as Compound (A-2)) in the presence of a base.

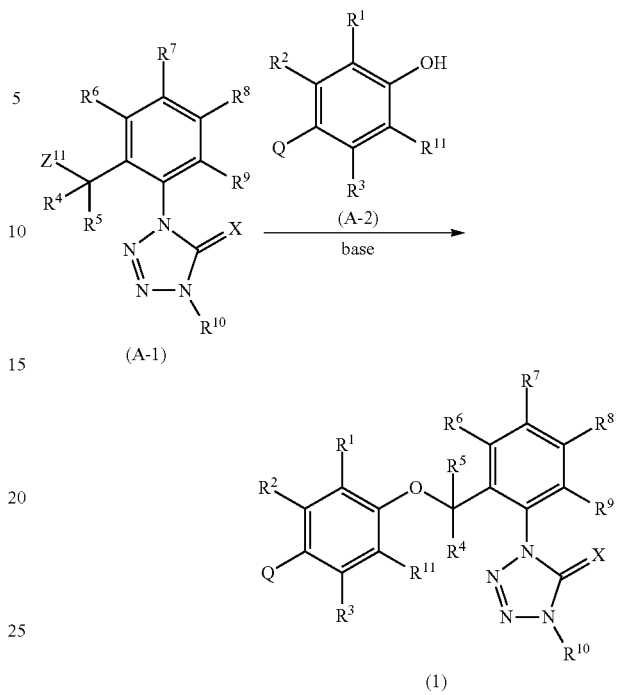

[wherein
$R^1$, $R^2$, $R^3$, $R^4$, $R^5$, $R^6$, $R^7$, $R^8$, $R^9$, $R^{10}$, $R^{11}$, X and Q are the same as defined above, $Z^{11}$ represents a leaving group such as a chlorine atom, a bromine atom, an iodine atom, a methanesulfonyloxy group, a trifluoromethanesulfonyloxy group, or a p-toluenesulfonyloxy group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (A-2) is used usually within a range of 1 to 10 molar ratio(s), and the base is used usually within a range of 1 to 10 molar ratio(s), as opposed to 1 mole of Compound (A-1).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (A-1).

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process B)

The present compound of the formula (1) can be prepared by reacting a compound of a formula (B-1) (hereinafter, described as Compound (B-1)) with a compound of a formula (B-2) (hereinafter, described as Compound (B-2)) in the presence of a base.

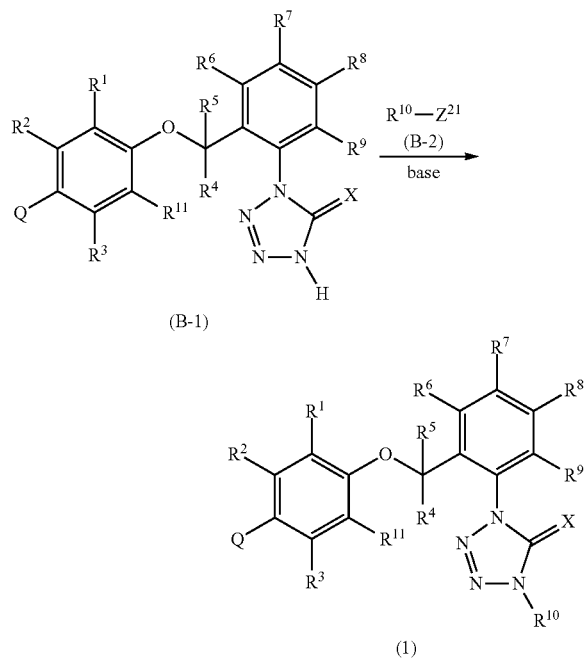

[wherein $R^1$, $R^2$, $R^3$, $R^4$, $R^5$, $R^6$, $R^7$, $R^8$, $R^9$, $R^{10}$, $R^{11}$, X and Q are the same as defined above, $Z^{21}$ represents a leaving group such as a chlorine atom, a bromine atom, an iodine atom, a methanesulfonyloxy group, a methoxysulfonyloxy group, a trifluoromethanesulfonyloxy group, or a p-toluenesulfonyloxy group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (B-2) to be used in the reaction can be usually used as a commercially available product. Specific examples include alkyl halides such as chlorodifluoromethane, methyl bromide, ethyl bromide, propyl bromide, methyl iodide, ethyl iodide, propyl bromide, aryl bromide, cyclopropyl bromide, 1,1-difluoro-2-iodoethane; alkyl or aryl sulfates such as dimethyl sulfate, methyl p-toluenesulfonate, ethyl p-toluenesulfonate, propyl p-toluenesulfonate, methyl methanesulfonate, ethyl methanesulfonate and propyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (B-2) is used usually within a range of 1 to 10 molar ratio(s), and the base is used usually within a range of 1 to 10 molar ratios, as opposed to 1 mole of Compound (B-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process C)

The present compound of the formula (1) wherein X represents a sulfur atom, i.e., the compound of a formula (1-S) (hereinafter, described as Compound (1-S)) can be prepared by reacting the present compound of the formula (1) wherein X represents an oxygen atom (hereinafter, described as Compound (1-O)) by well-known sulfurization.

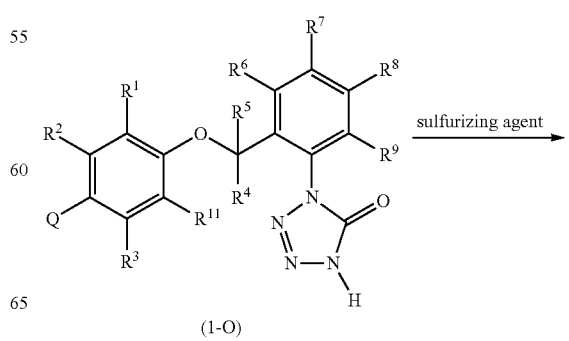

-continued

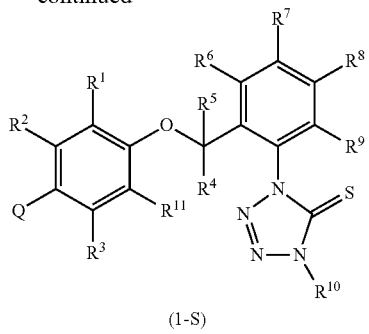

(1-S)

[wherein $R^1$, $R^2$, $R^3$, $R^4$, $R^5$, $R^6$, $R^7$, $R^8$, $R^9$, $R^{10}$, $R^{11}$ and Q are the same as defined above.]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; and mixed solvents thereof.

Examples of the sulfurating agent to be used in the reaction include phosphorus pentasulfide, Lawesson's reagent (2,4-bis(4-methoxyphenyl)-1,3,2,4-dithiadiphosphetane 2,4-disulfide).

In the reaction, the sulfurating agent is used within a range of 0.5 to 10 molar ratios as opposed to 1 mole of Compound (1-O).

The reaction temperature is usually within a range of −20 to 150° C. The reaction period of the reaction is usually within a range of 0.1 to 24 hours.

If necessary, organic bases such as pyridine and triethylamine and inorganic bases such as alkali metal hydroxides and alkali metal carbonates and the others may be added to the reaction and these compounds are used usually within a range of 0.5 to 10 molar ratios as opposed to 1 mole of Compound (1-O).

When the reaction is completed, the reaction mixtures are extracted with organic solvent(s), and the resulting organic layers are worked up (for example, drying and concentration) to isolate the present compound of the formula (1-S). The isolated present compound may be further purified, for example, by chromatography and recrystallization.

(Process D)

The present compound of the formula (1) wherein $R^6$ represents $R^{41}$, i.e., the compound of a formula (1-1) (hereinafter, described as Compound (1-1)), can be prepared by coupling Compound (D−1) (hereinafter, described as Compound (D-1)) with a compound of a formula (D-2) (hereinafter, described as Compound (D-2)) in the presence of a base and a catalyst.

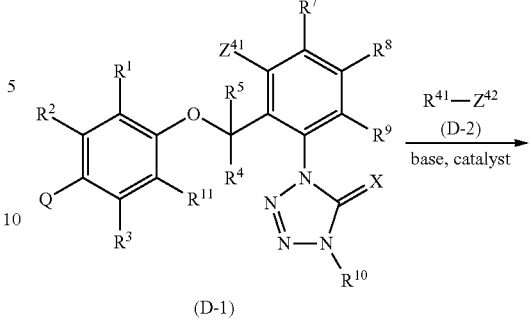

(D-1)

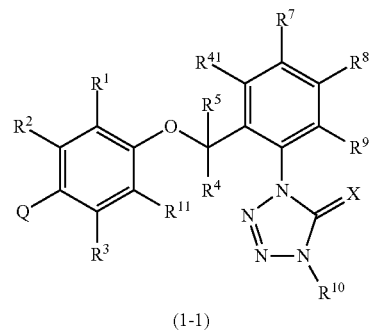

(1-1)

[wherein $R^1$, $R^2$, $R^3$, $R^4$, $R^5$, $R^6$, $R^7$, $R^8$, $R^9$, $R^{10}$, $R^{11}$, X and Q are the same as defined above, $Z^{41}$ represents a chlorine atom, a bromine atom, an iodine atom or a trifluoromethanesulfonyloxy group, $R^{41}$ represents an C1-C4 alkyl group or a C1-C4 haloalkyl group, an C2-C4 alkenyl group or a C2-C4 haloalkenyl group, and $Z^{42}$ represents a $B(OH)_2$, an alkoxyboryl group or a trifluoroborate salts $(BF_3^-K^+)$.]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Compound (D-2) to be used in the reaction may be usually used as a commercially available product, or may be prepared according to a method described in a review article of N. Miyaura and A. Suzuki, Chem. Rev. 1995, 95, 2457 and the others. Compound (D-2) to be used in the reaction can be also prepared, for example, by reacting an iodo compound ($R^{41}$—I) or a bromo compound ($R^{41}$—Br) with an alkyl lithium (such as butyl lithium), followed by reacting the resulting mixtures with borate esters to obtain boronate ester derivatives. Also, the obtained boronate ester derivatives can be hydrolyzed to the corresponding boronate esters derivatives as needed. Further, according to a method described in a review article of Molander et al. Acc. Chem. Res. 2007, 40, 275 and the others, the above-mentioned boronate ester derivatives can be fluorinated with potassium bifluoride and the like to obtain the trifluoroborate salts $(BF_3^-K^+)$.

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine ferrocenyl)palladium(II) dichloride, 1,3-bis(2,6-diisopropylphenyl)imidazole-2-ylidene (1,4-naphthoquinone) palladium dimer, aryl(chloro)(1,3-dimethyl-1,3-dihydro-2H-imidazole-2-ylidene)palladium or palladium(II) acetate/dicyclohexyl(2',4',6'-triisopropylbiphenyl-2-yl)phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (D-2) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (D-1).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-1). The isolated present compound may be further purified, for example, by chromatography and recrystallization.

According to the process for preparing the above-mentioned Compound (1-1), the present compound of the formula (1) wherein $R^7$ represents $R^{42}$, i.e., compound of a below-mentioned formula (1-1-2) (hereinafter, described as Compound (1-1-2)), can be prepared by coupling compound of a formula (D-3) (hereinafter, describes as Compound (D-3)) with compound of a formula (D-2-2) (hereinafter, describes as Compound (D-2-2)) in the presence of a base and the catalyst.

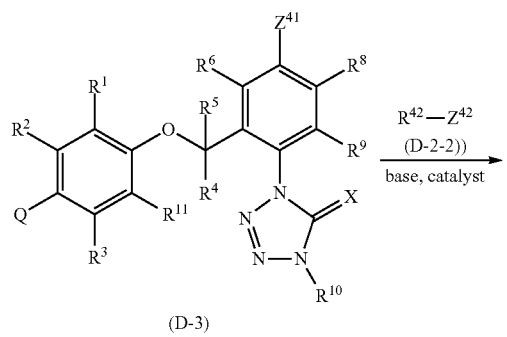

(D-3)

[wherein
$R^1$, $R^2$, $R^3$, $R^4$, $R^5$, $R^6$, $R^8$, $R^9$, $R^{10}$, $R^{11}$, X, Q, $Z^{41}$, $Z^{42}$ and X are the same as defined above, $R^{42}$ represents an C1-C3 alkyl group, a C1-C3 haloalkyl group, an C2-C3 alkenyl group or a C2-C3 haloalkenyl group]

According to the process for preparing the above-mentioned Compound (1-1), the present compound of the formula (1) wherein $R^8$ represents $R^{42}$, i.e., a compound of a below-mentioned formula (1-1-3) (hereinafter, described as Compound (1-1-3)), can be prepared by coupling a compound of a below-mentioned formula (D-4) (hereinafter, described as Compound (D-4)) with Compound (D-2-2) (hereinafter, described as Compound (D-2-2)) in the presence of a base and a catalyst.

[wherein
$R^1$, $R^2$, $R^3$, $R^4$, $R^5$, $R^6$, $R^7$, $R^9$, $R^{10}$, $R^{11}$, $R^{42}$, X, Q, $Z^{41}$, $Z^{42}$ and X are the same as defined above]

According to the process for preparing the above-mentioned Compound (1-1), the present compound of the formula (1) wherein $R^9$ represents $R^{42}$, i.e., a compound of a below-mentioned formula (1-1-4) (hereinafter, described as Compound (1-1-4)), can be prepared by coupling a compound of a below-mentioned formula (D-5) (hereinafter, described as Compound (D-5)) with Compound (D-2-2)

(hereinafter, described as Compound (D-2-2)) in the presence of a base and a catalyst.

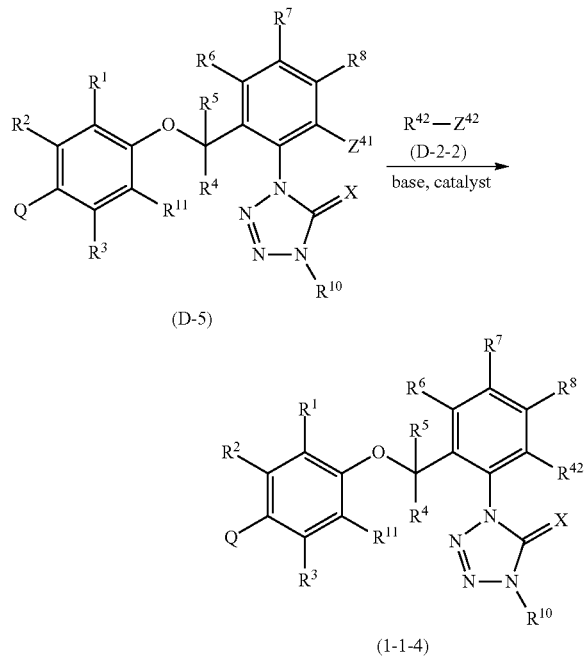

[wherein
$R^1$, $R^2$, $R^3$, $R^4$, $R^5$, $R^6$, $R^7$, $R^8$, $R^{10}$, $R^{11}$, $R^{42}$, X, Q, $Z^{41}$ and $Z^{42}$ are the same as defined above]

The present compound of the formula (1) wherein $R^6$ represents $R^{41}$, and one or more substituents selected from the group consisting of $R^7$, $R^8$ and $R^9$ is $R^{42}$ can be prepared according to the above-mentioned Process D.

Compound (1-1), Compound (1-1-2), Compound (1-1-3) and Compound (1-1-4) can be prepared by using other known coupling reaction in place of the above-mentioned coupling reaction of Process D.

(Process E)

The present compound of the formula (1) wherein $R^1$ represents $R^{51}$, i.e., the compound of a formula (1-2) (hereinafter, described as Compound (1-2)), can be prepared by coupling Compound (E-1) (hereinafter, described as Compound (E-1)) with a compound of a formula (E-2) (hereinafter, described as Compound (E-2)) in the presence of a base and a catalyst.

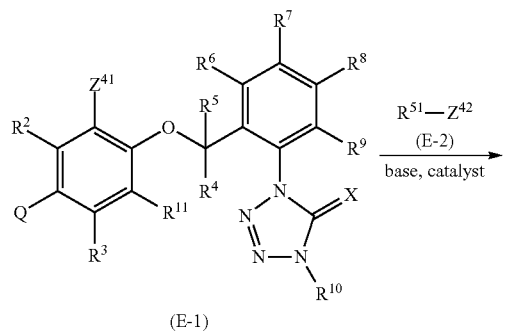

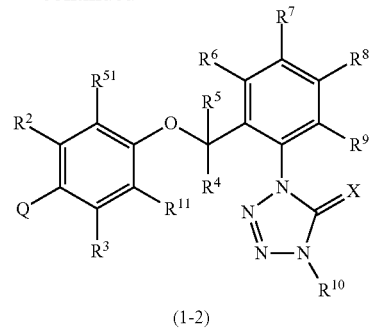

[wherein
$R^2$, $R^3$, $R^4$, $R^5$, $R^6$, $R^7$, $R^8$, $R^9$, $R^{10}$, $R^{11}$, $Z^{41}$, $Z^{42}$, X and Q are the same as defined above, $R^{51}$ represents an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group or a C3-C6 halocycloalkyl group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Compound (E-2) to be used in the reaction may be usually used as a commercially available product, or may be prepared according to a method described in a review article of N. Miyaura and A. Suzuki, Chem. Rev. 1995, 95, 2457 and the others. Compound (E-2) to be used in the reaction can be also prepared, for example, by reacting an iodo compound ($R^{51}$—I) or a bromo compound ($R^{51}$—Br) with an alkyl lithium (such as butyl lithium), followed by reacting the resulting mixtures with borate esters to obtain boronate ester derivatives. Also, the obtained boronate ester derivatives can be hydrolyzed to the corresponding boronate esters derivatives as needed. Further, according to a method described in a review article of Molander et al. Acc. Chem. Res. 2007, 40, 275 and the others, the above-mentioned boronate ester derivatives can be fluorinated with potassium bifluoride and the like to obtain the trifluoroborate salts ($BF_3^-K^+$).

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine ferrocenyl)palladium(II) dichloride, 1,3-bis(2,6-diisopropylphenyl)imidazole-2-ylidene (1,4-naphthoquinone) palladium dimer, aryl(chloro) (1,3-dimethyl-1,3-dihydro-2H-imidazole-2-ylidene)palladium or palladium(II) acetate/ dicyclohexyl(2',4',6'-triisopropylbiphenyl-2-yl)phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (E-2) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (E-1).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-2). The isolated present compound may be further purified, for example, by chromatography and recrystallization.

According to the process for preparing the above-mentioned Compound (1-2), the present compound of the formula (1) wherein $R^2$ represents $R^{51}$, i.e., a compound of a below-mentioned formula (1-2-2) (hereinafter, described as Compound (1-2-2)), can be prepared by coupling a compound of a below-mentioned formula (E-3) (hereinafter, described as Compound (E-3)) with Compound (E-2) (hereinafter, described as Compound (E-2)) in the presence of a base and a catalyst.

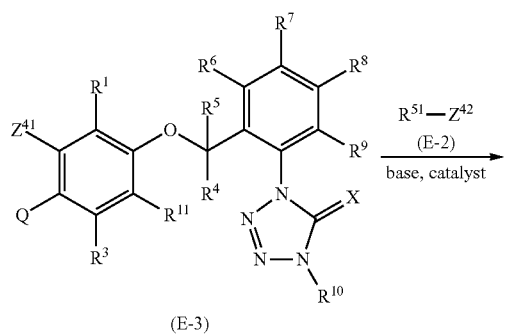

(E-3)

(1-2-2)

[wherein
$R^1$, $R^3$, $R^4$, $R^5$, $R^6$, $R^7$, $R^8$, $R^9$, $R^{10}$, $R^{11}$, $R^{51}$, X, Q, $Z^{41}$ and $Z^{42}$ are the same as defined above]

According to the process for preparing the above-mentioned Compound (1-2), the present compound of the formula (1) wherein $R^3$ represents $R^{51}$, i.e., a compound of a below-mentioned formula (1-2-3) (hereinafter, described as Compound (1-2-3)), can be prepared by coupling a compound of a below-mentioned formula (E-4) (hereinafter, described as Compound (E-4)) with Compound (E-2) (hereinafter, described as Compound (E-2)) in the presence of a base and a catalyst.

(E-4)

(1-2-3)

[wherein
$R^1$, $R^2$, $R^4$, $R^5$, $R^6$, $R^7$, $R^8$, $R^9$, $R^{10}$, $R^{11}$, $R^{51}$, X, Q, $Z^{41}$ and $Z^{42}$ are the same as defined above]

According to the process for preparing the above-mentioned Compound (1-2), the present compound of the formula (1) wherein $R^{11}$ represents $R^{51}$, i.e., a compound of a below-mentioned formula (1-2-4) (hereinafter, described as Compound (1-2-4)), can be prepared by coupling a compound of a below-mentioned formula (E-5) (hereinafter, described as Compound (E-5)) with Compound (E-2) (hereinafter, described as Compound (E-2)) in the presence of a base and a catalyst.

(E-5)

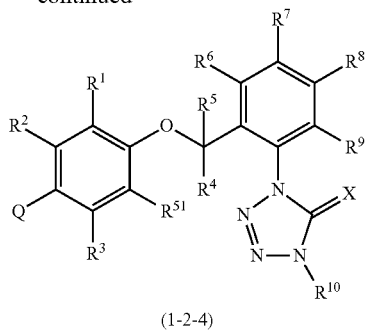

(1-2-4)

[wherein
$R^1$, $R^2$, $R^3$, $R^4$, $R^5$, $R^6$, $R^7$, $R^8$, $R^9$, $R^{10}$, $R^{51}$, X, Q, $Z^{41}$ and $Z^{42}$ are the same as defined above]

The present compound of the formula (1) wherein two or more substituents selected from the group consisting of $R^1$, $R^2$, $R^3$ and $R^{11}$ is $R^{51}$ can be prepared according to the above-mentioned Process E.

Compound (1-2), Compound (1-2-2), Compound (1-2-3) and Compound (1-2-4) can be prepared by using other known coupling reaction in place of the above-mentioned coupling reaction of Process E.

(Process F)

The present compound of the formula (1) wherein Q represents Q2, and $Z^1$ and $Z^2$ represent a hydrogen atom, i.e., a compound of a below-mentioned formula (1-3) (hereinafter, described as Compound (1-3)), can be prepared by reacting a compound of a below-mentioned formula (F-1) (hereinafter, described as Compound (F-1)) with hydrazines.

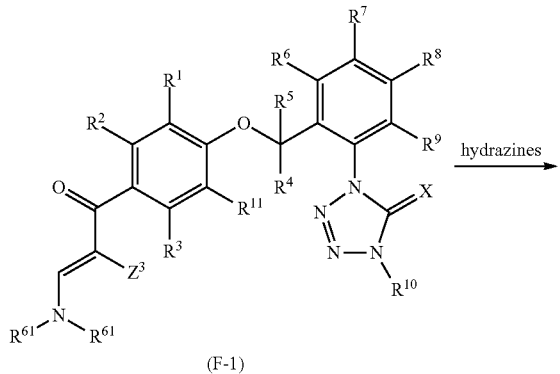

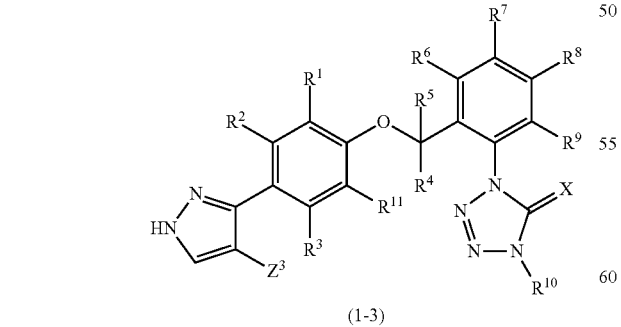

(1-3)

[wherein
$R^1$, $R^2$, $R^3$, $R^4$, $R^5$, $R^6$, $R^7$, $R^8$, $R^9$, $R^{10}$, $R^{11}$, X and Z are the same as defined above, and $R^{61}$ represents a methyl group or an ethyl group]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; water; and mixed solvents thereof.

Examples of the hydrazines to be used in the reaction include hydrazine monohydrate, hydrazine hydrochloride, hydroazine sulfate, anhydrous hydrazine and the others.

In the reaction, hydrazines is used usually within a range of 1 to 100 molar ratio(s) as opposed to 1 mole of Compound (F-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-3). Alternatively, the reaction is completed, the reaction mixtures are worked up (for example, concentration) to isolate the present compound of the formula (1-3). These isolated present compound may be further purified, for example, by chromatography and recrystallization.

(Process G)

The present compound of the formula (1) wherein Q represents Q2, and $Z^1$ represents a hydrogen atom, i.e., a compound of a below-mentioned formula (1-4) (hereinafter, described as Compound (1-4)), can be prepared by reacting a compound of a below-mentioned formula (G-1) (hereinafter, described as Compound (G-1)) with hydrazines.

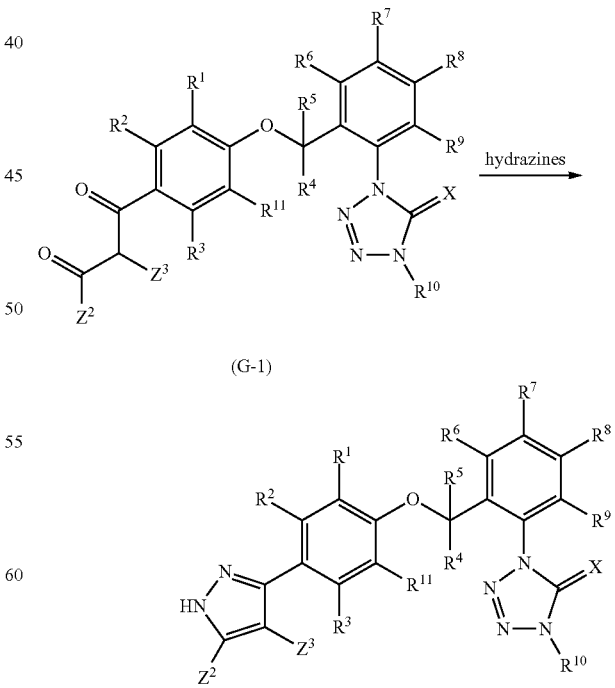

(G-1)

(1-4)

[wherein
R$^1$, R$^2$, R$^3$, R$^4$, R$^5$, R$^6$, R$^7$, R$^8$, R$^9$, R$^{10}$, R$^{11}$, X, Z$^2$ and Z$^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; water; and mixed solvents thereof.

Examples of the hydrazines to be used in the reaction include hydrazine monohydrate, hydrazine hydrochloride, hydroazine sulfate, anhydrous hydrazine and the others.

In the reaction, hydrazines is used usually within a range of 1 to 100 molar ratio(s) as opposed to 1 mole of Compound (G-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-4). The isolated present compound may be further purified, for example, by chromatography and recrystallization.

(Process H)

The present compound of the formula (1) wherein Q represents Q2, i.e., the compound of a formula (1-5) (hereinafter, described as Compound (1-5)), can be prepared by reacting Compound (1-4) (hereinafter, described as Compound (1-4)) with a compound of a formula (H-1) (hereinafter, described as Compound (H-1)) in the presence of a base.

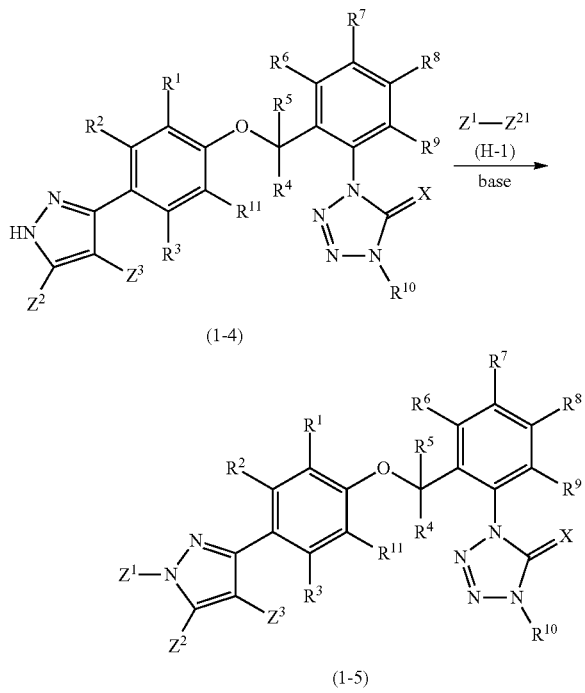

[wherein
R$^1$, R$^2$, R$^3$, R$^4$, R$^5$, R$^6$, R$^7$, R$^8$, R$^9$, R$^{10}$, R$^{11}$, Z$^1$, Z$^2$, Z$^3$, Z$^{21}$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (H-1) to be used in the reaction may be usually used as a commercially available product. Specific examples include halogenated alkyls such as chlorodifluoromethane, methyl bromide, ethyl bromide, propyl bromide, butyl bromide, pentyl bromide, hexyl bromide, methyl iodide, ethyl iodide, propyl iodide, isopropyl iodide, isobutyl iodide, isoamyl iodide, 2-propinyl iodide, 2-butynyl iodide, allyl bromide, cyclopropyl bromide, 2-propynyl bromide, 2-butynyl bromide, cyclopropylmethyl bromide, 1,1-difluoro-2-iodoethane and 1,1,1-trifluoro-2-iodoethane; alkyl or aryl sulfonates such as dimethyl sulfates, methyl p-toluenesulfonate, ethyl p-toluenesulfonate, propyl p-toluenesulfonate, methyl methanesulfonate, ethyl methanesulfonate, propyl methanesulfonate; carboxylic halides such as acetyl chloride; and sulfonic halides such as methanesulfonyl chloride, ethanesulfonyl chloride, isopropynyl sulfonyl chloride, cyclopropynyl sulfonyl chloride and N,N-dimethylsulfonyl chloride.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; and alkali metal alkoxides such as sodium tert-butoxide and potassium tert-butoxide.

In the reaction, Compound (H-1) is used usually within a range of 1 to 10 molar ratio(s), and the base is used usually within a range of 1 to 10 molar ratio(s), as opposed to 1 mole of Compound (1-4).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-5). The isolated present compound may be further purified, for example, by chromatography and recrystallization.

(Process I)

The present compound of the formula (1) wherein Q represents Q4, i.e., the compound of a formula (1-6) (hereinafter, described as Compound (1-6)), can be prepared by reacting Compound (1-4) (hereinafter, described as Compound (1-4)) with a compound of a formula (I-1) (hereinafter, described as Compound (I-1)) in the presence of a base.

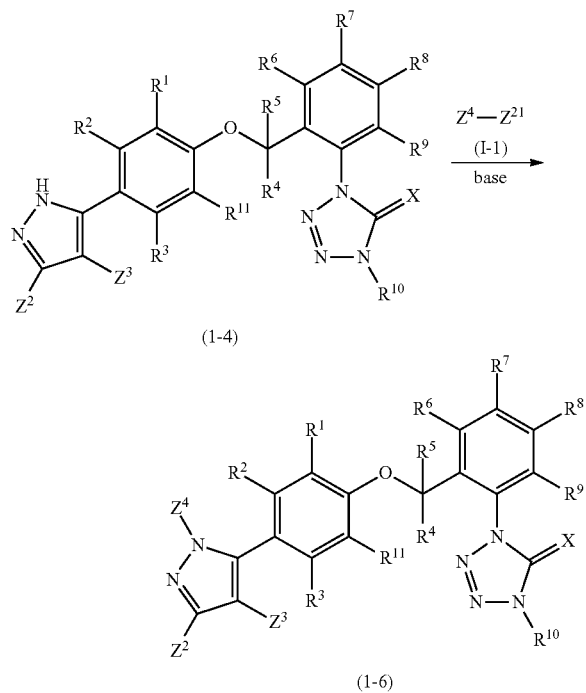

[wherein
R¹, R², R³, R⁴, R⁵, R⁶, R⁷, R⁸, R⁹, R¹⁰, R¹¹, Z², Z³, Z⁴, Z²¹ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (I-1) to be used in the reaction may be usually used as a commercially available product. Specific examples include halogenated alkyls such as chlorodifluoromethane, methyl bromide, ethyl bromide, propyl bromide, butyl bromide, pentyl bromide, hexyl bromide, methyl iodide, ethyl iodide, propyl iodide, isopropyl iodide, isobutyl iodide, isoamyl iodide, allyl bromide, cyclopropyl bromide and 1,1-difluoro-2-iodoethane; alkyl or aryl sulfonates such as dimethyl sulfates, methyl p-toluenesulfonate, ethyl p-toluenesulfonate, propyl p-toluenesulfonate, methyl methanesulfonate, ethyl methanesulfonate, propyl methanesulfonate; carboxylic halides such as acetyl chloride; and sulfonic halides such as methanesulfonyl chloride, ethanesulfonyl chloride, isopropynyl sulfonyl chloride, cyclopropynyl sulfonyl chloride and N,N-dimethylsulfonyl chloride.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; and alkali metal alkoxides such as sodium tert-butoxide and potassium tert-butoxide.

In the reaction, Compound (I-1) is used usually within a range of 1 to 10 molar ratio(s), and the base is used usually within a range of 1 to 10 molar ratio(s), as opposed to 1 mole of Compound (1-4).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-6). The isolated present compound may be further purified, for example, by chromatography and recrystallization.

(Process J)

The present compound of the formula (1) wherein Q represents Q1 and Y² represents R¹⁰⁰, i.e., the compound of a formula (1-8) (hereinafter, described as Compound (1-8)), can be prepared by reacting Compound (1-7) (hereinafter, described as Compound (1-7)) with a halogenating agent.

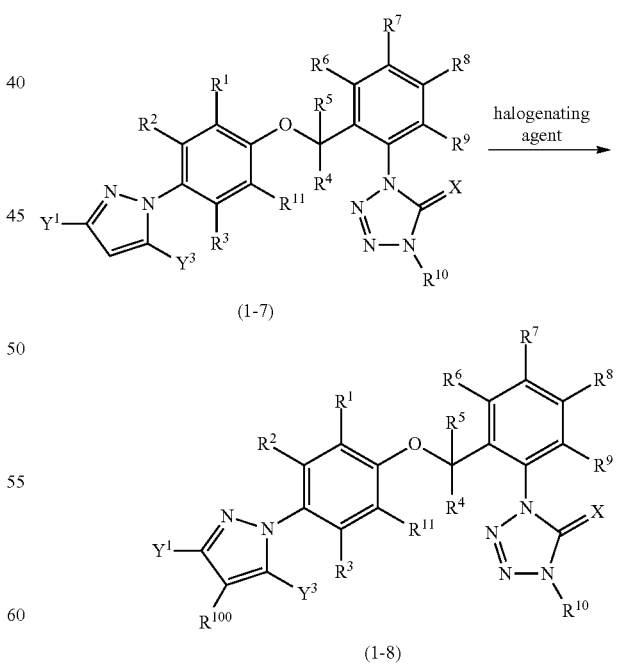

[wherein
R¹, R², R³, R⁴, R⁵, R⁶, R⁷, R⁸, R⁹, R¹⁰, R¹¹, Y¹, Y³ and X are the same as defined above, and R¹⁰⁰ represents a chlorine atom, a bromine atom, or an iodine atom.]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane and chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; water; and mixed solvents thereof.

Examples of the halogenating agent to be used in the reaction include N-chlorosuccinimide, N-bromosuccinimide, N-iodosuccinimide, chlorine, bromine, iodine and sulfuryl chloride.

In the reaction, the halogenating agent is used usually within a range of 1 to 10 molar ratio(s) as opposed to 1 mole of Compound (1-7).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-8). The isolated present compound may be further purified, for example, by chromatography and recrystallization.

According to the process for preparing the above-mentioned Compound (1-8), the present compound of the formula (1) wherein Q represents Q2 and $Z^3$ represents $R^{100}$, i.e., the compound of a formula (1-10) (hereinafter, described as Compound (1-10)), can be prepared by reacting Compound (1-9) (hereinafter, described as Compound (1-9)) with a halogenating agent.

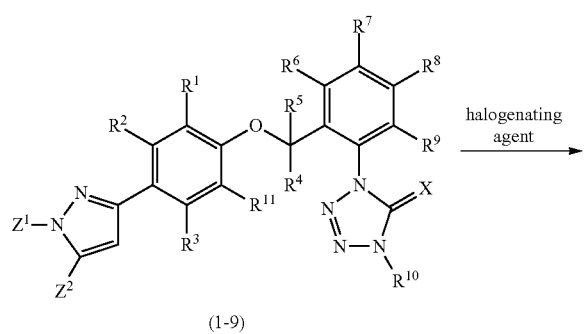

(1-9)

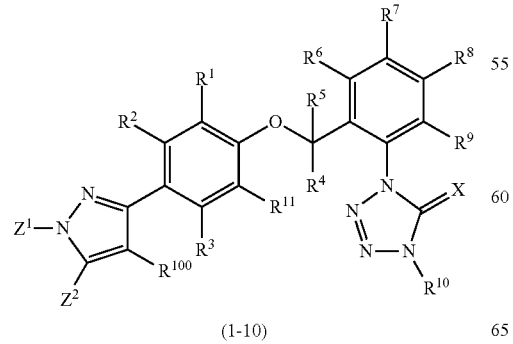

(1-10)

[wherein
$R^1$, $R^2$, $R^3$, $R^4$, $R^5$, $R^6$, $R^7$, $R^8$, $R^9$, $R^{10}$, $R^{11}$, $Z^1$, $Z^2$, $R^{100}$ and X are the same as defined above]

According to the process for preparing the above-mentioned Compound (1-8), the present compound of the formula (1) wherein Q represents Q4 and $Z^3$ represents $R^{10}$, i.e., the compound of a formula (1-12) (hereinafter, described as Compound (1-12)), can be prepared by reacting Compound (1-11) (hereinafter, described as Compound (1-11)) with a halogenating agent.

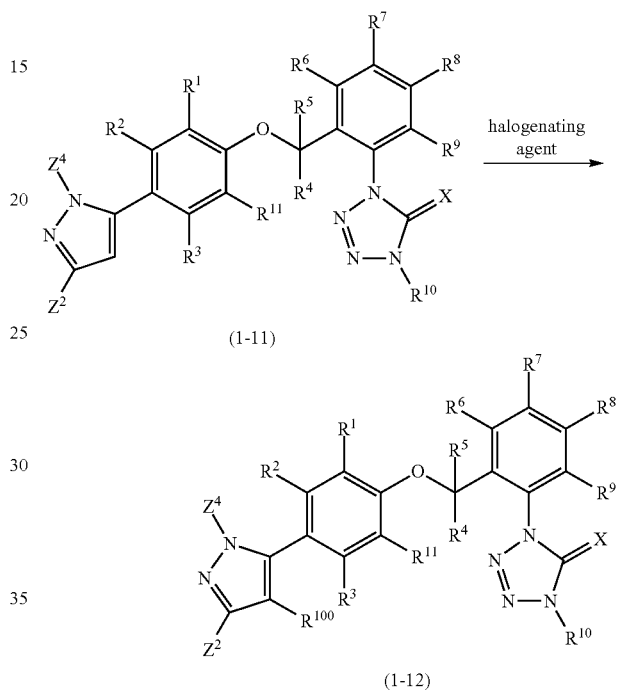

(1-11)

(1-12)

[wherein
$R^1$, $R^2$, $R^3$, $R^4$, $R^5$, $R^6$, $R^7$, $R^8$, $R^9$, $R^{10}$, $R^{11}$, $Z^2$, $Z^4$, $R^{100}$ and X are the same as defined above]

(Process K)

The present compound of the formula (1) wherein Q represents Q1 and $Y^2$ represents an aldehyde group, i.e., the compound of a formula (1-13) (hereinafter, described as Compound (1-13)), can be prepared by reacting Compound (1-7) (hereinafter, described as Compound (1-7)) with a formylating agent, which is prepared from N,N-dimethylformamide and phosphorus oxychloride, followed by reacting the resulting mixtures with water.

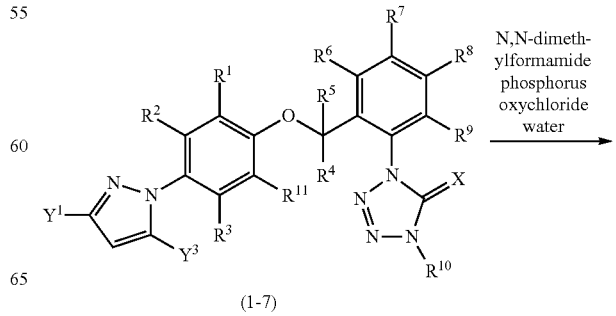

(1-7)

-continued

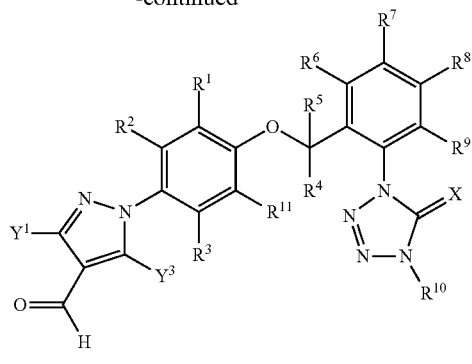

(1-13)

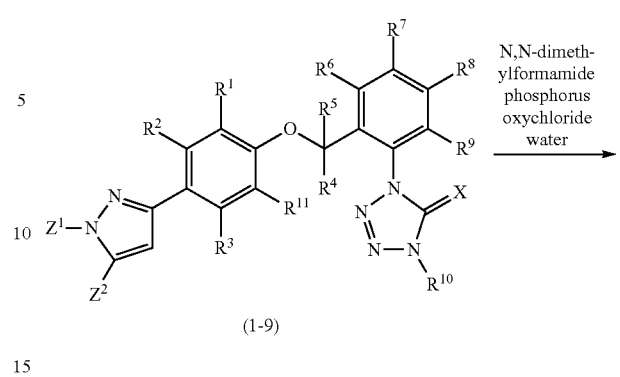

(1-9)

[wherein
R¹, R², R³, R⁴, R⁵, R⁶, R⁷, R⁸, R⁹, R¹⁰, R¹¹, Y¹, Y³ and X are the same as defined above]

This reaction is usually carried out in a solvent.

Examples of the solvent to be used in the reaction include hydrocarbons such as heptane, hexane, cyclohexane, pentane; ethers such as diethyl ether, tetrahydrofuran, 1,4-dioxane, ethyleneglycol dimethyl ether, methyl tert-butyl ether, diisopropyl ether; halogenated hydrocarbons such as carbon tetrachloride, chloroform, dichloromethane, 1,2-dichloroethane, tetrachloroethane and chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

In the reaction, the formylating agent is used as a mixture of 1 to 10 molar ratio(s) of N,N-dimethylformamide and 1 to 10 molar ratio(s) of phosphorus oxychloride, as opposed to 1 mole of Compound (1-7), and water is used within a range of 1 to 10 molar ratio(s) as opposed to 1 mole of Compound (1-7).

The reaction temperature is usually within a range of −20 to 150° C. The reaction period of the reaction is usually within a range of 0.1 to 24 hours.

When the reaction is completed, thereto is usually added 1 mole or more of water, and the reaction mixtures are extracted with organic solvent(s), and the resulting organic layers are worked up (for example, drying and concentration) to isolate the present compound of the formula (1-13). The isolated present compound may be further purified, for example, by chromatography and recrystallization.

According to the process for preparing the above-mentioned Compound (1-13), the present compound of the formula (1) wherein Q represents Q2 and Z³ represents an aldehyde group, i.e., the compound of a formula (1-14) (hereinafter, described as Compound (1-14)), can be prepared by reacting Compound (1-9) (hereinafter, described as Compound (1-9)) with formylating agent, which is prepared from N,N-dimethylformamide and phosphorus oxychloride, followed by reacting the resulting mixtures with water.

(1-14)

[wherein
R¹, R², R³, R⁴, R⁵, R⁶, R⁷, R⁸, R⁹, R¹⁰, R¹¹, Z¹, Z² and X are the same as defined above]

According to the process for preparing the above-mentioned Compound (1-13), the present compound of the formula (1) wherein Q represents Q4 and Z³ represents an aldehyde group, i.e., the compound of a formula (1-15) (hereinafter, described as Compound (1-15)), can be prepared by reacting Compound (1-11) (hereinafter, described as Compound (1-11)) with formylating agent, which is prepared from N,N-dimethylformamide and phosphorus oxychloride, followed by reacting the resulting mixtures with water.

(1-11)

-continued

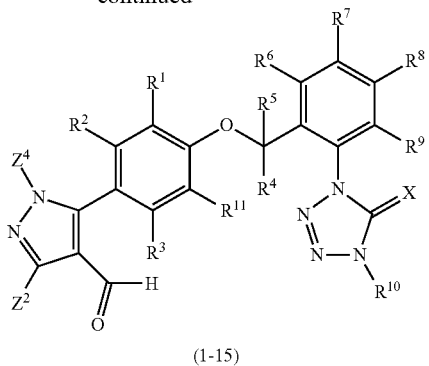

(1-15)

[wherein
$R^1$, $R^2$, $R^3$, $R^4$, $R^5$, $R^6$, $R^7$, $R^8$, $R^9$, $R^{10}$, $R^{11}$, $Z^2$, $Z^4$ and X are the same as defined above]
(Process L)

The present compound of the formula (1) wherein Q represents Q1 and $Y^2$ represents $R^{51}$, i.e., the compound of a formula (1-16) (hereinafter, described as Compound (1-16)), can be prepared by coupling Compound (1-8) (hereinafter, described as Compound (1-8)) with a compound of a formula (E-2) (hereinafter, described as Compound (E-2)) in the presence of a base and a catalyst.

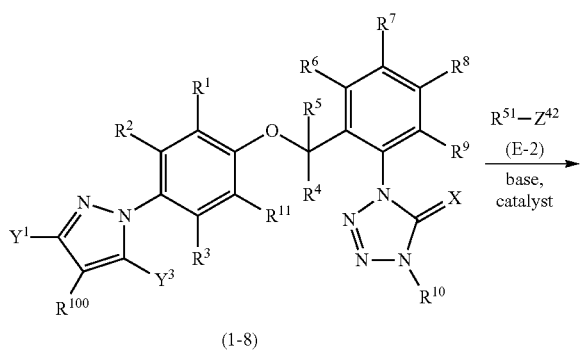

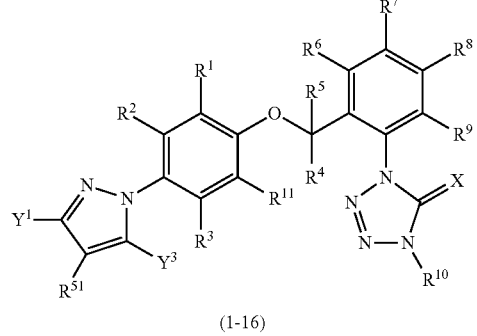

(1-16)

[wherein
$R^1$, $R^2$, $R^3$, $R^4$, $R^5$, $R^6$, $R^7$, $R^8$, $R^9$, $R^{10}$, $R^{11}$, $R^{51}$, $R^{100}$, $Y^1$, $Y^3$, X and $Z^{42}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Compound (E-2) to be used in the reaction may be usually used as a commercially available product, or may be prepared according to a method described in a review article of N. Miyaura and A. Suzuki, Chem. Rev. 1995, 95, 2457 and the others. Compound (E-2) to be used in the reaction can be also prepared, for example, by reacting an iodo compound ($R^{51}$—I) or a bromo compound ($R^{51}$—Br) with an alkyl lithium (such as butyl lithium), followed by reacting the resulting mixtures with borate esters to obtain boronate esters and further, as needed, hydrolyzing the obtained boronate esters. Further, according to a method described in a review article of Molander et al. Acc. Chem. Res. 2007, 40, 275 and the others, the above-mentioned boronate ester can be fluorinated with potassium bifluoride and the like to obtain the trifluoroborate salts ($BF_3^-K^+$).

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine ferrocenyl)palladium(II) dichloride, 1,3-bis(2,6-diisopropylphenyl)imidazole-2-ylidene (1,4-naphthoquinone) palladium dimer, aryl(chloro) (1,3-dimethyl-1,3-dihydro-2H-imidazole-2-ylidene)palladium or palladium(II) acetate/ dicyclohexyl(2',4',6'-triisopropylbiphenyl-2-yl)phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (E-2) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (1-8).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-16). The isolated present compound may be further purified, for example, by chromatography and recrystallization.

According to the process for preparing the above-mentioned Compound (1-16), the present compound of the formula (1) wherein Q represents Q2 and $Z^3$ represents $R^{51}$, i.e., the compound of a formula (1-17) (hereinafter, described as Compound (1-17)), can be prepared by reacting Compound (1-10) (hereinafter, described as Compound (1-10)) with a compound of a formula (E-2) (hereinafter, described as Compound (E-2)) in the presence of a base and a catalyst.

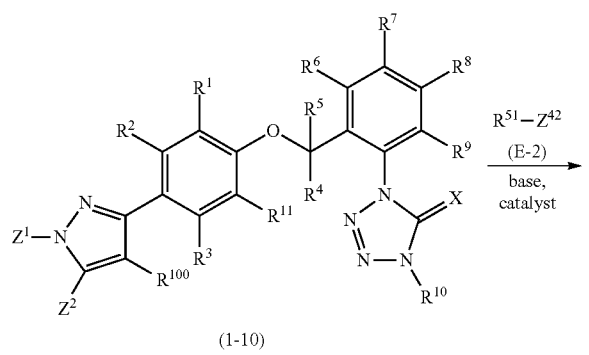

(1-10)

$R^{51}$—$Z^{42}$
(E-2)
base, catalyst
→

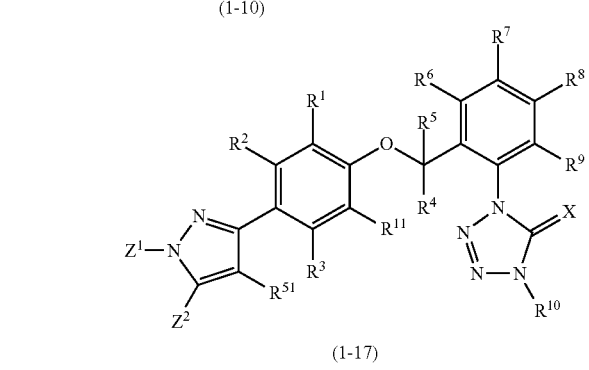

(1-17)

[wherein
$R^1$, $R^2$, $R^3$, $R^4$, $R^5$, $R^6$, $R^7$, $R^8$, $R^9$, $R^{10}$, $R^{11}$, $R^{51}$, $R^{100}$, X, $Z^1$, $Z^2$ and $Z^{42}$ are the same as defined above]

According to the process for preparing the above-mentioned Compound (1-16), the present compound of the formula (1) wherein Q represents Q4 and $Z^3$ represents $R^{51}$, i.e., the compound of a formula (1-18) (hereinafter, described as Compound (1-18)), can be prepared by reacting Compound (1-12) (hereinafter, described as Compound (1-12)) with a compound of a formula (E-2) (hereinafter, described as Compound (E-2)) in the presence of a base and a catalyst.

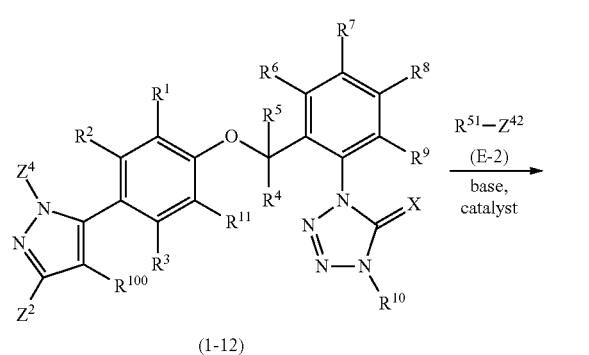

(1-12)

$R^{51}$—$Z^{42}$
(E-2)
base, catalyst
→

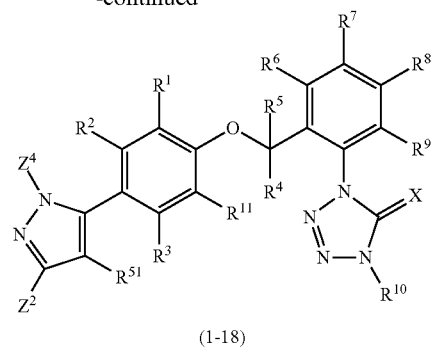

(1-18)

[wherein
$R^1$, $R^2$, $R^3$, $R^4$, $R^5$, $R^6$, $R^7$, $R^8$, $R^9$, $R^{10}$, $R^{11}$, $R^{51}$, $R^{100}$, X, $Z^2$, $Z^4$ and $Z^{42}$ are the same as defined above]

(Process M)

The present compound of the formula (1) wherein Q represents Q1 and $Y^2$ represents a difluoromethyl group, i.e., the compound of a formula (1-19) (hereinafter, described as Compound (1-19)), can be prepared by reacting Compound (1-13) with a fluorinating agent.

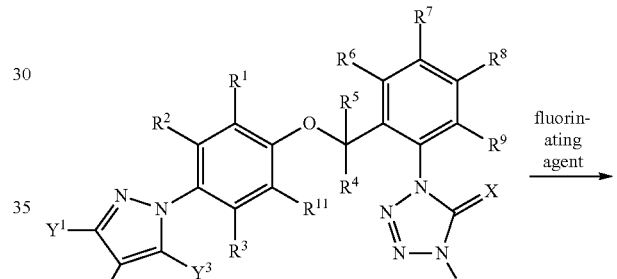

(1-13)

fluorinating agent
→

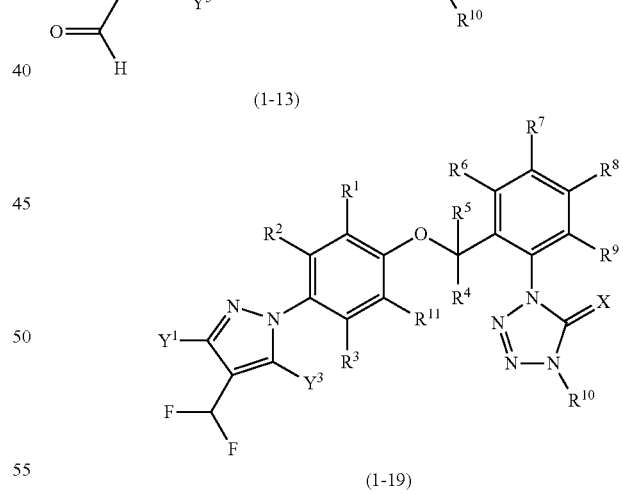

(1-19)

[wherein
$R^1$, $R^2$, $R^3$, $R^4$, $R^5$, $R^6$, $R^7$, $R^8$, $R^9$, $R^{10}$, $R^{11}$, $Y^1$, $Y^3$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

A fluorinating agent to be used in the reaction may be usually used as a commercially available product, and includes, for example, (diethylamino)-sulfur trifluoride, bis(methoxyethyl)-aminosulfur trifluoride, 4-tert-butyl-2,6-dimethylphenylsulfur trifluoride, (diethylamino)-difluorosulfonium tetrahydroborate, and difluoro(morphrino)sulfonium tetrahydroborate. In the reaction, a reaction accelerator may be also added, which includes, for example, (1.8-diazabicyclo[5.4.0]undec-7-ene and triethylamine trihydroborate.

In the reaction, the fluorinating agent is used usually within a range of 1 to 20 molar ratios, and the reaction accelerator is used usually within a range of 0 to 10 molar ratios, as opposed to 1 mole of Compound (1-13).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-19). The isolated present compound may be further purified, for example, by chromatography and recrystallization.

According to the process for preparing the above-mentioned Compound (1-19), the present compound of the formula (1) wherein Q represents Q2 and $Z^3$ represents a difluoromethyl group, i.e., the compound of a formula (1-20) (hereinafter, described as Compound (1-20)), can be prepared by reacting Compound (1-14) (hereinafter, described as Compound (1-14)) with a fluorinating agent.

[wherein $R^1$, $R^2$, $R^3$, $R^4$, $R^5$, $R^6$, $R^7$, $R^8$, $R^9$, $R^{10}$, $R^{11}$, $Z^1$, $Z^2$ and X are the same as defined above]

According to the process for preparing the above-mentioned Compound (1-19), the present compound of the formula (1) wherein Q represents Q4 and $Z^3$ represents a difluoromethyl group, i.e., the compound of a formula (1-21) (hereinafter, described as Compound (1-21)), can be prepared by reacting Compound (1-15) (hereinafter, described as Compound (1-15)) with a fluorinating agent.

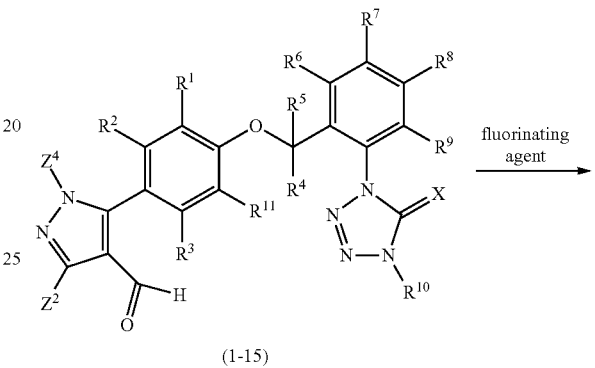

(1-15)

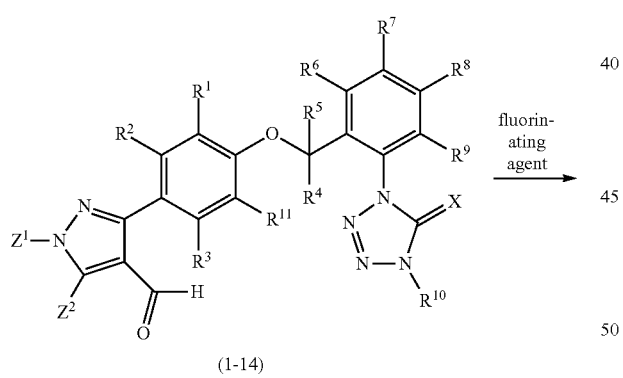

(1-14)

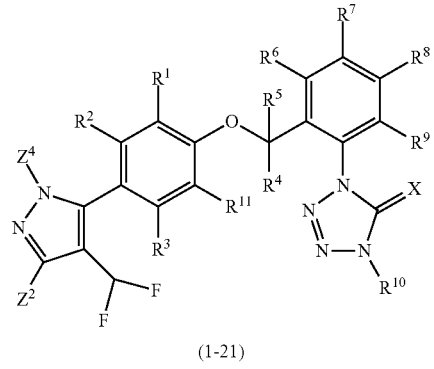

(1-21)

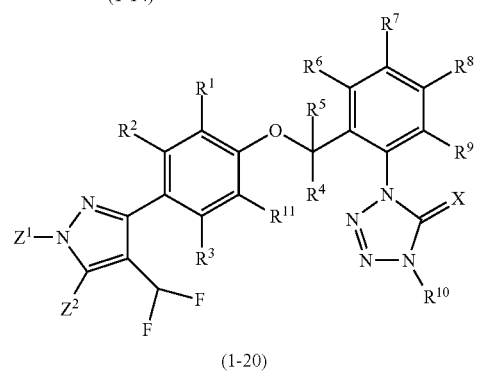

(1-20)

[wherein $R^1$, $R^2$, $R^3$, $R^4$, $R^5$, $R^6$, $R^7$, $R^8$, $R^9$, $R^{10}$, $R^{11}$, $Z^2$, $Z^4$ and X are the same as defined above]

(Process N)

The present compound of the formula (2) (hereinafter, described as Compound (2)) can be prepared by reacting a compound of a formula (A-1-2) (hereinafter, described as Compound (A-1-2)) with a compound of a formula (XV1-2) (hereinafter, described as Compound (XV1-2)) in the presence of a base.

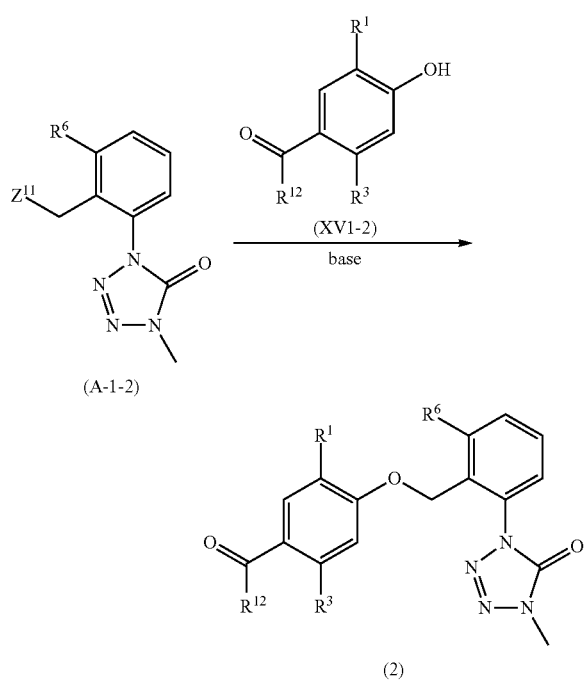

(A-1-2)

(2)

[wherein
R$^1$, R$^3$, R$^6$, R$^{12}$ and Z$^{11}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (XV1-2) is used usually within a range of 1 to 10 molar ratio(s), and the base is used usually within a range of 1 to 10 molar ratio(s), as opposed to 1 mole of Compound (A-1-2).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (A-1-2).

When the reaction is completed, the reaction mixtures are extracted with organic solvent(s), and the resulting organic layers are worked up (for example, drying and concentration) to isolate the present compound of the formula (2). Alternatively, the reaction mixtures are worked up (for example, drying and concentration) to isolate the present compound of the formula (2). These isolated present compound may be further purified, for example, by chromatography and recrystallization.

(Process O)

According to the process K, the present compound of the formula (1) wherein Q represents Q2, Z$^2$ represents a chlorine atom, and Z$^3$ represents an aldehyde group, i.e., the compound of a formula (1-14-1) (hereinafter, described as Compound (1-14-1)), can be prepared by reacting Compound (1-9) wherein Z$^2$ represents a hydroxy group, i.e., the compound of a formula (1-9-1) (hereinafter, described as Compound (1-9-1)) with a formylating agent, which is prepared from N,N-dimethylformamide and phosphorus oxychloride, followed by reacting the resulting mixtures with water.

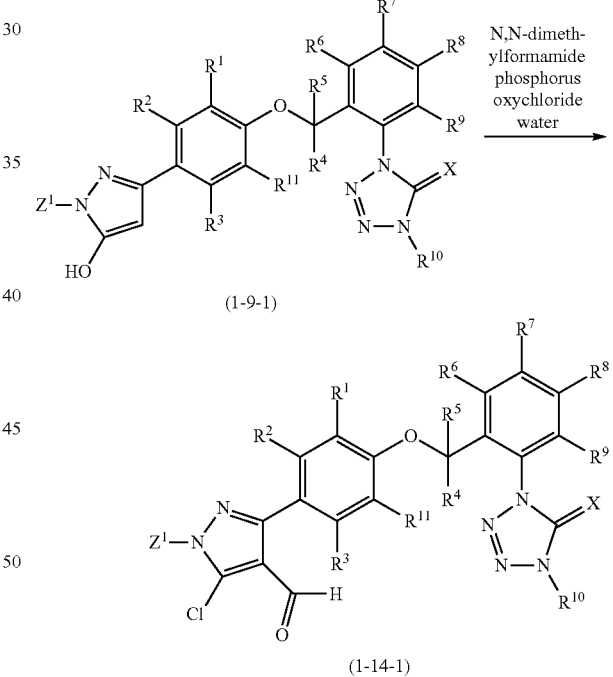

[wherein
R$^1$, R$^2$, R$^3$, R$^4$, R$^5$, R$^6$, R$^7$, R$^8$, R$^9$, R$^{10}$, R$^{11}$, Z$^1$ and X are the same as defined above]

(Process P)

The present compound of the formula (1) wherein Q represents Q2, Z$^2$ represents Z$^{2H}$ and Z$^3$ represents an aldehyde group, i.e., a compound of a formula (1-14-2) (hereinafter, described as Compound (1-14-2)) can be prepared by reacting a compound of a formula (1-14-1) with a compound of a formula (O-1) (hereinafter, described as Compound (O-1)) in the presence of a base.

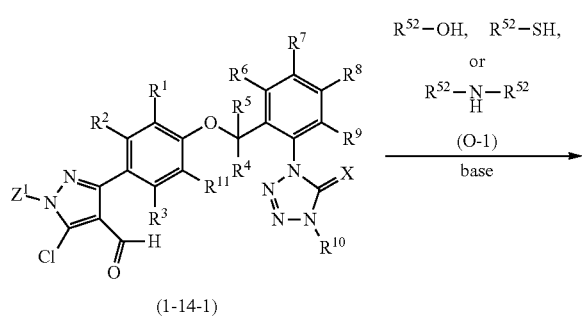

(1-14-1)

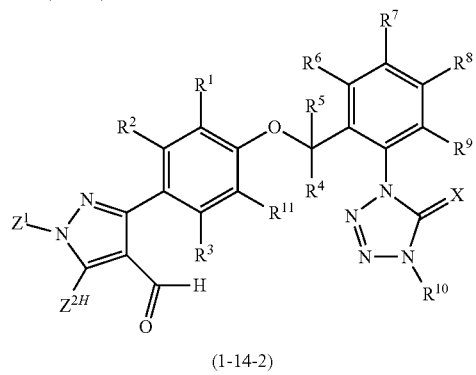

(1-14-2)

[wherein $R^1$, $R^2$, $R^3$, $R^4$, $R^5$, $R^6$, $R^7$, $R^8$, $R^9$, $R^{10}$, $R^{11}$, $Z^1$ and X are the same as defined above, $R^{52}$ represents an C1-C6 alkyl group, a C1-C6 haloalkyl group, an C2-C6 alkenyl group, a C2-C6 haloalkenyl group, an C2-C6 alkynyl group and a C2-C6 haloalkynyl group, and $Z^{2H}$ represents $OR^{52}$, $SR^{52}$ or $N(R^{52})_2$]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (O-1) is used usually within a range of 1 to 10 molar ratio(s), and the base is used usually within a range of 1 to 10 molar ratio(s), as opposed to 1 mole of Compound (1-14-1).

The reaction temperature is usually within a range of −20 to 150° C. The reaction period of the reaction is usually within a range of 0.1 to 24 hours.

In the reaction, metal salts of Compound (O-1) can be also used, which is previously prepared by reacting Compound (O-1) with alkali metal carbonates, alkali metal bicarbonates, alkali metal hydroxides, alkali metal halides, alkali metal hydrides or alkali metal alkoxides.

In the reaction, the metal salts of Compound (O-1) is used usually within a range of 1 to 10 molar ratio(s) as opposed to 1 mole of Compound (1-14-1).

When the reaction is completed, the reaction mixtures are extracted with organic solvent(s), and the resulting organic layers are worked up (for example, drying and concentration) to isolate the present compound of the formula (1-14-2). Alternatively, the reaction mixtures are worked up (for example, drying and concentration) to isolate the present compound of the formula (1-14-2). These isolated present compound may be further purified, for example, by chromatography and recrystallization.

(Process Q)

The present compound of the formula (1) wherein Q represents Q2, $Z^2$ represents $Z^{2H}$ and $Z^3$ represents a methyl group, i.e., a compound of a formula (1-14-3) (hereinafter, described as Compound (1-14-3)) can be prepared by reacting a compound of a formula (1-14-2) with a reducing agent in the presence of an acid.

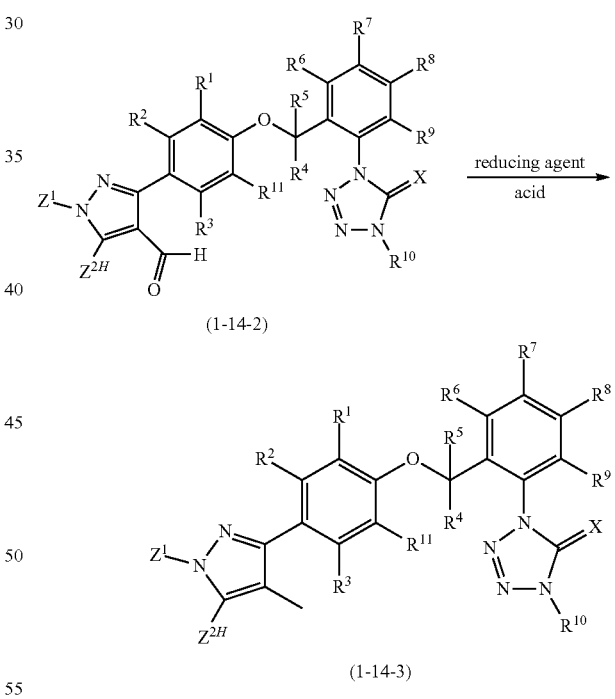

[wherein
$R^1$, $R^2$, $R^3$, $R^4$, $R^5$, $R^6$, $R^7$, $R^8$, $R^9$, $R^{10}$, $R^{11}$, $Z^1$, $Z^{2H}$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the reducing agent to be used in the reaction include metal boronate compounds such as lithium borohydride, sodium borohydride, potassium borohydride; and trialkylsilane compounds such as triethylsilane.

Examples of the acids to be used in the reaction include boron trifluoride and trifluoroacetic acid.

In the reaction, the reducing agent is used usually within a range of 1 to 10 molar ratio(s), and the acid is used usually within a range of 1 to 10 molar ratio(s), as opposed to 1 mole of Compound (1-14-2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-14-3). Alternatively, the reaction mixtures are worked up (for example, drying and concentration) to isolate the present compound of the formula (1-14-3). These isolated present compound may be further purified, for example, by chromatography and recrystallization.

(Process R)

The present compound of the formula (1) wherein Q represents Q2, $Z^1$ represents a hydrogen atom and $Z^2$ represents an C2-C6 alkoxycarbonyl group, i.e., a compound of a formula (1-4-R) (hereinafter, described as Compound (1-4-R)), can be prepared by reacting a compound of a formula (G-1-1) (hereinafter, described as Compound (G-1-1)) with hydrazines.

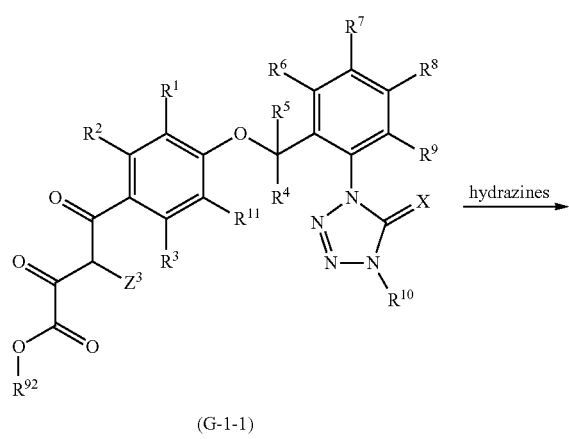

(G-1-1)

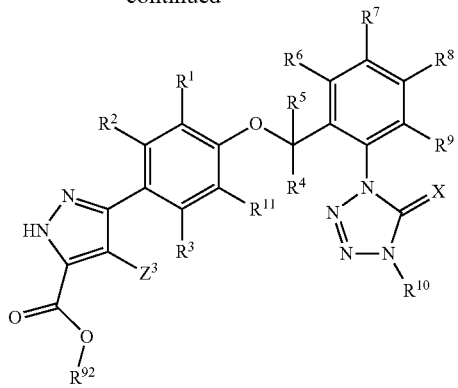

(1-4-R)

[wherein $R^1$, $R^2$, $R^3$, $R^4$, $R^5$, $R^6$, $R^7$, $R^8$, $R^9$, $R^{10}$, $R^{11}$, X and $Z^3$ are the same as defined above, and $R^{92}$ represents an C1-C5 alkyl group]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; water; and mixed solvents thereof.

Examples of the hydrazines to be used in the reaction include hydrazine monohydrate, hydrazine hydrochloride, hydroazine sulfate, anhydrous hydrazine and the others.

In the reaction, hydrazines is used usually within a range of 1 to 100 molar ratio(s) as opposed to 1 mole of Compound (G-1-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-4-R). The isolated present compound may be further purified, for example, by chromatography and recrystallization.

(Process S)

The present compound of the formula (1) wherein Q represents Q2 and $Z^2$ represents an C2-C6 alkoxycarbonyl group, i.e., a compound of a formula (1-5-S) (hereinafter, described as Compound (1-5-S)) can be prepared by reacting Compound (1-4-R) with Compound (H-1) optionally in the presence of a base.

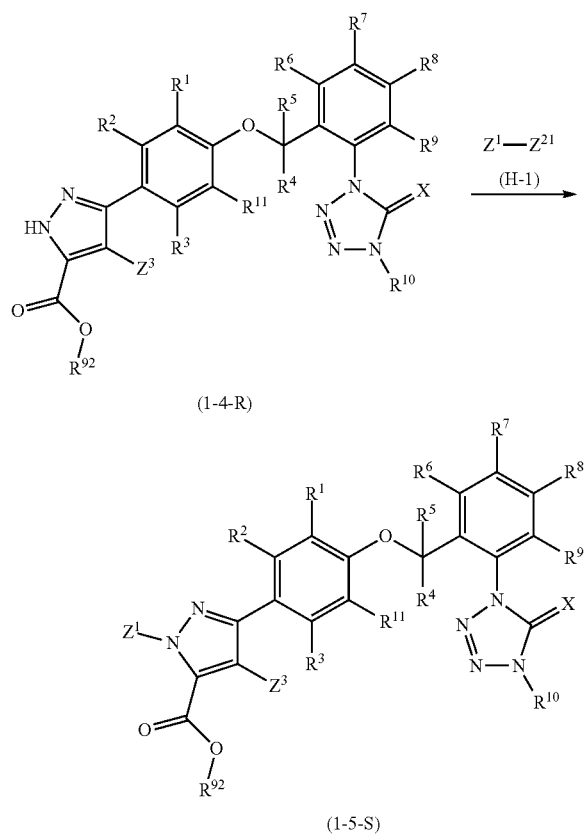

(1-4-R)

(1-5-S)

[wherein $R^1$, $R^2$, $R^3$, $R^4$, $R^5$, $R^6$, $R^7$, $R^8$, $R^9$, $R^{10}$, $R^{11}$, $R^{92}$, X, $Z^1$, $Z^3$ and $Z^{21}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (H-1) to be used in the reaction can be usually used as a commercially available product. Specific examples include alkyl halides such as chlorodifluoromethane, methyl bromide, ethyl bromide, propyl bromide, butyl bromide, propyl bromide, hexyl bromide, methyl iodide, ethyl iodide, propyl iodide, isopropyl iodide, isobutyl iodide, isoamyl iodide, 2-propinyl iodide, 2-butynyl iodide, allyl bromide, cyclopropyl bromide, 2-propynyl bromide, 2-butynyl bromide, cyclopropylmethyl bromide, 1,1-difluoro-2-iodoethane and 1,1,1-trifluoro-2-iodoethane; alkyl or aryl sulfonates such as dimethyl sulfates, methyl p-toluenesulfonate, ethyl p-toluenesulfonate, propyl p-toluenesulfonate, methyl methanesulfonate, ethyl methanesulfonate, propyl methanesulfonate; carboxylic halides such as acetyl chloride; and sulfonic halides such as methanesulfonyl chloride, ethanesulfonyl chloride, isopropynyl sulfonyl chloride, cyclopropynyl sulfonyl chloride and N,N-dimethylsulfonyl chloride.

In the reaction, a base may be used, which includes, for example, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (H-1) is used usually within a range of 1 to 10 molar ratio(s), and the base is used usually within a range of 1 to 10 molar ratios, as opposed to 1 mole of Compound (1-4-R).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-5-S). The isolated present compound may be further purified, for example, by chromatography and recrystallization.

(Process T)

The present compound of the formula (1) wherein Q represents Q4 and $Z^2$ represents an C2-C6 alkoxycarbonyl group, i.e., a compound of a formula (1-6-T) (hereinafter, described as Compound (1-6-T)) can be prepared by reacting a compound of a formula (1-4-T) (hereinafter, described as Compound (1-4-T)) with Compound (I-1) optionally in the presence of a base.

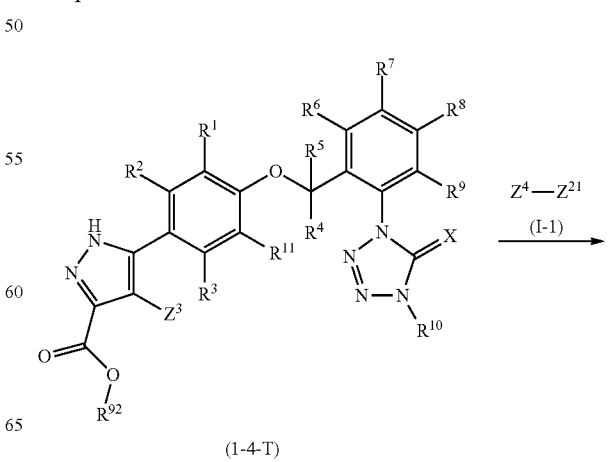

(1-4-T)

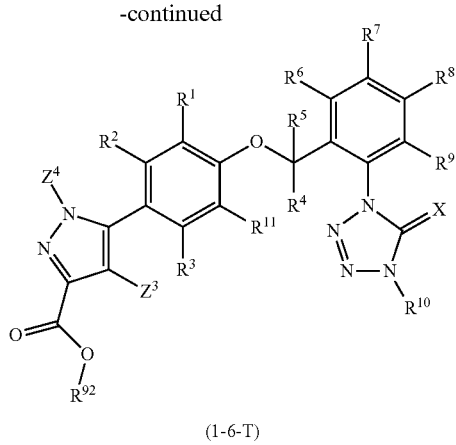

(1-6-T)

[wherein
R$^1$, R$^2$, R$^3$, R$^4$, R$^5$, R$^6$, R$^7$, R$^8$, R$^9$, R$^{10}$, R$^{11}$, R$^{92}$, X, Z$^3$, Z$^4$ and Z$^{21}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (I-1) to be used in the reaction can be usually used as a commercially available product. Specific examples include alkyl halides such as chlorodifluoromethane, methyl bromide, ethyl bromide, propyl bromide, butyl bromide, propyl bromide, hexyl bromide, methyl iodide, ethyl iodide, propyl iodide, isopropyl iodide, isobutyl iodide, isoamyl iodide, allyl bromide, cyclopropyl bromide and 1,1-difluoro-2-iodoethane; alkyl or aryl sulfonates such as dimethyl sulfates, methyl p-toluenesulfonate, ethyl p-toluenesulfonate, propyl p-toluenesulfonate, methyl methanesulfonate, ethyl methanesulfonate, propyl methanesulfonate; carboxylic halides such as acetyl chloride; and sulfonic halides such as methanesulfonyl chloride, ethanesulfonyl chloride, isopropynyl sulfonyl chloride, cyclopropynyl sulfonyl chloride and N,N-dimethylsulfonyl chloride.

In the reaction, a base may be used, which includes, for example, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (I-1) is used usually within a range of 1 to 10 molar ratio(s), and the base is used usually within a range of 1 to 10 molar ratios, as opposed to 1 mole of Compound (1-4-T).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-6-T). The isolated present compound may be further purified, for example, by chromatography and recrystallization.

(Process U)

The present compound of the formula (1) wherein Q represents Q2 and Z$^2$ represents an aminocarbonyl group, i.e., a compound of a formula (1-5-U) (hereinafter, described as Compound (1-5-U)) can be prepared by reacting Compound (1-5-S) with an amidating agent.

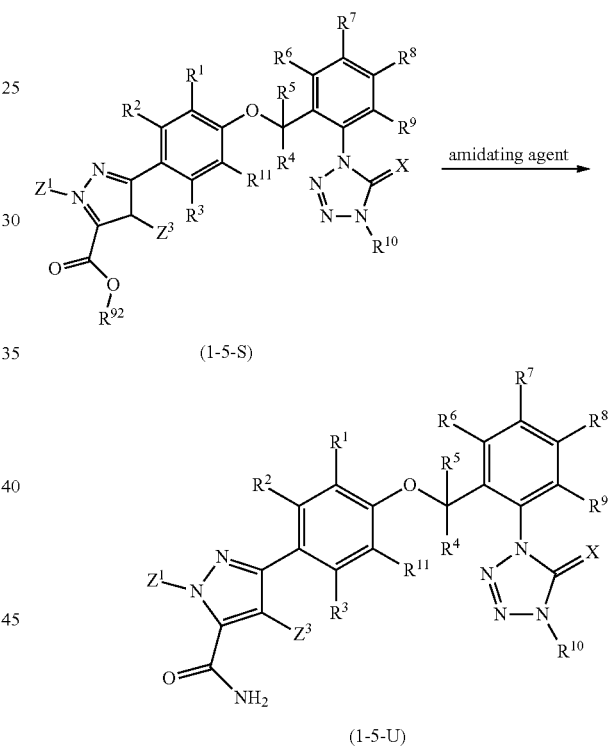

[wherein
R$^1$, R$^2$, R$^3$, R$^4$, R$^5$, R$^6$, R$^7$, R$^8$, R$^9$, R$^{10}$, R$^{11}$, R$^{92}$, X, Z$^1$ and Z$^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; water; and mixed solvents thereof.

Examples of the amidating agent to be used in the reaction include aqueous ammonia, ammonia hydrochloride salt, ammonia hydrosulfate salt and ammonia gas. Also the amidating agent can be used as solvent.

In the reaction, the amidating agent is used usually within a range of 1 to a large amount of molar ratio(s) as opposed to 1 mole of Compound (1-5-S).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate the present compound of the formula (1-5-U). Also, when any precipitates are formed, the precipitates are filtered off to isolate the present compound of the formula (1-5-U). These isolated present compounds may be further purified, for example, by chromatography and recrystallization.

(Process V)

The present compound of the formula (1) wherein Q represents Q2 and $Z^2$ represents a cyano group, i.e., a compound of a formula (1-5-V) (hereinafter, described as Compound (1-5-V)) can be prepared by reacting Compound (1-5-U) with a cyanating agent optionally in the presence of a base.

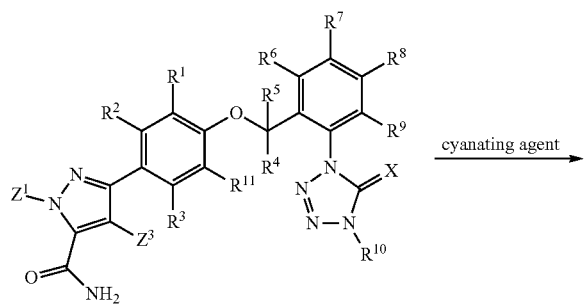

(1-5-U)

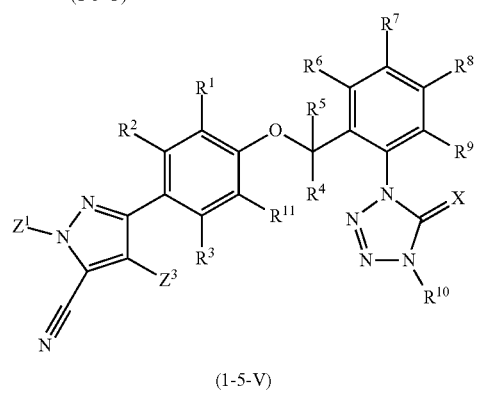

(1-5-V)

[wherein
$R^1$, $R^2$, $R^3$, $R^4$, $R^5$, $R^6$, $R^7$, $R^8$, $R^9$, $R^{10}$, $R^{11}$, X, $Z^1$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; and mixed solvents thereof.

Examples of the cyanating agent to be used in the reaction include phosphorous oxychloride, phosphorous pentachloride and phosphorous oxybromide.

In the reaction, a base may be used, which include, for example, organic bases such as triethylamine, pyridine, N-methylmorpholine, N-methylpiperidine, 4-dimethylaminopyridine, diisopropylethylamine, lutidine, collidine, diazabicycloundecene and diazabicyclononene. The base may be used also as a solvent.

In the reaction, the cyanating agent is used usually within a range of 1 to 20 molar ratio(s), and the base is used usually within a range of 1 to a large amount of molar ratio(s), as opposed to 1 mole of Compound (1-5-U).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate the present compound of the formula (1-5-V). Also, when any precipitates are formed, the precipitates are filtered off to isolate the present compound of the formula (1-5-V). These isolated present compounds may be further purified, for example, by chromatography and recrystallization.

(Process W)

Compound (1-5-U) can be prepared by reacting a compound of a formula (1-5-W) (hereinafter, described as Compound (1-5-W)) with an amidating agent.

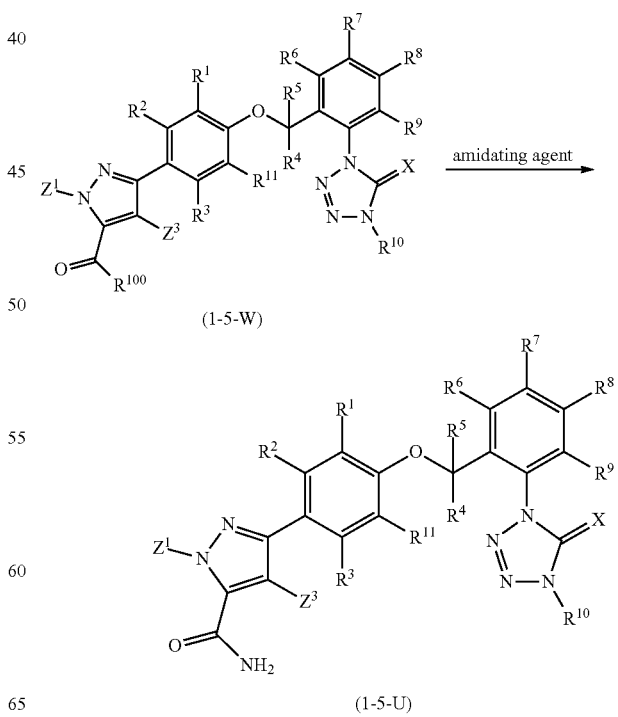

(1-5-W)

(1-5-U)

[wherein
R$^1$, R$^2$, R$^3$, R$^4$, R$^5$, R$^6$, R$^7$, R$^8$, R$^9$, R$^{10}$, R$^{11}$, R$^{100}$, X, Z$^1$ and Z$^3$ are the same as defined above]

The reaction can be carried out according to Process U.

A process for preparing a compound represented by a formula (3) is described below in detail.

The compound represented by formula (3) can be prepared, for example, according to the below-mentioned synthesis.

(Synthesis AA)

A compound represented by the formula (3) (hereinafter, described as Compound (3)) can be prepared by reacting a compound represented by the formula (4-3D) (hereinafter, described as Compound (4-3D)) or a compound represented by the formula (4-7) (hereinafter, described as Compound (4-7)) with an azidation agent.

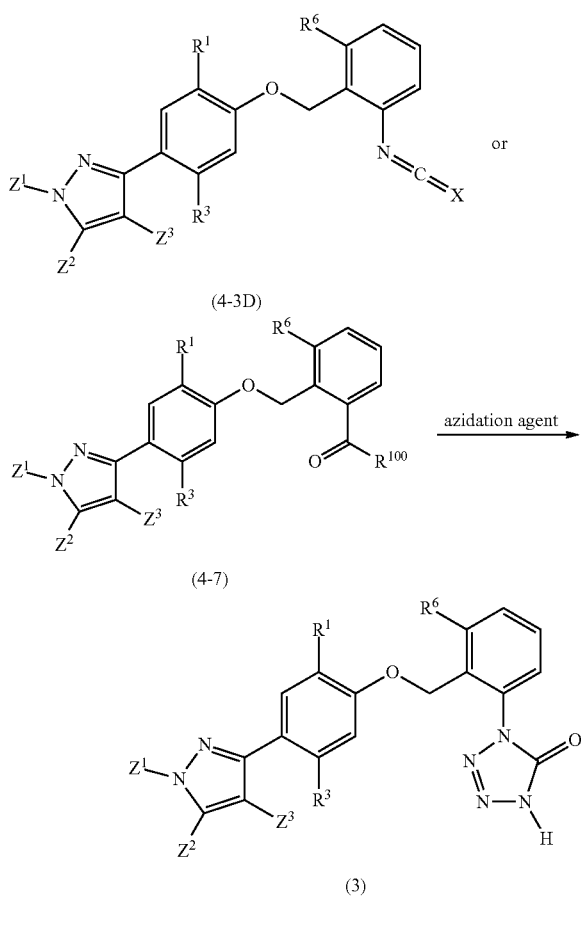

[wherein
R$^1$, R$^3$, R$^6$, R$^{100}$, X, Z$^2$ and Z$^3$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the azidation agent to be used in the reaction include inorganic azides such as sodium azide, barium azide and lithium azide; and organic azides such as trimethylsilyl azide and diphenylphosphoryl azide.

In the reaction, the azidation agent is used usually within a range of 1 to 10 molar ratio(s) as opposed to 1 mole of Compound (4-3D) or Compound (4-7).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.05 to 5 molar ratio(s) as opposed to 1 mole of Compound (4-3D) or Compound (4-7).

When the reaction is completed, the reaction mixtures are extracted with organic solvent(s), and the resulting organic layers are worked up (for example, drying and concentration) to isolate Compound (3). The isolated Compound (3) may be further purified, for example, by chromatography and recrystallization.

A process for preparing a compound represented by a formula (4) is described below in detail.

The compound represented by formula (4) can be prepared, for example, according to the below-mentioned synthesis.

(Synthesis A)

A compound represented by the formula (4) wherein L$^1$ represents a nitro group, i.e., a compound represented by the formula (4-1) (hereinafter, described as Compound (4-1)) can be prepared by reacting a compound represented by the formula (PA-1) (hereinafter, described as Compound (PA-1)) with a compound represented by the formula (PA-2) (hereinafter, described as Compound (PA-2)) in the presence of a base.

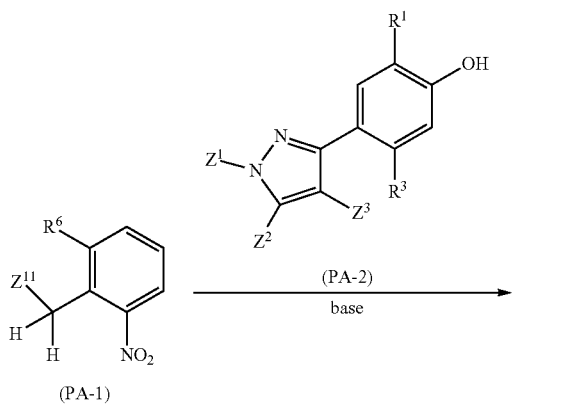

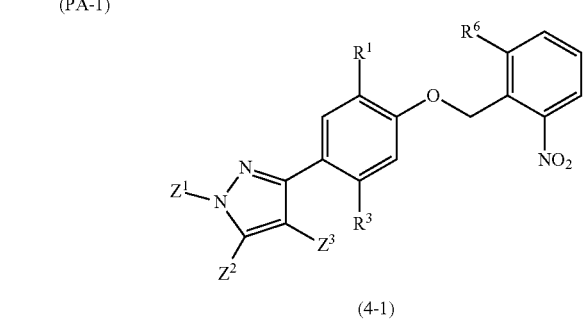

[wherein

R¹, R³, R⁶, Z¹, Z², Z³ and Z¹¹ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (PA-2) is used usually within a range of 1 to 10 molar ratio(s), and the base is used usually within a range of 0.5 to 5 molar ratios, as opposed to 1 mole of Compound (PA-1).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (PA-1).

When the reaction is completed, the reaction mixtures are extracted with organic solvent(s), and the resulting organic layers are worked up (for example, drying and concentration) to isolate Compound (4-1). The isolated Compound (4-1) may be further purified, for example, by chromatography and recrystallization.

(Synthesis B)

A compound represented by the formula (4) wherein L¹ represents an amino group, i.e., a compound represented by the formula (4-2) (hereinafter, described as Compound (4-2)) can be prepared by reacting the above-mentioned Compound (4-1) with a hydrogen gas in the presence of a catalyst.

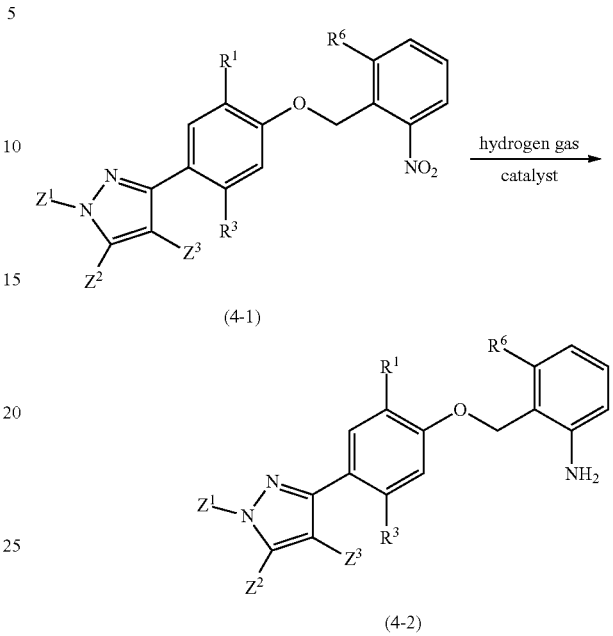

[wherein

R¹, R³, R⁶, Z¹, Z² and Z³ are the same as defined above]

This reaction is usually carried out in a solvent.

Examples of the solvent to be used in the reaction include alcohols such as methanol, ethanol, propanol, butanol; esters such as ethyl acetate, butyl acetate; halogenated hydrocarbons such as carbon tetrachloride, chloroform, dichloromethane, 1,2-dichloroethane, tetrachloroethane, chlorobenzene; ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; water; and mixed solvents thereof.

Examples of the catalyst to be used in the reaction include palladium on carbon (Pd/C), platinum on carbon (Pt/C), osmium on carbon (Os/C), ruthenium on carbon (Ru/C), rhodium on carbon (Rh/C) and Raney nickel.

The reaction temperature is usually within a range of −20 to 150° C. The reaction period of the reaction is usually within a range of 0.1 to 24 hours.

In the reaction, the catalyst is used usually within a range of 0.01 to 1 molar ratio(s), and the hydrogen gas is used usually within a range of 1 to a large amount of molar ratio(s), as opposed to 1 mole of Compound (4-1).

When the reaction is completed, the reaction mixtures are extracted with organic solvent(s), and the resulting organic layers are worked up (for example, drying and concentration) to isolate Compound (4-2). The isolated Compound (4-2) may be further purified, for example, by chromatography and recrystallization.

(Synthesis C)

Compound (4-2) can be prepared by reacting the above-mentioned Compound (4-1) with a reducing agent in the presence of an acid.

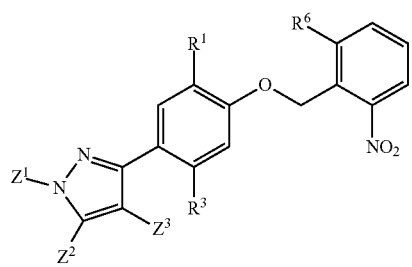

(4-1)

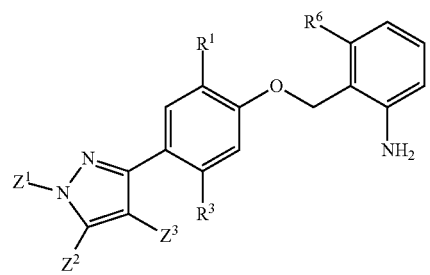

(4-2)

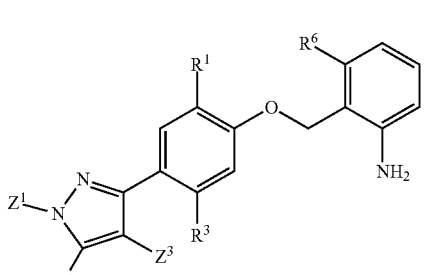

(4-2)

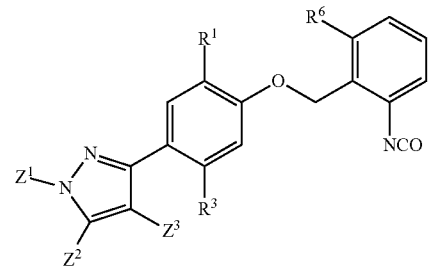

(4-3)

[wherein

R$^1$, R$^3$, R$^6$, Z$^1$, Z$^2$ and Z$^3$ are the same as defined above]

This reaction is usually carried out in a solvent.

Examples of the solvent to be used in the reaction include aliphatic carboxylic acids such as acetic acid; alcohols such as methanol, ethanol; water and mixed solvents thereof.

Examples of the reducing agent to be used in the reaction include iron, tin and zinc.

Examples of the acid to be used in the reaction include hydrochloric acid, sulfuric acid, acetic acid and aqueous ammonium chloride solution.

In the reaction, the reducing agent is used usually within a range of 1 to 30 molar ratio(s), and the acid is used usually within a range of 1 to 30 molar ratio(s), as opposed to 1 mole of Compound (4-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (4-2). The isolated Compound (4-2) may be further purified, for example, by distillation, chromatography and recrystallization.

(Synthesis D)

Compound (4) wherein L$^1$ represents an isocyanato group, i.e., a compound of a formula (4-3) (hereinafter, described as Compound (4-3)), can be prepared by reacting Compound (4-2) with phosgenes.

[wherein

R$^1$, R$^3$, R$^6$, Z$^1$, Z$^2$ and Z$^3$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene and triphosgene.

In the reaction, phosgenes are used usually within a range of 1 to 10 molar ratio(s) as opposed to 1 mole of Compound (4-2).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratio(s) as opposed to 1 mole of Compound (4-2).

When the reaction is completed, the reaction mixtures are extracted with organic solvent(s), and the resulting organic layers are worked up (for example, drying and concentration) to isolate Compound (4-3). The isolated Compound (4-3) may be further purified, for example, by distillation, chromatography and recrystallization.

(Synthesis E)

Compound (4-2) wherein $L^1$ is NSO, i.e., a compound of a formula (4-4) (hereinafter, described as Compound (4-4)) can be prepared by reacting Compound (4-2) with a thionyl chloride.

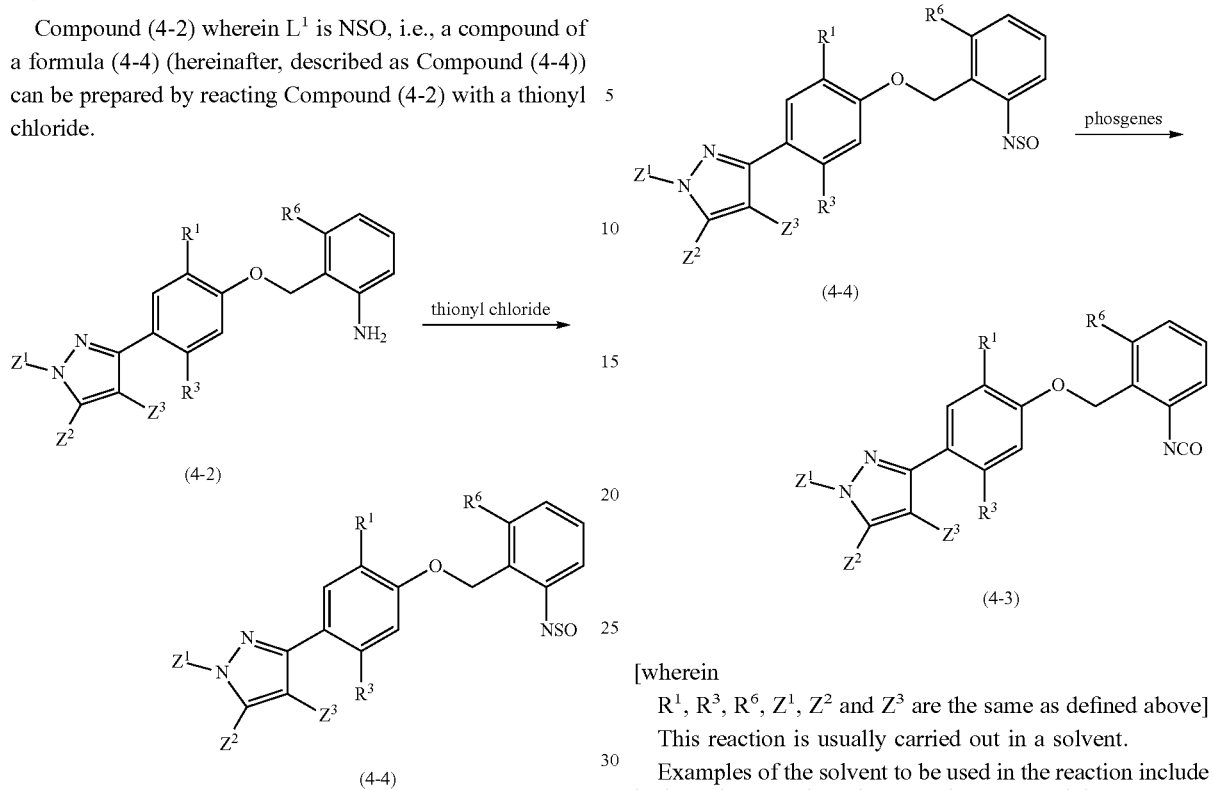

[wherein $R^1$, $R^3$, $R^6$, $Z^1$, $Z^2$ and $Z^3$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

In the reaction, thionyl chloride is used usually within a range of 1 to 10 molar ratio(s) as opposed to 1 mole of Compound (4-2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (4-4). The isolated Compound (4-4) may be further purified, for example, by distillation, chromatography and recrystallization.

(Synthesis F)

Compound (4-3) can be prepared by reacting Compound (4-4) with phosgenes.

[wherein $R^1$, $R^3$, $R^6$, $Z^1$, $Z^2$ and $Z^3$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene and triphosgene.

In the reaction, phosgenes are used usually within a range of 1 to 10 molar ratio(s) as opposed to 1 mole of Compound (4-4).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratio(s) as opposed to 1 mole of Compound (4-4).

When the reaction is completed, the reaction mixtures are extracted with organic solvent(s), and the resulting organic layers are worked up (for example, drying and concentration) to isolate Compound (4-3). The isolated Compound (4-3) may be further purified, for example, by distillation, chromatography and recrystallization.

(Synthesis G)

Compound (4) wherein $L^1$ represents an C2-C6 alkoxycarbonyl group, i.e., a compound of a formula (4-5) (hereinafter, described as Compound (4-5)) can be prepared by reacting Compound (PA-2) with Compound (PG-1) (hereinafter, described as Compound (PG-1)) in the presence of a base.

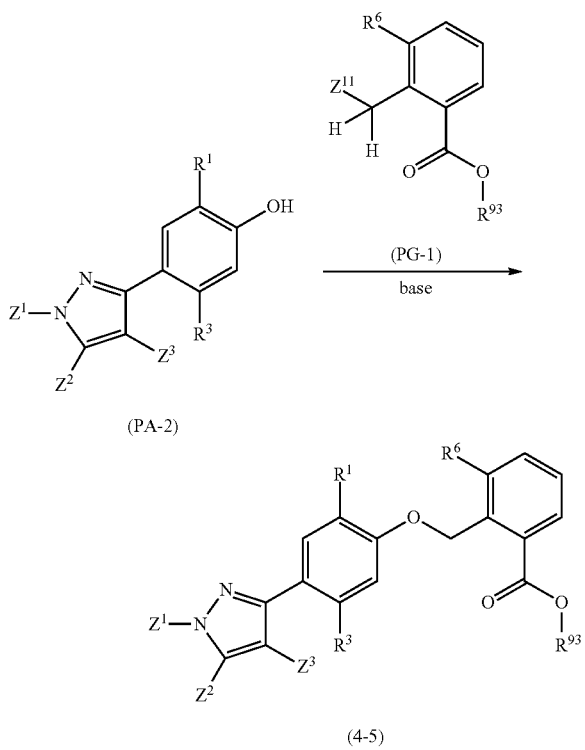

[wherein
$R^1$, $R^3$, $R^6$, $Z^1$, $Z^2$, $Z^3$ and $Z^{11}$ are the same as defined above, and $R^{93}$ represents an C1-C5 alkyl group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicyclounedecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (PG-1) is used usually within a range of 1 to 10 molar ratio(s), and the base is used usually within a range of 0.5 to 5 molar ratios, as opposed to 1 mole of Compound (PA-2).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (PA-2).

When the reaction is completed, the reaction mixtures are extracted with organic solvent(s), and the resulting organic layers are worked up (for example, drying and concentration) to isolate Compound (4-5). The isolated Compound (4-5) may be further purified, for example, by chromatography and recrystallization.

(Synthesis H)

Compound (4) wherein $L^1$ is a carboxyl group, i.e., a compound of a formula (4-6) (hereinafter, described as Compound (4-6)), can be prepared by reacting Compound (4-5) with a hydrolytic agent.

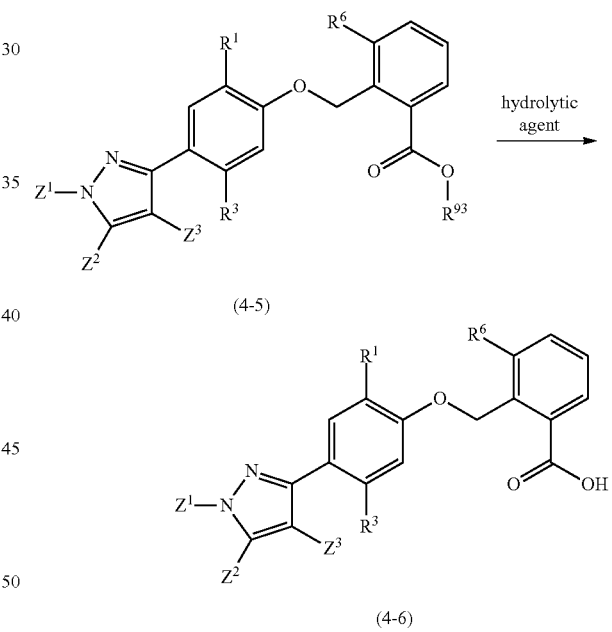

[wherein
$R^1$, $R^3$, $R^6$, $R^{93}$, $Z^1$, $Z^2$ and $Z^3$ are the same as defined above]

This reaction is usually carried out in a solvent.

Examples of the solvent to be used in the reaction include water; alcohols such as methanol, ethanol, propanol, butanol; hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; ketones such as acetone, methyl ethyl ketone, methyl isobutyl ketone; and mixed solvents thereof.

Examples of the hydrolytic agent to be used in the reaction include bases such as aqueous potassium hydroxide solution and aqueous sodium hydroxide solution; and acids such as hydrochloric acid and sulfuric acid.

In the reaction, the hydrolytic agent is used usually within a range of 0.5 to 20 molar ratio(s) as opposed to 1 mole of Compound (4-5).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (4-6). The isolated Compound (4-6) may be further purified, for example, by distillation, chromatography and recrystallization.

(Synthesis I)

Compound (4) wherein $L^1$ is a halocarbonyl group, i.e., a compound of a formula (4-7) (hereinafter, described as Compound (4-7)), can be prepared by reacting Compound (4-6) with a halogenating agent.

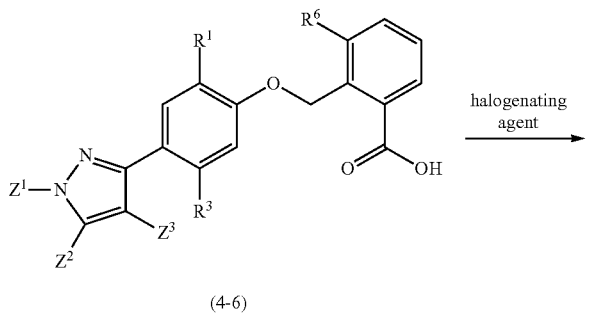

(4-6)

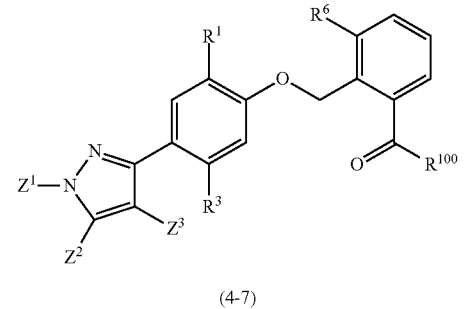

(4-7)

[wherein
$R^1$, $R^3$, $R^6$, $R^{100}$, $Z^1$, $Z^2$ and $Z^3$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include phosphorous oxychloride, phosphorous trichloride, phosphorous pentachloride, thionyl chloride, phosphorous oxybromide, phosphorous tribromide, phosphorous pentabromide, phosphorus triiodide, oxalyl dichloride, oxalyl dibromide, triphosgene, diphosgene, phosgene and sulfuryl chloride.

In the reaction, the halogenating agent is used usually within a range of 1 to 10 molar ratio(s) as opposed to 1 mole of Compound (4-6).

The reaction temperature is usually within a range of −20 to 150° C. The reaction period of the reaction is usually within a range of 0.1 to 24 hours.

A catalyst may be added to the reaction, which includes, for example, N,N-dimethylformide, triethylamine and diisopropylethylamine. The catalyst is used usually within a range of 0.001 to 1 molar ratio(s) as opposed to 1 mole of Compound (4-6).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratio(s) as opposed to 1 mole of Compound (4-6).

When the reaction is completed, the reaction mixtures are extracted with organic solvent(s), and the resulting organic layers are worked up (for example, drying and concentration) to isolate Compound (4-7). The isolated Compound (4-7) may be further purified, for example, by chromatography and recrystallization.

(Synthesis J)

Compound (4) wherein $L^1$ is a $C(O)N_3$ group, i.e., a compound of a formula (4-8) (hereinafter, described as Compound (4-8)), can be prepared by reacting Compound (4-7) with a sodium azide.

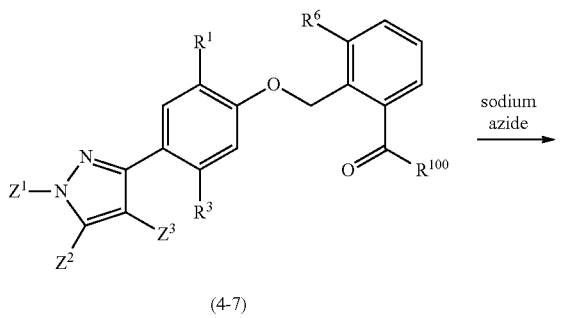

(4-7)

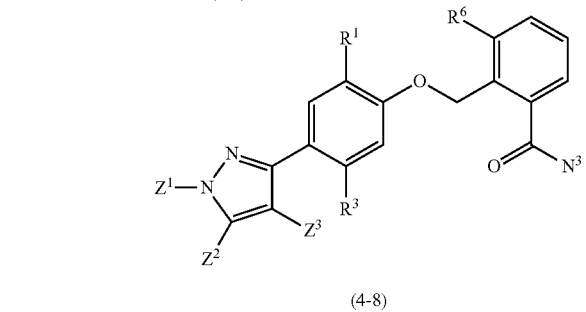

(4-8)

[wherein
$R^1$, $R^3$, $R^6$, $R^{100}$, $Z^1$, $Z^2$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

In the reaction, the sodium azide is used usually within a range of 1 to 10 molar ratio(s) as opposed to 1 mole of Compound (4-7).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (4-8). The isolated Compound (4-8) may be further purified, for example, by chromatography and recrystallization.

(Synthesis K)

Compound (4-3) can be prepared by heating Compound (4-8).

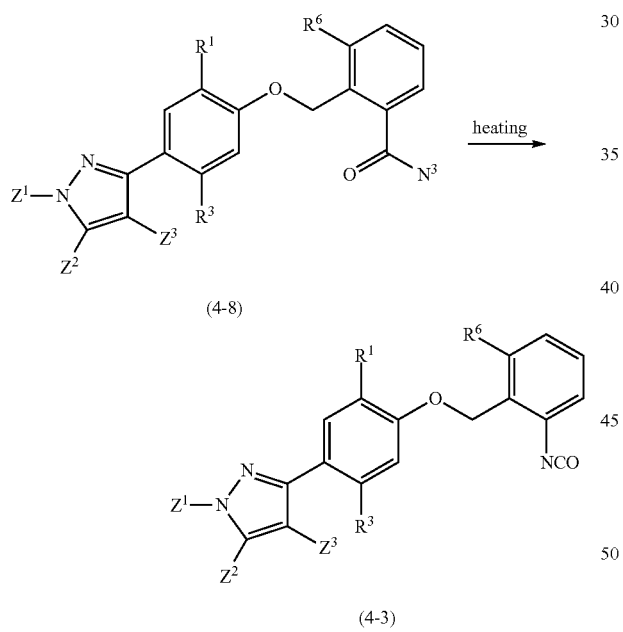

[wherein
$R^1$, $R^3$, $R^6$, $Z^1$, $Z^2$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

The reaction temperature is usually within a range of a room temperature to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (4-3). The isolated Compound (4-3) may be further purified, for example, by chromatography and recrystallization.

(Synthesis L)

Compound (4) wherein $L^1$ is a C(O)NH$_2$ group, i.e., a compound of a formula (4-9) (hereinafter, described as Compound (4-9)), can be prepared by reacting Compound (4-7) with an ammonia.

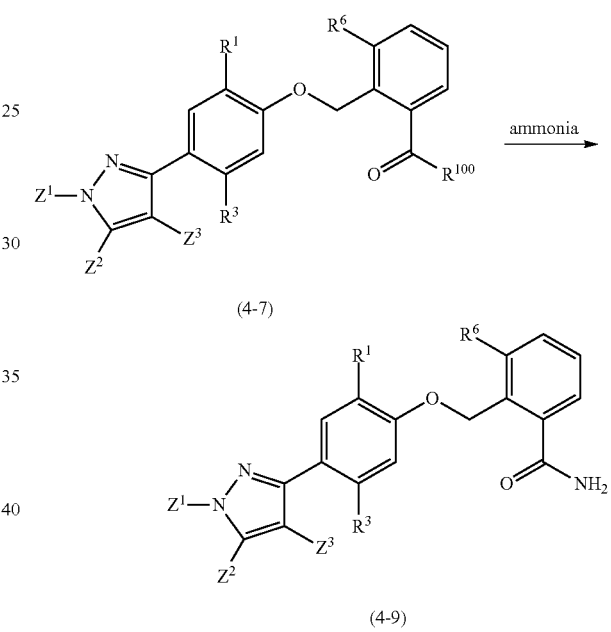

[wherein
$R^1$, $R^3$, $R^6$, $R^{100}$, $Z^1$, $Z^2$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

An ammonia to be used in the reaction may be in the form of a gas or a solution of ammonia dissolved in solvents such as water, methanol, ethanol, tetrahydrofuran, 1,4-dioxane and diethylether.

In the reaction, ammonia is used usually within a range of 1 to a large excess molar ratio(s) as opposed to 1 mole of Compound (4-7).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (4-9). The isolated Compound (4-9) may be further purified, for example, by chromatography and recrystallization.

(Synthesis M)

Compound (4-3) can be prepared also by reacting Compound (4-9) with hypochlorite or hypobromite.

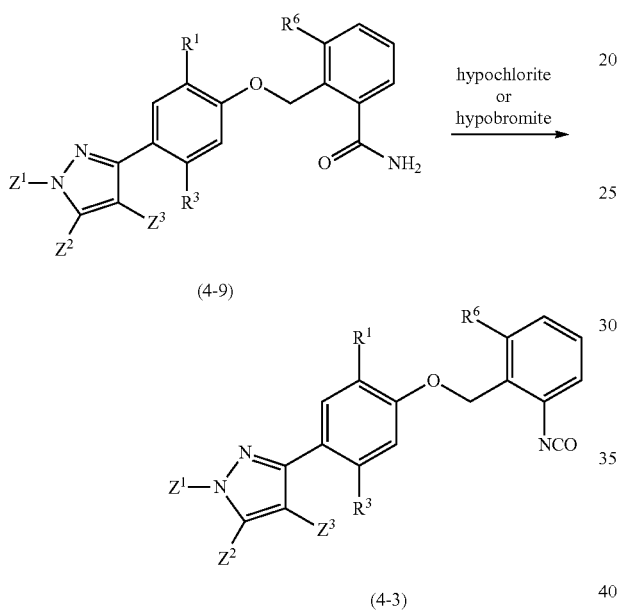

(4-9)

(4-3)

[wherein
$R^1$, $R^3$, $R^6$, $Z^1$, $Z^2$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; water; and mixed solvents thereof.

Examples of the hypochlorite or hypobromite to be used in the reaction include sodium hypobromite, sodium hypochlorite, potassium hypobromite, potassium hypochlorite, barium hypobromite, barium hypochlorite, calcium hypobromite and calcium hypochlorite.

Also chlorine or bromine is mixed with sodium hydroxide, potassium hydroxide, barium hydroxide, calcium hydroxide and the others to form a hypochlorite or a hypobromite, which also can be used.

The reaction temperature is usually within a range of 0 to 150° C. The reaction period of the reaction is usually within a range of 0.1 to 24 hours.

In the reaction, the hypochlorite or hypobromite is used usually within a range of 1 to 10 molar ratio(s) as opposed to 1 mole of Compound (4-9).

When the reaction is completed, the reaction mixtures are extracted with organic solvent(s), and the resulting organic layers are worked up (for example, drying and concentration) to isolate Compound (4-3). The isolated Compound (4-3) may be further purified, for example, by distillation, chromatography and recrystallization.

(Synthesis N)

Compound (4) wherein $L^1$ is a CONHOH group, i.e., a compound of a formula (4-10) (hereinafter, described as Compound (4-10)), can be prepared by reacting Compound (4-7) with hydroxylamine.

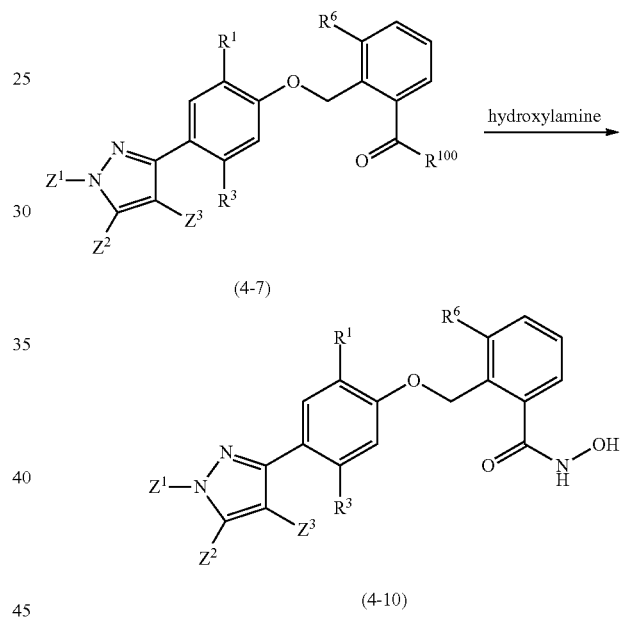

(4-7)

(4-10)

[wherein
$R^1$, $R^3$, $R^6$, $R^{100}$, $Z^1$, $Z^2$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

In the reaction, hydroxylamine is used usually within a range of 1 to 10 molar ratio(s) as opposed to 1 mole of Compound (4-7).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (4-10). The isolated Compound (4-10) may be further purified, for example, by chromatography and recrystallization.

(Synthesis O)

Compound (4-3) can be prepared also by reacting Compound (4-10) with an acid halide.

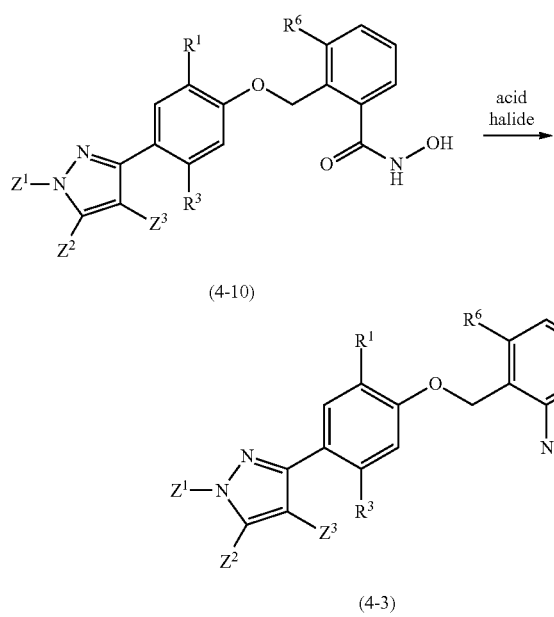

(4-10)

(4-3)

[wherein
$R^1$, $R^3$, $R^6$, $Z^1$, $Z^2$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; water; and mixed solvents thereof.

Examples of the acid halide to be used in the reaction include acid anhydride such as acetic anhydride and propionic anhydride; acid halides such as acetyl chloride, acetyl bromide and benzoyl chloride; sulfonyl chlorides such as p-toluenesulfonyl chloride and methanesulfonyl chloride; and sulfur trioxide-pyridine complex and thinoyl chloride.

If necessary, organic bases such as pyridine, triethylamine, tributylamine and diazabicycloundecene, and inorganic bases such as sodium hydroxide and potassium hydroxide may be added to the reaction, and these compounds are used usually within a range of 1 to 10 molar ratio(s) as opposed to 1 mole of Compound (4-10).

The reaction temperature is usually within a range of −20 to 150° C. The reaction period of the reaction is usually within a range of 0.1 to 24 hours.

In the reaction, the acid halide is used usually within a range of 1 to 10 molar ratio(s) as opposed to 1 mole of Compound (4-10).

When the reaction is completed, the reaction mixtures are extracted with organic solvent(s), and the resulting organic layers are worked up (for example, drying and concentration) to isolate Compound (4-3). The isolated Compound (4-3) may be further purified, for example, by chromatography and recrystallization.

(Synthesis P)

Compound (4) wherein $L^1$ is a C(O)NHCl group, i.e., a compound of a formula (4-11-1) (hereinafter, described as Compound (4-11-1)) or Compound (4) wherein $L^1$ is a C(O)NHBr group, i.e., compound of a formula (4-11-2) (hereinafter, described as Compound (4-11-2)) can be prepared by reacting Compound (4-9) with a halogenating agent.

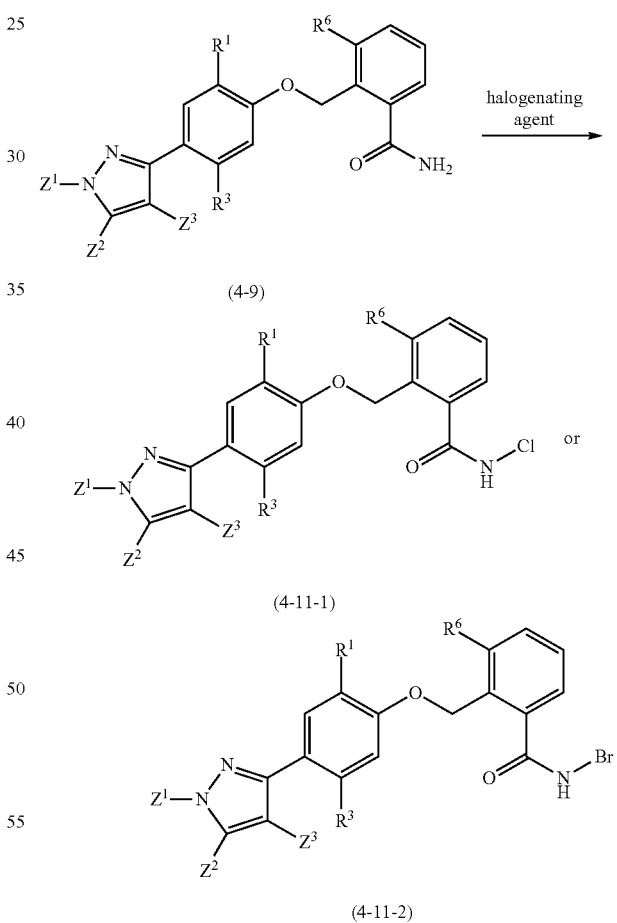

(4-9)

(4-11-1)

(4-11-2)

[wherein
$R^1$, $R^3$, $R^6$, $Z^1$, $Z^2$ and $Z^3$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include sodium hypochlorite, tert-butyl hypochlorite, trichloroisocyanuric acid, chlorine and sulfuryl chloride.

In the reaction, the halogenating agent is used usually within a range of 1 to 10 molar ratio(s) as opposed to 1 mole of Compound (4-9).

The reaction temperature is usually within a range of −20 to 150° C. The reaction period of the reaction is usually within a range of 0.1 to 24 hours.

A catalyst may be added to the reaction, and specific examples of the catalyst include dimethylformamide and the others. The catalyst is used usually within a range of 0.001 to 1 molar ratio(s) as opposed to 1 mole of Compound (4-9).

When the reaction is completed, the reaction mixtures are extracted with organic solvent(s), and the resulting organic layers are worked up (for example, drying and concentration) to isolate Compound (4-11-1) or Compound (4-11-2). The isolated Compound (4-11-1) or Compound (4-11-2) may be further purified, for example, by chromatography and recrystallization.

(Synthesis Q)

Compound (4-3) may be prepared also by reacting Compound (4-11-1) or Compound (4-11-2) with a base.

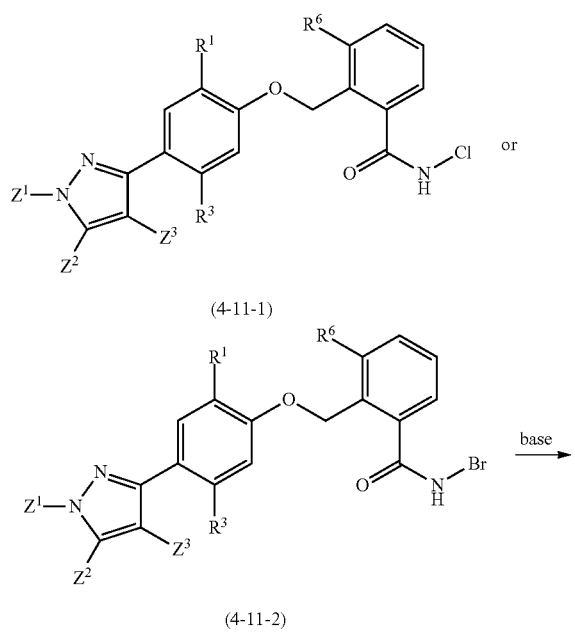

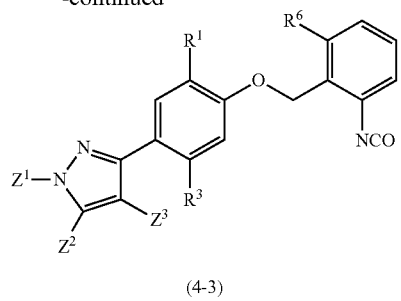

[wherein $R^1$, $R^3$, $R^6$, $R^{100}$, $Z^1$, $Z^2$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; water; and mixed solvents thereof.

Examples of the base to be used in the reaction include organic bases such as pyridine, triethylamine, tributylamine and diazabicycloundecene; and inorganic bases such as sodium hydroxide and potassium hydroxide.

In the reaction, the base is used usually within a range of 1 to 10 molar ratio(s) as opposed to 1 mole of Compound (4-11-1) or Compound (4-11-2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (4-3). The isolated Compound (4-3) may be further purified, for example, by chromatography and recrystallization.

(Synthesis R)

Compound (4) wherein $L^1$ is a halogen atom, i.e., a compound of a formula (4-12) (hereinafter, described as Compound (4-12)), can be prepared by reacting Compound (PA-2) with Compound (PR-1) (hereinafter, described as Compound (PR-1)) in the presence of a base.

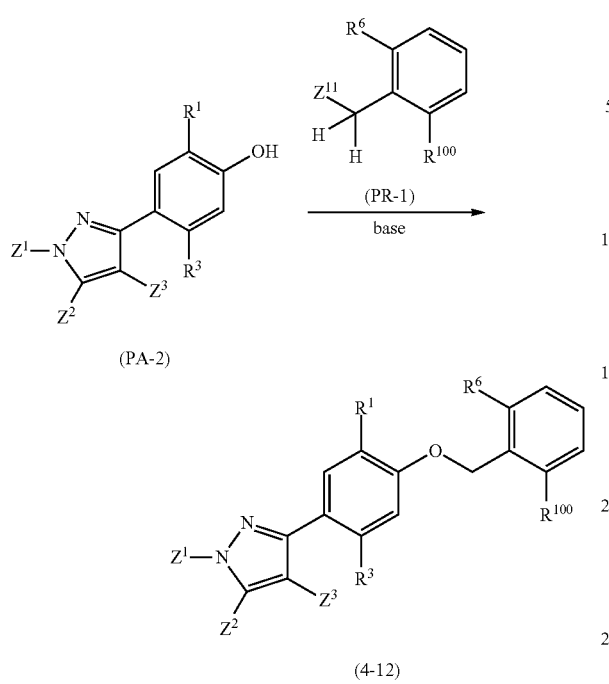

(PA-2)

(4-12)

[wherein
R$^1$, R$^3$, R$^6$, R$^{100}$, Z$^1$, Z$^2$, Z$^3$ and Z$^{11}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (PR-1) is used usually within a range of 1 to 10 molar ratio(s), and the base is used usually within a range of 0.5 to 5 molar ratios, as opposed to 1 mole of Compound (PA-2).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (PA-2).

When the reaction is completed, the reaction mixtures are extracted with organic solvent(s), and the resulting organic layers are worked up (for example, drying and concentration) to isolate Compound (4-12). The isolated Compound (4-12) may be further purified, for example, by chromatography and recrystallization.

(Synthesis S)

Compound (4-6) can be prepared also by reacting Compound (4-12) with metal or metallic compound, followed by reacting the resulting mixtures with a carbon homologation agent.

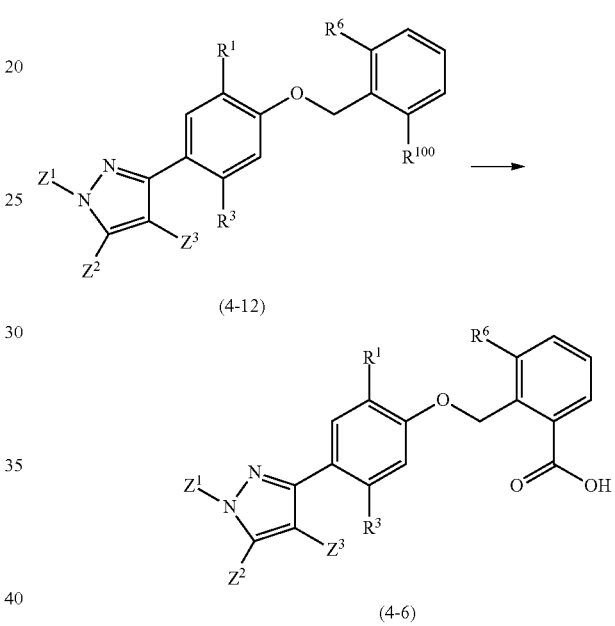

(4-12)

(4-6)

[wherein
R$^1$, R$^3$, R$^6$, R$^{100}$, Z$^1$, Z$^2$ and Z$^3$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; and mixed solvents thereof.

Examples of the metal or the metallic compound to be used in the reaction include magnesium, isopropylmagnesium bromide, isopropylmagnesium chloride, butyllithium, sec-butyllithium, tert-butyllithium and lithium diisopropylamide, and examples of the carbon homologation agent include carbon dioxide.

In the reaction, the metal or metallic compound is used usually within a range of 1 to 20 molar ratio(s), and the carbon homologation agent is used usually within a range of 1 to a large excess molar ratio(s), as opposed to 1 mole of Compound (4-12).

When carbon dioxide is used as carbon homologation agent, examples of the carbon dioxide include carbonic acid gas and dry ice.

The reaction temperature is usually within a range of −80 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (4-6). The isolated Compound (4-6) may be further purified, for example, by distillation, chromatography and recrystallization Next, methods for preparing intermediate compounds are described below in detail.

(Reference Process A)

A compound of a formula (XA3) (hereinafter, described as Compound (XA3)) can be prepared by reacting a compound of a formula (XA1) (hereinafter, described as Compound (XA1)) or a compound of a formula (XA2) (hereinafter, described as Compound (XA1)) with an azidation agent.

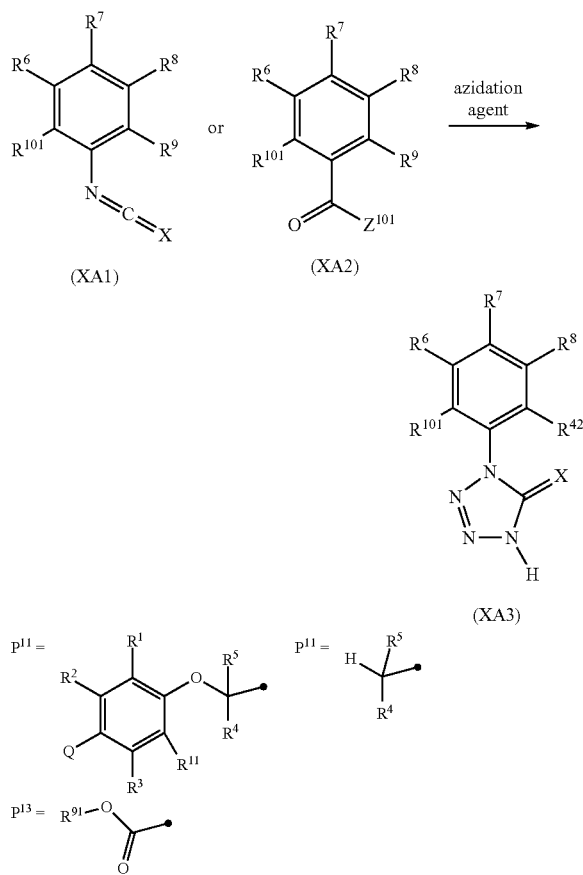

[wherein
$R^1$, $R^2$, $R^3$, $R^4$, $R^5$, $R^6$, $R^7$, $R^8$, $R^9$, $R^{11}$, X and Q are the same as defined above; $R^{101}$ represents $P^{11}$, $P^{12}$ or $P^{13}$; $R^{91}$ represents an C1-C12 alkyl group; $Z^{101}$ represents a chlorine atom or a bromine atom; and a dot represents a binding site]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the azidation agent to be used in the reaction include inorganic azides such as sodium azide, barium azide and lithium azide; and organic azides such as trimethylsilyl azide and diphenylphosphoryl azide.

In the reaction, the azidation agent is used usually within a range of 1 to 10 molar ratio(s) as opposed to 1 mole of Compound (XA1) or Compound (XA2).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.05 to 5 molar ratio(s) as opposed to 1 mole of Compound (XA1) or Compound (XA2).

When the reaction is completed, the reaction mixtures are extracted with organic solvent(s), and the resulting organic layers are worked up (for example, drying and concentration) to isolate Compound (XA3). The isolated Compound (XA3) may be further purified, for example, by chromatography and recrystallization.

(Reference Process B)

Compound (XA1) can be prepared by reacting a compound of a formula (XB1) (hereinafter, described as Compound (XB1)) with an isocyanation agent.

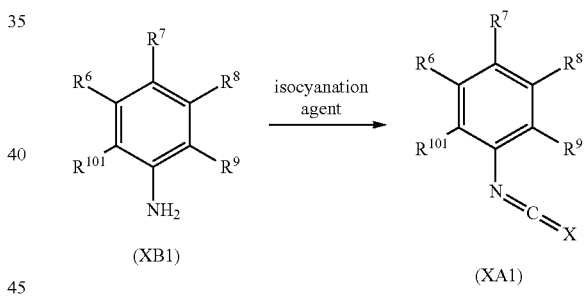

[wherein
$R^6$, $R^7$, $R^8$, $R^9$, $R^{101}$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the isocyanation agent to be used in the reaction include phosgene, diphosgene, triphosgene, thiophosgenes, N,N-carbodiimidazole and N,N-thio carbodiimidazole.

In the reaction, the isocyanation agent is used usually within a range of 1 to 10 molar ratio(s) as opposed to 1 mole of Compound (XB1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratios as opposed to 1 mole of Compound (XB1).

When the reaction is completed, the reaction mixtures are extracted with organic solvent(s), and the resulting organic layers are worked up (for example, drying and concentration) to isolate Compound (XA1). The isolated Compound (XA1) may be further purified, for example, by distillation, chromatography and recrystallization.

(Reference Process C)

Compound (XA2) can be prepared by reacting a compound of a formula (XC1) (hereinafter, described as Compound (XC1)) with a halogenating agent.

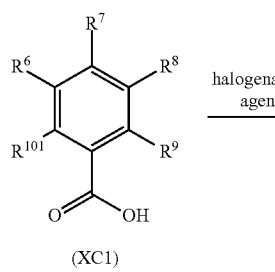

(XC1)  (XA2)

[wherein
$R^6$, $R^7$, $R^8$, $R^9$, $R^{101}$ and $Z^{101}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane and chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include phosphorous oxychloride, phosphorous trichloride, phosphorous pentachloride, thionyl chloride, phosphorous oxybromide, phosphorous tribromide, phosphorous pentabromide, phosphorus triiodide, oxalyl dichloride, oxalyl dibromide, triphosgene, diphosgene, phosgene and sulfuryl chloride.

In the reaction, the halogenating agent is used usually within a range of 1 to 10 molar ratio(s) as opposed to 1 mole of Compound (XC1).

The reaction temperature is usually within a range of −20 to 150° C. The reaction period of the reaction is usually within a range of 0.1 to 24 hours.

A catalyst may be added to the reaction, which includes, for example, N,N-dimethylformide. The catalyst is used usually within a range of 0.001 to 1 molar ratio(s) as opposed to 1 mole of Compound (XC1).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratios as opposed to 1 mole of Compound (XC1).

When the reaction is completed, the reaction mixtures are extracted with organic solvent(s), and the resulting organic layers are worked up (for example, drying and concentration) to isolate Compound (XA2). The isolated Compound (XA2) may be further purified, for example, by chromatography and recrystallization.

(Reference Process D)

Compound (XA1) can be prepared by reacting Compound (XB1) with a carbamating agent to form a compound of a formula (XD1) (hereinafter, described as Compound (XD1)), followed by reacting the resulting Compound (XD1) with an isocyanation agent.

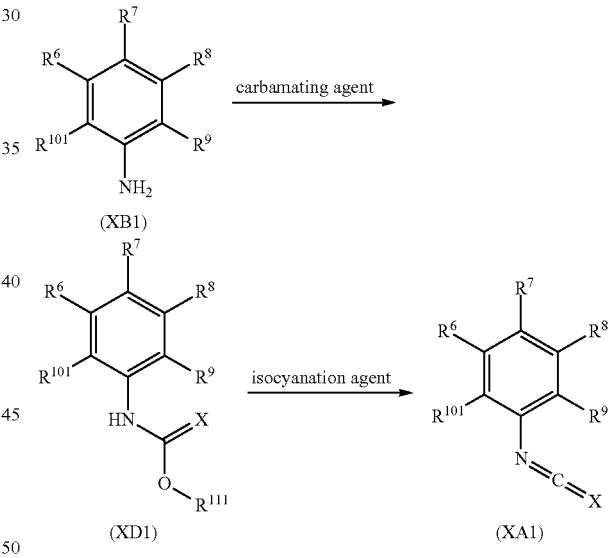

(XB1)

(XD1)  (XA1)

[wherein
$R^6$, $R^7$, $R^8$, $R^9$ and $R^{101}$ are the same as described above;
$R^{111}$ represents an C1-C12 alkyl group or a phenyl group]

Hereinafter, the process for preparing Compound (XD1) from Compound (XB1) is explained.

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the carbamating agent to be used in the reaction include phenyl chlorocarbonate, methyl chlorocarbonate, ethyl chlorocarbonate, propyl chlorocarbonate, isopropyl chlorocarbonate, butyl chlorocarbonate, tert-butyl chlorocarbonate, di-tert-butyl dicarbonate, dimethyl dicarbonate, diethyl dicarbonate, phenyl chlorothioformate, methyl chlorothioformate and ethyl chlorothioformate.

In the reaction, the carbamating agent is used usually within a range of 1 to 10 molar ratio(s) as opposed to 1 mole of Compound (XB1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali-metal carbonates such as lithium carbonate, sodium carbonate, potassium carbonate and cesium carbonate, alkali-metal bicarbonates such as lithium bicarbonate, sodium bicarbonate, potassium bicarbonate and cesium bicarbonate may be added to the reaction, and these compounds are used usually within a range of 0.05 to 5 molar ratios as opposed to 1 mole of Compound (XB1).

When the reaction is completed, the reaction mixtures are extracted with organic solvent(s), and the resulting organic layers are worked up (for example, drying and concentration) to isolate Compound (XD1). The isolated Compound (XD1) may be further purified, for example, by distillation, chromatography and recrystallization.

Hereinafter, the process for preparing Compound (XA1) from Compound (XD1) is explained.

This reaction is usually carried out in a solvent.

Examples of the solvent that can be used in the reaction include ethers such as tetrahydrofuran, dioxane, ethyleneglycol dimethyl ether, methyl tert-butyl ether; hydrocarbons such as toluene, xylene; halogenated hydrocarbons such as carbon tetrachloride, chloroform, 1,2-dichloroethane, chlorobenzene; nitriles such as acetonitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; and mixed solvents thereof.

Examples of the isocyanation agent to be used in the reaction include phosphorous pentachloride, phosphorous oxychloride, diphosphorus pentoxide, trichlorosilane, dichlorosilane, monochlorosilane, boron trichloride, 2-chloro-1,3,2-benzodioxaborole, diiodosilane, methyl trichlorosilane, dimethyl dichlorosilane and chlorotrimethylsilane.

In the reaction, the isocyanation agent is used usually within a range of 1 to 10 molar ratio(s) as opposed to 1 mole of Compound (XD1).

The reaction temperature is usually within a range of −20 to 250° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali-metal carbonates such as lithium carbonate, sodium carbonate, potassium carbonate and cesium carbonate, alkali-metal bicarbonates such as lithium bicarbonate, sodium bicarbonate, potassium bicarbonate and cesium bicarbonate may be added to the reaction, and these bases are used usually within a range of 0.05 to 5 molar ratios as opposed to 1 mole of Compound (XD1).

When the reaction is completed, the reaction mixtures are extracted with organic solvent(s), and the resulting organic layers are worked up (for example, drying and concentration) to isolate Compound (XA1). The isolated Compound (XA1) may be further purified, for example, by distillation, chromatography and recrystallization.

(Reference Process E)

A compound of a formula (XE2) (hereinafter, described as Compound (XE2)) can be prepared by reacting a compound of a formula (XE1) (hereinafter, described as Compound (XE1)) with hydrogen gas in the presence of a catalyst.

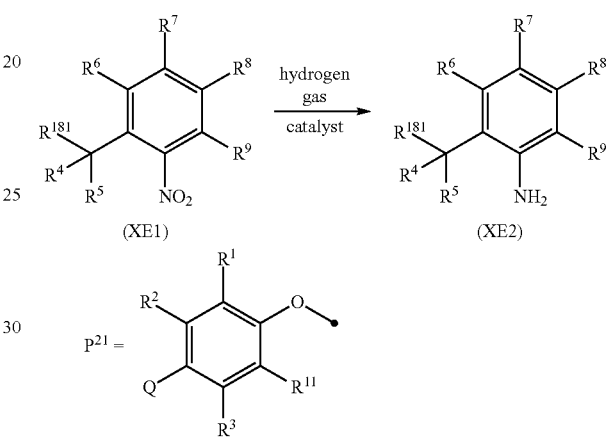

[wherein
$R^1$, $R^2$, $R^3$, $R^4$, $R^5$, $R^6$, $R^7$, $R^8$, $R^9$, $R^{11}$ and Q are the same as described above; $R^{181}$ represents a hydrogen atom or $P^{21}$; and a dot represents a binding site]

This reaction is usually carried out in a solvent.

Examples of the solvent that can be used in the reaction include alcohols such as methanol, ethanol, propanol, butanol: esters such as ethyl acetate, butyl acetate; halogenated hydrocarbons such as carbon tetrachloride, chloroform, dichloromethane, 1,2-dichloroethane, tetrachloroethane, chlorobenzene; ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; acetic acid; water; and mixed solvents thereof.

Examples of the catalyst to be used in the reaction includes palladium on carbon (Pd/C), platinum on carbon (Pt/C), osmium on carbon (Os/C), ruthenium on carbon (Ru/C), rhodium on carbon (Rh/C) and Raney nickel.

In the reaction, the catalyst is used usually within in a range of 0.1 to 1 molar ratio(s), and hydrogen gas is used usually in an excess amount, as opposed to 1 mole of Compound (XE1).

The reaction temperature is usually within a range of −20 to 150° C. The reaction period of the reaction is usually within a range of 0.1 to 24 hours.

When the reaction is completed, the catalyst is filtered off, and the resulting organic layers are worked up (for example, concentration) to isolate Compound (XE2). The isolated Compound (XE2) may be further purified, for example, by distillation, chromatography and recrystallization.

(Reference Process F)
Compound (XE2) can be prepared by reacting the above-mentioned Compound (XE1) with a reducing agent in the presence of an acid.

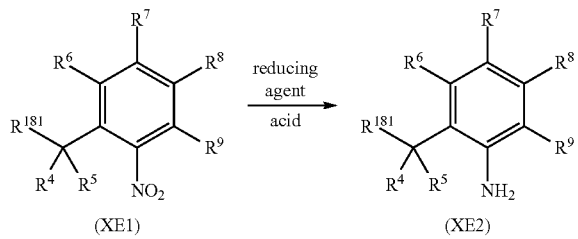

[wherein
$R^4$, $R^5$, $R^6$, $R^7$, $R^8$, $R^9$ and $R^{181}$ are the same as described above]

This reaction is usually carried out in a solvent.

Examples of the solvent to be used in the reaction include aliphatic carboxylic acids such as acetic acid; alcohols such as methanol, ethanol; water; and mixed solvents thereof.

Examples of the reducing agent to be used in the reaction include iron; tin compounds such as tin; and zinc compounds such as zinc.

Examples of the acid to be used in the reaction include hydrochloric acid, sulfuric acid, acetic acid, aqueous ammonium chloride solution.

In the reaction, the reducing agent is used usually within a range of 1 to 30 molar ratio(s), and the acid is used usually within a range of 1 to 100 molar ratio(s), as opposed to 1 mole of Compound (XE1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XE2). The isolated Compound (XE2) may be further purified, for example, by distillation, chromatography and recrystallization.

(Reference Process G)
A compound of a formula (XG2) (hereinafter, described as Compound (XG2)) can be prepared by reacting a compound of a formula (XG1) (hereinafter, described as Compound (XG1)) and Compound (B-2) in the presence of a base.

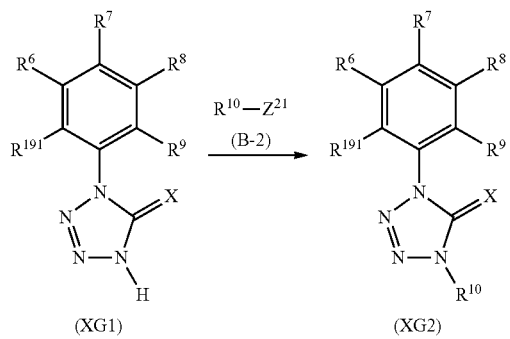

[wherein
$R^6$, $R^7$, $R^8$, $R^9$, $R^{10}$, X and $Z^{21}$ are the same as described above; and $R^{191}$ represents $P^{12}$ or $P^{13}$]

The reaction can be carried out according to the above-mentioned process B.

(Reference Process H)
A compound of a formula (XH2) (hereinafter, described as Compound (XH2)) can be prepared by reacting a compound of a formula (XH1) (hereinafter, described as Compound (XH1)) with a halogenating agent in the presence of a radical initiator.

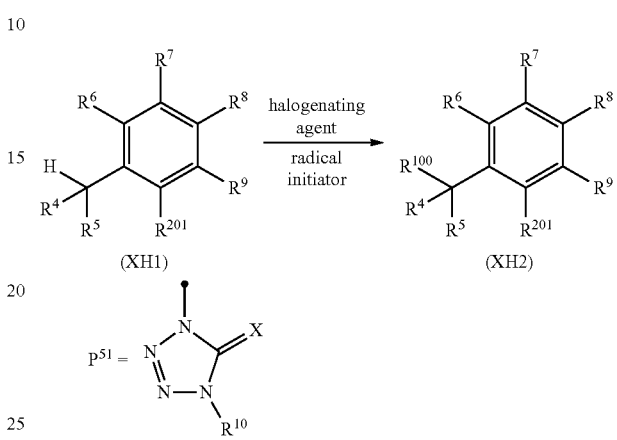

[wherein
$R^4$, $R^5$, $R^6$, $R^7$, $R^8$, $R^9$, $R^{10}$, $R^{100}$ and X are the same as described above; and $R^{201}$ represents $P^{51}$ or a nitro group]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, α,α,α-trichlorotoluene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include a chlorinating agent, a brominating agent or iodinating agent such as chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonamide and N-bromophthalimide.

Examples of the radical initiator to be used in the reaction include benzoyl peroxide, azobisisobutyronitrile (AIBN), 1,1-azobis(cyanocyclohexane)isobutyronitrile, diacylperoxide, dialkyl peroxydicarbonate, tert-alkyl peroxyester, monoperoxy carbonate, di(tert-alkylperoxy)ketal, ketone peroxide and triethylborane.

In the reaction, the halogenating agent is used usually within a range of 1 to 10 molar ratio(s), and the radical initiator is used usually within a range of 0.01 to 5 molar ratios, as opposed to 1 mole of Compound (XH1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). The isolated Compound (XH2) may be further purified, for example, by distillation, chromatography and recrystallization.

(Reference Process I)

A compound of a formula (XI2) (hereinafter, described as Compound (XI2)) can be prepared by reacting Compound (XH2) with a compound of a formula (XI1) (hereinafter, described as Compound (XI1)).

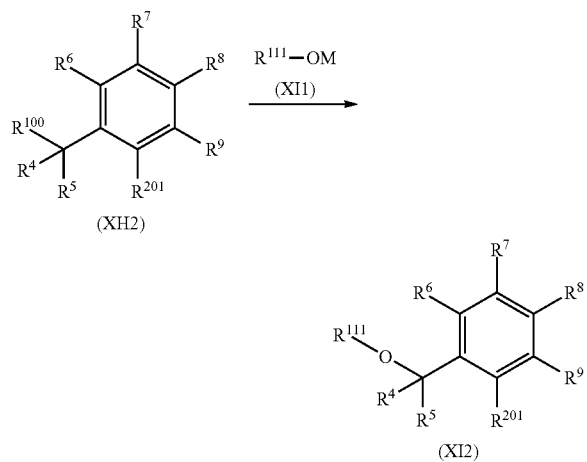

[wherein $R^4$, $R^5$, $R^6$, $R^7$, $R^8$, $R^9$, $R^{10}$, $R^{201}$ and $R^{111}$ are the same as described above; and M represents sodium, potassium or lithium]

This reaction is usually carried out in a solvent.

Examples of the solvent that can be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of Compound (XI1) include sodium methoxide, sodium ethoxide, sodium propoxide, sodium butoxide, sodium isopropoxide, sodium sec-butoxide, sodium tert-butoxide, potassium methoxide, potassium ethoxide, potassium propoxide, potassium butoxide, potassium isopropoxide, potassium sec-butoxide, potassium tert-butoxide and sodium phenoxide.

In the reaction, Compound (XI1) is used usually within a range of 1 to 10 molar ratio(s) as opposed to 1 mole of Compound (XH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XI2). The isolated Compound (XI2) may be further purified, for example, by distillation, chromatography and recrystallization.

(Reference Process J)

A compound of a formula (XJ1) (hereinafter, described as Compound (XJ1)) can be prepared by reacting Compound (XH2) and water in the presence of a base.

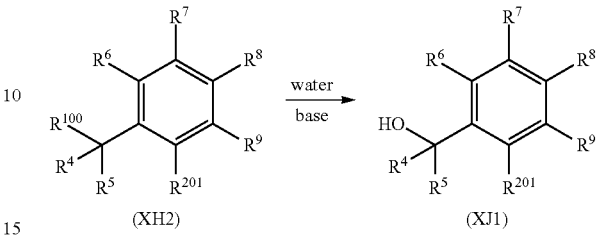

[wherein $R^4$, $R^5$, $R^6$, $R^7$, $R^8$, $R^9$, $R^{100}$ and $R^{201}$ are the same as described above]

This reaction is usually carried out in water or a solvent containing water.

Examples of the solvent that can be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicyclonundecene, diazabicyclononene; metallic organic acid salts such as lithium formate, lithium acetate, sodium formate, sodium acetate, potassium formate, potassium acetate; metal nitrates such as silver nitrate, sodium nitrate; alkali-metal bicarbonates such as lithium bicarbonate, sodium bicarbonate, potassium bicarbonate, cesium bicarbonate; alkali-metal hydroxides such as lithium hydroxide, sodium hydroxide, potassium hydroxide, cesium hydroxide; and alkali metal alkoxides such as sodium methoxide, sodium ethoxide, sodium tert-butoxide, potassium tert-butoxide.

In the reaction, the base is used usually within a range of 1 to 100 molar ratio(s) as opposed to 1 mole of Compound (XH2).

In the reaction, water is used usually within a range of 1 to a large excess molar ratio(s) as opposed to 1 mole of Compound (XH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XJ1). The isolated Compound (XJ1) may be further purified, for example, by distillation, chromatography and recrystallization.

(Reference Process K)

Compound (XH2) can be prepared by reacting Compound (XI2) and a halogenating agent.

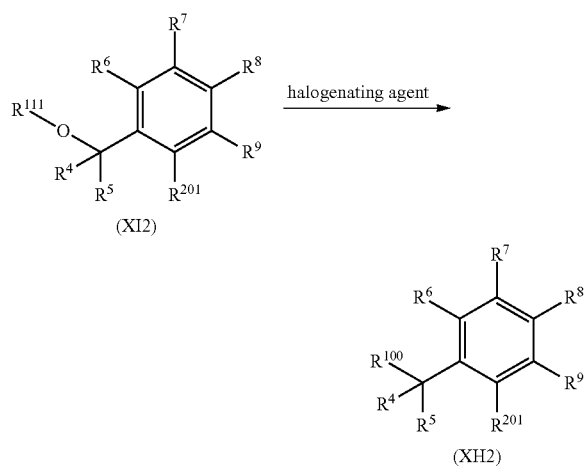

(XI2) → halogenating agent → (XH2)

[wherein
$R^4$, $R^5$, $R^6$, $R^7$, $R^8$, $R^9$, $R^{100}$, $R^{111}$ and $R^{201}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent include hydrochloric acid, hydrobromic acid and hydroiodic acid.

In the reaction, the halogenating agent is used usually in 1 or more molar ratio(s) as opposed to 1 mole of Compound (XI2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). The isolated Compound (XH2) may be further purified, for example, by distillation, chromatography and recrystallization.

(Reference Process L)

Compound (XH2) can be prepared by reacting a compound of a formula (XJ1) (hereinafter, described as Compound (XJ1)) and a halogenating agent.

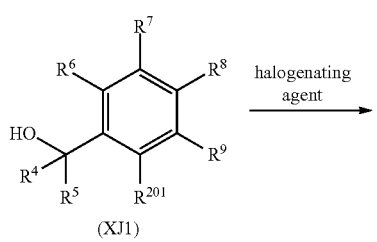

(XJ1) → halogenating agent →

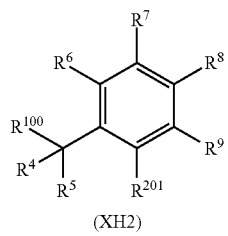

(XH2)

[wherein
$R^4$, $R^5$, $R^6$, $R^7$, $R^8$, $R^9$, $R^{100}$ and $R^{201}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorous oxychloride, phosphorous trichloride, phosphorous pentachloride, thionyl chloride, phosphorous oxybromide, phosphorous pentabromide, phosphorus triiodide, oxalyl dichloride, oxalyl dibromide, acetyl chloride, carbon tetrabromide, N-bromosuccinimide, lithium chloride, sodium iodide and acetyl bromide.

In the reaction, the halogenating agent is used usually within a range of 1 to 10 molar ratio(s) as opposed to 1 mole of Compound (XJ1).

To promote the reaction, an additive agent may be added depending on the halogenating agent used, and specifically includes zinc chloride for acetyl chloride; triphenylphosphine for carbon tetrabromide; dimethyl sulfide for N-bromosuccinimide; boron trifluoride diethyl etherate complex for sodium iodide; boron trifluoride diethyl etherate complex for acetyl bromide; triethylamine and methanesulfonyl chloride for lithium chloride; aluminium chloride for sodium iodide; and trimethylsilyl chloride for sodium iodide. The amount of the additive agent is used usually within a range of 0.01 to 5 molar ratios as opposed to 1 mole of Compound (XJ1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). The isolated Compound (XH2) may be further purified, for example, by distillation, chromatography and recrystallization.

(Reference process M)

A compound of a formula (XM2) (hereinafter, described as Compound (XM2)) can be prepared by reacting Compound (XJ1) with a compound of a formula (XM1) (hereinafter, described as Compound (XM1)) in the presence of a base.

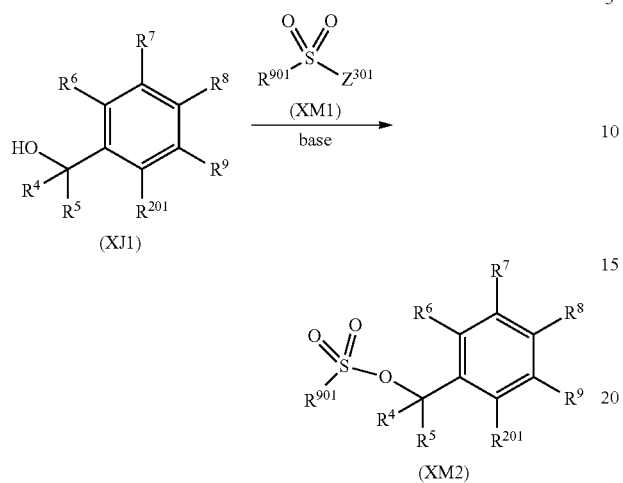

(XJ1)

(XM2)

[wherein $R^4$, $R^5$, $R^6$, $R^7$, $R^8$, $R^9$ and $R^{201}$ are the same as described above; $R^{901}$ represents a p-methylphenyl group, a methyl group or a trifluoromethyl group; $Z^{301}$ represents a fluorine atom, a chlorine atom, a bromine atom, an iodine atom, a methanesulfonyloxy group or a trifluoromethanesulfonyloxy group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal hydrides such as lithium hydride, sodium hydride, potassium hydride; alkali metal alkoxides such as sodium methoxide, sodium ethoxide, sodium tert-butoxide, potassium tert-butoxide.

In the reaction, Compound (XM1) is used usually within a range of 1 to 10 molar ratio(s), and the base is used usually within a range of 1 to 5 molar ratio(s), as opposed to 1 mole of Compound (XJ1).

The reaction temperature is usually within a range of −20 to 150° C. The reaction period of the reaction is usually within a range of 0.1 to 24 hours.

If necessary, an additive agent may be added to the reaction, and specifically, includes sodium iodide and tetrabutylammonium iodide and the others. These additive agents are used usually within a range of 0.001 to 1.2 molar ratios as opposed to 1 mole of Compound (XJ1).

When the reaction is completed, the reaction mixtures are extracted with organic solvent(s), and the resulting organic layers are worked up (for example, drying and concentration) to isolate Compound (XM2). The isolated Compound (XM2) may be further purified, for example, by chromatography and recrystallization.

(Reference Process N)

A compound of a formula (XN12) (hereinafter, described as Compound (XN12)) can be prepared by coupling a compound of a formula (XN11) (hereinafter, described as Compound (XN11)) with Compound (D-2) in the presence of a base and a catalyst.


(XN11)   (XN12)

[wherein $R^{501}$ represents a hydrogen atom or an $OR^{11}$ group; $R^4$, $R^5$, $R^7$, $R^8$, $R^9$, $R^{10}$, $R^{41}$, X, $Z^{41}$ and $Z^{42}$ are the same as described above]

The reaction can be carried out according to the above-mentioned Process D.

A compound of a formula (XN22) (hereinafter, described as Compound (XN22)) can be prepared by coupling a compound of a formula (XN21) (hereinafter, described as Compound (XN21)) with Compound (D-2-2) in the presence of a base and a catalyst.

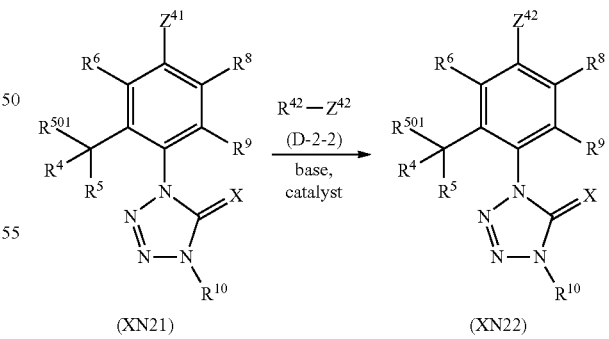

(XN21)   (XN22)

[wherein $R^4$, $R^5$, $R^6$, $R^8$, $R^9$, $R^{10}$, $R^{42}$, $R^{501}$, X, $Z^{41}$ and $Z^{42}$ are the same as described above]

The reaction can be carried out according to the above-mentioned Process D.

A compound of a formula (XN32) (hereinafter, described as Compound (XN32)) can be prepared by coupling a compound of a formula (XN31) (hereinafter, described as Compound (XN31)) with Compound (D-2-2) in the presence of a base and a catalyst.

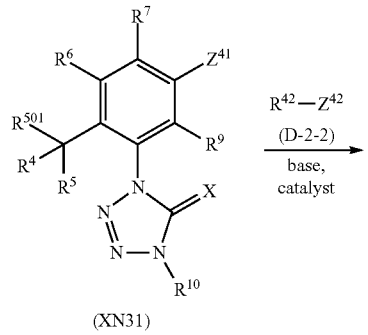

(XN31)

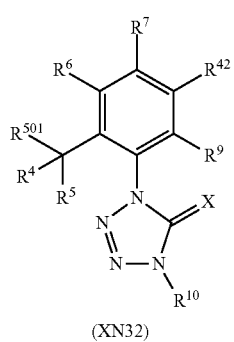

(XN32)

[wherein

R$^4$, R$^5$, R$^6$, R$^7$, R$^9$, R$^{10}$, R$^{42}$, R$^{501}$, X, Z$^{41}$ and Z$^{42}$ are the same as described above]

The reaction can be carried out according to the above-mentioned Process D.

A compound of a formula (XN42) (hereinafter, described as Compound (XN42)) can be prepared by coupling a compound of a formula (XN41) (hereinafter, described as Compound (XN41)) with Compound (D-2-2) in the presence of a base and a catalyst.

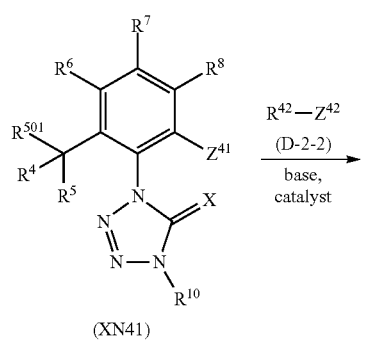

(XN41)

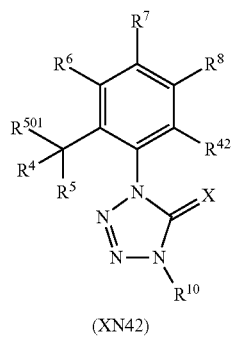

(XN42)

[wherein

R$^4$, R$^5$, R$^6$, R$^7$, R$^8$, R$^9$, R$^{10}$, R$^{42}$, R$^{501}$, X, Z$^{41}$ and Z$^{42}$ are the same as described above]

The reaction can be carried out according to the above-mentioned Process D.

(Reference Process O)

A compound of a formula (XO12) (hereinafter, described as Compound (XO12)) can be prepared by reacting a compound of a formula (XO11) (hereinafter, described as Compound (XO11)) with Compound (D-2) in the presence of a base and a catalyst.

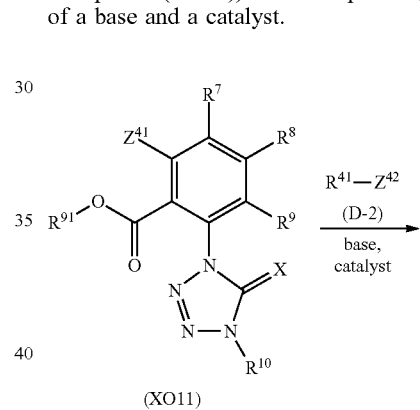

(XO11)

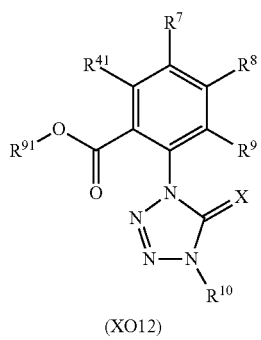

(XO12)

[wherein

R$^7$, R$^8$, R$^9$, R$^{10}$, R$^{41}$, R$^{91}$, X, Z$^{41}$ and Z$^{42}$ are the same as described above]

The reaction can be carried out according to the above-mentioned Process D.

A compound of a formula (XO22) (hereinafter, described as Compound (XO22)) can be prepared by reacting a compound of a formula (XO21) (hereinafter, described as Compound (XO21)) with Compound (D-2-2) in the presence of a base and a catalyst.

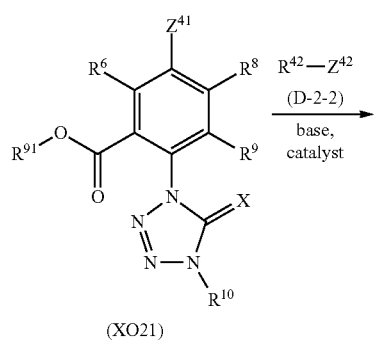

(XO21)

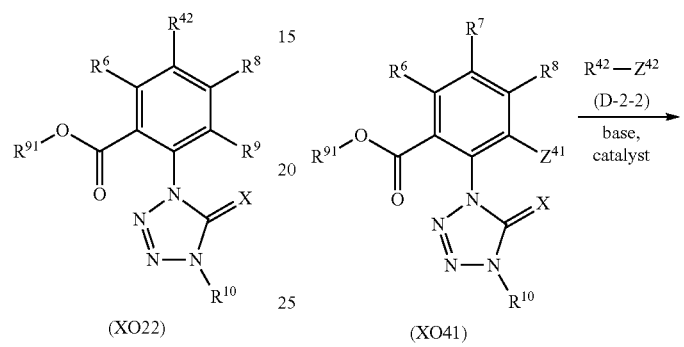

(XO22)   (XO41)

[wherein $R^6$, $R^7$, $R^9$, $R^{10}$, $R^{42}$, $R^{91}$, X, $Z^{41}$ and $Z^{42}$ are the same as described above]

The reaction can be carried out according to the above-mentioned Process D.

A compound of a formula (XO42) (hereinafter, described as Compound (XO42)) can be prepared by reacting a compound of a formula (XO41) (hereinafter, described as Compound (XO41)) with Compound (D-2-2) in the presence of a base and a catalyst.

[wherein $R^6$, $R^8$, $R^9$, $R^{10}$, $R^{42}$, $R^{91}$, X, $Z^{41}$ and $Z^{42}$ are the same as described above]

The reaction can be carried out according to the above-mentioned Process D.

A compound of a formula (XO32) (hereinafter, described as Compound (XO32)) can be prepared by reacting a compound of a formula (XO31) (hereinafter, described as Compound (XO31)) with Compound (D-2-2) in the presence of a base and a catalyst.

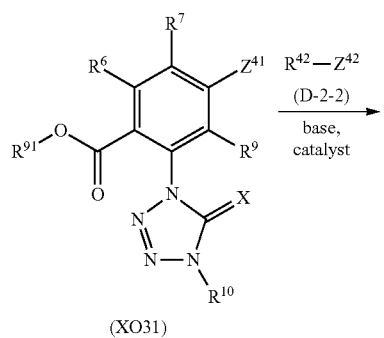

(XO31)

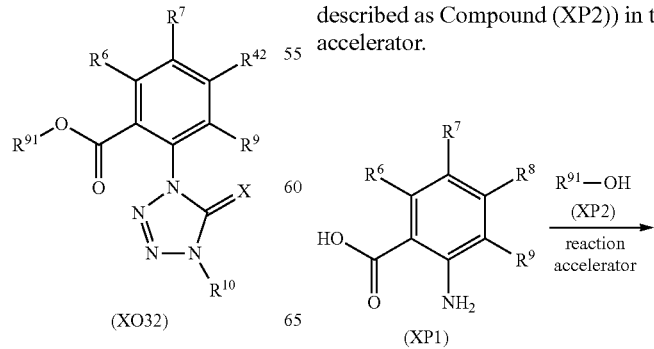

(XO32)   (XP1)

(XO42)

[wherein $R^6$, $R^7$, $R^8$, $R^{10}$, $R^{42}$, $R^{91}$, X, $Z^{41}$ and $Z^{42}$ are the same as described above]

The reaction can be carried out according to the above-mentioned Process D.

(Reference Process P)

A compound of a formula (XP3) (hereinafter, described as Compound (XP3)) can be prepared by reacting a compound of a formula (XP1) (hereinafter, described as Compound (XP1)) with a compound of a formula (XP2) (hereinafter, described as Compound (XP2)) in the presence of a reaction accelerator.

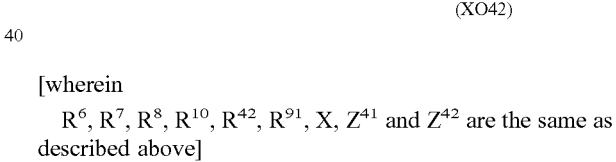

-continued

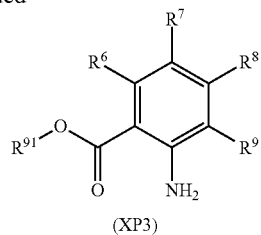

(XP3)

[wherein
R$^6$, R$^7$, R$^8$, R$^9$ and R$^{91}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof, and Compound (XP2) may be used as solvent.

Examples of Compound (XP2) to be used in the reaction include alcohols such as methanol, ethanol, propanol, isopropanol, butanol, sec-butanol, t-butanol, and pentanol.

Examples of the reaction accelerator to be used in the reaction include mineral acids such as hydrochloric acid, sulfuric acid; carbodiimides such as dicyclohexylcarbodiimide, diisopropylcarbodiimide, N'-(3-dimethylaminopropyl)-N-ethylcarbodiimide; organic acids such as methanesulfonic acid, toluenesulfonic acid; Mitsunobu reagents such as triphenylphosphine/diethyl azodicarboxylate; thionyl chloride; boron trifluoride-ethyl ether complex. In the reaction, the reaction accelerator is used usually within a range of 0.01 to 10 molar ratios as opposed to 1 mole of Compound (XP1).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate may be added to the reaction, and these compounds are used usually within a range of 0.001 to 5 molar ratios as opposed to 1 mole of Compound (XP1).

In the reaction, Compound (XP2) is used usually in a large excess molar ratios as opposed to 1 mole of Compound (XP1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XP3). The isolated Compound (XP3) may be further purified, for example, by distillation, chromatography and recrystallization.

(Reference Process Q)

Compound (XP3) can be prepared by reacting Compound (XP1) with a halogenating agent to form a below-mentioned compound of a formula (XQ1) (hereinafter, described as Compound (XQ1)), followed by reacting the resulting Compound (XQ1) with Compound (XP2).

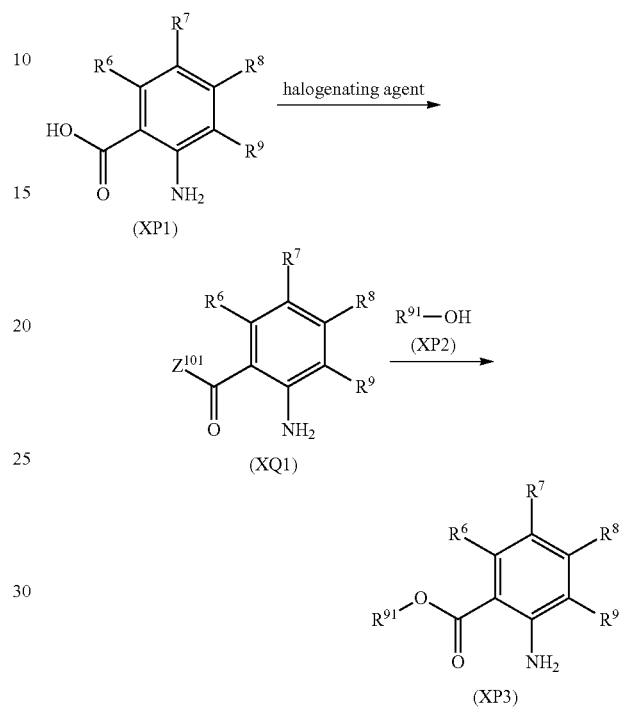

[wherein
R$^6$, R$^7$, R$^8$, R$^9$, R$^{91}$ and Z$^{101}$ are the same as described above]

The process for preparing Compound (XQ1) by reacting Compound (XP1) and a halogenating agent can be carried out according to Reference Process C.

Hereinafter, a process for preparing Compound (XP3) from Compound (XQ1) is explained.

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof, and Compound (XP2) may be used as solvent.

Examples of Compound (XP2) to be used in the reaction include alcohols such as methanol, ethanol, propanol, isopropanol, butanol, sec-butanol, t-butanol, and pentanol. In the reaction, Compound (XP2) is used usually within a range of 1 to 50 molar ratio(s) as opposed to 1 mole of Compound (XQ1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XP3). The isolated Compound (XP3) may be further purified, for example, by distillation, chromatography and recrystallization.

(Reference Process R)

Compound (XP3) can be prepared by reacting Compound (XP1) with an alkylating agent.

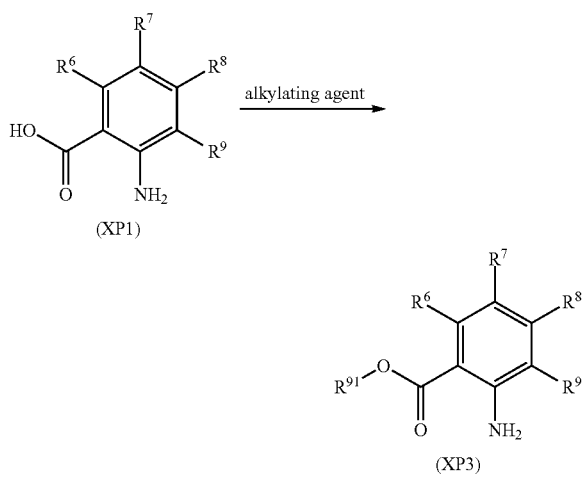

[wherein
$R^6$, $R^7$, $R^8$, $R^9$ and $R^{91}$ are the same as described above]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the alkylating agent to be used in the reaction include diazo compounds such as diazomethane, trimethylsilyldiazomethane; halogenated alkyls such as chlorodifluoromethane, methyl bromide, ethyl bromide, propyl bromide, methyl iodide, ethyl iodide, propyl iodide, aryl bromide, cyclopropyl bromide, benzyl bromide, 1,1-difluoro-2-iodomethane; dialkyl sulfates such as dimethyl sulfates, diethyl sulfates, di-propyl sulfates; and alkyl or aryl sulfonates such as methyl p-toluenesulfonate, ethyl p-toluenesulfonate, propyl p-toluenesulfonate, methyl methanesulfonate, ethyl methanesulfonate, propyl methanesulfonate.

In the reaction, the alkylating agent is used usually within a range of 1 to 10 molar ratios as opposed to 1 mole of Compound (XP1).

If necessary, an additive agent may be added to the reaction, and specifically, includes organic bases such as triethylamine, pyridine, N-methylmorpholine, N-methylpiperidine, 4-dimethylaminopyridine, diisopropylethylamine, lutidine, collidine, diazabicycloundecene and diazabicyclononene; alkali metal carbonates such as lithium carbonate, sodium carbonate, potassium carbonate and cesium carbonate; alkali metal bicarbonates such as lithium bicarbonate, sodium bicarbonate, potassium bicarbonate and cesium bicarbonate; and quaternary ammonium salts such as tetra(butyl)ammonium hydroxide. These additive agent is used usually within a range of 0.001 to 5 molar ratios as opposed to 1 mole of Compound (XP1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XP3). The isolated Compound (XP3) may be further purified, for example, by distillation, chromatography and recrystallization.

(Reference Process S)

A compound of a formula (XS2) (hereinafter, described as Compound (XS2)) can be prepared by reacting a compound of a formula (XS1) (hereinafter, described as Compound (XS1)) with a reducing agent.

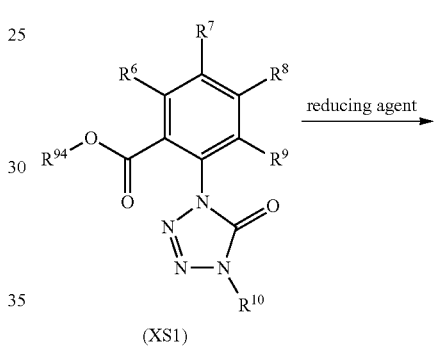

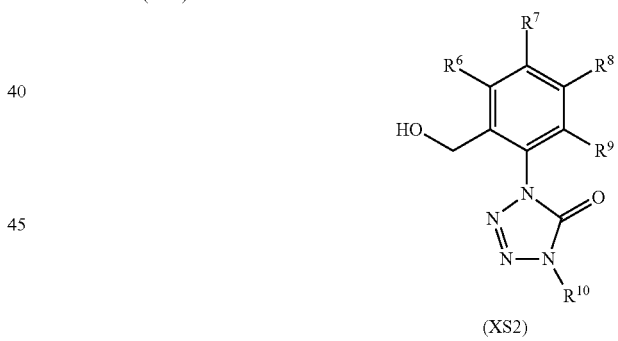

[wherein
$R^6$, $R^7$, $R^8$, $R^9$ and $R^{10}$ are the same as described above;
$R^{94}$ represents a hydrogen atom or an C1-C3 alkyl group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; alcohols such as methanol, ethanol, propanol, butanol; water; and mixed solvents thereof.

Examples of the reducing agent to be used in the reaction include lithium triethylborohydride, diisobutylaluminium hydride, lithium aminoborohydride, lithium borohydride, sodium borohydride, borane, borane-dimethyl sulfide complex and borane-tetrahydrofuran complex.

In the reaction, the reducing agent is used usually within a range of 1 to 10 molar ratio(s) as opposed to 1 mole of Compound (XS1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XS2). Compound (XS2) may be further purified, for example, by distillation, chromatography and recrystallization.

(Reference Process T)

A compound of a formula (XT2) (hereinafter, described as Compound (XT2)) can be prepared by reacting a compound of a formula (XT1) (hereinafter, described as Compound (XT1)) with a reducing agent.

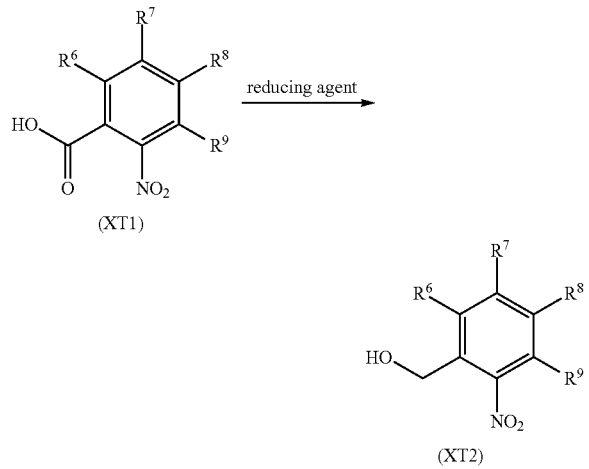

[wherein
$R^6$, $R^7$, $R^8$ and $R^9$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; water; and mixed solvents thereof.

Examples of the reducing agent to be used in the reaction include, borane, borane-tetrahydrofuran complex, borane-dimethyl sulfide complex. Also, borohydrides such as sodium borohydride and potassium borohydride are mixed with acids such as sulfuric acid, hydrochloric acid, methanesulfonic acid and boron trifluoride diethyl etherate complex to develop a borane, which also can be used.

In the reaction, the reducing agent is used usually within a range of 1 to 10 molar ratio(s) as opposed as 1 mole of Compound (XT1).

The reaction temperature is usually within a range of −20 to 100° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (XT2). The isolated Compound (XT2) may be further purified, for example, by distillation, chromatography and recrystallization.

(Reference Process U)

Compound (F-1) can be prepared by reacting a compound of a formula (XU1) (hereinafter, described as Compound (XU1)) with a compound of a formula (XU2) (hereinafter, described as Compound (XU2)).

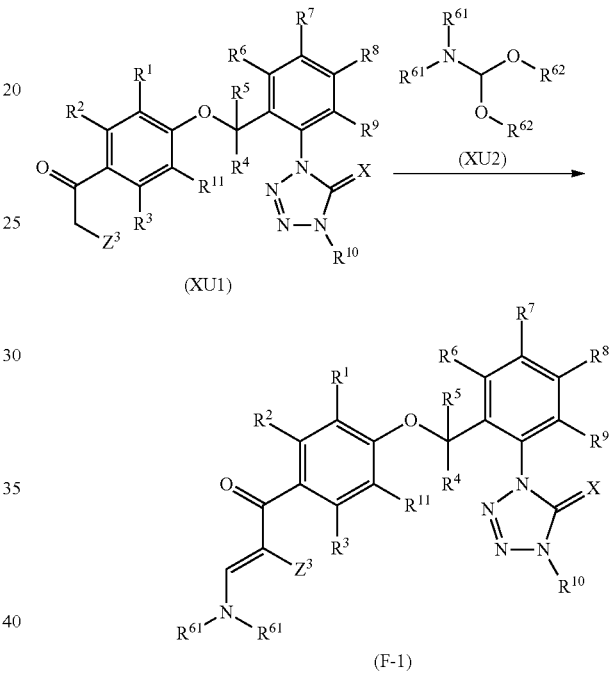

[wherein
$R^1$, $R^2$, $R^3$, $R^4$, $R^5$, $R^6$, $R^7$, $R^8$, $R^9$, $R^{10}$, $R^{11}$, $R^{61}$, X and $Z^3$ are the same as described above; $R^{62}$ represents a methyl group, an ethyl group, a propyl group, a butyl group or a benzyl group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; water; and mixed solvents thereof.

In the reaction, Compound (XU2) is used usually within a range of 1 to 10 molar ratio(s) as opposed as 1 mole of Compound (XU1).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (F-1). Alternatively, the reaction mixtures are worked up (for example, concentration) to isolate Compound (F-1). The isolated Compound (F-1) may be further purified, for example, by chromatography and recrystallization.

(Reference Process V)

Compound (XU1) can be prepared by reacting Compound (A-1) with a compound of a formula (XV1) (hereinafter, described as Compound (XV1)) in the presence of a base.

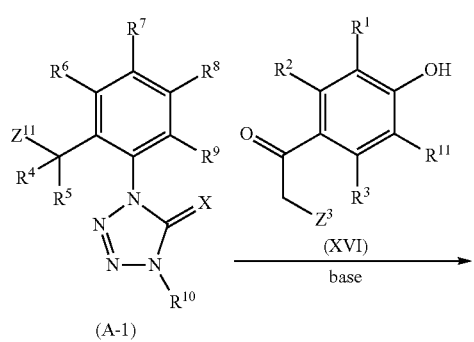

(A-1)

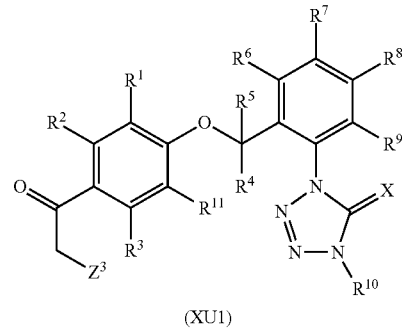

(XU1)

[wherein
$R^1$, $R^2$, $R^3$, $R^4$, $R^5$, $R^6$, $R^7$, $R^8$, $R^9$, $R^{10}$, $R^{11}$, X, $Z^3$ and $Z^{11}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (XV1) is used usually within a range of 1 to 10 molar ratio(s), and the base is used usually within a range of 1 to 10 molar ratio(s), as opposed as 1 mole of Compound (A-1).

The reaction temperature is usually within a range of -20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (A-1).

When the reaction is completed, the reaction mixtures are extracted with organic solvent(s), and the resulting organic layers are worked up (for example, drying and concentration) to isolate Compound (XU1). Alternatively, the reaction mixtures are worked up (for example, concentration) to isolate Compound (XU1). The isolated Compound (XU1) may be further purified, for example, by chromatography and recrystallization.

(Reference Process W)

Compound (G-1) can be prepared by reacting Compound (XU1) with a compound of a formula (XW1) (hereinafter, described as Compound (XW1)) in the presence of a base.

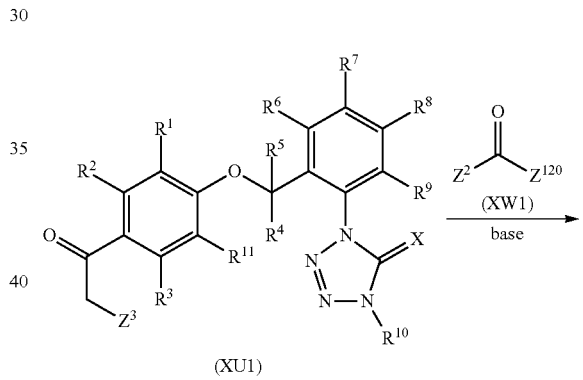

(XU1)

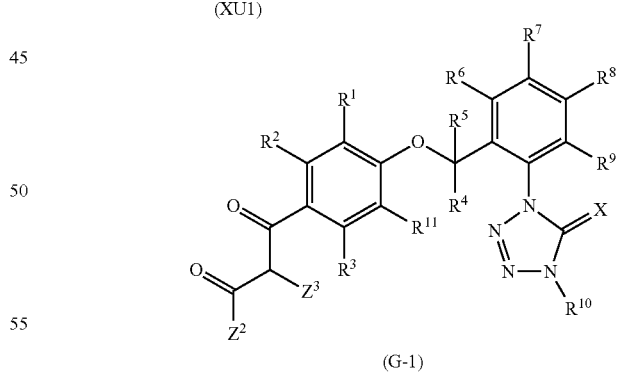

(G-1)

[wherein
$R^1$, $R^2$, $R^3$, $R^4$, $R^5$, $R^6$, $R^7$, $R^8$, $R^9$, $R^{10}$, $R^{11}$, X, $Z^2$ and $Z^3$ are the same as described above; and $Z^{120}$ represents a fluorine atom, a chlorine atom, a bromine atom, an iodine atom, an C1-C6 alkoxy group, an acetyloxy group or a phenoxy group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium methoxide, sodium ethoxide, sodium tert-butoxide, potassium tert-butoxide.

In the reaction, Compound (XW1) is used usually within a range of 1 to 10 molar ratio(s), and the base is used usually within a range of 1 to 10 molar ratio(s), as opposed as 1 mole of Compound (XU1).

The reaction temperature is usually within a range of −20 to 150° C. The reaction period of the reaction is usually within a range of 0.1 to 24 hours.

If necessary, an additive agent may be added to the reaction, and specifically includes, for example, 18-crown-6, dibenzo-18-crown-6 and the others. These additive agent is used usually within a range of 0.001 to 1.2 molar ratios as opposed to 1 mole of Compound (XU1).

When the reaction is completed, the reaction mixtures are extracted with organic solvent(s), and the resulting organic layers are worked up (for example, drying and concentration) to isolate Compound (G-1). The isolated Compound (G-1) may be further purified, for example, by chromatography and recrystallization.

(Reference Process X)

Compound (G-1-1) can be prepared by reacting Compound (XU1) with a compound of a formula (XX1) (hereinafter, described as Compound (XX1)) in the presence of a base.

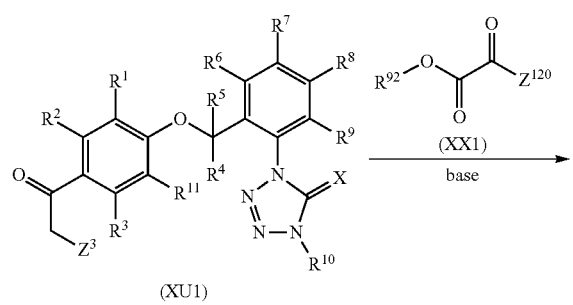

(XU1)

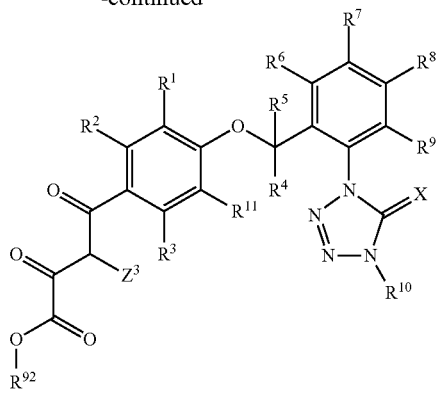

(G-1-1)

[wherein
$R^1$, $R^2$, $R^3$, $R^4$, $R^5$, $R^6$, $R^7$, $R^8$, $R^9$, $R^{10}$, $R^{11}$, $R^{92}$, X, $Z^3$ and $Z^{120}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium methoxide, sodium ethoxide, sodium tert-butoxide, potassium tert-butoxide.

In the reaction, Compound (XX1) is used usually within a range of 1 to 10 molar ratio(s), and the base is used usually within a range of 1 to 10 molar ratio(s), as opposed as 1 mole of Compound (XU1).

The reaction temperature is usually within a range of −20 to 150° C. The reaction period of the reaction is usually within a range of 0.1 to 24 hours.

If necessary, an additive agent may be added to the reaction, and specifically includes, for example, 18-crown-6, dibenzo-18-crown-6 and the others. These additive agent is used usually within a range of 0.001 to 1.2 molar ratios as opposed to 1 mole of Compound (XU1).

When the reaction is completed, the reaction mixtures are extracted with organic solvent(s), and the resulting organic layers are worked up (for example, drying and concentration) to isolate Compound (G-1-1). The isolated Compound (G-1-1) may be further purified, for example, by chromatography and recrystallization.

(Reference Process Y)

Compound (1-5-W) can be prepared by reacting a compound of a formula (1-5-Y) (hereinafter, described as Compound (1-5-Y)) with a halogenating agent.

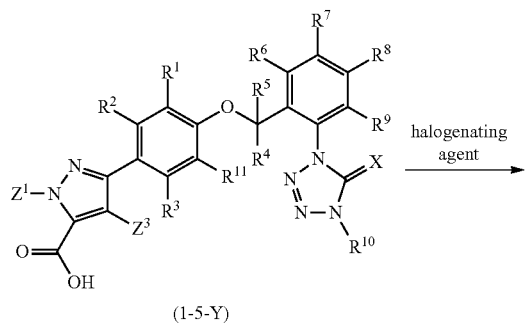

(1-5-Y)

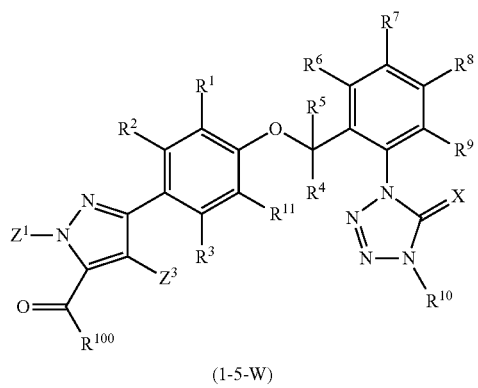

(1-5-W)

[wherein
R$^1$, R$^2$, R$^3$, R$^4$, R$^5$, R$^6$, R$^7$, R$^8$, R$^9$, R$^{10}$, R$^{11}$, R$^{100}$, X, Z$^1$ and Z$^3$ are the same as described above]

The reaction can be carried out according to Synthesis I.

(Reference Process Z)

Compound (1-5-Y) can be prepared by reacting a Compound (1-5-S) with a hydrolytic agent.

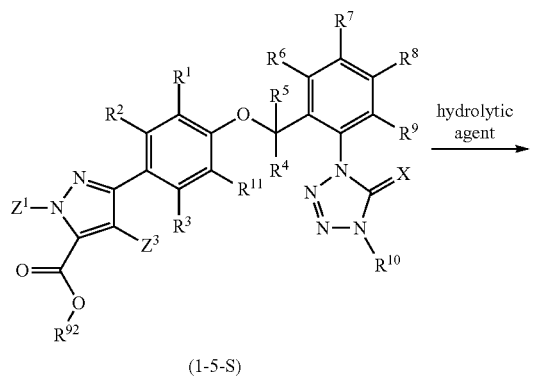

(1-5-S)

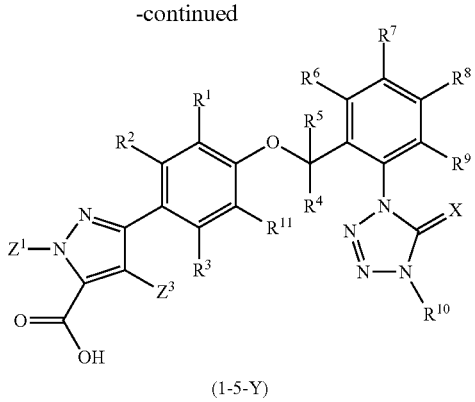

(1-5-Y)

[wherein
R$^1$, R$^2$, R$^3$, R$^4$, R$^5$, R$^6$, R$^7$, R$^8$, R$^9$, R$^{10}$, R$^{11}$, R$^{92}$, X, Z$^1$ and Z$^3$ are the same as described above]

The reaction can be carried out according to Synthesis H.

(Reference Process AA)

A compound of a formula (YA3) (hereinafter, described as Compound (YA3)) can be prepared by reacting a compound of a formula (YA1) (hereinafter, described as Compound (YA1)) with a compound of a formula (YA2) (hereinafter, described as Compound (YA2)).

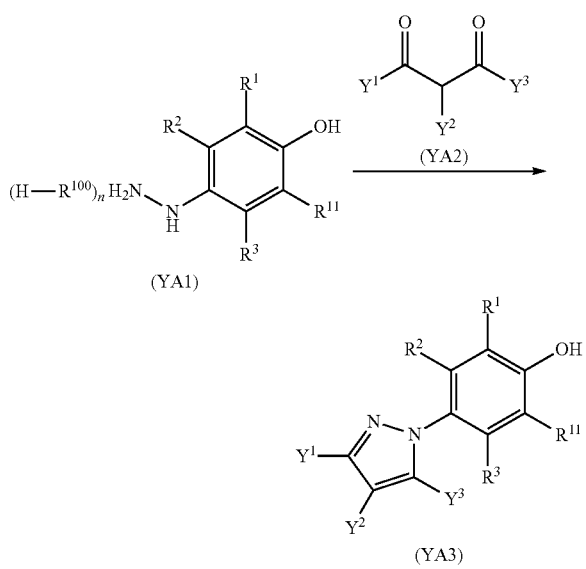

[wherein
R$^1$, R$^2$, R$^3$, R$^{11}$, R$^{100}$, Y$^1$, Y$^2$ and Y$^3$ are the same as described above; and n represents 0 or 1]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; alcohols such as methanol, ethanol, propanol, butanol; water; and mixed solvents thereof.

In the reaction, Compound (YA2) is used usually within a range of 1 to 10 molar ratio(s) as opposed as 1 mole of Compound (YA1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (YA3). Alternatively, the reaction mixtures are worked up (for example, concentration) to isolate Compound (YA3). The isolated Compound (YA3) may be further purified, for example, by chromatography and recrystallization.

(Reference Process AB)

Compound (YA1) can be prepared by reacting a compound of a formula (YB1) (hereinafter, described as Compound (YB1)) with a nitrosating agent, followed by reacting the resulting mixtures with a reducing agent.

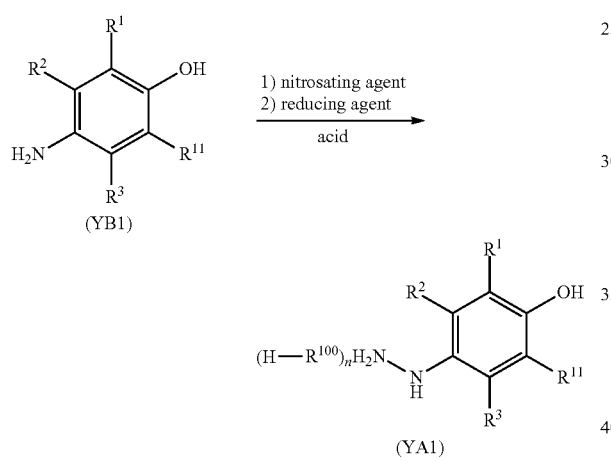

[wherein
$R^1$, $R^2$, $R^3$, $R^{11}$, $R^{100}$ and n are the same as described above]

This reaction is usually carried out in a solvent.

Examples of the solvent to be used in the reaction include alcohols such as methanol, ethanol, propanol, butanol; water; and mixed solvents thereof.

Examples of the nitrosating agent to be used in the reaction include sodium nitrite, potassium nitrite, tert-butyl nitrite and isoamyl nitrite.

Examples of the acid to be used in the reaction include acetic acid, hydrochloric acid and hydrobromic acid, and these aqueous solutions may be used as solvent.

Examples of the reducing agent to be used in the reaction include iron, zinc and tin, and specifically, include tin(II) chloride.

In the reaction, the nitrosating agent is used usually within a range of 1 to 10 molar ratio(s), the reducing agent is used usually within a range of 1 to 10 molar ratio(s) and the acid is used usually within a range of 1 to an excess molar ratio(s), as opposed as 1 mole of Compound (YB1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (YA1). Alternatively, the reaction mixtures are worked up (for example, concentration) to isolate Compound (YA1). The isolated Compound (YA1) may be further purified, for example, by chromatography and recrystallization.

(Reference Process AC)

Compound (YA3) can be prepared by reacting a compound of a formula (YC1) (hereinafter, described as Compound (YC1)) with an acid.

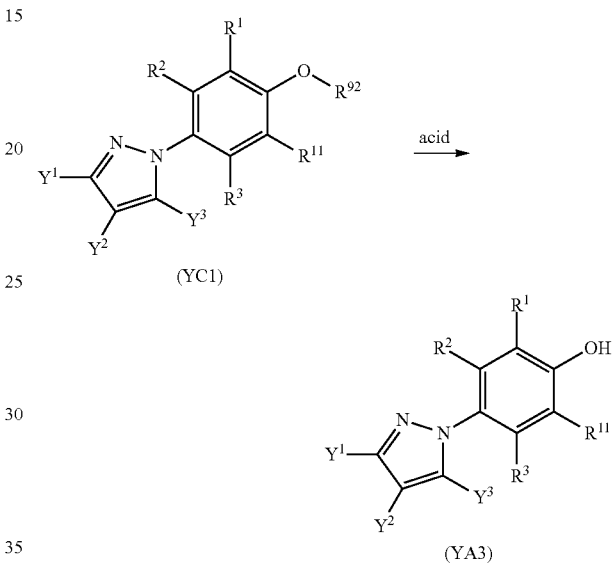

[wherein
$R^1$, $R^2$, $R^3$, $R^{11}$, $R^{92}$, $Y^1$, $Y^2$ and $Y^3$ are the same as described above]

This reaction is usually carried out in a solvent.

Examples of the solvent to be used in the reaction include alcohols such as methanol, ethanol, propanol, butanol; water; acetic acid; and mixed solvents thereof.

Examples of the acid to be used in the reaction include acetic acid, hydrochloric acid and hydrobromic acid, and these aqueous solutions may be used as solvent.

In the reaction, the acid is used usually in a range of a large excess molar ratios as opposed as 1 mole of Compound (YC1).

The reaction temperature is usually within a range of −20 to 150° C. The reaction period of the reaction is usually within a range of 0.1 to 100 hours.

When the reaction is completed, the reaction mixtures are extracted with organic solvent(s), and the resulting organic layers are worked up (for example, drying and concentration) to isolate Compound (YA3). Alternatively, the reaction mixtures are worked up (for example, concentration) to isolate Compound (YA3). The isolated Compound (YA3) may be further purified, for example, by chromatography and recrystallization.

(Reference Process AD)

Compound (YC1) can be prepared by reacting a compound of a formula (YD1) (hereinafter, described as Compound (YD1)) with a compound of a formula (YD2) (hereinafter, described as Compound (YD2)) in the presence of a copper reagent and a base.

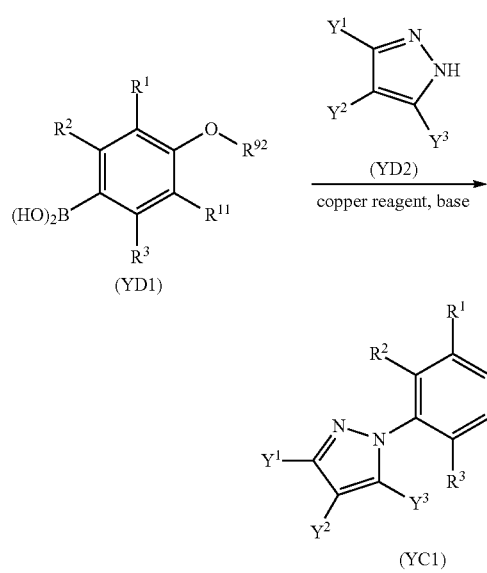

(YD1) + (YD2) → (YC1)

copper reagent, base

[wherein
$R^1$, $R^2$, $R^3$, $R^{11}$, $R^{92}$, $Y^1$, $Y^2$ and $Y^3$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; alcohols such as methanol, ethanol, propanol, butanol; water; and mixed solvents thereof.

Examples of the copper reagent to be used in the reaction include copper(II) acetate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (YD2) is used usually within a range of 1 to 10 molar ratio(s), the copper reagent is used usually within a range of 1 to 10 molar ratio(s), and the base is used usually within a range of 1 to 10 molar ratio(s), as opposed as 1 mole of Compound (YD1).

If necessary, dehydration agent such as molecular sieve may be used in the reaction, and the dehydration agent is used usually within a range of 100 to 500 percent by mass as opposed as 1 mole of Compound (YD1).

The reaction temperature is usually within a range of −20 to 150° C. The reaction period of the reaction is usually within a range of 0.1 to 120 hours.

When the reaction is completed, the reaction mixtures are extracted with organic solvent(s), and the resulting organic layers are worked up (for example, drying and concentration) to isolate Compound (YC1). The isolated Compound (YC1) may be further purified, for example, by chromatography and recrystallization.

(Reference Process AE)

A compound of a formula (YE2) (hereinafter, described as Compound (YE2)) can be prepared by reacting a compound of a formula (YE1) (hereinafter, described as Compound (YE1)) with an acid.

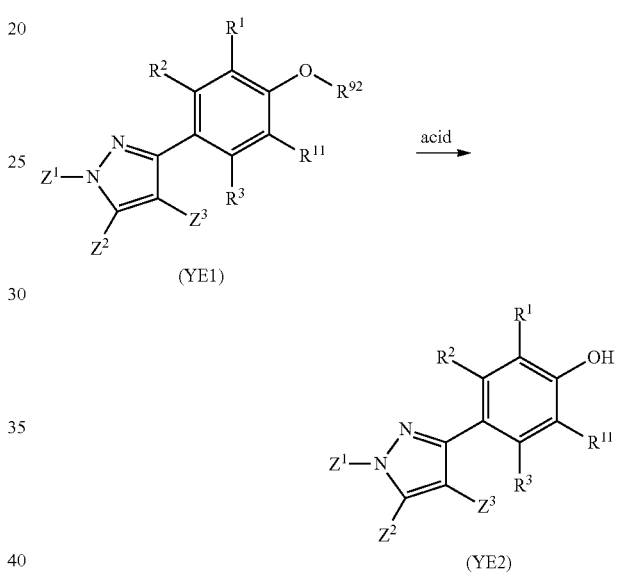

[wherein
$R^1$, $R^2$, $R^3$, $R^{11}$, $R^{92}$, $Z^1$, $Z^2$ and $Z^3$ are the same as described above]

The reaction can be carried out according to Reference Process AC.

(Reference Process AF)

A compound of a formula (YF2) (hereinafter, described as Compound (YF2)) can be prepared by reacting a compound of a formula (YF1) (hereinafter, described as Compound (YF1)) with an acid.

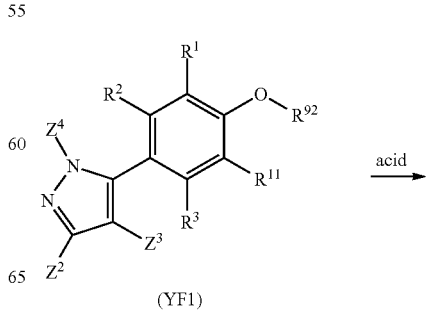

(YF1)

-continued

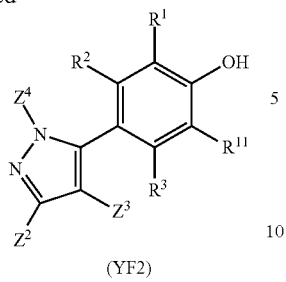

(YF2)

[wherein
$R^1$, $R^2$, $R^3$, $R^{11}$, $R^{92}$, $Z^2$, $Z^3$ and $Z^4$ are the same as described above]

The reaction can be carried out according to Reference Process AC.

(Reference Process AG)

Compound (YE1) can be prepared by reacting a compound of a formula (YG1) (hereinafter, described as Compound (YG1)) with Compound (H-1) in the presence of a base.

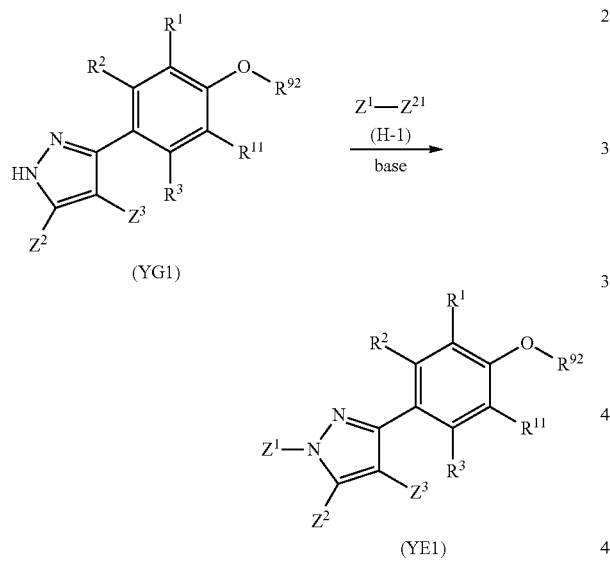

[wherein
$R^1$, $R^2$, $R^3$, $R^{11}$, $R^{92}$, $Z^1$, $Z^2$, $Z^3$ and $Z^{21}$ are the same as described above]

The reaction can be carried out according to Process H.

(Reference Process AH)

Compound (YF2) can be prepared by reacting Compound (YG1) with Compound (I-1) in the presence of a base.

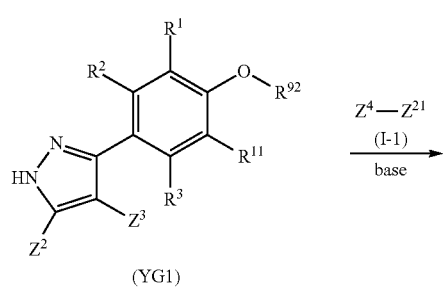

-continued

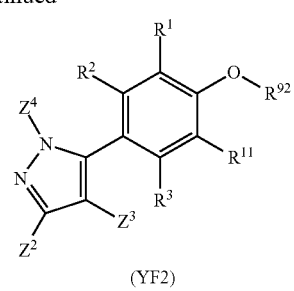

(YF2)

[wherein
$R^1$, $R^2$, $R^3$, $R^{11}$, $R^{92}$, $Z^2$, $Z^3$, $Z^4$ and $Z^{21}$ are the same as described above]

The reaction can be carried out according to Process I.

(Reference Process AI)

A compound of a formula (YI2) (hereinafter, described as Compound (YI2)) can be prepared by reacting a compound of a formula (YI1) (hereinafter, described as Compound (YI1)) with a hydrazine compound.

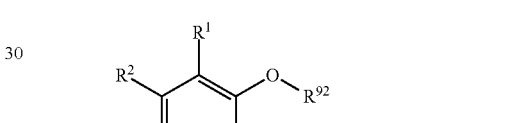

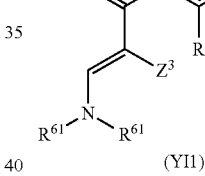

(YI1)

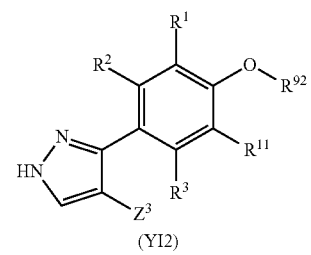

(YI2)

[wherein
$R^1$, $R^2$, $R^3$, $R^{11}$, $R^{61}$, $R^{92}$ and $Z^3$ are the same as described above]

The reaction can be carried out according to Process F.

(Reference Process AJ)

Compound (YG1) can be prepared by reacting a compound of a formula (YJ1) (hereinafter, described as Compound (YJ1)) with a hydrazine compound.

195

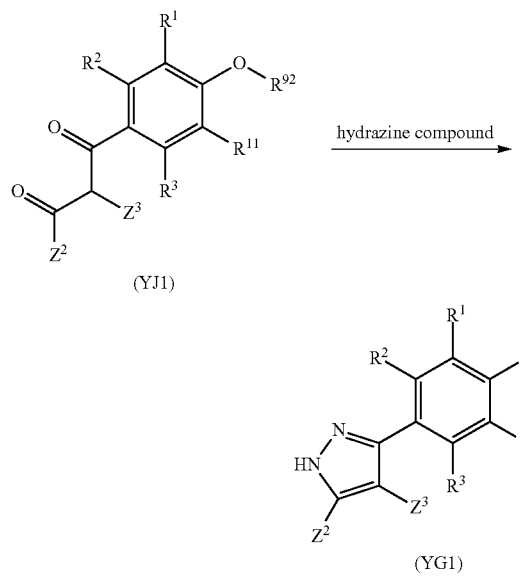

(YJ1)

hydrazine compound →

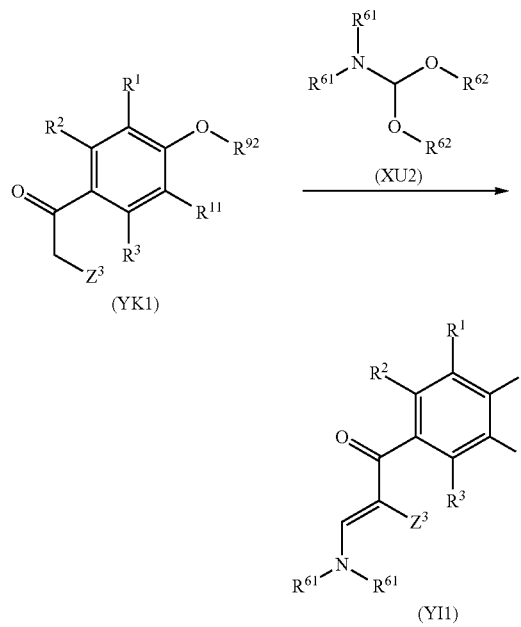

(YG1)

[wherein

R¹, R², R³, R¹¹, R⁹², Z² and Z³ are the same as described above]

The reaction can be carried out according to Process G.

(Reference Process AK)

Compound (YI1) can be prepared by reacting a compound of a formula (YK1) (hereinafter, described as Compound (YK1)) with Compound (XU2).

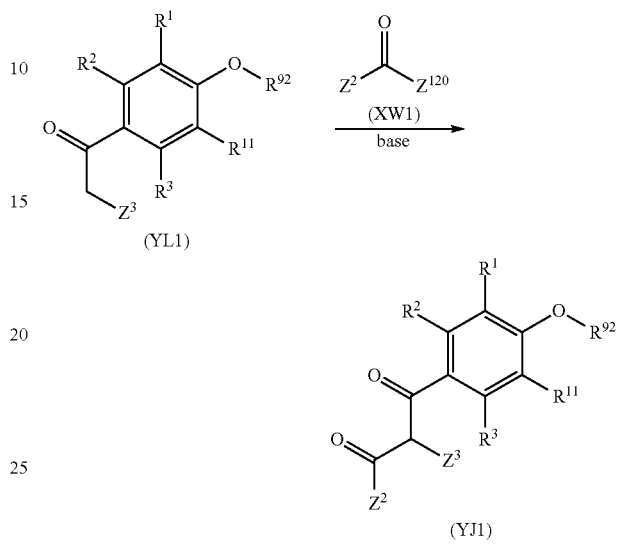

[wherein

R¹, R², R³, R⁶¹, R⁶², R⁹² and Z³ are the same as described above]

The reaction can be carried out according to Reference Process U.

196

(Reference Process AL)

Compound (YJ1) can be prepared by reacting a compound of a formula (YL1) (hereinafter, described as Compound (YL1)) with Compound (XW1) in the presence of a base.

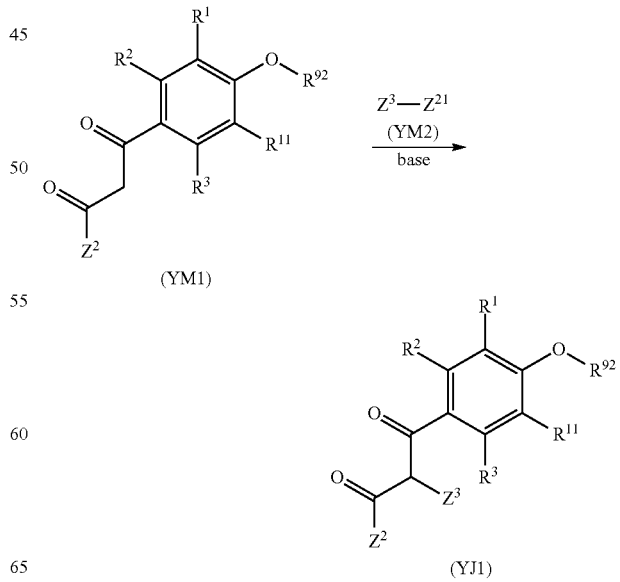

[wherein

R¹, R², R³, R¹¹, R⁹², Z², Z³ and Z¹²⁰ are the same as described above]

The reaction can be carried out according to Reference Process W.

(Reference Process AM)

Compound (YJ1) can be prepared also by reacting a compound of a formula (YM1) (hereinafter, described as Compound (YM1)) with a compound of a formula (YM2) (hereinafter, described as Compound (YM2)) in the presence of a base.

[wherein

R¹, R², R³, R¹¹, R⁹², Z², Z³ and Z²¹ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (YM2) to be used in the reaction can be usually used as a commercially available product. Specific examples include alkyl halides such as chlorodifluoromethane, methyl bromide, ethyl bromide, propyl bromide, methyl iodide, ethyl iodide, propyl bromide, aryl bromide, cyclopropyl bromide, 1,1-difluoro-2-iodoethane; alkyl or aryl sulfates such as dimethyl sulfate, methyl p-toluenesulfonate, ethyl p-toluenesulfonate, propyl p-toluenesulfonate, methyl methanesulfonate, ethyl methanesulfonate and propyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

If necessary, an additive agent may be added to the reaction, and specifically, includes tetrabutylammonium bromide and tetrabutylammonium fluoride and the others.

In the reaction, Compound (YM2) is used usually within a range of 1 to 10 molar ratio(s), the base is used usually within a range of 1 to 10 molar ratio(s), and the additive agent is used usually within a range of 0.01 to 1 molar ratio(s), as opposed to 1 mole of Compound (YM1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (YJ1). The isolated present Compound (YJ1) may be further purified, for example, by chromatography and recrystallization.

(Reference Process AN)

A compound of a formula (YN2) (hereinafter, described as Compound (YN2)) can be prepared by reacting a compound of a formula (YN1) (hereinafter, described as Compound (YN1)) with an acid.

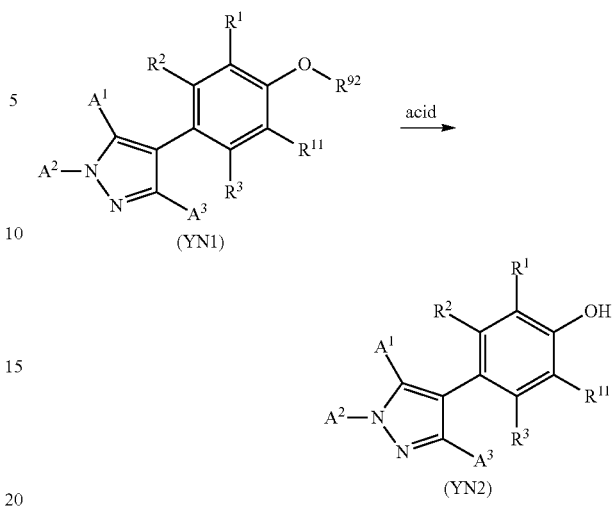

[wherein

R¹, R², R³, R¹¹, R⁹², A¹, A² and A³ are the same as described above]

The reaction can be carried out according to Reference Process AC.

(Reference Process AO)

Compound (YN1) can be prepared by coupling a compound of a formula (YO1) (hereinafter, described as Compound (YO1)) with a compound of a formula (YO2) (hereinafter, described as Compound (YO2)) in the presence of a base and a catalyst.

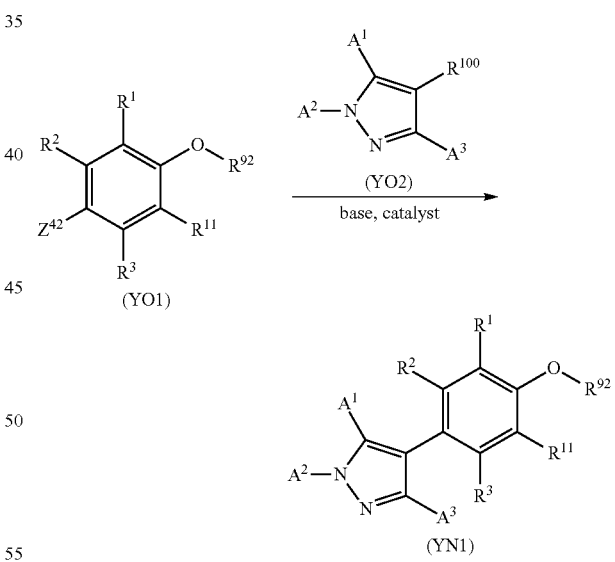

[wherein

R¹, R², R³, R¹¹, R⁹², R¹⁰⁰, A¹, A², A³ and Z⁴² are the same as described above]

The reaction can be carried out according to Process D.

(Reference Process AP)

Compound (YO2) can be prepared by coupling a compound of a formula (YP1) (hereinafter, described as Compound (YP1)) with a compound of a formula (YP2) (hereinafter, described as Compound (YP2)) in the presence of a base.

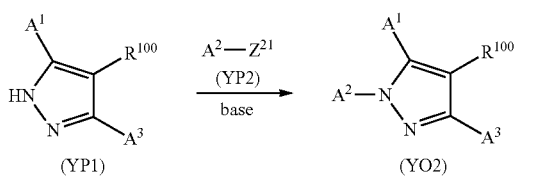

[wherein
R$^{100}$, A$^1$, A$^2$, A$^3$ and Z$^{21}$ are the same as described above]

The reaction can be carried out according to Process H.

(Reference Process AQ)

Compound (YE1) wherein Z$^3$ represents R$^{51}$, i.e., a compound of a formula (YE1-1) (hereinafter, described as Compound (YE1-1)) can be prepared by coupling a compound of a formula (YE1) wherein Z$^3$ represents R$^{100}$, i.e., a compound of a formula (YE1-2) (hereinafter, described as Compound (YE1-2)) with Compound (E-2) in the presence of a base and a catalyst.

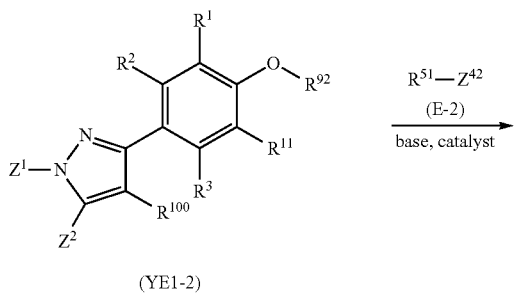

[wherein
R$^1$, R$^2$, R$^3$, R$^{11}$, R$^{51}$, R$^{92}$, R$^{100}$, Z$^1$, Z$^2$ and Z$^{42}$ are the same as described above]

The reaction can be carried out according to Process L.

(Reference Process AR)

Compound (YE1-2) can be prepared by reacting a compound of a formula (YE1) wherein Z$^3$ represents a hydrogen atom, i.e., a compound of a formula (YE1-3) (hereinafter, described as Compound (YE1-3)) with a halogenating agent.

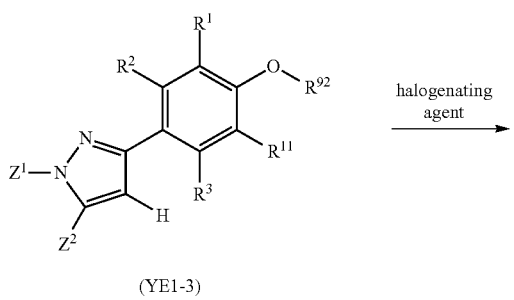

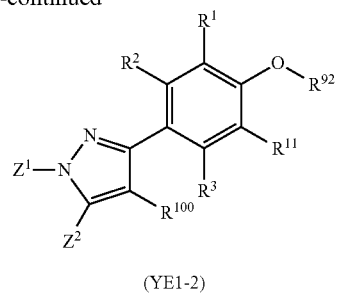

[wherein
R$^1$, R$^2$, R$^3$, R$^{11}$, R$^{92}$, R$^{100}$, Z$^1$ and Z$^2$ are the same as described above]

The reaction can be carried out according to Process J.

(Reference Process AS)

A compound of a formula (YE1) wherein Z$^1$ represents R$^{92}$ and Z$^2$ represents a chloro atom, i.e., a compound of a formula (YE1-11) (hereinafter, described as Compound (YE1-11)) can be prepared by reacting a compound of a formula (YE1) wherein Z$^1$ represents R$^{92}$ and Z$^2$ represents a hydroxy group, i.e., a compound of a formula (YE1-12) (hereinafter, described as Compound (YE1-12)) with a chlorinating agent.

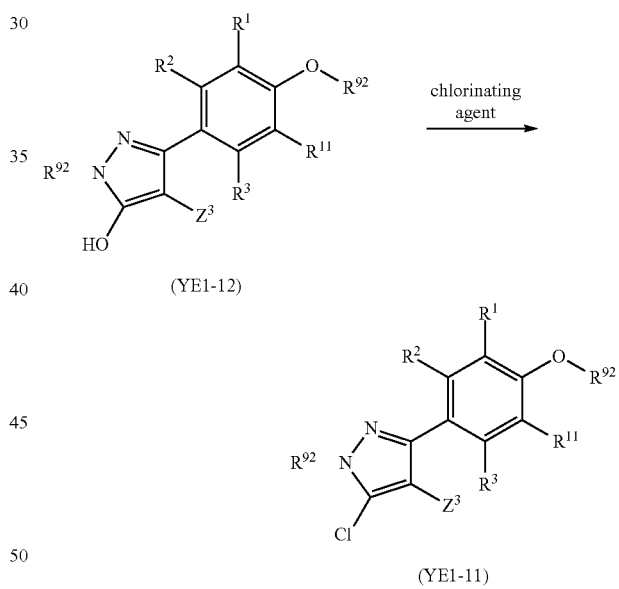

[wherein
R$^1$, R$^2$, R$^3$, R$^{11}$, R$^{92}$ and Z$^3$ are the same as described above]

This reaction is usually carried out in a solvent or in a solvent-free system.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

The chlorinating agent to be used in the reaction may be usually used as a commercially available product. Specific examples include thionyl chloride, phosphorous oxychloride, phosphorous pentachloride and mixtures thereof. If necessary, a base may be added to the reaction, and specifically, includes organic bases such as triethylamine, pyridine, N-methylmorpholine, N-methylpiperidine, 4-dimethylaminopyridine, diisopropylethylamine, lutidine, collidine, diazabicycloundecene and diazabicyclononene.

In the reaction, the chlorinating agent is used usually within a range of 1 to a large excess molar ratio(s), and the base is used usually within a range of 1 to 10 molar ratio(s), as opposed to 1 mole of Compound (YE1-12).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YE1-11). The isolated present Compound (YE1-11) may be further purified, for example, by chromatography and recrystallization.

(Reference Process AT)

Compound (YE1-12) can be prepared by reacting a compound of a formula (YE1-13) (hereinafter, described as Compound (YE1-13)) with Compound (AT1).

dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; water; and mixed solvents thereof. If necessary, an acid may be added to the reaction, and examples of the acid to be used in the reaction include hydrochloric acid, sulfuric acid, acetic acid, hydrobromic acid and p-toluenesulfonic acid.

In the reaction, Compound (AT1) is used usually within a range of 1 to 100 molar ratio(s), and the acid is used usually within a range of 1 to 100 molar ratio(s), as opposed to 1 mole of Compound (YE1-13).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying, concentration and filtration) to isolate Compound (YE1-12). The isolated present Compound (YE1-12) may be further purified, for example, by chromatography and recrystallization.

(Reference Process AU)

Compound (YE1-13) can be prepared by reacting Compound (YL1) with a compound of a formula (AU1) (hereinafter, described as Compound (AU1)) in the presence of a base.

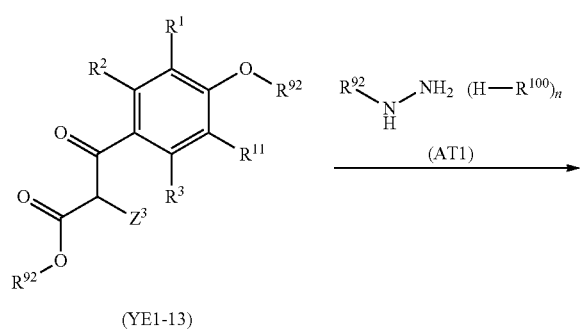

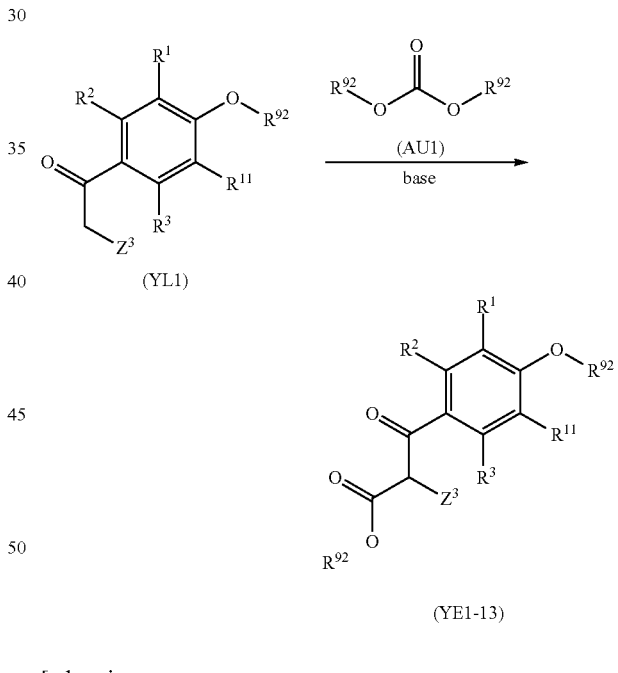

[wherein
R$^1$, R$^2$, R$^3$, R$^{11}$, R$^{92}$ and Z$^3$ are the same as described above; and n is 0 or 1]

This reaction is usually carried out in a solvent or in a solvent-free system.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform,

[wherein
R$^1$, R$^2$, R$^3$, R$^{11}$, R$^{92}$ and Z$^3$ are the same as described above]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (AU1) is used usually within a range of 1 to 10 molar ratio(s), and the base is used usually within a range of 1 to 10 molar ratio(s), as opposed to 1 mole of Compound (YL1).

The reaction temperature is usually within a range of −20 to 150° C. The reaction period of the reaction is usually within a range of 0.1 to 24 hours.

If necessary, an additive agent may be added to the reaction, and specifically includes, for example, 18-crown-6, dibenzo-18-crown-6 and the others. These additive agent is used usually within a range of 0.001 to 1.2 molar ratios as opposed to 1 mole of Compound (XL1).

When the reaction is completed, the reaction mixtures are extracted with organic solvent(s), and the resulting organic layers are worked up (for example, drying and concentration) to isolate Compound (YE1-13). The isolated present Compound (YE1-13) may be further purified, for example, by chromatography and recrystallization.

(Reference Process AV)

Compound (XV1-2) can be prepared by reacting a compound of a formula (XV1-3) (hereinafter, described as Compound (XV1-3)) in the presence of an acid.

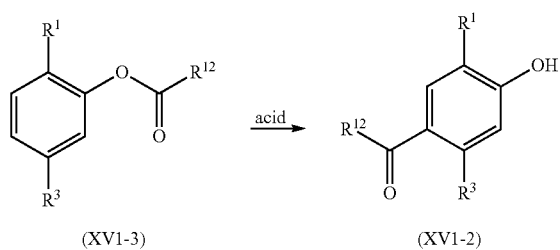

(XV1-3)          (XV1-2)

[wherein $R^1$, $R^3$ and $R^{12}$ are the same as described above]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as nitromethane, acetonitrile, propionitrile; and mixed solvents thereof.

Examples of the acid to be used in the reaction include aluminum trichloride, titanium chloride, iron trichloride, hydrogen fluoride, hypochlorous acid and polyphosphoric acid.

In the reaction, the acid is used usually within a range of 1 to 10 molar ratio(s) as opposed to 1 mole of Compound (XV1-3).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YV1-2). The isolated present Compound (YV1-2) may be further purified, for example, by chromatography and recrystallization.

(Reference Process AW)

Compound (XV1-3) can be prepared by reacting a compound of a formula (XV1-4) (hereinafter, described as Compound (XV1-4)) with a compound of a formula (AW1) (hereinafter, described as Compound (AW1)) in the presence of a base.

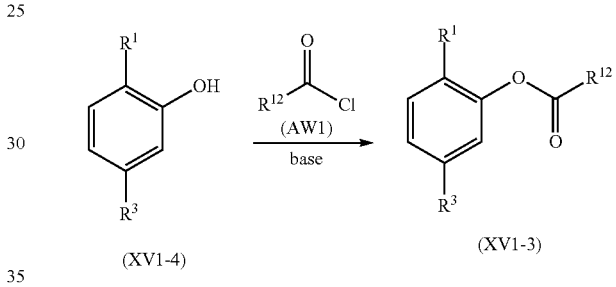

(XV1-4)                    (XV1-3)

[wherein $R^1$, $R^3$ and $R^{12}$ are the same as described above]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as nitromethane, acetonitrile, propionitrile; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (AW1) is used usually within a range of 1 to 10 molar ratio(s), and the base is used usually within a range of 1 to 10 molar ratio(s), as opposed to 1 mole of Compound (XV1-4).

The reaction temperature is usually within a range of −78 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YV1-3). The isolated present Compound (YV1-3) may be further purified, for example, by chromatography and recrystallization.

(Reference Process AX)

Compound (YE1) wherein $Z^1$ represents $R^{92}$, and $Z^2$ represents Rf, i.e., a compound of a formula (YE1-Rf) (hereinafter, described as Compound (YE1-Rf), can be prepared by reacting a compound of a formula (YE1-Rf1) (hereinafter, described as Compound (YE1-Rf1)) in the presence of an acid.

(YE1-Rf1)

(YE1-Rf)

[wherein
$R^1$, $R^2$, $R^3$, $R^{11}$, $R^{92}$ and $Z^3$ are the same as described above; and Rf represents a C1-C6 perfluoroalkyl group, a 1,1-difluoroethyl group, a 1,1-difluoropropyl group or a 2,2-difluoropropyl group]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; alcohols such as methanol, ethanol, isopropanol; water; and mixed solvents thereof.

Examples of the acid to be used in the reaction include acetic acid, hydrochloric acid and hydrobromic acid, and these aqueous solutions may be used as solvent.

In the reaction, the acid is used usually within a range of 1 to 10 molar ratio(s) as opposed to 1 mole of Compound (YE1-Rf1).

The reaction temperature is usually within a range of −78 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YE1-Rf). The isolated present Compound (YE1-Rf) may be further purified, for example, by chromatography and recrystallization.

(Reference Process AZ)

Compound (YE1-Rf1) and a compound of a formula (YF2) wherein $Z^2$ represents Rf and $Z^4$ represents $R^{92}$, i.e., a compound of a formula (YF2-Rf) (hereinafter, described as Compound (YF2-Rf)), can be prepared by reacting a compound of a formula (YJ1) wherein $Z^2$ represents Rf, i.e., a compound of a formula (YJ1-Rf) (hereinafter, described as Compound (YJ1-Rf)) with Compound (AT1).

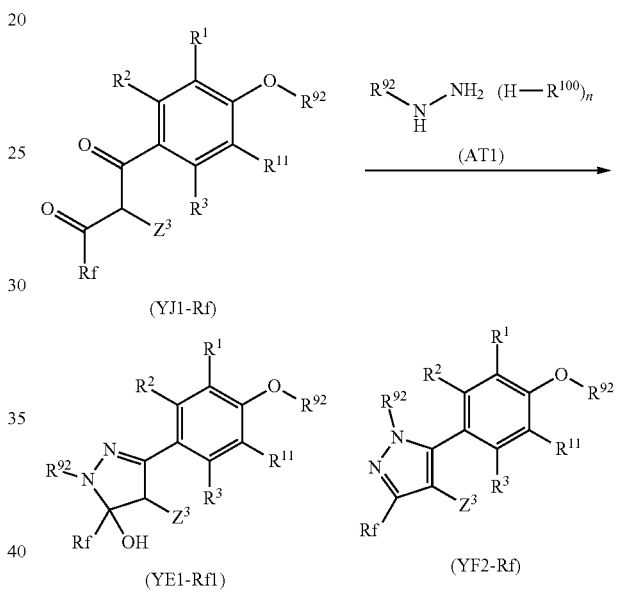

(YJ1-Rf)

(YE1-Rf1)

(YF2-Rf)

[wherein
$R^1$, $R^2$, $R^3$, $R^{11}$, $R^{92}$, $Z^3$ and Rf are the same as described above; and n is 0 or 1]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; alcohols such as methanol, ethanol, isopropanol; water; and mixed solvents thereof.

In the reaction, Compound (AT1) is used usually within a range of 1 to 10 molar ratio(s) as opposed to 1 mole of Compound (YJ1-Rf1).

The reaction temperature is usually within a range of −78 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YE1-Rf1) and Compound (YF2-Rf). The isolated present Compound (YE1-Rf1) and the isolated present Compound (YF2-Rf) may be further purified, for example, by chromatography and recrystallization.
(Reference Process BA)

Compound (YE1-11) wherein $Z^3$ represents an aldehyde group, i.e., a compound of a formula (YE1-11-1) (hereinafter, described as Compound (YE1-11-1)), a compound of a formula (YE1-12-2) (hereinafter, described as Compound (YE1-12-2)), and a compound of a formula (YE1-11-4) (hereinafter, described as Compound (YE1-11-4)) can be prepared by reacting a compound of a formula (YE1-12) wherein $Z^3$ represents a hydrogen atom, i.e., a compound of a formula (YE1-12-1)) (hereinafter, described as Compound (YE1-12-1)) with a formylating agent, which is prepared from N,N-dimethylformamide and phosphorus oxychloride, followed by reacting the resulting mixtures with water.

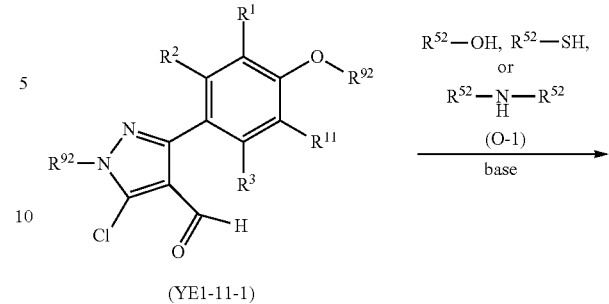

(YE1-11-1)

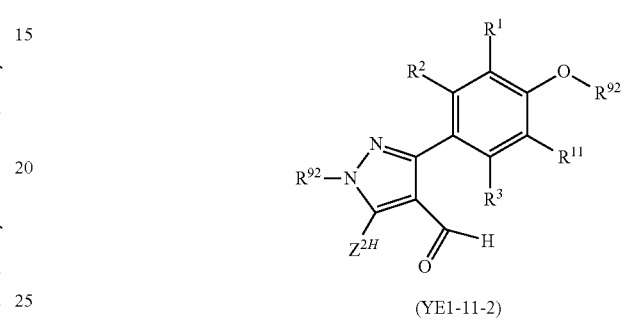

(YE1-11-2)

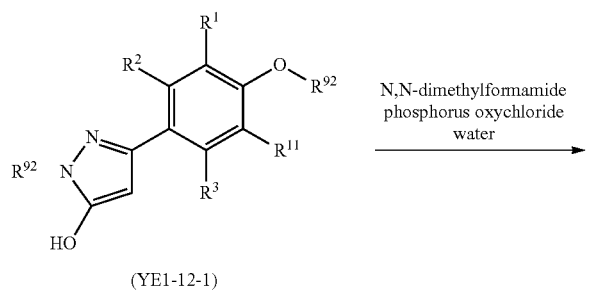

(YE1-12-1)

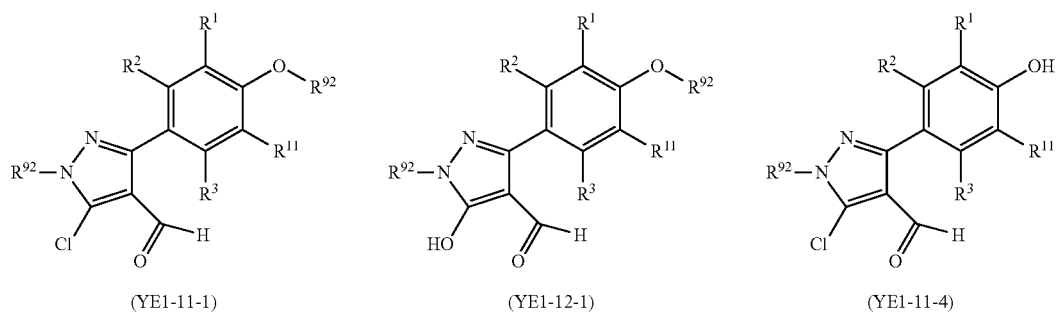

(YE1-11-1)  (YE1-12-1)  (YE1-11-4)

[wherein
$R^1$, $R^2$, $R^3$, $R^{11}$ and $R^{92}$ are the same as defined above]

The reaction can be carried out according to Process K.
(Reference Process BB)

Compound (YE1) wherein $Z^2$ represents $Z^{2H}$ and $Z^3$ represents an aldehyde group, i.e., a compound of a formula (YE1-11-2) (hereinafter, described as Compound (YE1-11-2)) can be prepared by reacting a compound of a formula (YE1-11-1) with Compound (O-1) in the presence of a base.

[wherein
$R^1$, $R^2$, $R^3$, $R^{11}$, $R^{52}$, $R^{92}$ and $Z^{2H}$ are the same as defined above]

The reaction can be carried out according to Process P.
(Reference Process BC)

Compound (YE1) wherein $Z^2$ represents $Z^{2H}$ and $Z^3$ represents a methyl group, i.e., a compound of a formula (YE1-11-3) (hereinafter, described as Compound (YE1-11-3)) can be prepared by reacting a compound of a formula (YE1-11-2) with a reducing agent in the presence of a base.

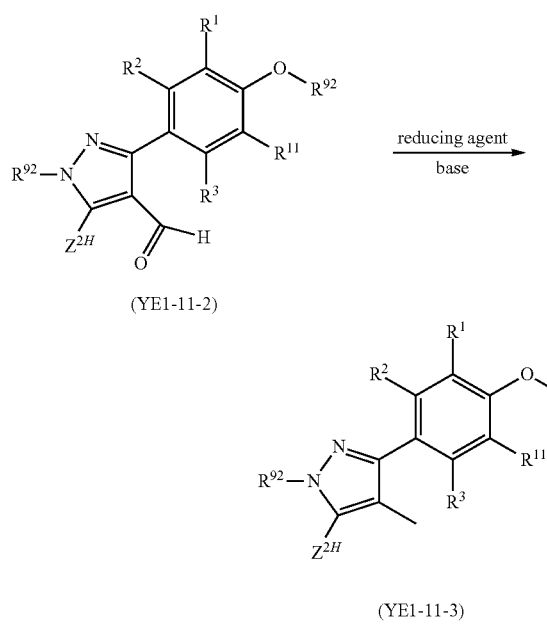

(YE1-11-2)

(YE1-11-3)

[wherein
R$^1$, R$^2$, R$^3$, R$^{11}$, R$^{92}$ and Z$^{2H}$ are the same as defined above]

The reaction can be carried out according to Process Q.

(Reference Process BD)

Compound (YG1) wherein Z$^2$ represents a hydroxy group, i.e., a compound of a formula (YG1-1) (hereinafter, described as Compound (YG1-1)) can be prepared by reacting a compound of a formula (YJ1) wherein Z$^2$ represents O—R$^{92}$, a compound of a formula (YJ1-1) (hereinafter, described as Compound (YJ1-1)) with a hydrazine compound.

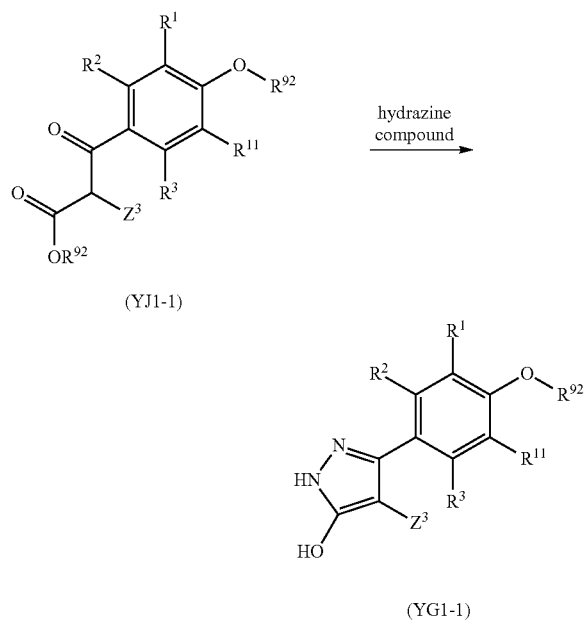

(YJ1-1)

(YG1-1)

[wherein
R$^1$, R$^2$, R$^3$, R$^{11}$, R$^{92}$ and Z$^3$ are the same as defined above]
The reaction can be carried out according to Process Q.

(Reference Process BE)

Compound (YE1) wherein Z$^1$ and Z$^2$ combines together with the carbon atoms to which they are attached to form a ring containing an oxygen atom, i.e., a compound of a formula (YG1-C) (hereinafter, described as Compound (YG1-C)) can be prepared by reacting Compound (YG1-1) with a compound of a formula (BE-1) (hereinafter, described as Compound (BE-1)) in the presence of a base.

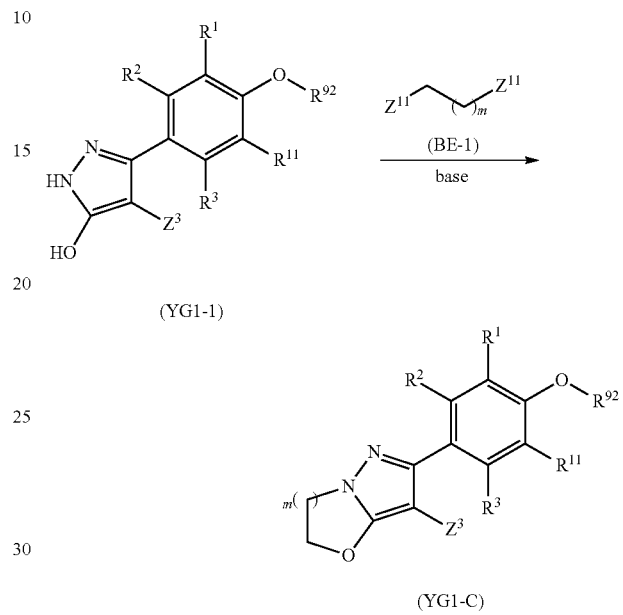

(YG1-1)

(YG1-C)

R$^1$, R$^2$, R$^3$, R$^{11}$, R$^{92}$, Z$^{11}$ and Z$^3$ are the same as defined above; m is an integer of 1 to 3; and a hydrogen atom of Compound (BE-1) may be substituted with atoms or groups selected from Group P$^1$]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (BE-1) is used usually within a range of 1 to 10 molar ratio(s), and the base is used usually within a range of 1 to 10 molar ratio(s), as opposed to 1 mole of Compound (XG1-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (YG1-C). The isolated present Compound (YG1-C) may be further purified, for example, by chromatography and recrystallization.

(Reference Process BF)

A compound of a formula (YE1-11-ORf) (hereinafter, described as Compound (YE1-11-ORf)) can be prepared by reacting Compound (YE1-12-2) with a fluoromethylating agent in the presence of a base.

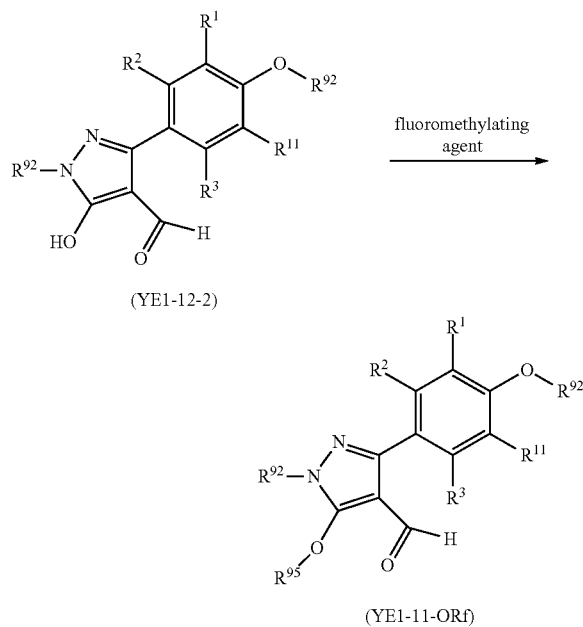

[$R^1$, $R^2$, $R^3$, $R^{11}$ and $R^{92}$ are the same as defined above; and $R^{95}$ represents a trifluoromethyl group or a difluoromethyl group]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the fluoromethylating agent to be used in the reaction include trifluoromethyl chloride, trifluoromethyl bromide, trifluoromethyl iodide, difluoromethylchloride, difluoromethylbromide, difluoromethyliodide, 3,3-dimethyl-1-(trifluoromethyl)-1,2-benziodoxole, 5-(trifluoromethyl)dibenzothiophene-tetrafluoroborate, 5-(trifluoromethyl)dibenzothiophene-trifluoromethanesulfonate, 3,3-dimethyl-1-(difluoromethyl)-1,2-benziodoxole, 5-(difluoromethyl)dibenzothiophene-tetrafluoroborate, 5-(difluoromethyl)dibenzothiophene-trifluoromethanesulfonate and bromodifluoromethyl dimethylphosphonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, the fluoromethylating agent is used usually within a range of 1 to 10 molar ratio(s), and the base is used usually within a range of 1 to 10 molar ratio(s), as opposed to 1 mole of Compound (YE1-12-2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (YE1-11-ORf). The isolated present Compound (YE1-11-ORf) may be further purified, for example, by chromatography and recrystallization.

Although a form used for the present compound may be the present compound as itself, the present compound is usually prepared by mixing the present compound with solid carriers, liquid carriers, gas carriers, surfactants and the others, and if necessary, adding stickers, dispersers and stabilizers, to formulate into wettable powders, water dispersible granules, flowables, granules, dry flowables, emulsifiable concentrates, aqueous solutions, oil solutions, smoking agents, aerosols, microcapsules and the others, In these formulations, the present compound is contained in a range of usually 0.1 to 99%, preferably 0.2 to 90% by weight.

Examples of the solid carrier include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, hexane, cyclohexane and kerosene), esters (for example, ethyl acetate and butyl acetate), nitriles (for example, acetonitrile and isobutyronitrile), ethers (for example, dioxane and diisopropylether), acid amides (for example, N,N-dimethyl formamide (DMF) and dimethylacetamide), halogenated hydrocarbons (for example, dichloroethane, trichloro ethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of other auxiliary agents for formulation include stickers, dispersers and stabilizers, specifically casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof and the others.

The method for applying the present compound is not particularly limited, as far as the applying form is a form by which the present compound may be applied substantially, and includes, for example, an application to plants such as a foliage application; an application to area for cultivating plants such as a soil-treatment; and an application to seed such as seed disinfection.

The application dose varies depending on weather conditions, dosage forms, timing of application, methods of application, areas to be applied, target diseases and target crops etc., but is in the range of usually from 1 to 500 g, and preferably from 2 to 200 g per 1,000 m² of the area to be applied. The emulsifiable concentrate, the wettable powder or the suspension concentrate, etc., is usually applied by diluting it with water. In this case, the concentration of the present compound after dilution is in the range of usually 0.0005 to 2% by weight, and preferably 0.005 to 1% by weight. The dust formulation or the granular formulation etc., is usually applied as itself without diluting it. In the application to seeds, the amount of the present compound is in the range of usually from 0.001 to 100 g, and preferably from 0.01 to 50 g per 1 kg of the seeds.

Herein, examples of the place where the pests live include paddy fields, fields, tea gardens, orchards, non-agricultural lands, houses, nursery trays, nursery boxes, nursery soils and nursery bed.

Also, in another embodiment, for example, the present compound can be administered to the inside (inside of the body) or the outside (body surface) of the below-mentioned vertebrate to exterminate systemically or unsystemically the living things or parasites which are parasitic on the vertebrate. Examples of a method of the internal medication include an oral administration, an anal administration, a transplanation, an administration via injection subcutaneously, intramuscularly or intravenously. Examples of a method of outside medication include a transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., but it is desirable in general to administer the present compound so that a dose of the active ingredient (the present compound or salts thereof) is in the range of generally from 0.1 mg to 2,000 mg and preferably 0.5 mg to 1,000 mg per 1 kg of body weight of the animal.

The present compound can be used as agent for controlling plant disease in agricultural lands such as fields, paddy fields, lawns, orchards. The compound of the present invention can control diseases occurred in the agricultural lands or the others for cultivating the following "plant".

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli, cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and Swiss chard),
lamiaceous vegetables (for example, *Perilla frutescens*, mint and basil),
strawberry, sweet potato, *Dioscorea japonica*, colocasia and the others;

Flowers:
Ornamental Foliage Plants:
Fruits:
pomaceous fruits (for example, apple, pear, Japanese pear, Chinese quince and quince),
stone fruits (for example, peach, plum, nectarine, *Prunus mume*, cherry fruit, apricot and prune),
citrus fruits (for example, Citrus unshiu, orange, lemon, lime and grapefruit),
nuts (for example, chestnut, walnuts, hazelnuts, almond, pistachio, cashew nuts and macadamia nuts),
berry fruits (for example, blueberry, cranberry, blackberry and raspberry),
grape, kaki persimmon, olive, Japanese plum, banana, coffee, date palm, coconuts, and the others;

Trees Other than Fruit Trees:
tea, mulberry, flowering plant,
roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate);
and the others.

The above-mentioned "plant" includes genetically modified crops.

The pests on which the present compound has a control efficacy include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), and take all disease (*Gaeumannomyces graminis*);

Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and rhizoctonia seeding blight (*Rhizoctonia solani*);

Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum gfaminicola*), gray leaf spot (*Cercospora zeae-maydis*), eyespot (*Kabatiella zeae*), and phaeosphaeria leaf spot (*Phaeosphaeria maydis*);

Cotton diseases: anthracnose (*Colletotrichum gossypii*), grey mildew (*Ramuraria areola*), alternaria leaf spot (*Alternaria macrospora, A. gossypii*);

Coffee diseases: rust (*Hemileia vastatrix*);

Rape seed diseases: sclerotinia rot (*Sclerotinia sclerotiorum*), black spot (*Alternaria brassicae*), and black leg (*Phoma lingam*);

Citrus diseases: melanose (*Diaporthe citri*), scab (*Elsinoe fawcetti*), and fruit rot (*Penicillium digitatum, P. italicum*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Colletotrichum acutatum*);

Pear diseases: scab (*Venturia nashicola, V. pirina*), black spot (*Alternaria alternata* Japanese pear pathotype) and rust (*Gymnosporangium haraeanum*);

Peach diseases: brown rot (*Monilinia fructicola*), scab (*Cladosporium carpophilum*) and *Phomopsis* rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.) and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*);

Eggplant disease: brown spot (*Phomopsis vexans*) and powdery mildew (*Erysiphe cichoracearum*);

Diseases of Cruciferous Vegetables: alternaria leaf spot (*Alternaria japonica*), white spot (*Cercosporella brassicae*), clubroot (*Plasmodiophora parasitica*), downy mildew (*Peronospora parasitica*);

Welsh onion diseases: rust (*Puccinia allii*);

Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia aerial blight (*Rhizoctonia solani*), septoria brown spot (*Septoria glycines*), and frog eye leaf spot (*Cercospora sojina*);

Kindney bean diseases: anthracnose (*Colletotrichum lindemthianum*);

Peanut diseases: early leaf spot (*Cercospora personata*), late leaf spot (*Cercospora arachidicola*) and southern blight (*Sclerotium rolfsii*);

Garden pea diseases: powdery mildew (*Erysiphe pisi*);

Potato diseases: early blight (*Alternaria solani*), late blight (*Phytophthora infestans*), and verticillium wilt (*verticillium albo-atrum, V. dahliae, V. nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theaesinensis*);

Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: cercospora leaf spot (*Cercospora beticola*), leaf blight (*Thanatephorus cucumeris*), root rot (*Thanatephorus cucumeris*) and aphanomyces root rot (*Aphanomyces sochlioides*);

Rose diseases: black spot (*Diplocarpon rosae*) and powdery mildew (*Sphaerotheca pannosa*);

Diseases of *Chrysanthemum*: leaf blight (*Septoria chrysanthemi-indici*) and white rust (*Puccinia horiana*);

Onion diseases: botrytis leaf blight (*Botrytis cinerea, B. byssoidea, B. squamosa*), gray-mold neck rot (*Botrytis slli*), and small sclerotial rot (*Botrytis squamosa*);

Various crops diseases: gray mold (*Botrytis cinerea*), and sclerotinia rot (*Sclerotinia sclerotiorum*);

Diseases of Japanese radish: alternaria leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola*).

Hemiptera:

Delphacidae (for example, *Laodelphax striatellus, Nilaparvata lugens*, or *Sogatella furcifera*);

Deltocephalidae (for example, *Nephotettix cincticeps*, or *Nephotettix virescens*);

Aphididae (for example, *Aphis gossypii, Myzus persicae, Brevicoryne brassicae, Macrosiphum euphorbiae, Aulacorthum solani, Rhopalosiphum padi, Toxoptera citricidus*);

Pentatomidae (for example, *Nezara antennata, Riptortus clavetus, Leptocorisa chinensis, Eysarcoris parvus, Halyomorpha mista*, or *Lygus lineolaris*);

Aleyrodidae (for example, *Trialeurodes vaporariorum*, or *Bemisia argentifolii*);

Coccoidea (for example, *Aonidiella aurantii, Comstockaspis perniciosa, Unaspis citri, Ceroplastes rubens*, or *Icerya purchasi*);

Tingidae;

Psyllidae;

Bed bugs (*Cimex lectularius*) and the others;

Lepidoptera:

Pyralidae (for example, *Chilo suppressalis, Tryporyza incertulas, Cnaphalocrocis medinalis, Notarcha derogata, Plodia interpunctella, Ostrinia furnacalis, Hellula undalis, Pediasia teterrellus*);

Noctuidae (for example, *Spodoptera litura, Spodoptera exigua, Pseudaletia separata, Mamestra brassicae, Agrotis ipsilon, Plusia nigrisigna, Trichoplusia* spp., *Heliothis* spp, or *Helicoverpa* spp.;

Pieridae (for example, *Pieris rapae*);
Tortricidae (for example, *Adoxophyes* spp., *Grapholita molesta*, *Cydia pomonella*, *Leguminivora glycinivorella*, *Matsumuraeses azukivora*, *Adophyes orana fasciata*, *Adoxophyes* sp., *Homona magnanima*, *Archips fuscocupreanus*, *Cydia pomonella*);
Gracillariidae (for example, *Caloptilia theivora*, *Phyllonorycter ringoneella*);
Carposinidae (for example, *Carposina niponensis*);
Lyonetiidae (for example, *Lyonetia* spp.);
Lymantriidae (for example, *Lymantria* spp., or *Euproctis* spp.);
Yponomeutidae (for example, *Plutella xylostella*);
Gelechiidae (for example, *Pectinophora gossypiefla* or *Phthorimaea operculella*);
Arctiidae (for example, *Hyphantria cunea*);
Tineidae (for example, *Tinea translucens*, or *Tineola bisselliella*); and the others;
Thysanoptera:
Thysanoptera (for example, *Frankliniella occidentalis*, *Thrips palmi*, *Scirtothrips dorsalis*, *Thrips tabaci*, *Frankliniella intonsa*, *Frankliniella fusca*);
Diptera:
*Musca domestica*, *Culex popiens pallens*, *Tabanus trigonus*, *Hylemya antiqua*, *Hylemya platura*, *Anopheles sinensis*, *Agromyza oryzae*, *Hydrellia griseola*, *Chlorops oryzae*, *Dacus cucurbitae*, *Ceratitis capitata*, *Liriomyza trifolii*, and the others;
Coleoptera:
*Epilachna vigintioctopunctata*, *Aulacophora femoralis*, *Phyllotreta striolata*, *Oulema oryzae*, *Echinocnemus squameus*, *Lissorhoptrus oryzophilus*, *Anthonomus grandis*, *Callosobruchus chinensis*, *Sphenophorus venatus*, *Popillia japonica*, *Anomala cuprea*, *Diabrotica* spp., *Leptinotarsa decemlineata*, *Agriotes* spp., *Lasioderma serricorne*, *Anthrenus verbasci*, *Tribolium castaneum*, *Lyctus brunneus*, *Anoplophora malasiaca*, *Tomicus piniperda*), and the others;
Orthoptera:
*Locusta migratoria*, *Gryllotalpa africana*, *Oxya yezoensis*, *Oxya japonica*, and the others;
Hymenoptera:
*Athalia rosae*, *Acromyrmex* spp., *Solenopsis* spp., and the others;
Nematodes:
*Aphelenchoides besseyi*, *Nothotylenchus acris*, *Heterodera glycines*, *Meloidogyne incognita*, *Pratylenchus*, *Nacobbus aberrans*, and the others;
Blattariae:
  *Blattella germanica*, *Periplaneta fuliginosa*, *Periplaneta americana*, *Periplaneta brunnea*, *Blatta orientalis*, and the others;
Acarina:
  Tetranychidae (for example, *Tetranychus urticae*, *Panonychus citri*, or *Oligonychus* spp.);
Eriophyidae (for example, *Aculops pelekassi*);
Tarsonemidae (for example, *Polyphagotarsonemus latus*);
Tenuipalpidae;
Tuckerellidae;
Acaridae (for example, *Tyrophagus putrescentiae*);
Pyroglyphidae (for example, *Dermatophagoides farinae*, or *Dermatophagoides ptrenyssnus*);
Cheyletidae (for example, *Cheyletus eruditus*, *Cheyletus malaccensis*, or *Cheyletus moorei*);
Dermanyssidae;
and the others.

Also the formulation comprising the present compound or salts thereof can be used in the field relating to a treatment of livestock diseases or livestock industry, and for example, can exterminate the living things or parasites which are parasitic on the inside and/or the outside of a vertebrate such as human being, cow, sheep, pig, poultry, dog, cat and fish, so as to maintain public health. Examples of the pests include *Isodes* spp. (for example, *Isodes scapularis*), *Boophilus* spp. (for example, *Boophilus microplus*), *Amblyomma* spp., *Hyalomma* spp., *Rhipicephalus* spp. (for example, *Rhipicephalus sanguineus*), *Haemaphysalis* spp. (for example, *Haemaphysalis longicornis*), *dermacentor* spp., *Ornithodoros* spp. (for example, *Ornithodoros moubata*), *Dermahyssus gallinae*, *Ornithonyssus sylviarum*, *Sarcoptes* spp. (for example, *Sarcoptes scabiei*), *Psoroptes* spp., *Chorioptes* spp., *Demodex* spp., *Eutrombicula* spp., *Ades* spp. (for example, *Aedes albopictus*), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., *Phthiraptera* (for example, *Damalinia* spp.), *Linognathus* spp., *Haematopinus* spp., *Ctenocephalides* spp. (for example, *Ctenocephalides felis*) *Xenosylla* spp., *monomorium pharaonis* and nematodes [for example, hairworm (for example, *Nippostrongylus brasiliensis*, *Trichostrongylus axei*, *Trichostrongylus colubriformis*), *Trichinella* spp. (for example, *Trichinella spiriralis*), *Haemonchus contortus*, *Nematodirus* spp. (for example, *Nematodirus battus*), *Ostertagia circumcincta*, *Cooperia* spp., *Hymenolepis nana*, and the others.

EXAMPLES

The following Examples including Preparation examples, Formulation examples and Test examples, serve to illustrate the present invention in more detail, which should not intend to limit the present invention.

The Preparation examples are shown below. $^1$H NMR means a proton nuclear magnetic resonance, spectrum and Tetramethyl silane is used as an internal standard and chemical shift ($\delta$) is expressed in ppm.

Preparation Example 1

A mixture of 1-(2-bromomethyl-3-fluorophenyl)-4-methyl-1,4-dihydrotetrazole-5-one (described in Reference Preparation example 1) 0.30 g, 2-methyl-4-(3,4,5-trimethyl-pyrazol-1-yl)-phenol (described in Reference Preparation example 28) 0.24 g, potassium carbonate 0.19 g and acetonitrile 10 ml was stirred with heating under reflux for four hours. After cooling to room temperature, the reaction mixtures was filtered, and the filtrates was then concentrated. The resulting residue was subjected to a silica gel column chromatography to give 1-{3-fluoro-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 1") 0.33 g.

Present compound 1

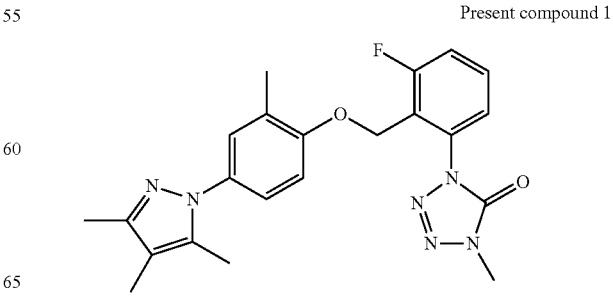

$^1$H-NMR (CDCl$_3$) δ: 7.52 (1H, td, J=8.2, 5.8 Hz), 7.35-7.27 (2H, m), 7.15-7.13 (1H, m), 7.10 (1H, dd, J=8.6, 2.3 Hz), 6.88 (1H, d, J=8.7 Hz), 5.29 (2H, d, J=1.0 Hz), 3.63 (3H, s), 2.22 (3H, s), 2.15 (3H, s), 2.01 (3H, s), 1.96 (3H, s).

Preparation Example 2

A mixture of 1-(2-bromomethyl-3-chlorophenyl)-4-methyl-1,4-dihydrotetrazole-5-one (described in Reference Preparation example 2) 0.30 g, 2-methyl-4-(3,4,5-trimethyl-pyrazol-1-yl)-phenol (described in Reference Preparation example 28) 0.23 g, potassium carbonate 0.17 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-chloro-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 1") 0.28 g.

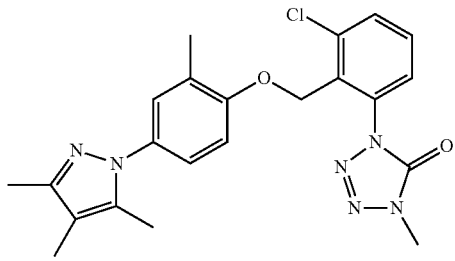

Present compound 2

$^1$H-NMR (CDCl$_3$) δ: 7.62 (1H, dd, J=8.1, 1.1 Hz), 7.48 (1H, t, J=8.1 Hz), 7.41 (1H, dd, J=7.8, 1.1 Hz), 7.15 (1H, d, J=2.4 Hz), 7.10 (1H, dd, J=8.7, 2.7 Hz), 6.87 (1H, d, J=8.5 Hz), 5.33 (2H, s), 3.62 (3H, s), 2.22 (3H, s), 2.16 (3H, s), 2.05 (3H, s), 1.96 (3H, s).

Preparation Example 3

A mixture of 1-(2-bromomethyl-3-bromophenyl)-4-methyl-1,4-dihydrotetrazole-5-one (described in Reference Preparation example 5) 2.5 g, 2-methyl-4-(3,4,5-trimethyl-pyrazol-1-yl)-phenol (described in Reference Preparation example 28) 1.6 g, potassium carbonate 1.29 g and acetonitrile 70 ml was stirred with heating under reflux for four hours. After cooling to room temperature, the reaction mixture was filtered, and the filtrate was then concentrated. The resulting residue was subjected to a silica gel column chromatography to give 1-{3-bromo-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 1") 3.1 g.

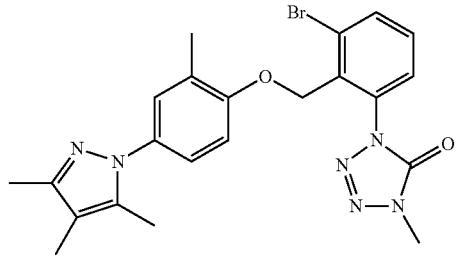

Present compound 3

$^1$H-NMR (CDCl$_3$) δ: 7.81 (1H, dd, J=7.7, 1.4 Hz), 7.46-7.38 (2H, m), 7.15 (1H, d, J=2.4 Hz), 7.10 (1H, dd, J=8.6, 2.5 Hz), 6.86 (1H, d, J=8.5 Hz), 5.32 (2H, s), 3.62 (3H, s), 2.23 (3H, s), 2.16 (3H, s), 2.06 (3H, s), 1.96 (3H, s).

Preparation Example 4

A mixture of 1-(2-bromomethyl-3-methylphenyl)-4-methyl-1,4-dihydrotetrazole-5-one (described in Reference Preparation example 14) 0.35 g, 2-methyl-4-(3,4,5-trimethyl-pyrazol-1-yl)-phenol (described in Reference Preparation example 28) 0.28 g, potassium carbonate 0.22 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-methyl-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 4") 0.24 g.

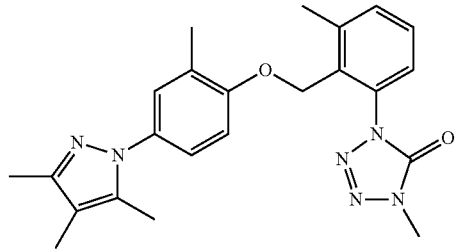

Present compound 4

$^1$H-NMR (CDCl$_3$) δ: 7.46-7.39 (2H, m), 7.31-7.27 (1H, m), 7.16 (1H, d, J=2.0 Hz), 7.11 (1H, dd, J=8.4, 2.6 Hz), 6.86 (1H, d, J=8.8 Hz), 5.05 (2H, s), 3.64 (3H, s), 2.51 (3H, s), 2.23 (3H, s), 2.17 (3H, s), 2.11 (3H, s), 1.97 (3H, s).

Preparation Example 5

A mixture of 1-(2-bromomethyl-3-ethylphenyl)-4-methyl-1,4-dihydrotetrazole-5-one (described in Reference Preparation example 17) 0.30 g, 2-methyl-4-(3,4,5-trimethyl-pyrazol-1-yl)-phenol (described in Reference Preparation example 28) 0.23 g, potassium carbonate 0.18 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-ethyl-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 5") 0.22 g.

Present compound 5

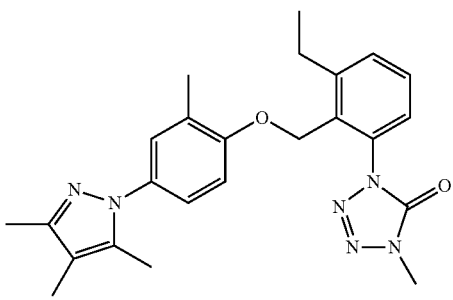

¹H-NMR (CDCl₃) δ: 7.51-7.44 (2H, m), 7.29 (1H, dd, J=7.2, 1.9 Hz), 7.16 (1H, d, J=2.4 Hz), 7.11 (1H, dd, J=8.6, 2.5 Hz), 6.87 (1H, d, J=8.7 Hz), 5.07 (2H, s), 3.61 (3H, s), 2.85 (2H, q, J=7.6 Hz), 2.23 (3H, s), 2.17 (3H, s), 2.09 (3H, s), 1.97 (3H, s), 1.28 (3H, t, J=7.6 Hz).

Preparation Example 6

A mixture of 1-(2-bromomethyl-3-trifluoromethylphenyl)-4-methyl-1,4-dihydrotetrazole-5-one (described in Reference Preparation example 11) 0.30 g, 2-methyl-4-(3,4,5-trimethyl-pyrazol-1-yl)-phenol (described in Reference Preparation example 28) 0.12 g, potassium carbonate 0.17 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-trifluoromethyl-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 6") 0.30 g.

Present compound 6

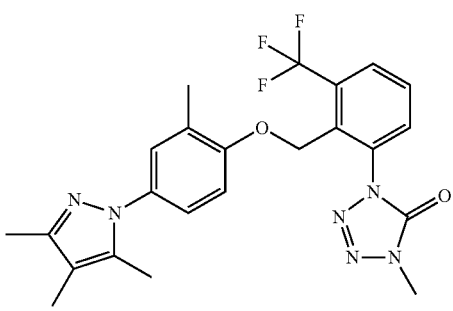

¹H-NMR (CDCl₃) δ: 7.92 (1H, dd, J=6.8, 2.4 Hz), 7.72-7.66 (2H, m), 7.15 (1H, d, J=2.4 Hz), 7.11 (1H, dd, J=8.6, 2.5 Hz), 6.85 (1H, d, J=8.7 Hz), 5.32 (2H, s), 3.57 (3H, s), 2.23 (3H, s), 2.16 (3H, s), 2.02 (3H, s), 1.97 (3H, s).

Preparation Example 7

A mixture of 1-(2-bromomethyl-3-methoxyphenyl)-4-methyl-1,4-dihydrotetrazole-5-one (described in Reference Preparation example 9) 0.35 g, 2-methyl-4-(3,4,5-trimethyl-pyrazol-1-yl)-phenol (described in Reference Preparation example 28) 0.27 g, potassium carbonate 0.21 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-methoxy-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 7") 0.18 g.

Present compound 7

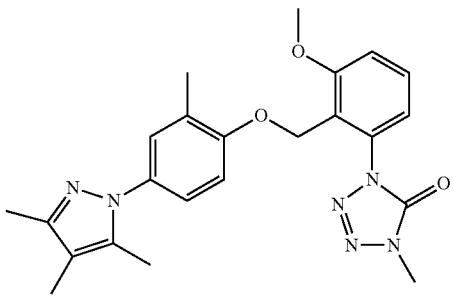

¹H-NMR (CDCl₃) δ: 7.45 (1H, t, J=8.2 Hz), 7.11 (1H, s), 7.07 (3H, d, J=8.0 Hz), 6.90 (1H, d, J=8.5 Hz), 5.28 (2H, s), 3.91 (3H, s), 3.60 (3H, s), 2.22 (3H, s), 2.14 (3H, s), 2.02 (3H, s), 1.95 (3H, s).

Preparation Example 8

A mixture of 1-(3-ethoxy-2-bromomethyl-phenyl)-4-methyl-1,4-dihydrotetrazole-5-one (described in Reference Preparation example 16) 0.30 g, 2-methyl-4-(3,4,5-trimethyl-pyrazol-1-yl)-phenol (described in Reference Preparation example 28) 0.22 g, potassium carbonate 0.17 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-ethoxy-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 8") 0.29 g.

Present compound 8

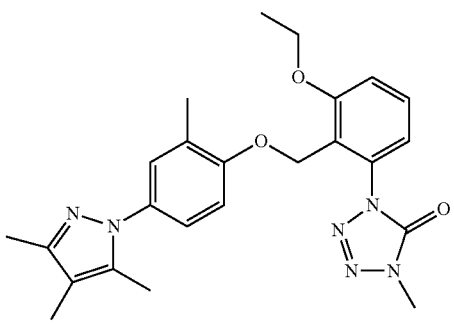

¹H-NMR (CDCl₃) δ: 7.44 (1H, t, J=8.2 Hz), 7.12-7.04 (4H, m), 6.92 (1H, d, J=8.5 Hz), 5.30 (2H, s), 4.14 (2H, q, J=7.0 Hz), 3.61 (3H, s), 2.22 (3H, s), 2.15 (3H, s), 2.02 (3H, s), 1.96 (3H, s), 1.44 (3H, t, J=7.0 Hz).

Preparation Example 9

A similar reaction to Preparation example 2 using 2-chloro-4-(3,4,5-trimethyl-pyrazol-1-yl)-phenol (described in Reference Preparation example 20) instead of 2-methyl-4-(3,4,5-trimethyl-pyrazol-1-yl)-phenol gave 1-{3-chloro-2-[2-chloro-4-(3,5-dimethyl-pyrazol-1-yl)-phenoxymethyl]-phenyl}-4-methyl-1,4-dihydrotetrazole-5-one (hereinafter, referred to as "Present compound 9").

Present compound 9

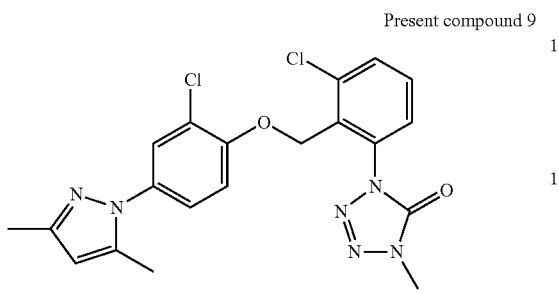

$^1$H-NMR (CDCl$_3$) δ: 7.60 (1H, dd, J=7.0, 2.4 Hz), 7.50-7.43 (2H, m), 7.42 (1H, d, J 2.7 Hz), 7.22 (1H, dd, J=8.7, 2.7 Hz), 6.96 (1H, d, J=8.7 Hz), 5.96 (1H, s), 5.53 (2H, s), 3.66 (3H, s), 2.27 (3H, s), 2.26 (3H, s).

Preparation Example 10

A similar reaction to Preparation example 2 using 2-chloro-4-(3,4,5-trimethyl-pyrazol-1-yl)-phenol (described in Reference Preparation example 19) instead of 2-methyl-4-(3,4,5-trimethyl-pyrazol-1-yl)-phenol gave 1-{3-chloro-2-[2-chloro-4-(3,4,5-trimethyl-pyrazol-1-yl)-phenoxymethyl]-phenyl}-4-methyl-1,4-dihydrotetrazole-5-one (hereinafter, referred to as "Present compound 10").

Present compound 10

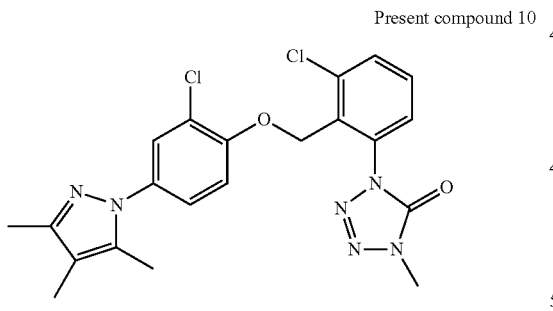

$^1$H-NMR (CDCl$_3$) δ: 7.60 (1H, dd, J=7.3, 2.2 Hz), 7.50-7.43 (2H, m), 7.39 (1H, d, J=2.7 Hz), 7.19 (1H, dd, J=8.8, 2.7 Hz), 6.95 (1H, d, J=8.8 Hz), 5.52 (2H, s), 3.65 (3H, s), 2.21 (3H, s), 2.17 (3H, s), 1.96 (3H, s).

Preparation Example 11

A similar reaction to Preparation example 2 using 3-chloro-4-(3,5-dimethyl-pyrazol-1-yl)-phenol (described in Reference Preparation example 29) instead of 2-methyl-4-(3,4,5-trimethyl-pyrazol-1-yl)-phenol gave 1-{3-chloro-2-[3-chloro-4-(3,5-dimethyl-pyrazol-1-yl)-phenoxymethyl]-phenyl}-4-methyl-1,4-dihydrotetrazole-5-one (hereinafter, referred to as "Present compound 11").

Present compound 11

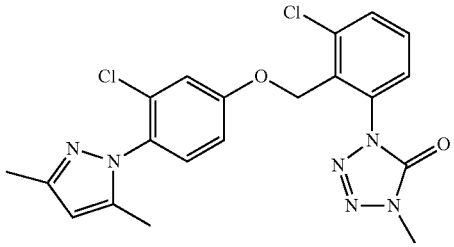

$^1$H-NMR (CDCl$_3$) δ: 7.62 (1H, dd, J=8.0, 1.5 Hz), 7.50 (1H, t, J=8.0 Hz), 7.42 (1H, dd, J=8.0, 1.2 Hz), 7.28 (1H, s), 6.98 (1H, d, J=2.7 Hz), 6.82 (1H, dd, J=8.7, 2.7 Hz), 5.96 (1H, s), 5.31 (2H, s), 3.66 (3H, s), 2.28 (3H, s), 2.09 (3H, s).

Preparation Example 12

A similar reaction to Preparation example 2 using 2-methyl-4-(3,5-dimethyl-pyrazol-1-yl)-phenol (described in Reference Preparation example 30) instead of 2-methyl-4-(3,4,5-trimethyl-pyrazol-1-yl)-phenol gave 1-{3-chloro-2-[2-methyl-4-(3,5-dimethyl-pyrazol-1-yl)-phenoxymethyl]-phenyl}-4-methyl-1,4-dihydrotetrazole-5-one (hereinafter, referred to as "Present compound 12").

Present compound 12

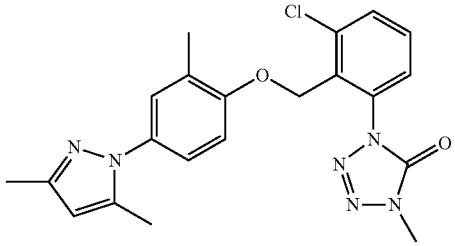

$^1$H-NMR (CDCl$_3$) δ: 7.62 (1H, dd, J=8.0, 1.2 Hz), 7.48 (1H, t, J=8.0 Hz), 7.41 (1H, dd, J=8.0, 1.2 Hz), 7.17 (1H, d, J=2.4 Hz), 7.12 (1H, dd, J=8.5, 2.7 Hz), 6.87 (1H, d, J=8.5 Hz), 5.95 (1H, s), 5.34 (2H, s), 3.67-3.59 (3H, m), 2.28 (3H, s), 2.24 (3H, s), 2.05 (3H, s).

Preparation Example 13

A similar reaction to Preparation example 2 using 2-methyl-4-(3-methyl-pyrazol-1-yl)-phenol (described in Reference Preparation example 36) instead of 2-methyl-4-(3,4,5-trimethyl-pyrazol-1-yl)-phenol gave 1-{3-chloro-2-[2-methyl-4-(3-methyl-pyrazol-1-yl)-phenoxymethyl]-phenyl}-4-methyl-1,4-dihydrotetrazole-5-one (hereinafter, referred to as "Present compound 13").

Present compound 13

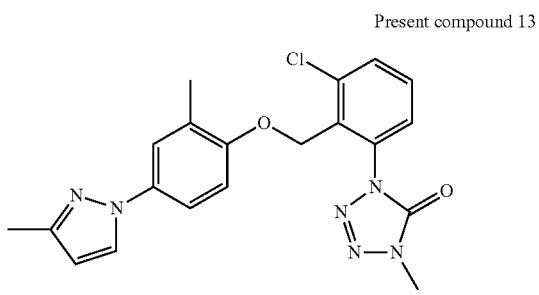 [SMILES: Cc1ccn(-c2ccc(OCc3c(Cl)cccc3-n3nnn(C)c3=O)c(C)c2)n1]

¹H-NMR (CDCl₃) δ: 7.68 (1H, d, J=2.2 Hz), 7.62 (1H, dd, J=8.0, 1.5 Hz), 7.47 (1H, t, J=8.0 Hz), 7.42-7.39 (2H, m), 7.34-7.30 (1H, m), 6.86 (1H, d, J=8.5 Hz), 6.19 (1H, d, J=2.2 Hz), 5.33 (2H, s), 3.60 (3H, s), 2.36 (3H, s), 2.07 (3H, s).

Preparation Example 14

A similar reaction to Preparation example 2 using 2-methyl-4-(3,4,5-trimethyl-pyrazol-1-yl)-phenol (described in Reference Preparation example 37) instead of 2-methyl-4-(3,4,5-trimethyl-pyrazol-1-yl)-phenol gave 1-{3-chloro-2-(2-methyl-4-pyrazol-1-yl-phenoxymethyl)-phenyl}-4-methyl-1,4-dihydrotetrazole-5-one (hereinafter, referred to as "Present compound 14").

Present compound 14

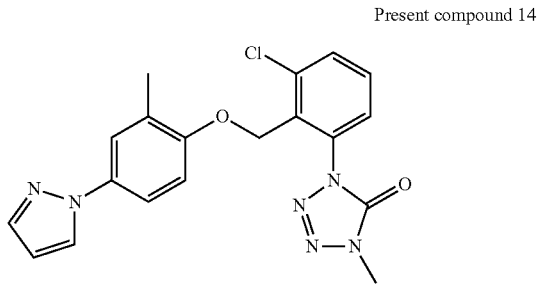 [SMILES: Cc1cc(-n2cccn2)ccc1OCc1c(Cl)cccc1-n1nnn(C)c1=O]

¹H-NMR (CDCl₃) δ: 7.81 (1H, d, J=2.2 Hz), 7.68 (1H, d, J=1.7 Hz), 7.62 (1H, dd, J=8.0, 1.3 Hz), 7.48 (1H, t, J=8.0 Hz), 7.45-7.37 (3H, m), 6.89 (1H, d, J=8.7 Hz), 6.42 (1H, t, J=2.2 Hz), 5.34 (2H, s), 3.61 (3H, s), 2.09 (3H, s).

Preparation Example 15

A similar reaction to Preparation example 2 using 2-methyl-4-(4-methyl-pyrazol-1-yl)-phenol (described in Reference Preparation example 34) instead of 2-methyl-4-(3,4,5-trimethyl-pyrazol-1-yl)-phenol gave 1-{3-chloro-2-[2-methyl-4-(4-methyl-pyrazol-1-yl)-phenoxymethyl]-phenyl}-4-methyl-1,4-dihydrotetrazole-5-one (hereinafter, referred to as "Present compound 15").

Present compound 15

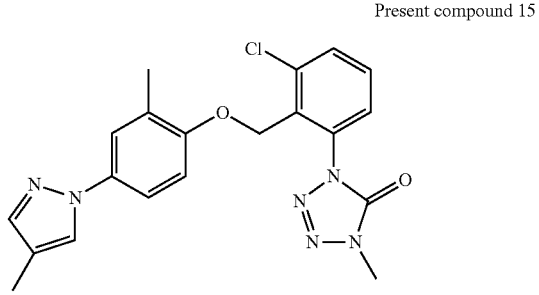 [SMILES: Cc1cnn(-c2ccc(OCc3c(Cl)cccc3-n3nnn(C)c3=O)c(C)c2)c1]

¹H-NMR (CDCl₃) δ: 7.71 (1H, d, J=7.8 Hz), 7.60-7.58 (1H, m), 7.56-7.48 (3H, m), 7.45 (1H, d, J=2.7 Hz), 7.32 (1H, dd, J=8.8, 2.7 Hz), 6.82 (1H, d, J=8.8 Hz), 5.18 (2H, s), 3.68 (3H, s), 2.23 (3H, s), 2.14 (3H, s).

Preparation Example 16

A similar reaction to Preparation example 2 using 2-chloro-4-(4-methyl-pyrazol-1-yl)-phenol (described in Reference Preparation example 44) instead of 2-methyl-4-(3,4,5-trimethyl-pyrazol-1-yl)-phenol gave 1-{3-chloro-2-[2-chloro-4-(4-methyl-pyrazol-1-yl)-phenoxymethyl]-phenyl}-4-methyl-1,4-dihydrotetrazole-5-one (hereinafter, referred to as "Present compound 16").

Present compound 16

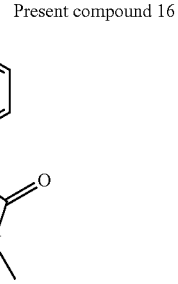

¹H-NMR (CDCl₃) δ: 7.64 (1H, d, J=2.7 Hz), 7.61-7.57 (2H, m), 7.50-7.40 (4H, m), 6.95 (1H, d, J=8.9 Hz), 5.51 (2H, s), 3.65 (3H, s), 2.14 (3H, s).

Preparation Example 17

A similar reaction to Preparation example 4 using 2-chloro-4-(3,5-dimethyl-pyrazol-1-yl)-phenol (described in Reference Preparation example 20) instead of 2-methyl-4-(3,4,5-trimethyl-pyrazol-1-yl)-phenol gave 1-{3-methyl-2-[2-chloro-4-(3,5-dimethyl-pyrazol-1-yl)-phenoxymethyl]-phenyl}-4-methyl-1,4-dihydrotetrazole-5-one (hereinafter, referred to as "Present compound 17").

Present compound 17

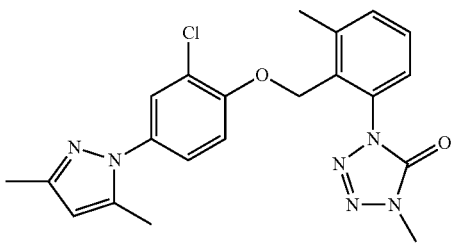

¹H-NMR (CDCl₃) δ: 7.45-7.38 (3H, m), 7.31-7.28 (1H, m), 7.22 (1H, dd, J=8.7, 2.6 Hz), 6.93 (1H, d, J=8.5 Hz), 5.96 (1H, s), 5.18 (2H, s), 3.68 (3H, s), 2.54 (3H, s), 2.27 (3H, s), 2.26 (3H, s).

Preparation Example 18

A similar reaction to Preparation example 4 using 3-chloro-4-(3,5-dimethyl-pyrazol-1-yl)-phenol (described in Reference Preparation example 29) instead of 2-methyl-4-(3,4,5-trimethyl-pyrazol-1-yl)-phenol gave 1-{3-methyl-2-[3-chloro-4-(3,5-dimethyl-pyrazol-1-yl)-phenoxymethyl]-phenyl}-4-methyl-1,4-dihydrotetrazole-5-one (hereinafter, referred to as "Present compound 18").

Present compound 18

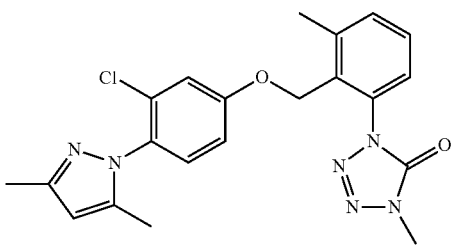

¹H-NMR (CDCl₃) δ: 7.47-7.40 (2H, m), 7.31-7.27 (2H, m), 7.01 (1H, d, J=2.8 Hz), 6.85 (1H, dd, J=8.8, 2.8 Hz), 5.97 (1H, s), 5.05 (2H, s), 3.67 (3H, s), 2.50 (3H, s), 2.29 (3H, s), 2.09 (3H, s).

Preparation Example 19

A similar reaction to Preparation example 4 using 4-(3,5-dimethyl-pyrazol-1-yl)-phenol (described in Reference Preparation example 31) instead of 2-methyl-4-(3,4,5-trimethyl-pyrazol-1-yl)-phenol gave 1-{3-methyl-2-[4-(3,5-dimethyl-pyrazol-1-yl)-phenoxymethyl]-phenyl}-4-methyl-1,4-dihydrotetrazole-5-one (hereinafter, referred to as "Present compound 19").

Present compound 19

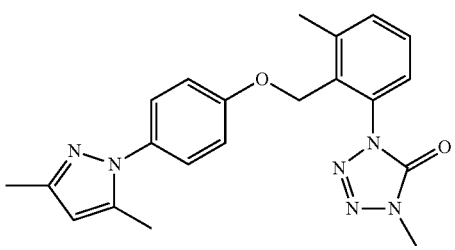

¹H-NMR (CDCl₃) δ: 7.45-7.39 (2H, m), 7.32-7.27 (3H, m), 6.94-6.89 (2H, m), 5.96 (1H, s), 5.05 (2H, s), 3.63 (3H, s), 2.50 (3H, s), 2.28 (3H, s), 2.24 (3H, s).

Preparation Example 20

A similar reaction to Preparation example 4 using 2-methyl-4-(3,5-dimethyl-pyrazol-1-yl)-phenol (described in Reference Preparation example 30) instead of 2-methyl-4-(3,4,5-trimethyl-pyrazol-1-yl)-phenol gave 1-{3-methyl-2-[2-methyl-4-(3,5-dimethyl-pyrazol-1-yl)-phenoxymethyl]-phenyl}-4-methyl-1,4-dihydrotetrazole-5-one (hereinafter, referred to as "Present compound 20").

Present compound 20

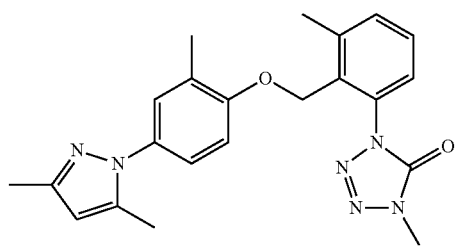

¹H-NMR (CDCl₃) δ: 7.45-7.40 (2H, m), 7.28 (1H, dd, J=6.9, 2.2 Hz), 7.18 (1H, d, J 2.2 Hz), 7.13 (1H, dd, J=8.6, 2.4 Hz), 6.86 (1H, d, J=8.6 Hz), 5.95 (1H, s), 5.06 (2H, s), 3.64 (3H, s), 2.51 (3H, s), 2.28 (3H, s), 2.24 (3H, s), 2.11 (3H, s).

Preparation Example 21

A similar reaction to Preparation example 4 using 3-methyl-4-(3,5-trimethyl-pyrazol-1-yl)-phenol (described in Reference Preparation example 32) instead of 2-methyl-4-(3,4,5-trimethyl-pyrazol-1-yl)-phenol gave 1-{3-methyl-2-[3-methyl-4-(3,5-dimethyl-pyrazol-1-yl)-phenoxymethyl]-phenyl}-4-methyl-1,4-dihydrotetrazole-5-one (hereinafter, referred to as "Present compound 21").

Present compound 21

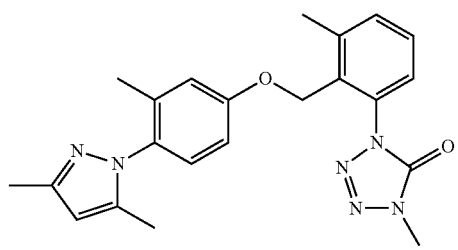

¹H-NMR (CDCl₃) δ: 7.44-7.39 (2H, m), 7.30-7.26 (1H, m), 7.11 (1H, d, J=8.5 Hz), 6.79-6.72 (2H, m), 5.93 (1H, s), 5.03 (2H, s), 3.64 (3H, s), 2.49 (3H, s), 2.27 (3H, s), 2.03 (3H, s), 1.99 (3H, s).

Preparation Example 22

A similar reaction to Preparation example 4 using 2-methyl-4-(3-methyl-pyrazol-1-yl)-phenol (described in Reference Preparation example 36) instead of 2-methyl-4-(3,4,5-trimethyl-pyrazol-1-yl)-phenol gave 1-{3-methyl-2-

[2-methyl-4-(3-methyl-pyrazol-1-yl)-phenoxymethyl]-phenyl}-4-methyl-1,4-dihydrotetrazole-5-one (hereinafter, referred to as "Present compound 22").

Present compound 22

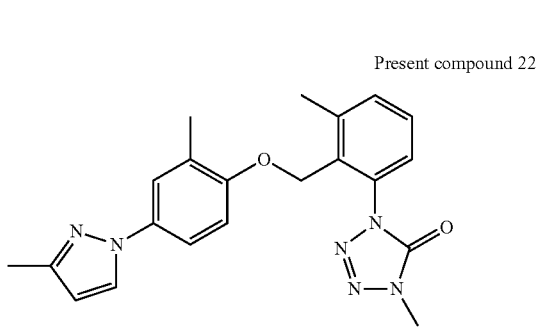 [SMILES: Cc1ccn(-c2ccc(OCc3c(C)cccc3-n3nnn(C)c3=O)c(C)c2)n1]

¹H-NMR (CDCl₃) δ: 7.69 (1H, d, J=2.3 Hz), 7.45-7.39 (3H, m), 7.3.3 (1H, dd, J=8.7, 2.7 Hz), 7.29-7.26 (1H, m), 6.85 (1H, d, J=8.7 Hz), 6.20 (1H, d, J=2.3 Hz), 5.05 (2H, s), 3.62 (3H, s), 2.51 (3H, s), 2.36 (3H, s), 2.13 (3H, s).

Preparation Example 23

A similar reaction to Preparation example 4 using 2-methyl-4-(5-methyl-pyrazol-1-yl)-phenol (described in Reference Preparation example 35) instead of 2-methyl-4-(3,4,5-trimethyl-pyrazol-1-yl)-phenol gave 1-{3-methyl-2-[2-methyl-4-(5-methyl-pyrazol-1-yl)-phenoxymethyl]-phenyl}-4-methyl-1,4-dihydrotetrazole-5-one (hereinafter, referred to as "Present compound 23").

Present compound 23

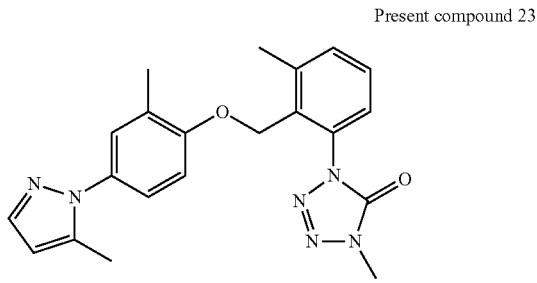 [SMILES: Cc1cc(-n2nccc2C)ccc1OCc1c(C)cccc1-n1nnn(C)c1=O]

¹H-NMR (CDCl₃) δ: 7.53 (1H, d, J=1.7 Hz), 7.46-7.41 (2H, m), 7.29 (1H, dd, J=7.0, 2.2 Hz), 7.21-7.19 (1H, m), 7.17 (1H, dd, J=8.5, 2.2 Hz), 6.89 (1H, d, J=8.5 Hz), 6.16 (1H, dd, J=1.7, 0.7 Hz), 5.07 (2H, s), 3.64 (3H, s), 2.52 (3H, s), 2.30 (3H, s), 2.13 (3H, s).

Preparation Example 24

A similar reaction to Preparation example 4 using 2-methyl-4-(4-methyl-pyrazol-1-yl)-phenol (described in Reference Preparation example 34) instead of 2-methyl-4-(3,4,5-trimethyl-pyrazol-1-yl)-phenol gave 1-{3-methyl-2-[2-methyl-4-(4-methyl-pyrazol-1-yl)-phenoxymethyl-phenyl}-4-methyl-1,4-dihydrotetrazole-5-one (hereinafter, referred to as "Present compound 24").

Present compound 24

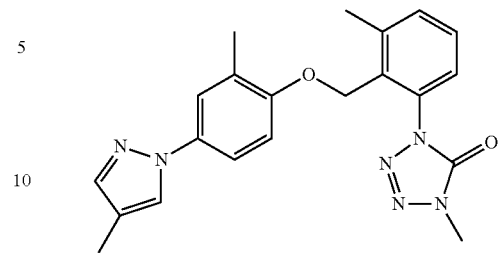

¹H-NMR (CDCl₃) δ: 7.60-7.59 (1H, m), 7.48 (1H, s), 7.45-7.39 (3H, m), 7.35 (1H, dd, J=8.8, 2.7 Hz), 7.29-7.26 (1H, m), 6.86 (1H, d, J=8.8 Hz), 5.06 (2H, s), 3.63 (3H, s), 2.51 (3H, s), 2.15 (3H, s), 2.13 (3H, s).

Preparation Example 25

A similar reaction to Preparation example 4 using 3-chloro-4-(pyrazol-1-yl)-phenol (described in Reference Preparation example 33) instead of 2-methyl-4-(3,4,5-trimethyl-pyrazol-1-yl)-phenol gave 1-{3-methyl-2-(3-chloro-4-pyrazol-1-yl-phenoxymethyl]-phenyl}-4-methyl-1,4-dihydrotetrazole-5-one (hereinafter, referred to as "Present compound 25").

Present compound 25

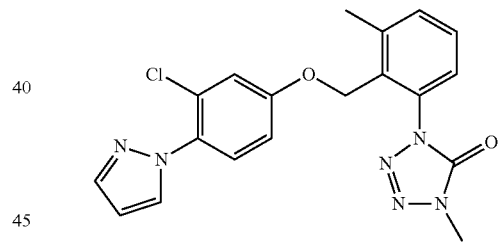

¹H-NMR (CDCl₃) δ: 7.74 (1H, d, J=2.4 Hz), 7.72 (1H, d, J=1.6 Hz), 7.47-7.41 (3H, m), 7.30 (1H, dd, J=7.3, 1.6 Hz), 7.02 (1H, d, J=2.7 Hz), 6.86 (1H, dd, J=8.9, 2.7 Hz), 6.44 (1H, t, J=2.2 Hz), 5.06 (2H, s), 3.67 (3H, s), 2.50 (3H, s).

Preparation Example 26

A similar reaction to Preparation example 4 using 2-methyl-4-(pyrazol-1-yl)-phenol (described in Reference Preparation example 37) instead of 2-methyl-4-(3,4,5-trimethyl-pyrazol-1-yl)-phenol gave 1-{3-methyl-2-(2-methyl-4-pyrazol-1-yl-phenoxymethyl]-phenyl}-4-methyl-1,4-dihydrotetrazole-5-one (hereinafter, referred to as "Present compound 26").

Present compound 26

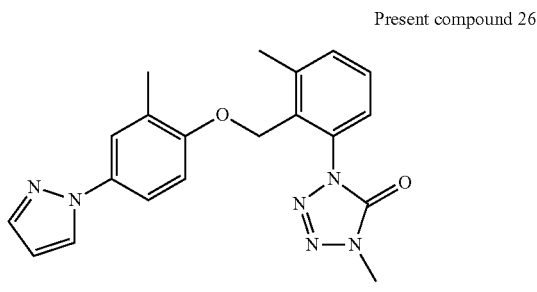 [SMILES: Cc1cc(-n2cccn2)ccc1OCc1c(C)cccc1-n1nnn(C)c1=O]

¹H-NMR (CDCl₃) δ: 7.81 (1H, d, J=2.4 Hz), 7.68 (1H, d, J=2.1 Hz), 7.47-7.37 (4H, m), 7.28 (1H, dd, J=7.0, 2.4 Hz), 6.88 (1H, d, J=8.8 Hz), 6.43 (1H, t, J=2.1 Hz), 5.07 (2H, s), 3.63 (3H, s), 2.52 (3H, s), 2.15 (3H, s).

Preparation Example 27

A mixture of 1-{3-methyl-2-(2-methyl-4-pyrazol-1-yl-phenoxymethyl]-phenyl}-4-methyl-1,4-dihydrotetrazole-5-one (Present compound 26) 0.5 g, N-chlorosuccinimide 0.19 g and chloroform 15 ml was stirred at room temperature for twelve hours. To the reaction mixture was added water and the resulting mixture was extracted with chloroform. The organic layer was washed with water, and was dried over anhydrous magnesium sulfate and was then concentrated under reduced pressure. The resulting residue was subjected to a silica gel column chromatography to give 1-{3-methyl-2-(2-methyl-4-(4-chloro-pyrazol-1-yl)-phenoxymethyl]-phenyl}-4-methyl-1,4-dihydrotetrazole-5-one (hereinafter, referred to as "Present compound 27") 0.51 g.

Present compound 27

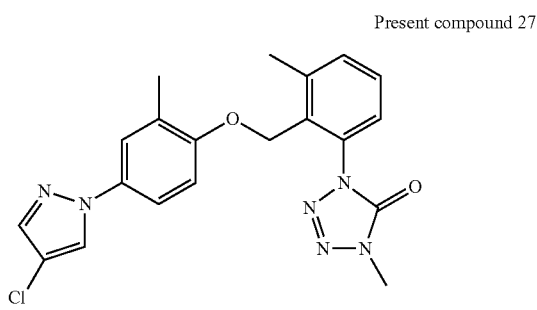 [SMILES: Cc1cc(-n2cc(Cl)cn2)ccc1OCc1c(C)cccc1-n1nnn(C)c1=O]

¹H-NMR (CDCl₃) δ: 7.80-7.78 (1H, m), 7.60-7.58 (1H, m), 7.47-7.37 (3H, m), 7.34 (1H, dd, J=8.5, 2.4 Hz), 7.30-7.25 (1H, m), 6.87 (1H, d, J=8.8 Hz), 5.07 (2H, s), 3.63 (3H, s), 2.51 (3H, s), 2.14 (3H, s).

Preparation Example 28

A similar reaction to Preparation example 27 using N-bromosuccinimide instead of N-chlorosuccinimide gave 1-{3-methyl-2-[2-methyl-4-(4-bromo-pyrazol-1-yl)-phenoxymethyl]-phenyl}-4-methyl-1,4-dihydrotetrazole-5-one (hereinafter, referred to as "Present compound 28").

Present compound 28

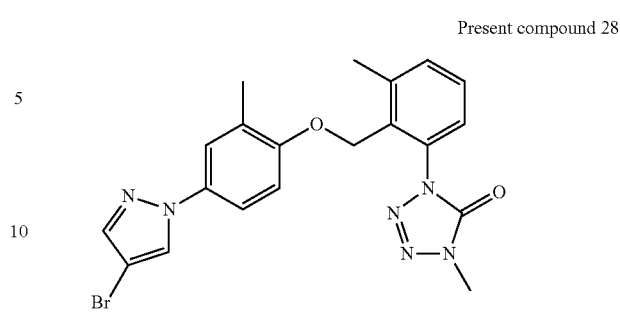

¹H-NMR (CDCl₃) δ: 7.82 (1H, s), 7.63 (1H, s), 7.46-7.39 (3H, m), 7.34 (1H, dd, J=8.6, 2.8 Hz), 7.30-7.26 (1H, m), 6.88 (1H, d, J=8.6 Hz), 5.07 (2H, s), 3.63 (3H, s), 2.51 (3H, s), 2.14 (3H, s).

Preparation Example 29

A similar reaction to Preparation example 4 using 2-chloro-4-(3-methyl-pyrazol-1-yl)-phenol (described in Reference Preparation example 39) instead of 2-methyl-4-(3,4,5-trimethyl-pyrazol-1-yl)-phenol gave 1-{3-methyl-2-[2-chloro-4-(3-methyl-pyrazol-1-yl)-phenoxymethyl]-phenyl}-4-methyl-1,4-dihydrotetrazole-5-one (hereinafter, referred to as "Present compound 29").

Present compound 29

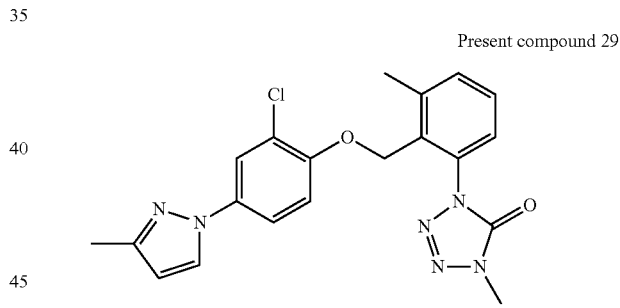

¹H-NMR (CDCl₃) δ: 7.68 (2H, dd, J=9.5, 2.4 Hz), 7.45-7.37 (3H, m), 7.29 (1H, dd, J=7.2, 1.8 Hz), 6.91 (1H, d, J=8.8 Hz), 6.22 (1H, d, J=2.4 Hz), 5.18 (2H, s), 3.67 (3H, s), 2.54 (3H, s), 2.36 (3H, s).

Preparation Example 30

A similar reaction to Preparation example 4 using 2,5-dimethyl-4-(3-methyl-pyrazol-1-yl)-phenol (described in Reference Preparation example 40) instead of 2-methyl-4-(3,4,5-trimethyl-pyrazol-1-yl)-phenol gave 1-{3-methyl-2-[2,5-dimethyl-4-(3-methyl-pyrazol-1-yl)-phenoxymethyl]-phenyl}-4-methyl-1,4-dihydrotetrazole-5-one (hereinafter, referred to as "Present compound 30").

Present compound 30

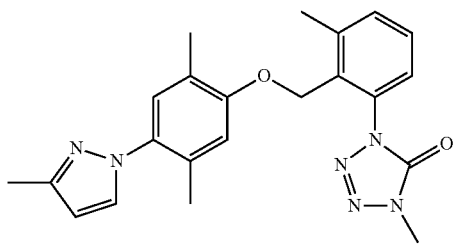

¹H-NMR (CDCl₃) δ: 7.45-7.39 (3H, m), 7.29-7.26 (1H, m), 7.06 (1H, s), 6.70 (1H, s), 6.17 (1H, d, J=2.4 Hz), 5.05 (2H, s), 3.66 (3H, s), 2.51 (3H, s), 2.35 (3H, s), 2.16 (3H, s), 2.05 (3H, s).

Preparation Example 31

A similar reaction to Preparation example 4 using 2,6-dimethyl-4-(3-methyl-pyrazol-1-yl)-phenol (described in Reference Preparation example 38) instead of 2-methyl-4-(3,4,5-trimethyl-pyrazol-1-yl)-phenol gave 1-{3-methyl-2-[2,6-dimethyl-4-(3-methyl-pyrazol-1-yl)-phenoxymethyl]-phenyl}-4-methyl-1,4-dihydrotetrazole-5-one (hereinafter, referred to as "Present compound 31").

Present compound 31

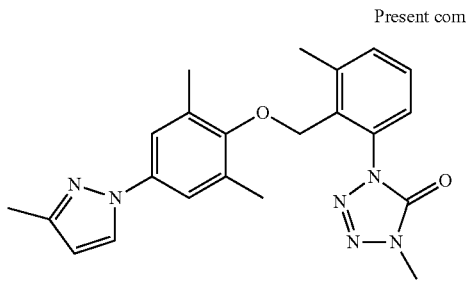

¹H-NMR (CDCl₃) δ: 7.71 (1H, d, J=2.4 Hz), 7.43-7.36 (2H, m), 7.23-7.19 (3H, m), 6.19 (1H, d, J=2.4 Hz), 4.99 (2H, s), 3.59 (3H, s), 2.54 (3H, s), 2.36 (3H, s), 2.07 (6H, s).

Preparation Example 32

A similar reaction to Preparation example 4 using 2-fluoro-4-(3-methyl-pyrazol-1-yl)-phenol (described in Reference Preparation example 43) instead of 2-methyl-4-(3,4,5-trimethyl-pyrazol-1-yl)-phenol gave 1-{3-methyl-2-[2-fluoro-4-(3-methyl-pyrazol-1-yl)-phenoxymethyl]-phenyl}-4-methyl-1,4-dihydrotetrazole-5-one (hereinafter, referred to as "Present compound 32").

Present compound 32

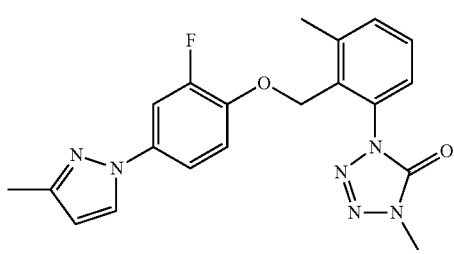

¹H-NMR (CDCl₃) δ: 7.69 (1H, d, J=2.2 Hz), 7.44-7.36 (3H, m), 7.29-7.24 (2H, m), 6.95 (1H, t, J=8.8 Hz), 6.21 (1H, d, J=2.2 Hz), 5.14 (2H, s), 3.67 (3H, s), 2.52 (3H, s), 2.35 (3H, s)

Preparation Example 33

A similar reaction to Preparation example 4 using 2-chloro-4-(4-methyl-pyrazol-1-yl)-phenol (described in Reference Preparation example 44) instead of 2-methyl-4-(3,4,5-trimethyl-pyrazol-1-yl)-phenol gave 1-{3-methyl-2-[2-chloro-4-(4-methyl-pyrazol-1-yl)-phenoxymethyl]-phenyl}-4-methyl-1,4-dihydrotetrazole-5-one (hereinafter, referred to as "Present compound 33").

Present compound 33

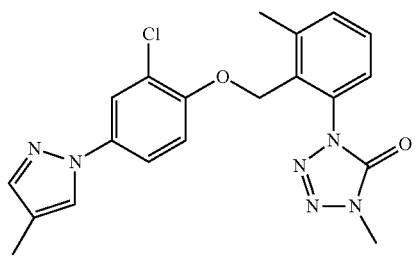

¹H-NMR (CDCl₃) δ: 7.66 (1H, d, J=2.7 Hz), 7.59 (1H, s), 7.49 (1H, s), 7.44-7.37 (3H, m), 7.31-7.27 (1H, m), 6.92 (1H, d, J=8.8 Hz), 5.17 (2H, s), 3.66 (3H, s), 2.54 (3H, s), 2.14 (3H, s).

Preparation Example 34

A similar reaction to Preparation example 4 using 2-chloro-4-(1-methyl-1H-pyrazol-4-yl)-phenol (described in Reference Preparation example 52) instead of 2-methyl-4-(3,4,5-trimethyl-pyrazol-1-yl)-phenol gave 1-{3-methyl-2-[2-chloro-4-(1-methyl-1H-pyrazole-4-yl)-phenoxymethyl]-phenyl}-4-methyl-1,4-dihydrotetrazole-5-one (hereinafter, referred to as "Present compound 34").

Present compound 34

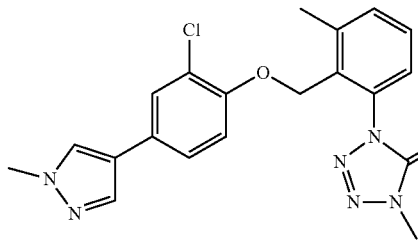

¹H-NMR (CDCl₃) δ: 7.67-7.66 (1H, m), 7.52 (1H, s), 7.44-7.37 (3H, m), 7.29 (1H, dd, J=7.3, 2.0 Hz), 7.26-7.23 (1H, m), 6.87 (1H, d, J=8.5 Hz), 5.16 (2H, s), 3.93 (3H, s), 3.67 (3H, s), 2.54 (3H, s).

Preparation Example 35

A similar reaction to Preparation example 4 using 2-methyl-4-(1-methyl-1H-pyrazol-4-yl)-phenol (described in Reference Preparation example 53) instead of 2-methyl- 4-(3,4,5-trimethyl-pyrazol-1-yl)-phenol gave 1-{3-methyl-2-[2-methyl-4-(1-methyl-1H-pyrazole-4-yl)-phenoxymethyl]-phenyl}-4-methyl-1,4-dihydrotetrazole-5-one (hereinafter, referred to as "Present compound 35").

Present compound 35

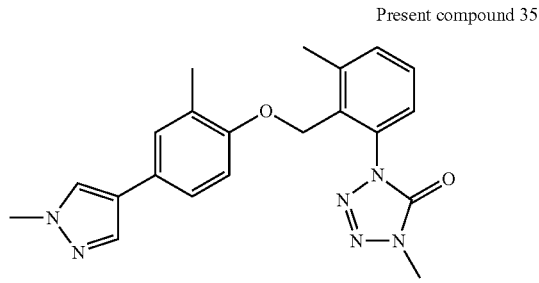 [SMILES: Cc1cc(-c2cnn(C)c2)ccc1OCc1c(C)cccc1-n1nnn(C)c1=O]

$^1$H-NMR (CDCl$_3$) δ: 7.68 (1H, s), 7.52 (1H, s), 7.45-7.39 (2H, m), 7.30-7.27 (1H, m), 7.24-7.21 (2H, m), 6.83 (1H, d, J=8.8 Hz), 5.04 (2H, s), 3.93 (3H, s), 3.62 (3H, s), 2.51 (3H, s), 2.11 (3H, s).

Preparation Example 36

A similar reaction to Preparation example 4 using 2,3-dimethyl-4-(3-methyl-pyrazol-1-yl)-phenol (described in Reference Preparation example 42) instead of 2-methyl-4-(3,4,5-trimethyl-pyrazol-1-yl)-phenol gave 1-{3-methyl-2-[2,3-dimethyl-4-(3-methyl-pyrazol-1-yl)-phenoxymethyl]-phenyl}-4-methyl-1,4-dihydrotetrazole-5-one (hereinafter, referred to as "Present compound 36").

Present compound 36

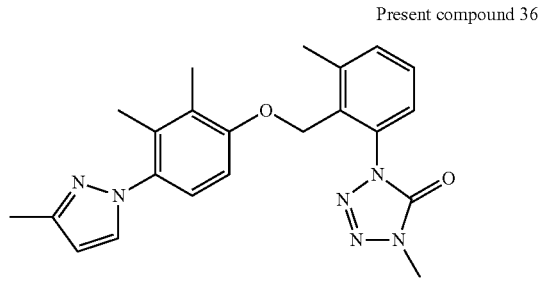 [SMILES: Cc1ccn(-c2ccc(OCc3c(C)cccc3-n3nnn(C)c3=O)c(C)c2C)n1]

$^1$H-NMR (CDCl$_3$) δ: 7.45-7.39 (2H, m), 7.38 (1H, d, J=2.2 Hz), 7.30-7.26 (1H, m), 7.09 (1H, d, J=8.5 Hz), 6.75 (1H, d, J=8.5 Hz), 6.17 (1H, d, J=2.2 Hz), 5.05 (2H, s), 3.65 (3H, s), 2.50 (3H, s), 2.35 (3H, s), 2.05 (3H, s), 1.98 (3H, s).

Preparation Example 37

A similar reaction to Preparation example 4 using 2-methyl-4-(3-trifluoromethyl-pyrazol-1-yl)-phenol (described in Reference Preparation example 45) instead of 2-methyl-4-(3,4,5-trimethyl-pyrazol-1-yl)-phenol gave 1-{3-methyl-2-[2-methyl-4-(3-trifluoromethyl-pyrazol-1-yl)-phenoxymethyl]-phenyl}-4-methyl-1,4-dihydrotetrazole-5-one (hereinafter, referred to as "Present compound 37").

Present compound 37

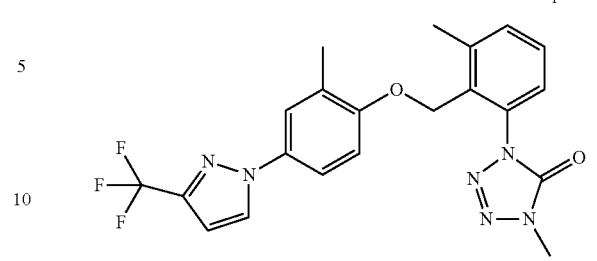

$^1$H-NMR (CDCl$_3$) δ: 7.83 (1H, t, J=1.1 Hz), 7.47-7.38 (4H, m), 7.32-7.28 (1H, m), 6.88 (1H, d, J=8.5 Hz), 6.68 (1H, d, J=2.2 Hz), 5.08 (2H, s), 3.63 (3H, s), 2.51 (3H, s), 2.15 (3H, s).

Preparation Example 38

A similar reaction to Preparation example 4 using 2-methyl-4-(4,5,6,7-tetrahydro-indazole-2-yl)-phenol (described in Reference Preparation example 50) instead of 2-methyl-4-(3,4,5-trimethyl-pyrazol-1-yl)-phenol gave 1-{3-methyl-2-[2-methyl-4-(4,5,6,7-tetrahydro-indazole-2-yl)-phenoxymethyl]-phenyl}-4-methyl-1,4-dihydrotetrazole-5-one (hereinafter, referred to as "Present compound 38").

Present compound 38

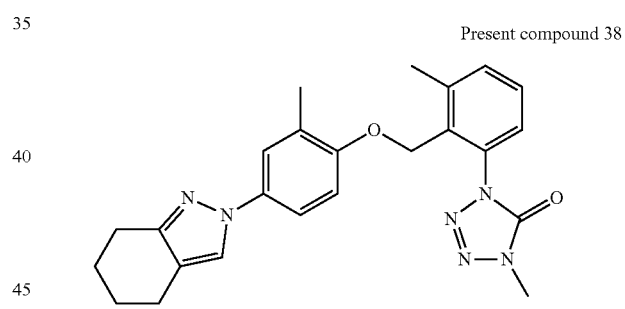

$^1$H-NMR (CDCl$_3$) δ: 7.50 (1H, s), 7.45-7.38 (3H, m), 7.32-7.27 (2H, m), 6.84 (1H, d, J=8.8 Hz), 5.05 (2H, s), 3.62 (3H, s), 2.76 (2H, t, J=6.2 Hz), 2.60 (2H, t, J=6.1 Hz), 2.51 (3H, s), 2.12 (3H, s), 1.89-1.82 (2H, m), 1.81-1.74 (2H, m).

Preparation Example 39

A similar reaction to Preparation example 4 using 2-methyl-4-(4,5,6,7-tetrahydro-indazole-1-yl)-phenol (described in Reference Preparation example 51) instead of 2-methyl-4-(3,4,5-trimethyl-pyrazol-1-yl)-phenol gave 1-{3-methyl-2-[2-methyl-4-(4,5,6,7-tetrahydro-indazole-1-yl)-phenoxymethyl]-phenyl}-4-methyl-1,4-dihydrotetrazole-5-one (hereinafter, referred to as "Present compound 39").

Present compound 39

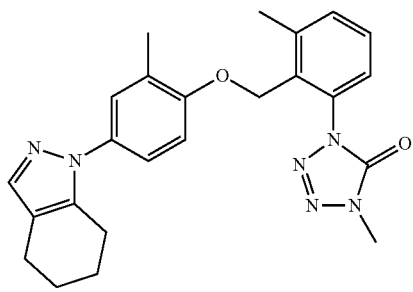

¹H-NMR (CDCl₃) δ: 7.45-7.39 (3H, m), 7.30-7.24 (2H, m), 7.19 (1H, dd, J=8.7, 2.6 Hz), 6.87 (1H, d, J=8.8 Hz), 5.06 (2H, s), 3.63 (3H, s), 2.66 (2H, t, J=5.4 Hz), 2.58 (2H, t, J=5.1 Hz), 2.51 (3H, s), 2.12 (3H, s), 1.83-1.74 (4H, m).

Preparation Example 40

A mixture of 1-(2-bromomethyl-3-methylphenyl)-4-methyl-1,4-dihydrotetrazole-5-one (described in Reference Preparation example 14) 0.30 g, 2-methyl-4-(1-methyl-1H-pyrazol-3-yl)-phenol (described in Reference Preparation example 60) 0.21 g, potassium carbonate 0.19 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-methyl-2-[2-methyl-4-(1-methyl-1H-pyrazol-3-yl)-phenoxymethyl]-phenyl}-4-methyl-1,4-dihydrotetrazole-5-one (hereinafter, referred to as "Present compound 40") 0.22 g.

Present compound 40

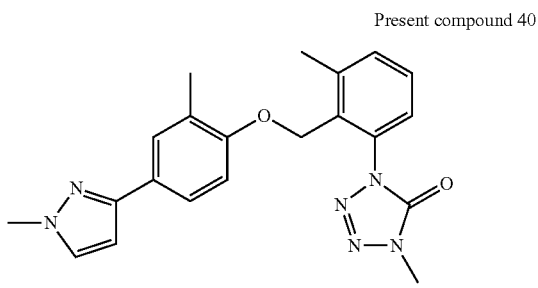 [SMILES: Cc1cc(-c2ccn(C)n2)ccc1OCc1c(C)cccc1-n1nnn(C)c1=O]

¹H-NMR (CDCl₃) δ: 7.58-7.56 (1H, m), 7.53 (1H, dd, J=8.2, 2.2 Hz), 7.44-7.39 (2H, m), 7.34 (1H, d, J=2.2 Hz), 7.28 (1H, d, J=2.4 Hz), 6.85 (1H, d, J=8.5 Hz), 6.44 (1H, d, J=2.2 Hz), 5.06 (2H, s), 3.93 (3H, s), 3.61 (3H, s), 2.51 (3H, s), 2.12 (3H, s).

Preparation Example 41

A similar reaction to Preparation example 4 using 2-methyl-4-(3,4-dimethyl-pyrazol-1-yl)-phenol (described in Reference Preparation example 46) instead of 2-methyl-4-(3,4,5-trimethyl-pyrazol-1-yl)-phenol gave 1-{3-methyl-2-[2-methyl-4-(3,4-dimethyl-pyrazol-1-yl)-phenoxymethyl]-phenyl}-4-methyl-1,4-dihydrotetrazole-5-one (hereinafter, referred to a "Present compound 41").

Present compound 41

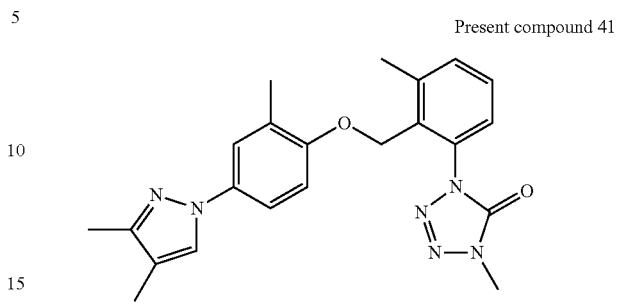

¹H-NMR (CDCl₃) δ: 7.52 (1H, s), 7.43-7.38 (3H, m), 7.31-7.27 (2H, m), 6.84 (1H, d, J=8.7 Hz), 5.04 (2H, s), 3.62 (3H, s), 2.51 (3H, s), 2.27 (3H, s), 2.12 (3H, s), 2.06 (3H, s).

Preparation Example 42

A similar reaction to Preparation example 4 using 2-chloro-4-(3,5-ditrifluoromethyl-pyrazol-1-yl)-phenol (described in Reference Preparation example 22) instead of 2-methyl-4-(3,4,5-trimethyl-pyrazol-1-yl)-phenol gave 1-{3-methyl-2-[2-chloro-4-(3,5-ditrifluoromethyl-pyrazol-1-yl)-phenoxymethyl]-phenyl}-4-methyl-1,4-dihydrotetrazole-5-one (hereinafter, referred to as "Present compound 42").

Present compound 42

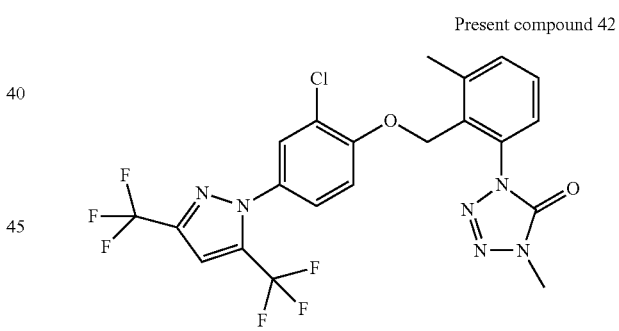

¹H-NMR (CDCl₃) δ: 7.51 (1H, d, J=2.7 Hz), 7.47-7.40 (2H, m), 7.35-7.31 (2H, m), 7.05 (1H, s), 7.00 (1H, d, J=8.8 Hz), 5.23 (2H, s), 3.67 (3H, s), 2.54 (3H, s).

Preparation Example 43

A similar reaction to Preparation example 4 using 2-chloro-4-(5-methyl-3-trifluoromethyl-pyrazol-1-yl)-phenol (described in Reference Preparation example 23) instead of 2-methyl-4-(3,4,5-trimethyl-pyrazol-1-yl)-phenol gave 1-{3-methyl-2-[2-chloro-4-(3-trifluoromethyl-5-methyl-pyrazol-1-yl)-phenoxymethyl]-phenyl}-4-methyl-1,4-dihydrotetrazole-5-one (hereinafter, referred to as "Present compound 43").

Present compound 43

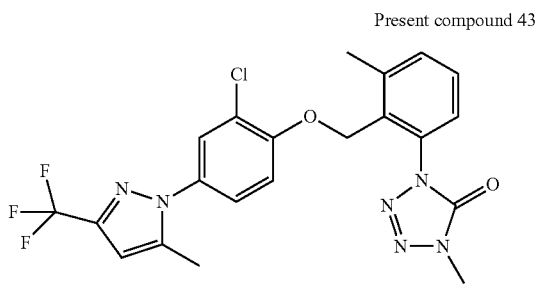 [SMILES: Cc1cccc(-n2nnn(C)c2=O)c1COc1ccc(-n2nc(C(F)(F)F)cc2C)cc1Cl]

¹H-NMR (CDCl₃) δ: 7.46 (1H, d, J=2.4 Hz), 7.45-7.40 (2H, m), 7.33-7.29 (1H, m), 7.28-7.24 (1H, m), 6.98-6.95 (1H, m), 6.43 (1H, s), 5.21 (2H, s), 3.68 (3H, s), 2.55 (3H, s), 2.32 (3H, s).

Preparation Example 44

A similar reaction to Preparation example 4 using 2-methyl-4-(1-ethyl-1H-pyrazol-3-yl)-phenol (described in Reference Preparation example 61) instead of 2-methyl-4-(3,4,5-trimethyl-pyrazol-1-yl)-phenol gave 1-{3-methyl-2-[2-methyl-4-(1-ethyl-1H-3-pyrazol-3-yl)-phenoxymethyl]-phenyl}-4-methyl-1,4-dihydrotetrazole-5-one (hereinafter, referred to as "Present compound 44").

Present compound 44

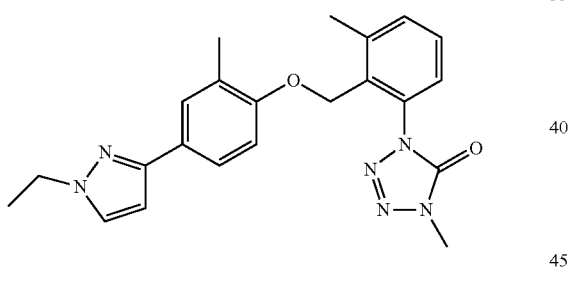

¹H-NMR (CDCl₃) δ: 7.58-7.57 (1H, m), 7.55-7.51 (1H, m), 7.43-7.39 (2H, m), 7.38 (1H, d, J=2.2 Hz), 7.30-7.27 (1H, m), 6.85 (1H, d, J=8.5 Hz), 6.44 (1H, d, J=2.2 Hz), 5.06 (2H, s), 4.20 (2H, q, J=7.3 Hz), 3.61 (3H, s), 2.51 (3H, s), 2.12 (3H, s), 1.51 (3H, t, J=7.2 Hz).

Preparation Example 45

A similar reaction to Preparation example 4 using 2-chloro-4-(3,5-diethyl-pyrazol-1-yl)-phenol (described in Reference Preparation example 24) instead of 2-methyl-4-(3,4,5-trimethyl-pyrazol-1-yl)-phenol gave 1-{3-methyl-2-[2-chloro-4-(3,5-diethyl-pyrazol-1-yl)-phenoxymethyl]-phenyl}-4-methyl-1,4-dihydrotetrazole-5-one (hereinafter, referred to as "Present compound 45").

Present compound 45

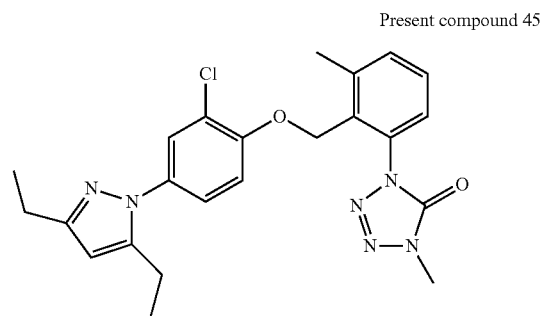 [SMILES: CCc1cc(CC)n(-c2ccc(OCc3c(C)cccc3-n3nnn(C)c3=O)c(Cl)c2)n1]

¹H-NMR (CDCl₃) δ: 7.45-7.38 (3H, m), 7.30 (1H, dd, J=7.3, 2.0 Hz), 7.22 (1H, dd, J=8.7, 2.6 Hz), 6.93 (1H, d, J=8.8 Hz), 6.02 (1H, s), 5.18 (2H, s), 3.68 (3H, s), 2.66 (2H, q, J=7.6 Hz), 2.59 (2H, q, J=7.5 Hz), 2.54 (3H, s), 1.29-1.24 (3H, m), 1.23-1.18 (3H, m).

Preparation Example 46

A similar reaction to Preparation example 4 using 2-chloro-4-(3,5-diisopropyl-pyrazol-1-yl)-phenol (described in Reference Preparation example 25) instead of 2-methyl-4-(3,4,5-trimethyl-pyrazol-1-yl)-phenol gave 1-{3-methyl-2-[2-chloro-4-(3,5-diisopropyl-pyrazol-1-yl)-phenoxymethyl]-phenyl}-4-methyl-1,4-dihydrotetrazole-5-one (hereinafter, referred to as "Present compound 46").

Present compound 46

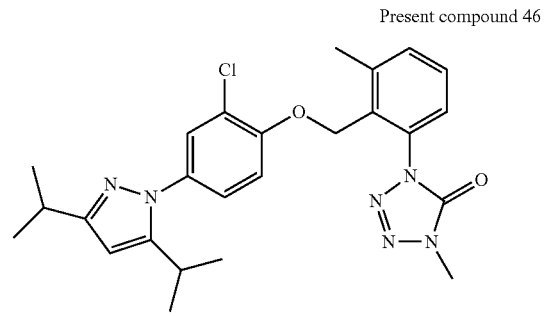 [SMILES: Cc1cccc(-n2nnn(C)c2=O)c1COc1ccc(-n2nc(C(C)C)cc2C(C)C)cc1Cl]

¹H-NMR (CDCl₃) δ: 7.45-7.38 (3H, m), 7.30 (1H, dd, J=7.3, 1.7 Hz), 7.22 (1H, dd, J=8.8, 2.4 Hz), 6.94 (1H, d, J=8.8 Hz), 6.00 (1H, s), 5.18 (2H, s), 3.68 (3H, s), 2.99-2.91 (2H, m), 2.54 (3H, s), 1.28 (6H, d, J=7.1 Hz), 1.16 (6H, d, J=6.8 Hz).

Preparation Example 47

A similar reaction to Preparation example 4 using 2-methyl-4-(1,5-dimethyl-1H-pyrazol-3-yl)-phenol (described in Reference Preparation example 63) instead of 2-methyl-4-(3,4,5-trimethyl-pyrazol-1-yl)-phenol gave 1-{3-methyl-2-[2-methyl-4-(1,5-dimethyl-1H-pyrazol-3-yl)-phenoxymethyl]-phenyl}-4-methyl-1,4-dihydrotetrazole-5-one (hereinafter, referred to as "Present compound 47").

Present compound 47

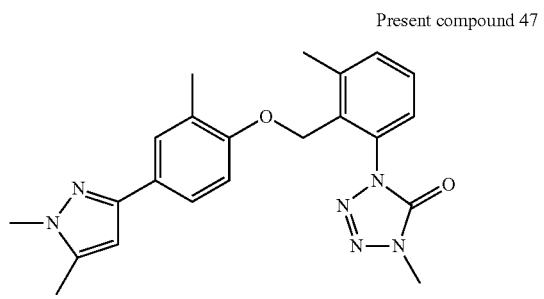 [SMILES: Cc1cc(-c2cc(C)n(C)n2)ccc1OCc1c(C)cccc1-n1nnn(C)c1=O]

¹H-NMR (CDCl₃) δ: 7.54-7.52 (1H, m), 7.48 (1H, dd, J=8.3, 2.3 Hz), 7.44-7.38 (2H, m), 7.30-7.26 (1H, m), 6.84 (1H, d, J=8.5 Hz), 6.23 (1H, s), 5.05 (2H, s), 3.80 (3H, s), 3.61 (3H, s), 2.51 (3H, s), 2.29 (3H, s), 2.11 (3H, s).

Preparation Example 48

A similar reaction to Preparation example 4 using 2-methyl-4-(1-isopropyl-1H-pyrazol-3-yl)-phenol (described in Reference Preparation example 62) instead of 2-methyl-4-(3,4,5-trimethyl-pyrazol-1-yl)-phenol gave 1-{3-methyl-2-[2-methyl-4-(1-isopropyl-1H-pyrazol-3-yl)-phenoxymethyl]-phenyl}-4-methyl-1,4-dihydrotetrazole-5-one (hereinafter, referred to as "Present compound 48").

Present compound 48

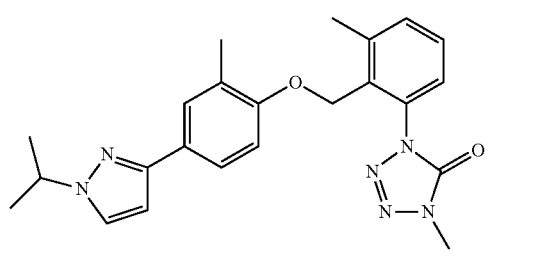

¹H-NMR (CDCl₃) δ: 7.58-7.57 (1H, m), 7.55-7.51 (1H, m), 7.45-7.38 (3H, m), 7.29-7.26 (1H, m), 6.85 (1H, d, J=8.5 Hz), 6.44 (1H, d, J=2.2 Hz), 5.06 (2H, s), 4.57-4.50 (1H, m), 3.61 (3H, s), 2.51 (3H, s), 2.12 (3H, s), 1.53 (6H, d, J=6.8 Hz).

Preparation Example 49

A similar reaction to Preparation example 4 using 2-methyl-4-(3-tert-butyl-pyrazol-1-yl)-phenol (described in Reference Preparation example 48) instead of 2-methyl-4-(3,4,5-trimethyl-pyrazol-1-yl)-phenol gave 1-{3-methyl-2-[2-methyl-4-(3-tert-butyl-pyrazol-1-yl)-phenoxymethyl]-phenyl}-4-methyl-1,4-dihydrotetrazole-5-one (hereinafter, referred to as "Present compound 49").

Present compound 49

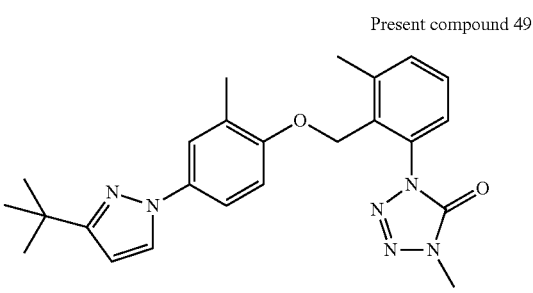 [SMILES: Cc1cc(-n2ccc(C(C)(C)C)n2)ccc1OCc1c(C)cccc1-n1nnn(C)c1=O]

¹H-NMR (CDCl₃) δ: 7.67 (1H, d, J=2.4 Hz), 7.45-7.39 (3H, m), 7.35 (1H, dd, J=8.7, 2.7 Hz), 7.28 (1H, dd, J=7.6, 2.8 Hz), 6.84 (1H, d, J=8.7 Hz), 6.26 (1H, d, J=2.2 Hz), 5.05 (2H, s), 3.63 (3H, s), 2.51 (3H, s), 2.13 (3H, s), 1.36 (9H, s).

Preparation Example 50

A similar reaction to Preparation example 5 using 2-methyl-4-(3,5-dimethyl-pyrazol-1-yl)-phenol (described in Reference Preparation example 30) instead of 2-methyl-4-(3,4,5-trimethyl-pyrazol-1-yl)-phenol gave 1-{3-ethyl-2-[2-methyl-4-(3,5-dimethyl-pyrazol-1-yl)-phenoxymethyl]-phenyl}-4-methyl-1,4-dihydrotetrazole-5-one (hereinafter, referred to as "Present compound 50").

Present compound 50

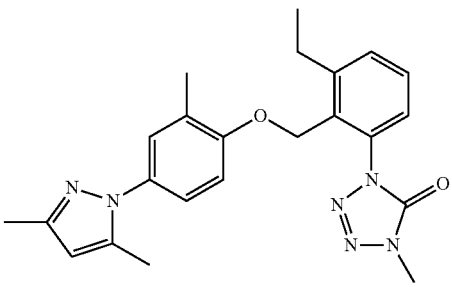

¹H-NMR (CDCl₃) δ: 7.51-7.43 (2H, m), 7.29 (1H, dd, J=7.2, 1.9 Hz), 7.19-7.11 (2H, m), 6.87 (1H, d, J=8.5 Hz), 5.95 (1H, s), 5.08 (2H, s), 3.61 (3H, s), 2.85 (2H, q, J=7.6 Hz), 2.28 (3H, s), 2.24 (3H, s), 2.10 (3H, s), 1.28 (3H, t, J=8.8 Hz).

Preparation Example 51

A similar reaction to Preparation example 5 using 2-chloro-4-(3,5-dimethyl-pyrazol-1-yl)-phenol (described in Reference Preparation example 20) instead of 2-methyl-4-(3,4,5-trimethyl-pyrazol-1-yl)-phenol gave 1-{3-ethyl-2-[2-chloro-4-(3,5-dimethyl-pyrazol-1-yl)-phenoxymethyl]-phenyl}-4-methyl-1,4-dihydrotetrazole-5-one (hereinafter, referred to as "Present compound 51").

Present compound 51

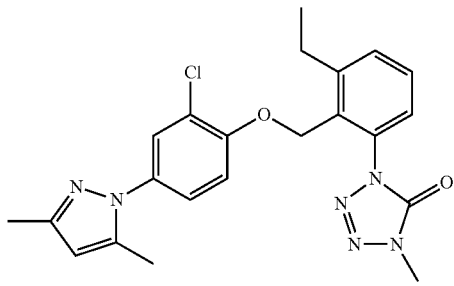

¹H-NMR (CDCl₃) δ: 7.50-7.42 (3H, m), 7.31 (1H, dd, J=7.4, 1.6 Hz), 7.23 (1H, dd, J=8.8, 2.7 Hz), 6.95 (1H, d, J=8.8 Hz), 5.96 (1H, s), 5.21 (2H, s), 3.65 (3H, s), 2.87 (2H, q, J=7.6 Hz), 2.27 (3H, s), 2.26 (3H, s), 1.30 (3H, t, J=7.6 Hz).

Preparation Example 52

A similar reaction to Preparation example 5 using 2-methyl-4-(3-methyl-pyrazol-1-yl)-phenol (described in Reference Preparation example 36) instead of 2-methyl-4-(3,4,5-trimethyl-pyrazol-1-yl)-phenol gave 1-{3-ethyl-2-[2-methyl-4-(3-methyl-pyrazol-1-yl)-phenoxymethyl]-phenyl}-4-methyl-1,4-dihydrotetrazole-5-one (hereinafter, referred to as "Present compound 52").

Present compound 52

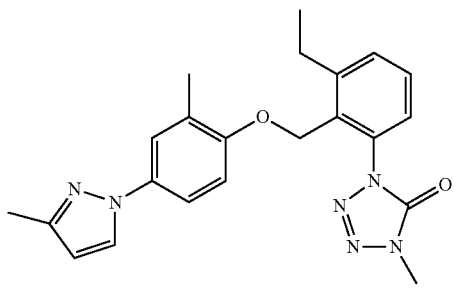

¹H-NMR (CDCl₃) δ: 7.69 (1H, d, J=2.2 Hz), 7.50-7.41 (3H, m), 7.34 (1H, dd, J=8.7, 2.9 Hz), 7.28 (1H, dd, J=7.1, 2.1 Hz), 6.86 (1H, d, J=8.7 Hz), 6.20 (1H, d, J=2.4 Hz), 5.07 (2H, s), 3.59 (3H, s), 2.85 (2H, q, J=7.6 Hz), 2.36 (3H, s), 2.12 (3H, s), 1.28 (3H, t, J=7.5 Hz).

Preparation Example 53

A similar reaction to Preparation example 5 using 2-methyl-4-(3,4-dimethyl-pyrazol-1-yl)-phenol (described in Reference Preparation example 46) instead of 2-methyl-4-(3,4,5-trimethyl-pyrazol-1-yl)-phenol gave 1-{3-ethyl-2-[2-methyl-4-(3,4-dimethyl-pyrazol-1-yl)-phenoxymethyl]-phenyl}-4-methyl-1,4-dihydrotetrazole-5-one (hereinafter, referred to as "Present compound 53").

Present compound 53

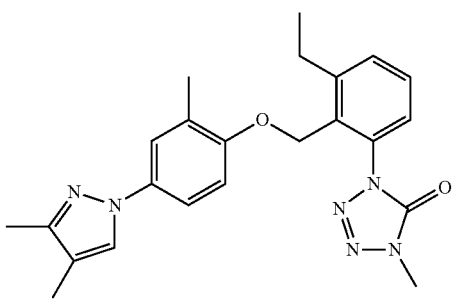

¹H-NMR (CDCl₃) δ: 7.52 (1H, s), 7.50-7.43 (1H, m), 7.38 (1H, d, J=2.7 Hz), 7.31-7.27 (3H, m), 6.84 (1H, d, J=8.8 Hz), 5.06 (2H, s), 3.59 (3H, s), 2.85 (2H, d, J=7.6 Hz), 2.27 (3H, s), 2.11 (3H, s), 2.06 (3H, s), 1.30-1.24 (3H, m).

Preparation Example 54

A similar reaction to Preparation example 5 using 2-chloro-4-(3,4,5-trimethyl-pyrazol-1-yl)-phenol (described in Reference Preparation example 19) instead of 2-methyl-4-(3,4,5-trimethyl-pyrazol-1-yl)-phenol gave 1-{3-ethyl-2-[2-chloro-4-(3,4,5-trimethyl-pyrazol-1-yl)-phenoxymethyl]-phenyl}-4-methyl-1,4-dihydrotetrazole-5-one (hereinafter, referred to as "Present compound 54").

Present compound 54

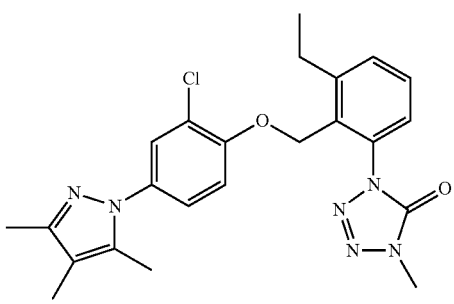

¹H-NMR (CDCl₃) δ: 7.50-7.40 (3H, m), 7.33-7.30 (1H, m), 7.21 (1H, dd, J=8.7, 2.7 Hz), 6.95 (1H, d, J=8.7 Hz), 5.20 (2H, s), 3.66 (3H, s), 2.87 (2H, q, J=7.6 Hz), 2.22 (3H, s), 2.18 (3H, s), 1.96 (3H, s), 1.30 (3H, t, J=7.5 Hz).

Preparation Example 55

A similar reaction to Preparation example 5 using 2-methyl-4-(1-ethyl-1H-pyrazol-3-yl)-phenol (described in Reference Preparation example 61) instead of 2-methyl-4-(3,4,5-trimethyl-pyrazol-1-yl)-phenol gave 1-{3-ethyl-2-[2-methyl-4-(1-ethyl-1H-pyrazol-3-yl)-phenoxymethyl]-phenyl}-4-methyl-1,4-dihydrotetrazole-5-one (hereinafter, referred to as "Present compound 55").

Present compound 55

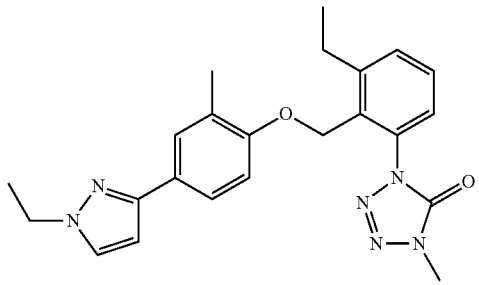

¹H-NMR (CDCl₃) δ: 7.57-7.42 (4H, m), 7.38 (1H, d, J=2.4 Hz), 7.30-7.27 (1H, m), 6.86 (1H, d, J=8.5 Hz), 6.44 (1H, d, J=2.2 Hz), 5.08 (2H, s), 4.20 (2H, q, J=7.3 Hz), 3.57 (3H, s), 2.88-2.82 (2H, m), 2.11 (3H, s), 1.51 (3H, t, J=7.2 Hz), 1.28 (3H, t, J=7.6 Hz).

Preparation Example 56

A similar reaction to Preparation example 5 using 2-chloro-4-(3,5-dimethyl-4-ethyl-pyrazol-1-yl)-phenol (described in Reference Preparation example 27) instead of 2-methyl-4-(3,4,5-trimethyl-pyrazol-1-yl)-phenol gave 1-{3-ethyl-2-[2-chloro-4-(3,5-dimethyl-4-ethyl-pyrazol-1-yl)-phenoxymethyl]-phenyl}-4-methyl-1,4-dihydrotetrazole-5-one (hereinafter, referred to a "Present compound 56").

Present compound 56

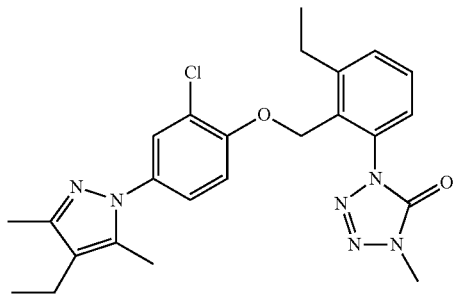

¹H-NMR (CDCl₃) δ: 7.50-7.41 (3H, m), 7.31 (1H, dd, J=7.5, 1.7 Hz), 7.23-7.20 (1H, m), 6.95 (1H, d, J=8.7 Hz), 5.20 (2H, s), 3.66 (3H, s), 2.87 (2H, q, J=7.5 Hz), 2.41 (2H, q, J=7.6 Hz), 2.24 (3H, s), 2.20 (3H, s), 1.30 (3H, t, J=7.6 Hz), 1.11 (3H, t, J=7.6 Hz).

Preparation Example 57

A similar reaction to Preparation example 5 using 2-methyl-4-(1-methyl-1H-pyrazol-3-yl)-phenol (described in Reference Preparation example 60) instead of 2-methyl-4-(3,4,5-trimethyl-pyrazol-1-yl)-phenol gave 1-{3-ethyl-2-[2-methyl-4-(1-methyl-1H-pyrazol-3-yl)-phenoxymethyl]-phenyl}-4-methyl-1,4-dihydrotetrazole-5-one (hereinafter, referred to as "Present compound 57").

Present compound 57

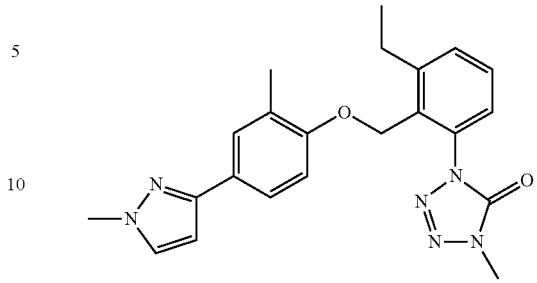

¹H-NMR (CDCl₃) δ: 7.56 (1H, s), 7.53 (1H, dd, J=8.3, 2.3 Hz), 7.49-7.43 (2H, m), 7.34 (1H, d, J=2.2 Hz), 7.29-7.26 (1H, m), 6.87 (1H, d, J=8.5 Hz), 6.45 (1H, d, J=2.2 Hz), 5.08 (2H, s), 3.93 (3H, s), 3.57 (3H, s), 2.85 (2H, q, J=7.6 Hz), 2.11 (3H, s), 1.28 (3H, t, J=7.7 Hz).

Preparation Example 58

A similar reaction to Preparation example 5 using 2-methyl-4-(1-isopropyl-1H-pyrazol-3-yl)-phenol (described in Reference Preparation example 62) instead of 2-methyl-4-(3,4,5-trimethyl-pyrazol-1-yl)-phenol gave 1-{3-ethyl-2-[2-methyl-4-(1-isopropyl-1H-pyrazol-3-yl)-phenoxymethyl]-phenyl}-4-methyl-1,4-dihydrotetrazole-5-one (hereinafter, referred to as "Present compound 58").

Present compound 58

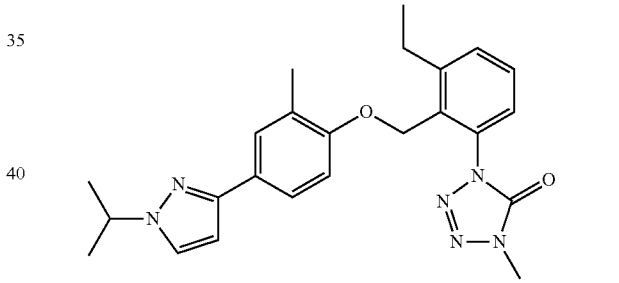

¹H-NMR (CDCl₃) δ: 7.58-7.56 (1H, m), 7.55-7.52 (1H, m), 7.48-7.43 (2H, m), 7.41 (1H, d, J=2.4 Hz), 7.28 (1H, dd, J=7.0, 2.2 Hz), 6.86 (1H, d, J=8.5 Hz), 6.44 (1H, d, J=2.4 Hz), 5.08 (2H, s), 4.58-4.50 (1H, m), 3.58 (3H, s), 2.85 (2H, q, J=7.4 Hz), 2.11 (3H, s), 1.53 (6H, d, J=6.8 Hz), 1.28 (3H, t, J=7.6 Hz).

Preparation Example 59

A mixture of 1-(2-bromomethyl-3-ethylphenyl)-4-methyl-1,4-dihydrotetrazole-5-one (described in Reference Preparation example 17) 0.30 g, 2-methyl-4-(1,5-dimethyl-1H-pyrazol-3-yl)-phenol (described in Reference Preparation example 63) 0.21 g, potassium carbonate 0.18 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-ethyl-2-[2-methyl-4-(1,5-dimethyl-1H-pyrazol-3-yl)-phenoxymethyl]-phenyl}-4-methyl-1,4-dihydrotetrazole-5-one (hereinafter, referred to as "Present compound 59") 0.33 g.

Present compound 59

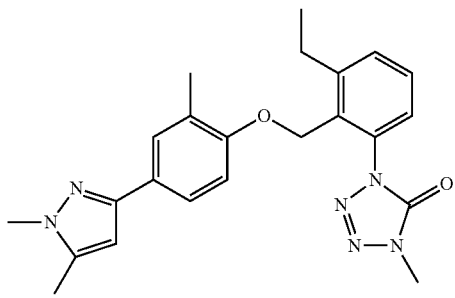

¹H-NMR (CDCl₃) δ: 7.54-7.52 (1H, m), 7.51-7.43 (3H, m), 7.29-7.26 (1H, m), 6.85 (1H, d, J=8.5 Hz), 6.23 (1H, s), 5.07 (2H, s), 3.80 (3H, s), 3.57 (3H, s), 2.89-2.81 (2H, m), 2.29 (3H, s), 2.10 (3H, s), 1.28 (3H, t, J=7.6 Hz).

Preparation Example 60

A similar reaction to Preparation example 7 using 2-chloro-4-(3,5-dimethyl-pyrazol-1-yl)-phenol (described in Reference Preparation example 20) instead of 2-methyl-4-(3,4,5-trimethyl-pyrazol-1-yl)-phenol gave 1-{3-methoxy-2-[2-chloro-4-(3,5-dimethyl-pyrazol-1-yl)-phenoxymethyl]-phenyl}-4-methyl-1,4-dihydrotetrazole-5-one (hereinafter, referred to as "Present compound 60").

Present compound 60

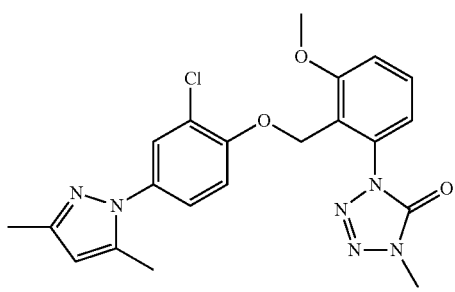

¹H-NMR (CDCl₃) δ: 7.46 (1H, t, J=8.3 Hz), 7.38 (1H, d, J=2.7 Hz), 7.19 (1H, dd, J=8.8, 2.7 Hz), 7.13-7.10 (1H, m), 7.07 (1H, d, J=8.3 Hz), 6.98 (1H, d, J=8.8 Hz), 5.95 (1H, s), 5.45 (2H, s), 3.94 (3H, s), 3.65 (3H, s), 2.26 (3H, s), 2.24 (3H, s).

Preparation Example 61

A similar reaction to Preparation example 7 using 2-chloro-4-(3,4,5-trimethyl-pyrazol-1-yl)-phenol (described in Reference Preparation example 19) instead of 2-methyl-4-(3,4,5-trimethyl-pyrazol-1-yl)-phenol gave 1-{3-methoxy-2-[2-chloro-4-(3,4,5-trimethyl-pyrazol-1-yl)-phenoxymethyl]-phenyl}-4-methyl-1,4-dihydrotetrazole-5-one (hereinafter, referred to as "Present compound 61").

Present compound 61

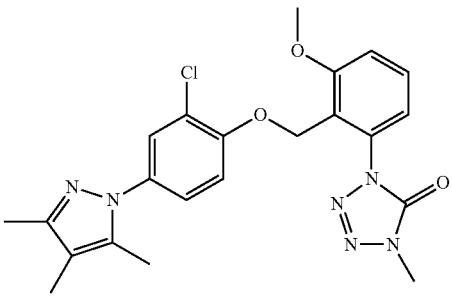

¹H-NMR (CDCl₃) δ: 7.45-7.37 (3H, m), 7.30 (1H, dd, J=7.6, 1.5 Hz), 7.20 (1H, dd, J=8.8, 2.6 Hz), 6.93 (1H, d, J=8.8 Hz), 5.18 (2H, s), 3.67 (3H, s), 2.54 (3H, s), 2.22 (3H, s), 2.18 (3H, s), 1.96 (3H, s).

Preparation Example 62

A similar reaction to Preparation example 7 using 2-methyl-4-(3,5-dimethyl-pyrazol-1-yl)-phenol (described in Reference Preparation example 30) instead of 2-methyl-4-(3,4,5-trimethyl-pyrazol-1-yl)-phenol gave 1-{3-methoxy-2-[2-methyl-4-(3,5-dimethyl-pyrazol-1-yl)-phenoxymethyl]-phenyl}-4-methyl-1,4-dihydrotetrazole-5-one (hereinafter, referred to as "Present compound 62").

Present compound 62

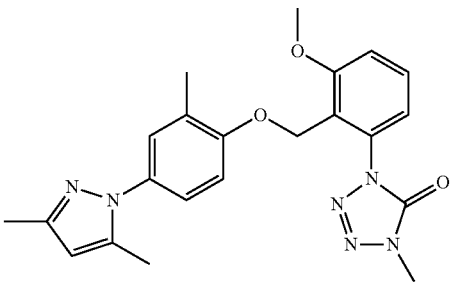

¹H-NMR (CDCl₃) δ: 7.47 (1H, t, J=8.2 Hz), 7.14-7.06 (4H, m), 6.90 (1H, d, J=8.5 Hz), 5.94 (1H, s), 5.29 (2H, s), 3.93 (3H, s), 3.61 (3H, s), 2.27 (3H, s), 2.23 (3H, s), 2.02 (3H, s).

Preparation Example 63

A similar reaction to Preparation example 7 using 2-methyl-4-(3-methyl-pyrazol-1-yl)-phenol (described in Reference Preparation example 36) instead of 2-methyl-4-(3,4,5-trimethyl-pyrazol-1-yl)-phenol gave 1-{3-methoxy-2-[2-methyl-4-(3-methyl-pyrazol-1-yl)-phenoxymethyl]-phenyl}-4-methyl-1,4-dihydrotetrazole-5-one (hereinafter, referred to a "Present compound 63").

Present compound 63

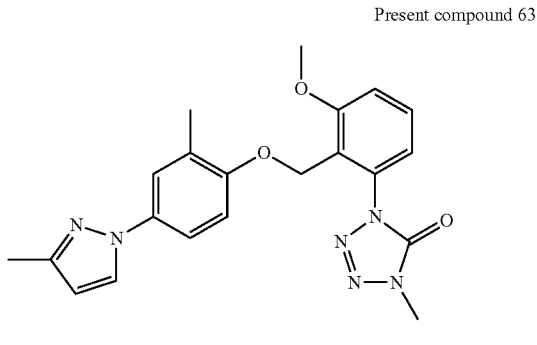

¹H-NMR (CDCl₃) δ: 7.67 (1H, d, J=2.2 Hz), 7.46 (1H, t, J=8.2 Hz), 7.37 (1H, d, J=2.7 Hz), 7.30 (1H, dd, J=8.7, 2.7 Hz), 7.08 (2H, dd, J=8.2, 5.0 Hz), 6.89 (1H, d, J=8.7 Hz), 6.18 (1H, d, J=2.2 Hz), 5.28 (2H, s), 3.93 (3H, s), 3.59 (3H, s), 2.36 (3H, s), 2.04 (3H, s).

Preparation Example 64

A similar reaction to Preparation example 7 using 2-chloro-4-(3-methyl-pyrazol-1-yl)-phenol (described in Reference Preparation example 39) instead of 2-methyl-4-(3,4,5-trimethyl-pyrazol-1-yl)-phenol gave 1-{3-methoxy-2-[2-chloro-4-(3-methyl-pyrazol-1-yl)-phenoxymethyl]-phenyl}-4-methyl-1,4-dihydrotetrazole-5-one (hereinafter, referred to as "Present compound 64").

Present compound 64

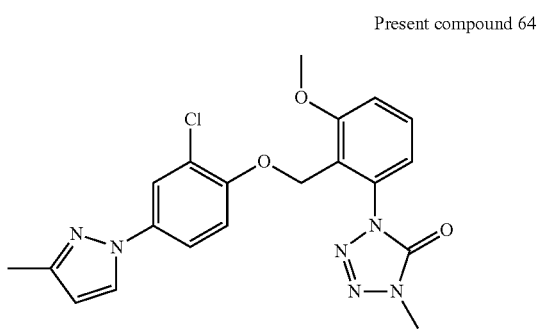 [SMILES: COc1cccc(-n2nnn(C)c2=O)c1COc1ccc(-n2ccc(C)n2)cc1Cl]

¹H-NMR (CDCl₃) δ: 7.66 (1H, d, J=2.2 Hz), 7.61 (1H, d, J=2.7 Hz), 7.45 (1H, t, J=8.3 Hz), 7.38 (1H, dd, J=9.0, 2.7 Hz), 7.10 (1H, d, J=7.8 Hz), 7.06 (1H, d, J=8.0 Hz), 6.96 (1H, d, J=9.0 Hz), 6.20 (1H, d, J=2.2 Hz), 5.44 (2H, s), 3.94 (3H, s), 3.64 (3H, s), 2.34 (3H, s).

Preparation Example 65

A similar reaction to Preparation example 7 using 2-methyl-4-(4-methyl-pyrazol-1-yl)-phenol (described in Reference Preparation example 34) instead of 2-methyl-4-(3,4,5-trimethyl-pyrazol-1-yl)-phenol gave 1-{3-methoxy-2-[2-methyl-4-(4-methyl-pyrazol-1-yl)-phenoxymethyl]-phenyl}-4-methyl-1,4-dihydrotetrazole-5-one (hereinafter, referred to as "Present compound 65").

Present compound 65

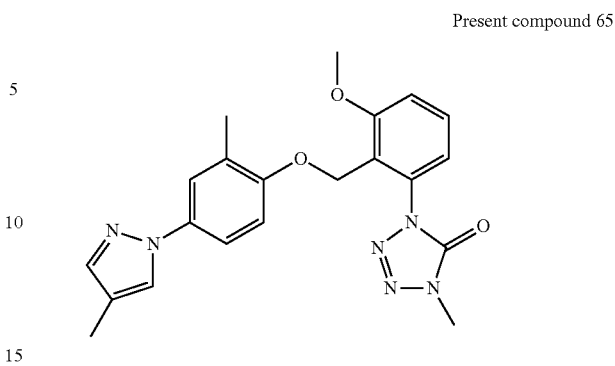

¹H-NMR (CDCl₃) δ: 7.58 (1H, s), 7.47 (2H, t, J=8.3 Hz), 7.37 (1H, d, J=2.7 Hz), 7.31 (1H, dd, J=8.5, 2.7 Hz), 7.08 (2H, dd, J=7.6, 6.6 Hz), 6.90 (1H, d, J=8.5 Hz), 5.28 (2H, s), 3.93 (3H, s), 3.59 (3H, s), 2.14 (3H, s), 2.04 (3H, s).

Preparation Example 66

A similar reaction to Preparation example 7 using 2-methyl-4-(5-methyl-pyrazol-1-yl)-phenol (described in Reference Preparation example 35) instead of 2-methyl-4-(3,4,5-trimethyl-pyrazol-1-yl)-phenol gave 1-{3-methoxy-2-[2-methyl-4-(5-methyl-pyrazol-1-yl)-phenoxymethyl]-phenyl}-4-methyl-1,4-dihydrotetrazole-5-one (hereinafter, referred to as "Present compound 66").

Present compound 66

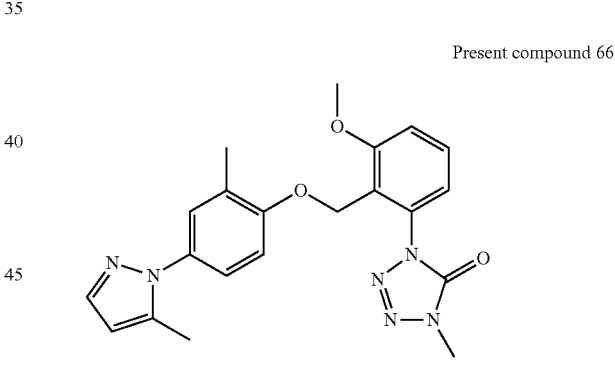

¹H-NMR (CDCl₃) δ: 7.51 (1H, s), 7.48 (1H, t, J=8.3 Hz), 7.15 (1H, s), 7.12-7.07 (3H, m), 6.93 (1H, d, J=8.5 Hz), 6.14 (1H, s), 5.30 (2H, s), 3.93 (3H, s), 3.62 (3H, s), 2.28 (3H, s), 2.03 (3H, s).

Preparation Example 67

A similar reaction to Preparation example 7 using 2-chloro-4-(1-methyl-1H-pyrazole-4-yl)-phenol (described in Reference Preparation example 52) instead of 2-methyl-4-(3,4,5-trimethyl-pyrazol-1-yl)-phenol gave 1-{3-methoxy-2-[2-chloro-4-(1-methyl-1H-pyrazol-4-yl)-phenoxymethyl]-phenyl}-4-methyl-1,4-dihydrotetrazole-5-one (hereinafter, referred to as "Present compound 67").

Present compound 67

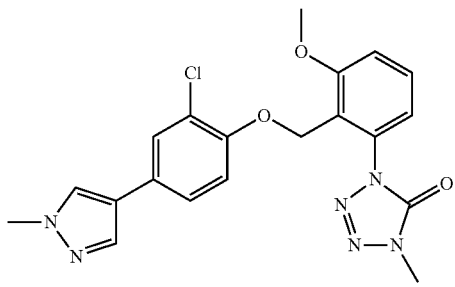

$^1$H-NMR (CDCl$_3$) δ: 7.64 (1H, s), 7.49 (1H, s), 7.45 (1H, t, J=8.3 Hz), 7.37 (1H, d, J=2.2 Hz), 7.21 (1H, dd, J=8.3, 2.2 Hz), 7.10 (1H, dd, J=8.0, 0.7 Hz), 7.06 (1H, d, J=8.5 Hz), 6.91 (1H, d, J=8.5 Hz), 5.43 (2H, s), 3.94 (3H, s), 3.92 (3H, s), 3.64 (3H, s).

Preparation Example 68

A similar reaction to Preparation example 7 using 2-methyl-4-(1-methyl-1H-pyrazole-4-yl)-phenol (described in Reference Preparation example 53) instead of 2-methyl-4-(3,4,5-trimethyl-pyrazol-1-yl)-phenol gave 1-{3-methoxy-2-[2-methyl-4-(1-methyl-1H-pyrazole-4-yl)-phenoxymethyl]-phenyl}-4-methyl-1,4-dihydrotetrazole-5-one (hereinafter, referred to as "Present compound 68").

Present compound 68

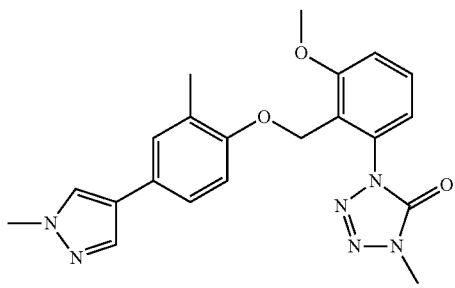

$^1$H-NMR (CDCl$_3$) δ: 7.66 (1H, s), 7.50 (1H, s), 7.46 (1H, t, J=8.2 Hz), 7.21-7.16 (2H, m), 7.07 (2H, t, J=8.3 Hz), 6.86 (1H, d, J=8.2 Hz), 5.26 (2H, s), 3.93 (3H, s), 3.92 (3H, s), 3.58 (3H, s), 2.02 (3H, s).

Preparation Example 69

A similar reaction to Preparation example 7 using 2-methyl-4-(pyrazol-1-yl)-phenol (described in Reference Preparation example 37) instead of 2-methyl-4-(3,4,5-trimethyl-pyrazol-1-yl)-phenol gave 1-{3-methoxy-2-[2-methyl-4-pyrazol-1-yl-phenoxymethyl]-phenyl}-4-methyl-1,4-dihydrotetrazole-5-one (hereinafter, referred to as "Present compound 69").

Present compound 69

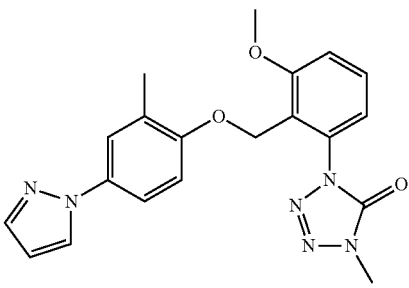

$^1$H-NMR (CDCl$_3$) δ: 7.79 (1H, d, J=2.4 Hz), 7.67 (1H, d, J=1.9 Hz), 7.47 (1H, t, J=8.2 Hz), 7.41 (1H, d, J=2.7 Hz), 7.36 (1H, dd, J=8.7, 2.7 Hz), 7.09 (1H, d, J=6.0 Hz), 7.07 (1H, d, J=5.6 Hz), 6.92 (1H, d, J=8.7 Hz), 6.41 (1H, t, J=1.9 Hz), 5.29 (2H, s), 3.93 (3H, s), 3.60 (3H, d, J=0.5 Hz), 2.05 (3H, s).

Preparation Example 70

A similar reaction to Preparation example 7 using 2-methyl-4-(1-propyl-1H-pyrazol-1-yl)-phenol (described in Reference Preparation example 55) instead of 2-methyl-4-(3,4,5-trimethyl-pyrazol-1-yl)-phenol gave 1-{3-methoxy-2-[2-methyl-4-(1-propyl-1H-pyrazol-1-yl)-phenoxymethyl]-phenyl}-4-methyl-1,4-dihydrotetrazole-5-one (hereinafter, referred to as "Present compound 70").

Present compound 70

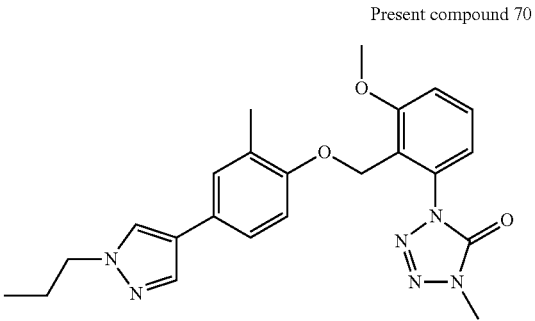 [SMILES: CCCn1cc(-c2ccc(OCc3c(OC)cccc3-n3nnn(C)c3=O)c(C)c2)cn1]

$^1$H-NMR (CDCl$_3$) δ: 7.68 (1H, d, J=0.7 Hz), 7.52 (1H, d, J=0.7 Hz), 7.46 (1H, t, J=8.2 Hz), 7.22-7.17 (2H, m), 7.10-7.05 (2H, m), 6.86 (1H, d, J=8.3 Hz), 5.26 (2H, s), 4.10-4.06 (2H, m), 3.93 (3H, s), 3.58 (3H, s), 2.02 (3H, s), 1.91 (2H, td, J=14.5, 7.4 Hz), 0.94 (3H, t, J=7.3 Hz).

Preparation Example 71

A similar reaction to Preparation example 7 using 2-methyl-4-(1-ethyl-1H-pyrazole-4-yl)-phenol (described in Reference Preparation example 54) instead of 2-methyl-4-(3,4,5-trimethyl-pyrazol-1-yl)-phenol gave 1-{3-methoxy-2-[2-methyl-4-(1-ethyl-1H-pyrazole-4-yl)-phenoxymethyl]-phenyl}-4-methyl-1,4-dihydrotetrazole-5-one (hereinafter, referred to as "Present compound 71").

Present compound 71

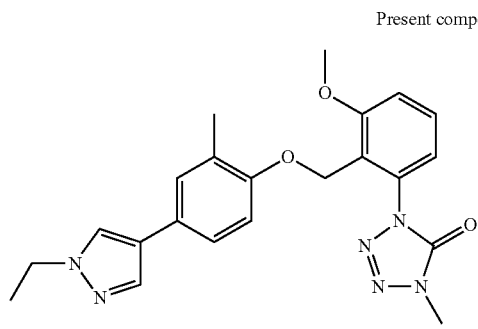

¹H-NMR (CDCl₃) δ: 7.67 (1H, s), 7.53 (1H, s), 7.46 (1H, t, J=8.2 Hz), 7.22-7.17 (2H, m), 7.08 (2H, t, J=8.4 Hz), 6.86 (1H, d, J=8.3 Hz), 5.26 (2H, s), 4.18 (2H, q, J=7.3 Hz), 3.93 (3H, s), 3.58 (3H, d, J=1.2 Hz), 2.02 (3H, s), 1.53-1.49 (3H, m).

Preparation Example 72

A similar reaction to Preparation example 7 using 2-chloro-4-(3,4,5-trimethyl-pyrazol-1-yl)-phenol (described in Reference Preparation example 19) instead of 2-methyl-4-(3,4,5-trimethyl-pyrazol-1-yl)-phenol gave 1-{3-methoxy-2-[2-chloro-4-(3,4,5-trimethyl-pyrazol-1-yl)-phenoxymethyl]-phenyl}-4-methyl-1,4-dihydrotetrazole-5-one (hereinafter, referred to as "Present compound 72").

Present compound 72

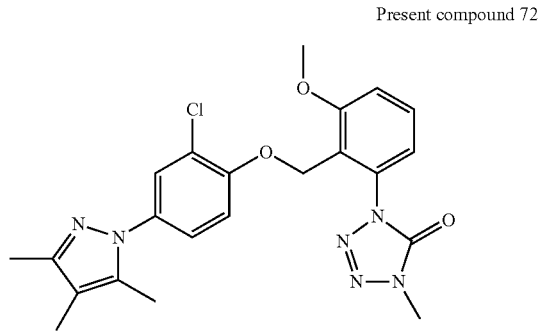 [SMILES: COc1cccc(-n2nnn(C)c2=O)c1COc1ccc(-n2nc(C)c(C)c2C)cc1Cl]

¹H-NMR (CDCl₃) δ: 7.46 (1H, t, J=8.2 Hz), 7.36 (1H, d, J=2.4 Hz), 7.16 (1H, dd, J=8.8, 2.4 Hz), 7.11 (1H, dd, J=7.9, 0.9 Hz), 7.07 (1H, d, J=8.5 Hz), 6.97 (1H, d, J=8.8 Hz), 5.45 (2H, s), 3.94 (3H, s), 3.65 (3H, s), 2.21 (3H, s), 2.16 (3H, s), 1.95 (3H, s).

Preparation Example 73

A similar reaction to Preparation example 7 using 2-methyl-4-(1-isopropyl-1H-pyrazole-4-yl)-phenol (described in Reference Preparation example 56) instead of 2-methyl-4-(3,4,5-trimethyl-pyrazol-1-yl)-phenol gave 1-{3-methoxy-2-[2-methyl-4-(1-isopropyl-1H-pyrazole-4-yl)-phenoxymethyl]-phenyl}-4-methyl-1,4-dihydrotetrazole-5-one (hereinafter, referred to as "Present compound 73").

Present compound 73

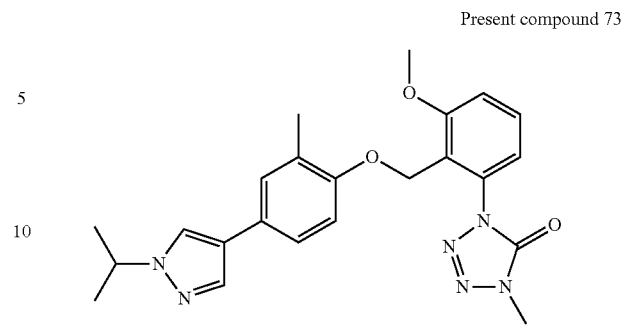

¹H-NMR (CDCl₃) δ: 7.68 (1H, s), 7.56 (1H, s), 7.45 (1H, t, J=8.2 Hz), 7.22-7.16 (2H, m), 7.07 (2H, dd, J=7.6, 6.9 Hz), 6.86 (1H, d, J=8.2 Hz), 5.26 (2H, s), 4.55-4.45 (1H, m), 3.92 (3H, s), 3.58 (3H, s), 2.02 (3H, s), 1.53 (6H, d, J=6.5 Hz).

Preparation Example 74

A similar reaction to Preparation example 7 using 2-methyl-4-(3-trifluoromethyl-pyrazol-1-yl)-phenol (described in Reference Preparation example 45) instead of 2-methyl-4-(3,4,5-trimethyl-pyrazol-1-yl)-phenol gave 1-{3-methoxy-2-[2-methyl-4-(3-trifluoromethyl-pyrazol-1-yl)-phenoxymethyl]-phenyl}-4-methyl-1,4-dihydrotetrazole-5-one (hereinafter, referred to as "Present compound 74").

Present compound 74

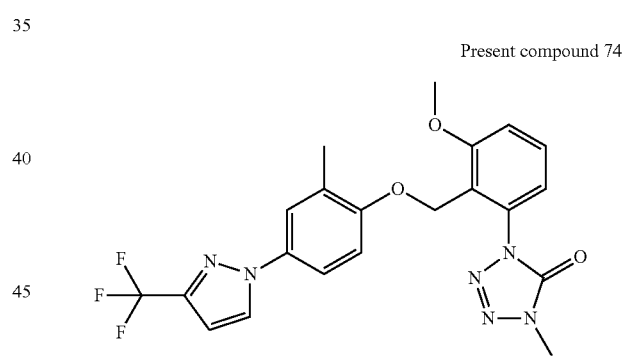

¹H-NMR (CDCl₃) δ: 7.81-7.79 (1H, m), 7.48 (1H, t, J=8.3 Hz), 7.40 (1H, d, J=2.4 Hz), 7.36 (1H, dd, J=8.7, 2.8 Hz), 7.09 (2H, t, J=7.6 Hz), 6.93 (1H, d, J=8.8 Hz), 6.66 (1H, d, J=2.4 Hz), 5.31 (2H, s), 3.94 (3H, s), 3.61 (3H, s), 2.05 (3H, s).

Preparation Example 75

A similar reaction to Preparation example 7 using 2,5-dimethyl-4-(3-methyl-pyrazol-1-yl)-phenol (described in Reference Preparation example 40) instead of 2-methyl-4-(3,4,5-trimethyl-pyrazol-1-yl)-phenol gave 1-{3-methoxy-2-[2,5-dimethyl-4-(3-methyl-pyrazol-1-yl)-phenoxymethyl]-phenyl}-4-methyl-1,4-dihydrotetrazole-5-one (hereinafter, referred to a "Present compound 75").

Present compound 75

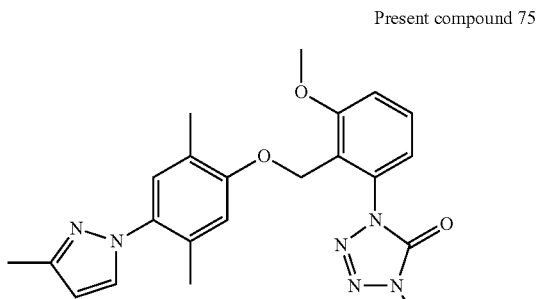

¹H-NMR (CDCl₃) δ: 7.47 (1H, t, J=8.2 Hz), 7.38 (1H, d, J=2.4 Hz), 7.10-7.06 (2H, m), 7.01 (1H, s), 6.75 (1H, s), 6.15 (1H, d, J=2.2 Hz), 5.27 (2H, s), 3.94 (3H, s), 3.62 (3H, s), 2.34 (3H, s), 2.14 (3H, s), 1.95 (3H, s).

Preparation Example 76

A similar reaction to Preparation example 7 using 2-chloro-4-(4-methyl-pyrazol-1-yl)-phenol (described in Reference Preparation example 44) instead of 2-methyl-4-(3,4,5-trimethyl-pyrazol-1-yl)-phenol gave 1-{3-methoxy-2-[2-chloro-4-(4-methyl-pyrazol-1-yl)-phenoxymethyl]-phenyl}-4-methyl-1,4-dihydrotetrazole-5-one (hereinafter, referred to as "Present compound 76").

Present compound 76

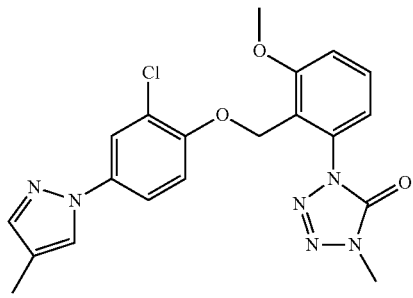

¹H-NMR (CDCl₃) δ: 7.60 (1H, d, J=2.7 Hz), 7.56 (1H, t, J=0.7 Hz), 7.48-7.43 (2H, m), 7.39 (1H, dd, J=8.8, 2.7 Hz), 7.10 (1H, dd, J=8.0, 1.0 Hz), 7.07 (1H, d, J=8.5 Hz), 6.97 (1H, d, J=8.8 Hz), 5.44 (2H, s), 3.94 (3H, s), 3.64 (3H, s), 2.13 (3H, s).

Preparation Example 77

A similar reaction to Preparation example 7 using 2-methyl-4-(1-isobutyl-1H-pyrazole-4-yl)-phenol (described in Reference Preparation example 58) instead of 2-methyl-4-(3,4,5-trimethyl-pyrazol-1-yl)-phenol gave 1-{3-methoxy-2-[2-methyl-4-(1-isobutyl-1H-pyrazole-4-yl)-phenoxymethyl]-phenyl}-4-methyl-1,4-dihydrotetrazole-5-one (hereinafter, referred to as "Present compound 77").

Present compound 77

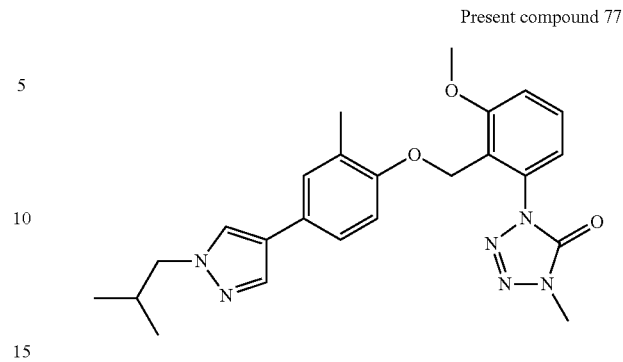

¹H-NMR (CDCl₃) δ: 7.68 (1H, s), 7.50 (1H, s), 7.46 (1H, t, J=8.2 Hz), 7.22-7.18 (2H, m), 7.07 (2H, dd, J=8.0, 7.3 Hz), 6.86 (1H, d, J=8.0 Hz), 5.27 (2H, s), 3.93 (3H, s), 3.91 (2H, d, J=7.3 Hz), 3.58 (3H, s), 2.27-2.17 (1H, m), 2.02 (3H, s), 0.93 (6H, d, J=6.6 Hz).

Preparation Example 78

A similar reaction to Preparation example 7 using 2-methyl-4-(1-butyl-1H-pyrazole-4-yl)-phenol (described in Reference Preparation example 57) instead of 2-methyl-4-(3,4,5-trimethyl-pyrazol-1-yl)-phenol gave 1-{3-methoxy-2-[2-methyl-4-(1-butyl-1H-pyrazole-4-yl)-phenoxymethyl]-phenyl}-4-methyl-1,4-dihydrotetrazole-5-one (hereinafter, referred to as "Present compound 78").

Present compound 78

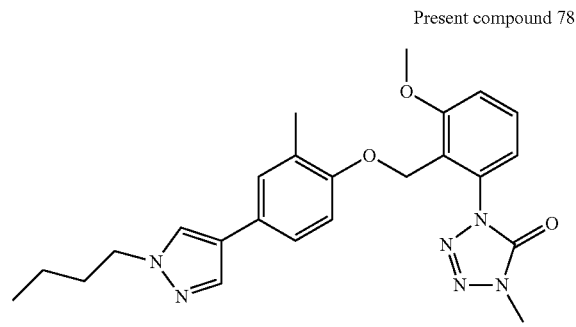 [SMILES: CCCCn1cc(-c2ccc(OCc3c(OC)cccc3-n3nnn(C)c3=O)c(C)c2)cn1]

¹H-NMR (CDCl₃) δ: 7.67 (1H, s), 7.51 (1H, s), 7.46 (1H, t, J=8.2 Hz), 7.21-7.17 (2H, m), 7.07 (2H, t, J=7.9 Hz), 6.86 (1H, d, J=8.3 Hz), 5.26 (2H, s), 4.12 (2H, t, J=7.2 Hz), 3.93 (3H, s), 3.58 (3H, s), 2.02 (3H, s), 1.90-1.83 (2H, m), 1.39-1.32 (2H, m), 0.95 (3H, t, J=7.3 Hz).

Preparation Example 79

A similar reaction to Preparation example 7 using 2-fluoro-4-(3-methyl-pyrazol-1-yl)-phenol (described in Reference Preparation example 43) instead of 2-methyl-4-(3,4,5-trimethyl-pyrazol-1-yl)-phenol gave 1-{3-methoxy-2-[2-fluoro-4-(3-methyl-pyrazol-1-yl)-phenoxymethyl]-phenyl}-4-methyl-1,4-dihydrotetrazole-5-one (hereinafter, referred to as "Present compound 79").

Present compound 79

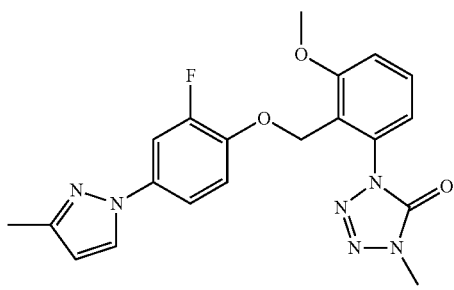

¹H-NMR (CDCl₃) δ: 7.67 (1H, d, J=2.4 Hz), 7.46 (1H, t, J=8.2 Hz), 7.36 (1H, dd, J=12.0, 2.5 Hz), 7.24-7.21 (1H, m), 7.09-7.05 (2H, m), 6.97 (1H, t, J=8.8 Hz), 6.20 (1H, d, J=2.4 Hz), 5.36 (2H, s), 3.92 (3H, s), 3.66 (3H, s), 2.34 (3H, s).

Preparation Example 80

A similar reaction to Preparation example 7 using 2-methyl-4-(1,3-dimethyl-1H-pyrazole-4-yl)-phenol (described in Reference Preparation example 59) instead of 2-methyl-4-(3,4,5-trimethyl-pyrazol-1-yl)-phenol gave 1-{3-methoxy-2-[2-methyl-4-(1,3-dimethyl-1H-pyrazole-4-yl)-phenoxymethyl]-phenyl}-4-methyl-1,4-dihydrotetrazole-5-one (hereinafter, referred to as "Present compound 80")

Present compound 80

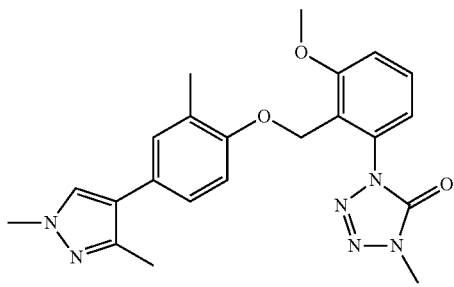

¹H-NMR (CDCl₃) δ: 7.46 (1H, t, J=8.2 Hz), 7.32 (1H, s), 7.12-7.05 (4H, m), 6.88 (1H, d, J=8.3 Hz), 5.27 (2H, s), 3.93 (3H, s), 3.85 (3H, s), 3.60 (3H, s), 2.35 (3H, s), 2.02 (3H, s).

Preparation Example 81

A similar reaction to Preparation example 7 using 2-methyl-4-(4,5,6,7-tetrahydro-indazole-2-yl)-phenol (described in Reference Preparation example 50) instead of 2-methyl-4-(3,4,5-trimethyl-pyrazol-1-yl)-phenol gave 1-{3-methoxy-2-[2-methyl-4-(4,5,6,7-tetrahydro-indazole-2-yl)-phenoxymethyl]-phenyl}-4-methyl-1,4-dihydrotetrazole-5-one (hereinafter, referred to as "Present compound 81").

Present compound 81

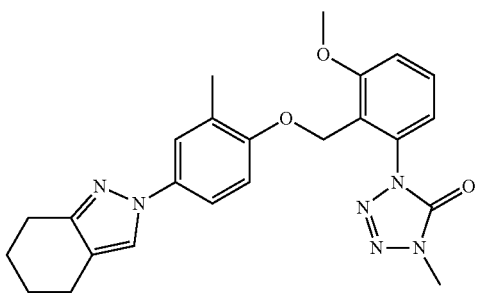

¹H-NMR (CDCl₃) δ: 7.49 (1H, s), 7.48-7.44 (1H, m), 7.36 (1H, d, J=2.7 Hz), 7.29 (1H, d, J=2.9 Hz), 7.08 (2H, dd, J=8.2, 5.0 Hz), 6.88 (1H, d, J=8.8 Hz), 5.26 (2H, s), 3.92 (3H, s), 3.59 (3H, s), 2.75 (2H, t, J=6.2 Hz), 2.60 (2H, t, J=6.1 Hz), 2.03 (3H, s), 1.88-1.81 (2H, m), 1.80-1.74 (2H, m).

Preparation Example 82

A similar reaction to Preparation example 7 using 2-methyl-4-(4,5,6,7-tetrahydro-indazole-1-yl)-phenol (described in Reference Preparation example 51) instead of 2-methyl-4-(3,4,5-trimethyl-pyrazol-1-yl)-phenol gave 1-{3-methoxy-2-[2-methyl-4-(4,5,6,7-tetrahydro-indazole-1-yl)-phenoxymethyl]-phenyl}-4-methyl-1,4-dihydrotetrazole-5-one (hereinafter, referred to as "Present compound 82").

Present compound 82

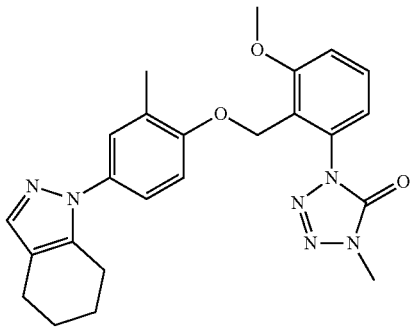

¹H-NMR (CDCl₃) δ: 7.47 (1H, t, J=8.2 Hz), 7.40 (1H, s), 7.21 (1H, d, J=2.4 Hz), 7.16 (1H, dd, J=8.5, 2.7 Hz), 7.09 (2H, dd, J=8.0, 4.4 Hz), 6.90 (1H, d, J=8.8 Hz), 5.28 (2H, s), 3.93 (3H, s), 3.61 (3H, s), 2.64 (2H, t, J=5.4 Hz), 2.57 (2H, t, J=5.4 Hz), 2.03 (3H, s), 1.82-1.73 (4H, m).

Preparation Example 83

A similar reaction to Preparation example 7 using 2,3-dimethyl-4-(3-methyl-pyrazol-1-yl)-phenol (described in Reference Preparation example 42) instead of 2-methyl-4-(3,4,5-trimethyl-pyrazol-1-yl)-phenol gave 1-{3-methoxy-2-[2,3-dimethyl-4-(3-methyl-pyrazol-1-yl)-phenoxymethyl]-phenyl}-4-methyl-1,4-dihydrotetrazole-5-one (hereinafter, referred to as "Present compound 83").

Present compound 83

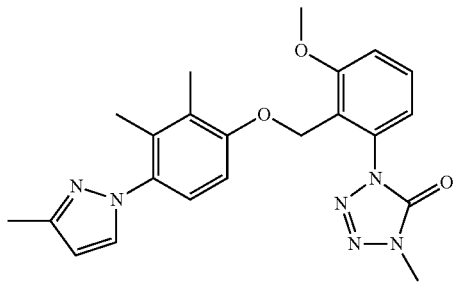

¹H-NMR (CDCl₃) δ: 7.46 (1H, t, J=8.3 Hz), 7.36 (1H, d, J=2.2 Hz), 7.10-7.03 (3H, m), 6.78 (1H, d, J=8.8 Hz), 6.15 (1H, d, J=2.2 Hz), 5.28 (2H, s), 3.93 (3H, s), 3.62 (3H, s), 2.34 (3H, s), 1.95 (6H, s).

Preparation Example 84

A mixture of 1-(2-bromomethyl-3-methoxyphenyl)-4-methyl-, 4-dihydrotetrazole-5-one (described in Reference Preparation example 9) 0.30 g, 2-methyl-4-(1-methyl-1H-pyrazol-3-yl)-phenol (described in Reference Preparation example 60) 0.19 g, potassium carbonate 0.18 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-methoxy-2-[2-methyl-4-(1-methyl-1H-pyrazol-3-yl)-phenoxymethyl]-phenyl}-4-methyl-1,4-dihydrotetrazole-5-one (hereinafter, referred to as "Present compound 84") 0.29 g.

Present compound 84

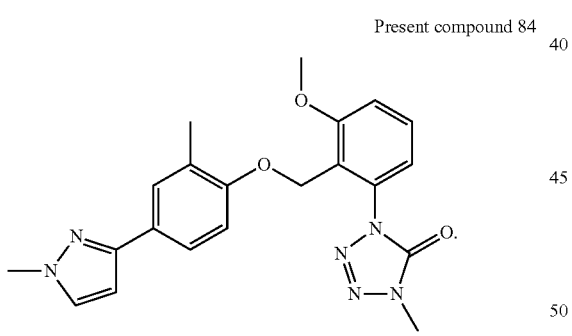

¹H-NMR (CDCl₃) δ: 7.52-7.44 (3H, m), 7.33 (1H, d, J=2.2 Hz), 7.08 (2H, dd, J=8.1, 5.7 Hz), 6.89 (1H, d, J=8.5 Hz), 6.43 (1H, d, J=2.2 Hz), 5.28 (2H, s), 3.92 (6H, s), 3.57 (3H, s), 2.03 (3H, s).

Preparation Example 85

A similar reaction to Preparation example 7 using 2-methyl-4-(3,4-dimethyl-pyrazol-1-yl)-phenol (described in Reference Preparation example 46) instead of 2-methyl-4-(3,4,5-trimethyl-pyrazol-1-yl)-phenol gave 1-{3-methoxy-2-[2-methyl-4-(3,4-dimethyl-pyrazol-1-yl)-phenoxymethyl]-phenyl}-4-methyl-1,4-dihydrotetrazole-5-one (hereinafter, referred to as "Present compound 85")

Present compound 85

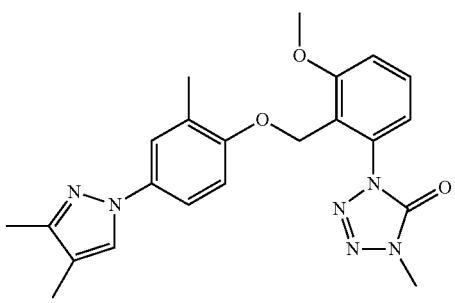

¹H-NMR (CDCl₃) δ: 7.50 (1H, s), 7.46 (1H, t, J=8.2 Hz), 7.34 (1H, d, J=2.7 Hz), 7.26 (1H, dd, J=8.3, 3.0 Hz), 7.08 (2H, dd, J=8.2, 4.3 Hz), 6.88 (1H, d, J=8.7 Hz), 5.26 (2H, s), 3.92 (3H, s), 3.59 (3H, s), 2.26 (3H, s), 2.05 (3H, s), 2.03 (3H, s).

Preparation Example 86

A similar reaction to Preparation example 7 using 2-methyl-4-(4,5-dimethyl-pyrazol-1-yl)-phenol (described in Reference Preparation example 47) instead of 2-methyl-4-(3,4,5-trimethyl-pyrazol-1-yl)-phenol gave 1-{3-methoxy-2-[2-methyl-4-(4,5-dimethyl-pyrazol-1-yl)-phenoxymethyl]-phenyl}-4-methyl-1,4-dihydrotetrazole-5-one (hereinafter, referred to as "Present compound 86").

Present compound 86

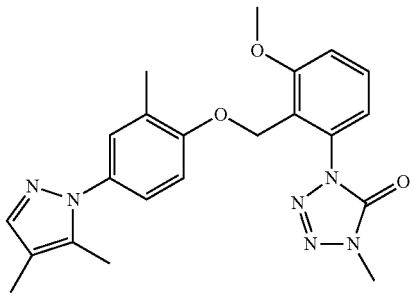

¹H-NMR (CDCl₃) δ: 7.48 (1H, t, J=8.2 Hz), 7.39 (1H, s), 7.13-7.07 (4H, m), 6.92 (1H, d, J=8.7 Hz), 5.29 (2H, s), 3.93 (3H, s), 3.61 (3H, s), 2.18 (3H, s), 2.04 (3H, s), 2.03 (3H, s).

Preparation Example 87

A similar reaction to Preparation example 7 using 2-methyl-4-(1-ethyl-1H-pyrazol-3-yl)-phenol (described in Reference Preparation example 61) instead of 2-methyl-4-(3,4,5-trimethyl-pyrazol-1-yl)-phenol gave 1-{3-methoxy-2-[2-methyl-4-(1-ethyl-1H-pyrazol-3-yl)-phenoxymethyl]-phenyl}-4-methyl-1,4-dihydrotetrazole-5-one (hereinafter, referred to as "Present compound 87").

Present compound 87

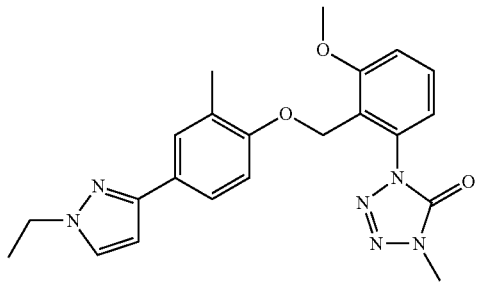

$^1$H-NMR (CDCl$_3$) δ: 7.53-7.43 (3H, m), 7.37 (1H, d, J=2.2 Hz), 7.08 (1H, d, J=4.1 Hz), 7.06 (1H, d, J=3.7 Hz), 6.88 (1H, d, J=8.5 Hz), 6.43 (1H, d, J=2.2 Hz), 5.28 (2H, s), 4.19 (2H, q, J=7.3 Hz), 3.92 (3H, s), 3.57 (3H, s), 2.03 (3H, s), 1.51 (3H, t, J=7.3 Hz).

Preparation Example 88

A similar reaction to Preparation example 7 using 2-chloro-4-(3,5-diisopropyl-pyrazol-1-yl)-phenol (described in Reference Preparation example 25) instead of 2-methyl-4-(3,4,5-trimethyl-pyrazol-1-yl)-phenol gave 1-{3-methoxy-2-[2-chloro-4-(3,5-diisopropyl-pyrazol-1-yl)-phenoxymethyl]-phenyl}-4-methyl-1,4-dihydrotetrazole-5-one (hereinafter, referred to as "Present compound 88").

Present compound 88

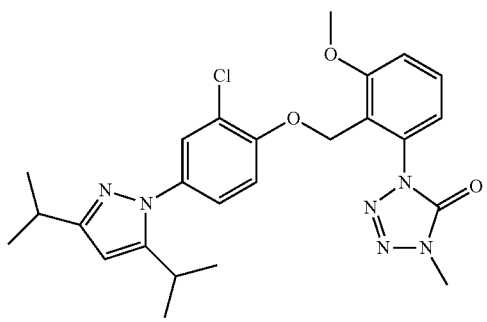

$^1$H-NMR (CDCl$_3$) δ: 7.47 (1H, t, J=8.2 Hz), 7.36 (1H, d, J=2.4 Hz), 7.19 (1H, dd, J=8.7, 2.4 Hz), 7.12 (1H, d, J=7.7 Hz), 7.07 (1H, d, J=8.5 Hz), 6.99 (1H, d, J=8.7 Hz), 5.99 (1H, s), 5.45 (2H, s), 3.95 (3H, s), 3.66 (3H, s), 3.00-2.87 (2H, m), 1.27 (6H, d, J=7.0 Hz), 1.15 (6H, d, J=6.8 Hz).

Preparation Example 89

A similar reaction to Preparation example 7 using 2-chloro-4-(3,5-diethyl-pyrazol-1-yl)-phenol (described in Reference Preparation example 24) instead of 2-methyl-4-(3,4,5-trimethyl-pyrazol-1-yl)-phenol gave 1-{3-methoxy-2-[2-chloro-4-(3,5-diethyl-pyrazol-1-yl)-phenoxymethyl]-phenyl}-4-methyl-1,4-dihydrotetrazole-5-one (hereinafter, referred to as "Present compound 89").

Present compound 89

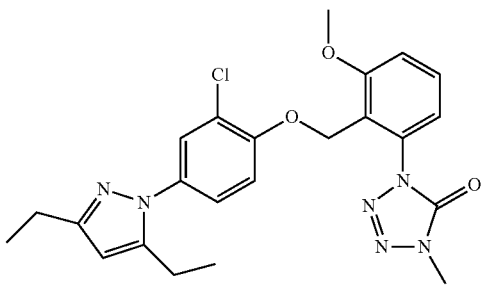

$^1$H-NMR (CDCl$_3$) δ: 7.46 (1H, t, J=8.2 Hz), 7.37 (1H, d, J=2.7 Hz), 7.18 (1H, dd, J=8.7, 2.7 Hz), 7.11 (1H, dd, J=8.1, 0.8 Hz), 7.07 (1H, t, J=4.2 Hz), 6.98 (1H, d, J=8.7 Hz), 6.01 (1H, s), 5.45 (2H, s), 3.94 (3H, s), 3.65 (3H, s), 2.65 (2H, q, J=7.6 Hz), 2.57 (2H, q, J=7.5 Hz), 1.26 (3H, t, J=7.6 Hz), 1.19 (3H, t, J=7.5 Hz).

Preparation Example 90

A similar reaction to Preparation example 7 using 2-methyl-4-(1,5-dimethyl-1H-pyrazol-3-yl)-phenol (described in Reference Preparation example 63) instead of 2-methyl-4-(3,4,5-trimethyl-pyrazol-1-yl)-phenol gave 1-{3-methoxy-2-[2-methyl-4-(1,5-dimethyl-1H-pyrazol-3-yl)-phenoxymethyl]-phenyl}-4-methyl-1,4-dihydrotetrazole-5-one (hereinafter, referred to as "Present compound 90").

Present compound 90

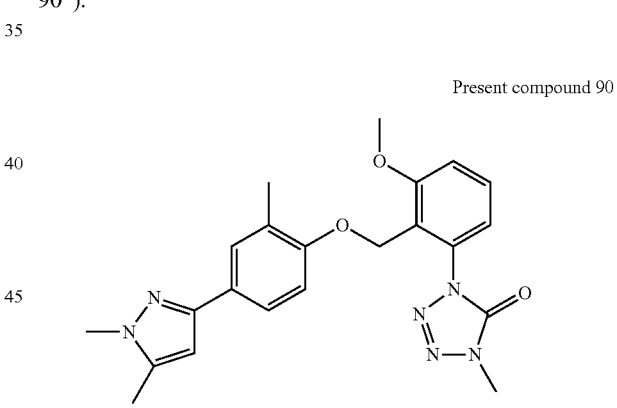

$^1$H-NMR (CDCl$_3$) δ: 7.49-7.43 (3H, m), 7.07 (2H, dd, J=8.2, 4.3 Hz), 6.87 (1H, d, J=8.2 Hz), 6.21 (1H, s), 5.27 (2H, s), 3.92 (3H, s), 3.79 (3H, s), 3.56 (3H, s), 2.28 (3H, s), 2.02 (3H, s).

Preparation Example 91

A similar reaction to Preparation example 7 using 2-methyl-4-(1-isopropyl-1H-pyrazol-3-yl)-phenol (described in Reference Preparation example 62) instead of 2-methyl-4-(3,4,5-trimethyl-pyrazol-1-yl)-phenol gave 1-{3-methoxy-2-[2-methyl-4-(1-isopropyl-1H-pyrazol-3-yl)-phenoxymethyl]-phenyl}-4-methyl-1,4-dihydrotetrazole-5-one (hereinafter, referred to as "Present compound 91").

Present compound 91

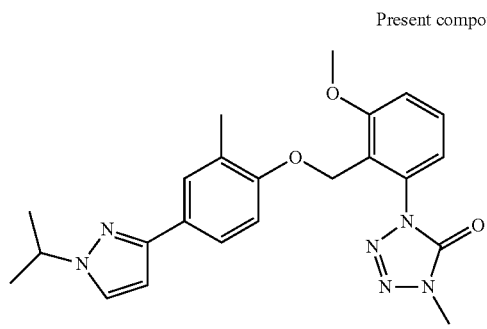

¹H-NMR (CDCl₃) δ: 7.54-7.48 (2H, m), 7.48-7.43 (1H, m), 7.40 (1H, d, J=2.4 Hz), 7.10-7.05 (2H, m), 6.88 (1H, d, J=8.5 Hz), 6.42 (1H, d, J=2.2 Hz), 5.28 (2H, s), 4.57-4.50 (1H, m), 3.92 (3H, s), 3.57 (3H, s), 2.03 (3H, s), 1.53 (6H, d, J=6.5 Hz).

Preparation Example 92

A similar reaction to Preparation example 7 using 2-methyl-4-(3-tert-butyl-pyrazol-1-yl)-phenol (described in Reference Preparation example 48) instead of 2-methyl-4-(3,4,5-trimethyl-pyrazol-1-yl)-phenol gave 1-{3-methoxy-2-[2-methyl-4-(3-tert-butyl-pyrazol-1-yl)-phenoxymethyl]-phenyl}-4-methyl-1,4-dihydrotetrazole-5-one (hereinafter, referred to a "Present compound 92").

Present compound 92

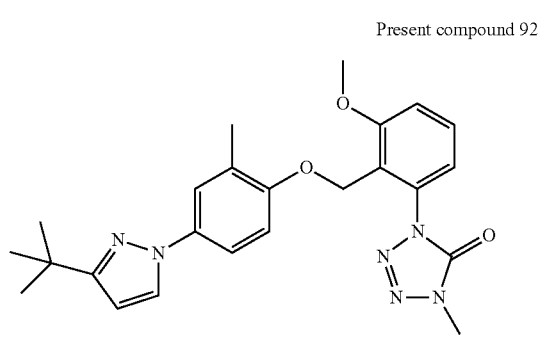 [SMILES: COc1cccc(-n2nnn(C)c2=O)c1COc1ccc(-n2ccc(C(C)(C)C)n2)cc1C]

¹H-NMR (CDCl₃) δ: 7.65 (1H, d, J=2.4 Hz), 7.47 (1H, t, J=8.3 Hz), 7.37 (1H, d, J=2.7 Hz), 7.32 (1H, dd, J=8.6, 2.8 Hz), 7.08 (2H, t, J=7.6 Hz), 6.88 (1H, d, J=8.7 Hz), 6.25 (1H, d, J=2.4 Hz), 5.28 (2H, s), 3.94 (3H, s), 3.60 (3H, s), 2.05 (3H, s), 1.35 (9H, s).

Preparation Example 93

A similar reaction to Preparation example 7 using 2-bromo-4-(1-methyl-1H-pyrazol-3-yl)-phenol (described in Reference Preparation example 64) instead of 2-methyl-4-(3,4,5-trimethyl-pyrazol-1-yl)-phenol gave 1-{3-methoxy-2-[2-bromo-4-(1-methyl-1H-pyrazol-3-yl)-phenoxymethyl]-phenyl}-4-methyl-1,4-dihydrotetrazole-5-one (hereinafter, referred to a "Present compound 93").

Present compound 93

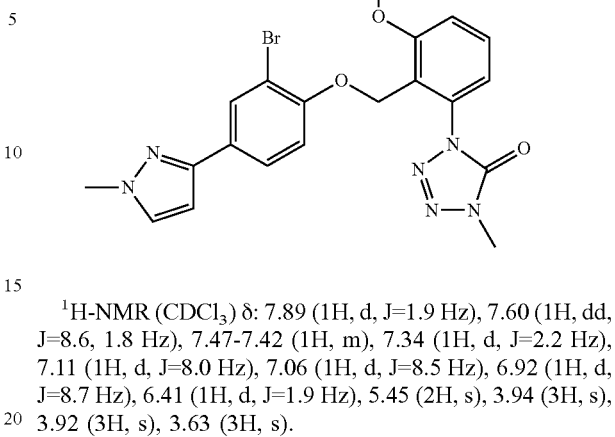

¹H-NMR (CDCl₃) δ: 7.89 (1H, d, J=1.9 Hz), 7.60 (1H, dd, J=8.6, 1.8 Hz), 7.47-7.42 (1H, m), 7.34 (1H, d, J=2.2 Hz), 7.11 (1H, d, J=8.0 Hz), 7.06 (1H, d, J=8.5 Hz), 6.92 (1H, d, J=8.7 Hz), 6.41 (1H, d, J=1.9 Hz), 5.45 (2H, s), 3.94 (3H, s), 3.92 (3H, s), 3.63 (3H, s).

Preparation Example 94

A similar reaction to Preparation example 7 using 2-chloro-4-(3,5-dimethyl-4-methoxy-pyrazol-1-yl)-phenol (described in Reference Preparation example 26) instead of 2-methyl-4-(3,4,5-trimethyl-pyrazol-1-yl)-phenol gave 1-{3-methoxy-2-[2-chloro-4-(3,5-dimethyl-4-methoxy-pyrazol-1-yl)-phenoxymethyl]-phenyl}-4-methyl-1,4-dihydrotetrazole-5-one (hereinafter, referred to as "Present compound 94").

Present compound 94

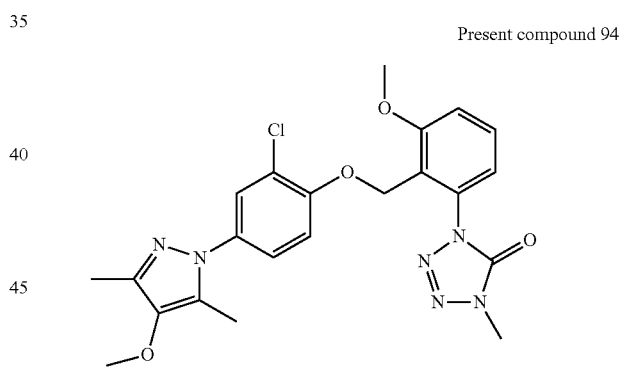

¹H-NMR (CDCl₃) δ: 7.47 (1H, t, J=8.2 Hz), 7.37 (1H, d, J=2.7 Hz), 7.19-7.16 (1H, m), 7.11 (1H, d, J=7.7 Hz), 7.07 (1H, d, J=8.2 Hz), 6.97 (1H, t, J=6.3 Hz), 5.45 (2H, s), 3.94 (3H, s), 3.76 (3H, d, J=0.5 Hz), 3.65 (3H, s), 2.26 (3H, s), 2.21 (3H, s).

Preparation Example 95

A similar reaction to Preparation example 7 using 2-trifluoromethyl-4-(3,4,5-trimethyl-pyrazol-1-yl)-phenol (described in Reference Preparation example 49) instead of 2-methyl-4-(3,4,5-trimethyl-pyrazol-1-yl)-phenol gave 1-{3-methoxy-2-[2-trifluoromethyl-4-(3,4,5-trimethyl-pyrazol-1-yl)-phenoxymethyl]-phenyl}-4-methyl-, 4-dihydrotetrazole-5-one (hereinafter, referred to as "Present compound 95").

Present compound 95

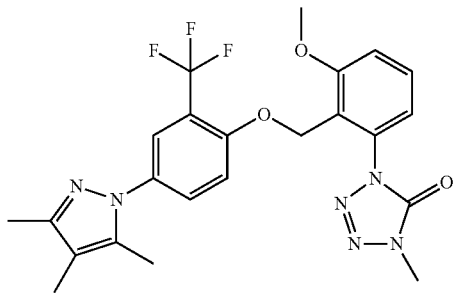

$^1$H-NMR (CDCl$_3$) δ: 7.53 (1H, d, J=2.7 Hz), 7.50-7.42 (2H, m), 7.15-7.06 (3H, m), 5.49 (2H, s), 3.95 (3H, s), 3.67 (3H, s), 2.22 (3H, s), 2.16 (3H, s), 1.96 (3H, s).

Preparation Example 96

A similar reaction to Preparation example 7 using 2-chloro-4-(3,5-dimethyl-4-ethyl-pyrazol-1-yl)-phenol (described in Reference Preparation example 27) instead of 2-methyl-4-(3,4,5-trimethyl-pyrazol-1-yl)-phenol gave 1-{3-methoxy-2-[2-chloro-4-(3,5-dimethyl-4-ethyl-pyrazol-1-yl)-phenoxymethyl]-phenyl}-4-methyl-1,4-dihydrotetrazole-5-one (hereinafter, referred to as "Present compound 96").

Present compound 96

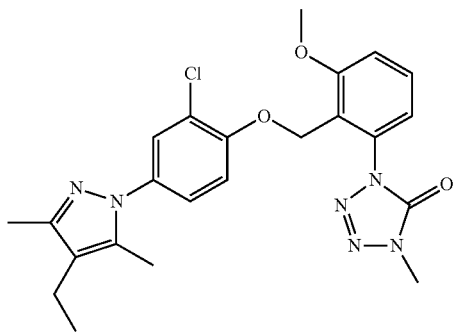

$^1$H-NMR (CDCl$_3$) δ: 7.47 (1H, t, J=8.2 Hz), 7.37 (1H, d, J=2.7 Hz), 7.18 (1H, dd, J=8.7, 2.2 Hz), 7.11 (1H, d, J=8.0 Hz), 7.07 (1H, d, J=8.5 Hz), 6.98 (1H, d, J=8.7 Hz), 5.45 (2H, s), 3.94 (3H, s), 3.65 (3H, d, J=0.5 Hz), 2.40 (2H, q, J=7.5 Hz), 2.23 (3H, s), 2.17 (3H, s), 1.10 (3H, t, J=7.5 Hz).

Preparation Example 97

To a mixture of 1-{2-[4-(3-dimethylamino-acryloyl)-2-methyl-phenoxymethyl]-3-methoxy-pheny}-4-methyl-1,4-dihydrotetrazole-5-one (described in Reference Preparation example 104) 13.4 g and ethanol 100 ml was added hydrazine one (1) hydrate 9 ml and the resulting mixture was stirred at room temperature for twenty four (24) hours. The reaction mixture was concentrated under reduced pressure so as to make ethanol in the reaction mixture about 10 ml. The resulting residue was subjected to a silica gel column chromatography to give 1-{3-methoxy-2-[2-methyl-4-(1H-pyrazol-3-yl)-phenoxymethyl]-phenyl}-4-methyl-1,4-dihydrotetrazole-5-one (hereinafter, referred to as "Present compound 97") 11.7 g.

Present compound 97

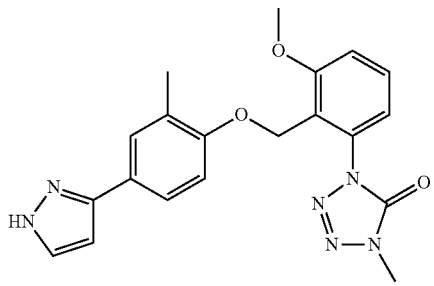

$^1$H-NMR (CDCl$_3$) δ: 7.57 (1H, d, J=2.2 Hz), 7.49-7.44 (3H, m), 7.08 (2H, dd, J=8.2, 4.6 Hz), 6.93-6.89 (1H, m), 6.49 (1H, d, J=2.2 Hz), 5.30 (2H, s), 3.92 (3H, s), 3.58 (3H, s), 2.03 (3H, s).

Preparation Examples 98 and 99

At room temperature, to a mixture of 1-{3-methoxy-2-[2-methyl-4-(1H-pyrazol-3-yl)-phenoxymethyl]-phenyl}-4-methyl-1,4-dihydrotetrazole-5-one (Present compound 97) 0.5 g and N,N-dimethylformamide 20 ml was added 55% sodium hydride 0.067 g and the resulting mixture was stirred for a half hour and thereto was added isobutyl bromide 0.23 g. The resulting mixture was stirred for seven hours and thereto was added water, and then the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-{3-methoxy-2-[2-methyl-4-(1-isobutyl-1H-pyrazol-3-yl)-phenoxymethyl]-phenyl}-4-methyl-1,4-dihydrotetrazole-5-one (hereinafter, referred to as "Present compound 98") 0.27 g and 1-{3-methoxy-2-[2-methyl-4-(1-isobutyl-1H-pyrazole-5-yl)-phenoxymethyl]-phenyl}-4-methyl-1,4-dihydrotetrazole-5-one (hereinafter, referred to as "Present compound 99") 0.06 g.

Present compound 98

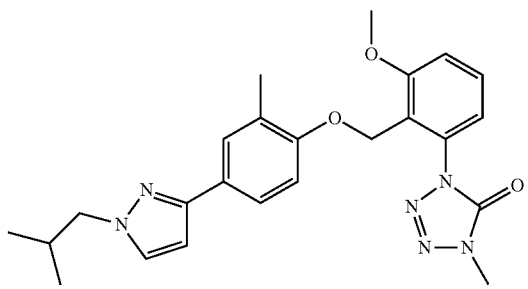

$^1$H-NMR (CDCl$_3$) δ: 7.53 (1H, s), 7.50 (1H, dd, J=8.3, 2.3 Hz), 7.46 (1H, t, J=8.2 Hz), 7.33 (1H, d, J=2.2 Hz), 7.07 (2H, dd, J=8.1, 5.0 Hz), 6.88 (1H, d, J=8.5 Hz), 6.41 (1H, d, J=2.4 Hz), 5.28 (2H, s), 3.92 (3H, s), 3.91 (2H, d, J=7.5 Hz), 3.58 (3H, s), 2.31-2.21 (1H, m), 2.03 (3H, s), 0.92 (6H, d, J=6.8 Hz).

Present compound 99

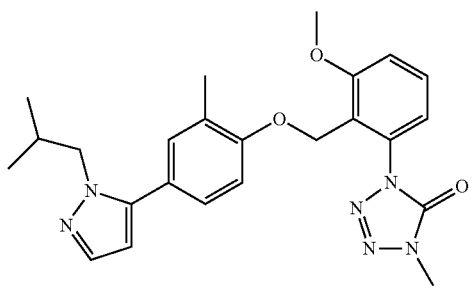

¹H-NMR (CDCl₃) δ: 7.53-7.46 (2H, m), 7.12-7.06 (4H, m), 6.93 (1H, d, J=8.5 Hz), 6.17 (1H, d, J=1.9 Hz), 5.31 (2H, s), 3.95 (3H, s), 3.89 (2H, d, J=7.2 Hz), 3.62 (3H, s), 2.20 (1H, s), 2.03 (3H, s), 0.77 (6H, d, J=6.5 Hz).

Preparation Examples 100 and 101

A similar reaction to Preparation example 98 using 3-methyl-butyl iodide instead of isobutyl bromide gave 1-{3-methoxy-2-{(2-methyl-4-[1-(3-methyl-butyl)-1H-pyrazol-3-yl)-phenoxymethyl]-phenyl}-4-methyl-1,4-dihydrotetrazole-5-one (hereinafter, referred to as "Present compound 100") and 1-{3-methoxy-2-{2-methyl-4-[1-(3-methyl-butyl)-1H-pyrazole-5-yl)-phenoxymethyl]-phenyl}-4-methyl-1,4-dihydrotetrazole-5-one (hereinafter, referred to as "Present compound 101")

Present compound 100

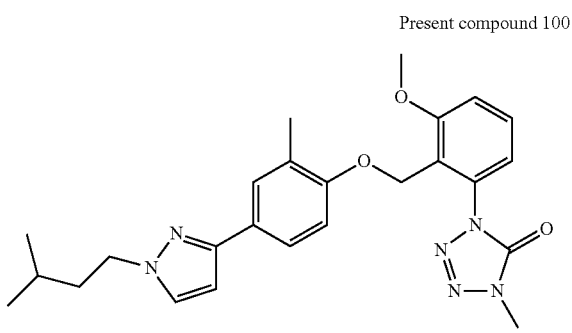 [SMILES: COc1cccc(-n2nnn(C)c2=O)c1COc1ccc(-c2ccn(CCC(C)C)n2)cc1C]

¹H-NMR (CDCl₃) δ: 7.52 (1H, s), 7.52-7.43 (2H, m), 7.35 (1H, d, J=1.9 Hz), 7.08 (2H, dd, J=8.2, 5.3 Hz), 6.88 (1H, d, J=8.5 Hz), 6.42 (1H, d, J=1.9 Hz), 5.28 (2H, s), 4.17-4.13 (2H, m), 3.92 (3H, s), 3.57 (3H, s), 2.03 (3H, s), 1.79 (2H, dd, J=14.9, 7.1 Hz), 1.66-1.56 (1H, m), 0.96 (3H, s), 0.95 (3H, s).

Present compound 101

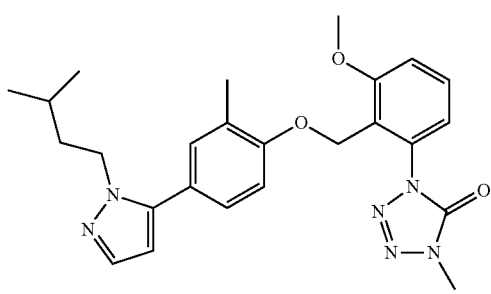

MS+; 463

Preparation Examples 102 and 103

A similar reaction to Preparation example 98 using iodopentane instead of isobutyl bromide gave 1-{3-methoxy-2-{(2-methyl-4-[1-(1-pentyl-1H-pyrazol-3-yl)-phenoxymethyl]-phenyl}-4-methyl-1,4-dihydrotetrazole-5-one (hereinafter, referred to as "Present compound 102") and 1-{3-methoxy-2-{2-methyl-4-[1-(1-pentyl-1H-pyrazole-5-yl)-phenoxymethyl]-phenyl}-4-methyl-1,4-dihydrotetrazole-5-one (hereinafter, referred to as "Present compound 103")

Present compound 102

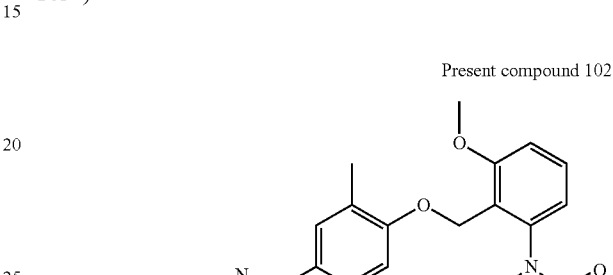

¹H-NMR (CDCl₃) δ: 7.53 (1H, s), 7.50 (1H, dd, J=8.5, 2.2 Hz), 7.46 (1H, t, J=8.2 Hz), 7.34 (1H, t, J=3.3 Hz), 7.07 (2H, dd, J=8.2, 5.1 Hz), 6.89 (1H, d, J=8.5 Hz), 6.42 (1H, t, J=1.1 Hz), 5.28 (2H, s), 4.11 (2H, t, J=7.2 Hz), 3.92 (3H, s), 3.57 (3H, d, J=0.5 Hz), 2.03 (3H, s), 1.92-1.85 (2H, m), 1.40-1.26 (4H, m), 0.90 (3H, t, J=7.0 Hz).

Present compound 103

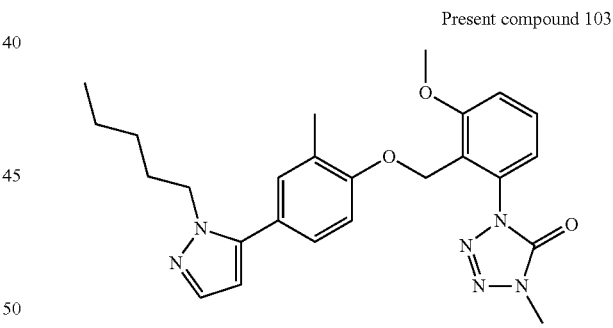

¹H-NMR (CDCl₃) δ: 7.51-7.46 (2H, m), 7.10 (4H, t, J=7.8 Hz), 6.94 (1H, d, J=8.5 Hz), 6.17 (1H, d, J=1.9 Hz), 5.31 (2H, s), 4.06 (2H, t, J=7.4 Hz), 3.95 (3H, s), 3.62 (3H, s), 2.03 (3H, s), 1.83-1.78 (2H, m), 1.29-1.18 (4H, m), 0.84 (3H, t, J=7.0 Hz).

Preparation Example 104

A similar reaction to Preparation example 98 using trifluoromethanesulfonic acid 2,2,2-trifluoroethyl ester instead of isobutyl bromide gave 1-(2-{4-{1-(2,2,2-trifluoroethyl)-1H-pyrazol-3-yl)-2-methyl-phenoxymethyl}-3-methoxy-phenyl)-4-methyl-1,4-dihydrotetrazole-5-one (hereinafter, referred to a "Present compound 104").

Present compound 104

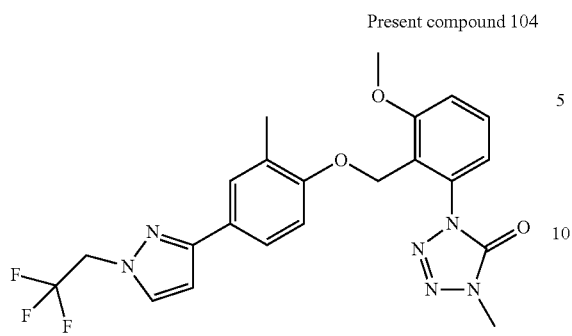

Present compound 106

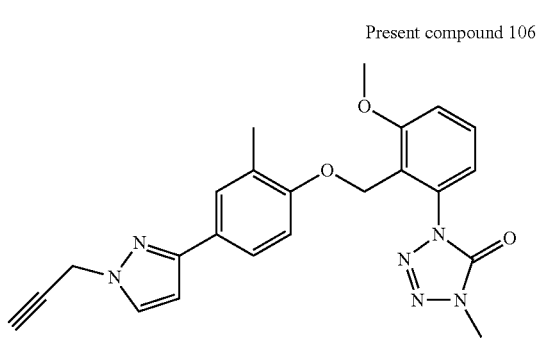 [SMILES: C#CCn1ccc(-c2ccc(OCc3c(OC)cccc3-n3nnn(C)c3=O)c(C)c2)n1]

¹H-NMR (CDCl₃) E: 7.57-7.55 (1H, m), 7.54-7.48 (3H, m), 7.13-7.10 (2H, m), 6.94 (1H, d, J=8.2 Hz), 6.59 (1H, d, J=2.5 Hz), 5.33 (2H, s), 4.75 (2H, q, J=8.5 Hz), 3.97 (3H, s), 3.62 (3H, s), 2.07 (3H, s).

Preparation Example 105

A similar reaction to Preparation example 98 using trifluoromethanesulfonic acid 2,2-difluoroethyl ester instead of isobutyl bromide gave 1-(2-4-{1-(2,2-difluoroethyl)-1H-pyrazol-3-yl)-2-methyl-phenoxymethyl}-3-methoxy-phenyl)-4-methyl-1,4-dihydrotetrazole-5-one (hereinafter, referred to as "Present compound 105").

¹H-NMR (CDCl₃) δ: 7.65-7.64 (1H, m), 7.57-7.47 (3H, m), 7.13-7.09 (2H, m), 6.93 (1H, d, J=8.2 Hz), 6.53 (1H, dd, J=2.3, 1.1 Hz), 5.33 (2H, s), 5.00 (2H, dd, J=2.7, 0.9 Hz), 3.96 (3H, d, J=0.9 Hz), 3.61 (3H, s), 2.55-2.54 (1H, m), 2.07 (3H, d, J=3.7 Hz).

Preparation Example 107

A similar reaction to Preparation example 98 using 1-bromo-2-butyne instead of isobutyl bromide gave 1-(3-methoxy-2-{2-methyl-4-[1-(2-butynyl)-1H-pyrazol-3-yl)-phenoxymethyl}-phenyl)-4-methyl-1,4-dihydrotetrazole-5-one (hereinafter, referred to as "Present compound 107").

Present compound 105

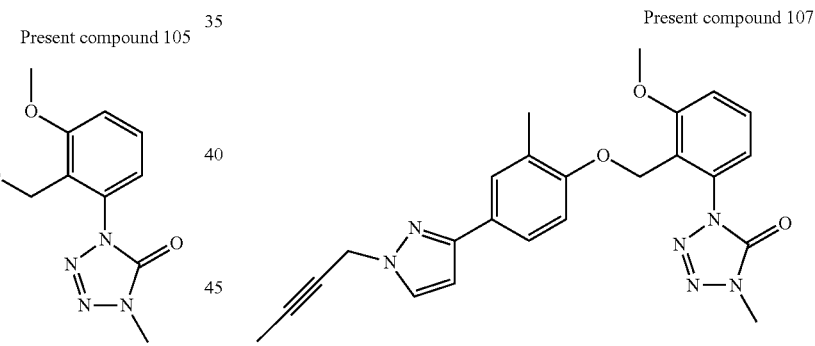

Present compound 107

¹H-NMR (CDCl₃) δ: 7.52-7.50 (1H, m), 7.46 (3H, dd, J=13.1, 5.3 Hz), 7.10-7.06 (2H, m), 6.90 (1H, d, J=8.2 Hz), 6.50 (1H, d, J=2.3 Hz), 6.13 (1H, tt, J=55.6, 4.4 Hz), 5.30 (2H, s), 4.46 (2H, td, J=13.4, 4.4 Hz), 3.93 (3H, s), 3.58 (3H, d, J=0.7 Hz), 2.04 (3H, s).

¹H-NMR (CDCl₃) δ: 7.64 (1H, d, J=2.3 Hz), 7.57 (1H, d, J=1.4 Hz), 7.54 (1H, dd, J=8.2, 2.3 Hz), 7.50 (1H, t, J=8.2 Hz), 7.13-7.09 (2H, m), 6.92 (1H, d, J=8.5 Hz), 6.51 (1H, d, J=2.5 Hz), 5.32 (2H, s), 4.95 (2H, q, J=2.4 Hz), 3.96 (3H, s), 3.61 (3H, s), 2.06 (3H, s), 1.92 (3H, t, J=2.4 Hz).

Preparation Example 106

A similar reaction to Preparation example 98 using 3-bromopropyne instead of isobutyl bromide gave 1-(3-methoxy-2-{2-methyl-4-{1-(2-propynyl)-1H-pyrazol-3-yl)-phenoxymethyl}-phenyl)-4-methyl-1,4-dihydrotetrazole-5-one (hereinafter, referred to as "Present compound 106").

Preparation Example 108

A similar reaction to Preparation example 98 using propyl iodide instead of isobutyl bromide gave 1-(3-methoxy-2-[2-methyl-4-(1-propyl-1H-pyrazol-3-yl)-phenoxymethyl}-phenyl)-4-methyl-1,4-dihydrotetrazole-5-one (hereinafter, referred to a "Present compound 108").

Present compound 108

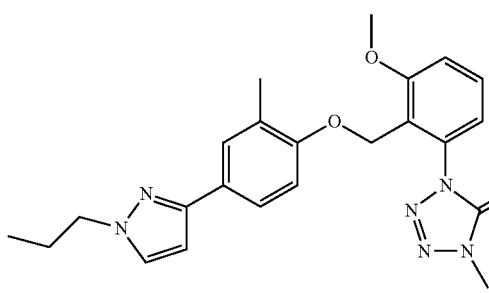

¹H-NMR (CDCl₃) δ: 7.57-7.56 (1H, m), 7.55-7.47 (2H, m), 7.39 (1H, d, J=2.3 Hz), 7.14-7.09 (2H, m), 6.92 (1H, d, J=8.5 Hz), 6.46 (1H, d, J=2.3 Hz), 5.32 (2H, s), 4.13 (2H, t, J=7.1 Hz), 3.96 (3H, s), 3.61 (3H, s), 2.07 (3H, s), 1.95 (2H, td, J=14.6, 7.4 Hz), 0.97 (3H, t, J=7.4 Hz).

Preparation Example 109

A similar reaction to Preparation example 98 using 4-methyl-bromopentane instead of isobutyl bromide gave 1-(3-methoxy-2-{(2-methyl-4-[1-(4-methyl-pentyl)-1H-pyrazol-3-yl)-phenoxymethyl}-phenyl)-4-methyl-1,4-dihydrotetrazole-5-one (hereinafter, referred to as "Present compound 109").

Present compound 109

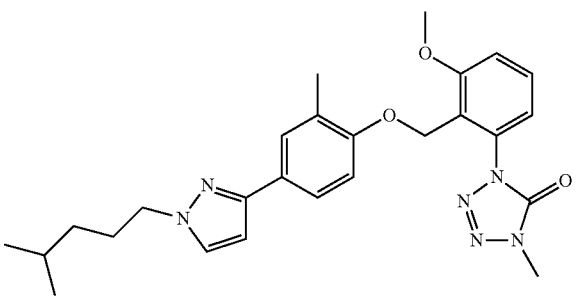

¹H-NMR (CDCl₃) δ: 7.57-7.56 (1H, m), 7.55-7.52 (1H, m), 7.49 (1H, t, J=8.2 Hz), 7.39 (1H, d, J=2.3 Hz), 7.14-7.09 (2H, m), 6.92 (1H, d, J=8.5 Hz), 6.46 (1H, d, J=2.3 Hz), 5.32 (2H, s), 4.14 (2H, t, J=7.3 Hz), 3.96 (3H, s), 3.61 (3H, s), 2.07 (3H, s), 1.96-1.88 (2H, m), 1.63-1.58 (1H, m), 1.27-1.21 (2H, m), 0.92 (6H, d, J=6.6 Hz).

Preparation Example 110

A similar reaction to Preparation example 98 using butyl bromide instead of isobutyl bromide gave 1-{3-methoxy-2-[2-methyl-4-(1-butyl-1H-pyrazol-3-yl)-phenoxymethyl}-phenyl)-4-methyl-1,4-dihydrotetrazole-5-one (hereinafter, referred to a "Present compound 110").

Present compound 110

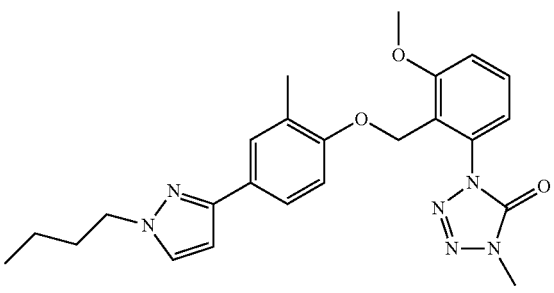

¹H-NMR (CDCl₃) δ: 7.53-7.52 (1H, m), 7.51-7.48 (1H, m), 7.46 (1H, t, J=8.1 Hz), 7.35 (1H, d, J=2.3 Hz), 7.09-7.06 (2H, m), 6.89 (1H, d, J=8.5 Hz), 6.42 (1H, d, J=2.3 Hz), 5.28 (2H, s), 4.14-4.11 (2H, m), 3.92 (3H, s), 3.58 (3H, s), 2.03 (3H, s), 1.91-1.83 (2H, m), 1.38-1.30 (2H, m), 0.94 (3H, t, J=7.4 Hz).

Preparation Example 111

A similar reaction to Preparation example 98 using N,N-dimethylsulfamoyl chloride instead of isobutyl bromide gave 1-{3-methoxy-2-[2-methyl-4-(1-N,N-dimethylsulfamoyl-1H-pyrazol-3-yl)-phenoxymethyl}-phenyl}-4-methyl-1,4-dihydrotetrazole-5-one (hereinafter, referred to as "Present compound 111").

Present compound 111

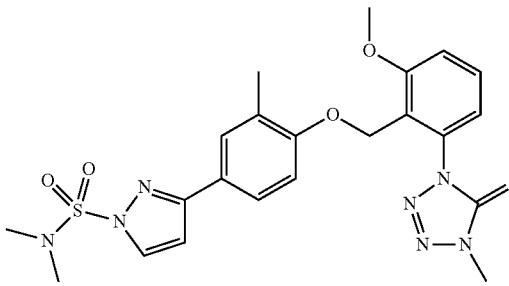

¹H-NMR (CDCl₃) δ: 7.96 (1H, d, J=2.7 Hz), 7.60-7.56 (2H, m), 7.47 (1H, t, J=8.2 Hz), 7.09 (2H, t, J=7.8 Hz), 6.91 (1H, d, J=8.9 Hz), 6.60 (1H, d, J=2.7 Hz), 5.32 (2H, s), 3.94 (3H, s), 3.60 (3H, s), 2.97 (6H, s), 2.04 (3H, s).

Preparation Example 112

At room temperature, to a mixture of 1-{3-methoxy-2-[2-methyl-4-(1H-pyrazol-3-yl)-phenoxymethyl]-phenyl}-4-methyl-1,4-dihydrotetrazole-5-one (Present compound 97) 0.5 g, methanesulfonyl chloride 0.19 g and tetrahydrofuran 20 ml was added pyridine 0.30 g and the resulting mixture was stirred for twenty four hours. Thereto was added water and then the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-{3-methoxy-2-[2-methyl-4-(1-methanesulfonyl-1H-pyrazol-3-yl)-phenoxymethyl]-phenyl}-4-methyl-1,4-dihydrotetrazole-5-one (hereinafter, referred to as "Present compound 112") 0.41 g.

Present compound 112

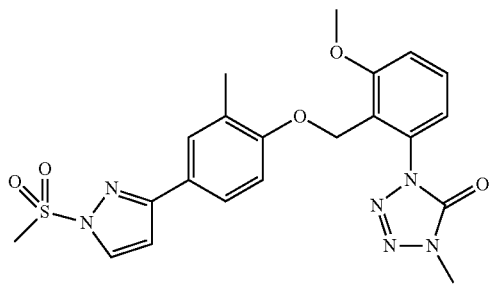

¹H-NMR (CDCl₃) δ: 8.02 (1H, d, J=2.9 Hz), 7.62 (1H, s), 7.59 (1H, dd, J=8.3, 2.3 Hz), 7.47 (1H, t, J=8.2 Hz), 7.09 (2H, t, J=7.6 Hz), 6.92 (1H, d, J=8.5 Hz), 6.67 (1H, d, J=2.9 Hz), 5.32 (2H, s), 3.94 (3H, s), 3.59 (3H, s), 3.35 (3H, s), 2.04 (3H, s).

Preparation Example 113

A similar reaction to Preparation example 112 using ethanesulfonyl chloride instead of methanesulfonyl chloride gave 1-{3-methoxy-2-[2-methyl-4-(1-ethanesulfonyl-1H-pyrazol-3-yl)-phenoxymethyl}-phenyl}-4-methyl-1,4-dihydrotetrazole-5-one (hereinafter, referred to as "Present compound 113").

Present compound 113

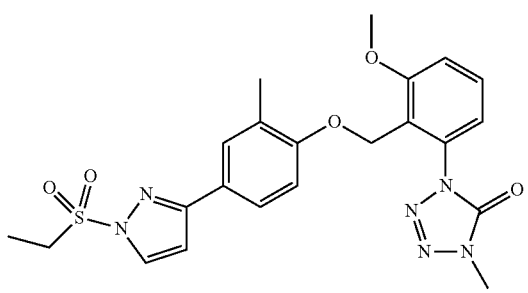

¹H-NMR (CDCl₃) δ: 8.06 (1H, d, J=2.7 Hz), 7.66-7.65 (1H, m), 7.64-7.61 (1H, m), 7.51 (1H, t, J=8.2 Hz), 7.14-7.10 (2H, m), 6.95 (1H, d, J=8.5 Hz), 6.70 (1H, d, J=2.7 Hz), 5.35 (2H, s), 3.98 (3H, s), 3.63 (3H, s), 3.57 (2H, q, J=7.4 Hz), 2.08 (3H, s), 1.30 (3H, t, J=7.2 Hz).

Preparation Example 114

A similar reaction to Preparation example 112 using, cyclopropanesulfonyl chloride instead of methanesulfonyl chloride gave 1-{3-methoxy-2-[2-methyl-4-(1-cyclopropanesulfonyl-1H-pyrazol-3-yl)-phenoxymethyl}-phenyl}-4-methyl-1,4-dihydrotetrazole-5-one (hereinafter, referred to as "Present compound 114").

Present compound 114

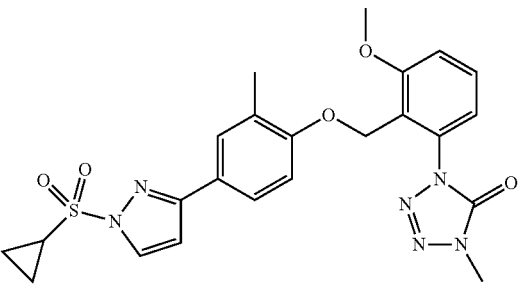

¹H-NMR (CDCl₃) δ: 8.00 (1H, d, J=2.7 Hz), 7.66-7.62 (2H, m), 7.51 (1H, t, J=8.1 Hz), 7.12 (2H, t, J=8.1 Hz), 6.95 (1H, d, J=8.2 Hz), 6.70 (1H, d, J=2.7 Hz), 5.35 (2H, s), 3.97 (3H, s), 3.63 (3H, s), 2.86-2.81 (1H, m), 2.08 (3H, s), 1.54-1.49 (2H, m), 1.22-1.16 (2H, m).

Preparation Example 115

A mixture of 1-{3-methoyl-2-[2-methyl-4-(3,5-dimethyl-pyrazol-1-yl)-phenoxymethyl]-phenyl}-4-methyl-1,4-dihydrotetrazole-5-one (Present compound 62) 3.0 g, N-bromosuccinimide 1.33 g and chloroform 100 ml was stirred at room temperature for twenty four hours. To the reaction mixture was added water and the resulting mixture was extracted with chloroform. The organic layer was washed with water, and was dried over anhydrous magnesium sulfate and was then concentrated under reduced pressure. The resulting residue was subjected to a silica gel column chromatography to give 1-{3-methoxy-2-[2-methyl-4-(4-bromo-3,5-dimethyl-pyrazol-1-yl)-phenoxymethyl]-phenyl}-4-methyl-1,4-dihydrotetrazole-5-one (hereinafter, referred to as "Present compound 115") 3.49 g.

Present compound 115

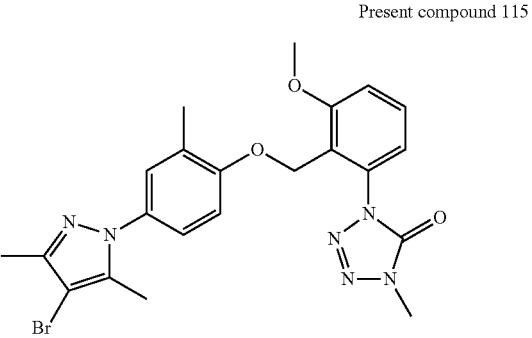 [SMILES: COc1cccc(-n2nnn(C)c2=O)c1COc1ccc(-n2nc(C)c(Br)c2C)cc1C]

¹H-NMR (CDCl₃) δ: 7.48 (1H, t, J=8.2 Hz), 7.11-7.05 (4H, m), 6.91 (1H, d, J=8.5 Hz), 5.29 (2H, s), 3.93 (3H, s), 3.62 (3H, s), 2.27 (3H, s), 2.23 (3H, s), 2.02 (3H, s).

Preparation Example 116

At 0° C., phosphorus oxychloride 2.92 g was added to N,N-dimethylformamide 100 ml and the resulting mixture was stirred for one hour and thereto was added 1-{3-methoxy-2-[2-methyl-4-(3,5-dimethyl-pyrazol-1-yl)-phenoxymethyl]-phenyl}-4-methyl-1,4-dihydrotetrazole-5-one (Present compound 62) 1.6 g. The resulting mixture was stirred at room temperature for two and a half hours, and then was heated to 100° C. and was stirred for two hours. At room temperature, to the reaction mixture was added water and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{3-methoxy-2-[2-methyl-4-(3,5-dimethyl-4-formyl-pyrazol-1-yl)-phenoxymethyl]-phenyl}-4-methyl-1,4-dihydrotetrazole-5-one (hereinafter, referred to as "Present compound 116") 1.5 g.

Present compound 116

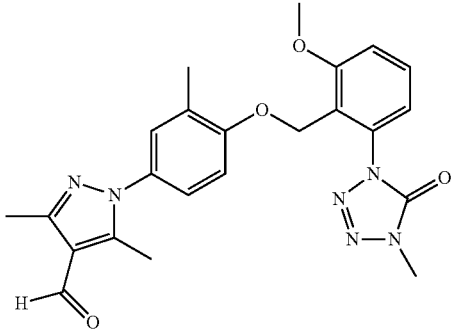

$^1$H-NMR (CDCl$_3$) δ: 9.99 (1H, d, J=0.5 Hz), 7.49 (1H, t, J=8.2 Hz), 7.12-7.08 (4H, m), 6.95 (1H, d, J=8.5 Hz), 5.31 (2H, s), 3.94 (3H, s), 3.63 (3H, s), 2.50 (3H, s), 2.49 (3H, s), 2.03 (3H, s).

Preparation Example 117

At room temperature, to a mixture of 1-{3-methoxy-2-[2-methyl-4-(3,5-dimethyl-4-formyl-pyrazol-1-yl)-phenoxymethyl]-phenyl}-4-methyl-1,4-dihydrotetrazole-5-one (Present compound 116) 0.5 g and chloroform 10 ml was added (diethylamino)sulfur trifluoride 2.4 g and the resulting mixture was stirred at 50° C. for two and a half hours. At room temperature, to the reaction mixtures was added water and the resulting mixture was extracted with chloroform. The organic layer was washed with water, and was dried over anhydrous magnesium sulfate and was then concentrated under reduced-pressure. The resulting residue was subjected to a silica gel column chromatography to give 1-{3-methoxy-2-[2-methyl-4-(4-difluoromethyl-3,5-dimethyl-4-formyl-pyrazol-1-yl)-phenoxymethyl]-phenyl}-4-methyl-1,4-dihydrotetrazole-5-one (hereinafter, referred to as "Present compound 117") 0.38 g.

Present compound 117

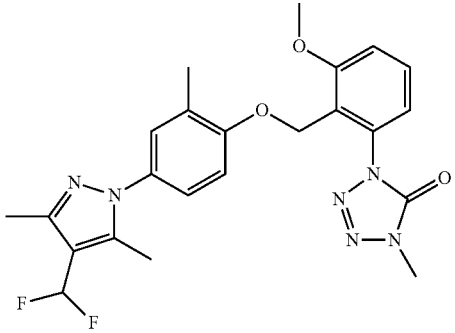

$^1$H-NMR (CDCl$_3$) δ: 7.48 (1H, t, J=8.2 Hz), 7.11-7.05 (4H, m), 6.92 (1H, d, J=8.5 Hz), 6.66 (1H, t, J=55.2 Hz), 5.30 (2H, s), 3.94 (3H, s), 3.62 (3H, s), 2.35 (3H, s), 2.28 (3H, s), 2.02 (3H, s).

Preparation Example 118

Under nitrogen atmosphere, a mixture of 1-{3-methoxy-2-[2-bromo-4-(1-methyl-1H-pyrazol-3-yl)-phenoxymethyl]-phenyl}-4-methyl-1,4-dihydrotetrazole-5-one (Present compound 93) 0.30 g, ethylboronic acid 0.14 g, 1,1'-bis(diphenylphosphino) ferrocene-palladium(II) dichloride dichloromethane complex 0.10 g, potassium phosphate 0.38 g, dioxane 5 ml, water 0.2 ml was stirred with heating under reflux for three hours. The resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{3-methoxy-2-[2-ethyl-4-(1-methyl-1H-pyrazol-3-yl)-phenoxymethyl]-phenyl}-4-methyl-1,4-dihydrotetrazole-5-one (hereinafter, referred to as "Present compound 118") 0.22 g.

Present compound 118

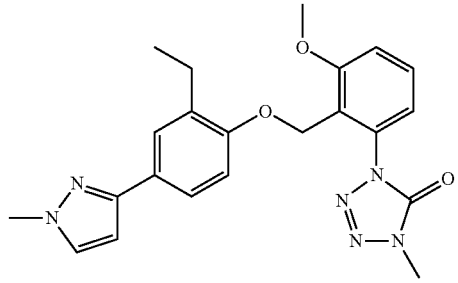

$^1$H-NMR (CDCl$_3$) δ: 7.55 (1H, d, J=2.2 Hz), 7.51 (1H, dd, J=8.5, 2.2 Hz), 7.47 (1H, t, J=8.2 Hz), 7.34 (1H, d, J=2.2 Hz), 7.08 (2H, dd, J=8.1, 5.2 Hz), 6.92 (1H, d, J=8.5 Hz), 6.44 (1H, d, J=2.4 Hz), 5.25 (2H, s), 3.93 (3H, s), 3.91 (3H, s), 3.59 (3H, s), 2.44 (2H, q, J=7.6 Hz), 1.08 (3H, t, J=7.5 Hz).

Preparation Example 119

A similar reaction to Preparation example 118 using propylboronic acid instead of ethylboronic acid gave 1-{3-methoxy-2-[2-propyl-4-(1-methyl-1H-pyrazol-3-yl)-phenoxymethyl]-phenyl}-4-methyl-1,4-dihydrotetrazole-5-one (hereinafter, referred to as "Present compound 119").

Present compound 119

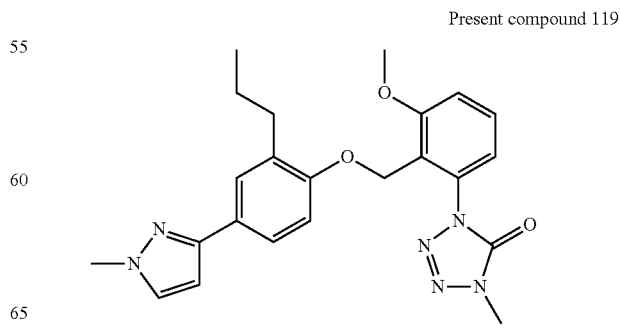

¹H-NMR (CDCl₃) δ: 7.54-7.49 (2H, m), 7.46 (1H, t, J=8.3 Hz), 7.33 (1H, d, J=2.4 Hz), 7.08 (1H, d, J=3.1 Hz), 7.06 (1H, d, J=2.7 Hz), 6.92 (1H, d, J=8.2 Hz), 6.43 (1H, d, J=2.4 Hz), 5.26 (2H, s), 3.92 (3H, s), 3.91 (3H, s), 3.60 (3H, s), 2.38 (2H, t, J=7.7 Hz), 1.51-1.43 (2H, m), 0.86 (3H, t, J=7.2 Hz).

Preparation Example 120

A similar reaction to Preparation example 118 using butylboronic acid instead of ethylboronic acid gave 1-{3-methoxy-2-[2-butyl-4-(1-methyl-1H-pyrazol-3-yl)-phenoxymethyl]-phenyl}-4-methyl-1,4-dihydrotetrazole-5-one (hereinafter, referred to as "Present compound 120").

Present compound 120

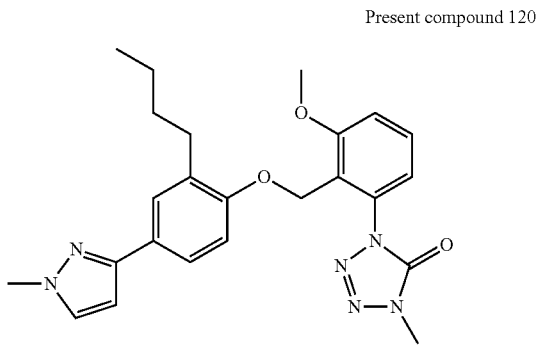 [SMILES: CCCCc1cc(-c2ccn(C)n2)ccc1OCc1c(OC)cccc1-n1nnn(C)c1=O]

¹H-NMR (CDCl₃) δ: 7.53-7.51 (2H, m), 7.49-7.44 (1H, m), 7.33 (1H, d, J=2.4 Hz), 7.07 (2H, dd, J=8.2, 5.1 Hz), 6.91 (1H, d, J=8.2 Hz), 6.44 (1H, d, J=1.9 Hz), 5.25 (2H, s), 3.93 (3H, s), 3.91 (3H, s), 3.60 (3H, s), 2.40 (2H, t, J=7.7 Hz), 1.48-1.40 (2H, m), 1.32-1.23 (2H, m), 0.85 (3H, t, J=7.2 Hz).

Preparation Example 121

A similar reaction to Preparation example 118 using cyclopropylboronic acid instead of ethylboronic acid gave 1-{3-methoxy-2-[2-cyclopropyl-4-(1-methyl-1H-pyrazol-3-yl)-phenoxymethyl]-phenyl}-4-methyl-1,4-dihydrotetrazole-5-one (hereinafter, referred to a "Present compound 121").

Present compound 121

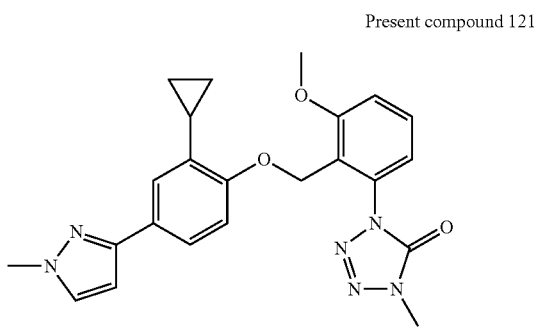 [SMILES: COc1cccc(-n2nnn(C)c2=O)c1COc1ccc(-c2ccn(C)n2)cc1C1CC1]

¹H-NMR (CDCl₃) δ: 7.48-7.44 (2H, m), 7.32 (1H, d, J=2.2 Hz), 7.16 (1H, d, J=1.9 Hz), 7.09 (1H, d, J=1.9 Hz), 7.07 (1H, d, J=2.4 Hz), 6.91 (1H, d, J=8.5 Hz), 6.41 (1H, d, J=2.2 Hz), 5.32 (2H, s), 3.92 (3H, s), 3.91 (3H, s), 3.57 (3H, s), 1.95-1.89 (1H, m), 0.84-0.81 (2H, m), 0.65-0.60 (2H, m).

Preparation Example 122

A similar reaction to Preparation example 8 using 2-methyl-4-(1-methyl-1H-pyrazol-3-yl)-phenol (described in Reference Preparation example 60) instead of 2-methyl-4-(3,4,5-trimethyl-pyrazol-1-yl)-phenol gave 1-{3-ethoxy-2-[2-methyl-4-(1-methyl-1H-pyrazol-3-yl)-phenoxymethyl]-phenyl}-4-methyl-1,4-dihydrotetrazole-5-one (hereinafter, referred to as "Present compound 122").

Present compound 122

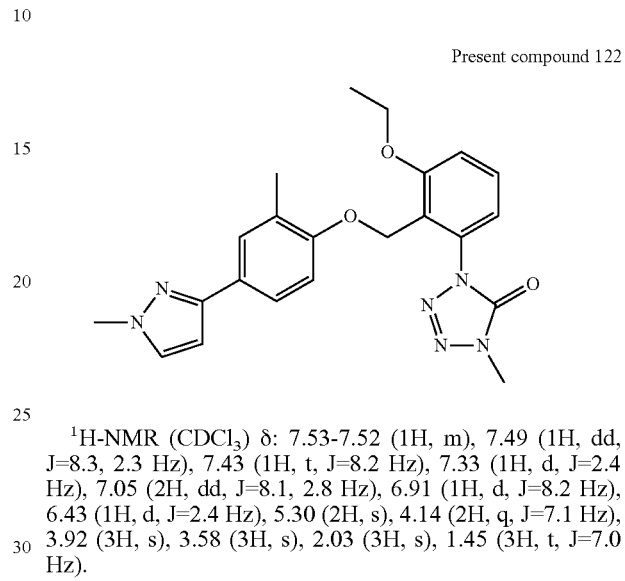

¹H-NMR (CDCl₃) δ: 7.53-7.52 (1H, m), 7.49 (1H, dd, J=8.3, 2.3 Hz), 7.43 (1H, t, J=8.2 Hz), 7.33 (1H, d, J=2.4 Hz), 7.05 (2H, dd, J=8.1, 2.8 Hz), 6.91 (1H, d, J=8.2 Hz), 6.43 (1H, d, J=2.4 Hz), 5.30 (2H, s), 4.14 (2H, q, J=7.1 Hz), 3.92 (3H, s), 3.58 (3H, s), 2.03 (3H, s), 1.45 (3H, t, J=7.0 Hz).

Preparation Example 123

A similar reaction to Preparation example 8 using 2-methyl-4-(1-ethyl-1H-pyrazol-3-yl)-phenol (described in Reference Preparation example 61) instead of 2-methyl-4-(3,4,5-trimethyl-pyrazol-1-yl)-phenol gave 1-{3-ethoxy-2-[2-methyl-4-(1-ethyl-1H-pyrazol-3-yl)-phenoxymethyl]-phenyl}-4-methyl-1,4-dihydrotetrazole-5-one (hereinafter, referred to as "Present compound 123").

Present compound 123

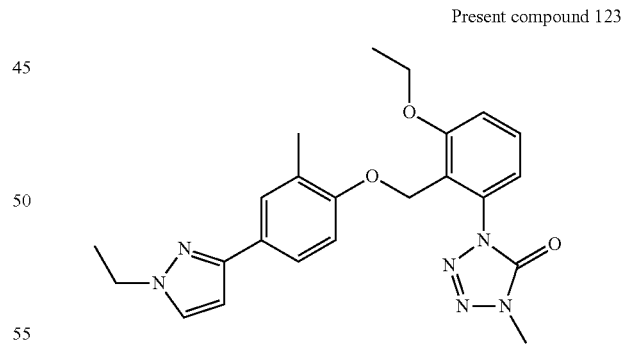

¹H-NMR (CDCl₃) δ: 7.54-7.52 (1H, m), 7.52-7.48 (1H, m), 7.43 (1H, t, J=8.2 Hz), 7.37 (1H, d, J=2.2 Hz), 7.09-7.05 (1H, m), 7.04 (1H, d, J=2.7 Hz), 6.91 (1H, d, J=8.2 Hz), 6.43 (1H, d, J=1.9 Hz), 5.30 (2H, s), 4.22-4.11 (4H, m), 3.58 (3H, d, J=0.5 Hz), 2.03 (3H, s), 1.51 (3H, t, J=7.2 Hz), 1.48-1.42 (3H, m).

Preparation Example 124

A similar reaction to Preparation example 8 using 2-methyl-4-(1,5-dimethyl-1H-pyrazol-3-yl)-phenol (described in Reference Preparation example 63) instead of 2-methyl-4-(3,4,5-trimethyl-pyrazol-1-yl)-phenol gave 1-{3-ethoxy-2-[2-methyl-4-(1,5-dimethyl-1H-pyrazol-3-yl)-phenoxymethyl]-phenyl}-4-methyl-1,4-dihydrotetrazole-5-one (hereinafter, referred to as "Present compound 124").

Present compound 124

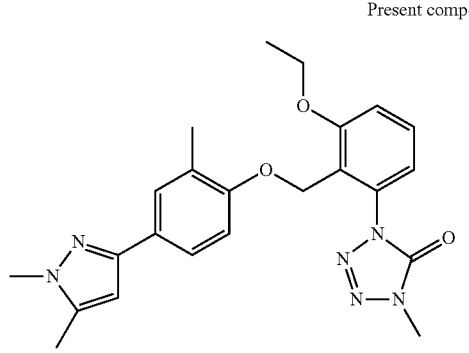

$^1$H-NMR (CDCl$_3$) δ: 7.50-7.48 (1H, m), 7.47-7.40 (2H, m), 7.06 (1H, d, J=2.9 Hz), 7.04 (1H, d, J=2.4 Hz), 6.90 (1H, d, J=8.5 Hz), 6.22 (1H, s), 5.29 (2H, s), 4.17-4.09 (2H, m), 3.79 (3H, s), 3.57 (3H, s), 2.28 (3H, s), 2.02 (3H, s), 1.44 (3H, t, J=6.9 Hz).

Preparation Example 125

A similar reaction to Preparation example 8 using 2-methyl-4-(3-methyl-pyrazol-1-yl)-phenol (described in Reference Preparation example 36) instead of 2-methyl-4-(3,4,5-trimethyl-pyrazol-1-yl)-phenol gave 1-{3-ethoxy-2-[2-methyl-4-(3-methyl-pyrazol-3-yl)-phenoxymethyl]-phenyl}-4-methyl-1,4-dihydrotetrazole-5-one (hereinafter, referred to as "Present compound 125").

Present compound 125

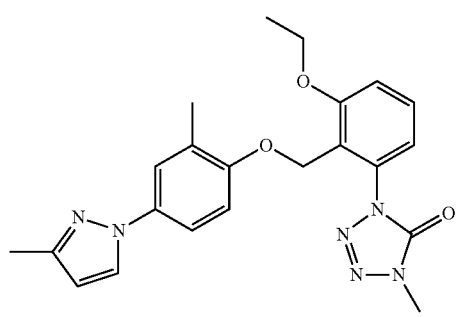

$^1$H-NMR (CDCl$_3$) δ: 7.67 (1H, d, J=2.4 Hz), 7.43 (1H, t, J=8.2 Hz), 7.37 (1H, d, J=2.7 Hz), 7.30 (1H, dd, J=8.7, 2.7 Hz), 7.06 (2H, dd, J=8.1, 3.7 Hz), 6.92 (1H, d, J=8.7 Hz), 6.18 (1H, d, J=2.2 Hz), 5.30 (2H, s), 4.18-4.11 (2H, m), 3.60 (3H, d, J=0.7 Hz), 2.36 (3H, s), 2.04 (3H, s), 1.47-1.43 (3H, m).

Preparation Example 126

A similar reaction to Preparation example 8 using 2-methyl-4-(3,5-dimethyl-pyrazol-1-yl)-phenol (described in Reference Preparation example 30) instead of 2-methyl-4-(3,4,5-trimethyl-pyrazol-1-yl)-phenol gave 1-{3-ethoxy-2-[2-methyl-4-(3,5-dimethyl-pyrazol-1-yl)-phenoxymethyl]-phenyl}-4-methyl-1,4-dihydrotetrazole-5-one (hereinafter, referred to as "Present compound 126").

Present compound 126

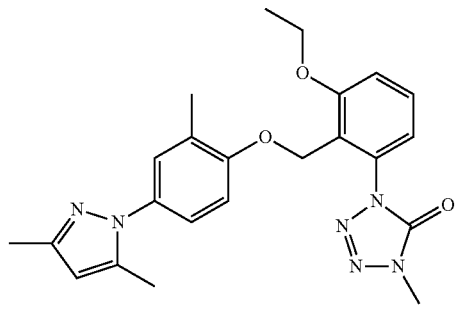

$^1$H-NMR (CDCl$_3$) δ: 7.44 (1H, t, J=8.2 Hz), 7.13-7.05 (4H, m), 6.93 (1H, d, J=8.5 Hz), 5.94 (1H, s), 5.30 (2H, s), 4.15 (2H, q, J=6.9 Hz), 3.62 (3H, s), 2.27 (3H, s), 2.23 (3H, d, J=0.5 Hz), 2.02 (3H, s), 1.45 (3H, t, J=7.0 Hz).

Preparation Example 127

A similar reaction to Preparation example 8 using 2-chloro-4-(3,5-dimethyl-pyrazol-1-yl)-phenol (described in Reference Preparation example 20) instead of 2-methyl-4-(3,4,5-trimethyl-pyrazol-1-yl)-phenol gave 1-{3-ethoxy-2-[2-chloro-4-(3,5-dimethyl-pyrazol-1-yl)-phenoxymethyl]-phenyl}-4-methyl-1,4-dihydrotetrazole-5-one (hereinafter, referred to as "Present compound 127").

Present compound 127

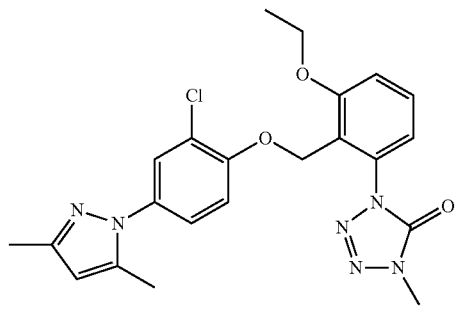

$^1$H-NMR (CDCl$_3$) δ: 7.44 (1H, t, J=8.2 Hz), 7.38 (1H, d, J=2.4 Hz), 7.19 (1H, dd, J=8.7, 2.7 Hz), 7.11-7.08 (1H, m), 7.05 (1H, d, J=8.5 Hz), 7.01 (1H, d, J=8.7 Hz), 5.95 (1H, s), 5.46 (2H, s), 4.16 (2H, q, J=7.2 Hz), 3.66 (3H, s), 2.26 (3H, s), 2.24 (3H, s), 1.47 (3H, t, J=7.0 Hz).

Preparation Example 128

A similar reaction to Preparation example 8 using 2-chloro-4-(3,4,5-trimethyl-pyrazol-1-yl)-phenol (described in Reference Preparation example 19) instead of 2-methyl-4-(3,4,5-trimethyl-pyrazol-1-yl)-phenol gave 1-{3-ethoxy-2-[2-chloro-4-(3,4,5-trimethyl-pyrazol-1-yl)-phenoxymethyl]-phenyl}-4-methyl-1,4-dihydrotetrazole-5-one (hereinafter, referred to as "Present compound 128").

Present compound 128

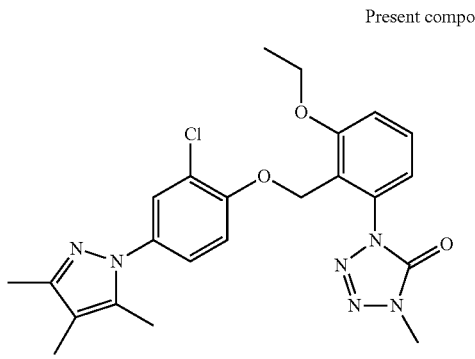

¹H-NMR (CDCl₃) δ: 7.43 (1H, t, J=8.2 Hz), 7.35 (1H, d, J=2.7 Hz), 7.17 (1H, dd, J=8.7, 2.4 Hz), 7.09 (1H, d, J=8.0 Hz), 7.04 (1H, d, J=8.5 Hz), 7.00 (1H, d, J=8.7 Hz), 5.45 (2H, s), 4.16 (2H, q, J=6.8 Hz), 3.65 (3H, s), 2.21 (3H, s), 2.16 (3H, s), 1.95 (3H, s), 1.46 (3H, t, J=7.0 Hz).

Preparation Example 129

A similar reaction to Preparation example 8 using 2-methyl-4-(3,4-dimethyl-pyrazol-1-yl)-phenol (described in Reference Preparation example 46) instead of 2-methyl-4-(3,4,5-trimethyl-pyrazol-1-yl)-phenol gave 1-{3-ethoxy-2-[2-methyl-4-(3,4-dimethyl-pyrazol-1-yl)-phenoxymethyl]-phenyl}-4-methyl-1,4-dihydrotetrazole-5-one (hereinafter, referred to as "Present compound 129").

Present compound 129

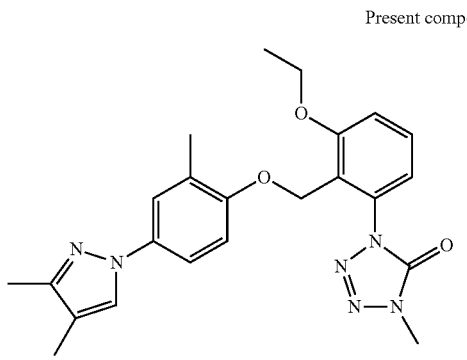

¹H-NMR (CDCl₃) δ: 7.50 (1H, s), 7.43 (1H, t, J=8.2 Hz), 7.33 (1H, d, J=2.7 Hz), 7.28-7.24 (1H, m), 7.06 (2H, dd, J=8.3, 3.3 Hz), 6.90 (1H, d, J=8.7 Hz), 5.28 (2H, s), 4.14 (2H, q, J=7.1 Hz), 3.59 (3H, s), 2.26 (3H, s), 2.05 (3H, s), 2.03 (3H, s), 1.45 (3H, t, J=6.9 Hz).

Preparation Example 130

A similar reaction to Preparation example 4 using 2-chloro-4-(3,5-dimethyl-4-methoxy-pyrazol-1-yl)-phenol (described in Reference Preparation example 26) instead of 2-methyl-4-(3,4,5-trimethyl-pyrazol-1-yl)-phenol gave 1-{3-methyl-2-[2-chloro-4-(3,5-dimethyl-4-methoxy-pyrazol-1-yl)-phenoxymethyl]-phenyl}-4-methyl-1,4-dihydrotetrazole-5-one (hereinafter, referred to as "Present compound 130").

Present compound 130

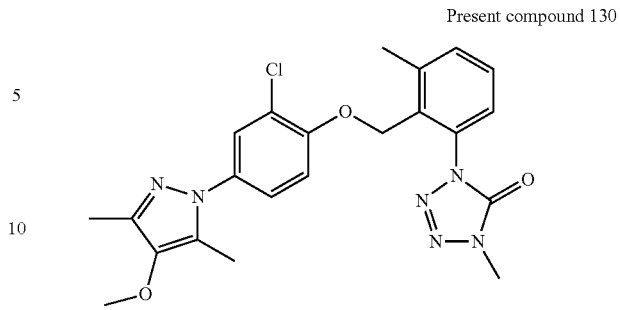

¹H-NMR (CDCl₃) δ: 7.45-7.38 (3H, m), 7.30 (1H, dd, J=7.4, 1.3 Hz), 7.21 (1H, dd, J=8.8, 2.6 Hz), 6.93 (1H, d, J=8.7 Hz), 5.18 (2H, s), 3.77 (3H, s), 3.68 (3H, s), 2.54 (3H, s), 2.27 (3H, s), 2.23 (3H, s).

Preparation Example 131

A similar reaction to Preparation example 4 using 2-chloro-4-(3,5-dimethyl-4-ethyl-pyrazol-1-yl)-phenol (described in Reference Preparation example 27) instead of 2-methyl-4-(3,4,5-trimethyl-pyrazol-1-yl)-phenol gave 1-{3-methyl-2-[2-chloro-4-(3,5-dimethyl-4-ethyl-pyrazol-1-yl)-phenoxymethyl]-phenyl}-4-methyl-1,4-dihydrotetrazole-5-one (hereinafter, referred to as "Present compound 131").

Present compound 131

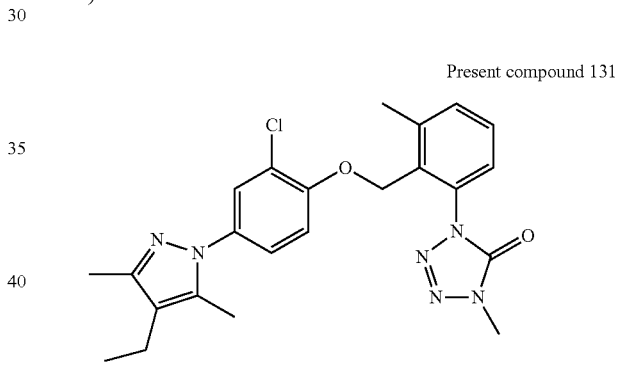

¹H-NMR (CDCl₃) δ: 7.44-7.38 (3H, m), 7.29 (1H, dd, J=7.4, 1.7 Hz), 7.21 (1H, dd, J=8.7, 2.5 Hz), 6.93 (1H, d, J=8.9 Hz), 5.18 (2H, s), 3.67 (3H, s), 2.54 (3H, s), 2.40 (2H, q, J=7.6 Hz), 2.24 (3H, s), 2.19 (3H, s), 1.10 (3H, t, J=7.6 Hz).

Preparation Examples 132 and 133

At room temperature, to a mixture of 1-{3-methoxy-2-[2-methyl-4-(1H-pyrazol-3-yl)-phenoxymethyl]-phenyl}-4-methyl-1,4-dihydrotetrazole-5-one (Present compound 97) 0.60 g and N,N-dimethylformamide 10 ml was added 55% sodium hydride 0.080 g and the resulting mixture was stirred for a half hour and thereto was added cyclopropylmethyl bromide 0.27 g. The resulting mixture was stirred at 80° C. for ten hours and thereto was added water, and then the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-{3-methoxy-2-[2-methyl-4-(1-cyclopropylmethyl-1H-pyrazol-3-yl)-phenoxymethyl]-phenyl}-4-methyl-1,4- dihydrotetrazole-5-one (hereinafter, referred to as "Present compound 132") 0.52 g and 1-{3-methoxy-2-[2-methyl-4-(1-cyclopropylmethyl-1H-pyrazole-5-yl)-phenoxymethyl]-phenyl}-4-methyl-1,4-dihydrotetrazole-5-one (hereinafter, referred to as "Present compound 133") 0.06 g.

Present compound 132

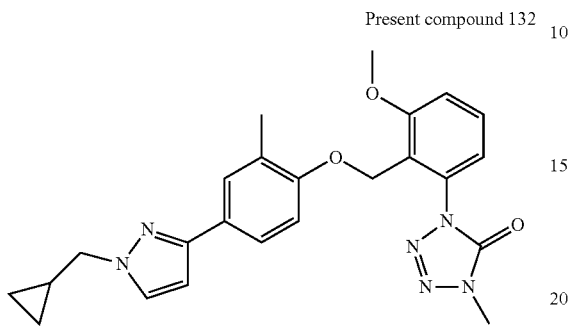

¹H-NMR (CDCl₃) δ: 7.54-7.52 (1H, m), 7.50 (2H, d, J=2.3 Hz), 7.46 (1H, t, J=8.1 Hz), 7.09 (1H, d, J=5.3 Hz), 7.07 (1H, d, J=4.6 Hz), 6.89 (1H, d, J=8.5 Hz), 6.45 (1H, d, J=2.3 Hz), 5.29 (2H, s), 4.01 (2H, d, J=7.1 Hz), 3.93 (3H, s), 3.58 (3H, s), 2.03 (3H, s), 1.36-1.31 (1H, m), 0.68-0.63 (2H, m), 0.41-0.37 (2H, m).

Present compound 133

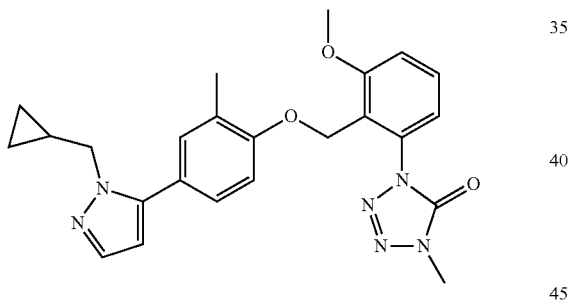

¹H-NMR (CDCl₃) δ: 7.52 (1H, d, J=1.8 Hz), 7.49 (1H, t, J=8.0 Hz), 7.14-7.08 (4H, m), 6.93 (1H, d, J=8.2 Hz), 6.19 (1H, d, J=1.8 Hz), 5.31 (2H, s), 3.96 (2H, d, J=6.9 Hz), 3.95 (3H, s), 3.63 (3H, s), 2.03 (3H, s), 1.23-1.15 (1H, m), 0.49 (2H, dt, J=6.3, 1.5 Hz), 0.21 (2H, dd, J=4.9, 1.0 Hz).

Preparation Example 134

A similar reaction to Preparation example 4 using 2-chloro-4-(3,5-bis-difluoromethyl-pyrazol-1-yl)-phenol (described in Reference Preparation example 21) instead of 2-methyl-4-(3,4,5-trimethyl-pyrazol-1-yl)-phenol gave 1-{3-methyl-2-[2-chloro-4-(3,5-bis-difluoromethyl-pyrazol-1-yl)-phenoxymethyl]-phenyl}-4-methyl-1,4-dihydrotetrazole-5-one (hereinafter, referred to as "Present compound 134").

Present compound 134

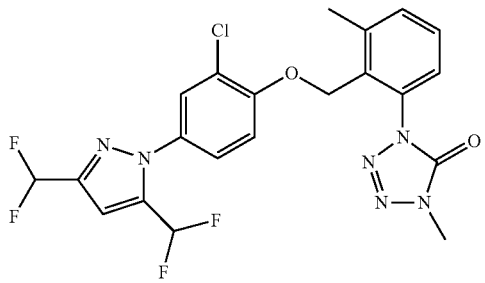

¹H-NMR (CDCl₃) δ: 7.52 (1H, d, J=2.7 Hz), 7.47-7.41 (2H, m), 7.33-7.29 (2H, m), 6.98 (1H, d, J=8.8 Hz), 6.94 (1H, s), 6.73 (1H, t, J=54.4 Hz), 6.61 (1H, t, J=53.2 Hz), 5.23 (2H, s), 3.69 (3H, d, J=10.7 Hz), 2.55 (3H, s).

Preparation Example 135

A similar reaction to Preparation example 1 using 2-chloro-4-(3,5-dimethyl-4-ethyl-pyrazol-1-yl)-phenol (described in Reference Preparation example 27) instead of 2-methyl-4-(3,4,5-trimethyl-pyrazol-1-yl)-phenol gave 1-{3-fluoro-2-[2-chloro-4-(3,5-dimethyl-4-ethyl-pyrazol-1-yl)-phenoxymethyl]-phenyl}-4-methyl-1,4-dihydrotetrazole-5-one (hereinafter, referred to as "Present compound 135").

Present compound 135

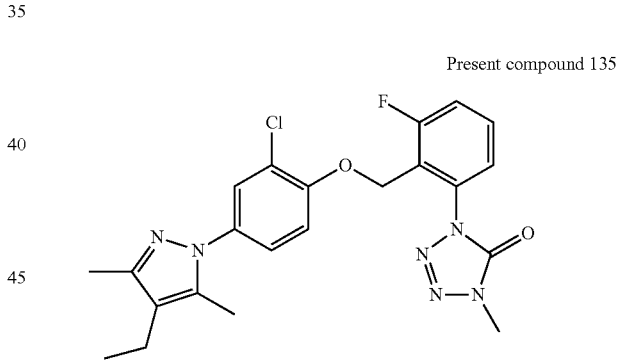

¹H-NMR (CDCl₃) δ: 7.54-7.48 (1H, m), 7.40 (1H, d, J=2.5 Hz), 7.38-7.36 (1H, m), 7.30-7.25 (1H, m), 7.21 (1H, dd, J=8.7, 2.5 Hz), 6.97 (1H, d, J=8.9 Hz), 5.45 (2H, d, J=0.9 Hz), 3.65 (3H, s), 2.40 (2H, q, J=7.6 Hz), 2.23 (3H, s), 2.18 (3H, s), 1.10 (3H, t, J=7.6 Hz).

Preparation Example 136

A similar reaction to Preparation example 2 using 2-chloro-4-(3,5-dimethyl-4-ethyl-pyrazol-1-yl)-phenol (described in Reference Preparation example 27) instead of 2-methyl-4-(3,4,5-trimethyl-pyrazol-1-yl)-phenol gave 1-{3-chloro-2-[2-chloro-4-(3,5-dimethyl-4-ethyl-pyrazol-1-yl)-phenoxymethyl]-phenyl}-4-methyl-1,4-dihydrotetrazole-5-one (hereinafter, referred to as "Present compound 136").

Present compound 136

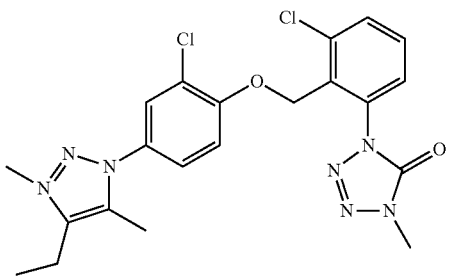

¹H-NMR (CDCl₃) δ: 7.60 (1H, dd, J=7.2, 2.2 Hz), 7.49-7.44 (2H, m), 7.40 (1H, d, J=2.7 Hz), 7.22-7.19 (1H, m), 6.95 (1H, d, J=8.7 Hz), 5.52 (2H, s), 3.65 (3H, s), 2.40 (2H, q, J=7.6 Hz), 2.24 (3H, s), 2.18 (3H, s), 1.10 (3H, t, J=7.5 Hz).

Preparation Example 137

A similar reaction to Preparation example 3 using 2-chloro-4-(3,5-dimethyl-4-ethyl-pyrazol-1-yl)-phenol (described in Reference Preparation example 27) instead of 2-methyl-4-(3,4,5-trimethyl-pyrazol-1-yl)-phenol gave 1-{3-bromo-2-[2-chloro-4-(3,5-dimethyl-4-ethyl-pyrazol-1-yl)-phenoxymethyl]-phenyl}-4-methyl-1,4-dihydrotetrazole-5-one (hereinafter, referred to as "Present compound 137").

Present compound 137

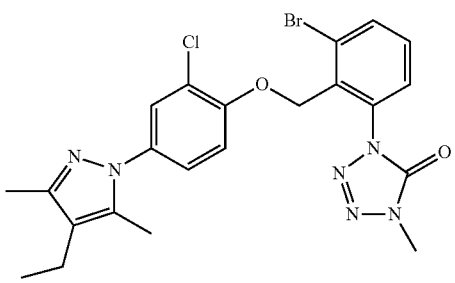

¹H-NMR (CDCl₃) δ: 7.78 (1H, dd, J=8.2, 1.0 Hz), 7.49-7.47 (1H, m), 7.41-7.37 (2H, m), 7.21 (1H, dd, J=8.7, 2.7 Hz), 6.95 (1H, d, J=8.7 Hz), 5.51 (2H, s), 3.65 (3H, s), 2.40 (2H, q, J=7.6 Hz), 2.24 (3H, s), 2.19 (3H, s), 1.10 (3H, t, J=7.5 Hz).

Preparation Example 138

Under nitrogen atmosphere, a mixture of 1-{3-methoxy-2-[2-methyl-4-(4-bromo-3,5-dimethyl-pyrazol-1-yl)-phenoxymethyl]-phenyl}-4-methyl-1,4-dihydrotetrazole-5-one (Present compound 115) 0.50 g, cyclopropylboronic acid 0.13 g, bis(triphenylphosphine)palladium-dichloride 0.07 g, tri(tert-butylphosphine) 0.10 g, potassium phosphate 0.85 g, dioxane 5 ml and water 0.5 ml was stirred at room temperature, and was then heated to 90° C. and was stirred at three hours. The reaction mixture was concentrated under reduced pressure and the resulting residue was subjected to a silica gel column chromatography to give 1-{3-methoxy-2-[2-methyl-4-(4-cyclopropyl-3,5-dimethyl-pyrazol-1-yl)-phenoxymethyl]-phenyl}-4-methyl-1,4-dihydrotetrazole-5-one (hereinafter, referred to as "Present compound 138") 0.33 g.

Present compound 138

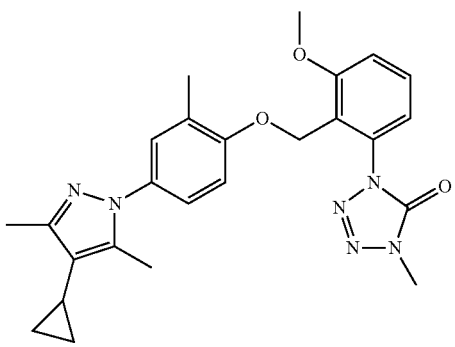

¹H-NMR (CDCl₃) δ: 7.47 (1H, t, J=8.2 Hz), 7.13-7.05 (4H, m), 6.90-6.88 (1H, m), 5.28 (2H, s), 3.92 (3H, s), 3.61 (3H, s), 2.28 (3H, s), 2.21 (3H, s), 2.01 (3H, s), 1.53-1.46 (1H, m), 0.84-0.79 (2H, m), 0.51-0.47 (2H, m).

Preparation Example 139

A mixture of 1-{3-methoxy-2-[2-methyl-4-(1-methyl-1H-pyrazol-3-yl)-phenoxymethyl]-phenyl}-4-methyl-1,4-dihydrotetrazole-5-one (Present compound 84) 1.0 g, N-bromosuccinimide 0.53 g and chloroform 15 ml was stirred at room temperature for seven hours. To the reaction mixture was added water 5 ml and the resulting mixture was separated with a separatory funnel. The organic layer was dehydrated over anhydrous magnesium sulfate, and was then filtered and was concentrated under reduced pressure. The resulting residue was subjected to a silica gel column chromatography to give 1-{3-methoxy-2-[2-methyl-4-(4-bromo-1-methyl-pyrazol-1-yl)-phenoxymethyl]-phenyl}-4-methyl-1,4-dihydrotetrazole-5-one (hereinafter, referred to as "Present compound 139") 1.0 g.

Present compound 139

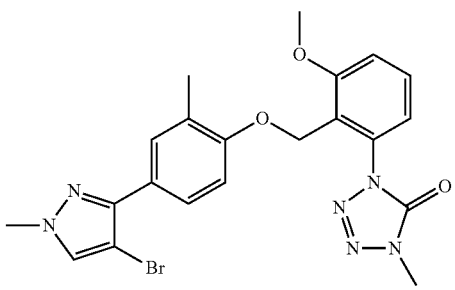

¹H-NMR (CDCl₃) δ: 7.62 (1H, dd, J=8.5, 2.2 Hz), 7.56 (1H, d, J=1.4 Hz), 7.46 (1H, t, J=8.2 Hz), 7.41 (1H, s), 7.10-7.06 (2H, m), 6.92 (1H, d, J=8.5 Hz), 5.29 (2H, s), 3.93 (3H, s), 3.90 (3H, s), 3.58 (3H, s), 2.04 (3H, s).

Preparation Example 140

At room temperature, a mixture of 1-{2-[4-(3-dimethyl-amino-acryloyl)-2-methyl-phenoxymethyl]-3-methoxy-pheny}-4-methyl-1,4-dihydrotetrazole-5-one (described in Reference Preparation example 115) 3.9 g and hydrazine one (1) hydrate 1.0 g was stirred for eight hours. The reaction mixture was concentrated under reduced pressure and the resulting residues was washed with hexane to give 1-{3-methoxy-2-[2-methyl-4-(4-methyl-1H-pyrazol-3-yl)-phenoxymethyl]-phenyl}-4-methyl-1,4-dihydrotetrazole-5-one (hereinafter, referred to as "Present compound 140") 3.9 g.

Present compound 140

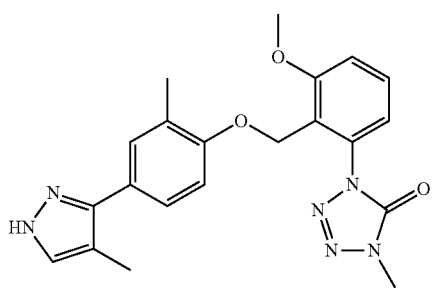

$^1$H-NMR (CDCl$_3$) δ: 7.47 (1H, t, J=8.2 Hz), 7.41 (1H, s), 7.30-7.23 (2H, m), 7.09 (2H, t, J=8.1 Hz), 6.94 (1H, d, J=8.0 Hz), 5.30 (2H, s), 3.94 (3H, s), 3.60 (3H, s), 2.19 (3H, s), 2.04 (3H, s).

Preparation Example 141

At room temperature, to a mixture of 1-{3-methoxy-2-[2-methyl-4-(4-methyl-1H-pyrazol-3-yl)-phenoxymethyl]-phenyl}-4-methyl-1,4-dihydrotetrazole-5-one (Present compound 140) 0.3 g and N,N-dimethylformamide 4 ml was added 55% sodium hydride 0.07 g and the resulting mixture was stirred for one hour, and thereto was added trifluoromethanesulfonic acid 2,2,2-trifluoroethyl ester 0.23 g. The resulting mixture was heated to 60° C. and was stirred for five hours. Thereto was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-{4-[4-methyl-1-(2,2,2-trifluoroethyl)-1H-pyrazol-3-yl)-2-methyl-phenoxymethyl}-3-methoxy-phenyl)-4-methyl-1,4-dihydrotetrazole-5-one (hereinafter, referred to as "Present compound 141") 0.3 g.

Present compound 141

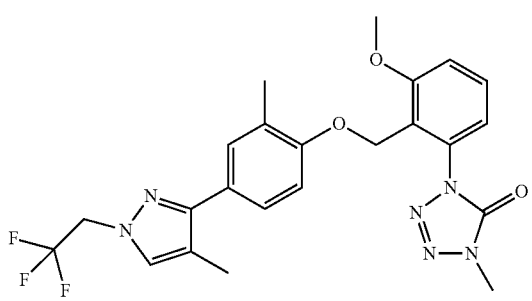

$^1$H-NMR (CDCl$_3$) δ: 7.50 (1H, t, J=8.1 Hz), 7.42-7.39 (2H, m), 7.33 (1H, s), 7.12 (1H, d, J=5.3 Hz), 7.10 (1H, d, J=4.8 Hz), 6.95 (1H, d, J=8.2 Hz), 5.33 (2H, s), 4.69 (2H, q, J=8.5 Hz), 3.96 (3H, s), 3.62 (3H, s), 2.23 (3H, s), 2.07 (3H, s).

Preparation Example 142

A similar reaction to Preparation example 141 using trifluoromethanesulfonic acid 2,2-difluoroethyl ester instead of trifluoromethanesulfonic acid 2,2,2-trifluoroethyl ester gave 1-(2-{4-[4-methyl-1-(2,2-difluoroethyl)-1H-pyrazol-3-yl)-2-methyl-phenoxymethyl}-3-methoxy-phenyl)-4-methyl-1,4-dihydrotetrazole-5-one (hereinafter, referred to a "Present compound 142").

Present compound 142

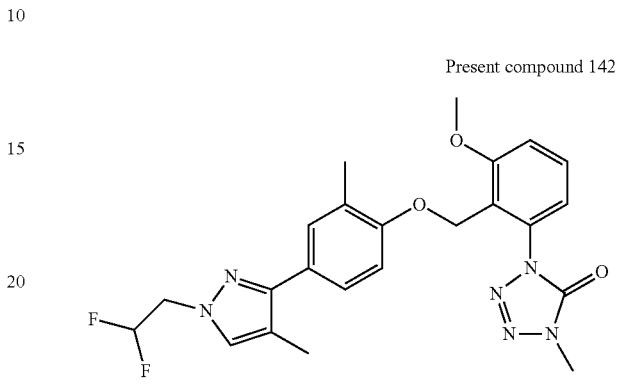

$^1$H-NMR (CDCl$_3$) δ: 7.48-7.43 (1H, m), 7.36 (2H, dd, J=11.0, 2.8 Hz), 7.12-7.06 (3H, m), 6.92 (1H, d, J=8.2 Hz), 6.09 (1H, tt, J=55.8, 4.4 Hz), 5.29 (2H, s), 4.40 (2H, td, J=13.5, 4.5 Hz), 3.93 (3H, s), 3.59 (3H, s), 2.19 (3H, s), 2.04 (3H, s).

Preparation Example 143

A similar reaction to Preparation example 141 using 3-bromopropyne instead of trifluoromethanesulfonic acid 2,2,2-trifluoroethyl ester gave 1-(2-{4-[4-methyl-1-(2-propynyl)-1H-pyrazol-3-yl)-2-methyl-phenoxymethyl}-3-methoxy-phenyl)-4-methyl-1,4-dihydrotetrazole-5-one (hereinafter, referred to a "Present compound 143").

Present compound 143

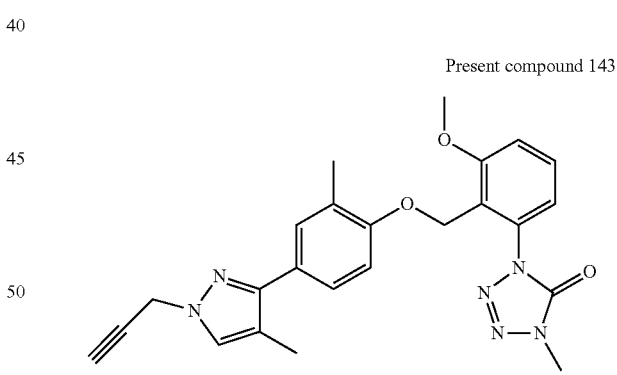

$^1$H-NMR (CDCl$_3$) δ: 7.48-7.35 (4H, m), 7.09 (1H, d, J=4.6 Hz), 7.07 (1H, d, J=3.9 Hz), 6.91 (1H, d, J=8.5 Hz), 5.29 (2H, s), 4.91 (2H, d, J=2.7 Hz), 3.93 (3H, s), 3.58 (3H, d, J=0.7 Hz), 2.49-2.47 (1H, m), 2.20 (3H, s), 2.03 (3H, s).

Preparation Example 144

A similar reaction to Preparation example 141 using 1-bromo-2-butyne instead of trifluoromethanesulfonic acid 2,2,2-trifluoroethyl ester gave 1-(2-{4-[4-methyl-1-(2-butynyl)-1H-pyrazol-3-yl)-2-methyl-phenoxymethyl}-3-methoxy-phenyl)-4-methyl-1,4-dihydrotetrazole-5-one (hereinafter, referred to as "Present compound 144").

Present compound 144

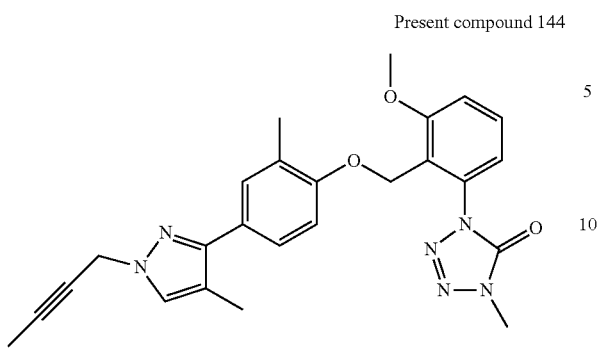

¹H-NMR (CDCl₃) δ: 7.46 (1H, t, J=8.2 Hz), 7.41-7.40 (2H, m), 7.37 (1H, dd, J=8.3, 2.3 Hz), 7.09-7.06 (2H, m), 6.90 (1H, d, J=8.2 Hz), 5.28 (2H, s), 4.85 (2H, q, J=2.4 Hz), 3.92 (3H, s), 3.58 (3H, s), 2.20 (3H, s), 2.03 (3H, s), 1.88 (3H, t, J=2.5 Hz).

Preparation Example 145

A similar reaction to Preparation example 141 using ethyl iodide instead of trifluoromethanesulfonic acid 2,2,2-trifluoroethyl ester gave 1-{3-methoxy-2-[2-methyl-4-(1-ethyl-4-methyl-1H-pyrazol-3-yl)-phenoxymethyl]-phenyl}-4-methyl-1,4-dihydrotetrazole-5-one (hereinafter, referred to a "Present compound 145").

Present compound 145

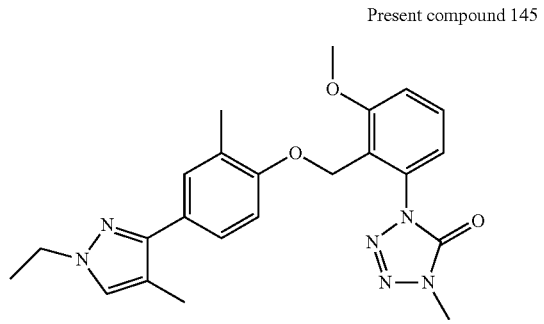 [SMILES: CCn1cc(C)c(-c2ccc(OCc3c(OC)cccc3-n3nnn(C)c3=O)c(C)c2)n1]

¹H-NMR (CDCl₃) δ: 7.48-7.44 (1H, m), 7.41-7.37 (2H, m), 7.20 (1H, s), 7.09-7.06 (2H, m), 6.90 (1H, d, J=8.5 Hz), 5.28 (2H, s), 4.16-4.10 (2H, m), 3.92 (3H, s), 3.58 (3H, s), 2.19 (3H, s), 2.03 (3H, s), 1.48 (3H, t, J=7.5 Hz).

Preparation Example 146

A similar reaction to Preparation example 5 using 2,5-dimethyl-4-(3-methyl-pyrazol-1-yl)-phenol (described in Reference Preparation example 40) instead of 2-methyl-4-(3,4,5-trimethyl-pyrazol-1-yl)-phenol gave 1-{3-ethyl-2-[2,5-dimethyl-4-(3-methyl-pyrazol-1-yl)-phenoxymethyl]-phenyl}-4-methyl-1,4-dihydrotetrazole-5-one (hereinafter, referred to as "Present compound 146").

Present compound 146

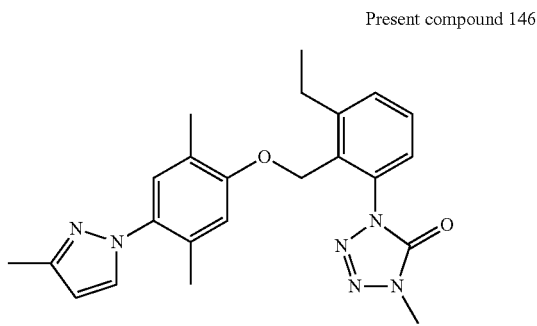 [SMILES: CCc1cccc(-n2nnn(C)c2=O)c1COc1cc(C)c(-n2ccc(C)n2)cc1C]

¹H-NMR (CDCl₃) δ: 7.50-7.44 (2H, m), 7.40 (1H, d, J=2.3 Hz), 7.29 (1H, dd, J=7.1, 2.1 Hz), 7.06 (1H, s), 6.71 (1H, s), 6.17 (1H, d, J=2.3 Hz), 5.06 (2H, s), 3.63 (3H, s), 2.85 (2H, q, J=7.6 Hz), 2.35 (3H, s), 2.17 (3H, s), 2.04 (3H, s), 1.28 (3H, t, J=7.6 Hz).

Preparation Example 147

A similar reaction to Preparation example 98 using bromoacetonitrile instead of isobutyl bromide gave 1-{3-methoxy-2-[2-methyl-4-(1-cyanomethyl-1H-pyrazol-3-yl)-phenoxymethyl]-phenyl}-4-methyl-1,4-dihydrotetrazole-5-one (hereinafter, referred to as "Present compound 147").

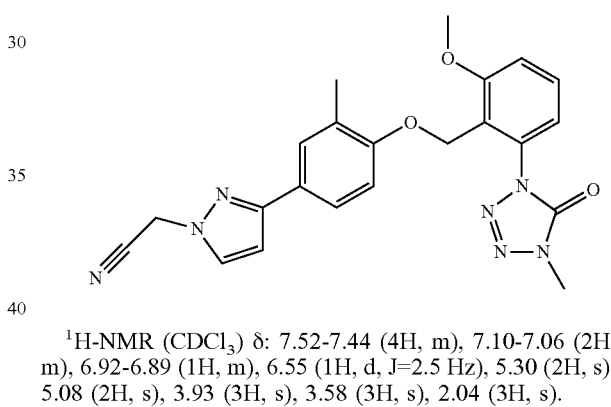

¹H-NMR (CDCl₃) δ: 7.52-7.44 (4H, m), 7.10-7.06 (2H, m), 6.92-6.89 (1H, m), 6.55 (1H, d, J=2.5 Hz), 5.30 (2H, s), 5.08 (2H, s), 3.93 (3H, s), 3.58 (3H, s), 2.04 (3H, s).

Preparation Example 148

A similar reaction to Preparation example 4 using 2-chloro-4-(1-methyl-1H-pyrazol-3-yl)-phenol (described in Reference Preparation example 119) instead of 2-methyl-4-(3,4,5-trimethyl-pyrazol-1-yl)-phenol gave 1-{3-methyl-2-[2-chloro-4-(1-methyl-1H-pyrazol-3-yl)-phenoxymethyl]-phenyl}-4-methyl-1,4-dihydrotetrazole-5-one (hereinafter, referred to as "Present compound 148").

Present compound 148

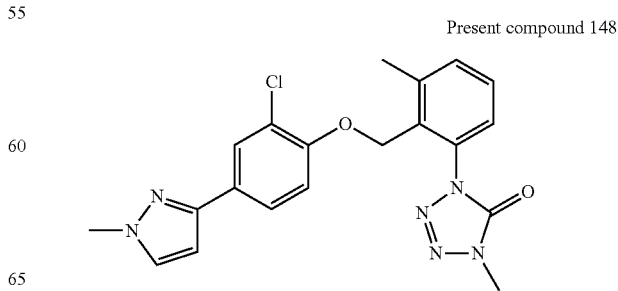

¹H-NMR (CDCl₃) δ: 7.77 (1H, d, J=2.3 Hz), 7.58 (1H, dd, J=8.5, 2.1 Hz), 7.43-7.37 (2H, m), 7.35 (1H, d, J=2.3 Hz), 7.29 (1H, dd, J=7.2, 1.9 Hz), 6.90 (1H, d, J=8.7 Hz), 6.43 (1H, d, J=2.3 Hz), 5.18 (2H, s), 3.92 (3H, s), 3.65 (3H, s), 2.54 (3H, s).

Preparation Example 149

A similar reaction to Preparation example 5 using 2-chloro-4-(1-methyl-1H-pyrazol-3-yl)-phenol (described in Reference Preparation example 119) instead of 2-methyl-4-(3,4,5-trimethyl-pyrazol-1-yl)-phenol gave 1-{3-ethyl-2-[2-chloro-4-(1-methyl-1H-pyrazol-3-yl)-phenoxymethyl]-phenyl}-4-methyl-1,4-dihydrotetrazole-5-one (hereinafter, referred to as "Present compound 149").

Present compound 149

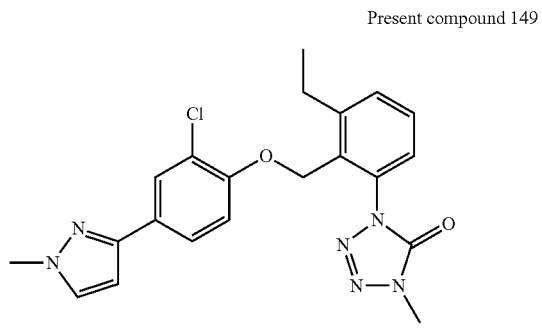 [SMILES: CCc1cccc(-n2nnn(C)c2=O)c1COc1ccc(-c2ccn(C)n2)cc1Cl]

¹H-NMR (CDCl₃) δ: 7.77 (1H, d, J=2.2 Hz), 7.58 (1H, dd, J=8.6, 2.1 Hz), 7.48-7.41 (2H, m), 7.35 (1H, d, J=2.2 Hz), 7.30 (1H, dd, J=7.5, 1.7 Hz), 6.92 (1H, d, J=8.5 Hz), 6.43 (1H, d, J=2.2 Hz), 5.20 (2H, s), 3.92 (3H, s), 3.63 (3H, s), 2.87 (2H, q, J=7.6 Hz), 1.30 (3H, t, J=7.6 Hz).

Preparation Example 150

A similar reaction to Preparation example 7 using 2-chloro-4-(1-methyl-1H-pyrazol-3-yl)-phenol (described in Reference Preparation example 119) instead of 2-methyl-4-(3,4,5-trimethyl-pyrazol-1-yl)-phenol gave 1-{3-methoxy-2-[2-chloro-4-(1-methyl-1H-pyrazol-3-yl)-phenoxymethyl]-phenyl}-4-methyl-1,4-dihydrotetrazole-5-one (hereinafter, referred to as "Present compound 150").

Present compound 150

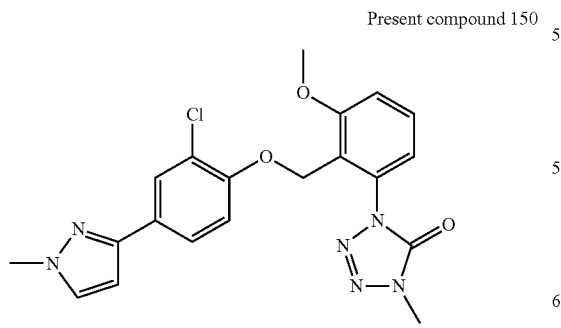

¹H-NMR (CDCl₃) δ: 7.73 (1H, d, J=2.3 Hz), 7.56 (1H, dd, J=8.6, 2.2 Hz), 7.46 (1H, t, J=8.2 Hz), 7.35 (1H, d, J=2.3 Hz), 7.12 (1H, dd, J=8.0, 0.9 Hz), 7.07 (1H, dd, J=8.5, 0.7 Hz), 6.96 (1H, d, J=8.5 Hz), 6.43 (1H, d, J=2.3 Hz), 5.46 (2H, s), 3.95 (3H, s), 3.93 (3H, s), 3.64 (3H, s).

Preparation Example 151

A similar reaction to Preparation example 5 using 2-methyl-4-(3-trifluoromethyl-pyrazol-1-yl)-phenol (described in Reference Preparation example 45) instead of 2-methyl-4-(3,4,5-trimethyl-pyrazol-1-yl)-phenol gave 1-{3-ethyl-2-[2-methyl-4-(3-trifluoromethyl-pyrazol-1-yl)-phenoxymethyl]-phenyl}-4-methyl-1,4-dihydrotetrazole-5-one (hereinafter, referred to as "Present compound 151").

Present compound 151

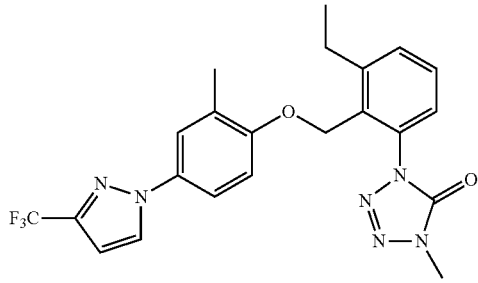

¹H-NMR (CDCl₃) δ: 7.83-7.82 (1H, m), 7.51-7.45 (3H, m), 7.42-7.39 (1H, m), 7.30 (1H, dd, J=7.3, 1.8 Hz), 6.90 (1H, d, J=8.7 Hz), 6.68 (1H, dd, J=2.5, 0.5 Hz), 5.10 (2H, s), 3.60 (3H, s), 2.85 (2H, q, J=7.6 Hz), 2.14 (3H, s), 1.29 (3H, t, J=7.6 Hz).

Preparation Example 152

A similar reaction to Preparation example 4 using 4-(1,4-dimethyl-1H-pyrazol-3-yl)-2-chloro-phenol (described in Reference Preparation example 125) instead of 2-methyl-4-(3,4,5-trimethyl-pyrazol-1-yl)-phenol gave 1-{3-methyl-2-[2-chloro-4-(1,4-dimethyl-1H-pyrazol-3-yl)-phenoxymethyl]-phenyl}-4-methyl-1,4-dihydrotetrazole-5-one (hereinafter, referred to a "Present compound 152").

Present compound 152

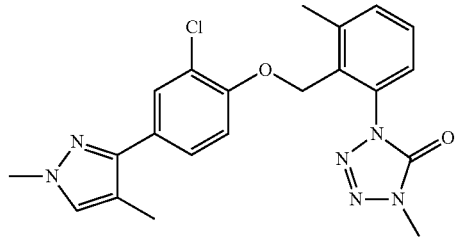

¹H-NMR (CDCl₃) δ: 7.66 (1H, d, J=2.2 Hz), 7.47 (1H, dd, J=8.3, 1.8 Hz), 7.43-7.37 (2H, m), 7.30-7.28 (1H, m), 7.16 (1H, s), 6.93 (1H, d, J=8.5 Hz), 5.18 (2H, s), 3.85 (3H, s), 3.65 (3H, s), 2.54 (3H, s), 2.18 (3H, s).

Preparation Example 153

A similar reaction to Preparation example 5 using 4-(1,4-dimethyl-1H-pyrazol-1-yl)-phenol (described in Reference Preparation example 125) instead of 2-methyl-4-(3,4,5-trimethyl-pyrazol-1-yl)-phenol gave 1-{3-ethyl-2-[2-chloro-4-(1,4-dimethyl-1H-pyrazol-3-yl)-phenoxymethyl]-phenyl}-4-methyl-1,4-dihydrotetrazole-5-one (hereinafter, referred to as "Present compound 153").

Present compound 153

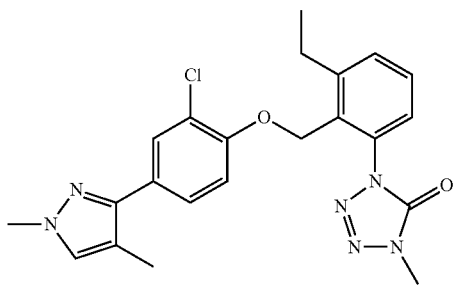

¹H-NMR (CDCl₃) δ: 7.66 (1H, d, J=2.2 Hz), 7.49-7.42 (3H, m), 7.31 (1H, dd, J=7.2, 1.7 Hz), 7.17 (1H, s), 6.94 (1H, d, J=8.7 Hz), 5.20 (2H, s), 3.87 (3H, s), 3.64 (3H, s), 2.88 (2H, q, J=7.6 Hz), 2.19 (3H, s), 1.30 (3H, t, J=7.5 Hz).

Preparation Example 154

A similar reaction to Preparation example 7 using 4-(1,4-dimethyl-1H-pyrazol-3-yl)-2-chloro-phenol (described in Reference Preparation example 125) instead of 2-methyl-4-(3,4,5-trimethyl-pyrazol-1-yl)-phenol gave 1-{3-methoxy-2-[2-chloro-4-(1,4-dimethyl-1H-pyrazol-3-yl)-phenoxymethyl]-phenyl}-4-methyl-1,4-dihydrotetrazole-5-one (hereinafter, referred to as "Present compound 154").

Present compound 154

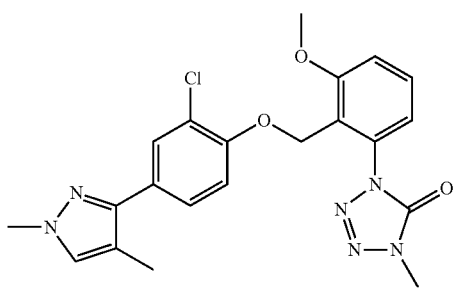

¹H-NMR (CDCl₃) δ: 7.61 (1H, d, J=2.2 Hz), 7.47-7.42 (2H, m), 7.16 (1H, s), 7.11 (1H, d, J=8.2 Hz), 7.06 (1H, d, J=8.5 Hz), 6.96 (1H, d, J=8.5 Hz), 5.44 (2H, s), 3.94 (3H, s), 3.86 (3H, s), 3.63 (3H, s), 2.17 (3H, d, J=0.7 Hz).

Preparation Example 155

A similar reaction to Preparation example 2 using 4-(1,4-dimethyl-1H-pyrazol-1-yl)-2-chloro-phenol (described in Reference Preparation example 125) instead of 2-methyl-4-(3,4,5-trimethyl-pyrazol-1-yl)-phenol gave 1-{3-chloro-2-[2-chloro-4-(1,4-dimethyl-1H-pyrazol-3-yl)-phenoxymethyl]-phenyl}-4-methyl-1,4-dihydrotetrazole-5-one (hereinafter, referred to as "Present compound 155").

Present compound 155

¹H-NMR (CDCl₃) δ: 7.65-7.64 (1H, m), 7.60-7.58 (1H, m), 7.48-7.44 (3H, m), 7.17 (1H, s), 6.94 (1H, d, J=8.5 Hz), 5.52 (2H, s), 3.86 (3H, s), 3.64 (3H, s), 2.18 (3H, s).

Preparation Example 156

A similar reaction to Preparation example 4 using 4-(1,4-dimethyl-1H-pyrazol-3-yl)-2-methyl-phenol (described in Reference Preparation example 124) instead of 2-methyl-4-(3,4,5-trimethyl-pyrazol-1-yl)-phenol gave 1-{3-methyl-2-[2-methyl-4-(1,4-dimethyl-1H-pyrazol-3-yl)-phenoxymethyl]-phenyl}-4-methyl-1,4-dihydrotetrazole-5-one (hereinafter, referred to as "Present compound 156").

Present compound 156

¹H-NMR (CDCl₃) δ: 7.44 (1H, d, J=1.8 Hz), 7.42-7.38 (3H, m), 7.28-7.26 (1H, m), 7.16 (1H, s), 6.87 (1H, d, J=8.5 Hz), 5.06 (2H, s), 3.86 (3H, s), 3.62 (3H, s), 2.51 (3H, s), 2.19 (3H, s), 2.12 (3H, s).

Preparation Example 157

A similar reaction to Preparation example 7 using 4-(1,4-dimethyl-1H-pyrazol-3-yl)-2-methylphenol (described in Reference Preparation example 124) instead of 2-methyl-4-(3,4,5-trimethyl-pyrazol-1-yl)-phenol gave 1-{3-methoxy-2-[2-methyl-4-(1,4-dimethyl-1H-pyrazol-3-yl)-phenoxymethyl]-phenyl}-4-methyl-1,4-dihydrotetrazole-5-one (hereinafter, referred to as "Present compound 157").

Present compound 157

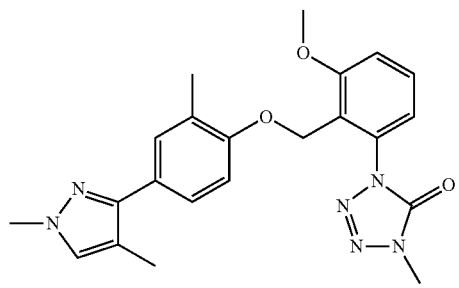

$^1$H-NMR (CDCl$_3$) δ: 7.45 (1H, t, J=8.2 Hz), 7.40 (1H, dd, J=2.1, 0.7 Hz), 7.36 (1H, ddd, J=8.5, 2.3, 0.5 Hz), 7.15 (1H, d, J=0.5 Hz), 7.09-7.05 (2H, m), 6.90 (1H, d, J=8.5 Hz), 5.28 (2H, s), 3.92 (3H, s), 3.86 (3H, s), 3.58 (3H, s), 2.18 (3H, d, J=0.7 Hz), 2.03 (3H, s).

Preparation Example 158

A similar reaction to Preparation example 2 using 4-(1,4-dimethyl-1H-pyrazol-3-yl)-2-methylphenol (described in Reference Preparation example 124) instead of 2-methyl-4-(3,4,5-trimethyl-pyrazol-1-yl)-phenol gave 1-{3-chloro-2-[2-methyl-4-(1,4-dimethyl-1H-pyrazol-3-yl)-phenoxymethyl]-phenyl}-4-methyl-1,4-dihydrotetrazole-5-one (hereinafter, referred to as "Present compound 158").

Present compound 158

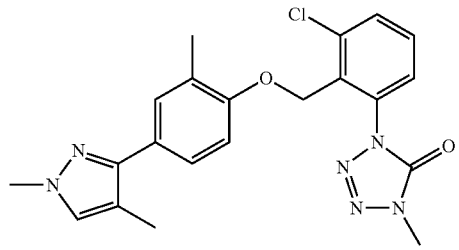

$^1$H-NMR (CDCl$_3$) δ: 7.62 (1H, dd, J=8.0, 1.1 Hz), 7.47 (1H, t, J=8.0 Hz), 7.43-7.38 (3H, m), 7.17 (1H, s), 6.88 (1H, d, J=8.5 Hz), 5.35 (2H, s), 3.87 (3H, s), 3.59 (3H, s), 2.19 (3H, s), 2.06 (3H, s).

Preparation Example 159

A similar reaction to Preparation example 5 using 4-(1,4-dimethyl-1H-pyrazol-3-yl)-2-methylphenol (described in Reference Preparation example 124) instead of 2-methyl-4-(3,4,5-trimethyl-pyrazol-1-yl)-phenol gave 1-{3-ethyl-2-[2-methyl-4-(1,4-dimethyl-1H-pyrazol-3-yl)-phenoxymethyl]-phenyl}-4-methyl-1,4-dihydrotetrazole-5-one (hereinafter, referred to as "Present compound 159").

Present compound 159

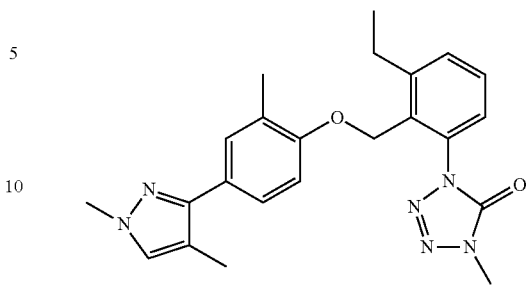

$^1$H-NMR (CDCl$_3$) δ: 7.49-7.44 (3H, m), 7.41 (1H, dd, J=8.4, 2.2 Hz), 7.29 (1H, dd, J=7.0, 2.2 Hz), 7.17 (1H, s), 6.89 (1H, d, J=8.5 Hz), 5.08 (2H, s), 3.88 (3H, s), 3.59 (3H, s), 2.86 (2H, q, J=7.6 Hz), 2.20 (3H, s), 2.11 (3H, s), 1.29 (3H, t, J=7.6 Hz).

Preparation Example 160

A similar reaction to Preparation example 3 using 4-(1,4-dimethyl-1H-pyrazol-3-yl)-2-methylphenol (described in Reference Preparation example 124) instead of 2-methyl-4-(3,4,5-trimethyl-pyrazol-1-yl)-phenol gave 1-{3-bromo-2-[2-methyl-4-(1,4-dimethyl-1H-pyrazol-3-yl)-phenoxymethyl]-phenyl}-4-methyl-1,4-dihydrotetrazole-5-one (hereinafter, referred to as "Present compound 160").

Present compound 160

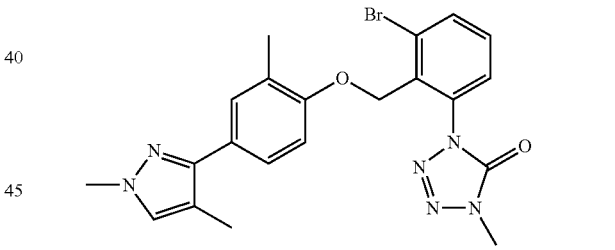

$^1$H-NMR (CDCl$_3$) δ: 7.82-7.79 (1H, m), 7.45-7.37 (4H, m), 7.17 (1H, s), 6.88 (1H, d, J=8.2 Hz), 5.34 (2H, s), 3.87 (3H, s), 3.59 (3H, s), 2.19 (3H, s), 2.08 (3H, s).

Preparation Example 161

A similar reaction to Preparation example 1 using 4-(1,4-dimethyl-1H-pyrazol-3-yl)-2-methylphenol (described in Reference Preparation example 124) instead of 2-methyl-4-(3,4,5-trimethyl-pyrazol-1-yl)-phenol gave 1-{3-fluoro-2-[2-methyl-4-(1,4-dimethyl-1H-pyrazol-3-yl)-phenoxymethyl]-phenyl}-4-methyl-1,4-dihydrotetrazole-5-one (hereinafter, referred to as "Present compound 161").

Present compound 161

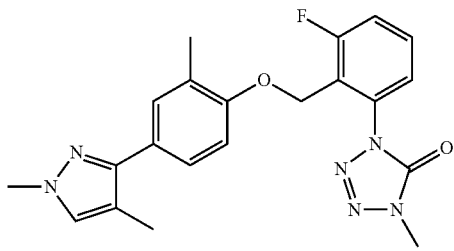

¹H-NMR (CDCl₃) δ: 7.54-7.47 (1H, m), 7.42 (1H, s), 7.39 (1H, dd, J=8.3, 2.3 Hz), 7.32 (1H, d, J=8.5 Hz), 7.29-7.27 (1H, m), 7.16 (1H, s), 6.89 (1H, d, J=8.5 Hz), 5.30 (2H, s), 3.87 (3H, s), 3.59 (3H, s), 2.19 (3H, s), 2.03 (3H, s).

Preparation Example 162

A similar reaction to Preparation example 1 using 4-(1,4,5-trimethyl-1H-pyrazol-3-yl)-2-methyl-phenol (described in Reference Preparation example 131) instead of 2-methyl-4-(3,4,5-trimethyl-pyrazol-1-yl)-phenol gave 1-{3-fluoro-2-[2-methyl-4-(1,4,5-trimethyl-1H-pyrazol-3-yl)-phenoxymethyl]-phenyl}-4-methyl-1,4-dihydrotetrazole-5-one (hereinafter, referred to a "Present compound 162").

Present compound 162

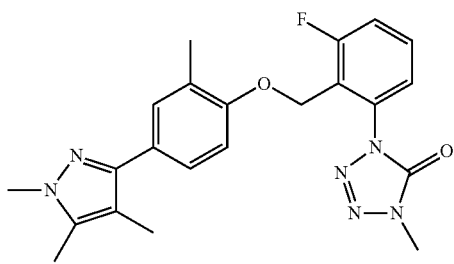

¹H-NMR (CDCl₃) δ: 7.50 (1H, td, J=8.2, 5.8 Hz), 7.38 (1H, s), 7.37-7.31 (2H, m), 7.29-7.27 (1H, m), 6.89 (1H, d, J=8.2 Hz), 5.30 (2H, s), 3.79 (3H, s), 3.59 (3H, s), 2.20 (3H, s), 2.09 (3H, s), 2.02 (3H, s).

Preparation Example 163

A similar reaction to Preparation example 4 using 4-(1,4,5-trimethyl-1H-pyrazol-3-yl)-2-methyl-phenol (described in Reference Preparation example 131) instead of 2-methyl-4-(3,4,5-trimethyl-pyrazol-1-yl)-phenol gave 1-{3-methyl-2-[2-methyl-4-(1,4,5-trimethyl-1H-pyrazol-3-yl)-phenoxymethyl]-phenyl}-4-methyl-1,4-dihydrotetrazole-5-one (hereinafter, referred to as "Present compound 163").

Present compound 163

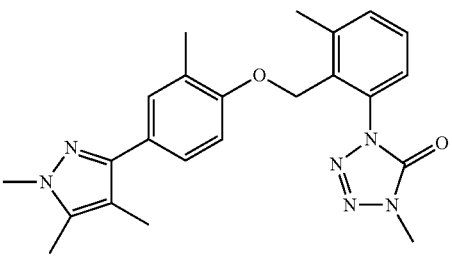

¹H-NMR (CDCl₃) δ: 8.48-8.44 (3H, m), 8.41 (1H, dd, J=8.2, 2.3 Hz), 8.31 (1H, dd, J=7.0, 2.9 Hz), 7.91 (1H, d, J=8.5 Hz), 6.10 (2H, s), 4.83 (3H, s), 4.66 (3H, s), 3.55 (3H, s), 3.24 (3H, s), 3.16 (3H, s), 3.14 (3H, s).

Preparation Example 164

A similar reaction to Preparation example 7 using 4-(1,4,5-trimethyl-1H-pyrazol-3-yl)-2-methyl-phenol (described in Reference Preparation example 131) instead of 2-methyl-4-(3,4,5-trimethyl-pyrazol-1-yl)-phenol gave 1-{3-methoxy-2-[2-methyl-4-(1,4,5-trimethyl-1H-pyrazol-3-yl)-phenoxymethyl]-phenyl}-4-methyl-1,4-dihydrotetrazole-5-one (hereinafter, referred to as "Present compound 164").

Present compound 164

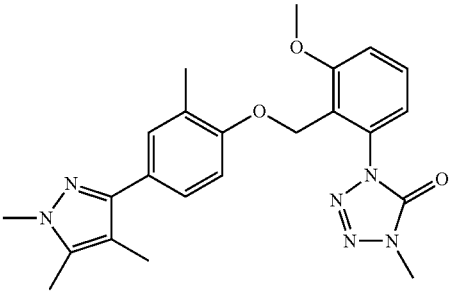

¹H-NMR (CDCl₃) δ: 7.46 (1H, t, J=8.2 Hz), 7.37 (1H, d, J=1.6 Hz), 7.33 (1H, dd, J=8.2, 2.3 Hz), 7.09 (1H, d, J=3.2 Hz), 7.07 (1H, d, J=2.5 Hz), 6.90 (1H, d, J=8.2 Hz), 5.28 (2H, s), 3.92 (3H, s), 3.79 (3H, s), 3.58 (3H, s), 2.20 (3H, s), 2.09 (3H, s), 2.03 (3H, s).

Preparation Example 165

A similar reaction to Preparation example 5 using 4-(1,4,5-trimethyl-1H-pyrazol-3-yl)-2-methyl-phenol (described in Reference Preparation example 131) instead of 2-methyl-4-(3,4,5-trimethyl-pyrazol-1-yl)-phenol gave 1-{3-ethyl-2-[2-methyl-4-(1,4,5-trimethyl-1H-pyrazol-3-yl)-phenoxymethyl]-phenyl}-4-methyl-1,4-dihydrotetrazole-5-one (hereinafter, referred to as "Present compound 165").

Present compound 165

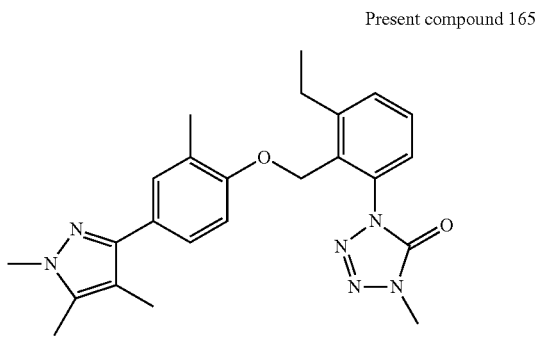

¹H-NMR (CDCl₃) δ: 7.49-7.43 (2H, m), 7.41-7.40 (1H, m), 7.37 (1H, dd, J=8.4, 2.2 Hz), 7.28 (1H, dd, J=7.0, 2.2 Hz), 6.88 (1H, d, J=8.5 Hz), 5.08 (2H, s), 3.80 (3H, s), 3.58 (3H, s), 2.85 (2H, q, J=7.6 Hz), 2.21 (3H, s), 2.11 (6H, s), 1.27 (3H, q, J=7.7 Hz).

Preparation Example 166

A similar reaction to Preparation example 2 using 4-(1,4,5-trimethyl-1H-pyrazol-3-yl)-2-methyl-phenol (described in Reference Preparation example 131) instead of 2-methyl-4-(3,4,5-trimethyl-pyrazol-1-yl)-phenol gave 1-{3-chloro-2-[2-methyl-4-(1,4,5-trimethyl-1H-pyrazol-3-yl)-phenoxymethyl]-phenyl}-4-methyl-1,4-dihydrotetrazole-5-one (hereinafter, referred to a "Present compound 166").

Present compound 166

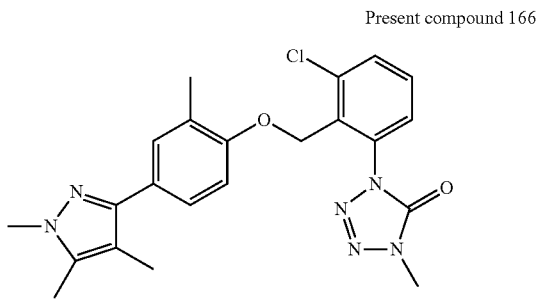 [SMILES: Cc1cc(-c2nn(C)c(C)c2C)ccc1OCc1c(F)cccc1-n1nnn(C)c1=O]

¹H-NMR (CDCl₃) δ: 7.61 (1H, dd, J=8.0, 1.4 Hz), 7.46 (1H, t, J=8.0 Hz), 7.41-7.39 (2H, m), 7.35 (1H, dd, J=8.2, 2.3 Hz), 6.88 (1H, d, J=8.2 Hz), 5.34 (2H, s), 3.79 (3H, s), 3.59 (3H, s), 2.20 (3H, s), 2.10 (3H, s), 2.05 (3H, s).

Preparation Example 167

A similar reaction to Preparation example 3 using 4-(1,4,5-trimethyl-1H-pyrazol-3-yl)-2-methyl-phenol (described in Reference Preparation example 131) instead of 2-methyl-4-(3,4,5-trimethyl-pyrazol-1-yl)-phenol gave 1-{3-bromo-2-[2-methyl-4-(1,4,5-trimethyl-1H-pyrazol-3-yl)-phenoxymethyl]-phenyl}-4-methyl-1,4-dihydrotetrazole-5-one (hereinafter, referred to a "Present compound 167").

Present compound 167

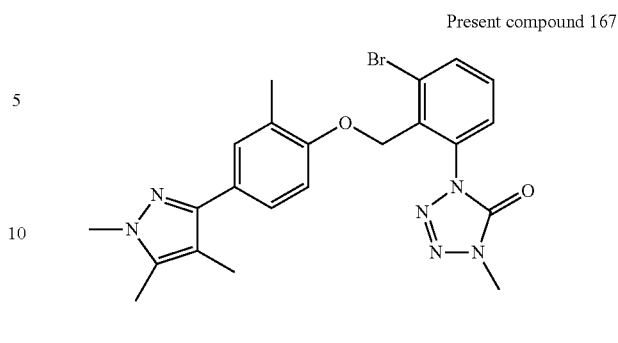

¹H-NMR (CDCl₃) δ: 7.80 (1H, dd, J=8.0, 1.4 Hz), 7.44 (1H, dd, J=8.0, 1.4 Hz), 7.40-7.38 (2H, m), 7.36 (1H, dd, J=8.1, 2.4 Hz), 6.87 (1H, d, J=8.2 Hz), 5.33 (2H, s), 3.79 (3H, s), 3.59 (3H, s), 2.20 (3H, s), 2.10 (3H, s), 2.07 (3H, s).

Preparation Example 168

A similar reaction to Preparation example 7 using 4-(5-chloro-1,4-dimethyl-1H-pyrazol-3-yl)-2-methyl-phenol (described in Reference Preparation example 140) instead of 2-methyl-4-(3,4,5-trimethyl-pyrazol-1-yl)-phenol gave 1-{3-methoxy-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 168").

Present compound 168

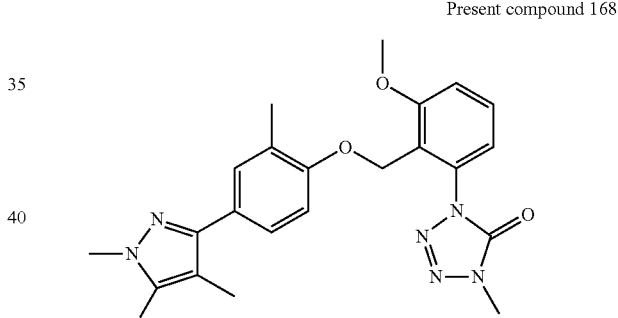

¹H-NMR (CDCl₃) δ: 7.49 (1H, t, J=8.2 Hz), 7.40-7.39 (1H, m), 7.37 (1H, dd, J=8.5, 2.3 Hz), 7.13-7.09 (2H, m), 6.94 (1H, d, J=8.5 Hz), 5.32 (2H, s), 3.96 (3H, s), 3.87 (3H, s), 3.62 (3H, s), 2.17 (3H, s), 2.06 (3H, s).

Preparation Example 169

A mixture of 1-(2-bromomethyl-3-methylphenyl)-4-methyl-1,4-dihydrotetrazole-5-one (described in Reference Preparation example 14) 3.1 g, 4-(5-chloro-1,4-dimethyl-1H-pyrazol-3-yl)-2-methyl-phenol (described in Reference Preparation example 140) 2.7 g, potassium carbonate 1.95 g and acetonitrile 70 ml was stirred with heating under reflux for four hours. After cooling to room temperature, the reaction mixture was filtered, and the filtrate was then concentrated under reduced pressure. The resulting residue was subjected to a silica gel column chromatography to give 1-{3-methyl-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 169").

Present compound 169

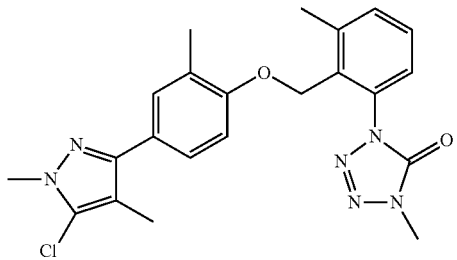

¹H-NMR (CDCl₃) δ: 7.45-7.39 (3H, m), 7.37 (1H, dd, J=8.5, 2.1 Hz), 7.28 (1H, dd, J=7.0, 2.4 Hz), 6.88 (1H, d, J=8.5 Hz), 5.06 (2H, s), 3.85 (3H, s), 3.62 (3H, s), 2.51 (3H, s), 2.15 (3H, s), 2.13 (3H, s).

Preparation Example 170

A similar reaction to Preparation example 4 using 2-methyl-4-(3,5-dimethyl-4-ethyl-pyrazol-1-yl)-phenol (described in Reference Preparation example 128) instead of 2-methyl-4-(3,4,5-trimethyl-pyrazol-1-yl)-phenol gave 1-{3-methyl-2-[2-methyl-4-(3,5-dimethyl-4-ethyl-1H-pyrazol-3-yl)-phenoxymethyl]-phenyl}-4-methyl-1,4-dihydrotetrazole-5-one (hereinafter, referred to as "Present compound 170").

Present compound 170

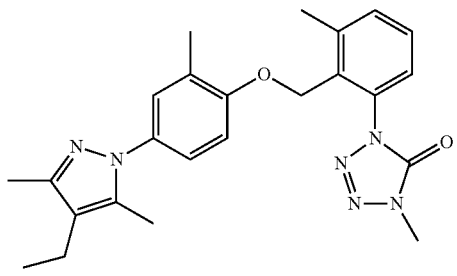

¹H-NMR (CDCl₃) δ: 7.45-7.40 (2H, m), 7.28 (1H, dd, J=7.0, 2.4 Hz), 7.17 (1H, d, J=2.3 Hz), 7.12 (1H, dd, J=8.5, 2.7 Hz), 6.86 (1H, d, J=8.5 Hz), 5.05 (2H, s), 3.64 (3H, s), 2.51 (3H, s), 2.41 (2H, q, J=7.6 Hz), 2.25 (3H, s), 2.18 (3H, s), 2.11 (3H, s), 1.11 (3H, t, J=7.6 Hz).

Preparation Example 171

A similar reaction to Preparation example 5 using 2-methyl-4-(3,5-dimethyl-4-ethyl-pyrazol-1-yl)-phenol (described in Reference Preparation example 128) instead of 2-methyl-4-(3,4,5-trimethyl-pyrazol-1-yl)-phenol gave 1-{3-ethyl-2-[2-methyl-4-(3,5-dimethyl-4-ethyl-1H-pyrazol-3-yl)-phenoxymethyl]-phenyl}-4-methyl-1,4-dihydrotetrazole-5-one (hereinafter, referred to a "Present compound 171").

Present compound 171

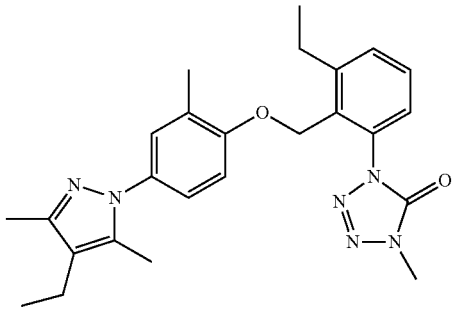

¹H-NMR (CDCl₃) δ: 7.50-7.44 (2H, m), 7.29 (1H, dd, J=7.2, 1.9 Hz), 7.17-7.16 (1H, m), 7.12 (1H, dd, J=8.5, 2.7 Hz), 6.87 (1H, d, J=8.5 Hz), 5.07 (2H, s), 3.61 (3H, s), 2.85 (2H, q, J=7.6 Hz), 2.41 (2H, q, J=7.6 Hz), 2.25 (3H, s), 2.18 (3H, s), 2.09 (3H, s), 1.28 (3H, t, J=7.6 Hz), 1.11 (3H, t, J=7.6 Hz).

Preparation Example 172

A similar reaction to Preparation example 7 using 2-methyl-4-(3,5-dimethyl-4-ethyl-pyrazol-1-yl)-phenol (described in Reference Preparation example 128) instead of 2-methyl-4-(3,4,5-trimethyl-pyrazol-1-yl)-phenol gave 1-{3-methoxy-2-[2-methyl-4-(3,5-dimethyl-4-ethyl-1H-pyrazol-3-yl)-phenoxymethyl]-phenyl}-4-methyl-1,4-dihydrotetrazole-5-one (hereinafter, referred to as "Present compound 172").

Present compound 172

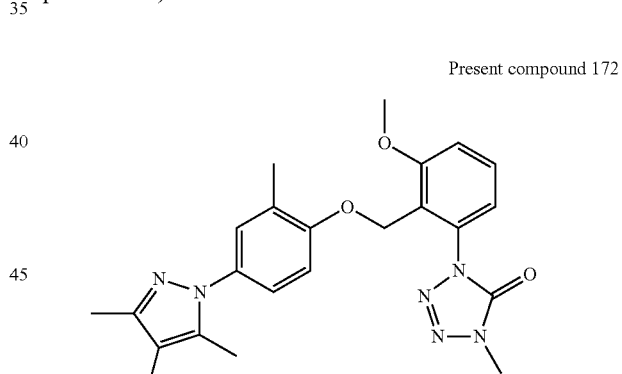

¹H-NMR (CDCl₃) δ: 7.47 (1H, t, J=8.2 Hz), 7.12-7.07 (4H, m), 6.90 (1H, d, J=8.5 Hz), 5.28 (2H, s), 3.93 (3H, s), 3.61 (3H, s), 2.40 (2H, q, J=7.6 Hz), 2.24 (3H, s), 2.16 (3H, s), 2.01 (3H, s), 1.11 (3H, t, J=7.5 Hz).

Preparation Example 173

A similar reaction to Preparation example 2 using 2-methyl-4-(3,5-dimethyl-4-ethyl-pyrazol-1-yl)-phenol (described in Reference Preparation example 128) instead of 2-methyl-4-(3,4,5-trimethyl-pyrazol-1-yl)-phenol gave 1-{3-chloro-2-[2-methyl-4-(3,5-dimethyl-4-ethyl-1H-pyrazol-3-yl)-phenoxymethyl]-phenyl}-4-methyl-1,4-dihydrotetrazole-5-one (hereinafter, referred to a "Present compound 173").

Present compound 173

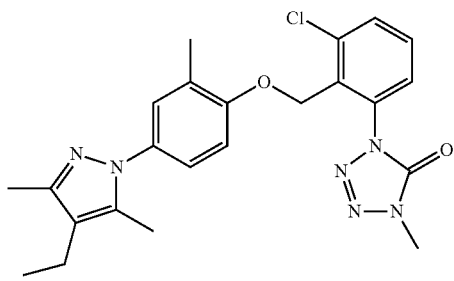

¹H-NMR (CDCl₃) δ: 7.62 (1H, dd, J=8.1, 1.3 Hz), 7.48 (1H, t, J=8.0 Hz), 7.41 (1H, dd, J=8.0, 1.4 Hz), 7.15 (1H, d, J=2.2 Hz), 7.11 (1H, dd, J=8.5, 2.7 Hz), 6.87 (1H, d, J=8.7 Hz), 5.33 (2H, s), 3.62 (3H, s), 2.41 (2H, q, J=7.6 Hz), 2.25 (3H, s), 2.17 (3H, s), 2.05 (3H, s), 1.11 (3H, t; J=7.5 Hz).

Preparation Example 174

A similar reaction to Preparation example 3 using 2-methyl-4-(3,5-dimethyl-4-ethyl-pyrazol-1-yl)-phenol (described in Reference Preparation example 128) instead of 2-methyl-4-(3,4,5-trimethyl-pyrazol-1-yl)-phenol gave 1-{3-bromo-2-[2-methyl-4-(3,5-dimethyl-4-ethyl-1H-pyrazol-3-yl)-phenoxymethyl]-phenyl}-4-methyl-1,4-dihydro-tetrazole-5-one (hereinafter, referred to a "Present compound 174").

Present compound 174

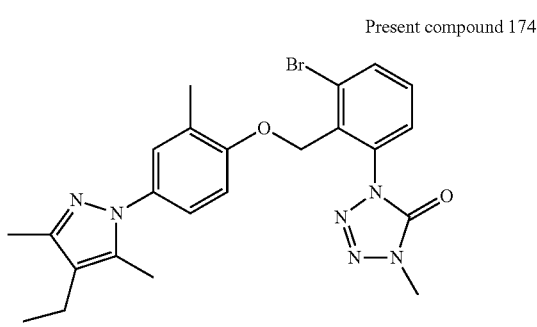 [SMILES: CCc1c(C)nn(-c2ccc(OCc3c(Br)cccc3-n3nnn(C)c3=O)c(C)c2)c1C]

¹H-NMR (CDCl₃) δ: 7.81 (1H, dd, J=7.8, 1.4 Hz), 7.46-7.38 (2H, m), 7.16 (1H, d, J=2.3 Hz), 7.11 (1H, dd, J=8.5, 2.5 Hz), 6.87 (1H, d, J=8.7 Hz), 5.32 (2H, s), 3.62 (3H, s), 2.41 (2H, q, J=7.6 Hz), 2.25 (3H, s), 2.17 (3H, s), 2.06 (3H, s), 1.11 (3H, t, J=7.6 Hz).

Preparation Example 175

A similar reaction to Preparation example 7 using 1-(4-hydroxy-3-methyl)-ethanone instead of 2-methyl-4-(3,4,5-trimethyl-pyrazol-1-yl)-phenol gave 1-[2-(4-acetyl-2-methyl-phenoxymethyl]-3-methoxy-phenyl)-4-methyl-1,4-dihydrotetrazole-5-one (hereinafter, referred to as "Present compound 175").

Present compound 175

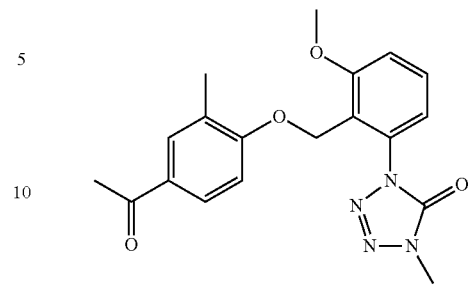

¹H-NMR (CDCl₃) δ: 7.76 (1H, dd, J=8.7, 2.2 Hz), 7.70 (1H, d, J=1.2 Hz), 7.48 (1H, t, J=8.2 Hz), 7.09 (2H, dd, J=11.7, 4.5 Hz), 6.91 (1H, d, J=8.7 Hz), 5.35 (2H, s), 3.94 (3H, s), 3.59 (3H, s), 2.52 (3H, s), 2.02 (3H, s).

Preparation Example 176

A similar reaction to Preparation example 7 using 1-(4-hydroxy-3-methyl-phenyl)-propane-1-one (described in Reference Preparation example 114) instead of 2-methyl-4-(3,4,5-trimethyl-pyrazol-1-yl)-phenol gave 1-[2-(4-propionyl-2-methyl-phenoxymethyl]-3-methoxy-phenyl)-4-methyl-1,4-dihydrotetrazole-5-one (hereinafter, referred to as "Present compound 176").

Present compound 176

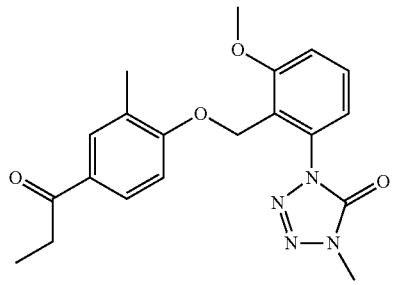

¹H-NMR (CDCl₃) δ: 7.77 (1H, dd, J=8.6, 2.3 Hz), 7.71 (1H, d, J=2.2 Hz), 7.48 (1H, t, J=8.2 Hz), 7.09 (2H, t, J=8.1 Hz), 6.90 (1H, d, J=8.5 Hz), 5.34 (2H, s), 3.94 (3H, s), 3.59 (3H, s), 2.92 (2H, q, J=7.2 Hz), 2.02 (3H, s), 1.19 (3H, t, J=7.2 Hz).

Preparation Example 177

A similar reaction to Preparation example 7 using 1-(4-hydroxy-3-methyl-phenyl)-2-methyl-propane-1-one (described in Reference Preparation example 152) instead of 2-methyl-4-(3,4,5-trimethyl-pyrazol-1-yl)-phenol gave 1-[2-(4-isobutyryl-2-methyl-phenoxymethyl]-3-methoxy-phenyl)-4-methyl-1,4-dihydrotetrazole-5-one (hereinafter, referred to as "Present compound 177").

Present compound 177

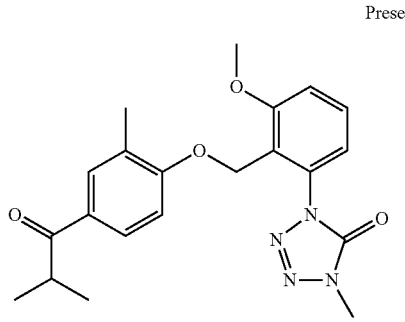

¹H-NMR (CDCl₃) δ: 7.77 (1H, dd, J=8.69, 2.29 Hz), 7.73-7.70 (1H, m), 7.48 (1H, t, J=8.21 Hz), 7.12-7.06 (2H, m), 6.91 (1H, d, J=8.69 Hz), 5.34 (2H, s), 3.94 (3H, s), 3.59 (3H, s), 3.54-3.46 (1H, m), 2.02 (3H, s), 1.18 (6H, d, J=6.76 Hz).

Preparation Example 178

A similar reaction to Preparation example 4 using 1-(4-hydroxy-3-methyl-phenyl)-ethanone instead of 2-methyl-4-(3,4,5-trimethyl-pyrazol-1-yl)-phenol gave 1-[2-(4-acetyl-2-methyl-phenoxymethyl]-3-methyl-phenyl)-4-methyl-1,4-dihydrotetrazole-5-one (hereinafter, referred to as "Present compound 178").

Present compound 178

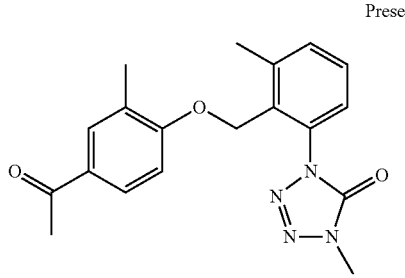

¹H-NMR (CDCl₃) δ: 7.79 (1H, dd, J=8.54, 2.24 Hz), 7.75 (1H, d, J=1.46 Hz), 7.46-7.40 (2H, m), 7.29 (1H, dd, J=7.32, 1.95 Hz), 6.86 (1H, d, J=8.54 Hz), 5.11 (2H, s), 3.62 (3H, s), 2.54 (3H, s), 2.50 (3H, s), 2.12 (3H, s).

Preparation Example 179

A similar reaction to Preparation example 4 using 1-(4-hydroxy-3-methyl-phenyl)-propane-1-one (described in Reference Preparation example 114) instead of 2-methyl-4-(3,4,5-trimethyl-pyrazol-1-yl)-phenol gave 1-[2-(2-methyl-4-propionyl-phenoxymethyl]-3-methyl-phenyl)-4-methyl-,4-dihydrotetrazole-5-one (hereinafter, referred to as "Present compound 179").

Present compound 179

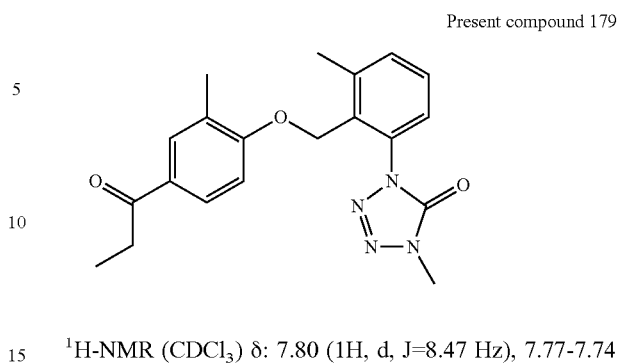

¹H-NMR (CDCl₃) δ: 7.80 (1H, d, J=8.47 Hz), 7.77-7.74 (1H, m), 7.47-7.39 (2H, m), 7.29 (1H, d J=7.33 Hz), 6.86 (1H, d, J=8.47 Hz), 5.11 (2H, s), 3.62 (3H, s), 2.94 (2H, q, J=7.33 Hz), 2.50 (3H, s), 2.12 (3H, s), 1.20 (3H, t, J=7.33 Hz).

Preparation Example 180

A similar reaction to Preparation example 4 using 1-(4-hydroxy-3-methyl-phenyl)-2-methyl-propane-1-one (described in Reference Preparation example 152) instead of 2-methyl-4-(3,4,5-trimethyl-pyrazol-1-yl)-phenol gave 1-[2-(4-isobutyryl-2-methyl-phenoxymethyl]-3-methyl-phenyl)-4-methyl-1,4-dihydrotetrazole-5-one (hereinafter, referred to as "Present compound 180").

Present compound 180

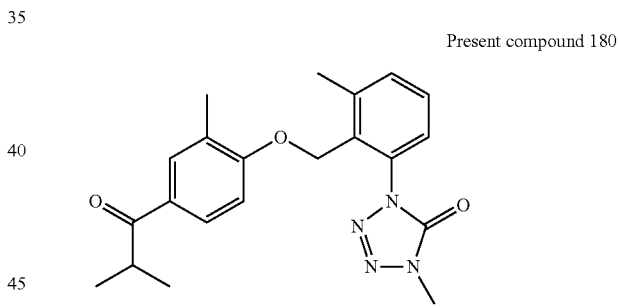

¹H-NMR (CDCl₃) δ: 7.81 (1H, d, J=8.70 Hz), 7.78-7.75 (1H, m), 7.47-7.39 (2H, m), 7.30-7.29 (1H, m), 6.88 (1H, d, J=8.70 Hz), 5.12 (2H, s), 3.63 (3H, s), 3.55-3.48 (1H, m), 2.51 (3H, s), 2.13 (3H, s), 1.20 (6H, d, J=6.87 Hz).

Preparation Example 181

A similar reaction to Preparation example 4 using cyclopropyl-(4-hydroxy-3-methyl-phenyl)-methanone (described in Reference Preparation example 150) instead of 2-methyl-4-(3,4,5-trimethyl-pyrazol-1-yl)-phenol gave 1-[2-(4-cyclopropanecarbonyl-2-methyl-phenoxymethyl]-3-methyl-phenyl)-4-methyl-1,4-dihydrotetrazole-5-one (hereinafter, referred to as "Present compound 181").

Present compound 181

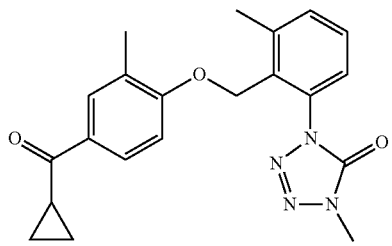

¹H-NMR (CDCl₃) δ: 7.88 (1H, dd, J=8.47, 2.06 Hz), 7.83-7.80 (1H, m), 7.47-7.41 (2H, m), 7.29 (1H, dd, J=7.21, 1.72 Hz), 6.89 (1H, d, J=8.47 Hz), 5.12 (2H, s), 3.63 (3H, s), 2.65-2.61 (1H, m), 2.51 (3H, s), 2.13 (3H, s), 1.22-1.18 (2H, m), 1.02-0.96 (2H, m).

Preparation Example 182

A similar reaction to Preparation example 4 using 1-(4-hydroxy-3-methyl-phenyl)-3,3-dimethyl-butane-1-one) (described in Reference Preparation example 151) instead of 2-methyl-4-(3,4,5-trimethyl-pyrazol-1-yl)-phenol gave 1-{2-[4-(3,3-dimethyl-butyryl)-2-methyl-phenoxymethyl]-3-methyl-phenyl}-4-methyl-1,4-dihydrotetrazole-5-one (hereinafter, referred to a "Present compound 182").

Present compound 182

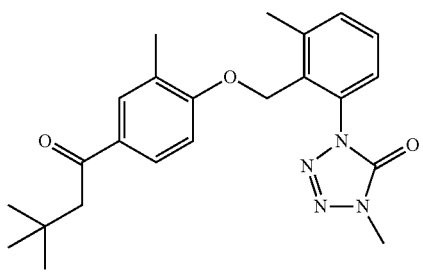

¹H-NMR (CDCl₃) δ: 7.77 (1H, dd, J=8.47, 2.06 Hz), 7.75-7.73 (1H, m), 7.47-7.39 (2H, m), 7.29 (1H, dd, J=7.21, 1.72 Hz), 6.85 (1H, d, J=8.47 Hz), 5.10 (2H, s), 3.62 (3H, s), 2.79 (2H, s), 2.50 (3H, s), 2.12 (3H, s), 1.05 (9H, s).

Preparation Example 183

A similar reaction to Preparation example 4 using cyclohexyl-(4-hydroxy-3-methyl-phenyl)-methanone instead of 2-methyl-4-(3,4,5-trimethyl-pyrazol-1-yl)-phenol gave 1-[2-(4-cyclohexanecarbonyl-2-methyl-phenoxymethyl)-3-methyl-phenyl}-4-methyl-1,4-dihydrotetrazole-5-one (hereinafter, referred to a "Present compound 183").

Present compound 183

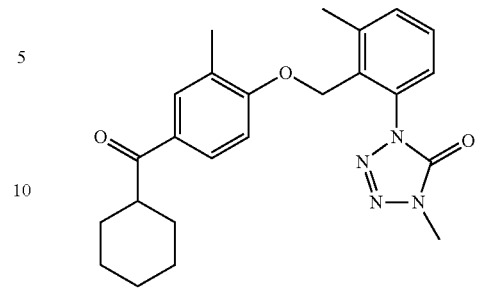

¹H-NMR (CDCl₃) δ: 7.79 (1H, dd, J=8.45, 2.29 Hz), 7.75-7.72 (1H, m), 7.46-7.36 (2H, m), 7.29 (1H, dd, J=7.24, 1.93 Hz), 6.86 (1H, d, J=8.45 Hz), 5.11 (2H, s), 3.62 (3H, s), 3.24-3.18 (1H, m), 2.50 (3H, s), 2.13 (3H, s), 1.89-1.79 (4H, m), 1.77-1.66 (2H, m), 1.54-1.29 (4H, m).

Preparation Example 184

A similar reaction to Preparation example 4 using 1-(4-hydroxy-3-methyl-phenyl)-pentane-1-one (described in Reference Preparation example 154) instead of 2-methyl-4-(3,4,5-trimethyl-pyrazol-1-yl)-phenol gave 1-[2-(2-methyl-4-pentanoyl-phenoxymethyl)-3-methyl-phenyl]-4-methyl-, 4-dihydrotetrazole-5-one (hereinafter, referred to as "Present compound 184").

Present compound 184

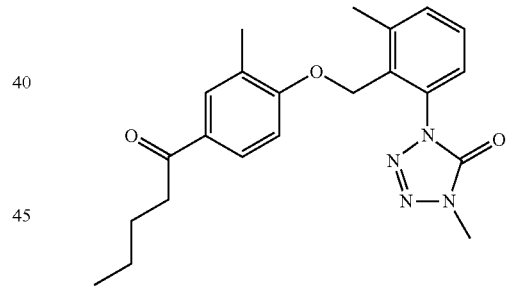

¹H-NMR (CDCl₃) δ: 7.80 (1H, dd, J=8.47, 2.06 Hz), 7.76-7.74 (1H, m), 7.47-7.39 (2H, m), 7.29 (1H, dd, J=7.21, 1.72 Hz), 6.86 (1H, d, J=8.47 Hz), 5.10 (2H, s), 3.62 (3H, s), 2.89 (2H, t, J=7.44 Hz), 2.50 (3H, s), 2.12 (3H, s), 1.73-1.66 (2H, m), 1.45-1.34 (2H, m), 0.94 (3H, t, J=7.33 Hz)

Preparation Example 185

A similar reaction to Preparation example 4 using 1-(3-bromo-4-hydroxy-phenyl)-ethanone (described in Reference Preparation example 149) instead of 2-methyl-4-(3,4,5-trimethyl-pyrazol-1-yl)-phenol gave 1-[2-(2-bromo-4-acetyl-phenoxymethyl)-3-methyl-phenyl]-4-methyl-, 4-dihydrotetrazole-5-one (hereinafter, referred to as "Present compound 185").

Present compound 185

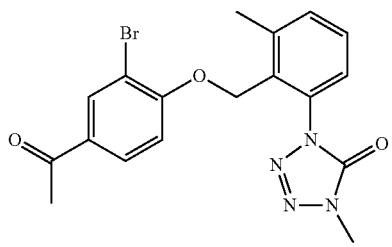

¹H-NMR (CDCl₃) δ: 8.13 (1H, d, J=2.17 Hz), 7.86 (1H, dd, J=8.69, 2.17 Hz), 7.47-7.38 (2H, m), 7.33-7.30 (1H, m), 6.90 (1H, d, J=8.69 Hz), 5.24 (2H, s), 3.67 (3H, s), 2.55-2.53 (6H, m).

Preparation Example 186

A mixture of 1-[2-(4-acetyl-2-bromo-phenoxymethyl)-3-methyl-phenyl]-4-methyl-1,4-dihydrotetrazole-5-one (Present compound 185) 0.4 g, cyclopropylboronic acid 0.1 g, [1,1'-bis(diphenylphosphino)ferrocene]palladium(II) dichloride dichloromethane complex 0.08 g, cesium fluoride 0.3 g and 1,4-dioxane 5 ml was stirred with heating under reflux for four hours. The reaction mixture was concentrated under reduced pressure and the resulting residue was subjected to a silica gel column chromatography to give 1-[2-(2-cyclopropyl-4-acetyl-phenoxymethyl)-3-methyl-phenyl]-4-methyl-1,4-dihydrotetrazole-5-one (hereinafter, referred to as "Present compound 186").

Present compound 186

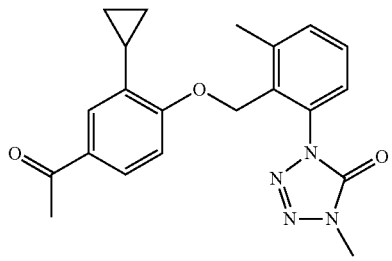

¹H-NMR (CDCl₃) δ: 7.76 (1H, dd, J=8.69, 2.17 Hz), 7.46-7.40 (3H, m), 7.30 (1H, dd, J=7.24, 1.93 Hz), 6.89 (1H, d, J=8.69 Hz), 5.16 (2H, s), 3.63 (3H, s), 3.53-3.45 (1H, m), 2.52 (3H, s), 1.19 (3H, s), 0.90-0.84 (2H, m), 0.65-0.60 (2H, m).

Preparation Example 187

A similar reaction to Preparation example 7 using 2-methyl-4-(1,3-dimethyl-1H-pyrazole-5-yl)-phenol (described in Reference Preparation example 134) instead of 2-methyl-4-(3,4,5-trimethyl-pyrazol-1-yl)-phenol gave 1-{2-[2-methyl-4-(1,3-dimethyl-1H-pyrazole-5-yl)-phenoxymethyl]-3-methoxy-phenyl}-4-methyl-1,4-dihydrotetrazole-5-one (hereinafter, referred to a "Present compound 187").

Present compound 187

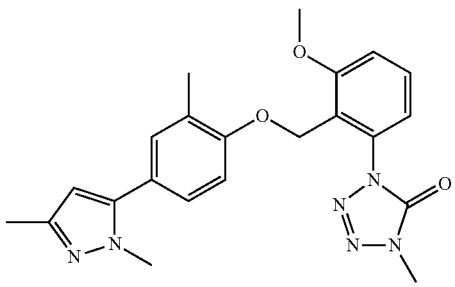

¹H-NMR (CDCl₃) δ: 7.48 (1H, t, J=8.2 Hz), 7.13-7.07 (4H, m), 6.92 (1H, d, J=8.5 Hz), 5.99 (1H, s), 5.30 (2H, s), 3.94 (3H, s), 3.78 (3H, s), 3.62 (3H, s), 2.28 (3H, s), 2.03 (3H, s).

Preparation Example 188

A similar reaction to Preparation example 2 using 2-methyl-4-(1,5-dimethyl-1H-pyrazol-3-yl)-phenol (described in Reference Preparation example 63) instead of 2-methyl-4-(3,4,5-trimethyl-pyrazol-1-yl)-phenol gave 1-{3-chloro-2-[2-methyl-4-(1,5-dimethyl-1H-pyrazol-3-yl)-phenoxymethyl]-phenyl}-4-methyl-1,4-dihydrotetrazole-5-one (hereinafter, referred to as "Present compound 188").

Present compound 188

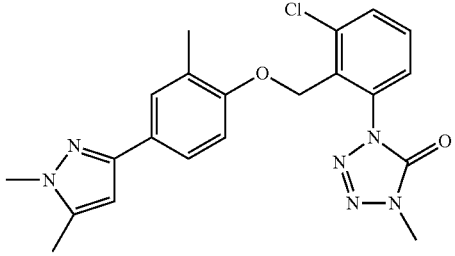

¹H-NMR (CDCl₃) δ: 7.61 (1H, dd, J=8.0, 1.1 Hz), 7.52-7.51 (1H, m), 7.49-7.44 (2H, m), 7.40 (1H, dd, J=8.0, 1.4 Hz), 6.85 (1H, d, J=8.5 Hz), 6.23 (1H, d, J=0.7 Hz), 5.33 (2H, s), 3.80 (3H, s), 3.57 (3H, s), 2.28 (3H, d, J=2.5 Hz), 2.05 (3H, s).

Preparation Example 189

A similar reaction to Preparation example 2 using 2-methyl-4-(1-methyl-5-trifluoromethyl-1H-pyrazol-3-yl)-phenol (described in Reference Preparation example 158) instead of 2-methyl-4-(3,4,5-trimethyl-pyrazol-1-yl)-phenol gave 1-{3-chloro-2-[2-methyl-4-(1-methyl-5-trifluoromethyl-1H-pyrazol-3-yl)-phenoxymethyl]-phenyl}-4-methyl-1,4-dihydrotetrazole-5-one (hereinafter, referred to as "Present compound 189").

Present compound 189

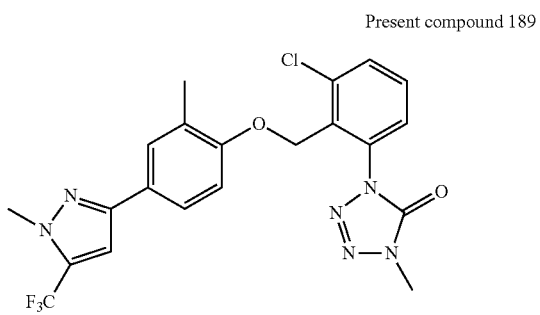 [SMILES: Cc1cc(-c2cc(C(F)(F)F)n(C)n2)ccc1OCc1c(Cl)cccc1-n1nnn(C)c1=O]

¹H-NMR (CDCl₃) δ: 7.62 (1H, dd, J=8.0, 1.4 Hz), 7.52-7.49 (2H, m), 7.47 (1H, t, J=8.0 Hz), 7.40 (1H, dd, J=8.0, 1.4 Hz), 6.87 (1H, d, J=8.5 Hz), 6.80 (1H, d, J=0.5 Hz), 5.34 (2H, s), 4.00 (3H, s), 3.59 (3H, s), 2.06 (3H, s).

Preparation Example 190

A mixture of 1-{3-methyl-2-[2-methyl-4-(1,5-dimethyl-1H-pyrazol-3-yl)-phenoxymethyl]-phenyl}-4-methyl-1,4-dihydrotetrazole-5-one (Present compound 47) 0.47 g, N-chlorosuccinimide 0.17 g and chloroform 10 ml was stirred at room temperature for twelve hours. The reaction mixture was extracted with chloroform and was washed with saturated saline, and the organic layer was dried over anhydrous magnesium sulfate and was then concentrated under reduced pressure. The resulting residue was subjected to a silica gel column chromatography to give 1-{3-methyl-2-[2-methyl-4-(4-chloro-1,5-dimethyl-1H-pyrazol-3-yl)-phenoxymethyl]-phenyl}-4-methyl-1,4-dihydrotetrazole-5-one (hereinafter, referred to as "Present compound 190") 0.34 g.

Present compound 190

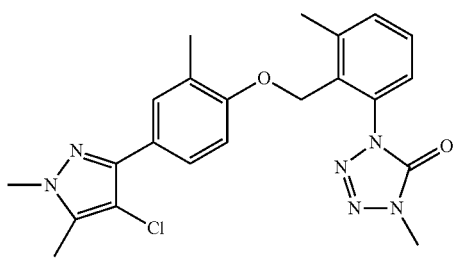

¹H-NMR (CDCl₃) δ: 7.66 (1H, dd, J=8.4, 2.2 Hz), 7.61-7.60 (1H, m), 7.44-7.39 (2H, m), 7.29-7.27 (1H, m), 6.89 (1H, d, J=8.5 Hz), 5.06 (2H, s), 3.82 (3H, s), 3.62 (3H, s), 2.51 (3H, s), 2.28 (3H, s), 2.13 (3H, s).

Preparation Example 191

A similar reaction to Preparation example 190 using 1-{(3-methoxy-2-[2-methyl-4-(1,5-dimethyl-1H-pyrazol-3-yl)-phenoxymethyl]-phenyl}-4-methyl-1,4-dihydrotetrazole-5-one (described in Reference Preparation example 90) instead of 1-{3-methyl-2-[2-methyl-4-(1,5-dimethyl-1H-pyrazol-3-yl)-phenoxymethyl]-phenyl}-4-methyl-1,4-dihydrotetrazole-5-one (Present compound 47) gave 1-{3-methoxy-2-[2-methyl-4-(4-chloro-1,5-dimethyl-1H-pyrazol-3-yl)-phenoxymethyl]-phenyl}-4-methyl-1,4-dihydrotetrazole-5-one (hereinafter, referred to as "Present compound 191").

Present compound 191

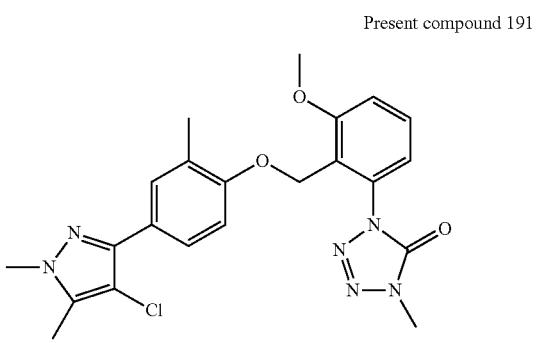

¹H-NMR (CDCl₃) δ: 7.63 (1H, dd, J=8.4, 2.2 Hz), 7.57-7.56 (1H, m), 7.46 (1H, t, J 8.2 Hz), 7.09-7.06 (2H, m), 6.92 (1H, d, J=8.7 Hz), 5.29 (2H, s), 3.93 (3H, s), 3.81 (3H, s), 3.58 (3H, s), 2.28 (3H, s), 2.03 (3H, s).

Preparation Example 192

A mixture of 1-(2-bromomethyl-3-methylphenyl)-4-methyl-1,4-dihydrotetrazole-5-one (described in Preparation example 14) 0.3 g, 2-methyl-4-(1-methyl-5-trifluoromethyl-1H-pyrazol-3-yl)-phenol 0.28 g, potassium carbonate 0.2 g and acetonitrile 10 ml was stirred with heating under reflux for five hours. The reaction mixture was concentrated under reduced pressure and the resulting residue was subjected to a silica gel column chromatography to give 1-{3-methyl-2-[2-methyl-4-(1-methyl-5-trifluoromethyl-1H-pyrazol-3-yl)-phenoxymethyl]-phenyl}-4-methyl-1,4-dihydrotetrazole-5-one (hereinafter, referred to as "Present compound 192") 0.32 g.

Present compound 192

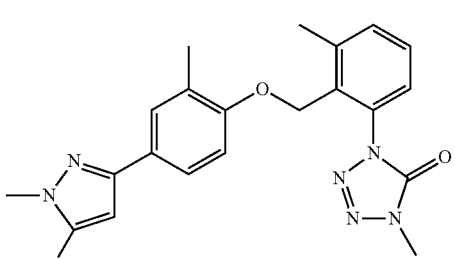

¹H-NMR (CDCl₃) δ: 7.54-7.54 (1H, m), 7.51 (1H, dd, J=8.4, 2.2 Hz), 7.45-7.40 (2H, m), 7.28 (1H, dd, J=7.0, 2.4 Hz), 6.87 (1H, d, J=8.2 Hz), 6.80 (1H, s), 5.07 (2H, s), 4.01 (3H, s), 3.62 (3H, s), 2.51 (3H, s), 2.13 (3H, s).

Preparation Example 193

A similar reaction to Preparation example 192 using 2,5-dimethyl-4-(1-methyl-5-trifluoromethyl-1H-pyrazol-3-yl)-phenol (described in Reference Preparation example 163) instead of 2-methyl-4-(1-methyl-5-trifluoromethyl-1H-pyrazol-3-yl)-phenol (described in Reference Preparation example 158) gave 1-{3-methyl-2-[2,5-dimethyl-4-(1-methyl-5-trifluoromethyl-1H-pyrazol-3-yl)-phenoxymethyl]-phenyl}-4-methyl-, 4-dihydrotetrazole-5-one (hereinafter, referred to as "Present compound 193") 0.32 g.

Present compound 193

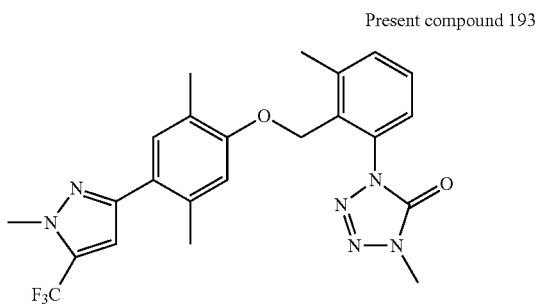 [SMILES: Cc1cc(-c2cc(C(F)(F)F)n(C)n2)c(C)cc1OCc1c(C)cccc1-n1nnn(C)c1=O]

¹H-NMR (CDCl₃) δ: 7.45-7.40 (2H, m), 7.29-7.26 (2H, m), 6.71 (1H, s), 6.68 (1H, d, J=0.5 Hz), 5.06 (2H, s), 4.02 (3H, s), 3.65 (3H, s), 2.51 (3H, s), 2.42 (3H, s), 2.08 (3H, s).

Preparation Example 194

A similar reaction to Preparation example 192 using 1-(2-bromomethyl-3-methoxyphenyl)-4-methyl-1,4-dihydrotetrazole-5-one (described in Reference Preparation example 90) instead of 1-(2-bromomethyl-3-methylphenyl)-4-methyl-1,4-dihydrotetrazole-5-one (described in Reference Preparation example 14) gave 1-{3-methoxy-2-[2-methyl-4-(1-methyl-5-trifluoromethyl-1H-pyrazol-3-yl)-phenoxymethyl]-phenyl}-4-methyl-1,4-dihydrotetrazole-5-one (hereinafter, referred to as "Present compound 194").

Present compound 194

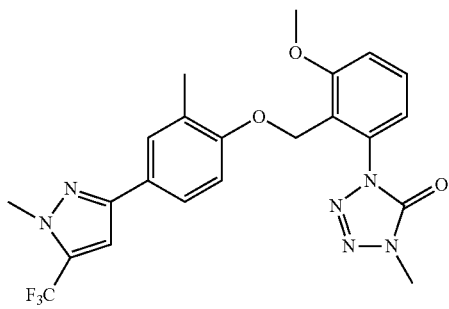

¹H-NMR (CDCl₃) δ: 7.49 (2H, s), 7.47 (1H, s), 7.10-7.06 (2H, m), 6.90 (1H, d, J=8.0 Hz), 6.78 (1H, d, J=0.5 Hz), 5.29 (2H, s), 4.00 (3H, s), 3.93 (3H, s), 3.58 (3H, s), 2.03 (3H, s).

Preparation Example 195

A similar reaction to Preparation example 2 using 2,5-dimethyl-4-(1-methyl-5-trifluoromethyl-1H-pyrazol-3-yl)-phenol (described in Reference Preparation example 163) instead of 2-methyl-4-(3,4,5-trimethyl-pyrazol-1-yl)phenol gave 1-{3-chloro-2-[2,5-dimethyl-4-(1-methyl-5-trifluoromethyl-1H-pyrazol-3-yl)-phenoxymethyl]phenyl}-4-methyl-1,4-dihydrotetrazole-5-one (hereinafter, referred to as "Present compound 195").

Present compound 195

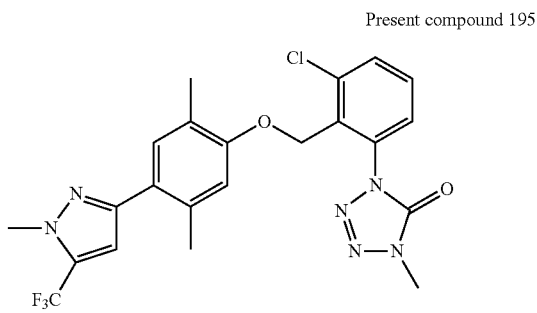 [SMILES: Cc1cc(-c2cc(C(F)(F)F)n(C)n2)c(C)cc1OCc1c(Cl)cccc1-n1nnn(C)c1=O]

¹H-NMR (CDCl₃) δ: 7.62 (1H, dd, J=8.0, 1.4 Hz), 7.47 (1H, t, J=8.0 Hz), 7.40 (1H, dd, J=7.8, 1.4 Hz), 7.26 (1H, s), 6.73 (1H, s), 6.67 (1H, d, J=0.5 Hz), 5.33 (2H, s), 4.02 (3H, s), 3.62 (3H, s), 2.41 (3H, s), 2.01 (3H, s).

Preparation Example 196

A similar reaction to Preparation example 7 using 2,5-dimethyl-4-(1-methyl-5-trifluoromethyl-1H-pyrazol-3-yl)-phenol (described in Reference Preparation example 163) instead of 2-methyl-4-(3,4,5-trimethyl-pyrazol-1-yl)phenol gave 1-{3-methoxy-2-[2,5-dimethyl-4-(1-methyl-5-trifluoromethyl-1H-pyrazol-3-yl)-phenoxymethyl]phenyl}-4-methyl-1,4-dihydrotetrazole-5-one (hereinafter, referred to as "Present compound 196").

Present compound 196

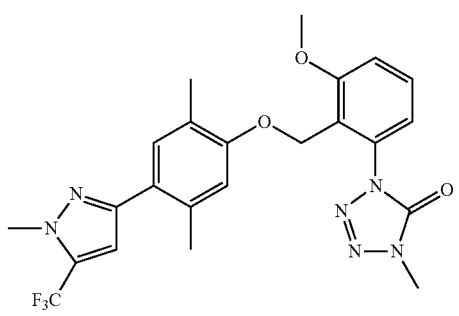

¹H-NMR (CDCl₃) δ: 7.47 (1H, t, J=8.2 Hz), 7.23 (1H, s), 7.10-7.06 (2H, m), 6.76 (1H, s), 6.66 (1H, d, J=0.5 Hz), 5.28 (2H, s), 4.01 (3H, d, J=0.7 Hz), 3.94 (3H, s), 3.60 (3H, s), 2.39 (3H, s), 1.97 (3H, s).

Preparation Example 197

A similar reaction to Preparation example 4 using 2-methyl-4-(3-cyclopropyl-1H-pyrazol-3-yl)-phenol (described in Reference Preparation example 133) instead of 2-methyl-4-(3,4,5-trimethyl-pyrazol-1-yl)phenol gave 1-{3-methyl-2-[2-methyl-4-(3-cyclopropyl-pyrazol-1-yl)-phenoxymethyl]phenyl}-4-methyl-1,4-dihydrotetrazole-5-one (hereinafter, referred to as "Present compound 197").

Present compound 197

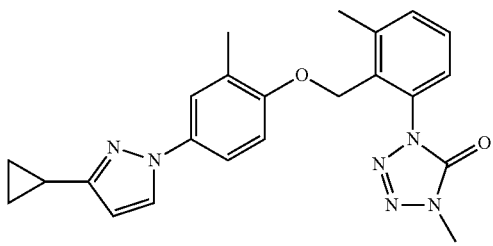

¹H-NMR (CDCl₃) δ: 7.67 (1H, d, J=2.3 Hz), 7.45-7.39 (3H, m), 7.33 (1H, dd, J=8.8, 2.6 Hz), 7.28 (1H, dd, J=7.1, 2.3 Hz), 6.84 (1H, d, J=8.4 Hz), 6.05 (1H, d, J=2.3 Hz), 5.05 (2H, s), 3.63 (3H, s), 2.51 (3H, s), 2.13 (3H, s), 2.06-1.99 (1H, m), 0.98-0.93 (2H, m), 0.80-0.76 (2H, m).

Preparation Example 198

A similar reaction to Preparation example 190 using 1-{(3-methyl-2-[2,5-dimethyl-4-(1-methyl-5-trifluoromethyl-1H-pyrazol-3-yl)-phenoxymethyl]-phenyl}-4-methyl-1,4-dihydrotetrazole-5-one (described in Reference Preparation example 193) instead of 1-{3-methyl-2-[2-methyl-4-(1,5-dimethyl-1H-pyrazol-3-yl)-phenoxymethyl]-phenyl}-4-methyl-1,4-dihydrotetrazole-5-one (Present compound 47) gave 1-{3-methyl-2-[2,5-dimethyl-4-(4-chloro-1-methyl-5-trifluoromethyl-1H-pyrazol-3-yl)-phenoxymethyl]-phenyl}-4-methyl-1,4-dihydrotetrazole-5-one (hereinafter, referred to as "Present compound 198").

Present compound 198

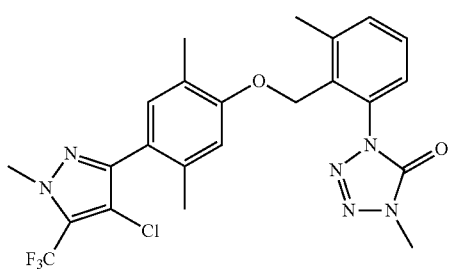

¹H-NMR (CDCl₃) δ: 7.41 (2H, d, J=5.3 Hz), 7.20 (1H, t, J=4.6 Hz), 7.11 (1H, s), 6.66 (1H, s), 5.12 (2H, s), 4.03 (3H, s), 3.67 (3H, s), 2.64 (3H, s), 2.38 (3H, s), 1.96 (3H, s).

Preparation Example 199

A similar reaction to Preparation example 7 using cyclopropyl-(4-hydroxy-3-methyl-phenyl)-methanone (described in Reference Preparation example 150) instead of 2-methyl-4-(3,4,5-trimethyl-pyrazol-1-yl)-phenol gave 1-[2-(4-cyclopropanecarbonyl-2-methyl-phenoxymethyl)-3-methoxy-phenyl]-4-methyl-1,4-dihydrotetrazole-5-one (hereinafter, referred to as "Present compound 199").

Present compound 199

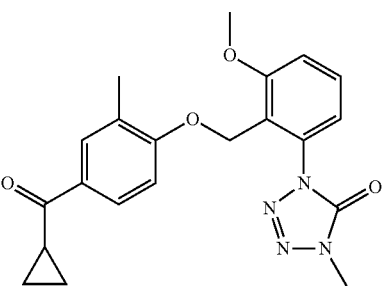

¹H-NMR (CDCl₃) δ: 7.84 (1H, dd, J=8.70, 2.18 Hz), 7.78-7.76 (1H, m), 7.48 (1H, t, J=8.13 Hz), 7.12-7.06 (2H, m), 6.93 (1H, d, J=8.70 Hz), 5.35 (2H, s), 3.94 (3H, s), 3.59 (3H, s), 2.65-2.58 (1H, m), 2.03 (3H, s), 1.20-1.16 (2H, m), 1.00-0.94 (2H, m).

Preparation Example 200

A similar reaction to Preparation example 5 using 2-methyl-4-(3-cyclopropyl-pyrazol-1-yl)-phenol (described in Reference Preparation example 133) instead of 2-methyl-4-(3,4,5-trimethyl-pyrazol-1-yl)-phenol gave 1-{3-ethyl-2-{2-methyl-4-(3-cyclopropyl-pyrazol-1-yl)-phenoxymethyl]-phenyl}-4-methyl-1,4-dihydrotetrazole-5-one (hereinafter, referred to as "Present compound 200").

Present compound 200

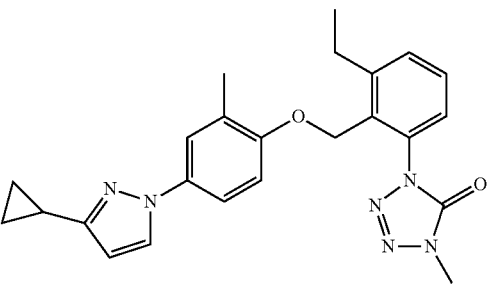

¹H-NMR (CDCl₃) δ: 7.67 (1H, d, J=2.5 Hz), 7.50-7.45 (2H, m), 7.44-7.41 (1H, m), 7.34 (1H, dd, J=8.8, 2.6 Hz), 7.29 (1H, dd, J=7.2, 1.9 Hz), 6.86 (1H, d, J=8.4 Hz), 6.06 (1H, d, J=2.3 Hz), 5.07 (2H, s), 3.60 (3H, s), 2.85 (2H, q, J=7.6 Hz), 2.11 (3H, s), 2.05-2.01 (1H, m), 1.28 (3H, t, J=7.8 Hz), 0.98-0.94 (2H, m), 0.80-0.76 (2H, m).

Preparation Example 201

A similar reaction to Preparation example 192 using 1-(2-bromomethyl-3-bromophenyl)-4-methyl-1,4-dihydrotetrazole-5-one (described in Reference Preparation example 5) instead of 1-(2-bromomethyl-3-methylphenyl)-4-methyl-,4-dihydrotetrazole-5-one (described in Reference Preparation example 14) gave 1-{3-bromo-2-[2-methyl-4-(1-methyl-5-trifluoromethyl-1H-pyrazol-3-yl)-phenoxymethyl]-phenyl}-4-methyl-1,4-dihydrotetrazole-5-one (hereinafter, referred to as "Present compound 201") 0.32 g.

Present compound 201

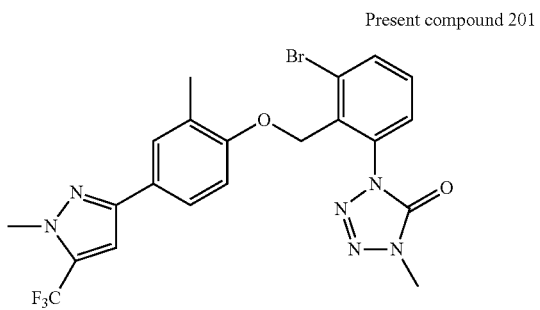 [SMILES: Cc1cc(-c2cc(C(F)(F)F)n(C)n2)ccc1OCc1c(Br)cccc1-n1nnn(C)c1=O]

¹H-NMR (CDCl₃) δ: 7.81 (1H, dd, J=7.8, 1.4 Hz), 7.52-7.49 (2H, m), 7.46-7.38 (2H, m), 6.87 (1H, d, J=8.2 Hz), 6.80 (1H, s), 5.33 (2H, s), 4.01 (3H, s), 3.59 (3H, s), 2.08 (3H, s).

Preparation Example 202

A similar reaction to Preparation example 192 using 1-(2-bromomethyl-3-ethylphenyl)-4-methyl-1,4-dihydrotetrazole-5-one (described in Reference Preparation example 17) instead of 1-(2-bromomethyl-3-methylphenyl)-4-methyl-1,4-dihydrotetrazole-5-one (described in Reference Preparation example 14) gave 1-{3-ethyl-2-[2-methyl-4-(1-methyl-5-trifluoromethyl-1H-pyrazol-3-yl)-phenoxymethyl]-phenyl}-4-methyl-1,4-dihydrotetrazole-5-one (hereinafter, referred to as "Present compound 202").

Present compound 202

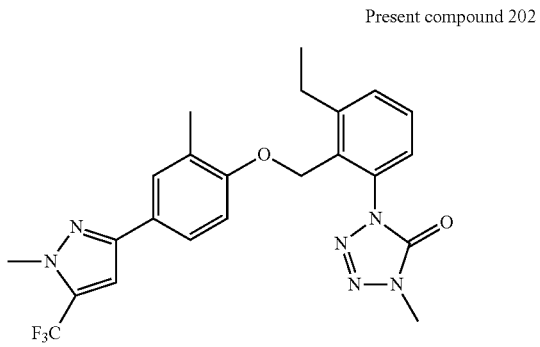 [SMILES: CCc1cccc(-n2nnn(C)c2=O)c1COc1ccc(-c2cc(C(F)(F)F)n(C)n2)cc1C]

¹H-NMR (CDCl₃) δ: 7.53-7.50 (2H, m), 7.48-7.43 (2H, m), 7.28 (1H, dd, J=7.1, 2.1 Hz), 6.88 (1H, d, J=8.2 Hz), 6.80 (1H, s), 5.09 (2H, s), 4.01 (3H, s), 3.58 (3H, s), 2.85 (2H, q, J=7.6 Hz), 2.11 (3H, s), 1.28 (3H, t, J=7.6 Hz).

Preparation Example 203

A similar reaction to Preparation example 4 using 2-methyl-4-(1-methyl-3-trifluoromethyl-1H-pyrazole-5-yl)-phenol (described in Reference Preparation example 164) instead of 2-methyl-4-(3,4,5-trimethyl-pyrazol-1-yl)-phenol gave 1-{3-methyl-2-[2-methyl-4-(1-methyl-3-trifluoromethyl-1H-pyrazole-5-yl)-phenoxymethyl]-phenyl}-4-methyl-,4-dihydrotetrazole-5-one (hereinafter, referred to as "Present compound 203").

Present compound 203

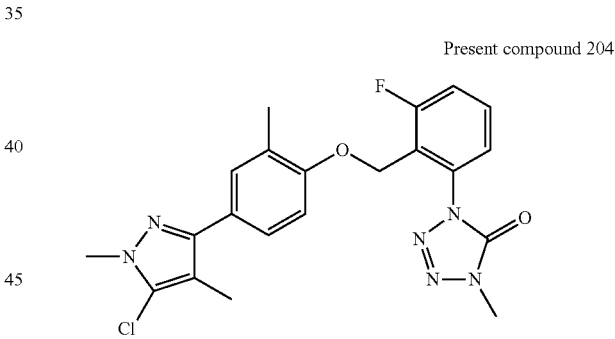

¹H-NMR (CDCl₃) δ: 7.47-7.42 (2H, m), 7.29 (1H, dd, J=7.1, 2.3 Hz), 7.18 (1H, dd, J=8.4, 2.2 Hz), 7.15-7.15 (1H, m), 6.92 (1H, d, J=8.2 Hz), 6.47 (1H, s), 5.09 (2H, s), 3.90 (3H, s), 3.65 (3H, s), 2.53 (3H, s), 2.14 (3H, s).

Preparation Example 204

A similar reaction to Preparation example 1 using 4-(5-chloro-1,4-dimethyl-1H-pyrazol-3-yl)-2-methyl-phenol (described in Reference Preparation example 140) instead of 2-methyl-4-(3,4,5-trimethyl-pyrazol-1-yl)-phenol gave 1-{3-fluoro-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 204").

Present compound 204

¹H-NMR (CDCl₃) δ: 7.54-7.48 (1H, m), 7.38-7.27 (4H, m), 6.90 (1H, d, J=8.5 Hz), 5.30 (2H, d, J=0.7 Hz), 3.85 (3H, s), 3.60 (3H, s), 2.14 (3H, s), 2.03 (3H, s).

Preparation Example 205

A similar reaction to Preparation example 2 using 4-(5-chloro-1,4-dimethyl-1H-pyrazol-3-yl)-2-methyl-phenol (described in Reference Preparation example 140) instead of 2-methyl-4-(3,4,5-trimethyl-pyrazol-1-yl)-phenol gave 1-{3-chloro-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 205").

Present compound 205

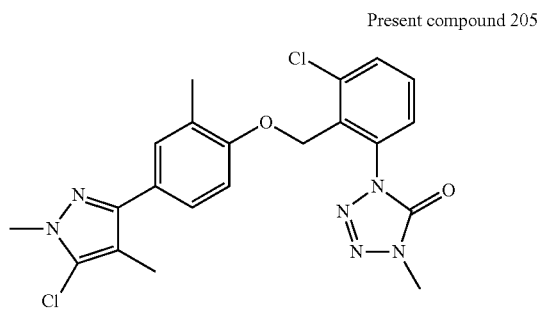 [SMILES: Cc1cc(-c2nn(C)c(Cl)c2C)ccc1OCc1c(F)cccc1-n1nnn(C)c1=O]

¹H-NMR (CDCl₃) δ: 7.62 (1H, dd, J=8.0, 1.4 Hz), 7.47 (1H, t, J=8.0 Hz), 7.41-7.39 (2H, m), 7.36 (1H, dd, J=8.4, 2.2 Hz), 6.89 (1H, d, J=8.5 Hz), 5.35 (2H, s), 3.85 (3H, s), 3.60 (3H, s), 2.14 (3H, s), 2.06 (3H, s).

Preparation Example 206

A similar reaction to Preparation example 5 using 4-(5-chloro-1,4-dimethyl-1H-pyrazol-3-yl)-2-methyl-phenol (described in Reference Preparation example 140) instead of 2-methyl-4-(3,4,5-trimethyl-pyrazol-1-yl)-phenol gave 1-{3-ethyl-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 206").

Present compound 206

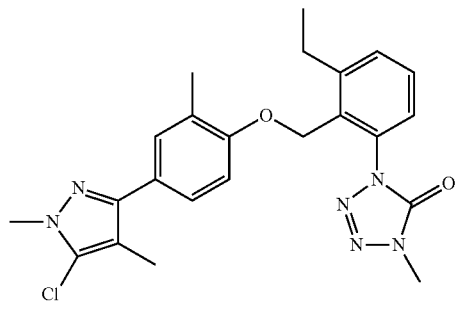

¹H-NMR (CDCl₃) δ: 7.50-7.44 (2H, m), 7.40 (1H, d, J=1.6 Hz), 7.39-7.36 (1H, m), 7.28 (1H, dd, J=7.1, 2.1 Hz), 6.89 (1H, d, J=8.2 Hz), 5.08 (2H, s), 3.85 (3H, s), 3.59 (3H, s), 2.85 (2H, q, J=7.6 Hz), 2.15 (3H, s), 2.11 (3H, s), 1.28 (3H, t, J=7.7 Hz).

Preparation Example 207

A similar reaction to Preparation example 4 using 2-methyl-4-(5-chloro-4-formyl-1-methyl-1H-pyrazol-3-yl)-phenol (described in Reference Preparation example 172) instead of 2-methyl-4-(3,4,5-trimethyl-pyrazol-1-yl)-phenol gave 1-{3-methyl-2-[2-methyl-4-(4-formyl-5-chloro-1-methyl-1H-pyrazol-3-yl)-phenoxymethyl]-phenyl}-4-methyl-1,4-dihydrotetrazole-5-one (hereinafter, referred to as "Present compound 207").

Present compound 207

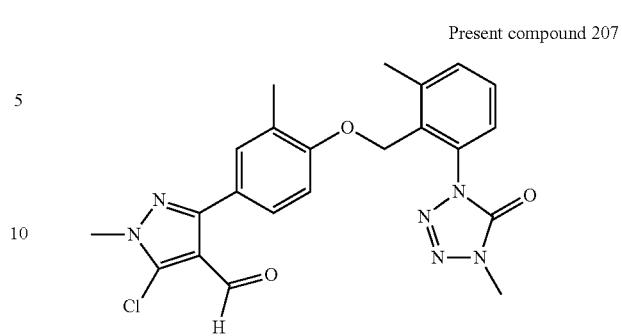

¹H-NMR (CDCl₃) δ: 9.92 (1H, d, J=0.5 Hz), 7.53 (1H, dd, J=8.3, 2.3 Hz), 7.49 (1H, d, J=1.9 Hz), 7.45-7.40 (2H, m), 7.28 (1H, dd, J=6.9, 2.3 Hz), 6.92 (1H, d, J=8.5 Hz), 5.08 (2H, s), 3.92 (3H, s), 3.64 (3H, s), 2.51 (3H, s), 2.14 (3H, s).

Preparation Example 208

A similar reaction to Preparation example 3 using 4-(5-chloro-1,4-dimethyl-1H-pyrazol-3-yl)-2-methyl-phenol (described in Reference Preparation example 140) instead of 2-methyl-4-(3,4,5-trimethyl-pyrazol-1-yl)-phenol gave 1-{3-bromo-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to a "Present compound 208").

Present compound 208

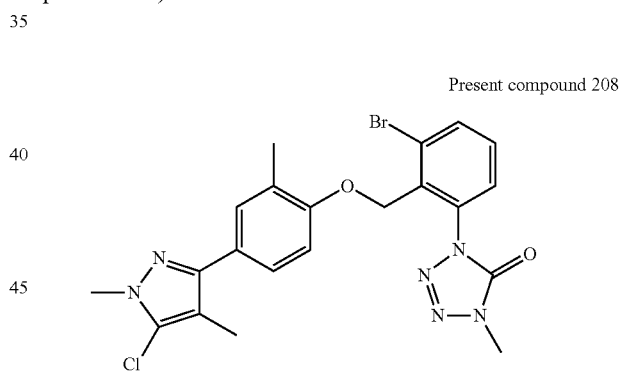

¹H-NMR (CDCl₃) δ: 7.80 (1H, dd, J=7.9, 1.5 Hz), 7.45-7.35 (4H, m), 6.88 (1H, d, J=8.5 Hz), 5.33 (2H, s), 3.85 (3H, s), 3.60 (3H, s), 2.14 (3H, s), 2.07 (3H, s).

Preparation Example 209

A similar reaction to Preparation example 6 using 4-(5-chloro-1,4-dimethyl-1H-pyrazol-3-yl)-2-methyl-phenol (described in Reference Preparation example 140) instead of 2-methyl-4-(3,4,5-trimethyl-pyrazol-1-yl)-phenol gave 1-{2-[2-methyl-4-(5-chloro-1,4-dimethyl-1H-pyrazol-3-yl)-phenoxymethyl]-3-trifluoromethyl-phenyl}-4-methyl-, 4-dihydrotetrazole-5-one (hereinafter, referred to as "Present compound 209").

Present compound 209

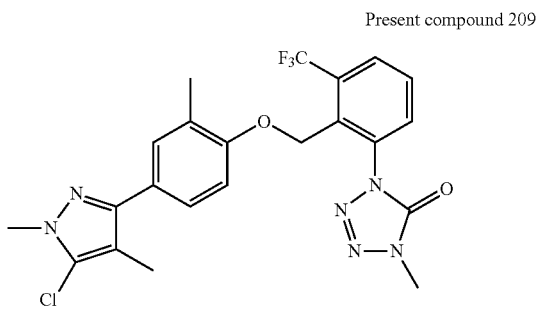 [SMILES: Cc1cc(-c2nn(C)c(Cl)c2C)ccc1OCc1c(-n2nnn(C)c2=O)cccc1C(F)(F)F]

¹H-NMR (CDCl₃) δ: 7.92 (1H, dd, J=7.0, 2.2 Hz), 7.71-7.66 (2H, m), 7.40-7.35 (2H, m), 6.88-6.86 (1H, m), 5.33 (2H, s), 3.85 (3H, s), 3.53 (3H, s), 2.15 (3H, s), 2.05 (3H, s).

Preparation Example 210

A similar reaction to Preparation example 8 using 4-(5-chloro-1,4-dimethyl-1H-pyrazol-3-yl)-2-methyl-phenol (described in Reference Preparation example 140) instead of 2-methyl-4-(3,4,5-trimethyl-pyrazol-1-yl)-phenol gave 1-{3-ethoxy-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to a "Present compound 210").

Present compound 210

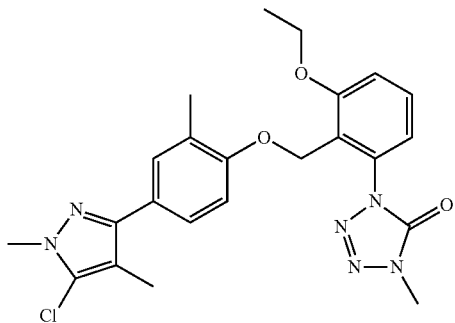

¹H-NMR (CDCl₃) δ: 7.45 (1H, t, J=8.2 Hz), 7.37-7.37 (1H, m), 7.36-7.33 (1H, m), 7.08 (1H, d, J=2.7 Hz), 7.06 (1H, d, J=2.1 Hz), 6.95 (1H, d, J=8.2 Hz), 5.32 (2H, s), 4.15 (2H, q, J=7.0 Hz), 3.86 (3H, s), 3.60 (3H, s), 2.15 (3H, s), 2.04 (3H, s), 1.46 (3H, t, J=7.0 Hz).

Preparation Example 211

A similar reaction to Preparation example 4 using 4-(1,4-dimethyl-5-methoxy-1H-pyrazol-3-yl)-2-methyl-phenol (described in Reference Preparation example 175) instead of 2-methyl-4-(3,4,5-trimethyl-pyrazol-1-yl)-phenol gave 1-{3-methyl-2-[2-methyl-4-(1,4-dimethyl-5-methoxy-1H-pyrazol-3-yl)-phenoxymethyl]-phenyl}-4-methyl-1,4-dihydrotetrazole-5-one (hereinafter, referred to as "Present compound 211").

Present compound 211

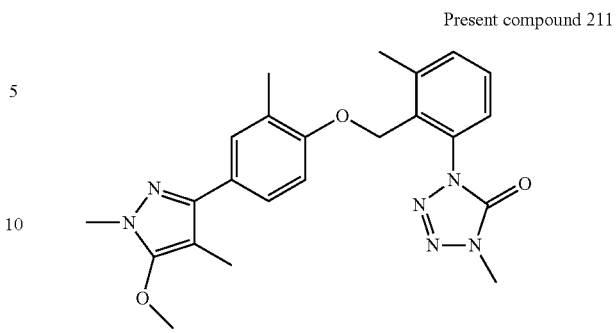

¹H-NMR (CDCl₃) δ: 7.44-7.39 (3H, m), 7.36 (1H, dd, J=8.5, 2.2 Hz), 7.29-7.26 (1H, m), 6.87 (1H, d, J=8.5 Hz), 5.06 (2H, s), 3.94 (3H, s), 3.71 (3H, s), 3.62 (3H, s), 2.51 (3H, s), 2.13 (3H, s), 2.12 (3H, s).

Preparation Example 212

A similar reaction to Preparation example 2 using 4-(1,4-dimethyl-5-methoxy-1H-pyrazol-3-yl)-2-methyl-phenol (described in Reference Preparation example 175) instead of 2-methyl-4-(3,4,5-trimethyl-pyrazol-1-yl)-phenol gave 1-{3-chloro-2-[2-methyl-4-(1,4-dimethyl-5-methoxy-1H-pyrazol-3-yl)-phenoxymethyl]-phenyl}-4-methyl-1,4-dihydrotetrazole-5-one (hereinafter, referred to as "Present compound 212").

Present compound 212

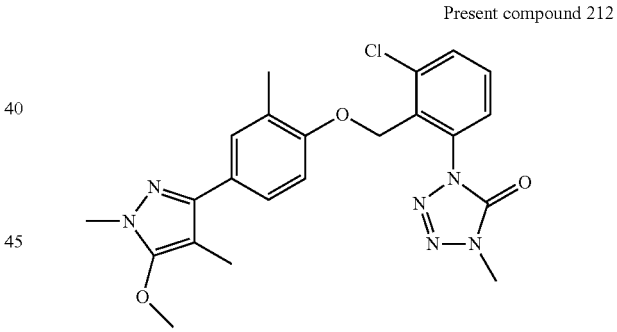

¹H-NMR (CDCl₃) δ: 7.61 (1H, dd, J=8.0, 1.2 Hz), 7.46 (1H, t, J=8.0 Hz), 7.41-7.39 (2H, m), 7.34 (1H, dd, J=8.5, 1.9 Hz), 6.87 (1H, d, J=8.5 Hz), 5.34 (2H, s), 3.93 (3H, s), 3.70 (3H, s), 3.59 (3H, s), 2.12 (3H, s), 2.06 (3H, s).

Preparation Example 213

A similar reaction to Preparation example 3 using 4-(1,4-dimethyl-5-methoxy-1H-pyrazol-3-yl)-2-methyl-phenol (described in Reference Preparation example 175) instead of 2-methyl-4-(3,4,5-trimethyl-pyrazol-1-yl)-phenol gave 1-{3-bromo-2-[2-methyl-4-(1,4-dimethyl-5-methoxy-1H-pyrazol-3-yl)-phenoxymethyl]-phenyl}-4-methyl-1,4-dihydrotetrazole-5-one (hereinafter, referred to as "Present compound 213").

Present compound 213

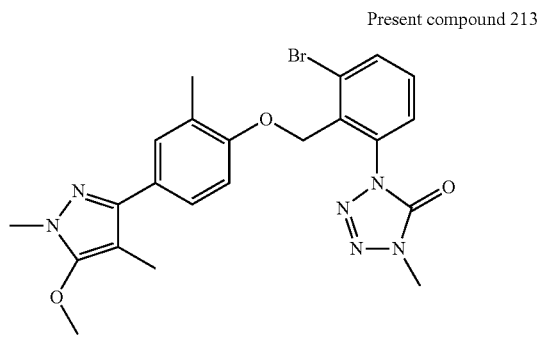 [SMILES: COc1c(C)c(-c2ccc(OCc3c(Br)cccc3-n3nnn(C)c3=O)c(C)c2)nn1C]

¹H-NMR (CDCl₃) δ: 7.80 (1H, dd, J=8.0, 1.0 Hz), 7.45-7.33 (4H, m), 6.87 (1H, d, J=8.2 Hz), 5.33 (2H, s), 3.93 (3H, d, J=0.5 Hz), 3.70 (3H, s), 3.59 (3H, s), 2.13 (3H, s), 2.07 (3H, s).

Preparation Example 214

A similar reaction to Preparation example 7 using 4-(1,4-dimethyl-5-methoxy-1H-pyrazol-3-yl)-2-methyl-phenol (described in Reference Preparation example 175) instead of 2-methyl-4-(3,4,5-trimethyl-pyrazol-1-yl)-phenol gave 1-{3-methoxy-2-[2-methyl-4-(1,4-dimethyl-5-methoxy-1H-pyrazol-3-yl)-phenoxymethyl]-phenyl}-4-methyl-1,4-dihydrotetrazole-5-one (hereinafter, referred to a "Present compound 214").

Present compound 214

¹H-NMR (CDCl₃) δ: 7.45 (1H, s), 7.34 (1H, s), 7.31 (1H, dd, J=8.4, 2.2 Hz), 7.07 (1H, d, J=4.4 Hz), 7.05 (1H, d, J=3.9 Hz), 6.89 (1H, d, J=8.2 Hz), 5.26 (2H, s), 3.91 (3H, s), 3.90 (3H, s), 3.68 (3H, s), 3.56 (3H, s), 2.10 (3H, s), 2.01 (3H, s).

Preparation Example 215

A similar reaction to Preparation example 5 using 4-(1,4-dimethyl-5-methoxy-1H-pyrazol-3-yl)-2-methyl-phenol (described in Reference Preparation example 175) instead of 2-methyl-4-(3,4,5-trimethyl-pyrazol-1-yl)-phenol gave 1-{3-ethyl-2-[2-methyl-4-(1,4-dimethyl-5-methoxy-1H-pyrazol-3-yl)-phenoxymethyl]-phenyl}-4-methyl-1,4-dihydrotetrazole-5-one (hereinafter, referred to as "Present compound 215").

Present compound 215

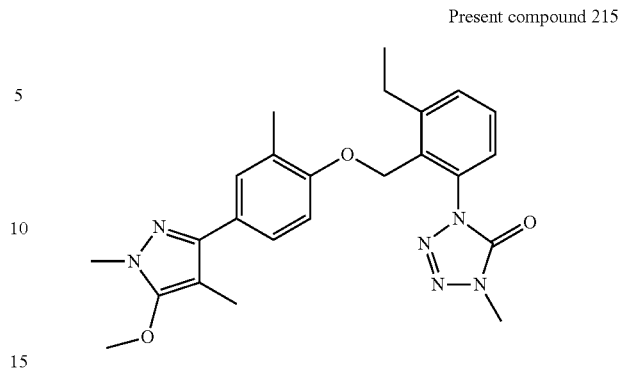

¹H-NMR (CDCl₃) δ: 7.49-7.43 (2H, m), 7.41-7.40 (1H, m), 7.36 (1H, d, J=8.5 Hz), 7.28 (1H, dd, J=7.0, 2.2 Hz), 6.88 (1H, d, J=8.5 Hz), 5.08 (2H, s), 3.94 (3H, s), 3.71 (3H, s), 3.59 (3H, s), 2.85 (2H, q, J=7.6 Hz), 2.13 (3H, s), 2.11 (3H, s), 1.27 (3H, q, J=7.6 Hz).

Preparation Example 216

A similar reaction to Preparation example 1 using 4-(1,4-dimethyl-5-methoxy-1H-pyrazol-3-yl)-2-methyl-phenol (described in Reference Preparation example 175) instead of 2-methyl-4-(3,4,5-trimethyl-pyrazol-1-yl)-phenol gave 1-{3-fluoro-2-[2-methyl-4-(1,4-dimethyl-5-methoxy-1H-pyrazol-3-yl)-phenoxymethyl]-phenyl}-4-methyl-1,4-dihydrotetrazole-5-one (hereinafter, referred to as "Present compound 216").

Present compound 216

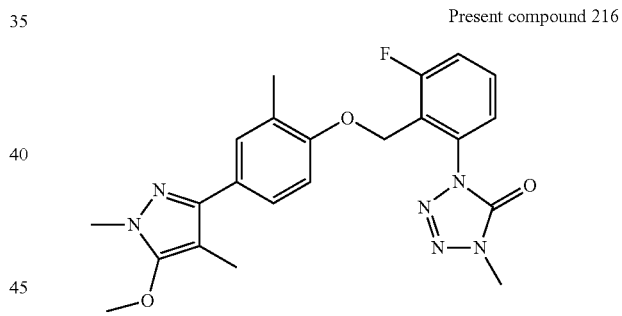

¹H-NMR (CDCl₃) δ: 7.52 (1H, td, J=8.2, 5.9 Hz), 7.39 (1H, d, J=1.4 Hz), 7.37-7.28 (3H, m), 6.90 (1H, d, J=8.5 Hz), 5.31 (2H, d, J=0.9 Hz), 3.94 (3H, s), 3.71 (3H, s), 3.61 (3H, s), 2.14 (3H, s), 2.03 (3H, s).

Preparation Example 217

At room temperature, to a mixture of 1-{3-methyl-2-[2-methyl-4-(4-formyl-5-chloro-1-methyl-1H-pyrazol-3-yl)-phenoxymethyl]-phenyl}-4-methyl-1,4-dihydrotetrazole-5-one (Present compound 207) 0.9 g and tetrahydrofuran 10 ml was added a solution of 20% sodium ethoxide in ethanol 0.81 g and the resulting mixture was stirred for three hours. To the reaction mixture was added water 10 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{3-methyl-2-[2-methyl-4-(4-formyl-5-ethoxy-1-methyl-1H-pyrazol-3- yl)-phenoxymethyl]-phenyl}-4-methyl-1,4-dihydrotetrazole-5-one (hereinafter, referred to as "Present compound 217") 0.7 g.

Present compound 217

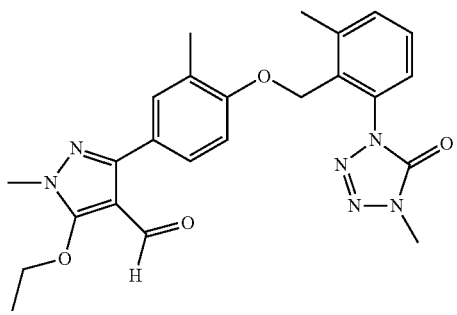

$^1$H-NMR (CDCl$_3$) δ: 9.73 (1H, s), 7.45-7.36 (4H, m), 7.28 (1H, dd, J=6.9, 2.5 Hz), 6.91 (1H, d, J=8.9 Hz), 5.08 (2H, s), 4.63 (2H, q, J=6.9 Hz), 3.72 (3H, s), 3.64 (3H, s), 2.52 (3H, s), 2.13 (3H, s), 1.44 (3H, t, J=7.0 Hz).

Preparation Example 218

At room temperature, to a mixture of 1-{3-methyl-2-[2-methyl-4-(4-formyl-5-ethoxy-1-methyl-1H-pyrazol-3-yl)-phenoxymethyl]-phenyl}-4-methyl-1,4-dihydrotetrazole-5-one (Present compound 217) 0.7 g and trifluoroacetic acid 20 ml was added to triethylsilane 0.5 g and the resulting mixture was stirred for fifteen hours. The solvent was distilled off under reduced pressure. To the residue was added water 10 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{3-methyl-2-[2-methyl-4-(1,4-dimethyl-5-ethoxy-1H-pyrazol-3-yl)-phenoxymethyl]-phenyl}-4-methyl-1,4-dihydrotetrazole-5-one (hereinafter, referred to as "Present compound 218") 0.6 g.

Present compound 218

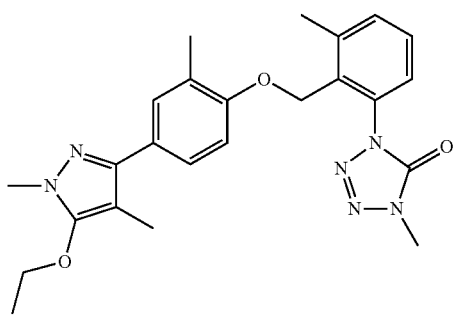

$^1$H-NMR (CDCl$_3$) δ: 7.44-7.39 (3H, m), 7.37 (1H, dd, J=8.3, 2.3 Hz), 7.29-7.27 (1H, m), 6.87 (1H, d, J=8.5 Hz), 5.06 (2H, s), 4.17-4.12 (2H, m), 3.71 (3H, s), 3.62 (3H, s), 2.51 (3H, s), 2.12 (3H, s), 2.11 (3H, s), 1.41 (3H, t, J=7.0 Hz).

Preparation Example 219

A similar reaction to Preparation example 4 using 4-(4-butyl-3,5-dimethyl-pyrazol-1-yl)-2-methyl-phenol (described in Reference Preparation example 204) instead of 2-methyl-4-(3,4,5-trimethyl-pyrazol-1-yl)-phenol gave 1-{3-methyl-2-[2-methyl-4-(4-butyl-3,5-dimethyl-pyrazol-1-yl)-phenoxymethyl]-phenyl}-4-methyl-1,4-dihydrotetrazole-5-one (hereinafter, referred to as "Present compound 219").

Present compound 219

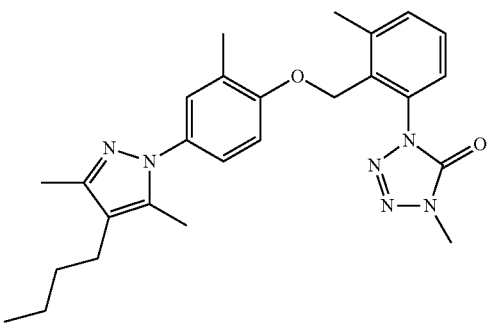

$^1$H-NMR (CDCl$_3$) δ: 7.45-7.40 (2H, m), 7.28 (1H, dd, J=6.9, 2.1 Hz), 7.17 (1H, dd, J=2.6, 0.8 Hz), 7.13-7.10 (1H, m), 6.85 (1H, d, J=8.7 Hz), 5.05 (2H, s), 3.64 (3H, s), 2.51 (3H, s), 2.37 (2H, t, J=7.6 Hz), 2.24 (3H, s), 2.16 (3H, s), 2.11 (3H, s), 1.48-1.42 (2H, m), 1.38-1.33 (2H, m), 0.94 (3H, t, J=7.2 Hz).

Preparation Example 220

A similar reaction to Preparation example 4 using 4-(5-difluoromethyl-1-methyl-1H-pyrazol-3-yl)-2-methyl-phenol (described in Reference Preparation example 201) instead of 2-methyl-4-(3,4,5-trimethyl-pyrazol-1-yl)-phenol gave 1-{3-methyl-2-[2-methyl-4-(5-difluoromethyl-1-methyl-1H-pyrazol-3-yl)-phenoxymethyl]-phenyl}-4-methyl-, 4-dihydrotetrazole-5-one (hereinafter, referred to as "Present compound 220").

Present compound 220

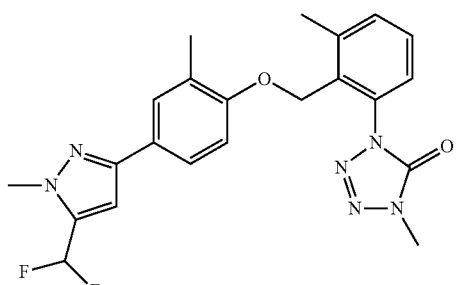

$^1$H-NMR (CDCl$_3$) δ: 7.54-7.54 (1H, m), 7.51 (1H, dd, J=8.3, 2.1 Hz), 7.45-7.39 (2H, m), 7.29-7.27 (1H, m), 6.86 (1H, d, J=8.5 Hz), 6.74 (1H, t, J=53.8 Hz), 6.67-6.66 (1H, m), 5.06 (2H, s), 4.00 (3H, s), 3.62 (3H, s), 2.51 (3H, s), 2.13 (3H, s).

Preparation Example 221

At room temperature, to a mixture of 1-{3-methyl-2-[2-methyl-4-(5-chloro-1,4-dimethyl-1H-pyrazol-3-yl)-phenoxymethyl]-phenyl}-4-methyl-1,4-dihydrotetrazole-5-one (Present compound 169) 0.36 g and toluene 10 ml was added to 2,4-bis(4-methoxyphenyl)-1,3,2,4-dithiaphosphetane-2,4-disulfide 0.5 g and the resulting mixture was stirred with heating under reflux for seven hours. Thereto was added water 5 ml at room temperature, and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{3-methyl-2-[2-methyl-4-(5-chloro-1,4-dimethyl-1H-pyrazol-3-yl)-phenoxymethyl]-phenyl}-4-methyl-1,4-dihydrotetrazole-5-thione (hereinafter, referred to as "Present compound 221").

Present compound 221

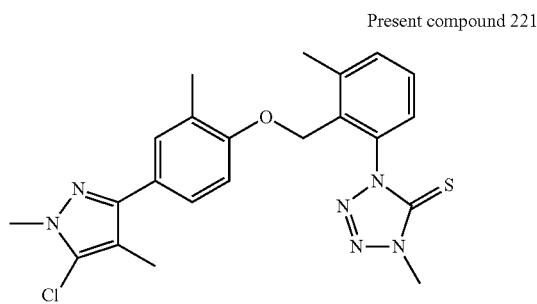 [SMILES: Cc1cc(-c2nn(C)c(Cl)c2C)ccc1OCc1c(C)cccc1-n1nnn(C)c1=S]

$^1$H-NMR (CDCl$_3$) δ: 7.49-7.47 (2H, m), 7.40-7.40 (1H, m), 7.35 (1H, dd, J=8.5, 2.2 Hz), 7.29-7.27 (1H, m), 6.84 (1H, d, J=8.2 Hz), 4.97 (2H, s), 3.91 (3H, d, J=0.5 Hz), 3.85 (3H, s), 2.53 (3H, s), 2.14 (3H, s), 2.13 (3H, s).

Preparation Example 222

A similar reaction to Preparation example 4 using 4-(7-methyl-2,3-dihydro-pyrazolo[5,1-b]oxazole-6-yl)-2-methyl-phenol instead of 2-methyl-4-(3,4,5-trimethyl-pyrazol-1-yl)-phenol gave 1-4-{3-methyl-2-[2-methyl-4-(7-methyl-2,3-dihydro-pyrazolo[5,1-b]oxazole-6-yl)-phenoxymethyl]-phenyl}-4-methyl-1,4-dihydrotetrazole-5-one (hereinafter, referred to a "Present compound 222").

Present compound 222

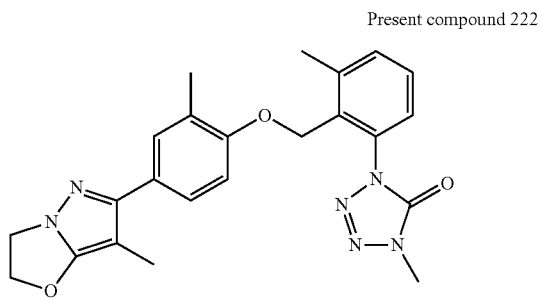 [SMILES: Cc1cc(-c2nn3c(c2C)OCC3)ccc1OCc1c(C)cccc1-n1nnn(C)c1=O]

$^1$H-NMR (CDCl$_3$) δ: 7.44-7.38 (4H, m), 7.29-7.24 (1H, m), 6.88 (1H, d, J=8.5 Hz), 5.06 (2H, s), 5.01 (2H, t, J=7.8 Hz), 4.30 (2H, t, J=7.8 Hz), 3.62 (3H, s), 2.51 (3H, s), 2.12 (3H, s), 2.06 (3H, s).

Preparation Example 223

A similar reaction to Preparation example 190 using 1-{3-ethyl-2-[2-methyl-4-(1,5-dimethyl-1H-pyrazol-3-yl)-phenoxymethyl]-phenyl}-4-methyl-1,4-dihydrotetrazole-5-one (described in preparation example 59) instead of 1-{3-methyl-2-[2-methyl-4-(1,5-dimethyl-1H-pyrazol-3-yl)-phenoxymethyl]-phenyl}-4-methyl-1,4-dihydrotetrazole-5-one (Present compound 47) gave 1-{3-ethyl-2-[2-methyl-4-(4-chloro-1,5-dimethyl-1H-pyrazol-3-yl)-phenoxymethyl]-phenyl}-4-methyl-1,4-dihydrotetrazole-5-one (hereinafter, referred to as "Present compound 223").

Present compound 223

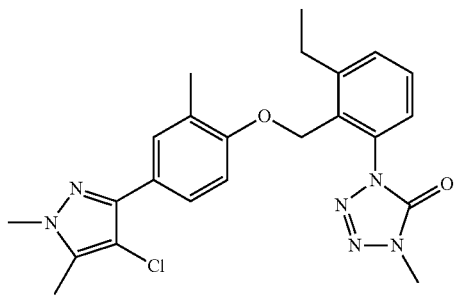

$^1$H-NMR (CDCl$_3$) δ: 7.66 (1H, dd, J=8.2, 2.2 Hz), 7.61 (1H, s), 7.49-7.43 (2H, m), 7.28 (1H, dd, J=7.1, 2.1 Hz), 6.90 (1H, d, J=8.5 Hz), 5.08 (2H, s), 3.82 (3H, s), 3.58 (3H, s), 2.85 (2H, q, J=7.6 Hz), 2.28 (3H, s), 2.11 (3H, s), 1.28 (3H, t, J=7.6 Hz).

Preparation Example 224

A similar reaction to Preparation example 4 using 2-methyl-4-(3-methyl-6,7-dihydro-5H-pyrazolo[5,1-b][1,3]oxazine-2-yl)-phenol (described in preparation example 197) instead of 2-methyl-4-(3,4,5-trimethyl-pyrazol-1-yl)-phenol gave 1-methyl-4-{3-methyl-2-[2-methyl-4-(3-methyl-6,7-dihydro-5H-pyrazolo[5,1-b][1,3]oxazine-2-yl)-phenoxymethyl]-phenyl}-1,4-dihydrotetrazole-5-one (hereinafter, referred to as "Present compound 224").

Present compound 224

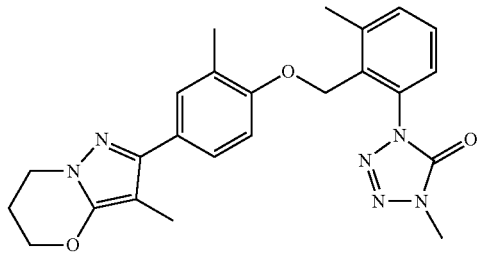

$^1$H-NMR (CDCl$_3$) δ: 7.44-7.38 (4H, m), 7.29-7.26 (1H, m), 6.87 (1H, d, J=8.5 Hz), 5.06 (2H, s), 4.30 (2H, t, J=5.1 Hz), 4.19 (2H, t, J=6.3 Hz), 3.62 (3H, s), 2.51 (3H, s), 2.29-2.24 (2H, m), 2.12 (3H, s), 2.03 (3H, s).

Preparation Example 225

A similar reaction to Preparation example 4 using 2-chloro-4-(1,4-dimethyl-5-methoxy-1H-pyrazol-3-yl)-phenol (described in reference preparation example 188) instead of 2-methyl-4-(3,4,5-trimethyl-pyrazol-1-yl)-phenol gave 1-{3-methyl-2-[2-chloro-4-(1,4-dimethyl-5-methoxy-1H-pyrazol-3-yl)-phenoxymethyl]-phenyl}-4-methyl-1,4-dihydrotetrazole-5-one (hereinafter, referred to as "Present compound 225").

Present compound 225

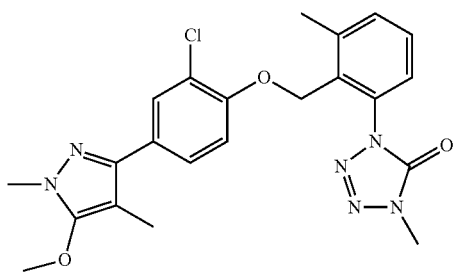

¹H-NMR (CDCl₃) δ: 7.62 (1H, d, J=2.2 Hz), 7.44-7.38 (3H, m), 7.31-7.28 (1H, m), 6.92 (1H, d, J=8.5 Hz), 5.18 (2H, s), 3.93 (3H, s), 3.70 (3H, s), 3.66 (3H, s), 2.54 (3H, s), 2.12 (3H, s).

Preparation Example 226

A similar reaction to Preparation example 190 using 1-{3-chloro-2-[2-methyl-4-(1,5-dimethyl-1H-pyrazol-3-yl)-phenoxymethyl]-phenyl}-4-methyl-1,4-dihydrotetrazole-5-one (described in preparation example 188) instead of 1-{3-methyl-2-[2-methyl-4-(1,5-dimethyl-1H-pyrazol-3-yl)-phenoxymethyl]-phenyl}-4-methyl-1,4-dihydrotetrazole-5-one gave 1-{3-chloro-2-[2-methyl-4-(5-chloromethyl-4-chloro-1-methyl-1H-pyrazol-3-yl)-phenoxymethyl]-phenyl}-4-methyl-1,4-dihydrotetrazole-5-one (hereinafter, referred to as "Present compound 226").

Present compound 226

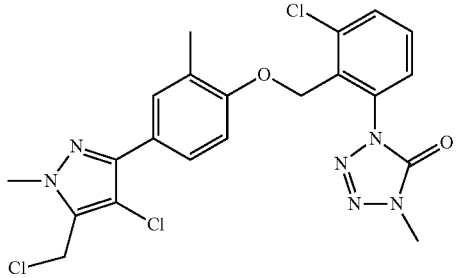

¹H-NMR (CDCl₃) δ: 7.66-7.61 (2H, m), 7.59 (1H, dd, J=2.2, 0.8 Hz), 7.47 (1H, t, J=8.0 Hz), 7.41 (1H, dd, J=8.0, 1.4 Hz), 6.90 (1H, d, J=8.5 Hz), 5.36 (2H, s), 4.65 (2H, s), 3.95 (3H, s), 3.60 (3H, s), 2.07 (3H, s).

Preparation Example 227

A similar reaction to Preparation example 190 using 1-{3-fluoro-2-[2-methyl-4-(1,5-dimethyl-1H-pyrazol-3-yl)-phenoxymethyl]-phenyl}-4-methyl-1,4-dihydrotetrazole-5-one (Present compound 237) instead of 1-{3-methyl-2-[2-methyl-4-(1,5-dimethyl-1H-pyrazol-3-yl)-phenoxymethyl]-phenyl}-4-methyl-1,4-dihydrotetrazole-5-one gave 1-{3-fluoro-2-[2-methyl-4-(4-chloro-1,5-dimethyl-1H-pyrazol-3-yl)-phenoxymethyl]-phenyl}-4-methyl-1,4-dihydrotetrazole-5-one (hereinafter, referred to as "Present compound 227").

Present comound 227

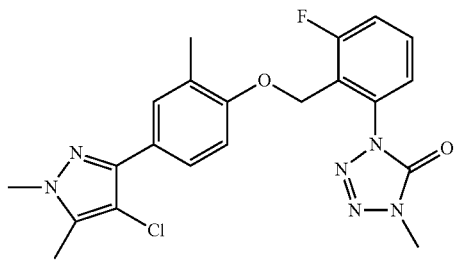

¹H-NMR (CDCl₃) δ: 7.65 (1H, dd, J=8.5, 2.3 Hz), 7.58 (1H, dd, J=1.6, 0.7 Hz), 7.53-7.48 (1H, m), 7.30 (2H, dd, J=17.1, 7.9 Hz), 6.90 (1H, d, J=8.5 Hz), 5.31 (2H, s), 3.81 (3H, s), 3.59 (3H, s), 2.28 (3H, s), 2.03 (3H, s).

Preparation Example 228

A similar reaction to Preparation example 4 using 4-(2,3-dihydro-pyrazolo[5,1-b]oxazole-6-yl)-2-methyl-phenol (described in reference preparation example 191) instead of 2-methyl-4-(3,4,5-trimethyl-pyrazol-1-yl)-phenol gave 1-methyl-4-{3-methyl-2-[2-methyl-4-(2,3-dihydro-pyrazolo[5,1-b]oxazole-6-yl)-phenoxymethyl]-phenyl}-1,4-dihydrotetrazole-5-one (hereinafter, referred to as "Present compound 228").

Present compound 228

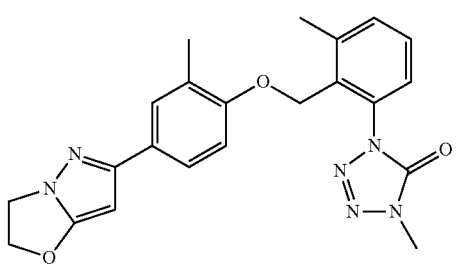

¹H-NMR (CDCl₃) δ: 7.52 (1H, d, J=1.4 Hz), 7.48 (1H, dd, J=8.5, 2.2 Hz), 7.44-7.39 (2H, m), 7.29-7.26 (1H, m), 6.85 (1H, d, J=8.5 Hz), 5.62 (1H, s), 5.06-5.02 (4H, m), 4.32 (2H, t, J=7.8 Hz), 3.61 (3H, s), 2.51 (3H, s), 2.11 (3H, s).

Preparation Example 229

A similar reaction to Preparation example 5 using 2-chloro-4-(1,4-dimethyl-5-methoxy-1H-pyrazol-3-yl)-phenol (described in reference preparation example 188) instead of 2-methyl-4-(3,4,5-trimethyl-pyrazol-1-yl)-phenol gave 1-{3-ethyl-2-[2-chloro-4-(1,4-dimethyl-5-methoxy-1H-pyrazol-3-yl)-phenoxymethyl]-phenyl}-4-methyl-1,4-dihydrotetrazole-5-one (hereinafter, referred to as "Present compound 229").

Present compound 229

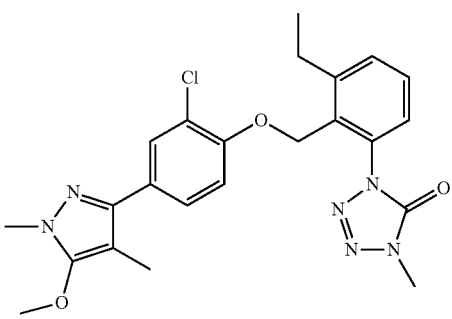

¹H-NMR (CDCl₃) δ: 7.62 (1H, d, J=2.1 Hz), 7.49-7.42 (3H, m), 7.31 (1H, dd, J=7.3, 1.8 Hz), 6.94 (1H, d, J=8.3 Hz), 5.20 (2H, s), 3.94 (3H, s), 3.71 (3H, s), 3.64 (3H, s), 2.88 (2H, q, J=7.6 Hz), 2.13 (3H, s), 1.30 (3H, t, J=7.6 Hz).

Preparation Example 230

At room temperature, to a mixture of 1-{3-methyl-2-[2-methyl-4-(1,5-dimethyl-1H-pyrazol-3-yl)-phenoxymethyl]-phenyl}-4-methyl-1,4-dihydrotetrazole-5-one (present compound 47) 1.5 g and chloroform 20 ml was added N-iodosuccinimide 0.9 g and the resulting mixture was stirred for twenty hours. Thereto was added water 5 ml at room temperature and the resulting mixture was extracted with chloroform. The organic layer was washed with water, and was dried over anhydrous magnesium sulfate and was then concentrated under reduced pressure. The resulting residue was subjected to a silica gel column chromatography to give 1-{3-methyl-2-[2-methyl-4-(1,5-dimethyl-4-iodo-1H-pyrazol-3-yl)-phenoxymethyl]-phenyl}-4-methyl-1,4-dihydrotetrazole-5-one (hereinafter, referred to as "Present compound 230") 1.5 g.

Present compound 230

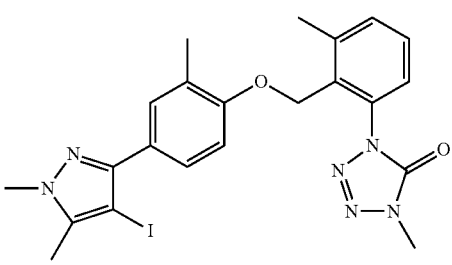

¹H-NMR (CDCl₃) δ: 7.59 (1H, dd, J=8.5, 2.3 Hz), 7.53 (1H, d, J=1.6 Hz), 7.45-7.39 (2H, m), 7.29-7.27 (1H, m), 6.90 (1H, d, J=8.5 Hz), 5.07 (2H, s), 3.89 (3H, s), 3.63 (3H, s), 2.51 (3H, s), 2.36 (3H, s), 2.13 (3H, s).

Preparation Example 231

A mixture of 1-{3-methyl-2-[2-methyl-4-(1,5-dimethyl-4-iodo-1H-pyrazol-3-yl)-phenoxymethyl]-phenyl}-4-methyl-1,4-dihydrotetrazole-5-one (Present compound 230) 0.4 g, zinc dicyanide 0.18 g, tetrakis(triphenylphosphine) 0.08 g and N-methylpyrrolidone 10 ml was stirred at 100° C. for five hours. Thereto was added water 5 ml at room temperature and the resulting mixture was extracted with chloroform. The organic layer was washed with water, and was dried over anhydrous magnesium sulfate and was then concentrated under reduced pressure. The resulting residue was subjected to a silica gel column chromatography to give 1-{3-methyl-2-[2-methyl-4-(1,5-dimethyl-4-cyano-1H-pyrazol-3-yl)-phenoxymethyl]-phenyl}-4-methyl-1,4-dihydrotetrazole-5-one (hereinafter, referred to as "Present compound 231") 0.2 g.

Present compound 231

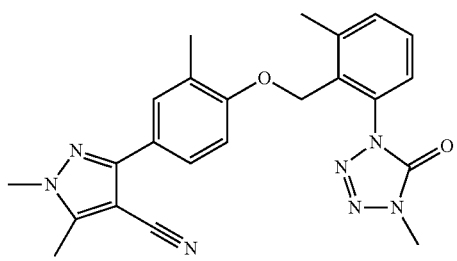

¹H-NMR (CDCl₃) δ: 7.73 (1H, dd, J=8.5, 2.1 Hz), 7.68 (1H, d, J=1.6 Hz), 7.46-7.40 (2H, m), 7.30-7.27 (1H, m), 6.90 (1H, d, J=8.5 Hz), 5.08 (2H, s), 3.84 (3H, s), 3.64 (3H, s), 2.52 (3H, s), 2.46 (3H, s), 2.14 (3H, s).

Preparation Example 232

A similar reaction to Preparation example 5 using 4-(1,4-dimethyl-5-ethoxy-1H-pyrazol-3-yl)-2-methyl-phenol (described in reference preparation example 178) instead of 2-methyl-4-(3,4,5-trimethyl-pyrazol-1-yl)-phenol gave 1-{3-ethyl-2-[2-methyl-4-(1,4-dimethyl-5-ethoxy-1H-pyrazol-3-yl)-phenoxymethyl]-phenyl}-4-methyl-1,4-dihydrotetrazole-5-one (hereinafter, referred to a "Present compound 232").

Present compound 232

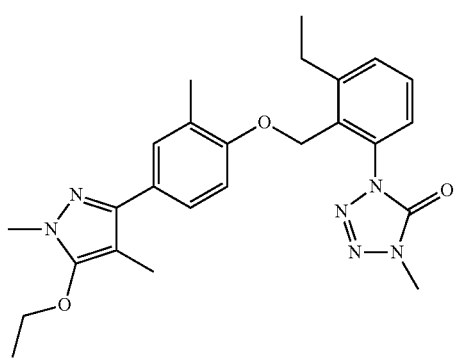

¹H-NMR (CDCl₃) δ: 7.49-7.43 (2H, m), 7.41-7.41 (1H, m), 7.38-7.35 (1H, m), 7.28 (1H, dd, J=7.0, 2.2 Hz), 6.88 (1H, d, J=8.2 Hz), 5.07 (2H, s), 4.14 (2H, q, J=7.1 Hz), 3.70 (3H, s), 3.58 (3H, s), 2.85 (2H, q, J=7.6 Hz), 2.11 (3H, s), 2.10 (3H, s), 1.41 (3H, t, J=7.1 Hz), 1.28 (3H, t, J=7.7 Hz).

Preparation Example 233

A similar reaction to Preparation example 1 using 4-(1,4-dimethyl-5-ethoxy-1H-pyrazol-3-yl)-2-methyl-phenol (described in reference preparation example 178) instead of 2-methyl-4-(3,4,5-trimethyl-pyrazol-1-yl)-phenol gave 1-{3-fluoro-2-[2-methyl-4-(1,4-dimethyl-5-ethoxy-1H-pyrazol-3-yl)-phenoxymethyl]-phenyl}-4-methyl-1,4-dihydrotetrazole-5-one (hereinafter, referred to as "Present compound 233").

Present compound 233

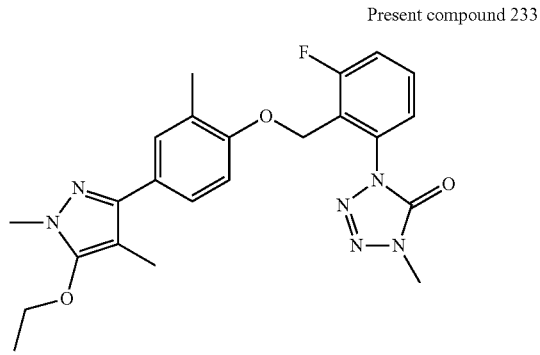 [SMILES: CCOc1c(C)c(-c2ccc(OCc3c(Cl)cccc3-n3nnn(C)c3=O)c(C)c2)nn1C]

$^1$H-NMR (CDCl$_3$) δ: 7.53-7.47 (1H, m), 7.39 (1H, d, J=1.6 Hz), 7.36-7.26 (3H, m), 6.88 (1H, d, J=8.5 Hz), 5.29 (2H, s), 4.14 (2H, q, J=7.1 Hz), 3.70 (3H, s), 3.59 (3H, s), 2.10 (3H, s), 2.02 (3H, s), 1.40 (3H, t, J=7.1 Hz).

Preparation Example 234

A similar reaction to Preparation example 2 using 4-(1,4-dimethyl-5-ethoxy-1H-pyrazol-3-yl)-2-methyl-phenol (described in reference preparation example 178) instead of 2-methyl-4-(3,4,5-trimethyl-pyrazol-1-yl)-phenol gave 1-{3-chloro-2-[2-methyl-4-(1,4-dimethyl-5-ethoxy-1H-pyrazol-3-yl)-phenoxymethyl]-phenyl}-4-methyl-1,4-dihydrotetrazole-5-one (hereinafter, referred to as "Present compound 234").

Present compound 234

$^1$H-NMR (CDCl$_3$) δ: 7.61 (1H, dd, J=8.0, 1.4 Hz), 7.46 (1H, t, J=8.0 Hz), 7.41-7.39 (2H, m), 7.36-7.34 (1H, m), 6.87 (1H, d, J=8.5 Hz), 5.34 (2H, s), 4.14 (2H, q, J=7.0 Hz), 3.70 (3H, s), 3.59 (3H, s), 2.10 (3H, s), 2.05 (3H, s), 1.41 (3H, t, J=7.1 Hz).

Preparation Example 235

A similar reaction to Preparation example 3 using 4-(1,4-dimethyl-5-ethoxy-1H-pyrazol-3-yl)-2-methyl-phenol (described in reference preparation example 178) instead of 2-methyl-4-(3,4,5-trimethyl-pyrazol-1-yl)-phenol gave 1-{3-bromo-2-[2-methyl-4-(1,4-dimethyl-5-ethoxy-1H-pyrazol-3-yl)-phenoxymethyl]-phenyl}-4-methyl-1,4-dihydrotetrazole-5-one (hereinafter, referred to as "Present compound 235").

Present compound 235

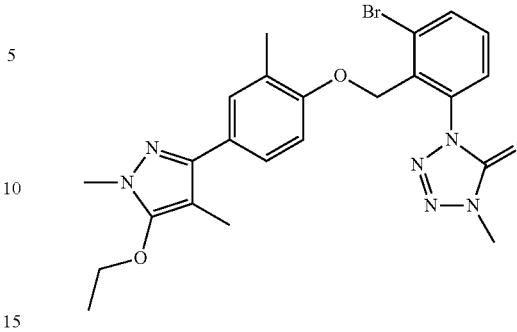

$^1$H-NMR (CDCl$_3$) δ: 7.80 (1H, dd, J=7.8, 1.4 Hz), 7.45-7.34 (4H, m), 6.87 (1H, d, J=8.5 Hz), 5.33 (2H, s), 4.14 (2H, q, J=7.1 Hz), 3.70 (3H, s), 3.59 (3H, s), 2.10 (3H, s), 2.06 (3H, s), 1.41 (3H, t, J=7.1 Hz).

Preparation Example 236

A similar reaction to Preparation example 7 using 4-(1,4-dimethyl-5-ethoxy-1H-pyrazol-3-yl)-2-methyl-phenol (described in reference preparation example 178) instead of 2-methyl-4-(3,4,5-trimethyl-pyrazol-1-yl)-phenol gave 1-{3-methoxy-2-[2-methyl-4-(1,4-dimethyl-5-ethoxy-1H-pyrazol-3-yl)-phenoxymethyl]-phenyl}-4-methyl-1,4-dihydrotetrazole-5-one (hereinafter, referred to as "Present compound 236").

Present compound 236

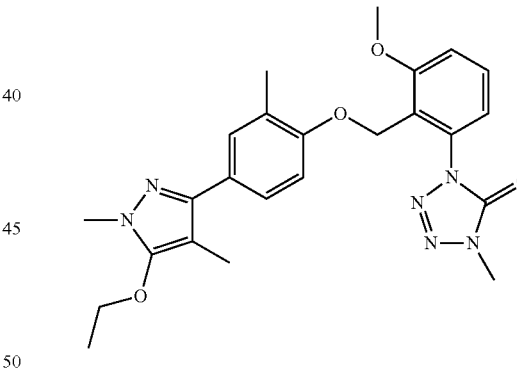

$^1$H-NMR (CDCl$_3$) δ: 7.46 (1H, t, J=8.2 Hz), 7.37 (1H, s), 7.33 (1H, dd, J=8.2, 2.3 Hz), 7.08 (2H, dd, J=8.1, 3.8 Hz), 6.90 (1H, d, J=8.5 Hz), 5.28 (2H, s), 4.16-4.09 (2H, m), 3.92 (3H, s), 3.70 (3H, s), 3.58 (3H, s), 2.10 (3H, s), 2.02 (3H, s), 1.40 (3H, t, J=7.1 Hz).

Preparation Example 237

A similar reaction to Preparation example 1 using 2-methyl-4-(1,5-dimethyl-1H-pyrazol-3-yl)-2-methyl-phenol (described in reference preparation example 63) instead of 2-methyl-4-(3,4,5-trimethyl-pyrazol-1-yl)-phenol gave 1-{3-fluoro-2-[2-methyl-4-(1,5-dimethyl-1H-pyrazol-3-yl)-phenoxymethyl]-phenyl}-4-methyl-1,4-dihydrotetrazole-5-one (hereinafter, referred to as "Present compound 237").

Present compound 237

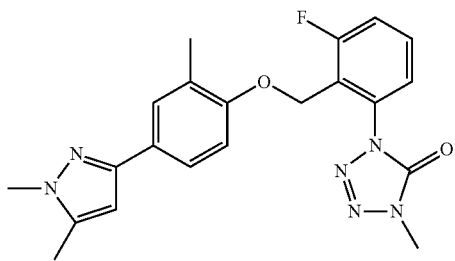

¹H-NMR (CDCl₃) δ: 7.62-7.60 (1H, m), 7.52 (1H, s), 7.48-7.44 (2H, m), 7.40 (1H, d, J=8.0 Hz), 6.85 (1H, d, J=8.2 Hz), 6.23 (1H, s), 5.33 (2H, s), 3.80 (3H, s), 3.57 (3H, s), 2.29 (3H, s), 2.05 (3H, s).

Preparation Example 238

A similar reaction to Preparation example 4 using 4-(1,4-dimethyl-5-methylthio-pyrazol-3-yl)-2-methyl-phenol (described in reference preparation example 181) instead of 2-methyl-4-(3,4,5-trimethyl-pyrazol-1-yl)-phenol gave 1-{3-methyl-2-[2-methyl-4-(1,4-dimethyl-5-methylthio-1H-pyrazol-3-yl)-phenoxymethyl]-phenyl}-4-methyl-, 4-dihydrotetrazole-5-one (hereinafter, referred to as "Present compound 238").

Present compound 238

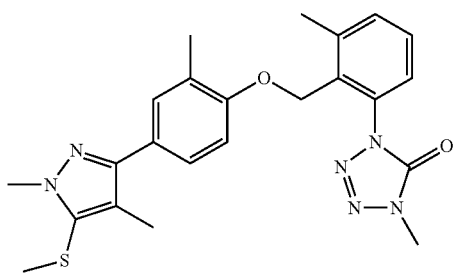

¹H-NMR (CDCl₃) δ: 7.44-7.38 (4H, m), 7.29-7.26 (1H, m), 6.88 (1H, d, J=8.5 Hz), 5.06 (2H, s), 3.98 (3H, s), 3.62 (3H, s), 2.51 (3H, s), 2.26 (6H, s), 2.13 (3H, s).

Preparation Example 239

At room temperature, to a mixture of 1-{3-methyl-2-[2-methyl-4-(4-formyl-5-ethoxy-1-methyl-1H-pyrazol-3-yl)-phenoxymethyl]-phenyl}-4-methyl-1,4-dihydrotetrazole-5-one (described in preparation example 217) 0.7 g, N,N-dimethylformamide 7 ml and 2-propyne-1-ol 0.1 g was added 55% sodium hydride 0.08 g. The resulting mixture was stirred for twelve hours and thereto was added water 5 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-(3-methyl-2-{2-methyl-4-[4-formyl-1-methyl-5-(2-propynyloxy)-1H-pyrazol-3-yl]-phenoxymethyl]-phenyl}-4-methyl-1,4-dihydrotetrazole-5-one (hereinafter, referred to as "Present compound 239") 0.15 g.

Present compound 239

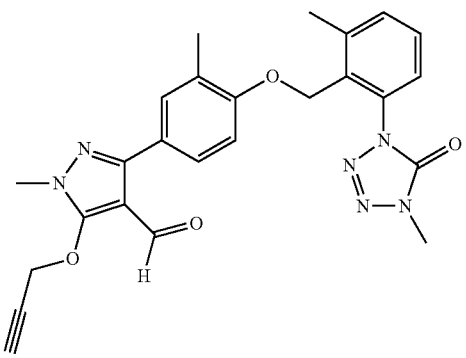

¹H-NMR (CDCl₃) δ: 9.74 (1H, s), 7.44-7.42 (2H, m), 7.38-7.36 (2H, m), 7.29 (1H, dd, J=7.1, 2.2 Hz), 6.91 (1H, d, J=8.2 Hz), 5.27 (2H, d, J=2.5 Hz), 5.08 (2H, s), 3.79 (3H, s), 3.64 (3H, s), 2.56 (1H, t, J=2.4 Hz), 2.52 (3H, s), 2.14 (3H, s).

Preparation Example 240

A similar reaction to Preparation example 239 using 2,2-difluoroethanol instead of 2-propyne-1-ol gave 1-(3-methyl-2-{2-methyl-4-[5-(2,2-difluoroethoxy)-4-formyl-1-methyl-1H-pyrazol-3-yl)-phenoxymethyl]-phenyl}-4-methyl-1,4-dihydrotetrazole-5-one (hereinafter, referred to as "Present compound 240").

Present compound 240

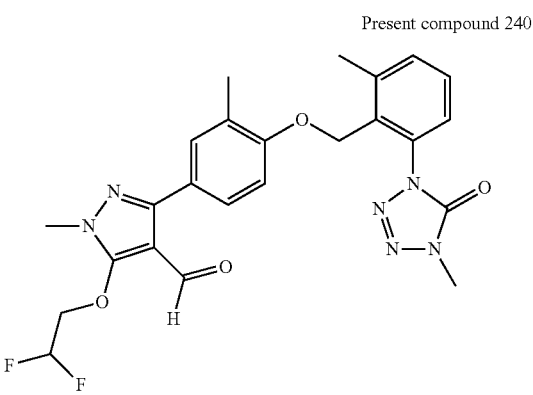 [SMILES: Cc1cc(-c2nn(C)c(OCC(F)F)c2C=O)ccc1OCc1c(C)cccc1-n1nnn(C)c1=O]

¹H-NMR (CDCl₃) δ: 9.72 (1H, s), 7.46-7.41 (2H, m), 7.34 (2H, t, J=5.5 Hz), 7.30 (1H, d, J=2.5 Hz), 6.92 (1H, d, J=8.2 Hz), 6.12 (1H, tt, J=54.6, 3.5 Hz), 5.08 (2H, s), 4.78 (2H, td, J=14.0, 3.6 Hz), 3.76 (3H, s), 3.64 (3H, s), 2.52 (3H, s), 2.14 (3H, s).

Preparation Example 241

To a mixture of 1-(3-methyl-2-{2-methyl-4-[5-(2,2-difluoroethoxy)-4-formyl-1-methyl-1H-pyrazol-3-yl)-phenoxymethyl]-phenyl}-4-methyl-1,4-dihydrotetrazole-5-one (present compound 240) 0.76 g and trifluoroacetic acid 7 ml was added triethylsilane 0.45 g. The resulting mixture was stirred for fifteen hours and the solvent was distilled off under reduced pressure. Thereto was added water 5 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-(3-methyl-2-{2-methyl-4-[5-(2,2-difluoromethoxy)-1,4-dimethyl-1H-pyrazol-3-yl)-phenoxymethyl]-phenyl}-4-methyl-1,4-dihydrotetrazole-5-one (hereinafter, referred to as "Present compound 241") 0.15 g.

Present compound 241

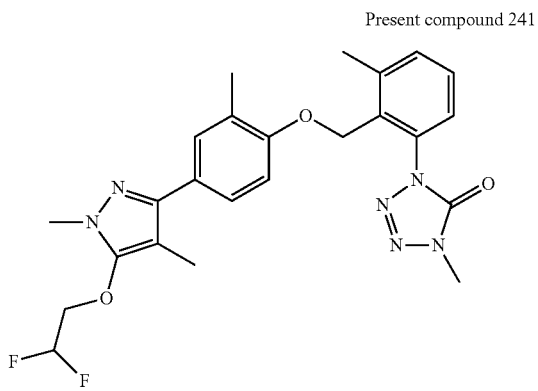 [SMILES: Cc1cc(-c2nn(C)c(OCC(F)F)c2C)ccc1OCc1c(C)cccc1-n1nnn(C)c1=O]

¹H-NMR (CDCl₃) δ: 7.43-7.39 (3H, m), 7.35 (1H, dd, J=8.4, 2.3 Hz), 7.29-7.27 (1H, m), 6.88 (1H, d, J=8.4 Hz), 6.07 (1H, tt, J=54.7, 4.0 Hz), 5.06 (2H, s), 4.27 (2H, td, J=13.4, 4.0 Hz), 3.73 (3H, s), 3.63 (3H, s), 2.51 (3H, s), 2.12 (6H, s).

Preparation Examples 242 and 243

At room temperature, a mixture of 1-{3-methyl-2-[2-methyl-4-(1,4-dimethyl-5-methylthio-1H-pyrazol-3-yl)-phenoxymethyl]-phenyl}-4-methyl-1,4-dihydrotetrazole-5-one (present compound 238) 1 g, chloroform 15 ml and m-chloroperoxybenzoic acid 0.65 g was stirred for fifteen hours. Thereto was added 5 ml and the resulting mixture was extracted with ethyl acetate. The organic layer was washed with water and aqueous sodium thiosulfate solution, and was dried over anhydrous magnesium sulfate and was then concentrated under reduced pressure. The resulting residue was subjected to a silica gel column chromatography to give 1-{3-methyl-2-[2-methyl-4-(1,4-dimethyl-5-methyl-sulfonyl-1H-pyrazol-3-yl)-phenoxymethyl]-phenyl}-4-methyl-1,4-dihydrotetrazole-5-one (hereinafter, referred to as "Present compound 242") 0.48 g and 1-{3-methyl-2-[2-methyl-4-(1,4-dimethyl-5-methyl-sulfinyl-1H-pyrazol-3-yl)-phenoxymethyl]-phenyl}-4-methyl-1,4-dihydrotetrazole-5-one (hereinafter, referred to as "Present compound 243") 0.28 g.

Present compound 242

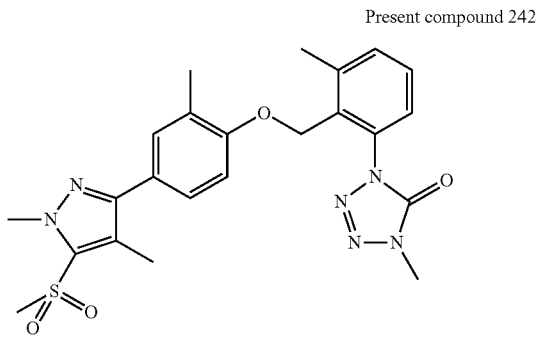 [SMILES: Cc1cc(-c2nn(C)c(S(C)(=O)=O)c2C)ccc1OCc1c(C)cccc1-n1nnn(C)c1=O]

¹H-NMR (CDCl₃) δ: 7.45-7.40 (2H, m), 7.33-7.27 (3H, m), 6.90 (1H, d, J=8.2 Hz), 5.07 (2H, s), 4.17 (3H, s), 3.63 (3H, s), 3.14 (3H, s), 2.51 (3H, s), 2.39 (3H, s), 2.13 (3H, s).

Present compound 243

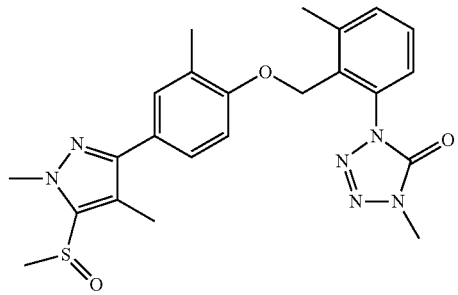

¹H-NMR (CDCl₃) δ: 7.45-7.39 (2H, m), 7.37-7.36 (1H, m), 7.35-7.32 (1H, m), 7.29-7.26 (1H, m), 6.89 (1H, d, J=8.4 Hz), 5.06 (2H, s), 4.15 (3H, s), 3.63 (3H, s), 3.00 (3H, s), 2.51 (3H, s), 2.29 (3H, s), 2.12 (3H, s).

Preparation Example 244

At room temperature, to a mixture of 1-(3-methyl-2-{2-methyl-4-[4-formyl-1-methyl-5-(2-propynyloxy)-1H-pyrazol-3-yl)-phenoxymethyl]-phenyl}-4-methyl-1,4-dihydrotetrazole-5-one (present compound 239) 0.44 g and trifluoroacetic acid 7 ml was added triethylsilane 0.27 g. The resulting mixture was stirred for fifteen hours and the solvent was distilled off under reduced pressure. Thereto was added water 5 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{3-methyl-2-(2-methyl-4-[1,4-dimethyl-5-(2-propynyloxy)-1H-pyrazol-3-yl]-phenoxymethyl)-phenyl}-4-methyl-1,4-dihydrotetrazole-5-one (hereinafter, referred to as "Present compound 244") 0.4 g.

Present compound 244

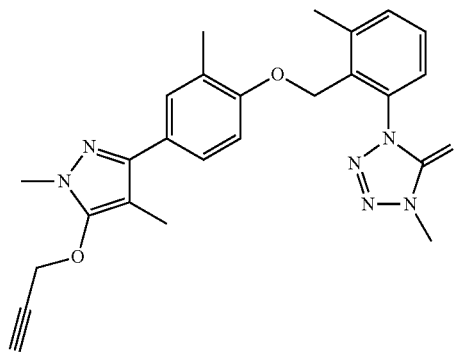

¹H-NMR (CDCl₃) δ: 7.45-7.39 (3H, m), 7.37 (1H, dd, J=8.4, 2.0 Hz), 7.29-7.27 (1H, m), 6.87 (1H, d, J=8.4 Hz), 5.06 (2H, s), 4.72 (2H, d, J=2.5 Hz), 3.77 (3H, s), 3.63 (3H, s), 2.59 (1H, t, J=2.5 Hz), 2.51 (3H, s), 2.14 (3H, s), 2.12 (3H, s).

Preparation Example 245

A similar reaction to Preparation example 4 using 2,5-dimethyl-4-(1-methyl-1H-pyrazol-3-yl)-phenol (described in reference preparation example 221) instead of 2-methyl-4-(3,4,5-trimethyl-pyrazol-1-yl)-phenol gave 1-{2-[2,5-dimethyl-4-(1-methyl-1H-pyrazol-3-yl)-phenoxymethyl]-3-methyl-phenyl}-4-methyl-1,4-dihydrotetrazole-5-one (hereinafter, referred to as "Present compound 245")

Present compound 245

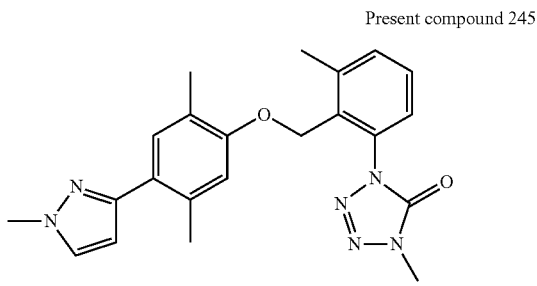 [SMILES: Cc1cc(-c2ccn(C)n2)c(C)cc1OCc1c(C)cccc1-n1nnn(C)c1=O]

$^1$H-NMR (CDCl$_3$) δ: 7.44-7.39 (2H, m), 7.37 (1H, d, J=2.1 Hz), 7.32 (1H, s), 7.28-7.26 (1H, m), 6.70 (1H, s), 6.32 (1H, d, J=1.8 Hz), 5.05 (2H, s), 3.94 (3H, s), 3.64 (3H, s), 2.51 (3H, s), 2.42 (3H, s), 2.07 (3H, s).

Preparation Example 246

A mixture of 1-(2-bromomethyl-3-methyl-4-fluorophenyl)-4-methyl-1,4-dihydrotetrazole-5-one (described in Reference Preparation example 217) 0.3 g, 2,5-dimethyl-4-(1-methyl-1H-pyrazol-3-yl)-phenol (described in Reference Preparation example 221) 0.25 g, potassium carbonate 0.18 g and acetonitrile 10 ml was stirred with heating under reflux for three hours. The reaction mixture was filtered, and the filtrate was then concentrated under reduced pressure. The resulting residue was subjected to a silica gel column chromatography to give 1-{2-[2,5-dimethyl-4-(1-methyl-1H-pyrazol-3-yl)-phenoxymethyl]-4-fluoro-3-methyl-phenyl}-4-methyl-1,4-dihydrotetrazole-5-one (hereinafter, referred to as "Present compound 246")

Present compound 246

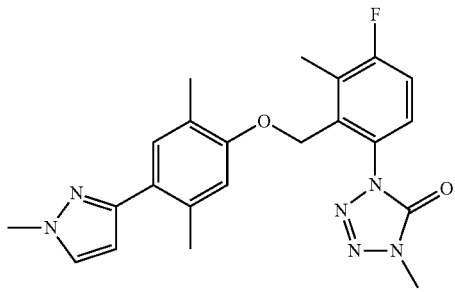

$^1$H-NMR (CDCl$_3$) δ: 7.37 (1H, d, J=2.1 Hz), 7.32 (1H, s), 7.28-7.25 (1H, m), 7.20 (1H, t, J=8.7 Hz), 6.68 (1H, s), 6.32 (1H, d, J=2.1 Hz), 5.02 (2H, s), 3.94 (3H, s), 3.65 (3H, s), 2.42 (3H, s), 2.40 (3H, d, J=2.1 Hz), 2.08 (3H, s).

Preparation Example 247

A similar reaction to Preparation example 4 using 4-(5-difluoromethoxy-1,4-dimethyl-1H-pyrazol-3-yl)-2-methyl-phenol (described in reference preparation example 224) instead of 2-methyl-4-(3,4,5-trimethyl-pyrazol-1-yl)-phenol gave 1-{2-[2-methyl-4-(5-difluoromethoxy-1,4-dimethyl-1H-pyrazol-3-yl)-phenoxymethyl]-3-methyl-phenyl}-4-methyl-1,4-dihydrotetrazole-5-one (hereinafter, referred to as "Present compound 247")

Present compound 247

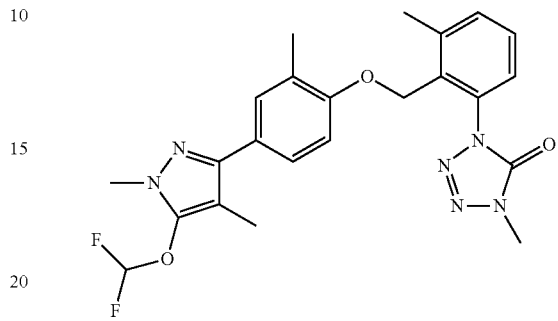

$^1$H-NMR (CDCl$_3$) δ: 7.47-7.41 (2H, m), 7.29 (1H, dd, J=6.9, 2.3 Hz), 7.07 (1H, dd, J=8.2, 2.1 Hz), 7.04 (1H, s), 6.92 (1H, d, J=8.2 Hz), 6.89 (1H, t, J=74.3 Hz), 5.08 (2H, s), 3.66 (3H, s), 3.63 (3H, s), 2.54 (3H, s), 2.14 (3H, s), 1.89 (3H, s).

Preparation Example 248

At room temperature, to a mixture of 1-{3-methyl-2-[2-chloro-4-(3,5-dimethyl-pyrazol-1-yl)-phenoxymethyl]-phenyl}-4-methyl-1,4-dihydrotetrazole-5-one (Present compound 17) 0.5 g and chloroform 10 ml wad added N-bromosuccinimide 0.23 g. The resulting mixture was stirred at room temperature for fifteen hours and thereto added water 5 ml. The resulting mixture was extracted with chloroform. The organic layer was washed with water, aqueous sodium thiosulfate solution and aqueous sodium carbonate solution, and was dried over anhydrous magnesium sulfate and was then concentrated under reduced pressure to give 1-{2-[4-(4-bromo-3,5-dimethyl-pyrazol-1-yl)-2-chloro-phenoxymethyl]-3-methyl-phenyl}-4-methyl-1,4-dihydrotetrazole-5-one (hereinafter, referred to as "Present compound 248") 0.5 g.

Present compound 248

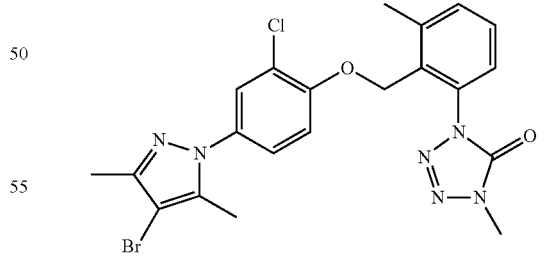

$^1$H-NMR (CDCl$_3$) δ: 7.46-7.39 (3H, m), 7.31-7.29 (1H, m), 7.20 (1H, dd, J=8.8, 2.6 Hz), 6.94 (1H, d, J=8.9 Hz), 5.19 (2H, s), 3.68 (3H, s), 2.54 (3H, s), 2.27 (3H, s), 2.27 (3H, s).

Preparation Example 249

A similar reaction to Preparation example 248 using N-iodosuccinimide instead of N-bromosuccinimide gave 1-{2-[4-(4-iodo-3,5-dimethyl-pyrazol-1-yl)-2-chloro-phenoxymethyl]-3-methyl-phenyl}-4-methyl-1,4-dihydrotetrazole-5-one (hereinafter, referred to a "Present compound 249").

Present compound 249

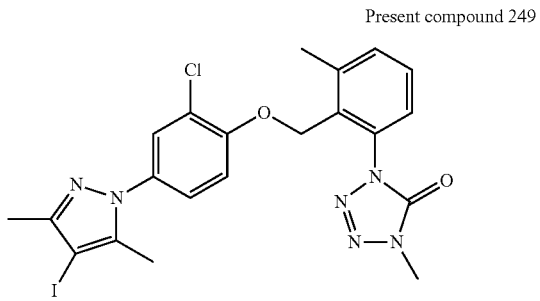 [SMILES: Cc1cccc(-n2nnn(C)c2=O)c1COc1ccc(-n2nc(C)c(I)c2C)cc1Cl]

$^1$H-NMR (CDCl$_3$) δ: 7.44-7.40 (3H, m), 7.30 (1H, dd, J=7.4, 1.7 Hz), 7.20 (1H, dd, J=8.7, 2.5 Hz), 6.95 (1H, d, J=8.7 Hz), 5.19 (2H, s), 3.68 (3H, s), 2.54 (3H, s), 2.30 (3H, s), 2.28 (3H, s).

Preparation Example 250

A similar reaction to Preparation example 190 using N-bromosuccinimide instead of N-chlorosuccinimide gave 1-{3-methyl-2-[2-methyl-4-(4-bromo-1,5-dimethyl-1H-pyrazol-3-yl)-phenoxymethyl]-phenyl}-4-methyl-1,4-dihydrotetrazole-5-one (hereinafter, referred to as "Present compound 250").

Present compound 250

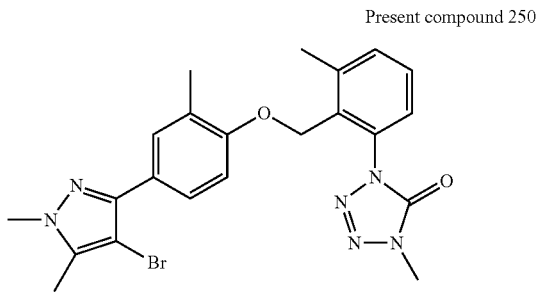

$^1$H-NMR (CDCl$_3$) δ: 7.65 (1H, dd, J=8.4, 2.3 Hz), 7.58 (1H, d, J=2.0 Hz), 7.44-7.39 (2H, m), 7.28-7.26 (1H, m), 6.89 (1H, d, J=8.6 Hz), 5.06 (2H, s), 3.84 (3H, s), 3.62 (3H, s), 2.51 (3H, s), 2.30 (3H, s), 2.12 (3H, s).

Preparation Example 251

A similar reaction to Preparation example 116 using 1-{3-methyl-2-[2-chloro-4-(3,5-dimethyl-pyrazol-1-yl)-phenoxymethyl]-phenyl}-4-methyl-1,4-dihydrotetrazole-5-one (present compound 17) instead of 1-{3-methoxy-2-[2-methyl-4-(3,5-dimethyl-pyrazol-1-yl)-phenoxymethyl]-phenyl}-4-methyl-1,4-dihydrotetrazole-5-one (present compound 62) gave 1-{3-methyl-2-[2-chloro-4-(3,5-dimethyl-4-formyl-pyrazol-1-yl)-phenoxymethyl]-phenyl}-4-methyl-1,4-dihydrotetrazole-5-one (hereinafter, referred to as "Present compound 251").

Present compound 251

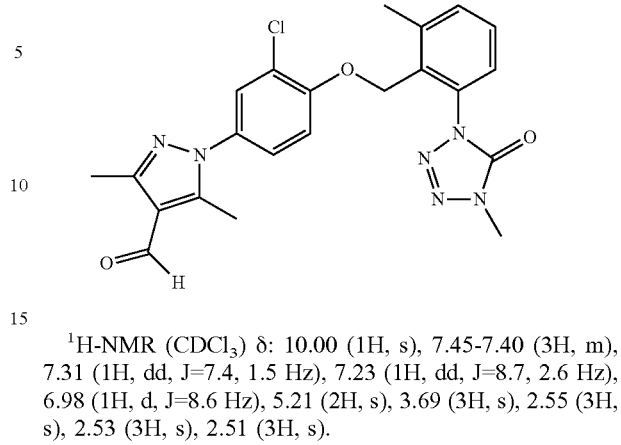

$^1$H-NMR (CDCl$_3$) δ: 10.00 (1H, s), 7.45-7.40 (3H, m), 7.31 (1H, dd, J=7.4, 1.5 Hz), 7.23 (1H, dd, J=8.7, 2.6 Hz), 6.98 (1H, d, J=8.6 Hz), 5.21 (2H, s), 3.69 (3H, s), 2.55 (3H, s), 2.53 (3H, s), 2.51 (3H, s).

Preparation Example 252

At room temperature, to a mixture of 3-methyl-4-{3-methyl-4-[2-methyl-6-(4-methyl-5-oxo-4,5-dihydro-tetrazol-1yl)-benzyloxy]-phenyl}-2,4-dioxo-butyric acid ethyl ester (described in Reference Preparation example 225) 3.8 g and tetrahydrofuran 70 ml was added hydrazine one hydrate 0.39 g and the resulting mixture was stirred for nine hours. The solvent was distilled off, and thereto was added water 100 ml, and the resulting mixture was stirred for a half hour. The precipitates were filtered and were washed with water 50 ml and hexane 50 ml and were then dried under reduced pressure to give 1-{3-methyl-2-[2-methyl-4-(5-ethoxycarbonyl-4-methyl-1H-pyrazol-3-yl)-phenoxymethyl]-phenyl}-4-methyl-1,4-dihydrotetrazole-5-one (hereinafter, referred to as "Present compound 252") 3.7 g.

Present compound 252

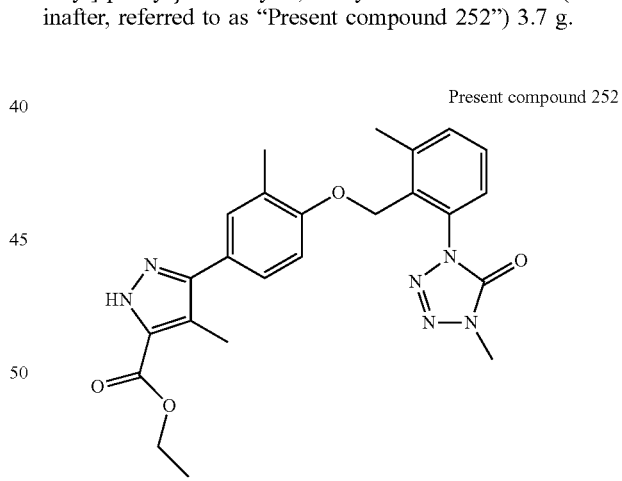

$^1$H-NMR (CDCl$_3$) δ: 7.46-7.40 (2H, m), 7.33-7.31 (2H, m), 7.28 (1H, dd, J=6.9, 2.4 Hz), 6.93-6.90 (1H, m), 5.08 (2H, s), 4.41 (2H, q, J=7.2 Hz), 3.64 (3H, s), 2.52 (3H, s), 2.41 (3H, s), 2.14 (3H, s), 1.42 (3H, t, J=7.2 Hz).

Preparation Examples 253 and 254

At 0° C., to a mixture of 1-{3-methyl-2-[2-methyl-4-(5-ethoxycarbonyl-4-methyl-1H-pyrazol-3-yl)-phenoxymethyl]-phenyl}-4-methyl-1,4-dihydrotetrazole-5-one (present compound 252) 0.5 g and N,N-dimethylformamide 10 ml was added 55% sodium hydride 0.056 g. The resulting mixture was stirred for one hour and thereto was added methyl iodide 0.13 ml. The resulting mixture was stirred at room temperature for twelve hours. Thereto was added water 5 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{3-methyl-2-[2-methyl-4-(5-ethoxycarbonyl-1,4-dimethyl-1H-pyrazol-3-yl)-phenoxymethyl]-phenyl}-4-methyl-1,4-dihydrotetrazole-5-one (hereinafter, referred to as "Present compound 253") 0.19 g and 1-{3-methyl-2-[2-methyl-4-(3-ethoxycarbonyl-1,4-dimethyl-1H-pyrazol-5-yl)-phenoxymethyl]-phenyl}-4-methyl-1,4-dihydrotetrazole-5-one (hereinafter, referred to as "Present compound 254") 0.21 g.

Present compound 253

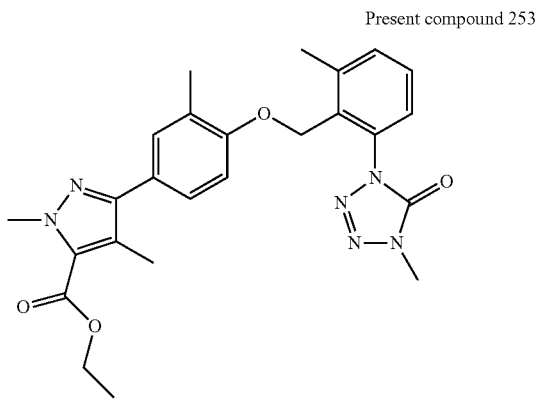 [SMILES: CCOC(=O)c1c(C)c(-c2ccc(OCc3c(C)cccc3-n3nnn(C)c3=O)c(C)c2)nn1C]

$^1$H-NMR (CDCl$_3$) δ: 7.45-7.40 (2H, m), 7.36-7.35 (1H, m), 7.32 (1H, dd, J=8.3, 1.9 Hz), 7.28 (1H, dd, J=6.9, 2.4 Hz), 6.90 (1H, d, J=8.4 Hz), 5.07 (2H, s), 4.40 (2H, q, J=7.1 Hz), 4.17 (3H, s), 3.64 (3H, s), 2.52 (3H, s), 2.36 (3H, s), 2.13 (3H, s), 1.42 (3H, t, J=7.1 Hz).

Present compound 254

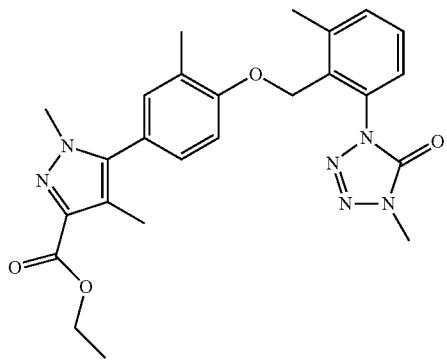

$^1$H-NMR (CDCl$_3$) δ: 7.47-7.42 (2H, m), 7.29 (1H, dd, J=7.0, 2.3 Hz), 7.06 (1H, dd, J=8.2, 2.3 Hz), 7.03-7.02 (1H, m), 6.93 (1H, d, J=8.4 Hz), 5.09 (2H, s), 4.43 (2H, q, J=7.1 Hz), 3.80 (3H, s), 3.66 (3H, s), 2.54 (3H, s), 2.19 (3H, s), 2.14 (3H, s), 1.42 (3H, t, J=7.1 Hz).

Preparation Example 255

A similar reaction to Preparation example 190 using 1-{2-[2,5-dimethyl-4-(1-methyl-1H-pyrazol-3-yl)-phenoxymethyl]-3-methyl-phenyl}-4-methyl-1,4-dihydrotetrazole-5-one (described in Preparation example 245) instead of 1-{3-methyl-2-[2-methyl-4-(1,5-dimethyl-1H-pyrazol-3-yl)-phenoxymethyl]-phenyl}-4-methyl-1,4-dihydrotetrazole-5-one (Present compound 47) gave 1-{2-[2,5-dimethyl-4-(4-chloro-1-methyl-1H-pyrazol-3-yl)-phenoxymethyl]-3-methyl-phenyl}-4-methyl-1,4-dihydrotetrazole-5-one (hereinafter, referred to as "Present compound 255").

Present compound 255

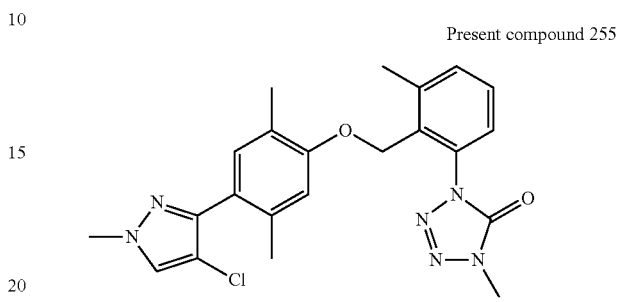

MS+: 439

Preparation Example 256

At room temperature, to a mixture of 1-{3-methyl-2-[2-methyl-4-(4-formyl-5-chloro-1-methyl-1H-pyrazol-3-yl)-phenoxymethyl]-phenyl}-4-methyl-1,4-dihydrotetrazole-5-one (present compound 207) 0.4 g and chloroform 10 ml was added (diethylamino)sulfur trifluoride 0.42 g. The resulting mixture was stirred for twelve hours and thereto was then added water 5 ml. The resulting mixture was extracted with chloroform. The organic layer was washed with water, and was dried over anhydrous magnesium sulfate and was then concentrated under reduced pressure. The resulting residue was subjected to a silica gel column chromatography to give 1-{3-methyl-2-[2-methyl-4-(5-chloro-4-difluoromethyl-1-methyl-1H-pyrazol-3-yl)-phenoxymethyl]-phenyl}-4-methyl-1,4-dihydrotetrazole-5-one (hereinafter, referred to as "Present compound 256") 0.17 g.

Present compound 256

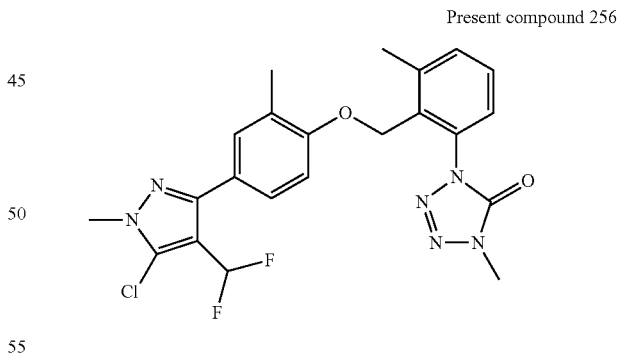

$^1$H-NMR (CDCl$_3$) δ: 7.43-7.40 (4H, m), 7.29-7.27 (1H, m), 6.90 (1H, d, J=8.9 Hz), 6.65 (1H, t, J=53.8 Hz), 5.07 (2H, s), 3.90 (3H, s), 3.63 (3H, s), 2.51 (3H, s), 2.13 (3H, s).

Preparation Example 257

A similar reaction to Preparation example 248 using N-chlorosuccinimide instead of N-bromosuccinimide gave 1-{2-[4-(4-chloro-3,5-dimethyl-pyrazol-1-yl)-2-chloro-phenoxymethyl]-3-methyl-phenyl}-4-methyl-1,4-dihydrotetrazole-5-one (hereinafter, referred to as "Present compound 257")

Present compound 257

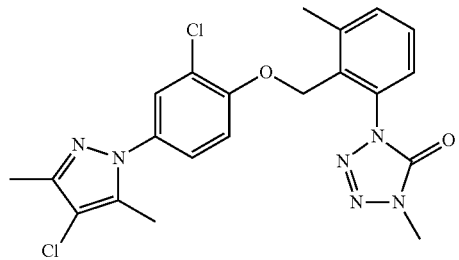

¹H-NMR (CDCl₃) δ: 7.46-7.40 (3H, m), 7.30 (1H, dd, J=7.5, 1.6 Hz), 7.21 (1H, dd, J=8.7, 2.6 Hz), 6.95 (1H, d, J=8.8 Hz), 5.19 (2H, s), 3.68 (3H, s), 2.54 (3H, s), 2.27 (3H, s), 2.26 (3H, s).

Preparation Example 258

A similar reaction to Preparation example 2 using 4-(1,4-dimethyl-5-methylthio-1H-pyrazol-3-yl)-2-methyl-phenol (described in Reference Preparation example 181) instead of 2-methyl-4-(3,4,5-trimethyl-pyrazol-1-yl)-phenol gave 1-{3-chloro-2-{2-methyl-4-(1,4-dimethyl-5-methyl-thio-1H-pyrazol-3-yl)-phenoxymethyl]-phenyl}-4-methyl-1,4-dihydrotetrazole-5-one (hereinafter, referred to as "Present compound 258").

Present compound 258

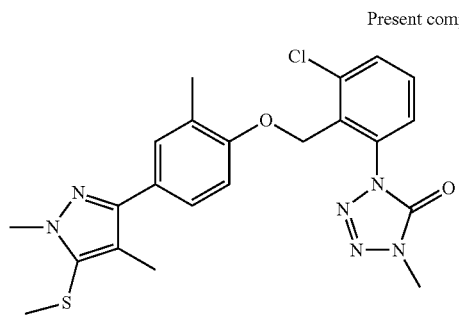

¹H-NMR (CDCl₃) δ: 7.62 (1H, t, J=4.0 Hz), 7.50-7.37 (4H, m), 6.89 (1H, d, J=8.5 Hz), 5.35 (2H, s), 3.98 (3H, s), 3.59 (3H, s), 2.26 (6H, s), 2.06 (3H, s).

Preparation Example 259

A similar reaction to Preparation example 7 using 4-(1,4-dimethyl-5-methylthio-1H-pyrazol-3-yl)-2-methyl-phenol (described in Reference Preparation example 181) instead of 2-methyl-4-(3,4,5-trimethyl-pyrazol-1-yl)-phenol gave 1-{3-methoxy-2-{2-methyl-4-(1,4-dimethyl-5-methyl-thio-1H-pyrazol-3-yl)-phenoxymethyl]-phenyl}-4-methyl-1,4-dihydrotetrazole-5-one (hereinafter, referred to as "Present compound 259").

Present compound 259

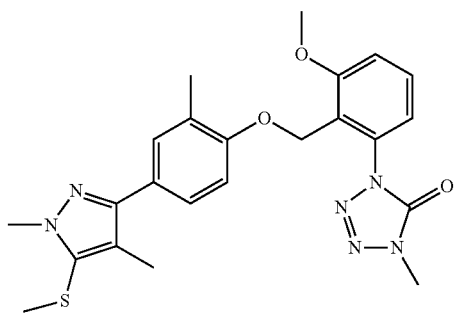

¹H-NMR (CDCl₃) δ: 7.46 (1H, t, J=8.2 Hz), 7.39-7.38 (1H, m), 7.36 (1H, dd, J=8.3, 2.2 Hz), 7.09-7.06 (2H, m), 6.91 (1H, d, J=8.4 Hz), 5.28 (2H, s), 3.97 (3H, s), 3.92 (3H, s), 3.58 (3H, s), 2.25 (3H, s), 2.25 (3H, s), 2.03 (3H, s).

Preparation Example 260

A similar reaction to Preparation example 5 using 4-(1,4-dimethyl-5-methylthio-1H-pyrazol-3-yl)-2-methyl-phenol (described in Reference Preparation example 181) instead of 2-methyl-4-(3,4,5-trimethyl-pyrazol-1-yl)-phenol gave 1-{3-ethyl-2-{(2-methyl-4-(1,4-dimethyl-5-methyl-thio-1H-pyrazol-3-yl)-phenoxymethyl]-phenyl}-4-methyl-1,4-dihydrotetrazole-5-one (hereinafter, referred to as "Present compound 260").

Present compound 260

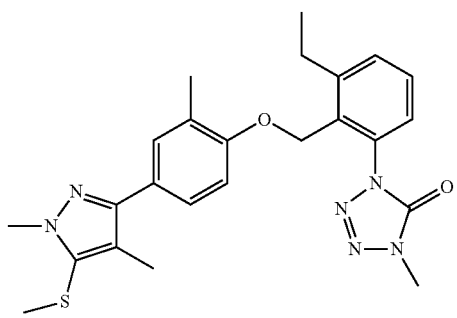

¹H-NMR (CDCl₃) δ: 7.49-7.42 (3H, m), 7.40 (1H, dd, J=8.5, 2.2 Hz), 7.28 (1H, dd, J=7.0, 2.0 Hz), 6.89 (1H, d, J=8.4 Hz), 5.08 (2H, s), 3.98 (3H, s), 3.59 (3H, s), 2.85 (2H, q, J=7.6 Hz), 2.26 (6H, s), 2.11 (3H, s), 1.28 (3H, t, J=7.6 Hz).

Preparation Example 261

A similar reaction to Preparation example 1 using 4-(1,4-dimethyl-5-methylthio-1H-pyrazol-3-yl)-2-methyl-phenol (described in Reference Preparation example 181) instead of 2-methyl-4-(3,4,5-trimethyl-pyrazol-1-yl)-phenol gave 1-{3-fluoro-2-{2-methyl-4-(1,4-dimethyl-5-methyl-thio-1H-pyrazol-3-yl)-phenoxymethyl]-phenyl}-4-methyl-,4-dihydrotetrazole-5-one (hereinafter, referred to as "Present compound 261").

Present compound 261

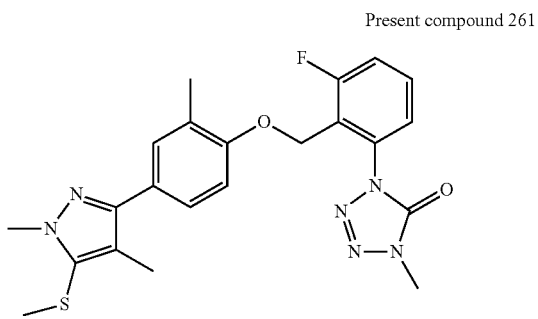

$^1$H-NMR (CDCl$_3$) δ: 7.53-7.47 (1H, m), 7.41-7.40 (1H, m), 7.38 (1H, dd, J=8.5, 1.9 Hz), 7.33-7.26 (2H, m), 6.89 (1H, d, J=8.4 Hz), 5.30 (2H, s), 3.98 (3H, s), 3.59 (3H, s), 2.26 (3H, s), 2.25 (3H, s), 2.02 (3H, s).

Preparation Example 262

2,4-Dimethyl-5-{3-methyl-4-[2-methyl-6-(4-methyl-5-oxo-4,5-dihydro-tetrazol-1-yl)-benzyloxy]-phenyl}-2H-pyrazole-3-carbonylchloride 2.1 g (described in Reference Preparation example 227) was dissolved in tetrahydrofuran 30 ml. To 28-30% aqueous ammonia solution 70 ml with stirring at room temperature was added dropwise the above-prepared tetrahydrofuran solution 30 ml, and the resulting mixture was stirred for another two hours. The precipitates were filtered and were washed with water 30 ml and hexane 30 ml, and were then dried under reduced pressure to give 1-{3-methyl-2-[2-methyl-4-(5-aminocarbonyl-1,4-dimethyl-1H-pyrazol-3-yl)-phenoxymethyl]-phenyl}-4-methyl-1,4-dihydrotetrazole-5-one (hereinafter, referred to as "Present compound 262") 2 g.

Present compound 262

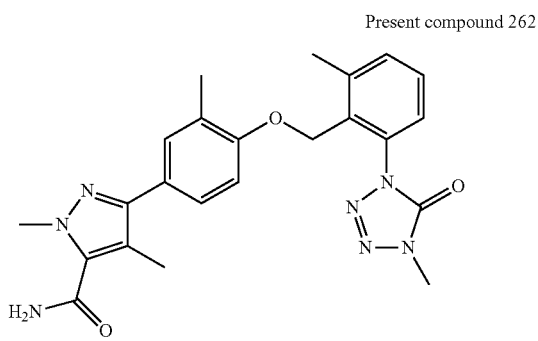

$^1$H-NMR (CDCl$_3$) δ: 7.45-7.40 (2H, m), 7.34-7.31 (2H, m), 7.30-7.27 (1H, m), 6.90 (1H, d, J=8.4 Hz), 5.75 (2H, br s), 5.07 (2H, s), 4.13 (3H, s), 3.64 (3H, s), 2.52 (3H, s), 2.36 (3H, s), 2.13 (3H, s).

Preparation Example 263

At 0° C., to a mixture of 1-{3-methyl-2-[2-methyl-4-(5-aminocarbonyl-1,4-dimethyl-1H-pyrazol-3-yl)-phenoxymethyl]-phenyl}-4-methyl-1,4-dihydrotetrazole-5-one (Present compound 262) 0.5 g and pyridine 10 ml was added phosphorus oxychloride 0.26 g. The resulting mixture was stirred at room temperature for three hours and thereto was added water 30 ml. The precipitates were filtered and were washed with water 10 ml and hexane 10 ml, and were then dried under reduced pressure to give 1-{3-methyl-2-[2-methyl-4-(5-cyano-1,4-dimethyl-1H-pyrazol-3-yl)-phenoxymethyl]-phenyl}-4-methyl-1,4-dihydrotetrazole-5-one (hereinafter, referred to as "Present compound 263") 0.38 g.

Present compound 263

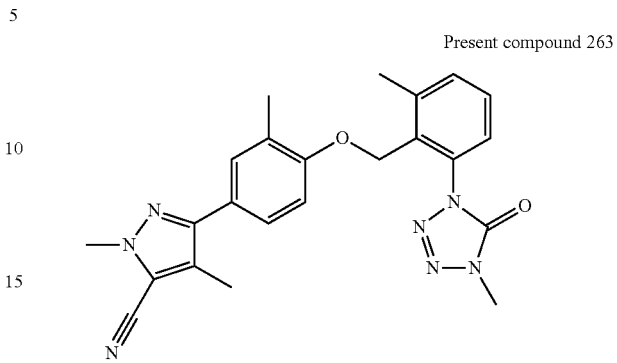

$^1$H-NMR (CDCl$_3$) δ: 7.46-7.40 (3H, m), 7.37 (1H, dd, J=8.4, 1.8 Hz), 7.28 (1H, dd, J=6.9, 2.2 Hz), 6.90 (1H, d, J=8.4 Hz), 5.07 (2H, s), 4.03 (3H, s), 3.64 (3H, s), 2.51 (3H, s), 2.33 (3H, s), 2.13 (3H, s).

Preparation Example 264

At room temperature, to a mixture of 1-{3-methyl-2-[2-methyl-4-(3,5-dimethyl-pyrazol-1-yl)-phenoxymethyl]-phenyl}-4-methyl-1,4-dihydrotetrazole-5-one (described in Preparation example 20) (Present compound 20) 0.3 g and chloroform 5 ml wad added N-bromosuccinimide 0.14 g. The resulting mixture was stirred at room temperature for twelve hours and thereto added water 5 ml. The resulting mixture was extracted with chloroform. The organic layer was washed with water, aqueous sodium thiosulfate solution and aqueous sodium carbonate solution, and was dried over anhydrous magnesium sulfate and was then concentrated under reduced pressure to give 1-{3-methyl-2-[2-methyl-4-(4-bromo-3,5-dimethyl-pyrazol-1-yl)-phenoxymethyl]-phenyl}-4-methyl-1,4-dihydrotetrazole-5-one (hereinafter, referred to as "Present compound 264") 0.3 g.

Present compound 264

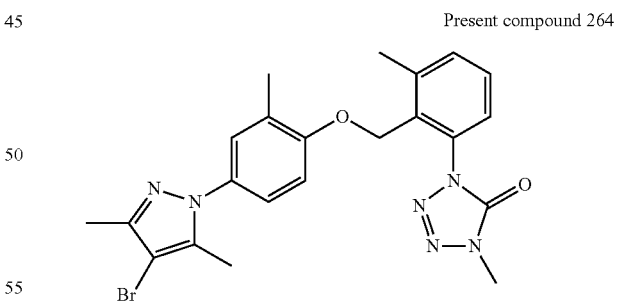

$^1$H-NMR (CDCl$_3$) δ: 7.46-7.41 (2H, m), 7.29 (1H, dd, J=7.1, 2.3 Hz), 7.15-7.15 (1H, m), 7.11 (1H, dd, J=8.5, 2.7 Hz), 6.87 (1H, d, J=8.7 Hz), 5.06 (2H, s), 3.65 (3H, s), 2.51 (3H, s), 2.28 (3H, s), 2.25 (3H, s), 2.12 (3H, s).

Preparation Example 265

A similar reaction to Preparation example 264 using N-chlorosuccinimide instead of N-bromosuccinimide gave 1-{3-methyl-2-[2-methyl-4-(4-chloro-3,5-dimethyl-pyrazol-1-yl)-phenoxymethyl]-phenyl}-4-methyl-1,4-dihydro-tetrazole-5-one (hereinafter, referred to as "Present compound 265").

Present compound 265

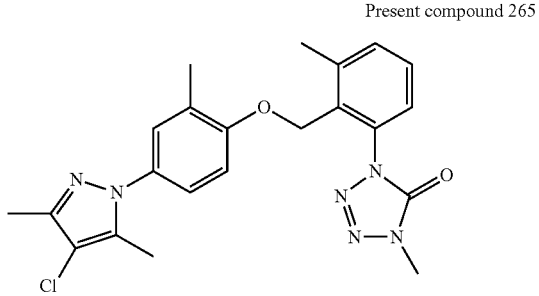 [SMILES: Cc1cccc(-n2nnn(C)c2=O)c1COc1ccc(-n2nc(C)c(Cl)c2C)cc1Cl]

¹H-NMR (CDCl₃) δ: 7.46-7.40 (2H, m), 7.29 (1H, dd, J=7.2, 1.9 Hz), 7.15 (1H, d, J=2.7 Hz), 7.11 (1H, dd, J=8.6, 2.6 Hz), 6.87 (1H, d, J=8.5 Hz), 5.06 (2H, s), 3.64 (3H, s), 2.51 (3H, s), 2.27 (3H, s), 2.24 (3H, s), 2.12 (3H, s).

Preparation Example 266

A similar reaction to Preparation example 239 using methanol instead of 2-propyne-1-ol gave 1-{3-methyl-2-[2-methyl-4-(4-formyl-5-methoxy-1-methyl-1H-pyrazol-3-yl)-phenoxymethyl]-phenyl}-4-methyl-1,4-dihydrotetrazole-5-one (hereinafter, referred to as "Present compound 266").

Present compound 266

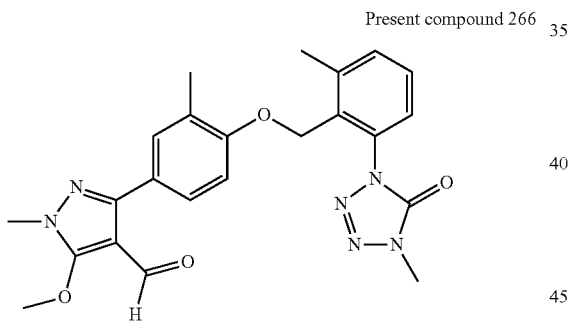

¹H-NMR (CDCl₃) δ: 9.73 (1H, s), 7.45-7.40 (2H, m), 7.37-7.35 (2H, m), 7.28 (1H, dd, J=6.8, 2.4 Hz), 6.91 (1H, d, J=9.2 Hz), 5.08 (2H, s), 4.29 (3H, s), 3.71 (3H, s), 3.64 (3H, s), 2.51 (3H, s), 2.13 (3H, s).

Preparation Example 267

A similar reaction to Preparation example 256 using 1-{(3-methyl-2-[2-methyl-4-(4-formyl-5-methoxy-1-methyl-1H-pyrazol-3-yl)-phenoxymethyl]-phenyl}-4-methyl-1,4-dihydrotetrazole-5-one (Present compound 266) instead of 1-{(3-methyl-2-[2-methyl-4-(4-formyl-5-chloro-1-methyl-1H-pyrazol-3-yl)-phenoxymethyl]-phenyl}-4-methyl-1,4-dihydrotetrazole-5-one (Present compound 207) gave 1-{3-methyl-2-[2-methyl-4-(4-difluoromethyl-5-methoxy-1-methyl-1H-pyrazol-3-yl)-phenoxymethyl]-phenyl}-4-methyl-1,4-dihydrotetrazole-5-one (hereinafter, referred to as "Present compound 267").

Present compound 267

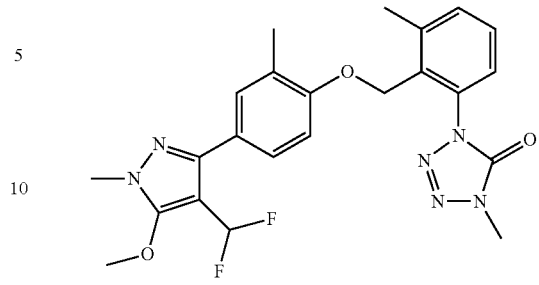

¹H-NMR (CDCl₃) δ: 7.45-7.40 (2H, m), 7.33-7.27 (3H, m), 6.89 (1H, d, J=8.5 Hz), 6.59 (1H, t, J=54.7 Hz), 5.07 (2H, s), 4.13 (3H, s), 3.71 (3H, s), 3.63 (3H, s), 2.51 (3H, s), 2.12 (3H, s).

Preparation Example 268

A similar reaction to Preparation example 5 using 1-(4-hydroxy-3-methyl-phenyl)-propane-1-one (described in Reference Preparation example 114) instead of 2-methyl-4-(3,4,5-trimethyl-pyrazol-1-yl)-phenol gave 1-[2-(2-methyl-4-propionyl-phenoxymethyl]-3-ethyl-phenyl}-4-methyl-, 4-dihydrotetrazole-5-one (hereinafter, referred to as "Present compound 268").

Present compound 268

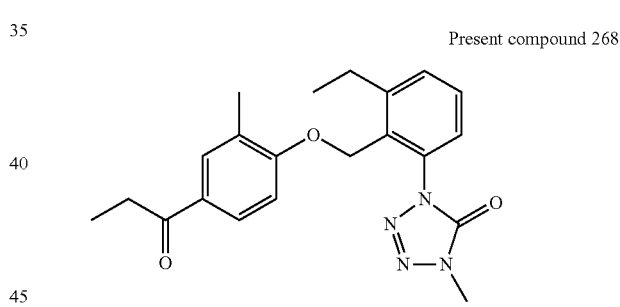

¹H-NMR (CDCl₃) δ: 7.81 (1H, dd, J=8.5, 2.2 Hz), 7.76-7.75 (1H, m), 7.52-7.45 (2H, m), 7.30 (1H, dd, J=7.5, 1.8 Hz), 6.88 (1H, d, J=8.6 Hz), 5.12 (2H, s), 3.59 (3H, s), 2.95 (2H, q, J=7.4 Hz), 2.84 (2H, q, J=7.6 Hz), 2.11 (3H, s), 1.28 (3H, t, J=7.6 Hz), 1.21 (3H, t, J=7.4 Hz).

Preparation Example 269

A similar reaction to Preparation example 97 using 1-{2-[4-(3-dimethylamino-acryloyl)-2-methyl-phenoxymethyl]-3-methyl-phenyl}-4-methyl-1,4-dihydro-tetrazole-5-one (described in Reference Preparation example 228) instead of 1-{2-[4-(3-dimethylamino-acryloyl)-2-methyl-phenoxymethyl]-3-methoxy-phenyl}-4-methyl-1,4-dihydro-tetrazole-5-one gave 1-{3-methyl-2-[2-methyl-4-(H-pyrazol-3-yl)-phenoxymethyl]-phenyl}-4-methyl-1,4-dihydrotetrazole-5-one (hereinafter, referred to a "Present compound 269").

Present compound 269

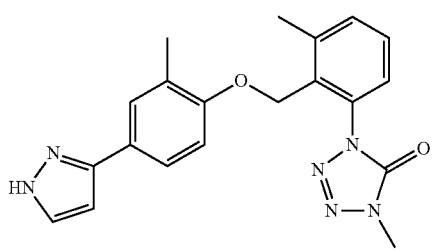

¹H-NMR (CDCl₃) δ: 7.59 (1H, d, J=2.3 Hz), 7.51-7.48 (2H, m), 7.45-7.39 (2H, m), 7.28 (1H, dd, J=6.9, 2.4 Hz), 6.89-6.87 (1H, m), 6.52 (1H, d, J=2.3 Hz), 5.07 (2H, s), 3.62 (3H, s), 2.51 (3H, s), 2.13 (3H, s).

Preparation Example 270

A similar reaction to Preparation example 252 using 3-methyl-4-{3-methyl-4-[2-ethyl-6-(4-methyl-5-oxo-4,5-dihydrotetrazol-1-yl)-benzyloxy]-phenyl}-2,4-dioxo-butyric acid ethyl ester (described in Reference Preparation example 229) instead of 3-methyl-4-{3-methyl-4-[2-methyl-6-(4-methyl-5-oxo-4,5-dihydrotetrazol-1-yl)-benzyloxy]-phenyl}-2,4-dioxo-butyric acid ethyl ester gave 1-{3-ethyl-2-[2-methyl-4-(5-ethoxycarbonyl-4-methyl-1H-pyrazol-3-yl)-phenoxymethyl]-phenyl}-4-methyl-1,4-dihydrotetrazole-5-one (hereinafter, referred to as "Present compound 270").

Present compound 270

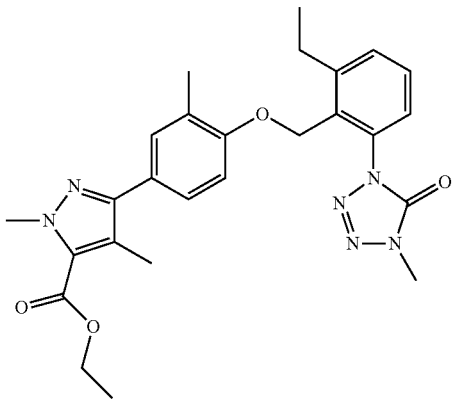 [SMILES: CCOC(=O)c1c(C)c(-c2ccc(OCc3c(CC)cccc3-n3nnn(C)c3=O)c(C)c2)nn1C]

¹H-NMR (CDCl₃) δ: 7.51-7.45 (2H, m), 7.34-7.32 (2H, m), 7.29 (1H, dd, J=7.1, 2.1 Hz), 6.93 (1H, d, J=8.0 Hz), 5.10 (2H, s), 4.42 (2H, q, J=7.2 Hz), 3.60 (3H, s), 2.86 (2H, q, J=7.6 Hz), 2.41 (3H, s), 2.13 (3H, s), 1.42 (3H, t, J=7.2 Hz), 1.29 (3H, t, J=7.6 Hz).

Preparation Example 271

A mixture of 1-{3-ethyl-2-[2-methyl-4-(5-ethoxycarbonyl-4-methyl-1H-pyrazol-3-yl)-phenoxymethyl]-phenyl}-4-methyl-1,4-dihydrotetrazole-5-one (Present compound 270) 3.3 g, dimethyl sulfate 2.6 g and toluene 50 ml was stirred at 100° C. for six hours. To the resulting mixture was added water 10 ml at room temperature, and the resulting mixture was extracted with ethyl acetate. The organic layers was washed with water and was dried over anhydrous magnesium sulfate and was then concentrated under reduced pressure. The resulting residue was subjected to a silica gel column chromatography to give 1-{3-ethyl-2-[2-methyl-4-(5-ethoxycarbonyl-1,4-dimethyl-1H-pyrazol-3-yl)-phenoxymethyl]-phenyl}-4-methyl-1,4-dihydrotetrazole-5-one (hereinafter, referred to as "Present compound 271") 1.8 g.

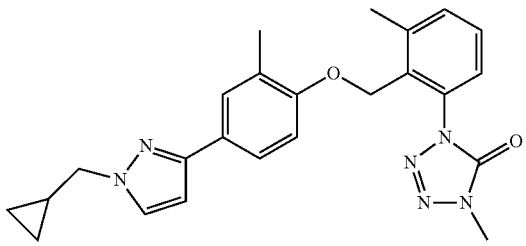

¹H-NMR (CDCl₃) δ: 7.50-7.44 (2H, m), 7.34-7.31 (2H, m), 7.29 (1H, dd, J=7.0, 2.2 Hz), 6.91 (1H, d, J=8.2 Hz), 5.08 (2H, s), 4.40 (2H, q, J=7.2 Hz), 4.17 (3H, s), 3.60 (3H, s), 2.85 (2H, q, J=7.6 Hz), 2.36 (3H, s), 2.12 (3H, s), 1.42 (3H, t, J=7.1 Hz), 1.29 (3H, t, J=7.6 Hz).

Preparation Example 272

A similar reaction to Preparation example 132 using 1-{3-methyl-2-[2-methyl-4-(1H-pyrazol-3-yl)-phenoxymethyl]-phenyl}-4-methyl-1,4-dihydrotetrazole-5-one (Present compound 269) instead of 1-{3-methoxy-2-[2-methyl-4-(1H-pyrazol-3-yl)-phenoxymethyl]-phenyl}-4-methyl-1,4-dihydrotetrazole-5-one (Present compound 97) gave 1-{3-methyl-2-[2-methyl-4-(1-cyclopropylmethyl-1H-pyrazol-3-yl)-phenoxymethyl]-phenyl}-4-methyl-1,4-dihydrotetrazole-5-one (hereinafter, referred to as "Present compound 272").

Present compound 272

¹H-NMR (CDCl₃) δ: 7.58-7.57 (1H, m), 7.53 (1H, dd, J=7.8, 1.9 Hz), 7.50 (1H, d, J 2.3 Hz), 7.43-7.39 (2H, m), 7.28-7.26 (1H, m), 6.85 (1H, d, J=8.4 Hz), 6.46 (1H, d, J=2.3 Hz), 5.05 (2H, s), 4.02 (2H, d, J=7.0 Hz), 3.61 (3H, s), 2.51 (3H, s), 2.12 (3H, s), 1.35-1.31 (1H, m), 0.68-0.63 (2H, m), 0.41-0.37 (2H, m).

Preparation Example 273

A similar reaction to Preparation example 262 using 2,4-dimethyl-5-{3-methyl-4-[2-ethyl-6-(4-methyl-5-oxo-4, 5-dihydro-tetrazol-1-yl)-benzyloxy]-phenyl}-2H-pyrazole-3-carbonyl chloride (described in Reference Preparation example 230) instead of 2,4-dimethyl-5-{3-methyl-4-[2-methyl-6-(4-methyl-5-oxo-4,5-dihydro-tetrazol-1-yl)-benzyloxy]-phenyl}-2H-pyrazole-3-carbonyl chloride gave 1-{3-ethyl-2-[2-methyl-4-(5-aminocarbonyl-1,4-dimethyl-1H-pyrazol-3-yl)-phenoxymethyl]-phenyl}-4-methyl-1,4-dihydrotetrazole-5-one (hereinafter, referred to as "Present compound 273").

Present compound 273

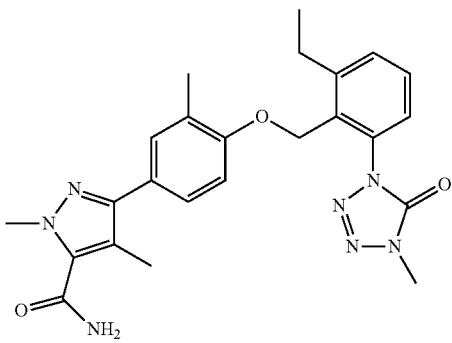

¹H-NMR (CDCl₃) δ: 7.50-7.44 (2H, m), 7.33-7.28 (3H, m), 6.91 (1H, d, J=8.2 Hz), 5.83 (2H, br s), 5.09 (2H, s), 4.12 (3H, s), 3.60 (3H, s), 2.85 (2H, q, J=7.6 Hz), 2.35 (3H, s), 2.12 (3H, s), 1.28 (3H, t, J=7.6 Hz).

Preparation Example 274

A similar reaction to Preparation example 263 using 1-{3-ethyl-2-[2-methyl-4-(5-aminocarbonyl-1,4-dimethyl-1H-pyrazol-3-yl)-phenoxymethyl]-phenyl}-4-methyl-1,4-dihydrotetrazole-5-one (described in Preparation example 273) (Present compound 273) instead of 1-{3-methyl-2-[2-methyl-4-(5-aminocarbonyl-1,4-dimethyl-1H-pyrazol-3-yl)-phenoxymethyl]-phenyl}-4-methyl-1,4-dihydrotetrazole-5-one (Present compound 262) gave 1-{3-ethyl-2-[2-methyl-4-(5-cyano-1,4-dimethyl-1H-pyrazol-3-yl)-phenoxymethyl]-phenyl}-4-methyl-1,4-dihydrotetrazole-5-one (hereinafter, referred to as "Present compound 274").

Present compound 274

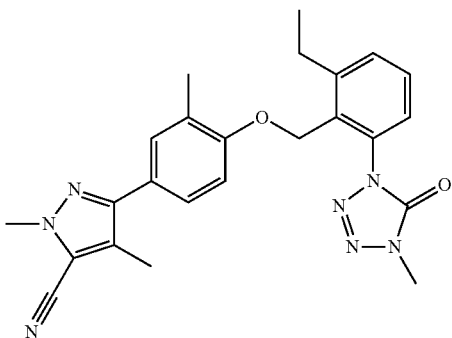

¹H-NMR (CDCl₃) δ: 7.51-7.44 (2H, m), 7.40-7.36 (2H, m), 7.29 (1H, dd, J=7.1, 2.1 Hz), 6.91 (1H, d, J=8.5 Hz), 5.09 (2H, s), 4.03 (3H, s), 3.60 (3H, s), 2.85 (2H, q, J=7.6 Hz), 2.34 (3H, s), 2.12 (3H, s), 1.29 (3H, t, J=7.6 Hz).

Preparation Example 275

At room temperature, to a mixture of 1-{3-methyl-2-[2-methyl-4-(1H-pyrazol-3-yl)-phenoxymethyl]-phenyl}-4-methyl-1,4-dihydrotetrazole-5-one (described in Preparation example 269) (Present compound 269) 0.4 g and N,N-dimethylformamide 4 ml was added 55% sodium hydride 0.056 g and the resulting mixture was stirred for one hour, and thereto was then added trifluoromethanesulfonic acid 2,2,2-trifluoroethyl ester 0.7 g. The resulting mixture was stirred at 55° C. for twenty four hours. Thereto was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-{4-[1-(2,2,2-trifluoroethyl)-1H-pyrazol-3-yl)-2-methyl-phenoxymethyl}-3-methyl-phenyl)-4-methyl-1,4-dihydrotetrazole-5-one (hereinafter, referred to as "Present compound 275") 0.22 g.

Present compound 275

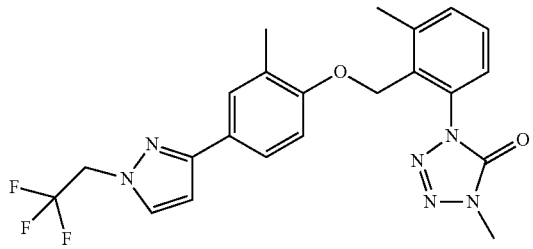

¹H-NMR (CDCl₃) δ: 7.57 (1H, s), 7.55-7.53 (1H, m), 7.50 (1H, d, J=2.3 Hz), 7.45-7.39 (2H, m), 7.29-7.27 (1H, m), 6.86 (1H, d, J=8.2 Hz), 6.57 (1H, d, J=2.5 Hz), 5.07 (2H, s), 4.73 (2H, q, J=8.4 Hz), 3.62 (3H, s), 2.51 (3H, s), 2.13 (3H, s).

Preparation Example 276

A similar reaction to Preparation example 275 using 3-bromopropyne instead of trifluoromethanesulfonic acid 2,2,2-trifluoroethyl ester gave 1-(2-{4-[1-(2-propynyl)-1H-pyrazol-3-yl)-2-methyl-phenoxymethyl]-3-methyl-phenyl)-4-methyl-1,4-dihydrotetrazole-5-one (hereinafter, referred to as "Present compound 276").

Present compound 276

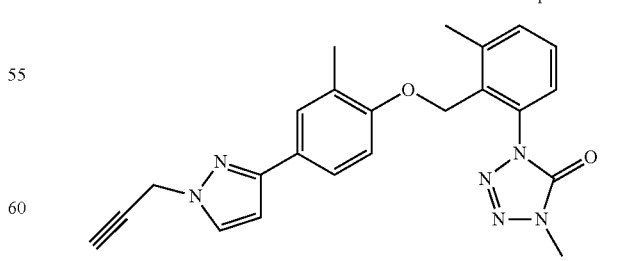

¹H-NMR (CDCl₃) δ: 7.58 (2H, d, J=21.1 Hz), 7.53-7.51 (1H, m), 7.43-7.37 (2H, m), 7.28-7.24 (1H, m), 6.84 (1H, d, J=8.2 Hz), 6.49 (1H, s), 5.04 (2H, s), 4.96 (2H, s), 3.60 (3H, s), 2.49 (4H, s), 2.10 (3H, s).

Preparation Example 277

A similar reaction to Preparation example 275 using 1-bromo-2-butyne instead of trifluoromethanesulfonic acid 2,2,2-trifluoroethyl ester gave 1-(2-{4-[1-(2-butynyl)-1H-pyrazol-3-yl]-2-methyl-phenoxymethyl]-3-methyl-phenyl)-4-methyl-1,4-dihydrotetrazole-5-one (hereinafter, referred to as "Present compound 277").

Present compound 277

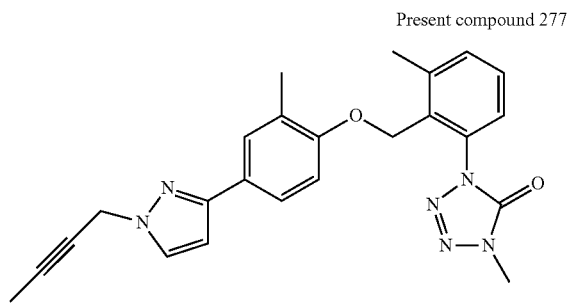 [SMILES: CC#CCn1ccc(-c2ccc(OCc3c(C)cccc3-n3nnn(C)c3=O)c(C)c2)n1]

$^1$H-NMR (CDCl$_3$) δ: 7.61 (1H, d, J=2.3 Hz), 7.57-7.57 (1H, m), 7.55-7.52 (1H, m), 7.44-7.39 (2H, m), 7.29-7.27 (1H, m), 6.85 (1H, d, J=8.5 Hz), 6.49 (1H, d, J=2.3 Hz), 5.06 (2H, s), 4.92 (2H, q, J=2.5 Hz), 3.61 (3H, s), 2.51 (3H, s), 2.12 (3H, s), 1.89 (3H, t, J=2.5 Hz).

Preparation Example 278

A similar reaction to Preparation example 2 using 1-(4-hydroxy-3-methyl-phenyl)-propane-1-one (described in Reference Preparation example 114) instead of 2-methyl-4-(3,4,5-trimethyl-pyrazol-1-yl)-phenol gave 1-[2-(2-methyl-4-propionyl-phenoxymethyl]-3-chloro-phenyl)-4-methyl-1,4-dihydrotetrazole-5-one (hereinafter, referred to as "Present compound 278").

Present compound 278

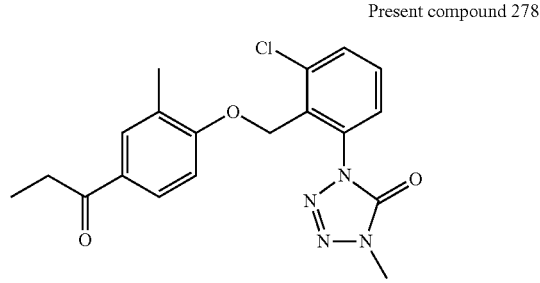 [SMILES: CCC(=O)c1ccc(OCc2c(Cl)cccc2-n2nnn(C)c2=O)c(C)c1]

$^1$H-NMR (CDCl$_3$) δ: 7.79 (1H, dd, J=8.5, 2.2 Hz), 7.74-7.73 (1H, m), 7.62 (1H, dd, J=8.2, 1.1 Hz), 7.48 (1H, t, J=7.9 Hz), 7.41 (1H, dd, J=7.9, 1.1 Hz), 6.87 (1H, d, J=8.6 Hz), 5.37 (2H, s), 3.59 (3H, s), 2.93 (2H, q, J=7.3 Hz), 2.05 (3H, s), 1.19 (3H, t, J=7.2 Hz).

Preparation Example 279

A similar reaction to Preparation example 252 using 3-methyl-4-{3-methyl-4-[2-chloro-6-(4-methyl-5-oxo-4,5-dihydro-tetrazol-1-yl)-benzyloxy]-phenyl}-2,4-dioxo-butyric acid ethyl ester (described in Reference Preparation example 231) instead of 3-methyl-4-{3-methyl-4-[2-methyl-6-(4-methyl-5-oxo-4,5-dihydro-tetrazol-1-yl)-benzyloxy]-phenyl}-2,4-dioxo-butyric acid ethyl ester gave 1-{3-chloro-2-[2-methyl-4-(5-ethoxycarbonyl-4-methyl-1H-pyrazol-3-yl)-phenoxymethyl]-phenyl)-4-methyl-1,4-dihydrotetrazole-5-one (hereinafter, referred to as "Present compound 279").

Present compound 279

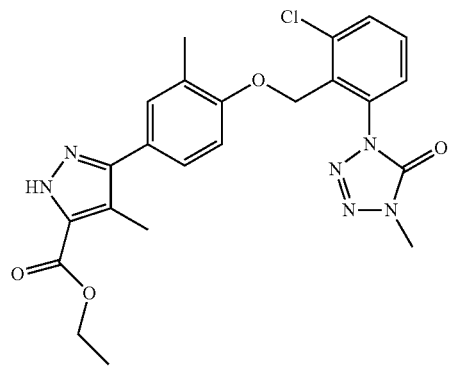

$^1$H-NMR (CDCl$_3$) δ: 7.62 (1H, dd, J=8.0, 1.4 Hz), 7.47 (1H, t, J=8.0 Hz), 7.40 (1H, dd, J=8.0, 1.4 Hz), 7.32-7.30 (2H, m), 6.91 (1H, d, J=8.9 Hz), 5.35 (2H, s), 4.40 (2H, q, J=7.2 Hz), 3.61 (3H, s), 2.40 (3H, s), 2.07 (3H, s), 1.40 (3H, t, J=7.2 Hz).

Preparation Example 280

A similar reaction to Preparation example 271 using 1-{3-chloro-2-[2-methyl-4-(5-ethoxycarbonyl-4-methyl-1H-pyrazol-3-yl)-phenoxymethyl]-phenyl)-4-methyl-1,4-dihydrotetrazole-5-one (Present compound 279) instead of 1-{3-ethyl-2-[2-methyl-4-(5-ethoxycarbonyl-4-methyl-1H-pyrazol-3-yl)-phenoxymethyl]-phenyl}-4-methyl-1,4-dihydrotetrazole-5-one gave 1-{3-chloro-2-[2-methyl-4-(5-ethoxycarbonyl-1,4-dimethyl-1H-pyrazol-3-yl)-phenoxymethyl]-phenyl}-4-methyl-1,4-dihydrotetrazole-5-one (hereinafter, referred to as "Present compound 280")

Present compound 280

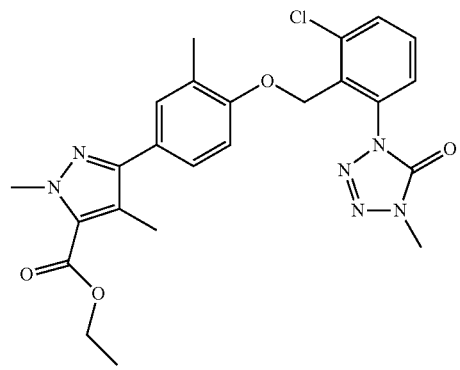

$^1$H-NMR (CDCl$_3$) δ: 7.62 (1H, dd, J=8.0, 1.4 Hz), 7.48 (1H, t, J=8.0 Hz), 7.41 (1H, dd, J=8.0, 1.4 Hz), 7.34-7.30 (2H, m), 6.90 (1H, d, J=8.2 Hz), 5.35 (2H, s), 4.40 (2H, q, J=7.1 Hz), 4.16 (3H, s), 3.61 (3H, s), 2.36 (3H, s), 2.07 (3H, s), 1.42 (3H, t, J=7.1 Hz).

Preparation Example 281

A similar reaction to Preparation example 262 using 2,4-Dimethyl-5-{3-methyl-4-[2-chloro-6-(4-methyl-5-oxo- 4,5-dihydro-tetrazol-1-yl)-benzyloxy]-phenyl}-2H-pyrazole-3-carbonylchloride (described in Reference Preparation example 234) instead of 2,4-Dimethyl-5-{3-methyl-4-[2-methyl-6-(4-methyl-5-oxo-4,5-dihydro-tetrazol-1-yl)-benzyloxy]-phenyl}-2H-pyrazole-3-carbonylchloride gave 1-{3-chloro-2-[2-methyl-4-(5-aminocarbonyl-1,4-dimethyl-1H-pyrazol-3-yl)-phenoxymethyl]-phenyl}-4-methyl-1,4-dihydrotetrazole-5-one (hereinafter, referred to as "Present compound 281").

Present compound 281

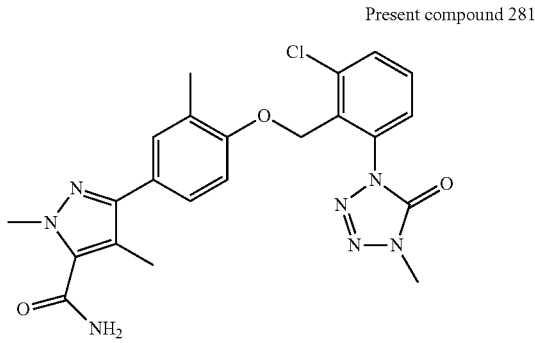 [SMILES: Cc1cc(-c2nn(C)c(C(N)=O)c2C)ccc1OCc1c(Cl)cccc1-n1nnn(C)c1=O]

¹H-NMR (DMSO-D₆) δ: 7.78 (1H, dd, J=8.0, 0.9 Hz), 7.63 (1H, t, J=8.1 Hz), 7.55 (1H, dd, J=8.0, 0.9 Hz), 7.40 (2H, br s), 7.29-7.27 (2H, m), 6.97 (1H, d, J=8.2 Hz), 5.16 (2H, s), 3.99 (3H, s), 3.51 (3H, s), 2.26 (3H, s), 1.97 (3H, s).

Preparation Example 282

A similar reaction to Preparation example 263 using 1-{3-chloro-2-[2-methyl-4-(5-aminocarbonyl-1,4-dimethyl-1H-pyrazol-3-yl)-phenoxymethyl]-phenyl}-4-methyl-1,4-dihydrotetrazole-5-one (Present compound 281) instead of 1-{(3-methyl-2-[2-methyl-4-(5-aminocarbonyl-1,4-dimethyl-1H-pyrazol-3-yl)-phenoxymethyl]-phenyl}-4-methyl-1,4-dihydrotetrazole-5-one (Present compound 262) gave 1-{3-chloro-2-[2-methyl-4-(5-cyano-1,4-dimethyl-1H-pyrazol-3-yl)-phenoxymethyl]-phenyl}-4-methyl-1,4-dihydrotetrazole-5-one (hereinafter, referred to as "Present compound 282").

Present compound 282

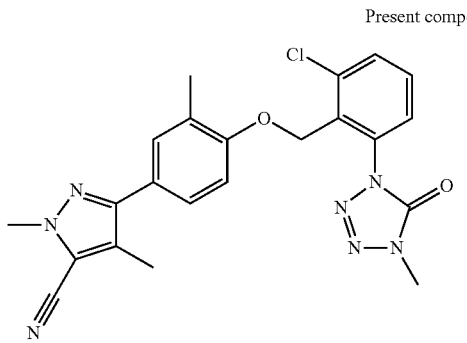

¹H-NMR (CDCl₃) δ: 7.61 (1H, dd, J=8.0, 1.4 Hz), 7.47 (1H, t, J=8.0 Hz), 7.40 (1H, dd, J=8.0, 1.4 Hz), 7.38-7.34 (2H, m), 6.89 (1H, d, J=8.5 Hz), 5.34 (2H, s), 4.01 (3H, s), 3.60 (3H, s), 2.32 (3H, s), 2.06 (3H, s).

Preparation Example 283

A similar reaction to Preparation example 116 using 1-{3-methyl-2-[2-methyl-4-(3,5-dimethyl-pyrazol-1-yl)-phenoxymethyl]-phenyl}-4-methyl-1,4-dihydrotetrazole-5-one (Present compound 20) instead of 1-{3-methoxy-2-[2-methyl-4-(3,5-dimethyl-pyrazol-1-yl)-phenoxymethyl]-phenyl}-4-methyl-1,4-dihydrotetrazole-5-one (Present compound 62) gave 1-{3-methyl-2-[2-methyl-4-(3,5-dimethyl-4-formyl-pyrazol-1-yl)-phenoxymethyl]-phenyl}-4-methyl-1,4-dihydrotetrazole-5-one (hereinafter, referred to as "Present compound 283").

Present compound 283

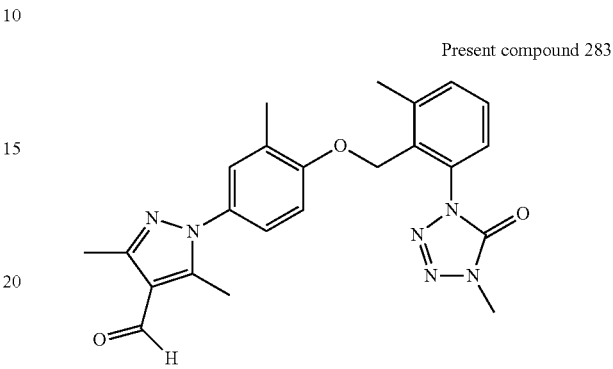

¹H-NMR (CDCl₃) δ: 10.00 (1H, s), 7.47-7.42 (2H, m), 7.29 (1H, dd, J=7.1, 1.7 Hz), 7.16-7.12 (2H, m), 6.90 (1H, d, J=8.4 Hz), 5.08 (2H, s), 3.66 (3H, s), 2.52-2.51 (9H, m), 2.13 (3H, s).

Preparation Example 284

A mixture of 1-{3-bromo-2-[2-methyl-4-(5-chloro-1,4-dimethyl-1H-pyrazol-3-yl)-phenoxymethyl]-phenyl}-4-methyl-1,4-dihydrotetrazole-5-one (Present compound 208) 0.9 g, tributyl-vinylstannane 0.6 g, teterakis-(triphenylphosphine)-palladium 0.4 g and toluene 10 ml was stirred with heating under reflux for seven hours. Thereto was added water 5 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{3-vinyl-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 284") 0.6 g.

Present compound 284

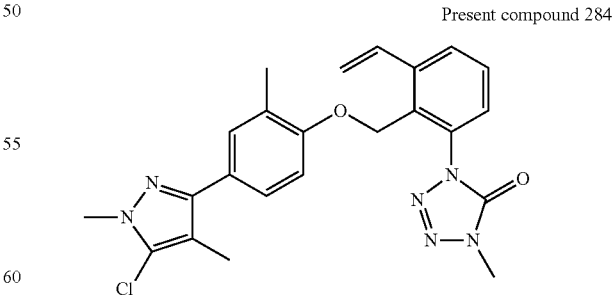

¹H-NMR (CDCl₃) δ: 7.71-7.69 (1H, m), 7.51 (1H, t, J=7.9 Hz), 7.41-7.40 (1H, m), 7.38-7.35 (2H, m), 7.06 (1H, dd, J=17.4, 10.9 Hz), 6.86 (1H, d, J=8.4 Hz), 5.74 (1H, dd, J=17.4, 1.1 Hz), 5.44 (1H, dd, J=10.9, 1.1 Hz), 5.10 (2H, s), 3.85 (3H, s), 3.63 (3H, s), 2.14 (3H, s), 2.12 (3H, s).

Preparation Example 285

To a mixture of 3,5-dimethyl-1-{3-methyl-4-[2-methyl-6-(4-methyl-5-oxo-4,5-dihydro-tetrazol-1-yl)-benzyloxy]-phenyl}-1H-pyrazole-4-carbaldehyde oxime (described in Reference Preparation example 235) and N,N-dimethylformamide 10 ml was added 2,4,6-trichloro-1,3,5-triazine 0.2 g, then the resulting mixture was stirred at room temperature for 7 hours and thereto was added water 30 ml. The precipitate was filtered and was washed with water 10 ml and was then dried under reduced pressure to give 3,5-Dimethyl-1-{3-methyl-4-[2-methyl-6-(4-methyl-5-oxo-4,5-dihydro-tetrazol-1-yl)-benzyloxy]-phenyl}-1H-pyrazole-4-carbonitrile (hereinafter, referred to as "Present compound 285") 0.4 g.

Present compound 285

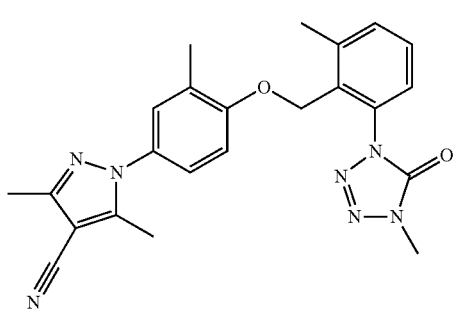

$^1$H-NMR (CDCl$_3$) δ: 7.47-7.41 (2H, m), 7.29 (1H, dd, J=7.2, 1.9 Hz), 7.14-7.11 (2H, m), 6.89 (1H, d, J=8.5 Hz), 5.08 (2H, s), 3.65 (3H, s), 2.51 (3H, s), 2.39 (3H, s), 2.39 (3H, s), 2.13 (3H, s).

Preparation Example 286

A similar reaction to Preparation example 4 using 1-(4-hydroxy-3-chloro-phenyl)-propane-1-one (described in Reference Preparation example 237) instead of 2-methyl-4-(3,4,5-trimethyl-pyrazol-1-yl)-phenol gave 1-[2-(2-chloro-4-propionyl-phenoxymethyl]-3-methyl-phenyl}-4-methyl-1,4-dihydrotetrazole-5-one (hereinafter, referred to as "Present compound 286").

Present compound 286

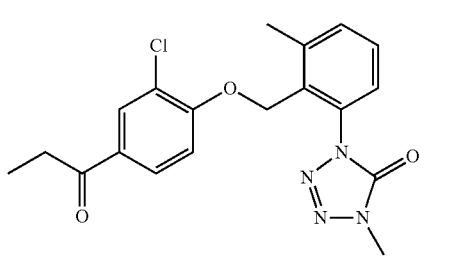

$^1$H-NMR (CDCl$_3$) δ: 7.97 (1H, d, J=2.3 Hz), 7.83 (1H, dd, J=8.6, 2.0 Hz), 7.46-7.39 (2H, m), 7.31 (1H, dd, J=7.4, 1.5 Hz), 6.93 (1H, d, J=8.8 Hz), 5.24 (2H, s), 3.67 (3H, s), 2.93 (2H, q, J=7.2 Hz), 2.53 (3H, s), 1.20 (3H, t, J=7.2 Hz).

Preparation Example 287

1-{3-chloro-2-[2-methyl-4-(3,5-dimethyl-4-formyl-pyrazol-1-yl)-phenoxymethyl]-phenyl}-4-methyl-1,4-dihydro-tetrazole-5-one (hereinafter, referred to as "Present compound 287") was obtained by reference to Preparation example 283.

Present compound 287

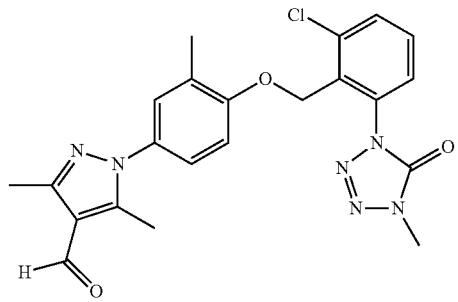

$^1$H-NMR (CDCl$_3$) δ: 9.98 (1H, s), 7.63-7.61 (1H, m), 7.51-7.46 (1H, m), 7.42-7.40 (1H, m), 7.13-7.11 (2H, m), 6.91 (1H, d, J=7.8 Hz), 5.34 (2H, s), 3.63 (3H, s), 2.49 (6H, s), 2.06 (3H, s).

Preparation Examples 288 and 289

A mixture of 1-{3-methyl-2-[2-methyl-4-(5-ethoxycarbonyl-4-methyl-1H-pyrazol-3-yl)-phenoxymethyl]-phenyl}-4-methyl-1,4-dihydrotetrazole-5-one (hereinafter, referred to as "Present compound 25") 3.8 g, diethyl sulfate 5.0 g and toluene 50 ml was stirred at 90° C. for six hours. To the resulting mixture was added water 10 ml at room temperature, and the resulting mixture was extracted with ethyl acetate. The organic layers was washed with water and was dried over anhydrous magnesium sulfate and was then concentrated under reduced pressure. The resulting residue was subjected to a silica gel column chromatography to give 1-{3-methyl-2-[2-methyl-4-(5-ethoxycarbonyl-1-ethyl-4-methyl-1H-pyrazol-3-yl)-phenoxymethyl]-phenyl}-4-methyl-1,4-dihydrotetrazole-5-one (hereinafter, referred to as "Present compound 288") and 1-{3-methyl-2-[2-methyl-4-(3-ethoxycarbonyl-1-ethyl-4-methyl-1H-pyrazol-3-yl)-phenoxymethyl]-phenyl}-4-methyl-1,4-dihydrotetrazole-5-one (hereinafter, referred to as "Present compound 289").

Present compound 288

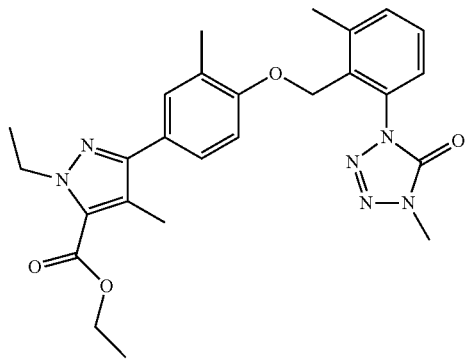

$^1$H-NMR (CDCl$_3$) δ: 7.45-7.40 (2H, m), 7.36-7.35 (1H, m), 7.33 (1H, dd, J=8.2, 2.3 Hz), 7.28 (1H, dd, J=6.8, 2.7 Hz), 6.90 (1H, d, J=8.2 Hz), 5.07 (2H, s), 4.59 (2H, q, J=7.2 Hz), 4.40 (2H, q, J=7.2 Hz), 3.64 (3H, s), 2.52 (3H, s), 2.36 (3H, s), 2.13 (3H, s), 1.43 (6H, q, J=7.1 Hz).

Present compound 289

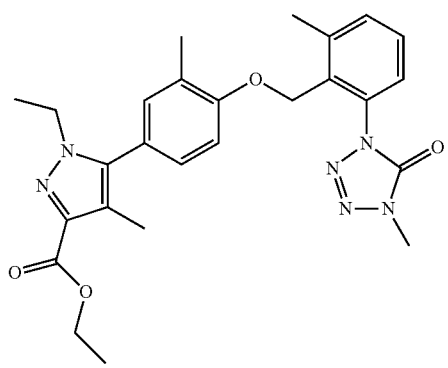

¹H-NMR (CDCl₃) δ: 7.46-7.41 (2H, m), 7.33-7.27 (3H, m), 6.92 (1H, d, J=7.9 Hz), 5.08 (2H, s), 4.44-4.39 (2H, m), 4.12 (2H, q, J=7.1 Hz), 3.64 (3H, s), 2.52 (3H, s), 2.41 (3H, s), 2.05 (3H, s), 1.42 (3H, t, J=7.1 Hz), 1.26 (3H, t, J=7.1 Hz).

Preparation Example 290

1-{3-chloro-2-[2-methyl-4-(4-cyano-3,5-dimethyl-pyrazol-1-yl)-phenoxymethyl]-phenyl}-4-methyl-1,4-dihydrotetrazole-5-one (hereinafter, referred to as "Present compound 290") was obtained by reference to Preparation example 285.

Present compound 290

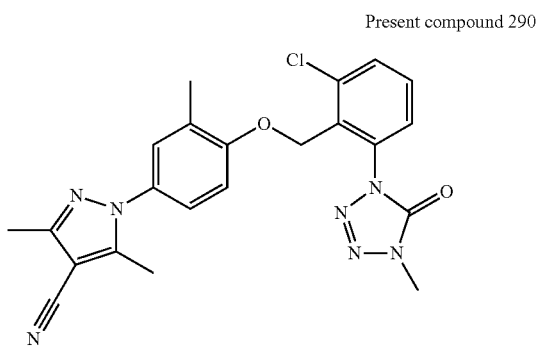 [SMILES: Cc1cc(-n2nc(C)c(C#N)c2C)ccc1OCc1c(Cl)cccc1-n1nnn(C)c1=O]

¹H-NMR (CDCl₃) δ: 7.62 (1H, dd, J=8.1, 1.3 Hz), 7.49 (1H, t, J=8.0 Hz), 7.41 (1H, dd, J=7.9, 1.3 Hz), 7.12-7.09 (2H, m), 6.90 (1H, d, J=8.2 Hz), 5.34 (2H, s), 3.63 (3H, s), 2.38 (3H, s), 2.38 (3H, s), 2.06 (3H, s).

Preparation Example 291

1-{3-methyl-2-[2-methyl-4-(5-aminocarbonyl-1-ethyl-4-methyl-1H-pyrazol-3-yl)-phenoxymethyl]-phenyl}-4-methyl-1,4-dihydrotetrazole-5-one (hereinafter, referred to as "Present compound 291") was obtained by reference to Preparation example 262.

Present compound 291

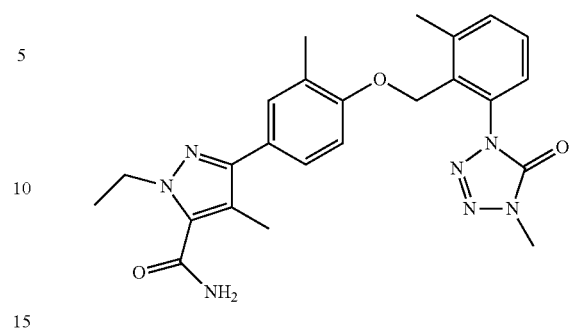

¹H-NMR (CDCl₃) δ: 7.43-7.40 (2H, m), 7.35-7.35 (1H, m), 7.31 (1H, dd, J=8.3, 2.2 Hz), 7.29-7.27 (1H, m), 6.90 (1H, d, J=8.4 Hz), 5.74 (2H, s), 5.07 (2H, s), 4.53 (2H, q, J=7.1 Hz), 3.64 (3H, s), 2.52 (3H, s), 2.35 (3H, s), 2.13 (3H, s), 1.45 (3H, t, J=7.1 Hz).

Preparation Example 292

1-{3-methyl-2-[2-methyl-4-(5-cyano-1-ethyl-4-methyl-1H-pyrazol-3-yl)-phenoxymethyl]-phenyl}-4-methyl-1,4-dihydrotetrazole-5-one (hereinafter, referred to as "Present compound 292") was obtained by reference to Preparation example 263.

Present compound 292

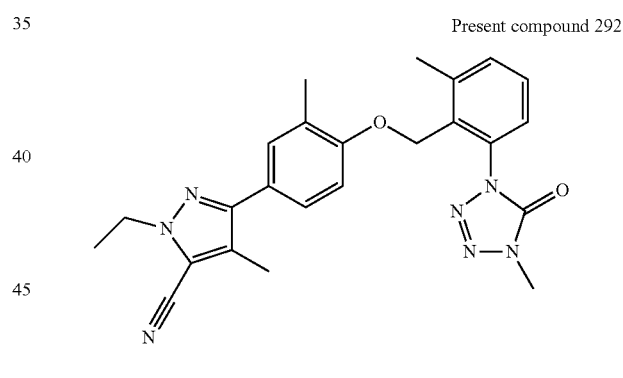

¹H-NMR (CDCl₃) δ: 7.45-7.40 (3H, m), 7.37 (1H, dd, J=8.4, 2.2 Hz), 7.28 (1H, dd, J=7.0, 2.4 Hz), 6.89 (1H, d, J=8.5 Hz), 5.07 (2H, s), 4.33 (2H, q, J=7.2 Hz), 3.63 (3H, s), 2.51 (3H, s), 2.33 (3H, s), 2.13 (3H, s), 1.54 (3H, t, J=7.2 Hz).

Preparation Example 293

1-{3-ethyl-2-[2-methyl-4-(4-cyano-3,5-dimethyl-pyrazol-1-yl)-phenoxymethyl]-phenyl}-4-methyl-1,4-dihydrotetrazole-5-one (hereinafter, referred to as "Present compound 293") was obtained by reference to Preparation example 285.

Present compound 293

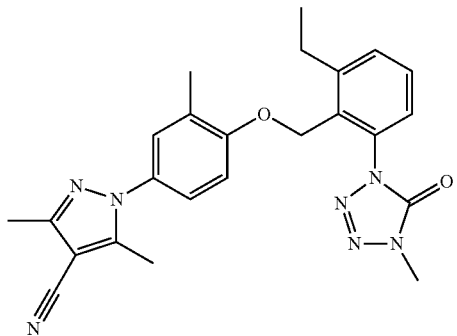

¹H-NMR (CDCl₃) δ: 7.51-7.45 (2H, m), 7.29 (1H, dd, J=7.2, 1.5 Hz), 7.13-7.11 (2H, m), 6.90 (1H, d, J=8.3 Hz), 5.09 (2H, s), 3.62 (3H, s), 2.84 (2H, q, J=7.6 Hz), 2.39 (6H, s), 2.11 (3H, s), 1.28 (3H, t, J=7.6 Hz).

Preparation Example 294

A similar reaction to Preparation example 5 using 1-(4-hydroxy-3-methyl-phenyl)-ethanone instead of 2-methyl-4-(3,4,5-trimethyl-pyrazol-1-yl)-phenol gave 1-[2-(4-acetyl-2-methyl-phenoxymethyl]-3-ethyl-phenyl}-4-methyl-1,4-dihydrotetrazole-5-one (hereinafter, referred to as "Present compound 294").

Present compound 294

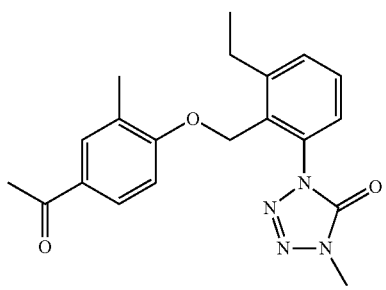

¹H-NMR (CDCl₃) δ: 7.81 (1H, dd, J=8.4, 2.3 Hz), 7.76-7.75 (1H, m), 7.52-7.45 (2H, m), 7.31 (1H, dd, J=7.2, 1.8 Hz), 6.89 (1H, d, J=8.6 Hz), 5.14 (2H, s), 3.60 (3H, s), 2.85 (2H, q, J=7.6 Hz), 2.56 (3H, s), 2.12 (3H, s), 1.29 (3H, t, J=7.6 Hz).

Preparation Example 295

A similar reaction to Preparation example 4 using 4-(4-Chloro-5-methoxy-1-methyl-1H-pyrazol-3-yl)-2-methyl-phenol (described in Reference Preparation example 244) instead of 2-methyl-4-(3,4,5-trimethyl-pyrazol-1-yl)-phenol gave 1-{2-[4-(4-Chloro-5-methoxy-1-methyl-1H-pyrazol-3-yl)-2-methyl-phenoxymethyl]-3-methyl-phenyl}-4-methyl-1,4-dihydro-tetrazol-5-one (hereinafter, referred to as "Present compound 295").

Present compound 295

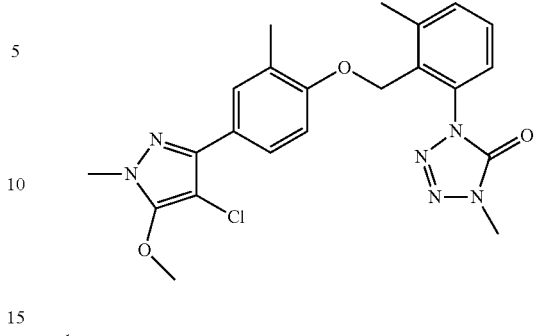

¹H-NMR (CDCl₃) δ: 7.62 (1H, dd, J=8.4, 2.3 Hz), 7.57 (1H, dd, J=2.0, 0.7 Hz), 7.45-7.39 (2H, m), 7.29-7.27 (1H, m), 6.89 (1H, d, J=8.4 Hz), 5.07 (2H, s), 4.11 (3H, s), 3.70 (3H, s), 3.62 (3H, s), 2.51 (3H, s), 2.12 (3H, s).

Preparation Example 296

1-{3-Ethyl-2-[2-methyl-4-(1H-pyrazol-3-yl)-phenoxymethyl]-phenyl}-4-methyl-1,4-dihydro-tetrazol-5-one (hereinafter, referred to as "Present compound 296") was obtained by reference to Preparation example 97.

Present compound 296

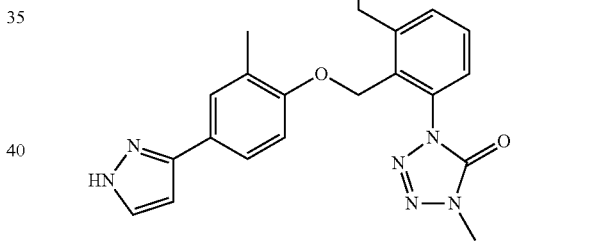

¹H-NMR (CDCl₃) δ: 7.58 (1H, d, J=2.1 Hz), 7.51-7.44 (4H, m), 7.29 (1H, dd, J=7.1, 2.1 Hz), 6.89 (1H, d, J=9.2 Hz), 6.52 (1H, d, J=2.1 Hz), 5.09 (2H, s), 3.58 (3H, s), 2.85 (2H, q, J=7.6 Hz), 2.12 (3H, s), 1.28 (3H, t, J=7.6 Hz).

Preparation Example 297

A similar reaction to Preparation example 285 using 5-methoxy-1-methyl-3-{3-methyl-4-[2-methyl-6-(4-methyl-5-oxo-4,5-dihydro-tetrazol-1-yl)-benzyloxy]-phenyl}-1H-pyrazole-4-carbaldehyde oxime (described in Reference Preparation example 245) instead of 3,5-Dimethyl-1-{3-methyl-4-[2-methyl-6-(4-methyl-5-oxo-4,5-dihydro-tetrazol-1-yl)-benzyloxy]-phenyl}-1H-pyrazole-4-carbaldehyde oxime gave 1-{2-[4-(4-cyano-5-methoxy-1-methyl-1H-pyrazol-3-yl)-2-methyl-phenoxymethyl]-3-methyl-phenyl}-4-methyl-1,4-dihydro-tetrazol-5-one (hereinafter, referred to as "Present compound 297").

Present compound 297

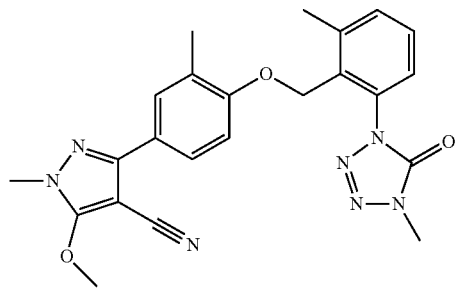

¹H-NMR (CDCl₃) δ: 7.68 (1H, dd, J=8.4, 2.2 Hz), 7.62-7.62 (1H, m), 7.45-7.40 (2H, m), 7.29-7.27 (1H, m), 6.89 (1H, d, J=8.5 Hz), 5.07 (2H, s), 4.33 (3H, s), 3.65 (3H, s), 3.63 (3H, s), 2.51 (3H, s), 2.13 (3H, s).

Preparation Example 298

1-{2-[4-(4-Chloro-5-methoxy-1-methyl-1H-pyrazol-3-yl)-2-methyl-phenoxymethyl]-3-ethyl-phenyl}-4-methyl-, 4-dihydro-tetrazol-5-one (hereinafter, referred to as "Present compound 298") was obtained by reference to Preparation example 295.

Present compound 299

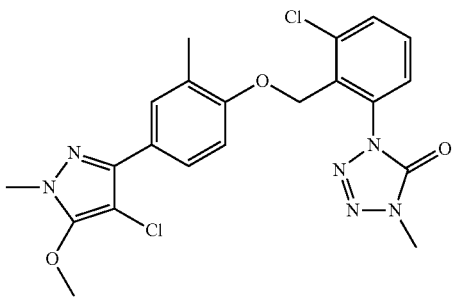

¹H-NMR (CDCl₃) δ: 7.63-7.59 (2H, m), 7.56 (1H, dd, J=2.2, 0.6 Hz), 7.47 (1H, t, J=8.0 Hz), 7.40 (1H, dd, J=8.0, 1.4 Hz), 6.89 (1H, d, J=8.5 Hz), 5.35 (2H, s), 4.11 (3H, s), 3.70 (3H, s), 3.59 (3H, s), 2.06 (3H, s).

Preparation Example 300

1-{2-[4-(4-Chloro-5-methoxy-1-methyl-1H-pyrazol-3-yl)-2-methyl-phenoxymethyl]-3-methoxy-phenyl}-4-methyl-1,4-dihydro-tetrazol-5-one (hereinafter, referred to as "Present compound 300") was obtained by reference to Preparation example 295.

Present compound 298

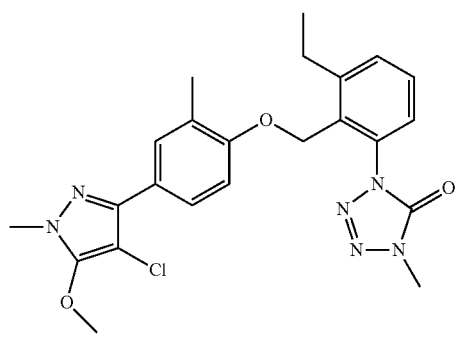

¹H-NMR (CDCl₃) δ: 7.62 (1H, d, J=8.5 Hz), 7.57 (1H, s), 7.49-7.43 (2H, m), 7.29-7.27 (1H, m), 6.89 (1H, d, J=8.5 Hz), 5.08 (2H, s), 4.11 (3H, s), 3.70 (3H, s), 3.58 (3H, s), 2.84 (2H, q, J=7.5 Hz), 2.11 (3H, s), 1.27 (3H, t, J=7.5 Hz).

Preparation Example 299

1-{2-[4-(4-Chloro-5-methoxy-1-methyl-1H-pyrazol-3-yl)-2-methyl-phenoxymethyl]-3-chloro-phenyl}-4-methyl-1,4-dihydro-tetrazol-5-one (hereinafter, referred to as "Present compound 299") was obtained by reference to Preparation example 295.

Present compound 300

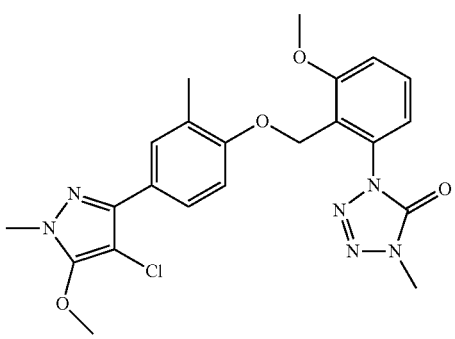

¹H-NMR (CDCl₃) δ: 7.58 (1H, dd, J=8.5, 2.3 Hz), 7.53 (1H, d, J=1.6 Hz), 7.46 (1H, t, J=8.1 Hz), 7.09-7.06 (2H, m), 6.91 (1H, d, J=8.7 Hz), 5.29 (2H, s), 4.10 (3H, s), 3.92 (3H, s), 3.69 (3H, s), 3.58 (3H, s), 2.03 (3H, s).

Preparation Example 301

1-{2-[4-(1-But-2-ynyl-1H-pyrazol-3-yl)-2-methyl-phenoxymethyl]-3-ethyl-phenyl}-4-methyl-, 4-dihydro-tetrazol-5-one (hereinafter, referred to as "Present compound 301") was obtained by reference to Preparation example 277.

Present compound 301

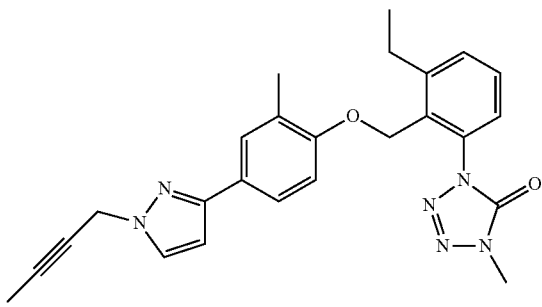

¹H-NMR (CDCl₃) δ: 7.61 (1H, d, J=2.3 Hz), 7.57-7.56 (1H, m), 7.53 (1H, dd, J=8.4, 2.2 Hz), 7.49-7.43 (2H, m), 7.28 (1H, dd, J=7.0, 2.2 Hz), 6.86 (1H, d, J=8.5 Hz), 6.48 (1H, d, J=2.3 Hz), 5.07 (2H, s), 4.92 (2H, q, J=2.4 Hz), 3.57 (3H, s), 2.85 (2H, q, J=7.6 Hz), 2.10 (3H, s), 1.89 (3H, t, J=2.5 Hz), 1.27 (3H, q, J=7.6 Hz).

Preparation Example 302

At room temperature, a mixture 3-{3-Methyl-4-[2-methyl-6-(4-methyl-5-oxo-4,5-dihydro-tetrazol-1-yl)-benzyloxy]-phenyl}-3-oxo-propionic acid ethyl ester (described in Reference Preparation example 247), toluene 70 ml and methylhydrazine 4 g was stirred for 12 hours. The resulting mixture was added water 100 ml and acidified with 10%-HClaq. The precipitates was filtered and was washed with water 10 ml and hexane 10 ml, and was then dried under reduced pressure to give the crude product 3 g of 1-{2-[4-(5-Hydroxy-1-methyl-1H-pyrazol-3-yl)-2-methyl-phenoxymethyl]-3-methyl-phenyl}-4-methyl-1,4-dihydro-tetrazol-5-one. At room temperature, to mixture of the crude product and N,N-dimethylformamide 40 ml was added 55%-sodium hydride 0.48 g and was stirred for one hour, and thereto was then added dimethyl sulfate 1.8 g and stirred at 100° C. for 4 hours. Thereto was added water 50 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{2-[4-(5-Methoxy-1-methyl-1H-pyrazol-3-yl)-2-methyl-phenoxymethyl]-3-methyl-phenyl}-4-methyl-1,4-dihydro-tetrazol-5-one (hereinafter, referred to as "Present compound 302")

Present compound 302

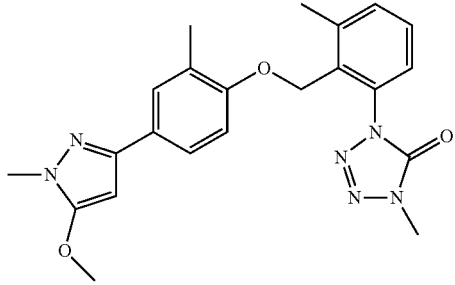

¹H-NMR (CDCl₃) δ: 7.53-7.53 (1H, m), 7.48 (1H, dd, J=8.4, 2.3 Hz), 7.44-7.39 (2H, m), 7.29-7.27 (1H, m), 6.84 (1H, d, J=8.4 Hz), 5.75 (1H, s), 5.05 (2H, s), 3.92 (3H, s), 3.67 (3H, s), 3.61 (3H, s), 2.51 (3H, s), 2.11 (3H, s).

Preparation Example 303

1-{3-ethyl-2-[2-methyl-4-(3,5-dimethyl-4-formyl-pyrazol-1-yl)-phenoxymethyl]-phenyl}-4-methyl-1,4-dihydro-tetrazole-5-one (hereinafter, referred to as "Present compound 303") was obtained by reference to Preparation example 283.

Present compound 303

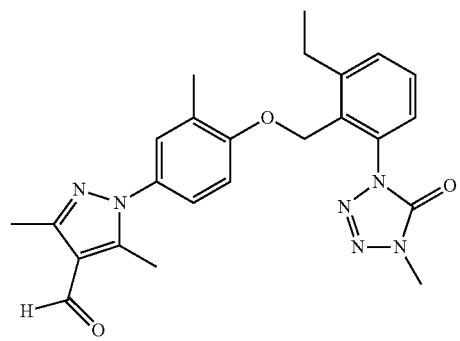

¹H-NMR (CDCl₃) δ: 9.99 (1H, s), 7.51-7.45 (2H, m), 7.29 (1H, d, J=7.3 Hz), 7.15-7.12 (2H, m), 6.91 (1H, d, J=8.2 Hz), 5.09 (2H, s), 3.62 (3H, s), 2.85 (2H, q, J=7.6 Hz), 2.50 (3H, s), 2.50 (3H, s), 2.11 (3H, s), 1.28 (3H, t, J=7.6 Hz).

Preparation Example 304

A similar reaction to Preparation example 139 using 1-{2-[4-(5-Methoxy-1-methyl-1H-pyrazol-3-yl)-2-methyl-phenoxymethyl]-3-methyl-phenyl}-4-methyl-1,4-dihydro-tetrazol-5-one (Present compound 302) instead of 1-{3-methoxy-2-[2-methyl-4-(1-methyl-1H-pyrazol-3-yl)-phenoxymethyl]-phenyl}-4-methyl-1,4-dihydrotetrazole-5-one (Present compound 84) gave 1-{2-[4-(4-bromo-5-methoxy-1-methyl-1H-pyrazol-3-yl)-2-methyl-phenoxymethyl]-3-methyl-phenyl}-4-methyl-1,4-dihydro-tetrazol-5-one (hereinafter, referred to as "Present compound 304").

Present compound 304

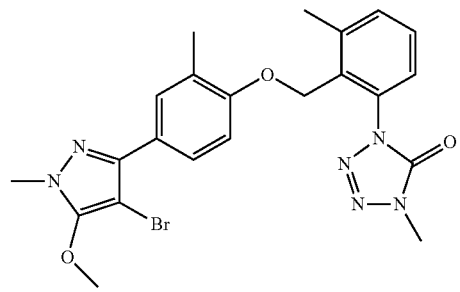

¹H-NMR (CDCl₃) δ: 7.62 (1H, dd, J=8.5, 2.3 Hz), 7.56 (1H, dd, J=2.1, 0.7 Hz), 7.46-7.40 (2H, m), 7.30-7.27 (1H, m), 6.90 (1H, d, J=8.5 Hz), 5.07 (2H, s), 4.10 (3H, s), 3.74 (3H, s), 3.63 (3H, s), 2.52 (3H, s), 2.13 (3H, s).

Preparation Example 305

A similar reaction to Preparation example 304 using 1-chloro methyl-4-fluoro-1,4-diazonia bicyclo[2.2.2]octane-bis-tetrafluoroborate instead of N-bromosuccinimide gave 1-{2-[4-(4-fluoro-5-methoxy-1-methyl-1H-pyrazol-3-yl)-2-methyl-phenoxymethyl]-3-methyl-phenyl}-4-methyl-, 4-dihydro-tetrazol-5-one (hereinafter, referred to as "Present compound 305").

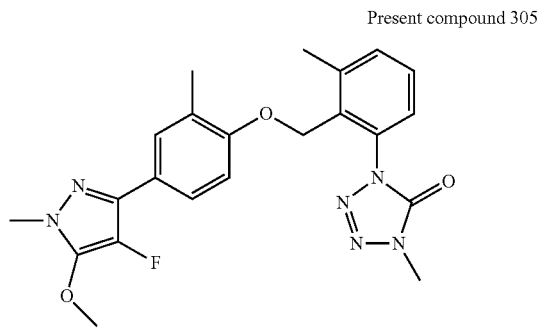 [SMILES: COc1c(F)c(-c2ccc(OCc3c(C)cccc3-n3nnn(C)c3=O)c(C)c2)nn1C]

Present compound 305

$^1$H-NMR (CDCl$_3$) δ: 7.57-7.55 (2H, m), 7.45-7.40 (2H, m), 7.29-7.27 (1H, m), 6.88 (1H, d, J=8.7 Hz), 5.07 (2H, s), 4.11 (3H, d, J=2.3 Hz), 3.64 (3H, s), 3.62 (3H, s), 2.51 (3H, s), 2.13 (3H, s).

Preparation Example 306

1-{2-[4-(4-bromo-1-methyl-1H-pyrazol-3-yl)-2-methyl-phenoxymethyl]-3-methyl-phenyl}-4-methyl-1,4-dihydro-tetrazol-5-one (hereinafter, referred to as "Present compound 306") was obtained by reference to Preparation example 139

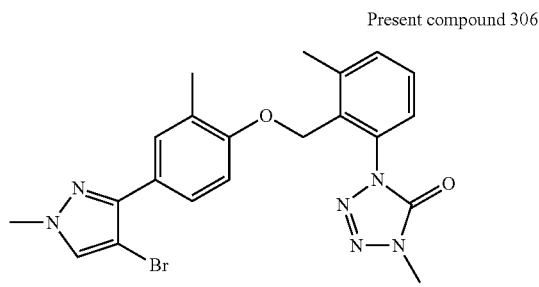 [SMILES: Cc1cc(-c2nn(C)cc2Br)ccc1OCc1c(C)cccc1-n1nnn(C)c1=O]

Present compound 306

$^1$H-NMR (CDCl$_3$) δ: 7.51 (1H, s), 7.47-7.41 (2H, m), 7.30-7.28 (1H, m), 7.19-7.16 (1H, m), 7.13 (1H, dd, J=2.2, 0.8 Hz), 6.95 (1H, d, J=8.2 Hz), 5.09 (2H, s), 3.79 (3H, s), 3.65 (3H, s), 2.53 (3H, s), 2.15 (3H, s).

Next, the Synthesis examples for preparing a compound represented by a formula (4) and a compound represented by a formula (3) are shown below.

Synthesis Example 1

A mixture of 4-(5-chloro-1,4-dimethyl-1H-pyrazol-3-yl)-2-methyl-phenol (described in Reference Preparation example 140) 2.1 g, 2-methyl-6-nitrobenzyl bromide (described in Reference Preparation example 219) 2 g, potassium carbonate 1.5 g and acetonitrile 100 ml was stirred with heating under reflux for twenty four hours. At room temperature, the reaction mixture was filtered and the filtrate was concentrated under reduced pressure and then was subjected to a silica gel column chromatography to give 5-chloro-1,4-dimethyl-3-[3-methyl-4-(2-methyl-6-nitrobenzyloxy)-phenyl]-1H-pyrazole 3.1 g.

5-chloro-1,4-dimethyl-3-[3-methyl-4-(2-methyl-6-nitrobenzyloxy)-phenyl]-1H-pyrazole

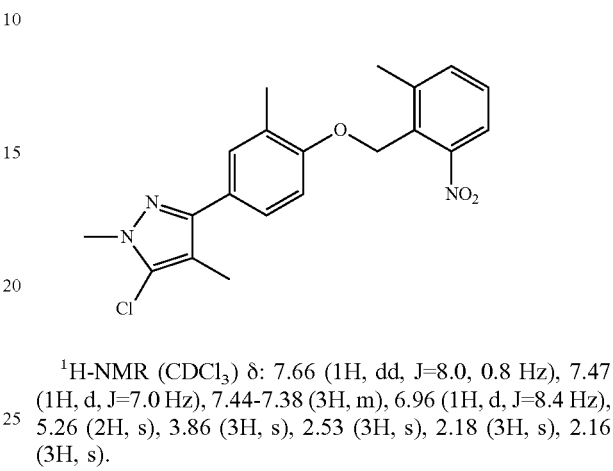

$^1$H-NMR (CDCl$_3$) δ: 7.66 (1H, dd, J=8.0, 0.8 Hz), 7.47 (1H, d, J=7.0 Hz), 7.44-7.38 (3H, m), 6.96 (1H, d, J=8.4 Hz), 5.26 (2H, s), 3.86 (3H, s), 2.53 (3H, s), 2.18 (3H, s), 2.16 (3H, s).

Synthesis Example 2

A similar reaction to Synthesis example 1 using 4-(1,4-dimethyl-5-ethoxy-1H-pyrazol-3-yl)-2-methyl-phenol (described in Reference Preparation example 178) instead of 4-(5-chloro-1,4-dimethyl-1H-pyrazol-3-yl)-2-methyl-phenol gave 5-ethoxy-1,4-dimethyl-3-[3-methyl-4-(2-methyl-6-nitrobenzyloxy)-phenyl]-1H-pyrazole.

5-ethoxy-1,4-dimethyl-3-[3-methyl-4-(2-methyl-6-nitrobenzyloxy)-phenyl]-1H-pyrazole

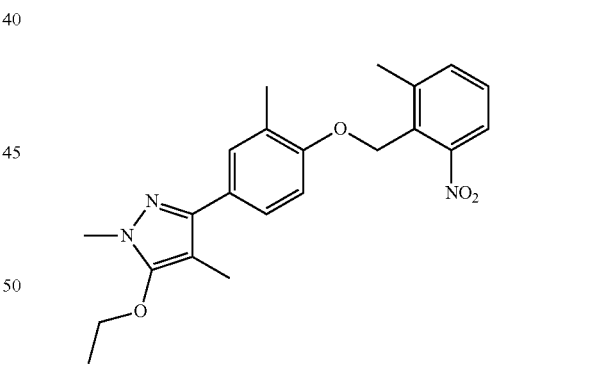

$^1$H-NMR (CDCl$_3$) δ: 7.66 (1H, d, J=7.7 Hz), 7.48-7.44 (2H, m), 7.42-7.38 (2H, m), 6.95 (1H, d, J=8.4 Hz), 5.25 (2H, s), 4.15 (2H, q, J=7.1 Hz), 3.71 (3H, s), 2.53 (3H, s), 2.18 (3H, s), 2.12 (3H, s), 1.42 (3H, t, J=7.1 Hz).

Synthesis Example 3

A similar reaction to Synthesis example 1 using 4-(1,4-dimethyl-5-methoxy-1H-pyrazol-3-yl)-2-methyl-phenol (described in Reference Preparation example 175) instead of 4-(5-chloro-1,4-dimethyl-1H-pyrazol-3-yl)-2-methyl-phenol gave 1,4-dimethyl-5-methoxy-3-[3-methyl-4-(2-methyl-6-nitrobenzyloxy)-phenyl]-1H-pyrazole.

1,4-dimethyl-5-methoxy-3-[3-methyl-4-(2-methyl-6-nitrobenzyloxy)-phenyl]-1H-pyrazole

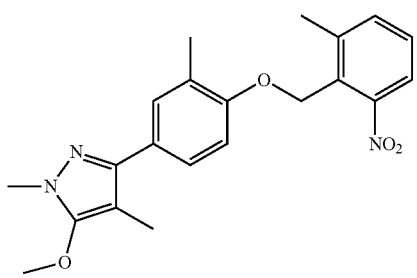

$^1$H-NMR (CDCl$_3$) δ: 7.66 (1H, d, J=7.7 Hz), 7.48-7.37 (4H, m), 6.95 (1H, d, J=8.4 Hz), 5.25 (2H, s), 3.94 (3H, s), 3.71 (3H, s), 2.53 (3H, s), 2.18 (3H, s), 2.14 (3H, s).

Synthesis Example 4

At room temperature, a mixture of 5-ethoxy-1,4-dimethyl-3-[3-methyl-4-(2-methyl-6-nitrobenzyloxy)-phenyl] 1H-pyrazole (described in Synthesis example 2) 2.1 g, 10% palladium-supported carbon (Pd/C) 0.21 g and ethanol 30 ml was stirred under hydrogen atmosphere for eight hours. The reaction mixture was filtered and the filtrate was concentrated under reduced pressure to give 2-[4-(5-ethoxy-1,4-dimethyl-1H-pyrazol-3-yl)-2-methyl-phenoxymethyl]-3-methyl-phenylamine 1.6 g.

2-[4-(5-ethoxy-1,4-dimethyl-1H-pyrazol-3-yl)-2-methyl-phenoxymethyl]-3-methyl-phenylamine

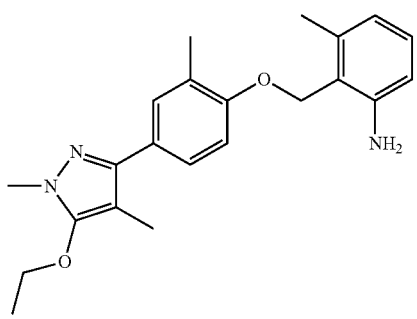 [SMILES: CCOc1c(C)c(-c2ccc(OCc3c(C)cccc3[N+](=O)[O-])c(C)c2)nn1C]

$^1$H-NMR (CDCl$_3$) δ: 7.47-7.47 (1H, m), 7.45-7.42 (1H, m), 7.09-7.04 (2H, m), 6.65 (1H, d, J=7.5 Hz), 6.62 (1H, d, J=7.9 Hz), 5.09 (2H, s), 4.15 (2H, q, J=6.8 Hz), 4.04 (2H, s), 3.72 (3H, s), 2.37 (3H, s), 2.23 (3H, s), 2.13 (3H, s), 1.42 (3H, t, J=6.8 Hz).

Synthesis Example 5

A similar reaction to Synthesis example 4 using 1,4-dimethyl-5-methoxy-3-[3-methyl-4-(2-methyl-6-nitrobenzyloxy)-phenyl]-1H-pyrazole (described in Synthesis example 3) instead of 5-ethoxy-1,4-dimethyl-3-[3-methyl-4-(2-methyl-6-nitrobenzyloxy)-phenyl]-1H-pyrazole gave 2-[4-(1,4-dimethyl-5-methoxy-1H-pyrazol-3-yl)-2-methyl-phenoxymethyl]-3-methyl-phenylamine.

2-[4-(1,4-dimethyl-5-methoxy-1H-pyrazol-3-yl)-2-methyl-phenoxymethyl]-3-methyl-phenylamine

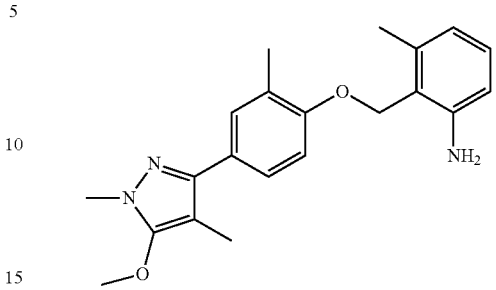

$^1$H-NMR (CDCl$_3$) δ: 7.46-7.45 (1H, m), 7.43 (1H, dd, J=8.6, 2.0 Hz), 7.09-7.05 (2H, m), 6.67-6.61 (2H, m), 5.09 (2H, s), 4.04 (2H, s), 3.94 (3H, s), 3.72 (3H, s), 2.37 (3H, s), 2.23 (3H, s), 2.15 (3H, s).

Synthesis Example 6

2-[4-(5-Ethoxy-1,4-dimethyl-1H-pyrazol-3-yl)-2-methyl-phenoxymethyl]-3-methyl-phenylamine (described in Synthesis example 4) 1.6 g, toluene 50 ml and triphosgene 1.9 g was stirred with heating under reflux for five hours. The reaction mixture was concentrated under reduced pressure to give 5-ethoxy-3-[4-(2-isocyanato-6-methyl-benzyloxy)-3-methyl-phenyl]-1,4-dimethyl-1H-pyrazole 1.7 g.

5-ethoxy-3-[4-(2-isocyanato-6-methyl-benzyloxy)-3-methyl-phenyl]-1,4-dimethyl-1H-pyrazole

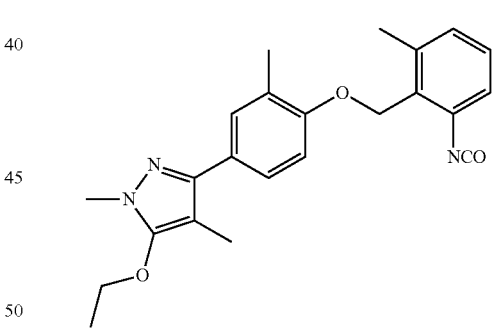

$^1$H-NMR (CDCl$_3$) δ: 7.46-7.43 (1H, m), 7.28-7.23 (1H, m), 7.21-7.14 (2H, m), 7.09-7.03 (2H, m), 5.11 (2H, s), 4.16 (2H, q, J=7.1 Hz), 3.72 (3H, s), 2.42 (3H, s), 2.21 (3H, s), 2.13 (3H, s), 1.42 (3H, t, J=7.1 Hz).

Synthesis Example 7

A similar reaction to Synthesis example 6 using 2-[4-(1,4-dimethyl-5-methoxy-1H-pyrazol-3-yl)-2-methyl-phenoxymethyl]-3-methyl-phenylamine (Synthesis example 5) instead of 2-[4-(5-ethoxy-1,4-dimethyl-1H-pyrazol-3-yl)-2-methyl-phenoxymethyl]-3-methyl-phenylamine gave 3-[4-(2-isocyanato-6-methyl-benzyloxy)-3-methyl-phenyl]-1,4-dimethyl-5-methoxy-1H-pyrazole.

3-[4-(2-isocyanato-6-methyl-benzyloxy)-3-methyl-phenyl]-1,4-dimethyl-5-methoxy-1H-pyrazole

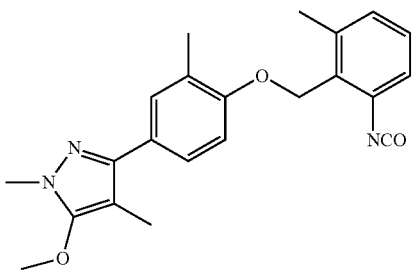

$^1$H-NMR (CDCl$_3$) δ: 7.47-7.44 (1H, m), 7.28-7.23 (1H, m), 7.19-7.16 (2H, m), 7.09-7.02 (2H, m), 5.12 (2H, s), 3.96 (3H, s), 3.74 (3H, s), 2.42 (3H, s), 2.21 (3H, s), 2.16 (3H, s).

Synthesis Example 8

At 0° C., to a mixture of N,N-dimethylformamide 15 ml and aluminum trichloride 0.76 g was added sodium azide 0.34 g. After the resulting mixture was stirred for one hour, thereto was added 5-ethoxy-3-[4-(2-isocyanato-6-methyl-benzyloxy)-3-methyl-phenyl]-1,4-dimethyl-1H-pyrazole (described in Synthesis example 6) 1.7 g. The reaction mixture was stirred at 75° C. for eight hours. The reaction mixture was cooled to room temperature, and thereto was added ice water 10 ml, followed by addition of sodium nitrite 0.52 g and further 10% aqueous hydrochloric acid solution 10 ml. The resulting mixture was extracted with ethyl acetate. The organic layer was washed with water, and was dried over anhydrous magnesium sulfate and was then concentrated under reduced pressure. The resulting residue was subjected to a silica gel column chromatography to give 1-{2-[4-(5-ethoxy-1,4-dimethyl-1H-pyrazol-3-yl)-2-methyl-phenoxymethyl]-3-methyl-phenyl}-1,4-dihydrotetrazole-5-one 0.7 g.

1-{2-[4-(5-ethoxy-1,4-dimethyl-1H-pyrazol-3-yl)-2-methyl-phenoxymethyl]-3-methyl-phenyl}-1,4-dihydrotetrazole-5-one

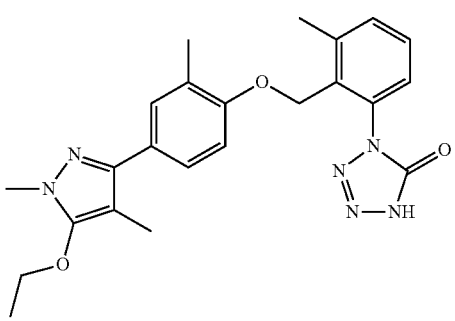 [SMILES: CCOc1c(C)c(-c2ccc(OCc3c(C)cccc3-n3nn[nH]c3=O)c(C)c2)nn1C]

$^1$H-NMR (CDCl$_3$) δ: 7.43-7.38 (2H, m), 7.33 (1H, dd, J=8.4, 1.9 Hz), 7.31-7.30 (1H, m), 7.29-7.27 (1H, m), 6.90 (1H, d, J=8.2 Hz), 5.15 (2H, s), 4.26 (2H, q, J=7.0 Hz), 3.82 (3H, s), 2.55 (3H, s), 2.12 (3H, s), 2.07 (3H, s), 1.45 (3H, t, J=7.1 Hz).

Synthesis Example 9

A similar reaction to Synthesis example 8 using 3-[4-(2-isocyanato-6-methyl-benzyloxy)-3-methyl-phenyl]-1,4-dimethyl-5-methoxy-1H-pyrazole (Synthesis example 7) instead of 5-ethoxy-3-[4-(2-isocyanato-6-methyl-benzyloxy)-3-methyl-phenyl]-1,4-dimethyl-1H-pyrazole gave 1-{2-[4-(5-methoxy-1,4-dimethyl-1H-pyrazol-3-yl)-2-methyl-phenoxymethyl]-3-methyl-phenyl}-1,4-dihydrotetrazole-5-one.

1-{2-[4-(5-methoxy-1,4-dimethyl-1H-pyrazol-3-yl)-2-methyl-phenoxymethyl]-3-methyl-phenyl}-1,4-dihydrotetrazole-5-one

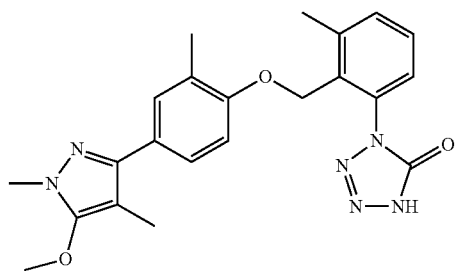 [SMILES: COc1c(C)c(-c2ccc(OCc3c(C)cccc3-n3nn[nH]c3=O)c(C)c2)nn1C]

$^1$H-NMR (CDCl$_3$) δ: 7.44-7.40 (2H, m), 7.39-7.35 (2H, m), 7.30 (1H, dd, J=6.8, 2.2 Hz), 6.89 (1H, d, J=8.2 Hz), 5.08 (2H, s), 3.94 (3H, s), 3.73 (3H, s), 2.52 (3H, s), 2.11 (3H, s), 2.10 (3H, s).

Synthesis Example 10

At room temperature, a mixture of 5-chloro-1,4-dimethyl-3-[3-methyl-4-(2-methyl-6-nitrobenzyloxy)-phenyl]-1H-pyrazole (described in Synthesis example 1) 2.9 g, 5% platinum carbon (Pt/C) 0.3 g, ethanol 70 ml and ethyl acetate 30 ml was stirred under hydrogen atmosphere for nine and a half hours. The reaction mixture was filtered and the filtrate was concentrated under reduced pressure to give 2-[4-(5-chloro-1,4-dimethyl-1H-pyrazol-3-yl)-2-methyl-phenoxymethyl]-3-methyl-phenylamine 2.6 g.

2-[4-(5-chloro-1,4-dimethyl-1H-pyrazol-3-yl)-2-methyl-phenoxymethyl]-3-methyl-phenylamine

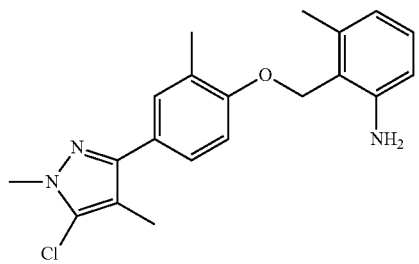 [SMILES: Cc1cc(-c2nn(C)c(Cl)c2C)ccc1OCc1c(C)cccc1N]

$^1$H-NMR (CDCl$_3$) δ: 7.46-7.42 (2H, m), 7.09-7.05 (2H, m), 6.66 (1H, d, J=7.3 Hz), 6.62 (1H, d, J=8.0 Hz), 5.10 (2H, s), 4.03 (2H, br s), 3.86 (3H, s), 2.37 (3H, s), 2.23 (3H, s), 2.16 (3H, s).

Synthesis Example 11

A similar reaction to Synthesis example 6 using 2-[4-(5-chloro-1,4-dimethyl-1H-pyrazol-3-yl)-2-methyl-phenoxymethyl]-3-methyl-phenylamine (Synthesis example 10) instead of 2-[4-(5-ethoxy-1,4-dimethyl-1H-pyrazol-3-yl)-2-methyl-phenoxymethyl]-3-methyl-phenylamine gave 3-[4-(2-isocyanato-6-methyl-benzyloxy)-3-methyl-phenyl]-1,4-dimethyl-5-chloro-1H-pyrazole.

3-[4-(2-isocyanato-6-methyl-benzyloxy)-3-methyl-phenyl]-1,4-dimethyl-5-chloro-1H-pyrazole

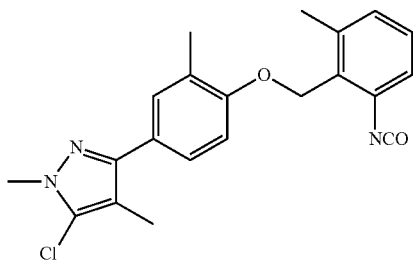

$^1$H-NMR (CDCl$_3$) δ: 7.47-7.43 (2H, m), 7.22 (1H, d, J=7.8 Hz), 7.18-7.16 (1H, m), 7.06 (2H, dd, J=15.5, 7.9 Hz), 5.12 (2H, s), 3.86 (3H, s), 2.42 (3H, s), 2.21 (3H, s), 2.17 (3H, s).

Synthesis Example 12

A similar reaction to Synthesis example 8 using 3-[4-(2-isocyanato-6-methyl-benzyloxy)-3-methyl-phenyl]-1,4-dimethyl-5-chloro-1H-pyrazole (Synthesis example 11) instead of 5-ethoxy-3-[4-(2-isocyanato-6-methyl-benzyloxy)-3-methyl-phenyl]-1,4-dimethyl-1H-pyrazole gave 1-{2-[4-(5-chloro-1,4-dimethyl-1H-pyrazol-3-yl)-2-methyl-phenoxymethyl]-3-methyl-phenyl}-1,4-dihydrotetrazole-5-one.

1-{2-[4-(5-chloro-1,4-dimethyl-1H-pyrazol-3-yl)-2-methyl-phenoxymethyl]-3-methyl-phenyl}-1,4-dihydrotetrazole-5-one

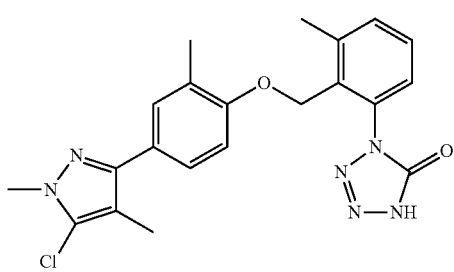 [SMILES: Cc1cc(-c2nn(C)c(Cl)c2C)ccc1OCc1c(C)cccc1-n1nn[nH]c1=O]

$^1$H-NMR (CDCl$_3$) δ: 7.45-7.40 (2H, m), 7.38-7.34 (2H, m), 7.28 (1H, dd, J=6.3, 2.9 Hz), 6.87 (1H, d, J=8.5 Hz), 5.07 (2H, s), 3.85 (3H, s), 2.52 (3H, s), 2.12 (3H, s), 2.11 (3H, s)

Next, regarding an intermediate for preparing the above-mentioned Present compounds, Reference Preparation examples are shown below.

Reference Preparation Example 1

1-(2-bromomethyl-3-fluorophenyl)-4-methyl-1,4-dihydrotetrazole-5-one was prepared according to the below-mentioned steps (1) to (3).

<Step (1)>

Anhydrous aluminium trichloride 21.9 g. was added to N,N-dimethylformamide 250 ml under ice-cooling, and the mixture was stirred for fifteen minutes. Thereto was added sodium azide 10.7 g and the mixture was stirred for fifteen minutes. Thereto was then added 1-fluoro-3-isocyanato-2-methylbenzene 22.5 g and the resulting mixture was heated at 80° C. for three and a half hours. After cooling, the reaction solution was added to a mixture of sodium nitrite 34 g, water 2 L and ice 500 g with stirring. The mixture was acidified with 10% hydrochloric acid and was extracted with ethyl acetate. The organic layer was washed with water and saturated saline and then was dried over anhydrous magnesium sulfate and was then concentrated under reduced pressure to give 1-(2-methyl-3-fluorophenyl)-1,4-dihydrotetrazole-5-one 27.5 g.

1-(2-methyl-3-fluorophenyl)-1,4-dihydrotetrazole-5-one

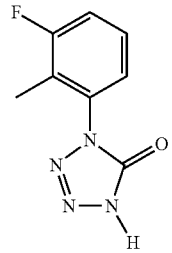

$^1$H-NMR (CDCl$_3$) δ: 2.21 (3H, s), 7.07-7.36 (3H, m), 12.93 (1H, s).

<Step (2)>

To a mixture of the above-mentioned 1-(2-methyl-3-fluorophenyl)-1,4-dihydrotetrazole-5-one 10.00 g and N,N-dimethylformamide 100 ml was added 55% sodium hydride 2.47 g under ice-cooling. The reaction mixture was raised to room temperature and was stirred for one hour. To the reaction mixture was added methyl iodide 3.5 ml under ice-cooling. The mixture was raised to room temperature and was stirred for fourteen hours. To the reaction mixture was added water and the mixture was extracted with ethyl acetate. The organic layer was washed with 10% hydrochloric acid, water and saturated saline, and was dried over anhydrous magnesium sulfate and was then concentrated under reduced pressure. The resulting residue was subjected to a silica gel column chromatography to give 1-(2-methyl-3-fluorophenyl)-4-methyl-1,4-dihydrotetrazole-5-one 2.19 g.

1-(2-methyl-3-fluorophenyl)-4-methyl-1,4-dihydro-tetrazole-5-one

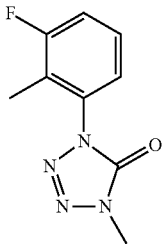

¹H-NMR (CDCl₃) δ: 2.19 (3H, s), 3.70 (3H, s), 7.16-7.20 (2H, m), 7.29 (1H, dt, J=5.9, 8.3 Hz).
<Step (3)>
To a mixture of the above-mentioned 1-(2-methyl-3-fluorophenyl)-4-methyl-1,4-dihydrotetrazole-5-one 2.19 g, 1,1'-azobis(cyclohexane-1-carbonitrile) 0.52 g, N-bromosuccinimide 2.16 g and chlorobenzene 40 ml was stirred with heating under reflux for five hours. After cooling the mixture, to the reaction solution was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-fluorophenyl)-4-methyl-1,4-dihydrotetrazole-5-one 2.36 g.

1-(2-bromomethyl-3-fluorophenyl)-4-methyl-1,4-dihydrotetrazole-5-one

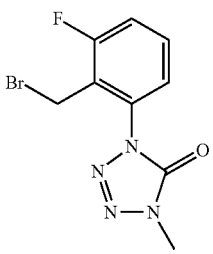 [SMILES: Cn1nnn(-c2cccc(F)c2CBr)c1=O]

¹H-NMR (CDCl₃) δ: 3.75 (3H, s), 4.64 (2H, s), 7.23-7.30 (2H, m), 7.47 (1H, dt, J=5.9, 8.0 Hz).

Reference Preparation Example 2

1-(2-bromomethyl-3-chlorophenyl)-4-methyl-1,4-dihydrotetrazole-5-one was prepared according to the below-mentioned steps (1) to (3).
<Step (1)>
Anhydrous aluminium trichloride 21.9 g was added to N,N-dimethylformamide 250 ml under ice-cooling, and the mixture was stirred for fifteen minutes. Thereto was added sodium azide 10.7 g and the mixture was stirred for fifteen minutes. Thereto was then added 1-chloro-3-isocyanato-2-methylbenzene 25.0 g and the resulting mixture was heated at 80° C. for five hours. After cooling, the reaction solution was added to a mixture of sodium nitrite 35 g, water 2 L and ice 500 g with stirring. The mixture was acidified with 10% hydrochloric acid and was extracted with ethyl acetate. The organic layer was washed with water and saturated saline and then was dried over anhydrous magnesium sulfate and was then concentrated under reduced pressure to give 1-(2-methyl-3-chlorophenyl)-1,4-dihydrotetrazole-5-one 17.0 g.

1-(2-methyl-3-chlorophenyl)-1,4-dihydrotetrazole-5-one

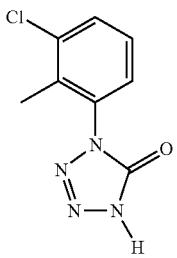

¹H-NMR (CDCl₃) δ: 2.32 (3H, s), 7.28-7.36 (2H, m), 7.57 (1H, dd, J=6.8, 2.2 Hz), 13.08 (1H, s).
<Step (2)>
To a mixture of the above-mentioned 1-(2-methyl-3-chlorophenyl)-1,4-dihydrotetrazole-5-one 10.00 g and N,N-dimethylformamide 100 ml was added 60% sodium hydride 2.30 g under ice-cooling. The reaction mixture was raised to room temperature and was stirred for one hour. To the reaction mixture was added methyl iodide 3.2 ml under ice-cooling. The mixture was raised to room temperature and was stirred for fourteen hours. To the reaction mixture was added water and the mixture was extracted with ethyl acetate. The organic layer was washed with 10% hydrochloric acid, water and saturated saline, and was dried over anhydrous magnesium sulfate and was then concentrated under reduced pressure. The resulting residue was subjected to a silica gel column chromatography to give 1-(2-methyl-3-chlorophenyl)-4-methyl-1,4-dihydrotetrazole-5-one 1.56 g.

1-(2-methyl-3-chlorophenyl)-4-methyl-1,4-dihydrotetrazole-5-one

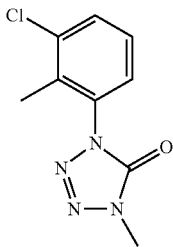

¹H-NMR (CDCl₃) δ: 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).
<Step (3)>
To a mixture of the above-mentioned 1-(2-methyl-3-chlorophenyl)-4-methyl-1,4-dihydrotetrazole-5-one 1.56 g, 1,1'-azobis(cyclohexane-1-carbonitrile) 0.34 g, N-bromosuccinimide 1.42 g and chlorobenzene 30 ml was stirred with heating under reflux for five hours. After cooling the mixture, to the reaction solution was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-chlorophenyl)-4-methyl-1,4-dihydrotetrazole-5-one 1.94 g.

1-(2-bromomethyl-3-chlorophenyl)-4-methyl-1,4-dihydrotetrazole-5-one

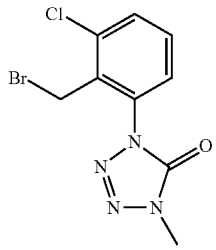

$^1$H-NMR (CDCl$_3$) δ: 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Preparation Example 3

A mixture of 3-chloro-2-methybenzoic acid 21.5 g, oxalyl dichloride 17.6 g, N,N-dimethylformamide about 50 mg and tetrahydrofuran 300 ml was stirred at 25° C. for one hour. The reaction mixture was concentrated under reduced pressure to give 3-chloro-2-methylbenzoyl chloride.

A mixture of aluminium trichloride 33.6 g, sodium azide 49.2 g and tetrahydrofuran 100 ml was stirred with heating under reflux for two hours. After the reaction mixture was ice-cooled, and thereto was added a mixture of 3-chloro-2-methylbenzoyl chloride and tetrahydrofuran 100 ml and the resulting mixture was stirred with heating under reflux for ten hours. After cooling the mixture, to a mixture of sodium nitrite 75.6 g and water 500 ml was added the reaction mixture with stirring. The mixture was acidified with concentrated hydrochloric acid and was then extracted with ethyl acetate. The organic layer was dried over anhydrous sodium sulfate and was then concentrated under reduced pressure to give 1-(2-methyl-3-chlorophenyl)-1,4-dihydrotetrazole-5-one.

A mixture of the above-mentioned 1-(2-methyl-3-chlorophenyl)-1,4-dihydrotetrazole-5-one, potassium carbonate 57.5 g, dimethyl sulfate 19.1 g and N,N-dimethylformamide 150 ml was stirred at 25° C. for one hour. To the reaction mixture was added aqueous saturated sodium bicarbonate solution and the mixture was extracted with ethyl acetate. The organic layer was washed with aqueous saturated sodium bicarbonate solution and was dried over anhydrous sodium sulfate. The resulting mixture was concentrated under reduced pressure to give 1-(2-methyl-3-chlorophenyl)-4-methyl-1,4-dihydrotetrazole-5-one 21.6 g.

Reference Preparation Example 4

Under cooling, to a mixture of methyl chloroformate 30 ml and tetrahydrofuran 50 ml was added dropwise 3-amino-1-chloro-2-methylbenzene 5.00 g and the mixture was, stirred at 25° C. for a half hour. To the reaction mixture was added water and the resulting mixture was extracted with ethyl acetate. The organic layer was washed with aqueous saturated sodium bicarbonate solution and was dried over anhydrous sodium sulfate. The mixture was concentrated under reduced pressure to give 1-chloro-2-methyl-3-methoxycarbonylaminobenzene 5.80 g.

A mixture of 1-chloro-2-methyl-3-methoxycarbonylaminobenzene 5.80 g, phosphorus pentachloride 7.53 g and chlorobenzene 50 ml was stirred with heating under reflux for one hour. The reaction mixture was concentrated under reduced pressure to give 1-chloro-3-isocyanato-2-methylbenzene.

A mixture of aluminium trichloride 4.71 g, sodium azide 6.89 g and tetrahydrofuran 100 ml was stirred with heating under reflux for one hour. After the reaction mixture was ice-cooled, thereto was added a mixture of the above-mentioned 1-chloro-3-isocyanato-2-methylbenzene and tetrahydrofuran 10 ml and the resulting mixture was stirred with heating under reflux for five hours. After cooling the mixture, to a mixture of sodium nitrite 10.59 g and water 300 ml was added the reaction mixture with stirring. The mixture was acidified with concentrated hydrochloric acid and was extracted with ethyl acetate. The organic layer was dried over anhydrous sodium sulfate and was then concentrated under reduced pressure to give 1-(2-methyl-3-chlorophenyl)-1,4-dihydrotetrazole-5-one.

A mixture of the above-mentioned 1-(2-methyl-3-chlorophenyl)-1,4-dihydrotetrazole-5-one, potassium carbonate 16.11 g, dimethyl sulfate 5.34 g and N,N-dimethylformamide 150 ml was stirred at 25° C. for one hour. To the reaction mixture was added aqueous saturated sodium bicarbonate solution and the mixture was extracted with ethyl acetate. The organic layer was washed with aqueous saturated sodium bicarbonate solution and was dried over anhydrous sodium sulfate. The mixture was concentrated under reduced pressure to give 1-(2-methyl-3-chlorophenyl)-4-methyl-1,4-dihydrotetrazole-5-one 4.80 g.

Reference Preparation Example 5

1-(2-Bromomethyl-3-bromophenyl)-4-methyl-1,4-dihydrotetrazole-5-one was prepared according to the below-mentioned steps (1) to (4).

<Step (1)>

A mixture of 1-bromo-2-methyl-3-aminobenzene 25.0 g, triphosgene 60.0 g and toluene 400 ml was stirred with heating under reflux for three hours. The reaction mixture after standing to cool was concentrated under reduced pressure to give 1-bromo-3-isocyanato-2-methylbenzene 30.3 g.

1-bromo-3-isocyanato-2-methylbenzene

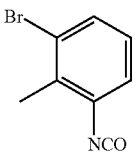

$^1$H-NMR (CDCl$_3$) δ: 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

<Step (2)>

Anhydrous aluminium trichloride 19.7 g was added to N,N-dimethylformamide 220 ml under ice-cooling, and the mixture was stirred for fifteen minutes. Thereto was added sodium azide 9.6 g and the mixture was stirred for fifteen minutes. Thereto was then added the above mentioned 1-bromo-3-isocyanato-2-methylbenzene (described in Reference preparation example 1) 30.3 g and the resulting mixture was heated at 80° C. for five hours. After cooling, the reaction solution was added to a mixture of sodium nitrite 33 g, water 2 L and ice 500 g with stirring. The mixture was acidified with 10% hydrochloric acid and was extracted with ethyl acetate. The organic layer was washed with water and saturated saline and then was dried over anhydrous magnesium sulfate and was then concentrated under reduced pressure to give 1-(2-methyl-3-bromophenyl)-1,4-dihydrotetrazole-5-one 31.4 g.

1-(2-methyl-3-bromophenyl)-1,4-dihydrotetrazole-5-one

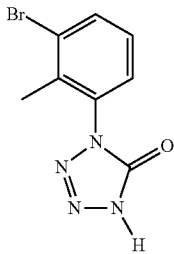

$^1$H-NMR (DMSO-d$_6$) δ: 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

<Step (3)>

To a mixture of the above-mentioned 1-(2-methyl-3-bromophenyl)-1,4-dihydrotetrazole-5-one (described in Synthesis example 9) 31.40 g and N,N-dimethylformamide 250 ml was added 60% sodium hydride 5.90 g under ice-cooling. The reaction mixture was raised to room temperature and was stirred for one hour. To the reaction mixture was added methyl iodide 8.4 ml under ice-cooling. The mixture was raised to room temperature and was stirred for fourteen hours. To the reaction mixture was added water and the mixture was extracted with ethyl acetate. The organic layer was washed with 10% hydrochloric acid, water and saturated saline, and was dried over anhydrous magnesium sulfate and was then concentrated under reduced pressure. The resulting residue was subjected to a silica gel column chromatography to give 1-(2-methyl-3-bromophenyl)-4-methyl-1,4-dihydrotetrazole-5-one 8.47 g.

1-(2-methyl-3-bromophenyl)-4-methyl-1,4-dihydrotetrazole-5-one

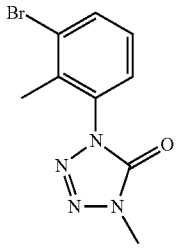

$^1$H-NMR (CDCl$_3$) δ: 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

<Step (4)>

To a mixture of the above-mentioned 1-(2-methyl-3-bromophenyl)-4-methyl-1,4-dihydrotetrazole-5-one 8.47 g, 1,1'-azobis(cyclohexane-1-carbonitrile) 1.54 g, N-bromosuccinimide 6.44 g and chlorobenzene 125 ml was stirred with heating under reflux for five hours. After cooling the mixture, to the reaction solution was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-bromophenyl)-4-methyl-1,4-dihydrotetrazole-5-one 7.52 g.

1-(2-bromomethyl-3-bromophenyl)-4-methyl-1,4-dihydrotetrazole-5-one

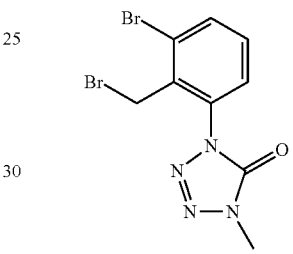

$^1$H-NMR (CDCl$_3$) δ: 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Preparation Example 6

A mixture of 3-bromo-2-methybenzoic acid 146.0 g, oxalyl dichloride 94.8 g, N,N-dimethylformamide about 15 mg and tetrahydrofuran 500 ml was stirred at 25° C. for one hour. The reaction mixture was concentrated under reduced pressure to give 3-bromo-2-methylbenzoyl chloride.

A mixture of aluminium trichloride 181.0 g, sodium azide 265.0 g and tetrahydrofuran 300 ml was stirred with heating under reflux for two hours. After the reaction mixture was ice-cooled, and thereto was added a mixture of 3-bromo-2-methylbenzoyl chloride and tetrahydrofuran 200 ml and the resulting mixture was stirred with heating under reflux for ten hours. After cooling the mixture, to a mixture of sodium nitrite 407 g and water 1,500 ml was added the reaction mixture with stirring. The mixture was acidified with concentrated hydrochloric acid and was then extracted with ethyl acetate. The organic layer was dried over anhydrous sodium sulfate and was then concentrated under reduced pressure to give 1-(2-methyl-3-bromophenyl)-1,4-dihydrotetrazole-5-one.

A mixture of the above-mentioned 1-(2-methyl-3-bromophenyl)-1,4-dihydrotetrazole-5-one, potassium carbonate 310.0 g, dimethyl sulfate 103.0 g and N,N-dimethylformamide 500 ml was stirred at 25° C. for one hour. To the reaction mixture was added aqueous saturated sodium bicarbonate solution and the mixture was extracted with ethyl acetate. The organic layer was washed with aqueous saturated sodium bicarbonate solution and was dried over anhydrous sodium sulfate. The resulting mixture was concentrated under reduced pressure to give 1-(2-methyl-3-bromophenyl)-4-methyl-1,4-dihydrotetrazole-5-one 142.0 g.

Reference Preparation Example 7

A mixture of 3-iodo-2-methybenzoic acid 10.00 g, oxalyl dichloride 5.33 g, N,N-dimethylformamide 5 drops and tetrahydrofuran 200 ml was stirred at 25° C. for one hour. The reaction mixture was concentrated under reduced pressure to give 3-iodo-2-methylbenzoyl chloride.

A mixture of aluminium trichloride 10.20 g, sodium azide 14.90 g and tetrahydrofuran 100 ml was stirred with heating under reflux for two hours. After the reaction mixture was ice-cooled, and thereto was added a mixture of 3-iodo-2-methylbenzoyl chloride and tetrahydrofuran 100 ml and the resulting mixture was stirred with heating under reflux for ten hours. After cooling the mixture, to a mixture of sodium nitrite 22.90 g and water 200 ml was added the reaction mixture with stirring. The mixture was acidified with concentrated hydrochloric acid and was then extracted with ethyl acetate. The organic layer was dried over anhydrous sodium sulfate and was then concentrated under reduced pressure to give 1-(2-methyl-3-iodophenyl)-1,4-dihydrotetrazole-5-one.

A mixture of the above-mentioned 1-(2-methyl-3-iodophenyl)-1,4-dihydrotetrazole-5-one, potassium carbonate 17.40 g, dimethyl sulfate 5.78 g and N,N-dimethylformamide 150 ml was stirred at 25° C. for one hour. To the reaction mixture was added aqueous saturated sodium bicarbonate solution and the mixture was extracted with ethyl acetate. The organic layer was washed with aqueous saturated sodium bicarbonate solution and was dried over anhydrous sodium sulfate. The resulting mixture was concentrated under reduced pressure to give 1-(2-methyl-3-iodophenyl)-4-methyl-1,4-dihydrotetrazole-5-one 8.10 g.

1-(2-methyl-3-iodophenyl)-4-methyl-1,4-dihydrotetrazole-5-one

$^1$H-NMR (CDCl$_3$) δ: 2.37 (3H, s), 3.72 (3H, s), 7.04 (1H, t, J=8.0 Hz), 7.32 (1H, d, J=7.7 Hz), 7.99 (1H, d, 8.0 Hz).

Reference Preparation Example 8

To a mixture of 1-(2-methyl-3-iodophenyl)-4-methyl-1,4-dihydrotetrazole-5-one (described in Reference Preparation example 7) 8.10 g, 1,1'-azobis(cyclohexane-1-carbonitrile) 1.25 g, N-bromosuccinimide 5.24 g and chlorobenzene 100 ml was stirred with heating under reflux for five hours. After cooling the mixture, to the reaction solution was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-iodophenyl)-4-methyl-1,4-dihydrotetrazole-5-one 3.11 g.

1-(2-bromomethyl-3-iodophenyl)-4-methyl-1,4-dihydrotetrazole-5-one

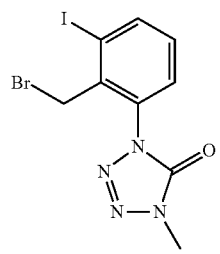 [SMILES: Cn1nnn(-c2cccc(I)c2CBr)c1=O]

$^1$H-NMR (CDCl$_3$) δ: 3.75 (3H, s), 4.71 (2H, s), 7.17 (1H, t, J=8.0 Hz), 7.39 (1H, d, J=8.0 Hz), 8.04 (1H, d, J=8.0 Hz).

Reference Preparation Example 9

1-(2-Bromomethyl-3-methoxyphenyl)-4-methyl-1,4-dihydrotetrazole-5-one was prepared according to steps (1) to (4).

<Step 1>

A mixture of 3-amino-1-methoxy-2-methylbenzene 15.0 g, triphosgene 48.7 g and toluene 350 ml was stirred with heating under reflux for three hours. The reaction mixture after standing to cool was concentrated under reduced pressure to give 1-methoxy-3-isocyanato-2-methylbenzene 17.0 g.

1-methoxy-3-isocyanato-2-methylbenzene

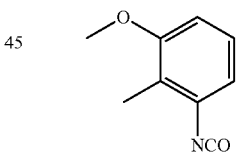

$^1$H-NMR (CDCl$_3$) δ: 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

<Step 2>

Anhydrous aluminium trichloride 16.0 g was added to N,N-dimethylformamide 180 ml under ice-cooling, and the mixture was stirred for fifteen minutes. Thereto was added sodium azide 7.8 g and the mixture was stirred for fifteen minutes. Thereto was then added 1-methoxy-3-isocyanato-2-methylbenzene 17.0 g and the resulting mixture was heated at 80° C. for four and a half hours. After cooling, the reaction solution was added to a mixture of sodium nitrite 25 g, water 2 L and ice 500 g with stirring. The mixture was acidified with 10% hydrochloric acid and was extracted with ethyl acetate. The organic layer was washed with water and saturated saline and then was dried over anhydrous magnesium sulfate and was then concentrated under reduced pressure to give 1-(2-methyl-3-methoxyphenyl)-1,4-dihydrotetrazole-5-one 16.2 g.

1-(2-methyl-3-methoxyphenyl)-1,4-dihydrotetrazole-5-one

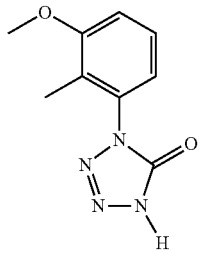

$^1$H-NMR (DMSO-d$_6$) δ: 1.99 (3H, s), 3.87 (3H, s), 7.01 (1H, d, J=8.1 Hz), 7.17 (1H, d, J=8.1 Hz). 7.36 (1H, t, J=8.3 Hz), 14.63 (1H, s).

<Step 3>

To a mixture of the above-mentioned 1-(2-methyl-3-methoxyphenyl)-1,4-dihydrotetrazole-5-one 10.00 g and N,N-dimethylformamide 100 ml was added 55% sodium hydride 2.47 g under ice-cooling. The reaction mixture was raised to room temperature and was stirred for one hour. To the reaction mixture was added methyl iodide 3.5 ml under ice-cooling. The mixture was raised to room temperature and was stirred for fourteen hours. To the reaction mixture was added water and the mixture was extracted with ethyl acetate. The organic layer was washed with 10% hydrochloric acid, water and saturated saline, and was dried over anhydrous magnesium sulfate and was then concentrated under reduced pressure. The resulting residue was subjected to a silica gel column chromatography to give 1-(2-methyl-3-methoxyphenyl)-4-methyl-1,4-dihydrotetrazole-5-one 2.19 g.

1-(2-methyl-3-methoxyphenyl)-4-methyl-1,4-dihydrotetrazole-5-one

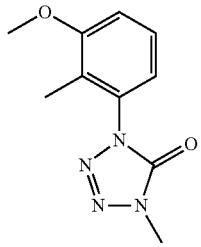 [SMILES: COc1cccc(-n2nnn(C)c2=O)c1C]

$^1$H-NMR (CDCl$_3$) δ: 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz)

<Step 4>

To a mixture of the above-mentioned 1-(2-methyl-3-methoxyphenyl)-4-methyl-1,4-dihydrotetrazole-5-one 2.19 g, 1,1'-azobis(cyclohexane-1-carbonitrile) 0.52 g, N-bromosuccinimide 2.16 g and chlorobenzene 40 ml was stirred with heating under reflux for five hours. After cooling the mixture, to the reaction solution was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-methoxyphenyl)-4-methyl-1,4-dihydrotetrazole-5-one 2.36 g.

1-(2-bromomethyl-3-methoxyphenyl)-4-methyl-1,4-dihydrotetrazole-5-one

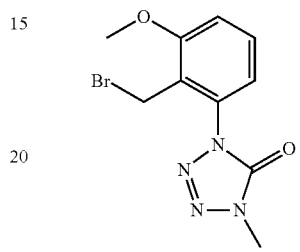

$^1$H-NMR (CDCl$_3$) δ: 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Preparation Example 10

A mixture of 3-trifluoromethyl-2-methybenzoic acid 5.00 g, oxalyl dichloride 3.42 g, N,N-dimethylformamide about 50 mg and tetrahydrofuran 200 ml was stirred at 25° C. for one hour. The reaction mixture was concentrated under reduced pressure to give 3-trifluoromethyl-2-methylbenzoyl chloride.

A mixture of aluminium trichloride 6.53 g, sodium azide 9.55 g and tetrahydrofuran 100 ml was stirred with heating under reflux for two hours. After the reaction mixture was ice-cooled, and thereto was added a mixture of 3-trifluoromethyl-2-methylbenzoyl chloride and tetrahydrofuran 100 ml and the resulting mixture was stirred with heating under reflux for ten hours. After cooling the mixture, to a mixture of sodium nitrite 14.7 g and water 200 ml was added the reaction mixture with stirring. The mixture was acidified with concentrated hydrochloric acid and was then extracted with ethyl acetate. The organic layer was dried over anhydrous sodium sulfate and was then concentrated under reduced pressure to give 1-(2-methyl-3-trifluoromethylphenyl)-1,4-dihydrotetrazole-5-one.

A mixture of the above-mentioned 1-(2-methyl-3-trifluoromethylphenyl)-1,4-dihydrotetrazole-5-one, potassium carbonate 11.20 g, dimethyl sulfate 3.71 g and N,N-dimethylformamide 150 ml was stirred at 25° C. for one hour. To the reaction mixture was added aqueous saturated sodium bicarbonate solution and the mixture was extracted with ethyl acetate. The organic layer was washed with aqueous saturated sodium bicarbonate solution and was dried over anhydrous sodium sulfate. The resulting mixture was concentrated under reduced pressure to give 1-(2-methyl-3-trifluoromethylphenyl)-4-methyl-1,4-dihydrotetrazole-5-one 5.13 g.

1-(2-methyl-3-trifluoromethylphenyl)-4-methyl-1,4-dihydrotetrazole-5-one

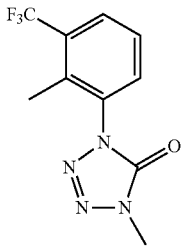 [SMILES: Cc1c(-n2nnn(C)c2=O)cccc1C(F)(F)F]

$^1$H-NMR (CDCl$_3$) δ: 2.42 (3H, s), 3.75 (3H, s), 7.52 (1H, t, J=8.2 Hz), 7.62 (1H, dd, J=1.2, 7.7 Hz), 8.02 (1H, dd, J=1.2, 8.2 Hz).

Reference Preparation Example 11

To a mixture of 1-(2-methyl-3-trifluoromethylphenyl)-4-methyl-1,4-dihydrotetrazole-5-one (described in Reference Preparation example 10) 1.00 g, 1,1'-azobis(cyclohexane-1-carbonitrile) 0.38 g, N-bromosuccinimide 0.79 g and chlorobenzene 30 ml was stirred with heating under reflux for five hours. After cooling the mixture, to the reaction solution was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-trifluoromethylphenyl)-4-methyl-1,4-dihydrotetrazole-5-one 1.21 g.

1-(2-bromomethyl-3-trifluoromethylphenyl)-4-methyl-1,4-dihydrotetrazole-5-one

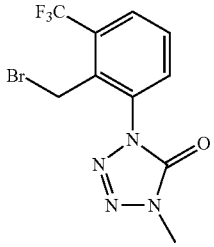 [SMILES: Cn1nnn(-c2cccc(C(F)(F)F)c2CBr)c1=O]

$^1$H-NMR (CDCl$_3$) δ: 3.77 (3H, s), 4.75 (2H, s), 7.62 (1H, d, J=5.5 Hz), 7.63 (1H, d, J=3.4 Hz), 7.85 (1H, dd, J=3.6, 5.8 Hz).

Reference Preparation Example 12

A mixture of 3-nitro-2-methybenzoic acid 5.0 g, oxalyl dichloride 3.9 g, N,N-dimethylformamide about 50 mg and tetrahydrofuran 200 ml was stirred at 25° C. for one hour. The reaction mixture was concentrated under reduced pressure to give 3-nitro-2-methylbenzoic acid chloride.

A mixture of aluminium trichloride 7.4 g, sodium azide 11.0 g and tetrahydrofuran 100 ml was stirred with heating under reflux for two hours. After the reaction mixture was ice-cooled, and thereto was added a mixture of the above-mentioned 3-nitro-2-methylbenzoyl chloride and tetrahydrofuran 100 ml and the resulting mixture was stirred with heating under reflux for ten hours. After cooling the mixture, to a mixture of sodium nitrite 16.6 g and water 200 ml was added the reaction mixture with stirring. The mixture was acidified with concentrated hydrochloric acid and was then extracted with ethyl acetate. The organic layer was dried over anhydrous sodium sulfate and was then concentrated under reduced pressure to give 1-(2-methyl-3-nitrophenyl)-1,4-dihydrotetrazole-5-one.

A mixture of the above-mentioned 1-(2-methyl-3-nitrophenyl)-1,4-dihydrotetrazole-5-one, potassium carbonate 12.6 g, dimethyl sulfate 13.8 g and N,N-dimethylformamide 150 ml was stirred at 25° C. for one hour. To the reaction mixture was added aqueous saturated sodium bicarbonate solution and the mixture was extracted with ethyl acetate. The organic layer was washed with aqueous saturated sodium bicarbonate solution and was dried over anhydrous sodium sulfate. The resulting mixture was concentrated under reduced pressure to give 1-(2-methyl-3-nitrophenyl)-4-methyl-1,4-dihydrotetrazole-5-one 5.3 g.

1-(2-methyl-3-nitrophenyl)-4-methyl-1,4-dihydrotetrazole-5-one

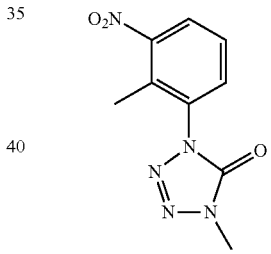

$^1$H-NMR (CDCl$_3$) δ: 2.42 (3H, s), 3.75 (3H, s), 7.52 (1H, t, J=8.2 Hz), 7.62 (1H, dd, J=1.2, 7.7 Hz), 8.02 (1H, d, J=1.2, 8.2 Hz).

Reference Preparation Example 13

To a mixture of 1-(2-methyl-3-nitrophenyl)-4-methyl-1,4-dihydrotetrazole-5-one (described in Reference Preparation example 12) 1.00 g, 1,1'-azobis(cyclohexane-1-carbonitrile) 0.42 g, N-bromosuccinimide 0.87 g and chlorobenzene 30 ml was stirred with heating under reflux for five hours. After cooling the mixture, to the reaction solution was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-nitrophenyl)-4-methyl-1,4-dihydrotetrazole-5-one 1.00 g.

1-(2-bromomethyl-3-nitrophenyl)-4-methyl-1,4-dihydrotetrazole-5-one

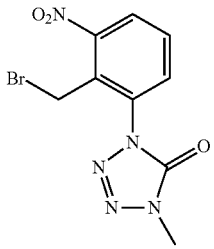 [SMILES: Cn1nnn(-c2cccc([N+](=O)[O-])c2CBr)c1=O]

$^1$H-NMR (CDCl$_3$) δ: 3.72 (3H, s), 5.63 (2H, s), 7.61 (1H, t, J=8.0 Hz), 7.70 (1H, d, J=8.1 Hz), 7.97 (1H, d, J=8.1 Hz).

Reference Preparation Example 14

A mixture of 1-(2-bromomethyl-3-bromophenyl)-4-methyl-1,4-dihydrotetrazole-5-one (described in Reference Preparation example 5) 45.0 g, sodium methoxide 37.4 g and tetrahydrofuran 600 ml was stirred at 25° C. for three hours. To the reaction mixture was added aqueous saturated sodium bicarbonate solution and the resulting mixture was extracted with ethyl acetate. The organic layer was washed with aqueous saturated sodium bicarbonate solution, and was dried over anhydrous sodium sulfate. The mixture was concentrated under reduced pressure to give 1-(2-methoxymethyl-3-bromophenyl)-4-methyl-1,4-dihydrotetrazole-5-one.

1-(2-methoxymethyl-3-bromophenyl)-4-methyl-1,4-dihydrotetrazole-5-one

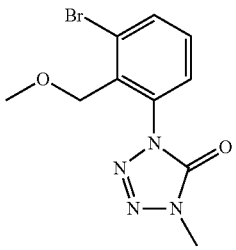 [SMILES: COCc1c(Br)cccc1-n1nnn(C)c1=O]

$^1$H-NMR (CDCl$_3$) δ: 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

A mixture of the above-prepared 1-(2-methoxymethyl-3-bromophenyl)-4-methyl-1,4-dihydrotetrazole-5-one, methylboronic acid 23.2 g, cesium fluoride 66.7 g, [1,1'-bis(diphenylphosphino)ferrocene]palladium(II) dichloride dichloromethane adduct 10.6 g and dioxane 500 ml was stirred at 90° C. for five and a half hours. After cooling the reaction mixture, the mixture was filtered and the filtrate was concentrated under reduced pressure. The resulting residue was subjected to a silica gel column chromatography to give 1-(2-methoxymethyl-3-methylphenyl)-4-methyl-1,4-dihydrotetrazole-5-one.

1-(2-methoxymethyl-3-methylphenyl)-4-methyl-1,4-dihydrotetrazole-5-one

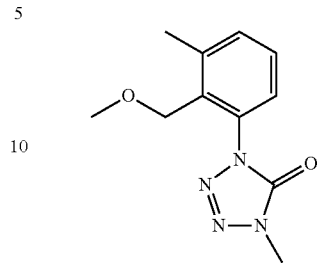

$^1$H-NMR (CDCl$_3$) δ: 2.48 (3H, s), 3.23 (3H, s), 3.72 (3H, s), 4.42 (2H, s), 7.21 (1H, t, J=5.1 Hz), 7.35 (2H, d, J=4.8 Hz).

A mixture of the above-prepared 1-(2-methoxymethyl-3-methylphenyl)-4-methyl-1,4-dihydrotetrazole-5-one, acetic acid 50 ml and 25% hydrogen bromide-acetic acid solution 50 ml was stirred at 65° C. for one hour. To the reaction mixture was added saturated saline, and the mixture was extracted with ethyl acetate. The organic layer was washed with aqueous saturated sodium bicarbonate solution and was dried over anhydrous sodium sulfate. The mixture was concentrated under reduced pressure to give 1-(2-bromomethyl-3-methylphenyl)-4-methyl-1,4-dihydrotetrazole-5-one 27.9 g.

1-(2-bromomethyl-3-methylphenyl)-4-methyl-1,4-dihydrotetrazole-5-one

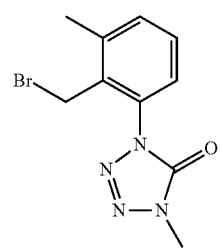 [SMILES: Cc1cccc(-n2nnn(C)c2=O)c1CBr]

$^1$H-NMR (CDCl$_3$) δ: 2.51 (3H, s), 3.75 (3H, s), 4.51 (2H, s), 7.22-7.24 (1H, m), 7.36-7.39 (2H, m).

Reference Preparation Example 15

1-(2-Bromomethyl-3-methylphenyl)-4-methyl-1,4-dihydrotetrazole-5-one (described in Reference Preparation example 14) can be prepared also according to the below-mentioned steps (1) to (5).

<Step (1)>

To a mixture of 2-amino-6-methylbenzoic acid ethyl ester 15.1 g, ethyl acetate 150 ml and ethanol 150 ml was added a solution of 2.0 M trimethylsilyl diazomethane in diethyl ether under ice-cooling. The resulting mixture was stirred at room temperature for four hours and was concentrated under reduced pressure to give 2-amino-6-methylbenzoic acid methyl ester 16.5 g.

2-amino-6-methylbenzoic acid methyl ester

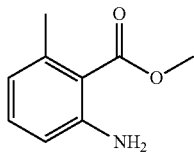

¹H-NMR (CDCl₃) δ: 6.94 (1H, t, J=8.0 Hz), 6.40-6.38 (2H, m), 4.96 (2H, s), 3.75 (3H, s), 2.29 (3H, s).

<Step (2)>

To a mixture of the above-prepared 2-amino-6-methylbenzoic acid methyl ester 16.5 g and toluene 300 ml was added triphosgene 44.5 g at room temperature and the resulting mixture was stirred with heating under reflux for two and a half hours. The reaction mixture was concentrated under reduced pressure to give 2-isocyanato-6-methylbenzoic acid methyl ester.

2-isocyanato-6-methylbenzoic acid methyl ester

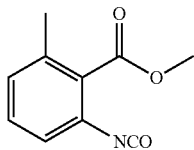

¹H-NMR (CDCl₃) δ: 7.28-7.24 (1H, m), 7.07-7.04 (1H, m), 6.98-6.95 (1H, m), 3.97 (3H, s), 2.36 (3H, s).

<Step (3)>

Under ice-cooling, to N,N-dimethylformamide 200 ml was added aluminum trichloride 16.0 g and the resulting mixture was stirred for a half hour. Thereto was added sodium azide 7.2 g and the resulting mixture was stirred for a half hour and thereto was then added the above-prepared 2-isocyanato-6-methylbenzoic acid methyl ester and the resulting mixture was heated at 80° C. for eight hours. After cooling the mixture, to the reaction solution was added sodium nitrite 11.5 g and ice water 300 ml. The mixture was acidified with 10% hydrochloric acid and was extracted with ethyl acetate. The organic layer was washed with water and saturated saline, and was dried over anhydrous magnesium sulfate and was then concentrated under reduced pressure to give 2-methyl-6-(5-oxo-4,5-dihydrotetrazol-1-yl)benzoic acid methyl ester.

To a mixture of 2-methyl-6-(5-oxo-4,5-dihydrotetrazol-1-yl)benzoic acid methyl ester and N,N-dimethylformamide 300 ml was added potassium carbonate 42.0 g and dimethyl sulfate 18.9 g at room temperature, and the resulting mixture was stirred for 24 hours. To the reaction solution was added water and the resulting mixture was extracted with ethyl acetate. The organic layer was washed with water and aqueous saturated sodium bicarbonate solution and was dried over anhydrous magnesium sulfate, and was then concentrated under reduced pressure. The resulting residue was subjected to a silica gel column chromatography to give 2-methyl-6-(4-methyl-5-oxo-4,5-dihydrotetrazol-1-yl)-benzoic acid methyl ester 13.9 g.

2-methyl-6-(4-methyl-5-oxo-4,5-dihydrotetrazol-1-yl)-benzoic acid methyl ester

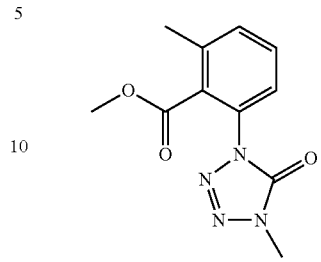

¹H-NMR (CDCl₃) δ: 7.50-7.46 (2H, m), 7.35-7.33 (1H, m), 3.83 (3H, s), 3.69 (3H, s), 2.48 (3H, s).

<Step (4)>

At 0° C., to a mixture of the above-mentioned 2-methyl-6-(4-methyl-5-oxo-4,5-dihydrotetrazol-1-yl)-benzoic acid methyl ester 25.0 g and tetrahydrofuran 300 ml was added a 1.0 M solution of lithium triethylborohydride in tetrahydrofuran 201 ml and the mixture was stirred at room temperature for a half hour. To the reaction solution was added water, and the resulting mixture was acidified with 10% hydrochloric acid and was extracted with ethyl acetate. The organic layer was washed with water and then was dried over anhydrous magnesium sulfate and was then concentrated under reduced pressure to give 1-(2-hydroxymethyl-3-methylphenyl)-4-methyl-1,4-dihydrotetrazole-5-one 21.2 g.

1-(2-hydroxymethyl-3-methylphenyl)-4-methyl-1,4-dihydrotetrazole-5-one

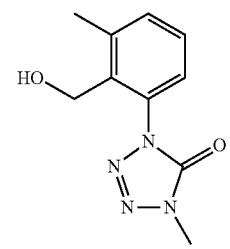 [SMILES: Cc1cccc(-n2nnn(C)c2=O)c1CO]

¹H-NMR (CDCl₃) δ: 7.39-7.34 (2H, m), 7.21 (1H, dd, J=6.5, 2.8 Hz), 4.48 (2H, s), 3.75 (3H, s), 2.57 (3H, s), 1.59 (1H, br s).

<Step (5)>

To a mixture of the above-prepared 1-(2-hydroxymethyl-3-methylphenyl)-4-methyl-1,4-dihydrotetrazole-5-one 21.2 g and chloroform 300 ml was added phosphorus tribromide 52.1 g, and the resulting mixture was stirred at room temperature for one hour. To the reaction solution was added ice water 200 ml and the resulting mixture was extracted with ethyl acetate. The organic layer was washed with water and saline, and was dried over anhydrous magnesium sulfate and was then concentrated under reduced pressure to give 1-(2-bromomethyl-3-methylphenyl)-4-methyl-1,4-dihydrotetrazole-5-one 26.0 g.

Reference Preparation Example 16

1-(3-ethoxy-2-bromomethyl-phenyl)-4-methyl-1,4-dihydrotetrazole-5-one was prepared according to the below-mentioned steps (1) to (6).

Step (1)

A mixture of 2-methyl-3-nitrophenol 33.5 g, iodoethane 41 g, potassium carbonate 90 g and acetone 400 ml was stirred with heating under reflux for ten hours. The mixture was cooled to room temperature and was filtered. The filtrate was then concentrated. The resulting mixture was extracted with ethyl acetate and the organic layer was washed with water and saturated saline, and was dried over anhydrous magnesium sulfate and was then concentrated under reduced pressure. The resulting residue was subjected to a silica gel column chromatography to give 1-ethoxy-2-methyl-3-nitrobenzene 39.9 g.

1-ethoxy-2-methyl-3-nitrobenzene

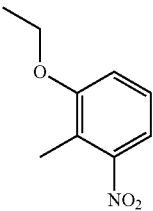

$^1$H-NMR (CDCl$_3$) δ: 7.39 (1H, dd, J=8.2, 1.0 Hz), 7.24 (1H, t, J=8.3 Hz), 7.02 (1H, d, J=8.2 Hz), 4.08 (2H, q, J=7.0 Hz), 2.37 (3H, s), 1.50-1.42 (3H, m).

Step (2)

A mixture of the above-prepared 1-ethoxy-2-methyl-3-nitrobenzene 39.9 g, palladium-carbon (palladium 5%) 4 g and ethanol 200 ml was stirred with additing of hydrogen for eighteen hours. The resulting mixture was filtered and the filtrate was concentrated to give 3-ethoxy-2-methylaniline 33.0 g.

3-ethoxy-2-methylaniline

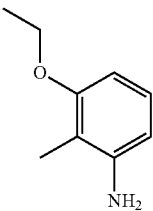

$^1$H-NMR (CDCl$_3$) δ: 6.95 (1H, t, J=8.1 Hz), 6.35 (1H, d, J=2.9 Hz), 6.33 (1H, d, J=3.1 Hz), 4.02-3.97 (2H, m), 3.61 (2H, br s), 2.05 (3H, s), 1.40 (3H, t, J=7.1 Hz).

Step (3)

At room temperature, to a mixture of the above-prepared 3-ethoxy-2-methylaniline 33.0 g and toluene 400 ml was added triphosgene 25 g, and the resulting mixture was stirred with heating reflux for four hours. The reaction mixture was concentrated under reduced pressure to give 1-ethoxy-3-isocyanato-2-methylbenzene 37.2 g.

1-ethoxy-3-isocyanato-2-methylbenzene

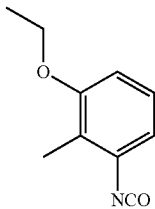

$^1$H-NMR (CDCl$_3$) δ: 7.07 (1H, t, J=8.2 Hz), 6.70 (1H, d, J=7.7 Hz), 6.68 (1H, d, J=8.2 Hz), 4.02 (2H, q, J=7.0 Hz), 2.20 (3H, s), 1.42 (3H, t, J=7.0 Hz).

Step (4)

At 0° C., to a mixture of N,N-dimethylformamide 350 ml and aluminium trichloride 33.6 g was added sodium azide 15 g, and the resulting mixture was stirred for one hour. Thereto was then added 1-ethoxy-3-isocyanato-2-methylbenzene 37.2 g and the reaction mixture was heated to 80° C. and was stirred for five hours. The reaction mixture was cooled and at 0° C., to the reaction mixture was added ice water 100 ml, followed by an addition of a mixture of sodium nitrite 23 g and water 150 ml. The mixture was acidified with an aqueous 10% hydrochloric acid solution to make it pH about 4. The resulting mixture was extracted with ethyl acetate. The organic layer was washed with water and saturated saline and then was dried over anhydrous magnesium sulfate and was then concentrated under reduced pressure. The resulting residue was subjected to a silica gel column chromatography to give 1-(3-ethoxy-2-methyl-phenyl)-1,4-dihydrotetrazole-5-one 39.0 g.

1-(3-ethoxy-2-methyl-phenyl)-1,4-dihydrotetrazole-5-one

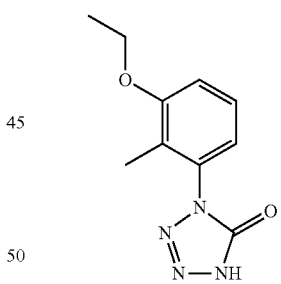

$^1$H-NMR (CDCl$_3$) δ: 7.30 (1H, t, J=8.1 Hz), 6.99 (1H, d, J=8.5 Hz), 6.96 (1H, d, J=8.0 Hz), 4.10 (2H, q, J=6.9 Hz), 2.13 (3H, s), 1.46 (3H, t, J=7.0 Hz).

Step (5)

At 0° C., to a mixture of N,N-dimethylformamide 400 ml, the above-prepared 1-(3-ethoxy-2-methyl-phenyl)-1,4-dihydrotetrazole-5-one 39.0 g, potassium carbonate 36.7 g and N,N-dimethylformamide 400 ml was added dimethyl sulfate 44.7 g. The resulting mixture was raised to room temperature and was stirred for seven hours. Thereto was added water 100 ml and the resulting mixture was extracted with ethyl acetate. The organic layer was washed with water and saturated saline and then was dried over anhydrous magnesium sulfate and was then concentrated under reduced pressure. The resulting residue was subjected to a silica gel column chromatography to give 1-(3-ethoxy-2-methyl-phenyl)-4-methyl-1,4-dihydrotetrazole-5-one 38.2 g.

1-(3-ethoxy-2-methyl-phenyl)-4-methyl-1,4-dihydrotetrazole-5-one

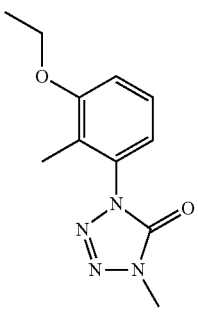 [SMILES: CCOc1cccc(-n2nnn(C)c2=O)c1C]

$^1$H-NMR (CDCl$_3$) δ: 7.29-7.23 (1H, m), 6.96 (1H, d, J=8.2 Hz), 6.93 (1H, d, J=8.2 Hz), 4.08 (2H, q, J=6.9 Hz), 3.72 (3H, s), 2.11 (3H, s), 1.45 (3H, t, J=7.1 Hz).

<Step (6)>

A mixture of the above-prepared 1-(3-ethoxy-2-methyl-phenyl)-4-methyl-1,4-dihydrotetrazole-5-one 38.2 g, 1,1'-azobis(cyclohexane-1-carbonitrile) 7.95 g, N-bromosuccinimide 33.4 g and chlorobenzene 380 ml was stirred at 120° C. for five hours. After cooling the reaction solution, thereto was added water and the resulting mixture was extracted with ethyl acetate. The organic layer was washed with water and saturated saline and then was dried over anhydrous magnesium sulfate and was then concentrated under reduced pressure. The resulting residue was subjected to a silica gel column chromatography to give 1-(3-ethoxy-2-bromomethyl-phenyl)-4-methyl-1,4-dihydrotetrazole-5-one 38.2 g.

1-(3-ethoxy-2-bromomethyl-phenyl)-4-methyl-1,4-dihydrotetrazole-5-one

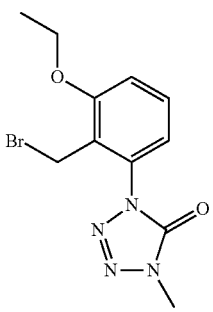 [SMILES: CCOc1cccc(-n2nnn(C)c2=O)c1CBr]

$^1$H-NMR (CDCl$_3$) δ: 7.40 (1H, t, J=8.2 Hz), 7.01 (2H, t, J=8.3 Hz), 4.64 (2H, s), 4.17 (2H, q, J=7.0 Hz), 3.74 (3H, s), 1.49 (3H, t, J=6.9 Hz).

Reference Preparation Example 17

A mixture of 1-(2-methoxymethyl-3-bromophenyl)-4-methyl-1,4-dihydrotetrazole-5-one (described in Reference Preparation example 14) 29.8 g, tributylvinyltin 35.2 g, tetrakis(triphenylphosphine)palladium 11.6 g and toluene 500 ml was stirred with heating under reflux for fourteen hours. After cooling the reaction solution, thereto was added aqueous saturated ammonium chloride solution and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-methoxymethyl-3-ethenylphenyl)-4-methyl-1,4-dihydrotetrazole-5-one 19.7 g.

1-(2-methoxymethyl-3-ethenylphenyl)-4-methyl-1,4-dihydrotetrazole-5-one

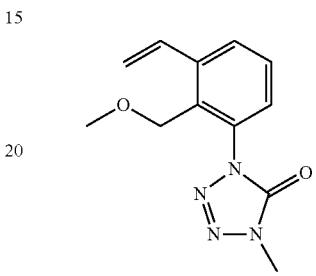

$^1$H-NMR (CDCl$_3$) δ(ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

A mixture of the above-prepared 1-(2-methoxymethyl-3-ethenylphenyl)-4-methyl-1,4-dihydrotetrazole-5-one 19.7 g, palladium fibroin complex 3.02 g and methanol 1 L was stirred at room temperature under hydrogen atmosphere for eleven hours. The reaction mixture was filtered and the filtrate was concentrated under reduced pressure. The resulting residue was subjected to a silica gel column chromatography to give 1-(2-methoxymethyl-3-ethylphenyl)-4-methyl-1,4-dihydrotetrazole-5-one 19.3 g.

1-(2-methoxymethyl-3-ethylphenyl)-4-methyl-1,4-dihydrotetrazole-5-one

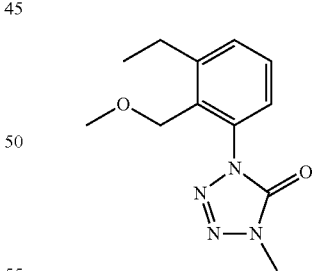

$^1$H-NMR (CDCl$_3$) δ(ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

A mixture of the above-prepared 1-(2-methoxymethyl-3-ethylphenyl)-4-methyl-1,4-dihydrotetrazole-5-one 19.3 g, acetic acid 40 ml and 25% hydrogen bromide-acetic acid solution 40 ml was stirred at 65° C. for one and a half hours. To the reaction mixture was added saturated saline, and the resulting mixture was extracted with ethyl acetate. The organic layer was washed with aqueous saturated sodium bicarbonate solution and was dried over anhydrous sodium sulfate. The mixture was concentrated under reduced pressure to give 1-(2-bromomethyl-3-ethylphenyl)-4-methyl-1,4-dihydrotetrazole-5-one 23.3 g.

1-(2-bromomethyl-3-ethylphenyl)-4-methyl-1,4-dihydrotetrazole-5-one

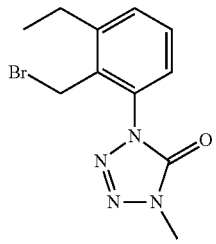 [SMILES: CCc1cccc(-n2nnn(C)c2=O)c1CBr]

¹H-NMR (CDCl₃) δ(ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Preparation Example 18

1-(2-Bromomethyl-3-difluoromethylphenyl)-4-methyl-1,4-dihydrotetrazole-5-one was prepared according to the below-mentioned steps (1) to (8).
<Step (1)>
A mixture of sodium borohydride 9.4 g and tetrahydrofuran 150 ml was stirred at room temperature for thirty minutes at 25° C. Thereto was added 2-methyl-3-nitrobenzoic acid 30.8 g and the resulting mixture was stirred at 25° C. for thirty minutes. The mixed solution was ice-cooled and thereto was added slowly methanesulfonic acid 11.0 ml over forty five minutes. The reaction mixture was stirred at 25° C. for three days. To the reaction mixture was added water and the mixture was extracted with ethyl acetate. The organic layer was washed with 10% hydrochloric acid and saturated saline, and was dried over anhydrous magnesium sulfate and was then concentrated under reduced pressure to give 3-hydroxymethyl-2-methyl-1-nitrobenzene 27.0 g.

3-hydroxymethyl-2-methyl-1-nitrobenzene

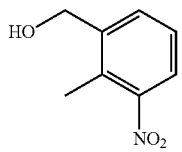

¹H-NMR (CDCl₃) δ(ppm): 1.81 (1H, s), 2.44 (3H, s), 4.79 (2H, s), 7.34 (1H, t, J=7.8 Hz), 7.65 (1H, d, 7.6 Hz), 7.72 (1H, d, J=8.1 Hz).
<Step (2)>
A mixture of the above-mentioned 3-hydroxymethyl-2-methyl-1-nitrobenzene 17.0 g, manganese dioxide 65.0 g and chloroform 170 ml was stirred with heating under reflux for five hours. The reaction mixture after standing to cool was filtered through Celite and the filtrate was concentrated under reduced pressure to give 3-formyl-2-methyl-1-nitrobenzene 14.0 g.

3-formyl-2-methyl-1-nitrobenzene

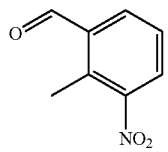

¹H-NMR (CDCl₃) δ(ppm): 2.78 (3H, s), 7.53 (1H, t, J=8.1 Hz), 7.97 (1H, dd, J=1.5, 8.1 Hz), 8.06 (1H, dd, J=1.5, 7.8 Hz), 10.39 (1H, s).
<Step (3)>
To a mixture of the above-mentioned 3-formyl-2-methyl-1-nitrobenzene 13.0 g and chloroform 200 ml under cooling at −78° C. was added dropwise N,N-diethylaminosulfur trifluoride 31.7 g, and the mixture was stirred at room temperature for sixteen hours. To the reaction mixture was added water and the mixture was extracted with chloroform. The organic layer was washed with saturated saline, and was dried over anhydrous magnesium sulfate and was then concentrated under reduced pressure. The resulting residue was subjected to a silica gel column chromatography to give 3-difluoromethyl-2-methyl-1-nitrobenzene 6.8 g.

3-difluoromethyl-2-methyl-1-nitrobenzene

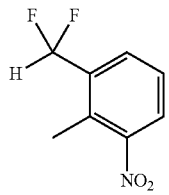

¹H-NMR (CDCl₃) δ(ppm): 2.54 (3H, s), 6.84 (1H, t, J=54.6 Hz), 7.45 (1H, t, J=7.7 Hz), 7.78 (1H, d, J=7.7 Hz), 7.89 (1H, d, J=8.0 Hz)
<Step (4)>
A mixture of the above-mentioned 3-difluoromethyl-2-methyl-1-nitrobenzene 6.80 g, 5% platinum-activated carbon 0.30 g and methanol 50 ml was stirred at 35° C. under hydrogen atmosphere for eight hours. The reaction mixture was filtered through Celite and the filtrate was concentrated under reduced pressure. The resulting residue was subjected to a silica gel column chromatography to give 3-difluoromethyl-2-methyl-1-aminobenzene 3.87 g.

3-difluoromethyl-2-methyl-1-aminobenzene

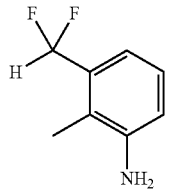

$^1$H-NMR (CDCl$_3$) δ(ppm): 2.20 (3H, s), 3.71 (2H, s), 6.72 (1H, t, J=55.5 Hz), 6.79 (1H, d, J=8.0 Hz), 6.92 (1H, d, J=7.7 Hz), 7.09 (1H, t, J=7.7 Hz).

<Step (5)>

A mixture of the above-prepared 3-difluoromethyl-2-methyl-1-aminobenzene 3.87 g, triphosgene 10.96 g and toluene 80 ml was stirred with heating under reflux for three and a half hours. The reaction mixture after standing to cool was concentrated under reduced pressure to give 3-difluoromethyl-2-methyl-1-isocyanatobenzene.

3-difluoromethyl-2-methyl-1-isocyanatobenzene

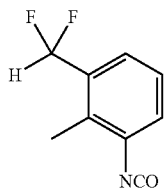

$^1$H-NMR (CDCl$_3$) δ(ppm): 2.39 (3H, s), 6.74 (1H, t, J=55.1 Hz), 7.21-7.27 (2H, m), 7.34 (1H, d, J=7.2 Hz).

<Step (6)>

Anhydrous aluminium trichloride 3.62 g was added to N,N-dimethylformamide 40 ml under ice-cooling, and the resulting mixture was stirred for twenty minutes. Thereto was added sodium azide 1.76 g and the mixture was stirred for fifteen minutes. Thereto was then added the above-prepared 3-difluoromethyl-2-methyl-1-isocyanatobenzene (described in <step (5)>) and the resulting mixture was heated at 80° C. for four hours. After cooling, the reaction solution was added to a mixture of sodium nitrite 6 g, water 0.5 L and ice 100 g with stirring. The resulting mixture was acidified with 10% hydrochloric acid and was extracted with ethyl acetate. The organic layer was washed with water and saturated saline and then was dried over anhydrous magnesium sulfate and was then concentrated under reduced pressure to give 1-(2-methyl-3-difluoromethylphenyl)-1,4-dihydrotetrazole-5-one 3.22 g.

<Step (7)>

A mixture of the above-prepared 1-(2-methyl-3-difluoromethylphenyl)-1,4-dihydrotetrazole-5-one 3.22 g, potassium carbonate 3.93 g, methyl iodide 4.04 g and N,N-dimethylformamide 70 ml was stirred at 25° C. for five hours. To the reaction mixture was added water and the mixture was extracted with ethyl acetate. The organic layer was washed with 10% hydrochloric acid, water and saturated saline, and was dried over anhydrous magnesium sulfate and was then concentrated under reduced pressure. The resulting residue was subjected to a silica gel column chromatography to give 1-(2-methyl-3-difluoromethylphenyl)-4-methyl-1,4-dihydrotetrazole-5-one 1.14 g.

1-(2-methyl-3-difluoromethylphenyl)-4-methyl-1,4-dihydrotetrazole-5-one

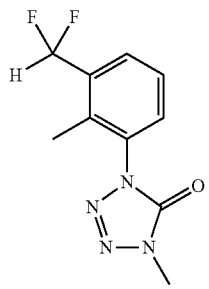 [SMILES: Cc1c(C(F)F)cccc1-n1nnn(C)c1=O]

$^1$H-NMR (CDCl$_3$) δ(ppm): 2.31 (3H, s), 3.73 (3H, s), 6.83 (1H, t, J=55.1 Hz), 7.44-7.46 (2H, m), 7.68-7.71 (1H, m).

<Step (8)>

To a mixture of the above-prepared 1-(2-methyl-3-difluoromethylphenyl)-4-methyl-1,4-dihydrotetrazole-5-one 1.14 g, 1,1'-azobis(cyclohexane-1-carbonitrile) 0.23 g, N-bromosuccinimide 0.97 g and chlorobenzene 20 ml was stirred with heating under reflux for five hours. After cooling the reaction solution, thereto was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-difluoromethylphenyl)-4-methyl-1,4-dihydrotetrazole-5-one 1.21 g.

1-(2-bromomethyl-3-difluoromethylphenyl)-4-methyl-1,4-dihydrotetrazole-5-one

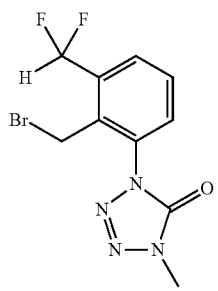 [SMILES: Cn1nnn(-c2cccc(C(F)F)c2CBr)c1=O]

$^1$H-NMR (CDCl$_3$) δ(ppm): 3.76 (3H, s), 4.66 (2H, s), 6.99 (1H, t, J=54.8 Hz), 7.55 (1H, d, J=8.0 Hz), 7.60 (1H, t, J=7.7 Hz), 7.56 (1H, d, J=7.5 Hz).

Reference Preparation Example 19

A mixture of 2-chloro-4-hydrazinophenol hydrochloride salt (described in Reference Preparation example 112) 3.0 g, 3-methyl-2,4-pentanedione 1.5 g, ethanol 100 ml was stirred with heating under reflux for twelve hours. The solvent was distilled off and thereto was added ethyl acetate 200 ml, and the resulting mixture was stirred for one hour. The precipitates were filtered and were washed with hexane, and were then dried under reduced pressure to give 2-chloro-4-(3,4,5-trimethyl-pyrazol-1-yl)-phenol 3.3 g.

2-chloro-4-(3,4,5-trimethyl-pyrazol-1-yl)-phenol

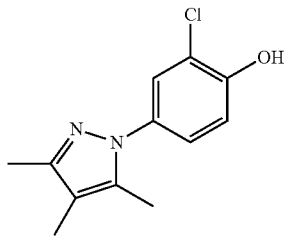 [SMILES: Cc1nn(-c2ccc(O)c(Cl)c2)c(C)c1C]

$^1$H-NMR (DMSO-D$_6$) δ: 7.43 (1H, d, J=2.7 Hz), 7.24 (1H, dd, J=8.7, 2.6 Hz), 7.07 (1H, d, J=8.8 Hz), 2.15 (3H, s), 2.13 (3H, s), 1.92 (3H, s).

Reference Preparation Example 20

A similar reaction to Reference Preparation example 19 using acetylacetone instead of 3-methyl-2,4-pentanedione gave 2-chloro-4-(3,5-dimethyl-pyrazol-1-yl)-phenol.

2-chloro-4-(3,5-dimethyl-pyrazol-1-yl)-phenol

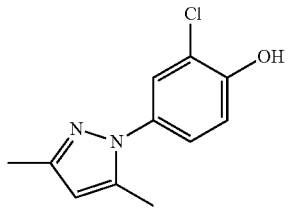

$^1$H-NMR (DMSO-D$_6$) δ: 8.66 (1H, br s), 7.46 (1H, d, J=2.6 Hz), 7.26 (1H, dd, J=8.7, 2.6 Hz), 7.10 (1H, d, J=8.8 Hz), 6.07 (1H, s), 2.23 (3H, s), 2.14 (3H, s)

Reference Preparation Example 21

A similar reaction to Reference Preparation example 19 using 1,1,5,5-tetrafluoro-2,4-pentanedione instead of 3-methyl-2,4-pentanedione gave 2-chloro-4-(3,5-bis-difluoromethyl-pyrazol-1-yl)-phenol.

2-chloro-4-(3,5-bis-difluoromethyl-pyrazol-1-yl)-phenol

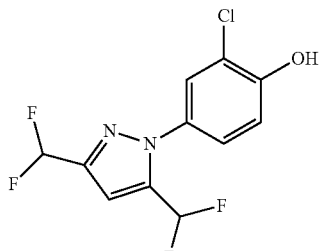

$^1$H-NMR (CDCl$_3$) δ: 7.53 (1H, d, J=2.4 Hz), 7.33 (1H, dd, J=8.7, 2.6 Hz), 7.15 (1H, d, J=8.8 Hz), 6.94 (1H, s), 6.87-6.47 (2H, m), 5.81 (1H, s).

Reference Preparation Example 22

A similar reaction to Reference Preparation example 19 using 1,1,1,5,5,5-hexafluoro-2,4-pentanedione instead of 3-methyl-2,4-pentanedione gave 2-chloro-4-(3,5-di-trifluoromethyl-pyrazol-1-yl)-phenol.

2-chloro-4-(3,5-di-trifluoromethyl-pyrazol-1-yl)-phenol

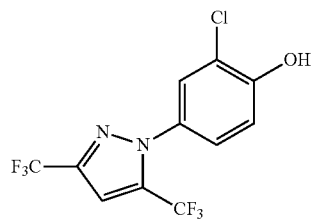 [SMILES: Oc1ccc(-n2nc(C(F)(F)F)cc2C(F)(F)F)cc1Cl]

$^1$H-NMR (CDCl$_3$) δ: 7.52 (1H, d, J=2.4 Hz), 7.35-7.31 (1H, m), 7.14 (1H, d, J=8.8 Hz), 7.06 (1H, s), 5.93 (1H, s).

Reference Preparation Example 23

A similar reaction to Reference Preparation example 19 using 1,1,1-trifluoro-2,4-pentanedione instead of 3-methyl-2,4-pentanedione gave 2-chloro-4-(5-methyl-3-trifluoromethyl-pyrazol-1-yl)-phenol.

2-chloro-4-(5-methyl-3-trifluoromethyl-pyrazol-1-yl)-phenol

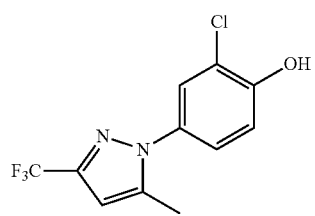 [SMILES: Cc1cc(C(F)(F)F)nn1-c1ccc(O)c(Cl)c1]

$^1$H-NMR (CDCl$_3$) δ: 7.47 (1H, d, J=2.7 Hz), 7.27 (1H, d, J=2.3 Hz), 7.25 (1H, d, J=2.7 Hz), 7.11 (1H, d, J=8.8 Hz), 6.44 (1H, s), 5.79 (1H, s), 2.32 (2H, s).

Reference Preparation Example 24

A similar reaction to Reference Preparation example 19 using heptane-3,5-dione instead of 3-methyl-2,4-pentanedione gave 2-chloro-4-(3,5-diethyl-pyrazol-1-yl)-phenol.

2-chloro-4-(3,5-diethyl-pyrazol-1-yl)-phenol

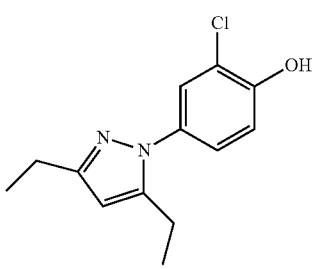 [SMILES: CCc1cc(CC)n(-c2ccc(O)c(Cl)c2)n1]

¹H-NMR (DMSO-D₆) δ: 10.56 (1H, br s), 7.42 (1H, d, J=2.7 Hz), 7.24-7.21 (1H, m), 7.07 (1H, d, J=8.8 Hz), 6.10 (1H, s), 2.60-2.52 (4H, m), 1.20-1.16 (3H, m), 1.11 (3H, dd, J=7.9, 7.0 Hz).

Reference Preparation Example 25

A similar reaction to Reference Preparation example 19 using 2,6-dimethyl-heptane-3,5-dione instead of 3-methyl-2,4-pentanedione gave 2-chloro-4-(3,5-diisopropyl-pyrazol-1-yl)-phenol.

2-chloro-4-(3,5-diisopropyl-pyrazol-1-yl)-phenol

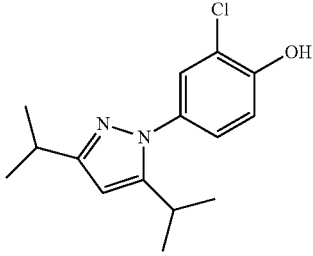 [SMILES: CC(C)c1cc(C(C)C)n(-c2ccc(O)c(Cl)c2)n1]

¹H-NMR (DMSO-D₆) δ: 7.41-7.39 (1H, m), 7.21-7.17 (1H, m), 7.10-7.07 (1H, m), 6.12 (1H, s), 2.93-2.83 (2H, m), 1.21 (3H, d, J=1.2 Hz), 1.19 (3H, d, J=1.2 Hz), 1.10 (3H, s), 1.09 (3H, s).

Reference Preparation Example 26

A mixture of iodosobenzene 2.5 g, boron trifluoride-ethyl ether 1.6 g, methanol 20 ml and 2,4-pentanedione 1.14 g was stirred at room temperature for five hours. The resulting mixture was concentrated under reduced pressure and was extracted with tert-butyl methyl ether. The organic layer was washed with aqueous sodium bicarbonate solution and water, and was dried over anhydrous sodium sulfate. The resulting mixture was concentrated under reduced and thereto was added ethanol 30 ml and 2-chloro-4-hydrazino-phenol hydrochloride salt 2 g (described in Reference Preparation example 112), and the resulting mixture was then stirred with heating under reflux for sixteen hours. The reaction mixture was concentrated under reduced pressure and thereto was added ethyl acetate 100 ml, and the resulting mixture was stirred at room temperature for two hours. The precipitates was filtered and was dried under reduced pressure to give 2-chloro-4-(3,5-dimethyl-4-methoxy-pyrazol-1-yl)-phenol 0.75 g.

2-chloro-4-(3,5-dimethyl-4-methoxy-pyrazol-1-yl)-phenol

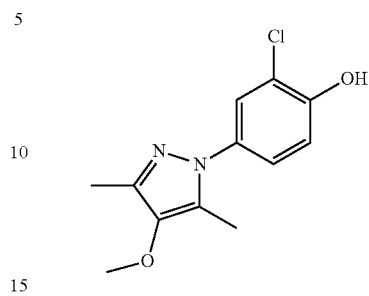

MS+; 253

Reference Preparation Example 27

A similar reaction to Reference Preparation example 19 using 3-ethyl-2,4-pentanedione instead of 3-methyl-2,4-pentanedione gave 2-chloro-4-(3,5-dimethyl-4-ethyl-pyrazol-1-yl)-phenol.

2-chloro-4-(3,5-dimethyl-4-ethyl-pyrazol-1-yl)-phenol

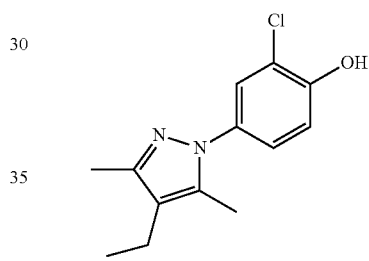

¹H-NMR (DMSO-D₆) δ: 7.45 (1H, s), 7.27-7.23 (1H, m), 7.11-7.07 (1H, m), 2.37 (2H, q, J=7.5 Hz), 2.17 (3H, s), 2.16 (3H, s), 1.05 (3H, t, J=7.6 Hz).

Reference Preparation Example 28

A mixture of 1-(4-methoxy-3-methyl-phenyl)-3,4,5-trimethyl-1H-pyrazole (described in Reference Preparation example 65) 7.3 g, 47% hydrobromic acid 50 ml and acetic acid 50 ml was stirred with heating under reflux for thirty hours. The solvent was distilled off and to the resulting residue was added ethyl acetate 400 ml, and the resulting mixture was stirred at room temperature for one hour. The precipitates was filtered and was washed with hexane, and was concentrated under reduced pressure to give 2-methyl-4-(3,4,5-trimethyl-pyrazol-1-yl)-phenol 6.1 g.

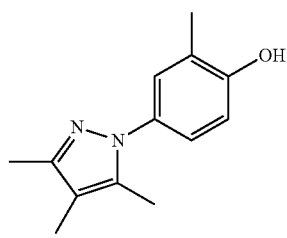 [SMILES: Cc1cc(-n2nc(C)c(C)c2C)ccc1O]

¹H-NMR (DMSO-D₆) δ: 7.22 (1H, d, J=2.2 Hz), 7.14 (1H, dd, J=8.4, 2.3 Hz), 6.91 (1H, d, J=8.3 Hz), 2.22 (3H, s), 2.17 (3H, s), 2.16 (3H, s), 1.97 (3H, s).

Reference Preparation Example 29

A similar reaction to Reference Preparation example 28 using 1-(2-chloro-4-methoxy-phenyl)-3,5-dimethyl-1H-pyrazole instead of 1-(4-methoxy-3-methyl-phenyl)-3,4,5-trimethyl-1H-pyrazole gave 3-chloro-4-(3,5-dimethyl-pyrazol-1-yl)-phenol.

3-chloro-4-(3,5-dimethyl-pyrazol-1-yl)-phenol

¹H-NMR (CDCl₃) δ: 10.65 (1H, br s), 7.02 (1H, d, J=8.5 Hz), 6.76 (1H, d, J=2.7 Hz), 6.55-6.52 (1H, m), 5.99 (1H, s), 2.32 (3H, s), 2.09 (3H, s).

Reference Preparation Example 30

A similar reaction to Reference Preparation example 28 using 1-(4-methoxy-3-methyl-phenyl)-3,5-dimethyl-1H-pyrazole (described in Reference Preparation example 66) instead of 1-(4-methoxy-3-methyl-phenyl)-3,4,5-trimethyl-1H-pyrazole gave 2-methyl-4-(3,5-dimethyl-pyrazol-1-yl)-phenol.

2-methyl-4-(3,5-dimethyl-pyrazol-1-yl)-phenol

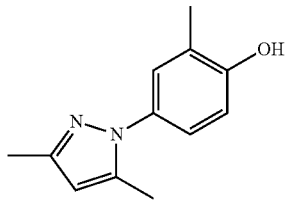

¹H-NMR (DMSO-D₆) δ: 9.68 (1H, br s), 7.19 (1H, s), 7.10 (1H, dd, J=8.8, 2.3 Hz), 6.87 (1H, d, J=8.8 Hz), 6.13 (1H, s), 2.20 (6H, s), 2.16 (3H, s).

Reference Preparation Example 31

A similar reaction to Reference Preparation example 28 using 1-(4-methoxy-phenyl)-3,5-dimethyl-1H-pyrazole (described in Reference Preparation example 74) instead of 1-(4-methoxy-3-methyl-phenyl)-3,4,5-trimethyl-1H-pyrazole gave 4-(3,5-dimethyl-pyrazol-1-yl)-phenol.

4-(3,5-dimethyl-pyrazol-1-yl)-phenol

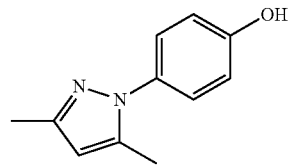

¹H-NMR (DMSO-D₆) δ: 9.69-9.67 (1H, m), 7.22 (2H, dd, J=6.6, 2.1 Hz), 6.83 (2H, dd, J=6.6, 2.1 Hz), 5.98 (1H, s), 2.18 (3H, s), 2.14 (3H, s).

Reference Preparation Example 32

A similar reaction to Reference Preparation example 28 using 1-(4-methoxy-2-methyl-phenyl)-3,5-dimethyl-1H-pyrazole (described in Reference Preparation example 75) instead of 1-(4-methoxy-3-methyl-phenyl)-3,4,5-trimethyl-1H-pyrazole gave 3-methyl-4-(3,5-dimethyl-pyrazol-1-yl)-phenol.

3-methyl-4-(3,5-dimethyl-pyrazol-1-yl)-phenol

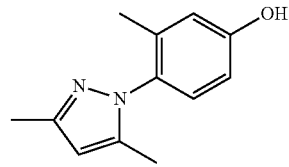

¹H-NMR (DMSO-D₆) δ: 7.13 (1H, d, J=8.5 Hz), 6.78 (1H, d, J=2.4 Hz), 6.73 (1H, dd, J=5.9, 2.7 Hz), 6.20 (1H, s), 2.23 (3H, s), 2.02 (3H, s), 1.88 (3H, s).

Reference Preparation Example 33

A similar reaction to Reference Preparation example 28 using 1-(2-chloro-4-methoxy-phenyl)-1H-pyrazole (described in Reference Preparation example 76) instead of 1-(4-methoxy-3-methyl-phenyl)-3,4,5-trimethyl-1H-pyrazole gave 3-chloro-4-(pyrazol-1-yl)-phenol.

3-chloro-4-(pyrazol-1-yl)-phenol

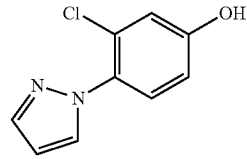 [SMILES: Oc1ccc(-n2cccn2)c(Cl)c1]

¹H-NMR (DMSO-D₆) δ: 7.96 (1H, d, J=2.2 Hz), 7.68-7.67 (1H, m), 7.34 (1H, d, J=8.7 Hz), 6.98 (1H, d, J=2.7 Hz), 6.85 (1H, dd, J=8.7, 2.7 Hz), 6.47-6.45 (1H, m).

Reference Preparation Example 34

A similar reaction to Reference Preparation example 28 using 1-(4-methoxy-3-methyl-phenyl)-4-methyl-1H-pyrazole (described in Reference Preparation example 67) instead of 1-(4-methoxy-3-methyl-phenyl)-3,4,5-trimethyl-1H-pyrazole gave 2-methyl-4-(4-methyl-pyrazol-1-yl)-phenol.

2-methyl-4-(4-methyl-pyrazol-1-yl)-phenol

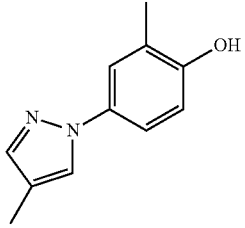

$^1$H-NMR (DMSO-D$_6$) δ: 8.04-8.03 (1H, m), 7.46 (1H, d, J=2.8 Hz), 7.44 (1H, s), 7.34 (1H, dd, J=8.6, 2.8 Hz), 6.82 (1H, d, J=8.6 Hz), 2.16 (3H, s), 2.07 (3H, s).

Reference Preparation Example 35

A similar reaction to Reference Preparation example 28 using 1-(4-methoxy-3-methyl-phenyl)-5-methyl-1H-pyrazole (described in Reference Preparation example 68) instead of 1-(4-methoxy-3-methyl-phenyl)-3,4,5-trimethyl-1H-pyrazole gave 2-methyl-4-(5-methyl-pyrazol-1-yl)-phenol.

2-methyl-4-(5-methyl-pyrazol-1-yl)-phenol

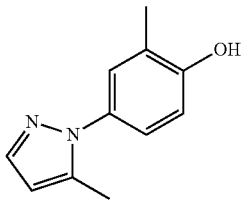

$^1$H-NMR (DMSO-D$_6$) δ: 7.50 (1H, d, J=1.5 Hz), 7.17 (1H, d, J=2.4 Hz), 7.09 (1H, dd, J=8.5, 2.7 Hz), 6.87 (1H, d, J=8.5 Hz), 6.22 (1H, d, J=1.5 Hz), 2.24 (3H, s), 2.16 (3H, s).

Reference Preparation Example 36

A similar reaction to Reference Preparation example 28 using 1-(4-methoxy-3-methyl-phenyl)-3-methyl-1H-pyrazole (described in Reference Preparation example 68) instead of 1-(4-methoxy-3-methyl-phenyl)-3,4,5-trimethyl-1H-pyrazole gave 2-methyl-4-(3-methyl-pyrazol-1-yl)-phenol.

2-methyl-4-(3-methyl-pyrazol-1-yl)-phenol

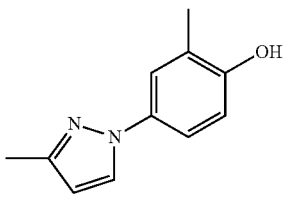

$^1$H-NMR (DMSO-D$_6$) δ: 8.13 (1H, d, J=2.4 Hz), 7.46 (1H, d, J=2.7 Hz), 7.35 (1H, dd, J=8.5, 2.7 Hz), 6.81 (1H, d, J=8.5 Hz), 6.23 (1H, d, J=2.4 Hz), 2.23 (3H, s), 2.17 (3H, s).

Reference Preparation Example 37

A similar reaction to Reference Preparation example 28 using 1-(4-methoxy-3-methyl-phenyl)-1H-pyrazole (described in Reference Preparation example 69) instead of 1-(4-methoxy-3-methyl-phenyl)-3,4,5-trimethyl-1H-pyrazole gave 2-methyl-4-(pyrazol-1-yl)-phenol.

2-methyl-4-(pyrazol-1-yl)-phenol

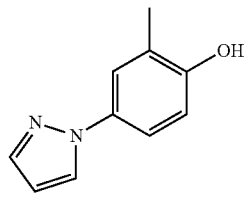

$^1$H-NMR (DMSO-D$_6$) δ: 8.27 (1H, d, J=2.2 Hz), 7.65-7.63 (1H, m), 7.52 (1H, d, J=2.7 Hz), 7.41 (1H, dd, J=8.5, 2.7 Hz), 6.85 (1H, d, J=8.5 Hz), 6.46 (1H, t, J=2.2 Hz), 5.36 (1H, br s), 2.18 (3H, s).

Reference Preparation Example 38

A similar reaction to Reference Preparation example 28 using 1-(3,5-dimethyl-4-methoxy-phenyl)-1H-pyrazole (described in Reference Preparation example 77) instead of 1-(4-methoxy-3-methyl-phenyl)-3,4,5-trimethyl-1H-pyrazole gave 2,6-dimethyl-4-(3-methyl-pyrazol-1-yl)-phenol.

2,6-dimethyl-4-(3-methyl-pyrazol-1-yl)-phenol

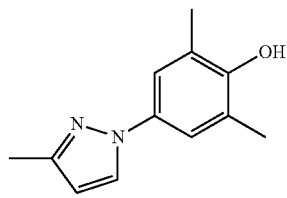

$^1$H-NMR (DMSO-D$_6$) δ: 8.14 (1H, d, J=2.2 Hz), 7.33 (1H, s), 7.31 (2H, s), 6.23 (1H, d, J=2.2 Hz), 2.23 (3H, s), 2.20 (6H, s).

Reference Preparation Example 39

A similar reaction to Reference Preparation example 28 using 1-(3-chloro-4-methoxy-phenyl)-3-methyl-1H-pyrazole (described in Reference Preparation example 78) instead of 1-(4-methoxy-3-methyl-phenyl)-3,4,5-trimethyl-1H-pyrazole gave 2-chloro-4-(3-methyl-pyrazol-1-yl)-phenol.

2-chloro-4-(3-methyl-pyrazol-1-yl)-phenol

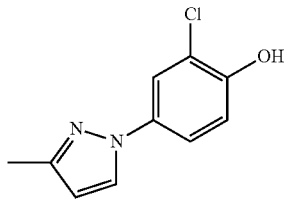

¹H-NMR (DMSO-D₆) δ: 8.25 (1H, d, J=2.2 Hz), 7.75 (1H, d, J=2.7 Hz), 7.56 (1H, dd, J=8.8, 2.7 Hz), 7.02 (1H, d, J=8.8 Hz), 6.27 (1H, d, J=2.2 Hz), 2.24 (3H, s).

Reference Preparation Example 40

A similar reaction to Reference Preparation example 28 using 1-(2,5-dimethyl-4-methoxy-phenyl)-3-methyl-1H-pyrazole (described in Reference Preparation example 81) instead of 1-(4-methoxy-3-methyl-phenyl)-3,4,5-trimethyl-1H-pyrazole gave 2,5-dimethyl-4-(3-methyl-pyrazol-1-yl)-phenol.

2,5-dimethyl-4-(3-methyl-pyrazol-1-yl)-phenol

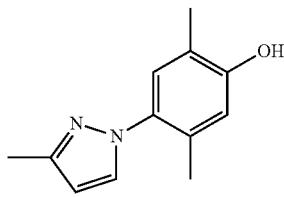

¹H-NMR (DMSO-D₆) δ: 7.74 (1H, d, J=2.2 Hz), 7.00 (1H, s), 6.70 (1H, s), 6.22 (1H, d, J=2.2 Hz), 2.23 (3H, s), 2.10 (3H, s), 2.02 (3H, s).

Reference Preparation Example 41

A similar reaction to Reference Preparation example 28 using 1-(3-chloro-4-methoxy-phenyl)-5-methyl-1H-pyrazole (described in Reference Preparation example 78) instead of 1-(4-methoxy-3-methyl-phenyl)-3,4,5-trimethyl-1H-pyrazole gave 2-chloro-4-(5-methyl-pyrazol-1-yl)-phenol.

2-chloro-4-(5-methyl-pyrazol-1-yl)-phenol

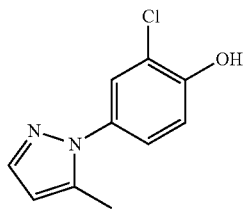

¹H-NMR (DMSO-D₆) δ: 10.54 (1H, s), 7.50-7.49 (1H, m), 7.48-7.47 (1H, m), 7.28 (1H, ddd, J=8.7, 2.6, 0.7 Hz), 7.06 (1H, d, J=8.5 Hz), 6.22 (1H, dd, J=1.7, 0.7 Hz), 2.27 (3H, s).

Reference Preparation Example 42

A similar reaction to Reference Preparation example 28 using 1-(2,3-dimethyl-4-methoxy-phenyl)-3-methyl-1H-pyrazole (described in Reference Preparation example 82) instead of 1-(4-methoxy-3-methyl-phenyl)-3,4,5-trimethyl-1H-pyrazole gave 2,3-dimethyl-4-(3-methyl-pyrazol-1-yl)-phenol.

2,3-dimethyl-4-(3-methyl-pyrazol-1-yl)-phenol

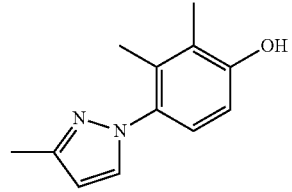

¹H-NMR (DMSO-D₆) δ: 7.68 (1H, d, J=2.2 Hz), 6.92 (1H, d, J=8.3 Hz), 6.72 (1H, d, J=8.3 Hz), 6.22 (1H, d, J=2.2 Hz), 2.23 (3H, s), 2.10 (3H, s), 1.90 (3H, s).

Reference Preparation Example 43

A similar reaction to Reference Preparation example 28 using 1-(3-fluoro-4-methoxy-phenyl)-3-methyl-1H-pyrazole (described in Reference Preparation example 80) instead of 1-(4-methoxy-3-methyl-phenyl)-3,4,5-trimethyl-1H-pyrazole gave 2-fluoro-4-(3-methyl-pyrazol-1-yl)-phenol.

2-fluoro-4-(3-methyl-pyrazol-1-yl)-phenol

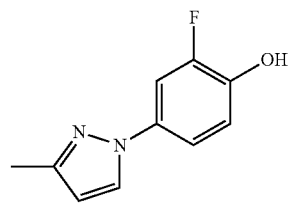

¹H-NMR (DMSO-D₆) δ: 8.24 (1H, d, J=2.4 Hz), 7.59 (1H, dd, J=12.6, 2.6 Hz), 7.41 (1H, dq, J=8.8, 1.2 Hz), 7.01 (1H, t, J=8.8 Hz), 6.28 (1H, d, J=2.4 Hz), 2.24 (3H, s).

Reference Preparation Example 44

A similar reaction to Reference Preparation example 28 using 1-(3-chloro-4-methoxy-phenyl)-4-methyl-1H-pyrazole (described in Reference Preparation example 79) instead of 1-(4-methoxy-3-methyl-phenyl)-3,4,5-trimethyl-1H-pyrazole gave 2-chloro-4-(4-methyl-pyrazol-1-yl)-phenol.

2-chloro-4-(4-methyl-pyrazol-1-yl)-phenol

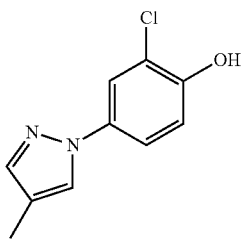

$^1$H-NMR (DMSO-D$_6$) δ: 8.16-8.15 (1H, m), 7.74 (1H, dd, J=2.6, 0.9 Hz), 7.55 (1H, dq, J=8.8, 1.2 Hz), 7.49 (1H, s), 7.03 (1H, d, J=8.8 Hz), 2.07 (3H, s).

Reference Preparation Example 45

A similar reaction to Reference Preparation example 28 using 1-(4-methoxy-3-methyl-phenyl)-3-trifluoromethyl-1H-pyrazole (described in Reference Preparation example 72) instead of 1-(4-methoxy-3-methyl-phenyl)-3,4,5-trimethyl-1H-pyrazole gave 2-methyl-4-(3-trifluoromethyl-pyrazol-1-yl)-phenol.

2-methyl-4-(3-trifluoromethyl-pyrazol-1-yl)-phenol

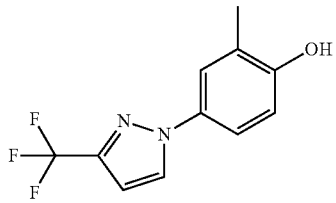 [SMILES: Cc1cc(-n2ccc(C(F)(F)F)n2)ccc1O]

$^1$H-NMR (CDCl$_3$) δ: 7.83-7.80 (1H, m), 7.45 (1H, d, J=2.2 Hz), 7.32 (1H, dd, J=8.5, 2.4 Hz), 6.82 (1H, d, J=8.5 Hz), 6.68 (1H, d, J=2.2 Hz), 5.46 (1H, s), 2.29 (3H, s).

Reference Preparation Example 46

A similar reaction to Reference Preparation example 28 using 1-(4-methoxy-3-methyl-phenyl)-3,4-dimethyl-1H-pyrazole (described in Reference Preparation example 70) instead of 1-(4-methoxy-3-methyl-phenyl)-3,4,5-trimethyl-1H-pyrazole gave 2-methyl-4-(3,4-dimethyl-pyrazol-1-yl)-phenol.

2-methyl-4-(3,4-dimethyl-pyrazol-1-yl)-phenol

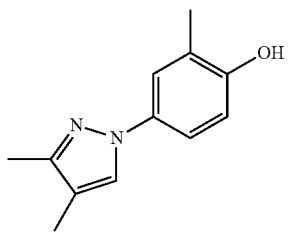

$^1$H-NMR (DMSO-D$_6$) δ: 7.94 (1H, s), 7.41 (1H, d, J=2.2 Hz), 7.29 (1H, dd, J=8.5, 2.7 Hz), 6.80 (1H, d, J=8.5 Hz), 2.15 (6H, s), 1.99 (3H, s).

Reference Preparation Example 47

A similar reaction to Reference Preparation example 28 using 1-(4-methoxy-3-methyl-phenyl)-4,5-dimethyl-1H-pyrazole (described in Reference Preparation example 70) instead of 1-(4-methoxy-3-methyl-phenyl)-3,4,5-trimethyl-1H-pyrazole gave 2-methyl-4-(4,5-dimethyl-pyrazol-1-yl)-phenol.

2-methyl-4-(4,5-dimethyl-pyrazol-1-yl)-phenol

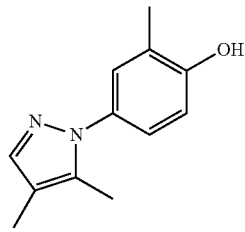

$^1$H-NMR (DMSO-D$_6$) δ: 7.51 (1H, s), 7.17 (1H, d, J=2.2 Hz), 7.08 (1H, dd, J=8.5, 2.4 Hz), 6.88 (1H, d, J=8.5 Hz), 2.16 (3H, s), 2.15 (3H, s), 2.01 (3H, s).

Reference Preparation Example 48

A similar reaction to Reference Preparation example 28 using 1-(4-methoxy-3-methyl-phenyl)-3-tert-butyl-1H-pyrazole (described in Reference Preparation example 73) instead of 1-(4-methoxy-3-methyl-phenyl)-3,4,5-trimethyl-1H-pyrazole gave 2-methyl-4-(3-tert-butyl-pyrazol-1-yl)-phenol.

2-methyl-4-(3-tert-butyl-pyrazol-1-yl)-phenol

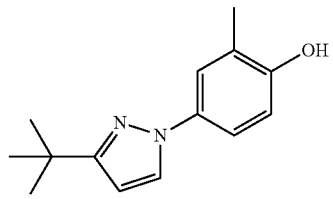 [SMILES: Cc1cc(-n2ccc(C(C)(C)C)n2)ccc1O]

$^1$H-NMR (DMSO-D$_6$) δ: 8.11 (1H, d, J=2.4 Hz), 7.46 (1H, d, J=2.7 Hz), 7.36 (1H, dd, J=8.5, 2.7 Hz), 6.82 (1H, d, J=8.5 Hz), 6.33 (1H, d, J=2.2 Hz), 2.17 (3H, s), 1.29 (9H, s).

Reference Preparation Example 49

A similar reaction to Reference Preparation example 28 using 1-(4-methoxy-3-trifluoromethyl-phenyl)-3,4,5-trimethyl-1H-pyrazole (described in Reference Preparation example 83) instead of 1-(4-methoxy-3-methyl-phenyl)-3,4,5-trimethyl-1H-pyrazole gave 2-trifluoromethyl-4-(3,4,5-trimethyl-pyrazol-1-yl)-phenol.

2-trifluoromethyl-4-(3,4,5-trimethyl-pyrazol-1-yl)-phenol

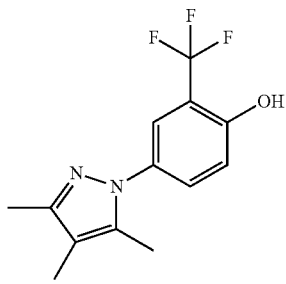 [SMILES: Cc1nn(-c2ccc(O)c(C(F)(F)F)c2)c(C)c1C]

¹H-NMR (DMSO-D₆) δ: 10.96 (1H, s), 7.59-7.55 (2H, m), 7.16-7.12 (1H, m), 2.16 (3H, s), 2.15 (3H, s), 1.94 (3H, s).

Reference Preparation Example 50

A similar reaction to Reference Preparation example 28 using 2-(4-methoxy-3-methyl-phenyl)-4,5,6,7-tetrahydro-2H-indazole (described in Reference Preparation example 71) instead of 1-(4-methoxy-3-methyl-phenyl)-3,4,5-trimethyl-1H-pyrazole gave 2-methyl-4-(4,5,6,7-tetrahydro-indazole-2-yl)-phenol.

2-methyl-4-(4,5,6,7-tetrahydro-indazole-2-yl)-phenol

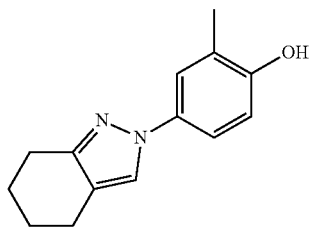 [SMILES: Cc1cc(-n2cc3c(n2)CCCC3)ccc1O]

¹H-NMR (DMSO-D₆) δ: 7.92 (1H, s), 7.43 (1H, d, J=2.7 Hz), 7.31 (1H, dd, J=8.7, 2.7 Hz), 6.79 (1H, d, J=8.7 Hz), 2.61 (2H, t, J=6.2 Hz), 2.55-2.51 (2H, m), 2.16-2.13 (3H, m), 1.79-1.72 (2H, m), 1.72-1.65 (2H, m).

Reference Preparation Example 51

A similar reaction to Reference Preparation example 28 using 1-(4-methoxy-3-methyl-phenyl)-4,5,6,7-tetrahydro-1H-indazole (described in Reference Preparation example 71) instead of 1-(4-methoxy-3-methyl-phenyl)-3,4,5-trimethyl-1H-pyrazole gave 2-methyl-4-(4,5,6,7-tetrahydro-indazole-1-yl)-phenol.

2-methyl-4-(4,5,6,7-tetrahydro-indazole-1-yl)-phenol

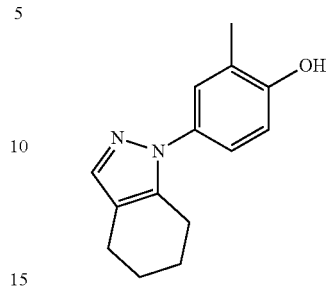

¹H-NMR (DMSO-D₆) δ: 7.39 (1H, s), 7.20 (1H, s), 7.12-7.09 (1H, m), 6.84 (1H, d, J=8.5 Hz), 2.64-2.59 (2H, m), 2.52-2.48 (2H, m), 2.16 (3H, s), 1.75-1.65 (4H, m).

Reference Preparation Example 52

A similar reaction to Reference Preparation example 28 using 4-(3-chloro-4-methoxy-phenyl)-1-methyl-1H-pyrazole (described in Reference Preparation example 85) instead of 1-(4-methoxy-3-methyl-phenyl)-3,4,5-trimethyl-1H-pyrazole gave 2-chloro-4-(1-methyl-1H-pyrazole-4-yl)-phenol.

2-chloro-4-(1-methyl-1H-pyrazole-4-yl)-phenol

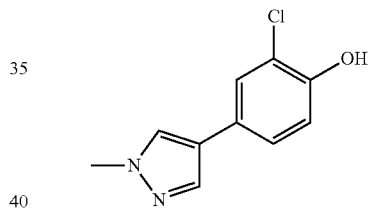

¹H-NMR (DMSO-D₆) δ: 8.04 (1H, s), 7.77 (1H, s), 7.53 (1H, d, J=2.0 Hz), 7.32 (1H, dd, J=8.5, 2.2 Hz), 6.94 (1H, d, J=8.5 Hz), 3.83 (3H, s).

Reference Preparation Example 53

A similar reaction to Reference Preparation example 28 using 4-(4-methoxy-3-methyl-phenyl)-1-methyl-1H-pyrazole (described in Reference Preparation example 84) instead of 1-(4-methoxy-3-methyl-phenyl)-3,4,5-trimethyl-1H-pyrazole gave 2-methyl-4-(1-methyl-1H-pyrazole-4-yl)-phenol.

2-methyl-4-(1-methyl-1H-pyrazole-4-yl)-phenol

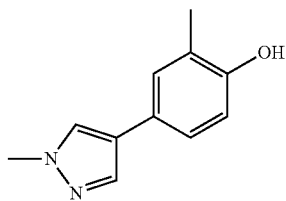

¹H-NMR (DMSO-D₆) δ: 7.92 (1H, s), 7.68 (1H, s), 7.24 (1H, s), 7.15 (1H, d, J=8.2 Hz), 6.73 (1H, d, J=8.5 Hz), 3.82 (3H, d, J=0.7 Hz), 2.12 (3H, s).

Reference Preparation Example 54

A similar reaction to Reference Preparation example 28 using 4-(4-methoxy-3-methyl-phenyl)-1-ethyl-1H-pyrazole (described in Reference Preparation example 86) instead of 1-(4-methoxy-3-methyl-phenyl)-3,4,5-trimethyl-1H-pyrazole gave 2-methyl-4-(1-ethyl-1H-pyrazole-4-yl)-phenol.

2-methyl-4-(1-ethyl-1H-pyrazole-4-yl)-phenol

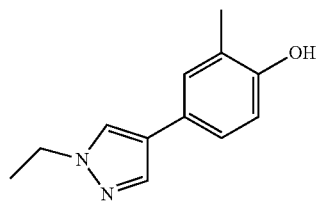

¹H-NMR (DMSO-D₆) δ: 7.99 (1H, s), 7.70 (1H, s), 7.26 (1H, d, J=1.2 Hz), 7.17 (1H, dd, J=8.2, 2.4 Hz), 6.74 (1H, d, J=8.2 Hz), 4.11 (2H, q, J=7.2 Hz), 2.13 (3H, s), 1.38 (3H, dd, J=7.8, 6.9 Hz).

Reference Preparation Example 55

A similar reaction to Reference Preparation example 28 using 4-(4-methoxy-3-methyl-phenyl)-1-propyl-1H-pyrazole (described in Reference Preparation example 87) instead of 1-(4-methoxy-3-methyl-phenyl)-3,4,5-trimethyl-1H-pyrazole gave 2-methyl-4-(1-propyl-1H-pyrazole-4-yl)-phenol.

2-methyl-4-(1-propyl-1H-pyrazole-4-yl)-phenol

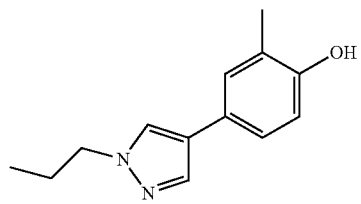 [SMILES: CCCn1cc(-c2ccc(O)c(C)c2)cn1]

¹H-NMR (DMSO-D₆) δ: 7.98 (1H, s), 7.71 (1H, s), 7.26 (1H, s), 7.19-7.14 (1H, m), 6.74 (1H, d, J=8.2 Hz), 4.03 (2H, t, J=6.9 Hz), 2.12 (3H, s), 1.83-1.73 (2H, m), 0.84 (3H, t, J=7.2 Hz).

Reference Preparation Example 56

A similar reaction to Reference Preparation example 28 using 4-(4-methoxy-3-methyl-phenyl)-1-isopropyl-1H-pyrazole (described in Reference Preparation example 88) instead of 1-(4-methoxy-3-methyl-phenyl)-3,4,5-trimethyl-1H-pyrazole gave 2-methyl-4-(1-isopropyl-1H-pyrazole-4-yl)-phenol.

2-methyl-4-(1-isopropyl-1H-pyrazole-4-yl)-phenol

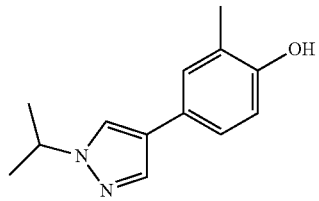 [SMILES: Cc1cc(-c2cnn(C(C)C)c2)ccc1O]

¹H-NMR (DMSO-D₆) δ: 8.03 (1H, d, J=1.5 Hz), 7.70 (1H, d, J=1.7 Hz), 7.27 (1H, s), 7.17 (1H, d, J=8.3 Hz), 6.75-6.72 (1H, m), 4.46 (1H, dt, J=14.0, 6.0 Hz), 2.13 (3H, s), 1.43 (3H, d, J=2.4 Hz), 1.41 (3H, d, J=2.4 Hz).

Reference Preparation Example 57

A similar reaction to Reference Preparation example 28 using 4-(4-methoxy-3-methyl-phenyl)-1-butyl-1H-pyrazole (described in Reference Preparation example 89) instead of 1-(4-methoxy-3-methyl-phenyl)-3,4,5-trimethyl-1H-pyrazole gave 2-methyl-4-(1-butyl-1H-pyrazole-4-yl)-phenol.

2-methyl-4-(1-butyl-1H-pyrazole-4-yl)-phenol

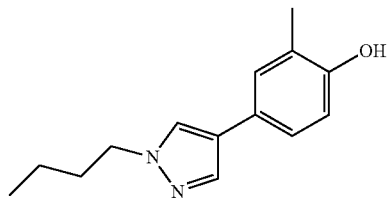 [SMILES: CCCCn1cc(-c2ccc(O)c(C)c2)cn1]

¹H-NMR (DMSO-D₆) δ: 7.97 (1H, s), 7.69 (1H, s), 7.26 (1H, s), 7.16 (1H, d, J=8.2 Hz), 6.73 (1H, d, J=8.2 Hz), 4.07 (2H, t, J=6.8 Hz), 2.15-2.10 (3H, m), 1.79-1.72 (2H, m), 1.25 (2H, dd, J=14.9, 7.6 Hz), 0.89 (3H, t, J=7.4 Hz).

Reference Preparation Example 58

A similar reaction to Reference Preparation example 28 using 4-(4-methoxy-3-methyl-phenyl)-1-isobutyl-1H-pyrazole instead of 1-(4-methoxy-3-methyl-phenyl)-3,4,5-trimethyl-1H-pyrazole gave 2-methyl-4-(1-isobutyl-1H-pyrazole-4-yl)-phenol.

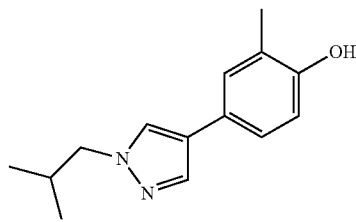 [SMILES: Cc1cc(-c2cnn(CC(C)C)c2)ccc1O]

¹H-NMR (DMSO-D₆) δ: 9.17 (1H, s), 7.94 (1H, s), 7.69 (1H, s), 7.26 (1H, s); 7.16 (1H, d, J=8.2 Hz), 6.73 (1H, d, J=8.2 Hz), 3.88 (2H, d, J=7.0 Hz), 2.12 (3H, s), 0.84 (6H, d, J=6.5 Hz).

Reference Preparation Example 59

A similar reaction to Reference Preparation example 28 using 4-(4-methoxy-3-methyl-phenyl)-1,3-dimethyl-1H-pyrazole (described in Reference Preparation example 90) instead of 1-(4-methoxy-3-methyl-phenyl)-3,4,5-trimethyl-1H-pyrazole gave 2-methyl-4-(1,3-dimethyl-1H-pyrazole-4-yl)-phenol.

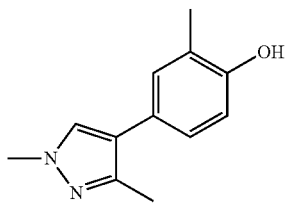

$^1$H-NMR (DMSO-D$_6$) δ: 7.83 (1H, s), 7.10 (1H, s), 7.03 (1H, d, J=8.2 Hz), 6.80 (1H, d, J=8.2 Hz), 3.80 (3H, s), 2.27 (3H, s), 2.14 (3H, s).

Reference Preparation Example 60

A mixture of 3-(4-methoxy-3-methyl-phenyl)-1-methyl-1H-pyrazole (described in Reference Preparation example 91) 2.9 g, 47% hydrobromic acid 21 ml and acetic acid 21 ml was stirred with heating under reflux for twenty hours. The solvent was distilled off and to the resulting residue was added ethyl acetate 100 ml, and the resulting mixture was stirred at room temperature for one hour. The precipitates was filtered and was washed with hexane, and was concentrated under reduced pressure to give 2-methyl-4-(1-methyl-1H-pyrazol-3-yl)-phenol 2.45 g.

2-methyl-4-(1-methyl-1H-pyrazol-3-yl)-phenol

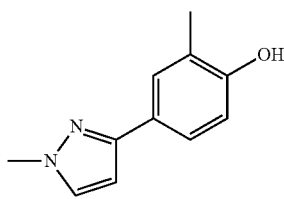

$^1$H-NMR (DMSO-D$_6$) δ: 9.30 (1H, br s), 7.64 (1H, s), 7.48 (1H, s), 7.38 (1H, d, J=8.3 Hz), 6.76 (1H, d, J=8.0 Hz), 6.50-6.49 (1H, m), 3.83 (3H, s), 2.14 (3H, s).

Reference Preparation Example 61

A similar reaction to Reference Preparation example 60 using 3-(4-methoxy-3-methyl-phenyl)-1-ethyl-1H-pyrazole (described in Reference Preparation example 92) instead of 3-(4-methoxy-3-methyl-phenyl)-1-methyl-1H-pyrazole gave 2-methyl-4-(1-ethyl-1H-pyrazol-3-yl)-phenol.

2-methyl-4-(1-ethyl-1H-pyrazol-3-yl)-phenol

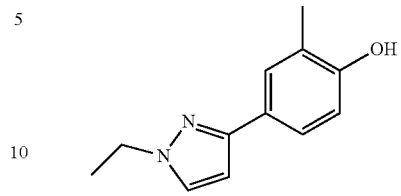

$^1$H-NMR (DMSO-D$_6$) δ: 9.30 (1H, br s), 7.68 (1H, d, J=2.2 Hz), 7.48 (1H, d, J=2.2 Hz), 7.39 (1H, dd, J=8.3, 2.2 Hz), 6.76 (1H, d, J=8.3 Hz), 6.49 (1H, d, J=2.2 Hz), 4.12 (2H, q, J=6.2 Hz), 2.14 (3H, s), 1.38 (3H, t, J=7.2 Hz).

Reference Preparation Example 62

A similar reaction to Reference Preparation example 60 using 3-(4-methoxy-3-methyl-phenyl)-1-isopropyl-1H-pyrazole (described in Reference Preparation example 93) instead of 3-(4-methoxy-3-methyl-phenyl)-1-methyl-1H-pyrazole gave 2-methyl-4-(1-isopropyl-1H-pyrazol-3-yl)-phenol.

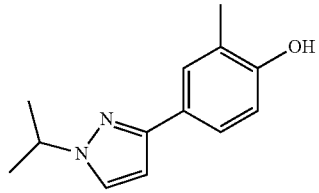 [SMILES: Cc1cc(-c2ccn(C(C)C)n2)ccc1O]

$^1$H-NMR (DMSO-D$_6$) δ: 9.30 (1H, br s), 7.71 (1H, d, J=2.2 Hz), 7.49-7.48 (1H, m), 7.39 (1H, dd, J=8.2, 2.2 Hz), 6.76 (1H, d, J=8.2 Hz), 6.49 (1H, d, J=2.2 Hz), 4.53-4.42 (1H, m), 2.15 (3H, s), 1.43 (6H, d, J=6.5 Hz).

Reference Preparation Example 63

A similar reaction to Reference Preparation example 60 using 3-(4-methoxy-3-methyl-phenyl)-1,5-dimethyl-1H-pyrazole (described in Reference Preparation example 95) instead of 3-(4-methoxy-3-methyl-phenyl)-1-methyl-1H-pyrazole gave 2-methyl-4-(1,5-dimethyl-1H-pyrazol-3-yl)-phenol.

2-methyl-4-(1,5-dimethyl-1H-pyrazol-3-yl)-phenol

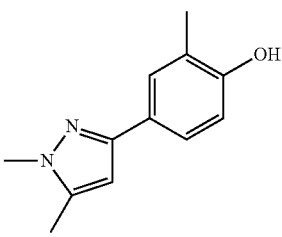

$^1$H-NMR (DMSO-D$_6$) δ: 9.31 (1H, br s), 7.43 (1H, d, J=1.7 Hz), 7.33 (1H, dd, J=8.2, 2.2 Hz), 6.75 (1H, d, J=8.2 Hz), 6.29 (1H, s), 3.71 (3H, s), 2.24 (3H, s), 2.13 (3H, s).

Reference Preparation Example 64

A similar reaction to Reference Preparation example 60 using 3-(3-bromo-4-methoxy-phenyl)-1-methyl-1H-pyrazole (described in Reference Preparation example 94) instead of 3-(4-methoxy-3-methyl-phenyl)-1-methyl-1H-pyrazole gave 2-bromo-4-(1-methyl-1H-pyrazol-3-yl)-phenol.

2-bromo-4-(1-methyl-1H-pyrazol-3-yl)-phenol

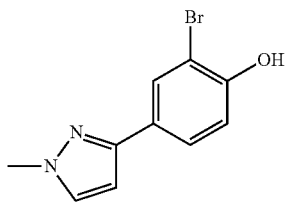

$^1$H-NMR (DMSO-D$_6$) δ: 7.87-7.86 (1H, m), 7.69 (1H, d, J=2.2 Hz), 7.60-7.57 (1H, m), 6.97 (1H, d, J=8.5 Hz), 6.61-6.60 (1H, m), 3.85 (3H, s).

Reference Preparation Example 65

A mixture of 4-methoxy-3-methyl-phenylboronic acid 10 g, 3,4,5-trimethyl-1H-pyrazole (described in Reference Preparation example 103) 7.3 g, copper(II) acetate 18.4 g, pyridine 10.0 g, molecular sieves 4 A 20.0 g and acetonitrile 300 ml was stirred with heating under reflux for thirty hours. The reaction mixture was filtered through Celite and was concentrated under reduced pressure. The resulting residue was subjected to a silica gel column chromatography to give 1-(4-methoxy-3-methyl-phenyl)-3,4,5-trimethyl-1H-pyrazole 7.3 g.

1-(4-methoxy-3-methyl-phenyl)-3,4,5-trimethyl-1H-pyrazole

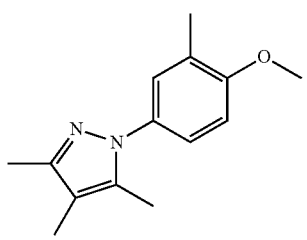

$^1$H-NMR (CDCl$_3$) δ: 7.19-7.17 (1H, m), 7.14 (1H, dd, J=8.5, 2.7 Hz), 6.84 (1H, d, J=8.5 Hz), 0.3.86 (3H, s), 2.24 (6H, s), 2.16 (3H, s), 1.97 (3H, s).

Reference Preparation Example 66

A similar reaction to Reference Preparation example 65 using 3,5-dimethyl-1H-pyrazole instead of 3,4,5-trimethyl-1H-pyrazole gave 1-(4-methoxy-3-methyl-phenyl)-3,5-dimethyl-1H-pyrazole.

1-(4-methoxy-3-methyl-phenyl)-3,5-dimethyl-1H-pyrazole

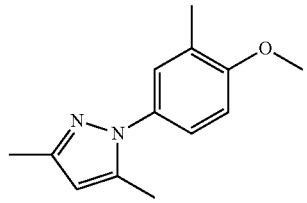

$^1$H-NMR (CDCl$_3$) δ: 7.20 (1H, d, J=2.0 Hz), 7.16 (1H, dd, J=8.5, 2.7 Hz), 6.84 (1H, d, J=8.5 Hz), 5.95 (1H, s), 3.86 (3H, s), 2.29 (3H, s), 2.24 (3H, s), 2.24 (3H, s).

Reference Preparation Example 67

A similar reaction to Reference Preparation example 65 using 4-methyl-1H-pyrazole instead of 3,4,5-trimethyl-1H-pyrazole gave 1-(4-methoxy-3-methyl-phenyl)-4-methyl-1H-pyrazole.

1-(4-methoxy-3-methyl-phenyl)-4-methyl-1H-pyrazole

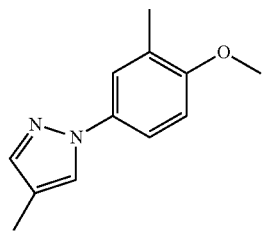

$^1$H-NMR (CDCl$_3$) δ: 7.60 (1H, s), 7.48 (1H, s), 7.44 (1H, d, J=2.7 Hz), 7.38 (1H, dd, J=8.7, 2.7 Hz), 6.85 (1H, d, J=8.7 Hz), 3.85 (3H, s), 2.26 (3H, s), 2.15 (3H, s).

Reference Preparation Example 68

A similar reaction to Reference Preparation example 65 using 3-methyl-1H-pyrazole instead of 3,4,5-trimethyl-1H-pyrazole gave 1-(4-methoxy-3-methyl-phenyl)-3-methyl-1H-pyrazole and 1-(4-methoxy-3-methyl-phenyl)-5-methyl-1H-pyrazole.

1-(4-methoxy-3-methyl-phenyl)-3-methyl-1H-pyrazole

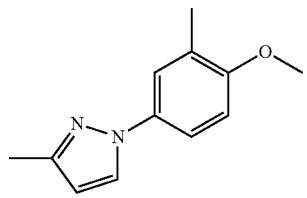

¹H-NMR (CDCl₃) δ: 7.70 (1H, d, J=2.2 Hz), 7.44 (1H, d, J=2.7 Hz), 7.37 (1H, dd, J=8.6, 2.7 Hz), 6.84 (1H, d, J=8.6 Hz), 6.20 (1H, d, J=2.2 Hz), 3.85 (3H, s), 2.37 (3H, s), 2.26 (3H, s).

1-(4-methoxy-3-methyl-phenyl)-5-methyl-1H-pyrazole

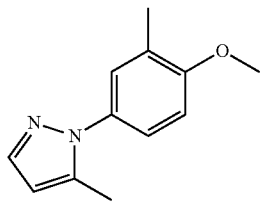

¹H-NMR (CDCl₃) δ: 7.54 (1H, d, J=1.7 Hz), 7.23-7.17 (2H, m), 6.87 (1H, d, J=8.5 Hz), 6.17-6.15 (1H, m), 3.88 (3H, s), 2.29 (3H, s), 2.26 (3H, s).

Reference Preparation Example 69

A similar reaction to Reference Preparation example 65 using 1H-pyrazole instead of 3,4,5-trimethyl-1H-pyrazole gave 1-(4-methoxy-3-methyl-phenyl)-1H-pyrazole.

1-(4-methoxy-3-methyl-phenyl)-1H-pyrazole

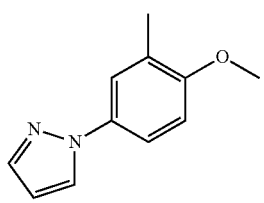

¹H-NMR (CDCl₃) δ: 7.82-7.81 (1H, m), 7.69 (1H, d, J=1.5 Hz), 7.48 (1H, d, J=2.2 Hz), 7.42 (1H, dd, J=8.6, 2.7 Hz), 6.86 (1H, d, J=8.6 Hz), 6.43 (1H, t, J=2.2 Hz), 3.86 (3H, s), 2.28 (3H, s).

Reference Preparation Example 70

A similar reaction to Reference Preparation example 65 using 3,4-dimethyl-1H-pyrazole instead of 3,4,5-trimethyl-1H-pyrazole gave 1-(4-methoxy-3-methyl-phenyl)-3,4-dimethyl-1H-pyrazole and 1-(4-methoxy-3-methyl-phenyl)-4,5-dimethyl-1H-pyrazole.

1-(4-methoxy-3-methyl-phenyl)-3,4-dimethyl-1H-pyrazole

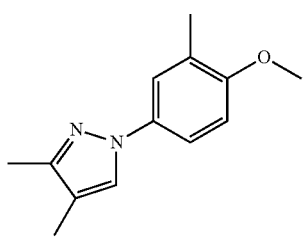

¹H-NMR (CDCl₃) δ: 7.52 (1H, s), 7.41 (1H, d, J=2.7 Hz), 7.32 (1H, dd, J=8.7, 2.9 Hz), 6.82 (1H, d, J=8.7 Hz), 3.84 (3H, s), 2.27 (3H, s), 2.25 (3H, s), 2.06 (3H, s).

1-(4-methoxy-3-methyl-phenyl)-4,5-dimethyl-1H-pyrazole

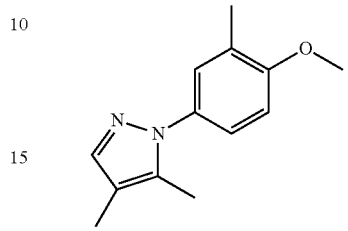

¹H-NMR (CDCl₃) δ: 7.41 (1H, s), 7.20-7.15 (2H, m), 6.86 (1H, d, J=8.5 Hz), 3.87 (3H, s), 2.25 (3H, s), 2.19 (3H, s), 2.05 (3H, s).

Reference Preparation Example 71

A similar reaction to Reference Preparation example 65 using 4,5,6,7-tetrahydroindazole instead of 3,4,5-trimethyl-1H-pyrazole gave 2-(4-methoxy-3-methyl-phenyl)-4,5,6,7-tetrahydro-2H-indazole and 1-(4-methoxy-3-methyl-phenyl)-4,5,6,7-tetrahydro-1H-indazole.

2-(4-methoxy-3-methyl-phenyl)-4,5,6,7-tetrahydro-2H-indazole

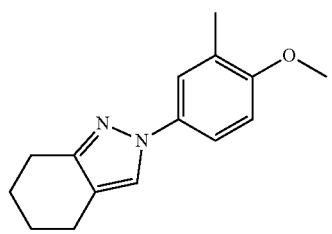 [SMILES: COc1ccc(-n2cc3c(n2)CCCC3)cc1C]

¹H-NMR (CDCl₃) δ: 7.51 (1H, s), 7.43 (1H, d, J=2.7 Hz), 7.34 (1H, dd, J=8.7, 2.8 Hz), 6.83 (1H, d, J=8.8 Hz), 3.85 (3H, s), 2.77 (2H, t, J=6.2 Hz), 2.61 (2H, t, J=6.1 Hz), 2.25 (3H, s), 1.89-1.82 (2H, m), 1.81-1.74 (2H, m).

1-(4-methoxy-3-methyl-phenyl)-4,5,6,7-tetrahydro-1H-indazole

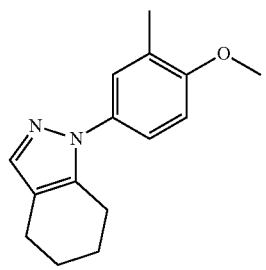 [SMILES: COc1ccc(-n2ncc3c2CCCC3)cc1C]

$^1$H-NMR (CDCl$_3$) δ: 7.42 (1H, s), 7.29-7.25 (1H, m), 7.22 (1H, dd, J=8.5, 2.7 Hz), 6.85 (1H, d, J=8.5 Hz), 3.86 (3H, s), 2.66 (2H, t, J=5.2 Hz), 2.58 (2H, t, J=5.2 Hz), 2.25 (3H, s), 1.83-1.74 (4H, m).

Reference Preparation Example 72

A similar reaction to Reference Preparation example 65 using 3-trifluoromethyl-1H-pyrazole instead of 3,4,5-trimethyl-1H-pyrazole gave 1-(4-methoxy-3-methyl-phenyl)-3-trifluoromethyl-1H-pyrazole.

1-(4-methoxy-3-methyl-phenyl)-3-trifluoromethyl-1H-pyrazole

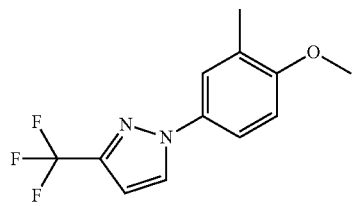 [SMILES: COc1ccc(-n2ccc(C(F)(F)F)n2)cc1C]

$^1$H-NMR (CDCl$_3$) δ: 7.83 (1H, dd, J=2.3, 0.9 Hz), 7.48 (1H, d, J=2.4 Hz), 7.43 (1H, dd, J=8.8, 2.7 Hz), 6.87 (1H, d, J=8.8 Hz), 6.68 (1H, d, J=2.4 Hz), 3.87 (3H, s), 2.28 (3H, s).

Reference Preparation Example 73

A similar reaction to Reference Preparation example 65 using 3-tert-butyl-1H-pyrazole instead of 3,4,5-trimethyl-1H-pyrazole gave 1-(4-methoxy-3-methyl-phenyl)-3-tert-butyl-1H-pyrazole.

1-(4-methoxy-3-methyl-phenyl)-3-tert-butyl-1H-pyrazole

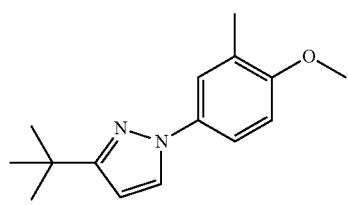 [SMILES: COc1ccc(-n2ccc(C(C)(C)C)n2)cc1C]

$^1$H-NMR (CDCl$_3$) δ: 7.68 (1H, d, J=2.4 Hz), 7.44 (1H, d, J=2.2 Hz), 7.38 (1H, dd, J=8.5, 2.7 Hz), 6.85-6.81 (1H, m), 6.27 (1H, d, J=2.4 Hz), 3.84 (3H, s), 2.26 (3H, s), 1.37 (9H, s).

Reference Preparation Example 74

A similar reaction to Reference Preparation example 65 using 4-methoxy-phenylboronic acid instead of 4-methoxy-3-methyl-phenylboronic acid, and using 3,5-dimethyl-1H-pyrazole instead of 3,4,5-trimethyl-1H-pyrazole gave 1-(4-methoxy-phenyl)-3,5-dimethyl-1H-pyrazole.

1-(4-methoxy-phenyl)-3,5-dimethyl-1H-pyrazole

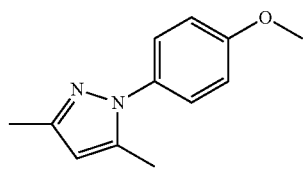

$^1$H-NMR (CDCl$_3$) δ: 7.32 (2H, dt, J=9.6, 2.8 Hz), 6.95 (2H, dt, J=9.6, 2.8 Hz), 5.96 (1H, s), 3.84 (3H, s), 2.29 (3H, s), 2.24 (3H, s).

Reference Preparation Example 75

A similar reaction to Reference Preparation example 65 using 4-methoxy-2-methyl-phenylboronic acid instead of 4-methoxy-3-methyl-phenylboronic acid, and using 3,5-dimethyl-1H-pyrazole instead of 3,4,5-trimethyl-1H-pyrazole gave 1-(4-methoxy-2-methyl-phenyl)-3,5-dimethyl-1H-pyrazole.

1-(4-methoxy-2-methyl-phenyl)-3,5-dimethyl-1H-pyrazole

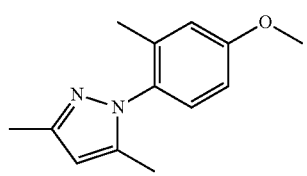

$^1$H-NMR (CDCl$_3$) δ: 7.14 (1H, d, J=8.5 Hz), 6.82-6.75 (2H, m), 5.94 (1H, s), 3.86-3.80 (3H, m), 2.28 (3H, s), 2.03 (3H, s), 2.01 (3H, s).

Reference Preparation Example 76

A similar reaction to Reference Preparation example 65 using 2-chloro-4-methoxy-phenylboronic acid instead of 4-methoxy-3-methyl-phenylboronic acid, and using 1H-pyrazole instead of 3,4,5-trimethyl-1H-pyrazole gave 1-(2-chloro-4-methoxy-phenyl)-1H-pyrazole.

1-(2-chloro-4-methoxy-phenyl)-1H-pyrazole

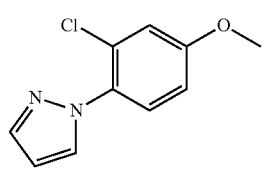

$^1$H-NMR (CDCl$_3$) δ: 7.74 (2H, dd, J=7.8, 2.1 Hz), 7.45 (1H, d, J=8.8 Hz), 7.03 (1H, d, J=2.9 Hz), 6.90 (1H, dd, J=8.8, 2.9 Hz), 6.45 (1H, t, J=2.1 Hz), 3.85 (3H, s).

Reference Preparation Example 77

A similar reaction to Reference Preparation example 65 using 3,5-dimethyl-4-methoxy-phenylboronic acid instead of 4-methoxy-3-methyl-phenylboronic acid, and using 3-methyl-1H-pyrazole instead of 3,4,5-trimethyl-1H-pyrazole gave 1-(3,5-dimethyl-4-methoxy-phenyl)-3-methyl-1H-pyrazole and 1-(3,5-dimethyl-4-methoxy-phenyl)-5-methyl-1H-pyrazole.

1-(3,5-dimethyl-4-methoxy-phenyl)-3-methyl-1H-pyrazole

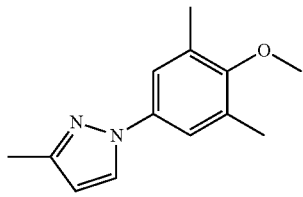

$^1$H-NMR (CDCl$_3$) δ: 7.72 (1H, d, J=2.2 Hz), 7.28 (2H, s), 6.20 (1H, d, J=2.2 Hz), 3.73 (3H, s), 2.37 (3H, s), 2.33 (6H, s).

1-(3,5-dimethyl-4-methoxy-phenyl)-5-methyl-1H-pyrazole

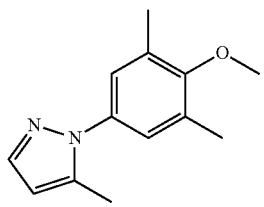 [SMILES: COc1c(C)cc(-n2nccc2C)cc1C]

$^1$H-NMR (CDCl$_3$) δ: 7.53 (1H, d, J=1.7 Hz), 7.08 (2H, s), 6.16-6.15 (1H, m), 3.75 (3H, s), 2.32 (6H, s), 2.32 (3H, s).

Reference Preparation Example 78

A similar reaction to Reference Preparation example 65 using 3-chloro-4-methoxy-phenylboronic acid instead of 4-methoxy-3-methyl-phenylboronic acid, and using 3-methyl-1H-pyrazole instead of 3,4,5-trimethyl-1H-pyrazole gave 1-(3-chloro-4-methoxy-phenyl)-3-methyl-1H-pyrazole and 1-(3-chloro-4-methoxy-phenyl)-5-methyl-1H-pyrazole.

1-(3-chloro-4-methoxy-phenyl)-3-methyl-1H-pyrazole

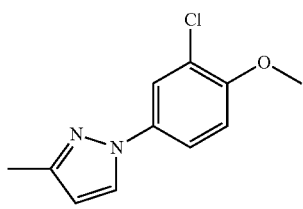

$^1$H-NMR (CDCl$_3$) δ: 7.70 (2H, t, J=2.3 Hz), 7.49 (1H, dd, J=9.0, 2.7 Hz), 6.96 (1H, d, J=9.0 Hz), 6.23 (1H, d, J=2.3 Hz), 3.93 (3H, s), 2.37 (3H, s)

1-(3-chloro-4-methoxy-phenyl)-5-methyl-1H-pyrazole

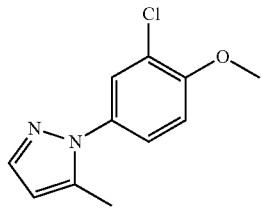

$^1$H-NMR (CDCl$_3$) δ: 7.55 (1H, d, J=1.7 Hz), 7.49 (1H, d, J=2.6 Hz), 7.31 (1H, dd, J=8.8, 2.6 Hz), 7.00 (1H, d, J=8.8 Hz), 6.18-6.17 (1H, m), 3.95 (3H, s), 2.32 (3H, s).

Reference Preparation Example 79

A similar reaction to Reference Preparation example 65 using 3-chloro-4-methoxy-phenylboronic acid instead of 4-methoxy-3-methyl-phenylboronic acid, and using 4-methyl-1H-pyrazole instead of 3,4,5-trimethyl-1H-pyrazole gave 1-(3-chloro-4-methoxy-phenyl)-4-methyl-1H-pyrazole.

1-(3-chloro-4-methoxy-phenyl)-4-methyl-1H-pyrazole

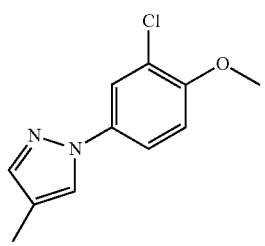

$^1$H-NMR (CDCl$_3$) δ: 7.69 (1H, d, J=2.7 Hz), 7.61-7.60 (1H, m), 7.51-7.48 (2H, m), 6.97 (1H, d, J=9.0 Hz), 3.93 (3H, s), 2.15 (3H, s).

Reference Preparation Example 80

A similar reaction to Reference Preparation example 65 using 3-fluoro-4-methoxy-phenylboronic acid instead of 4-methoxy-3-methyl-phenylboronic acid, and using 3-methyl-1H-pyrazole instead of 3,4,5-trimethyl-1H-pyrazole gave 1-(3-fluoro-4-methoxy-phenyl)-3-methyl-1H-pyrazole.

1-(3-fluoro-4-methoxy-phenyl)-3-methyl-1H-pyrazole

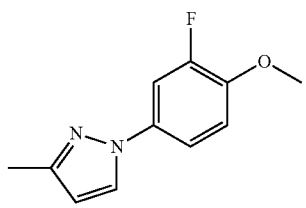

¹H-NMR (CDCl₃) δ: 7.70 (1H, d, J=2.4 Hz), 7.44 (1H, dd, J=12.2, 2.7 Hz), 7.33 (1H, dq, J=8.9, 1.4 Hz), 6.99 (1H, t, J=8.9 Hz), 6.22 (1H, d, J=2.4 Hz), 3.91 (3H, s), 2.36 (3H, s).

Reference Preparation Example 81

A similar reaction to Reference Preparation example 65 using 2,5-dimethyl-4-methoxy-phenylboronic acid instead of 4-methoxy-3-methyl-phenylboronic acid, and using 3-methyl-1H-pyrazole instead of 3,4,5-trimethyl-1H-pyrazole gave 1-(2,5-dimethyl-4-methoxy-phenyl)-3-methyl-1H-pyrazole.

1-(2,5-dimethyl-4-methoxy-phenyl)-3-methyl-1H-pyrazole

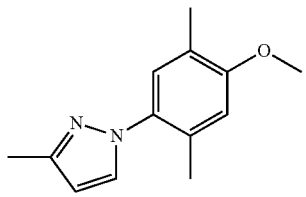

¹H-NMR (CDCl₃) δ: 7.40 (1H, d, J=2.2 Hz), 7.09 (1H, s), 6.69 (1H, s), 6.17 (1H, d, J=2.2 Hz), 3.86 (3H, s), 2.36 (3H, s), 2.18 (3H, s), 2.18 (3H, s).

Reference Preparation Example 82

A similar reaction to Reference Preparation example 65 using 2,3-dimethyl-4-methoxy-phenylboronic acid instead of 4-methoxy-3-methyl-phenylboronic acid, and using 3-methyl-1H-pyrazole instead of 3,4,5-trimethyl-1H-pyrazole gave 1-(2,3-dimethyl-4-methoxy-phenyl)-3-methyl-1H-pyrazole.

1-(2,3-dimethyl-4-methoxy-phenyl)-3-methyl-1H-pyrazole

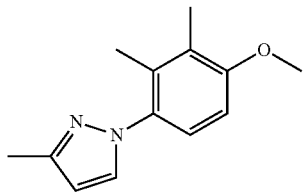

¹H-NMR (CDCl₃) δ: 7.38 (1H, d, J=2.2 Hz), 7.12 (1H, d, J=8.8 Hz), 6.74 (1H, d, J=8.8 Hz), 6.17 (1H, d, J=2.2 Hz), 3.85 (3H, s), 2.36 (3H, s), 2.19 (3H, s), 2.01 (3H, s).

Reference Preparation Example 83

A similar reaction to Reference Preparation example 65 using 4-methoxy-3-trifluoromethyl-phenylboronic acid instead of 4-methoxy-3-methyl-phenylboronic acid gave 1-(4-methoxy-3-trifluoromethyl-phenyl)-3,4,5-trimethyl-1H-pyrazole.

1-(4-methoxy-3-trifluoromethyl-phenyl)-3,4,5-trimethyl-1H-pyrazole

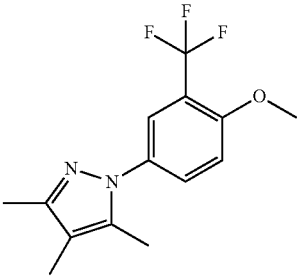

¹H-NMR (CDCl₃) δ: 7.62 (1H, d, J=2.7 Hz), 7.52 (1H, dd, J=8.9, 2.7 Hz), 7.06 (1H, d, J=8.7 Hz), 3.95 (3H, s), 2.23 (3H, s), 2.18 (3H, s), 1.97 (3H, s).

Reference Preparation Example 84

Under nitrogen atmosphere, a mixture of 4-methoxy-3-methyl-phenylboronic acid 1.62 g, 4-bromo-1-methyl-1H-pyrazole 1.57 g, 1,1'-bis(diphenylphosphino)ferrocene-palladium(II) dichloride dichloromethane complex 0.79 g, sodium carbonate 3.51 g, dioxane 100 ml and water 30 ml was stirred with heating under reflux for four hours. The resulting mixture was extracted with ethyl acetate. The organic layer was washed with water, and was dried over anhydrous magnesium sulfate and was then concentrated under reduced pressure. The resulting residue was subjected to a silica gel column chromatography to give 4-(4-methoxy-3-methyl-phenyl)-1-methyl-1H-pyrazole 1.3 g.

4-(4-methoxy-3-methyl-phenyl)-1-methyl-1H-pyrazole

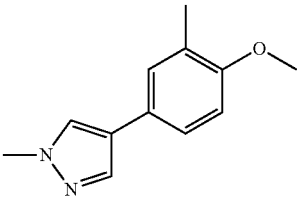

¹H-NMR (CDCl₃) δ: 7.68 (1H, s), 7.52 (1H, s), 7.28-7.24 (2H, m), 6.82 (1H, d, J=8.3 Hz), 3.93 (3H, s), 3.84 (3H, s), 2.24 (3H, s).

Reference Preparation Example 85

A similar reaction to Reference Preparation example 84 using 3-chloro-4-methoxy-phenylboronic acid instead of 4-methoxy-3-methyl-phenylboronic acid gave 1-(3-chloro-4-methoxy-phenyl)-1-methyl-1H-pyrazole.

1-(3-chloro-4-methoxy-phenyl)-1-methyl-1H-pyrazole

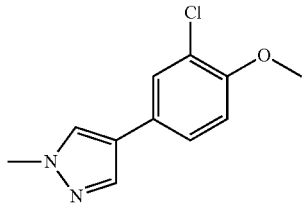

$^1$H-NMR (CDCl$_3$) δ: 7.68 (1H, s), 7.54 (1H, s), 7.47 (1H, d, J=2.2 Hz), 7.31 (1H, dd, J=8.5, 2.2 Hz), 6.92 (1H, d, J=8.5 Hz), 3.94 (3H, s), 3.91 (3H, s).

Reference Preparation Example 86

A similar reaction to Reference Preparation example 84 using 4-bromo-1-ethyl-1H-pyrazole (described in Reference Preparation example 106) instead of 4-bromo-1-methyl-1H-pyrazole gave 4-(4-methoxy-3-methyl-phenyl)-1-ethyl-1H-pyrazole.

4-(4-methoxy-3-methyl-phenyl)-1-ethyl-1H-pyrazole

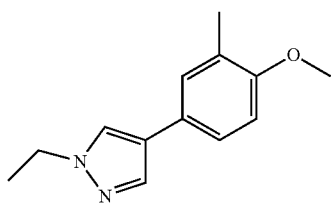 [SMILES: CCn1cc(-c2ccc(OC)c(C)c2)cn1]

$^1$H-NMR (CDCl$_3$) δ: 7.70 (1H, s), 7.56 (1H, s), 7.28-7.24 (2H, m), 6.82 (1H, d, J=8.5 Hz), 4.19 (2H, q, J=7.3 Hz), 3.84 (3H, s), 2.24 (3H, s), 1.52 (3H, t, J=7.3 Hz).

Reference Preparation Example 87

A similar reaction to Reference Preparation example 84 using 4-bromo-1-propyl-1H-pyrazole (described in Reference Preparation example 107) instead of 4-bromo-1-methyl-1H-pyrazole gave 4-(4-methoxy-3-methyl-phenyl)-1-propyl-1H-pyrazole.

4-(4-methoxy-3-methyl-phenyl)-1-propyl-1H-pyrazole

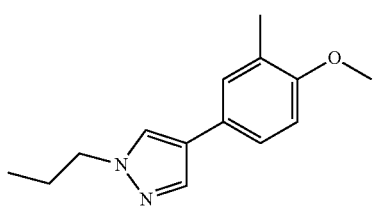 [SMILES: CCCn1cc(-c2ccc(OC)c(C)c2)cn1]

$^1$H-NMR (CDCl$_3$) δ: 7.70 (1H, s), 7.54 (1H, s), 7.29-7.24 (2H, m), 6.82 (1H, d, J=8.3 Hz), 4.09 (2H, t, J=7.1 Hz), 3.84 (3H, s), 2.24 (3H, s), 1.92 (2H, td, J=14.5, 7.2 Hz), 0.94 (3H, t, J=7.3 Hz).

Reference Preparation Example 88

A similar reaction to Reference Preparation example 84 using 4-bromo-1-isopropyl-1H-pyrazole (described in Reference Preparation example 108) instead of 4-bromo-1-methyl-1H-pyrazole gave 4-(4-methoxy-3-methyl-phenyl)-1-isopropyl-1H-pyrazole.

4-(4-methoxy-3-methyl-phenyl)-1-isopropyl-1H-pyrazole

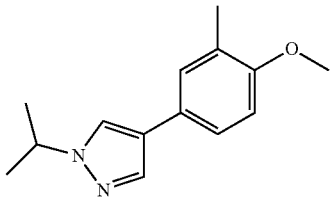 [SMILES: COc1ccc(-c2cnn(C(C)C)c2)cc1C]

$^1$H-NMR (CDCl$_3$) δ: 7.71 (1H, s), 7.59 (1H, s), 7.29-7.26 (2H, m), 6.82 (1H, d, J=8.7 Hz), 4.57-4.46 (1H, m), 3.84 (3H, s), 2.25 (3H, s), 1.54 (6H, d, J=6.5 Hz).

Reference Preparation Example 89

A similar reaction to Reference Preparation example 84 using 4-bromo-1-butyl-1H-pyrazole (described in Reference Preparation example 110) instead of 4-bromo-1-methyl-1H-pyrazole gave 4-(4-methoxy-3-methyl-phenyl)-1-isopropyl-1H-pyrazole.

4-(4-methoxy-3-methyl-phenyl)-1-isopropyl-1H-pyrazole

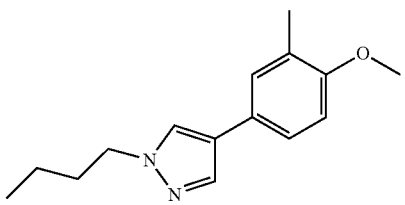 [SMILES: CCCCn1cc(-c2ccc(OC)c(C)c2)cn1]

$^1$H-NMR (CDCl$_3$) δ: 7.69 (1H, s), 7.54 (1H, s), 7.29-7.24 (2H, m), 6.82 (1H, d, J=8.3 Hz), 4.13 (2H, t, J=7.1 Hz), 3.84 (3H, s), 2.24 (3H, s), 1.91-1.84 (2H, m), 1.36 (2H, td, J=14.9, 7.5 Hz), 0.95 (3H, t, J=7.3 Hz).

Reference Preparation Example 90

A similar reaction to Reference Preparation example 84 using 4-bromo-1,3-dimethyl-1H-pyrazole instead of 4-bromo-1-methyl-1H-pyrazole gave 4-(4-methoxy-3-methyl-phenyl)-1,3-dimethyl-1H-pyrazole.

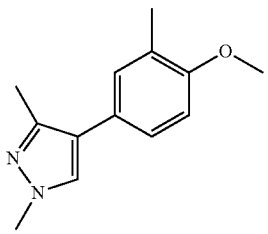 [SMILES: COc1ccc(-c2cn(C)nc2C)cc1C]

¹H-NMR (CDCl₃) δ: 7.35 (1H, s), 7.19-7.14 (2H, m), 6.84 (1H, d, J=8.2 Hz), 3.86 (3H, s), 3.85 (3H, s), 2.37 (3H, s), 2.25 (3H, s).

Reference Preparation Example 91

At room temperature, to a mixture of 3-(4-methoxy-3-methyl-phenyl)-1H-pyrazole (described in Reference Preparation example 96) 5.38 g and N,N-dimethylformamide 100 ml was added 55% sodium hydride 1.5 g and the resulting mixture was stirred for a half hour and thereto was added methyl iodide 7.9 g. The resulting mixture was stirred for twelve hours and thereto was added water, and then the resulting mixture was extracted with ethyl acetate. The organic layer was washed with water, and was dried over anhydrous magnesium sulfate and was then concentrated under reduced pressure. The resulting residue was subjected to a silica gel column chromatography to give 3-(4-methoxy-3-methyl-phenyl)-1-methyl-1H-pyrazole 2.9 g and 5-(4-methoxy-3-methyl-phenyl)-1-methyl-1H-pyrazole 1.0 g.

3-(4-methoxy-3-methyl-phenyl)-1-methyl-1H-pyrazole

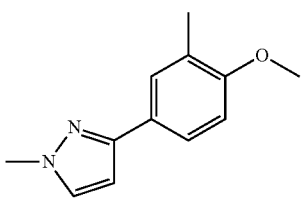

¹H-NMR (CDCl₃) δ: 7.61-7.58 (1H, m), 7.56 (1H, dd, J=8.3, 2.2 Hz), 7.34 (1H, d, J=2.2 Hz), 6.84 (1H, d, J=8.3 Hz), 6.45 (1H, d, J=2.2 Hz), 3.93 (3H, s), 3.85 (3H, s), 2.26 (3H, s).

5-(4-methoxy-3-methyl-phenyl)-1-methyl-1H-pyrazole

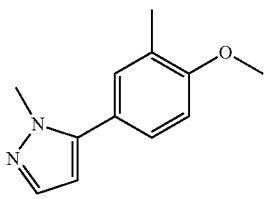

¹H-NMR (CDCl₃) δ: 7.49 (1H, d, J=1.7 Hz), 7.22-7.19 (2H, m), 6.89 (1H, d, J=8.5 Hz), 6.24 (1H, d, J=1.7 Hz), 3.88 (3H, s), 3.87 (3H, s), 2.26 (3H, s).

Reference Preparation Example 92

A similar reaction to Reference Preparation example 91 using ethyl iodide instead of methyl iodide gave 3-(4-methoxy-3-methyl-phenyl)-1-ethyl-1H-pyrazole.

3-(4-methoxy-3-methyl-phenyl)-1-ethyl-1H-pyrazole

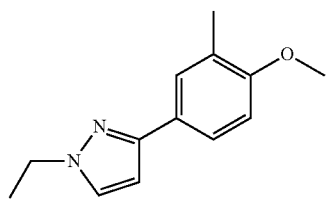 [SMILES: CCn1ccc(-c2ccc(OC)c(C)c2)n1]

¹H-NMR (CDCl₃) δ: 7.60 (1H, s), 7.57 (1H, dd, J=8.5, 2.2 Hz), 7.38 (1H, d, J=2.4 Hz), 6.84 (1H, d, J=8.2 Hz), 6.45 (1H, d, J=2.2 Hz), 4.20 (2H, q, J=7.3 Hz), 3.85 (3H, s), 2.26 (3H, s), 1.52 (3H, t, J=7.4 Hz).

Reference Preparation Example 93

A similar reaction to Reference Preparation example 91 using isopropyl iodide instead of methyl iodide gave 3-(4-methoxy-3-methyl-phenyl)-1-isopropyl-1H-pyrazole.

3-(4-methoxy-3-methyl-phenyl)-1-isopropyl-1H-pyrazole

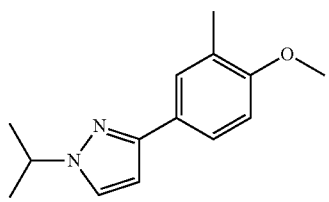 [SMILES: COc1ccc(-c2ccn(C(C)C)n2)cc1C]

¹H-NMR (CDCl₃) δ: 7.60 (1H, s), 7.58-7.54 (1H, m), 7.42 (1H, d, J=2.4 Hz), 6.84 (1H, d, J=8.2 Hz), 6.45 (1H, d, J=2.4 Hz), 4.60-4.50 (1H, m), 3.85 (3H, s), 2.26 (3H, s), 1.54 (6H, d, J=6.8 Hz).

Reference Preparation Example 94

A similar reaction to Reference Preparation example 91 using 3-(3-bromo-4-methoxy-phenyl)-1H-pyrazole (described in Reference Preparation example 97) instead of 3-(4-methoxy-3-methyl-phenyl)-1H-pyrazole gave 3-(3-bromo-4-methoxy-phenyl)-1-methyl-1H-pyrazole and 5-(3-bromo-4-methoxy-phenyl)-1-methyl-1H-pyrazole.

3-(3-bromo-4-methoxy-phenyl)-1-methyl-1H-pyrazole

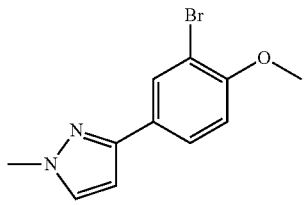

$^1$H-NMR (CDCl$_3$) δ: 7.99 (1H, d, J=2.2 Hz), 7.69 (1H, dd, J=8.5, 2.2 Hz), 7.36 (1H, d, J=2.4 Hz), 6.92 (1H, d, J=8.7 Hz), 6.45 (1H, d, J=2.4 Hz), 3.94 (3H, s), 3.92 (3H, s).

5-(3-bromo-4-methoxy-phenyl)-1-methyl-1H-pyrazole

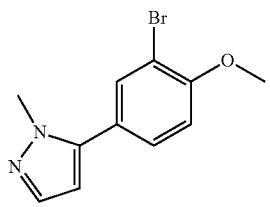

$^1$H-NMR (CDCl$_3$) δ: 7.61 (1H, d, J=1.9 Hz), 7.50 (1H, d, J=1.7 Hz), 7.33 (1H, dd, J=8.5, 2.2 Hz), 6.99-6.96 (1H, m), 6.26 (1H, d, J=1.7 Hz), 3.95 (3H, s), 3.87 (3H, s).

Reference Preparation Example 95

A similar reaction to Reference Preparation example 91 using 3-(4-methoxy-3-methyl-phenyl)-5-methyl-1H-pyrazole (described in Reference Preparation example 98) instead of 3-(4-methoxy-3-methyl-phenyl)-1H-pyrazole gave 3-(4-methoxy-3-methyl-phenyl)-1,3-dimethyl-1H-pyrazole and 5-(4-methoxy-3-methyl-phenyl)-1,3-dimethyl-1H-pyrazole.

3-(4-methoxy-3-methyl-phenyl)-1,3-dimethyl-1H-pyrazole

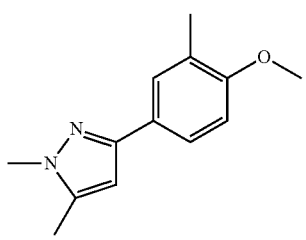

$^1$H-NMR (CDCl$_3$) δ: 7.56-7.55 (1H, m), 7.53-7.50 (1H, m), 6.82 (1H, d, J=8.5 Hz), 6.24 (1H, d, J=0.7 Hz), 3.84 (3H, s), 3.80 (3H, s), 2.29 (3H, s), 2.25 (3H, s).

5-(4-methoxy-3-methyl-phenyl)-1,3-dimethyl-1H-pyrazole

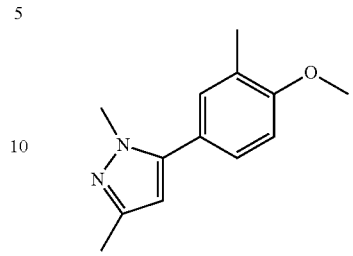

$^1$H-NMR (CDCl$_3$) δ: 7.20-7.17 (2H, m), 6.88 (1H, d, J=8.2 Hz), 6.02 (1H, s), 3.87 (3H, s), 3.79 (3H, s), 2.29 (3H, s), 2.26 (3H, s).

Reference Preparation Example 96

At room temperature, to a mixture of 3-dimethylamino-1-(4-methoxy-3-methyl-phenyl)-propenone (described in Reference Preparation example 99) 7.69 g and ethanol 100 ml was added hydrazine one hydrate 9.8 ml and the resulting mixture was stirred for twenty four hours. The reaction mixture was concentrated under reduced pressure so as to make ethanol in the reaction mixture about 10 ml. The resulting residue was subjected to a silica gel column chromatography to give 3-(4-methoxy-3-methyl-phenyl)-1,3-dimethyl-1H-pyrazole 5.4 g.

3-(4-methoxy-3-methyl-phenyl)-1,3-dimethyl-1H-pyrazole

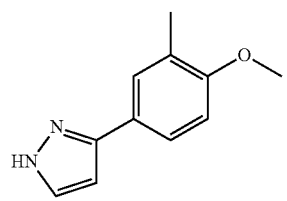

$^1$H-NMR (CDCl$_3$) δ: 11.91 (1H, br s), 7.58 (1H, d, J=2.2 Hz), 7.54-7.50 (2H, m), 6.84-6.80 (1H, m), 6.51 (1H, d, J=2.0 Hz), 3.85 (3H, s), 2.24 (3H, s).

Reference Preparation Example 97

A similar reaction to Reference Preparation example 96 using 3-dimethylamino-1-(3-bromo-4-methoxy-phenyl)-propenone (described in Reference Preparation example 100) instead of 3-dimethylamino-1-(4-methoxy-3-methyl-phenyl)-propenone gave 3-(3-bromo-4-methoxy-phenyl)-1H-pyrazole.

3-(3-bromo-4-methoxy-phenyl)-1H-pyrazole

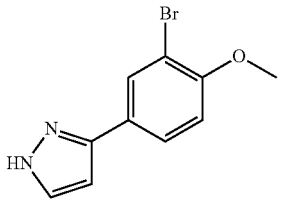

$^1$H-NMR (CDCl$_3$) δ: 7.97 (1H, d, J=1.9 Hz), 7.70-7.66 (1H, m), 7.61 (1H, d, J=2.4 Hz), 6.93 (1H, d, J=8.5 Hz), 6.55 (1H, d, J=2.2 Hz), 3.93 (3H, s).

Reference Preparation Example 98

A similar reaction to Reference Preparation example 96 using 1-(4-methoxy-3-methylphenyl)-butane-1,3-dione (described in Reference Preparation example 101) instead of 3-dimethylamino-1-(4-methoxy-3-methyl-phenyl)-propenone gave 3-(4-methoxy-3-methyl-phenyl)-5-methyl-1H-pyrazole.

3-(4-methoxy-3-methyl-phenyl)-5-methyl-1H-pyrazole

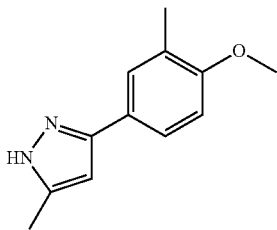

$^1$H-NMR (CDCl$_3$) δ: 7.49-7.46 (2H, m), 6.83-6.80 (1H, m), 6.26 (1H, s), 3.84 (3H, s), 2.31 (3H, s), 2.23 (3H, s).

Reference Preparation Example 99

A mixture of 1-(4-methoxy-3-methyl)-ethanone (described in Reference Preparation example 102) 5.76 g and N,N-dimethylformamide diethylacetal 7.46 ml was stirred with heating under reflux for twenty four hours. The resulting mixture was concentrated under reduce pressure to give 3-dimethylamino-1-(4-ethoxy-3-methyl-phenyl)-propenone 4.78 g.

3-dimethylamino-1-(4-ethoxy-3-methyl-phenyl)-propenone

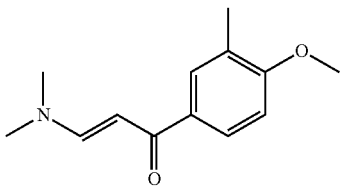

$^1$H-NMR (DMSO-D$_6$) δ: 7.76 (1H, dd, J=8.5, 2.2 Hz), 7.72 (1H, s), 7.64 (1H, d, J=12.4 Hz), 6.95 (1H, d, J=8.5 Hz), 5.80 (1H, d, J=12.4 Hz), 3.83 (3H, s), 3.11 (3H, br s), 2.90 (3H, br s), 2.18 (3H, s).

Reference Preparation Example 100

A similar reaction to Reference Preparation example 99 using 1-(3-bromo-4-methoxy)-ethanone instead of 1-(4-methoxy-3-methyl)-ethanone gave 3-dimethylamino-1-(3-bromo-4-methoxy-phenyl)-propenone.

3-dimethylamino-1-(3-bromo-4-methoxy-phenyl)-propenone

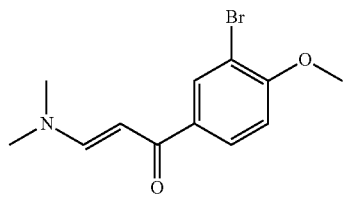

$^1$H-NMR (CDCl$_3$) δ: 8.12 (1H, d, J=2.2 Hz), 7.89 (1H, dd, J=8.5, 2.2 Hz), 7.80 (1H, d, J=12.2 Hz), 6.91 (1H, d, J=8.5 Hz), 5.65 (1H, d, J=12.2 Hz), 3.94 (3H, s), 3.15 (3H, s), 2.96 (3H, s).

Reference Preparation Example 101

At room temperature, to tetrahydrofuran 50 ml was added 55% sodium hydride 3.07 g and ethyl acetate 5.90 g and the resulting mixture was stirred for a half hour. Then, thereto was added 1-(4-methoxy-3-methyl)-ethanone (described in Reference Preparation example 102) 5.50 g, dibenzo-18-crown-6 0.024 g and ethanol 1 ml and the resulting mixture was stirred with heating under reflux for six hours. To the reaction mixture was added water and the resulting mixture was acidified with aqueous 10% hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 1-(4-methoxy-3-methyl-phenyl)-butane-1,3-dione 6.50 g.

1-(4-methoxy-3-methyl-phenyl)-butane-1,3-dione

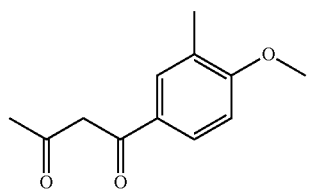

$^1$H-NMR (CDCl$_3$: 23° C.) δ: 7.76 (1H, dd, J=8.6, 2.3 Hz), 7.69 (1H, d, J=1.4 Hz), 6.85 (1H, d, J=8.5 Hz), 6.12 (1H, s), 3.89 (3H, s), 2.25 (3H, s), 2.17 (3H, s).

Reference Preparation Example 102

A mixture of 1-(4-hydroxy-3-methyl)-ethanone 5.0 g, methyl iodide 5.70 g, potassium carbonate 20.0 g and acetone 200 ml was stirred with heating under reflux for six hours. The reaction mixture was filtered and was extracted with ethyl acetate. The organic layer was washed with water and was dried over anhydrous magnesium sulfate, and was then concentrated under reduced pressure to give 1-(4-methoxy-3-methyl)-ethanone 5.3 g.

1-(4-methoxy-3-methyl)-ethanone

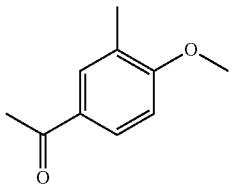

$^1$H-NMR (CDCl$_3$) δ: 7.82 (1H, dd, J=8.5, 1.7 Hz), 7.79-7.76 (1H, m), 6.85 (1H, d, J=8.5 Hz), 3.90 (3H, s), 2.55 (3H, s), 2.25 (3H, s).

Reference Preparation Example 103

At 0° C., to a mixture of water 5 ml and acetic acid 5 ml was added 3-methyl-2,4-pentanedione 5.88 g and hydrazine one hydrate 2.41 g, and the resulting mixture was stirred for five hours. The precipitates was filtered and were washed with water and hexane, and were dried under reduced pressure to give 3,4,5-toriemthyl-1H-pyrazole 3.68 g.

3,4,5-toriemthyl-1H-pyrazole

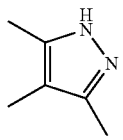

$^1$H-NMR (CDCl$_3$) δ: 2.19 (6H, s), 1.90 (3H, s).

Reference Preparation Example 104

A mixture of 1-[2-(4-acetyl-2-methyl-phenoxymethyl]-3-methoxy-phenyl)-4-methyl-1,4-dihydrotetrazole-5-one (described in Preparation example 175) 11.5 g and N,N-dimethylformamide diethylacetal 14 ml was stirred with heating under reflux for seventy two (72) hours. The resulting mixture was concentrated under reduced pressure to give 1-{2-[4-(3-dimethylamino-acryloyl)-2-methyl-phenoxymethyl]-3-methoxy-phenyl}-4-methyl-, 4-dihydrotetrazole-5-one 13.1 g.

1-{2-[4-(3-dimethylamino-acryloyl)-2-methyl-phenoxymethyl]-3-methoxy-phenyl}-4-methyl-1,4-dihydrotetrazole-5-one

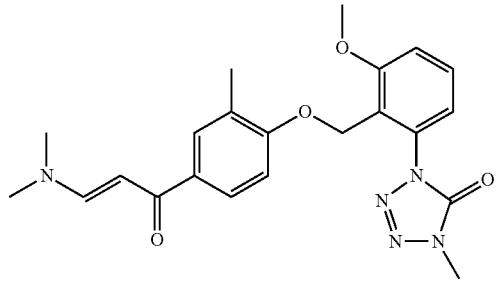 [SMILES: COc1cccc(-n2nnn(C)c2=O)c1COc1ccc(C(=O)/C=C/N(C)C)cc1C]

$^1$H-NMR (CDCl$_3$) δ: 7.76 (1H, d, J=12.3 Hz), 7.71 (1H, dd, J=8.6, 2.3 Hz), 7.68-7.66 (1H, m), 7.47 (1H, t, J=8.2 Hz), 7.10-7.06 (2H, m), 6.88 (1H, d, J=8.5 Hz), 5.69 (1H, d, J=12.3 Hz), 5.32 (2H, s), 3.93 (3H, s), 3.57 (3H, s), 3.09 (3H, br s), 2.96 (3H, br s), 2.02 (3H, s).

Reference Preparation Example 106

At room temperature, to a mixture of 4-bromo-1H-pyrazole (described in Reference Preparation example 111) 3.0 g and tetrahydrofuran 80 ml was added 55% sodium hydride 1.07 g and the resulting mixture was stirred for a half hour and thereto was added ethyl iodide, and the resulting mixture was stirred for twelve hours. To the reaction mixture was added water, and then the resulting mixture was extracted with ethyl acetate. The organic layer was washed with water, and was dried over anhydrous magnesium sulfate and was then concentrated under reduced pressure. The resulting residue was subjected to a silica gel column chromatography to give 4-bromo-1-ethyl-1H-pyrazole 2.72 g.

4-bromo-1-ethyl-1H-pyrazole

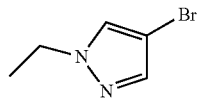

$^1$H-NMR (CDCl$_3$) δ: 7.45 (1H, s), 7.41 (1H, s), 4.15 (2H, td, J=7.5, 6.8 Hz), 1.47 (3H, td, J=7.3, 0.7 Hz).

Reference Preparation Example 107

A similar reaction to Reference Preparation example 106 using propyl iodide instead of ethyl iodide gave 4-bromo-1-propyl-1H-pyrazole.

4-bromo-1-propyl-1H-pyrazole

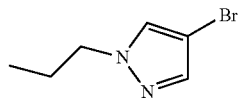

$^1$H-NMR (CDCl$_3$) δ: 7.45 (1H, s), 7.39 (1H, s), 4.06 (2H, t, J=7.1 Hz), 1.87 (2H, td, J=14.5, 7.3 Hz), 0.91 (3H, t, J=7.3 Hz).

Reference Preparation Example 108

A similar reaction to Reference Preparation example 106 using isopropyl iodide instead of ethyl iodide gave 4-bromo-1-isopropyl-1H-pyrazole.

4-bromo-1-isopropyl-1H-pyrazole

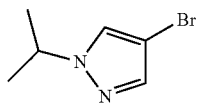

$^1$H-NMR (CDCl$_3$) δ: 7.45 (1H, s), 7.43 (1H, s), 4.50-4.44 (1H, m), 1.49 (6H, d, J=6.8 Hz).

Reference Preparation Example 109

A similar reaction to Reference Preparation example 106 using isobutyl iodide instead of ethyl iodide gave 4-bromo-1-isobutyl-1H-pyrazole.

4-bromo-1-isobutyl-1H-pyrazole

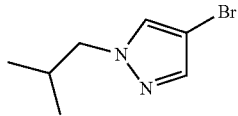

$^1$H-NMR (CDCl$_3$) δ: 7.45 (1H, s), 7.37 (1H, s), 3.88 (2H, d, J=7.3 Hz), 2.22-2.12 (1H, m), 0.90 (6H, d, J=6.8 Hz).

Reference Preparation Example 110

A similar reaction to Reference Preparation example 106 using butyl iodide instead of ethyl iodide gave 4-bromo-1-butyl-1H-pyrazole.

4-bromo-1-butyl-1H-pyrazole

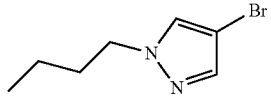

$^1$H-NMR (CDCl$_3$) δ: 7.44 (1H, s), 7.39 (1H, s), 4.09 (2H, t, J=7.2 Hz), 1.82 (2H, ddd, J=13.3, 8.8, 5.0 Hz), 1.32 (2H, td, J=14.9, 7.5 Hz), 0.94 (3H, t, J=7.3 Hz).

Reference Preparation Example 111

At room temperature, to a mixture of 1H-pyrazole 50 g and water 700 ml was added N-bromosuccinimide 137.0 g and the resulting mixture was stirred for twelve hours. The reaction mixture was extracted with ethyl acetate. The organic layer was washed with water, and was dried over anhydrous magnesium sulfate and was then concentrated under reduced pressure to give 4-bromo-1H-pyrazole 80 g.

4-bromo-1H-pyrazole

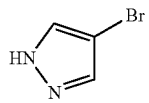

$^1$H-NMR (CDCl$_3$) δ: 7.61 (2H, s).

Reference Preparation Example 112

At 0° C., to a mixture of 3-amino-2-chlorophenol 100 g and concentrated hydrochloric acid 250 ml was added slowly aqueous solution 300 ml containing sodium nitrite 67.0 g and followed by addition of water 400 ml. The resulting mixture was stirred for two hours and thereto was added slowly anhydrous tin(II) chloride 292 g and concentrated hydrochloric acid 250 ml and the resulting mixture was stirred for one hour. At room temperature, the resulting mixture was stirred for additional twelve hours, and then the precipitates were filtered. The filtrate was washed with aqueous 10% hydrochloric acid and hexane and was dried under reduced pressure to give 2-chloro-4-hydrazinophenol hydrochloride salt 105 g.

2-chloro-4-hydrazinophenol hydrochloride salt

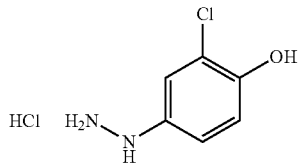

$^1$H-NMR (DMSO-D$_6$) δ: 10.00 (3H, s), 9.90 (1H, s), 7.92 (1H, br s), 7.07 (1H, d, J=2.7 Hz), 6.93 (1H, d, J=8.8 Hz), 6.85 (1H, dd, J=8.8, 2.7 Hz).

Reference Preparation Example 113

At 0° C., to a mixture of O-cresol 10 g and chloroform 100 ml was added propionyl chloride 10 g and triethylamine 28 g. The resulting mixture was raised to room temperature and was stirred for two hours. Then the reaction mixture was extracted with chloroform and the organic layer was washed with water and was dried over anhydrous magnesium sulfate, and was then concentrated under reduced pressure. The resulting residue was subjected to a silica gel column chromatography to give propionic acid o-tolyl ester 14 g.

Propionic acid o-tolyl ester

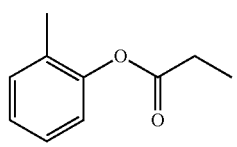

¹H-NMR (CDCl₃) δ: 7.24-7.18 (2H, m), 7.15-7.11 (1H, m), 7.01-6.99 (1H, m), 2.61 (2H, q, J=7.6 Hz), 2.17 (3H, s), 1.29 (3H, t, J=7.6 Hz).

Reference Preparation Example 114

At 0° C., to a mixture of nitromethane 150 ml and propionic acid o-tolyl ester (described in Reference Preparation example 113) 14 g was added aluminum trichloride 30 g. The resulting mixture was heated to 50° C. and was stirred for twelve hours. To the reaction mixture was added ice water 200 ml and the resulting mixture was extracted with ethyl acetate. The organic layer was washed with water and was dried over anhydrous magnesium sulfate, and was then concentrated under reduced pressure. The resulting residue was subjected to a silica gel column chromatography to give 1-(4-hydroxy-3-methyl-phenyl)-propane-1-one 8.8 g.

1-(4-hydroxy-3-methyl-phenyl)-propane-1-one

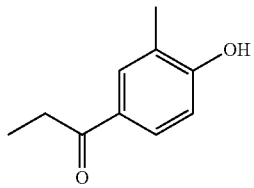

¹H-NMR (CDCl₃) δ: 7.80 (1H, d, J=1.9 Hz), 7.75 (1H, dd, J=8.5, 2.2 Hz), 6.86 (1H, d, J=8.5 Hz), 6.65 (1H, s), 2.96 (2H, q, J=7.2 Hz), 2.30 (3H, s), 1.22 (3H, td, J=7.3, 1.3 Hz).

Reference Preparation Example 115

A mixture of 1-[2-(4-propionyl-2-methyl-phenoxymethyl]-3-methoxy-phenyl)-4-methyl-, 4-dihydrotetrazole-5-one (described in Preparation example 176) 3.5 g and N,N-dimethylformamide-diethyl acetal 2.6 g was stirred at 100° C. for thirty hours and was concentrated under reduced pressure to give 1-{2-[4-(3-dimethylamino-2-methyl-acryloyl)-2-methyl-phenoxymethyl]-3-methoxy-phenyl}-4-methyl-1,4-dihydrotetrazole-5-one 3.9 g.

1-{2-[4-(3-dimethylamino-2-methyl-acryloyl)-2-methyl-phenoxymethyl]-3-methoxy-phenyl}-4-methyl-1,4-dihydrotetrazole-5-one

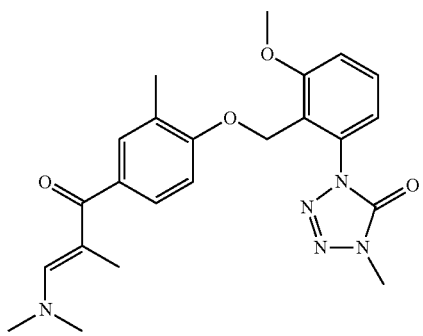 [SMILES: COc1cccc(-n2nnn(C)c2=O)c1COc1ccc(C(=O)/C(C)=C/N(C)C)cc1C]

¹H-NMR (CDCl₃) δ: 7.49-7.44 (1H, m), 7.19-7.18 (2H, m), 7.10-7.05 (2H, m), 6.91 (1H, s), 6.82 (1H, d, J=8.9 Hz), 5.28 (2H, s), 3.93 (3H, s), 3.60 (3H, s), 3.04 (6H, s), 2.11 (3H, s), 1.99 (3H, s).

Reference Preparation Example 116

A similar reaction to Reference Preparation example 99 using 1-1-(3-chloro-4-methoxy)-ethanone instead of 1-(4-methoxy-3-methyl)-ethanone gave 3-dimethylamino-1-(3-chloro-4-methoxy-phenyl)-propenone.

3-dimethylamino-1-(3-chloro-4-methoxy-phenyl)-propenone

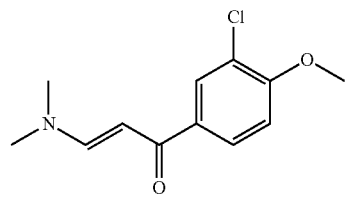

¹H-NMR (CDCl₃) δ: 7.95 (1H, d, J=2.2 Hz), 7.84 (1H, dd, J=8.7, 2.2 Hz), 7.80 (1H, d, J=12.3 Hz), 6.94 (1H, d, J=8.7 Hz), 5.65 (1H, d, J=12.3 Hz), 3.95 (3H, s), 3.14 (3H, s), 2.95 (3H, s).

Reference Preparation Example 117

A similar reaction to Reference Preparation example 96 using 3-dimethylamino-1-(3-chloro-4-methoxy-phenyl)-propenone (described in Reference Preparation example 116) instead of 3-dimethylamino-1-(4-methoxy-3-methyl-phenyl)-propenone gave 3-(3-chloro-4-methoxy-phenyl)-1H-pyrazole.

3-(3-chloro-4-methoxy-phenyl)-1H-pyrazole

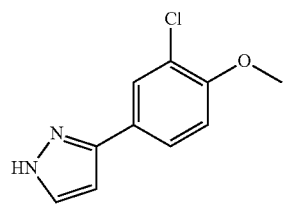

¹H-NMR (CDCl₃) δ: 7.78 (1H, d, J=1.9 Hz), 7.61-7.59 (2H, m), 6.92 (1H, d, J=8.7 Hz), 6.54 (1H, dd, J=2.2, 0.7 Hz), 3.92 (3H, s).

Reference Preparation Example 118

A similar reaction to Reference Preparation example 91 using 3-(3-chloro-4-methoxy-phenyl)-1H-pyrazole (described in Reference Preparation example 117) instead of 3-(4-methoxy-3-methyl-phenyl)-1H-pyrazole gave 3-(3-chloro-4-methoxy-phenyl)-1-methyl-1H-pyrazole and 5-(3-chloro-4-methoxy-phenyl)-1-methyl-1H-pyrazole.

3-(3-chloro-4-methoxy-phenyl)-1-methyl-1H-pyrazole

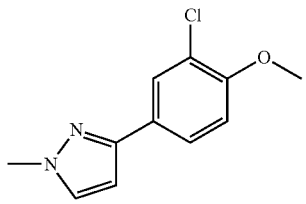

¹H-NMR (CDCl₃) δ: 7.81 (1H, d, J=2.2 Hz), 7.64 (1H, dd, J=8.6, 2.1 Hz), 7.36 (1H, d, J=2.2 Hz), 6.95 (1H, d, J=8.5 Hz), 6.45 (1H, d, J=2.2 Hz), 3.94 (3H, s), 3.93 (3H, s)

5-(3-chloro-4-methoxy-phenyl)-1-methyl-1H-pyrazole

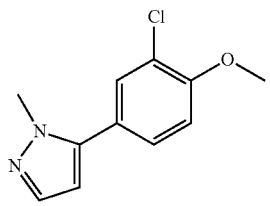

¹H-NMR (CDCl₃) δ: 7.50 (1H, d, J=1.9 Hz), 7.44 (1H, d, J=2.2 Hz), 7.29-7.26 (1H, m), 7.01 (1H, d, J=8.5 Hz), 6.26 (1H, d, J=1.9 Hz), 3.96 (3H, s), 3.87 (3H, s).

Reference Preparation Example 119

A similar reaction to Reference Preparation example 60 using 3-(3-chloro-4-methoxy-phenyl)-1-methyl-1H-pyrazole (described in Reference Preparation example 118) instead of 3-(4-methoxy-3-methyl-phenyl)-1H-pyrazole gave 2-chloro-4-(1-methyl-1H-pyrazol-3-yl)-phenol.

2-chloro-4-(1-methyl-1H-pyrazol-3-yl)-phenol

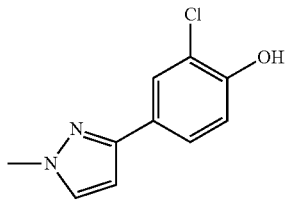

¹H-NMR (DMSO-D₆) δ: 7.70 (2H, dd, J=7.2, 1.7 Hz), 7.55 (1H, dd, J=8.5, 1.4 Hz), 6.98 (1H, d, J=8.5 Hz), 6.61-6.60 (1H, m), 3.85 (3H, s).

Reference Preparation Example 120

At room temperature, a mixture of 3-(4-methoxy-3-methyl-phenyl)-1-methyl-1H-pyrazole (described in Reference Preparation example 91) 3 g, N-bromosuccinimide 2.9 g and chloroform 50 ml was stirred for sixteen hours. To the reaction mixture was added water and the resulting mixture was extracted with chloroform. The organic layer was washed with water and was dried over-anhydrous magnesium sulfate, and was then concentrated under reduced pressure. The resulting residue was subjected to a silica gel column chromatography to give 3-(4-methoxy-3-methyl-phenyl)-4-bromo-1-methyl-1H-pyrazole 3.9 g.

3-(4-methoxy-3-methyl-phenyl)-4-bromo-1-methyl-1H-pyrazole

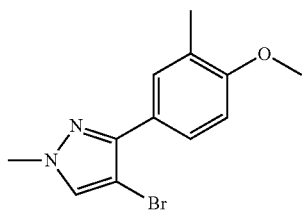

¹H-NMR (CDCl₃) δ: 7.69 (1H, dd, J=8.5, 2.4 Hz), 7.63 (1H, d, J=2.2 Hz), 7.43 (1H, s), 6.87 (1H, d, J=8.5 Hz), 3.91 (3H, s), 3.86 (3H, s), 2.26 (3H, s).

Reference Preparation Example 121

A similar reaction to Reference Preparation example 120 using 3-(3-chloro-4-methoxy-phenyl)-1-methyl-1H-pyrazole (described in Reference Preparation example 118) instead of 3-(4-methoxy-3-methyl-phenyl)-1-methyl-1H-pyrazole gave 3-(4-methoxy-3-chloro-phenyl)-4-bromo-1-methyl-1H-pyrazole.

3-(4-methoxy-3-chloro-phenyl)-4-bromo-1-methyl-1H-pyrazole

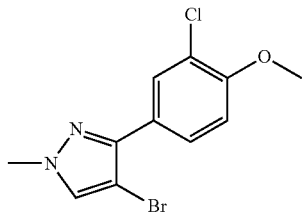

¹H-NMR (CDCl₃) δ: 7.92-7.91 (1H, m), 7.79-7.76 (1H, m), 7.44 (1H, s), 6.98 (1H, d, J=8.5 Hz), 3.94 (3H, s), 3.92 (3H, s).

Reference Preparation Example 122

A mixture of 3-(4-methoxy-3-methyl-phenyl)-4-bromo-1-methyl-1H-pyrazole (described in Reference Preparation example 120) 3.9 g, 1,4-dioxane 80 ml, water 20 ml, methylboronic acid 3.3 g, 1,1'-bis(diphenylphosphino)ferrocene-palladium(II) dichloride dichloromethane adducts 1.4 g and potassium phosphate 11.8 g was stirred with heating under reflux for six hours. The reaction mixture was extracted with ethyl acetate. The organic layer was washed with water, and was dried over anhydrous magnesium sulfate and was then concentrated under reduced pressure. The resulting residue was subjected to a silica gel column chromatography to give 3-(4-methoxy-3-methyl-phenyl)-1,4-dimethyl-1H-pyrazole 2.4 g.

3-(4-methoxy-3-methyl-phenyl)-1,4-dimethyl-1H-pyrazole

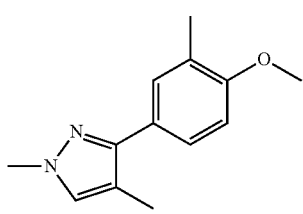

$^1$H-NMR (CDCl$_3$) δ: 7.47 (1H, s), 7.43 (1H, dd, J=8.2, 2.2 Hz), 7.16 (1H, s), 6.86 (1H, d, J=8.2 Hz), 3.87 (3H, s), 3.85 (3H, s), 2.26 (3H, s), 2.20 (3H, s).

Reference Preparation Example 123

A similar reaction to Reference Preparation example 122 using 3-(4-methoxy-3-chloro-phenyl)-4-bromo-1-methyl-1H-pyrazole (described in Reference Preparation example 121) instead of 3-(4-methoxy-3-methyl-phenyl)-4-bromo-1-methyl-1H-pyrazole gave 3-(4-methoxy-3-chloro-phenyl)-1,4-dimethyl-1H-pyrazole.

3-(4-methoxy-3-chloro-phenyl)-1,4-dimethyl-1H-pyrazole

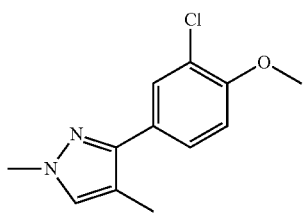

$^1$H-NMR (CDCl$_3$) δ: 7.70 (1H, d, J=2.2 Hz), 7.53 (1H, dd, J=8.5, 2.2 Hz), 7.18 (1H, s), 6.97 (1H, d, J=8.5 Hz), 3.93 (3H, s), 3.88 (3H, s), 2.20 (3H, s).

Reference Preparation Example 124

A mixture of 3-(4-methoxy-3-methyl-phenyl)-1,4-dimethyl-1H-pyrazole (described in Reference Preparation example 122) 2.4 g, 47% hydrobromic acid 18 ml and acetic acid 18 ml was stirred with heating under reflux for sixteen hours. The solvent was distilled off and to the resulting residue was added ethyl acetate 50 ml, and the resulting mixture was stirred at room temperature for one hour. The precipitates were filtered and were washed with hexane, and were dried under reduced pressure to give 4-(1,4-dimethyl-1H-pyrazol-3-yl)-2-methyl-phenol 2.1 g.

4-(1,4-dimethyl-1H-pyrazol-3-yl)-2-methyl-phenol

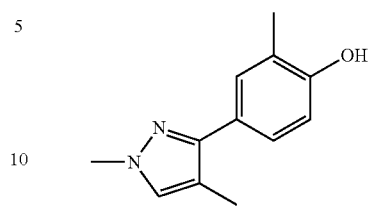

$^1$H-NMR (DMSO-D$_6$) δ: 7.58 (1H, s), 7.34 (1H, s), 7.25 (1H, dd, J=8.2, 2.2 Hz), 6.83 (1H, d, J=8.5 Hz), 3.81 (3H, s), 2.16 (3H, s), 2.13 (3H, s)

Reference Preparation Example 125

A similar reaction to Reference Preparation example 124 using 3-(4-methoxy-3-chloro-phenyl)-1,4-dimethyl-1H-pyrazole (described in Reference Preparation example 123) instead of 3-(4-methoxy-3-methyl-phenyl)-1,4-dimethyl-1H-pyrazole gave 4-(1,4-dimethyl-1H-pyrazol-3-yl)-2-chloro-phenol.

4-(1,4-dimethyl-1H-pyrazol-3-yl)-2-chloro-phenol

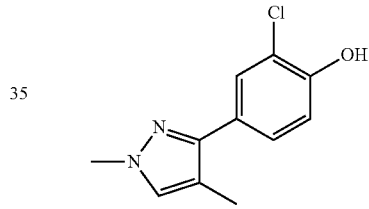

$^1$H-NMR (DMSO-D$_6$) δ: 7.54 (1H, d, J=2.2 Hz), 7.52 (1H, s), 7.41 (1H, dd, J=8.5, 1.9 Hz), 7.01 (1H, d, J=8.5 Hz), 3.79 (3H, s), 2.13 (3H, s).

Reference Preparation Example 126

At room temperature, to a mixture of 3-ethyl-2,4-pentanedione 5 g and ethanol 50 ml was added hydrazine one hydrate 2.9 g and the resulting mixture was stirred for five hours. The ethanol was distilled off and the resulting residue was subjected to a silica gel column chromatography to give 3,5-dimethyl-4-ethyl-1H-pyrazole 6.0 g.

3,5-dimethyl-4-ethyl-1H-pyrazole

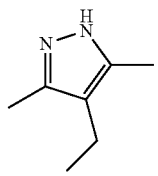

¹H-NMR (CDCl₃) δ: 2.36 (2H, q, J=7.6 Hz), 2.20 (6H, s), 1.07 (3H, t, J=7.6 Hz).

Reference Preparation Example 127

A similar reaction to Reference Preparation example 65 using 3,5-dimethyl-4-ethyl-1H-pyrazole (described in Reference Preparation example 126) instead of 3,4,5-trimethyl-1H-pyrazole gave 1-(4-methoxy-3-methyl-phenyl)-3,5-dimethyl-4-ethyl-1H-pyrazole.

1-(4-methoxy-3-methyl-phenyl)-3,5-dimethyl-4-ethyl-1H-pyrazole

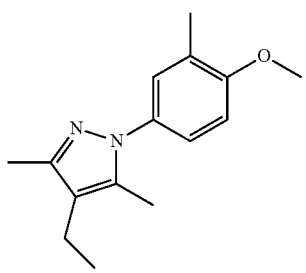

¹H-NMR (CDCl₃) δ: 7.19 (1H, d, J=2.7 Hz), 7.14 (1H, dd, J=8.5, 2.7 Hz), 6.84 (1H, d, J=8.7 Hz), 3.86 (3H, s), 2.41 (2H, q, J=7.6 Hz), 2.26 (3H, s), 2.24 (3H, s), 2.17 (3H, s), 1.11 (3H, t, J=7.5 Hz).

Reference Preparation Example 128

A similar reaction to Reference Preparation example 28 using 1-(4-methoxy-3-methyl-phenyl)-3,5-dimethyl-4-ethyl-1H-pyrazole (described in Reference Preparation example 127) instead of 1-(4-methoxy-3-methyl-phenyl)-3,4,5-trimethyl-1H-pyrazole gave 2-methyl-4-(3,5-dimethyl-4-ethyl-pyrazol-1-yl)-phenol.

2-methyl-4-(3,5-dimethyl-4-ethyl-pyrazol-1-yl)-phenol

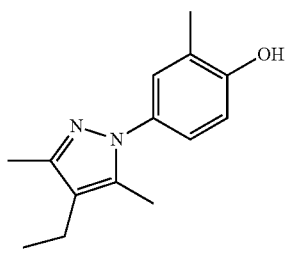 [SMILES: CCc1c(C)nn(-c2ccc(O)c(C)c2)c1C]

¹H-NMR (DMSO-D₆) δ: 7.24 (1H, d, J=2.5 Hz), 7.15 (1H, dd, J=8.5, 2.7 Hz), 6.93-6.91 (1H, m), 2.43 (2H, q, J=7.6 Hz), 2.25 (3H, s), 2.17 (3H, s), 2.17 (3H, s), 1.07 (3H, t, J=7.6 Hz)

Reference Preparation Example 129

At room temperature, a mixture of 3-(4-methoxy-3-methyl-phenyl)-1,5-dimethyl-1H-pyrazole (described in Reference Preparation example 95) 5.9 g, N-bromosuccinimide 5.8 g and chloroform 100 ml was stirred for seventeen hours. To the reaction mixture was added water and the resulting mixture was extracted with chloroform. The organic layer was washed with water and was dried over anhydrous magnesium sulfate, and was then concentrated under reduced pressure. The resulting residue was subjected to a silica gel column chromatography to give 3-(4-methoxy-3-methyl-phenyl)-4-bromo-1,5-dimethyl-1H-pyrazole 4.0 g.

3-(4-methoxy-3-methyl-phenyl)-4-bromo-1,5-dimethyl-1H-pyrazole

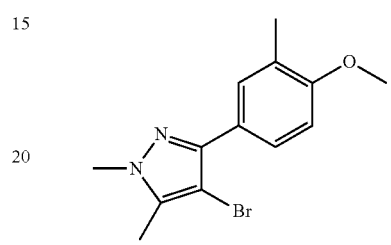

¹H-NMR (CDCl₃) δ: 7.67 (1H, dd, J=8.5, 2.2 Hz), 7.62 (1H, d, J=1.9 Hz), 6.87 (1H, d, J=8.5 Hz), 3.86 (3H, s), 3.84 (3H, s), 2.31 (3H, s), 2.26 (3H, s).

Reference Preparation Example 130

A mixture of 3-(4-methoxy-3-methyl-phenyl)-4-bromo-1,5-dimethyl-1H-pyrazole (described in Reference Preparation example 129) 1.3 g, 1,4-dioxane 30 ml, water 5 ml, methylboronic acid 1.0 g, 1,1'-bis(diphenylphosphino)ferrocene-palladium(II) dichloride dichloromethane adducts 0.4 g and potassium phosphate 3.7 g was stirred with heating under reflux for nine hours. The reaction mixture was extracted with ethyl acetate. The organic layer was washed with water, and was dried over anhydrous magnesium sulfate and was then concentrated under reduced pressure. The resulting residue was subjected to a silica gel column chromatography to give 3-(4-methoxy-3-methyl-phenyl)-1,4,5-trimethyl-1H-pyrazole 0.6 g.

3-(4-methoxy-3-methyl-phenyl)-1,4,5-trimethyl-1H-pyrazole

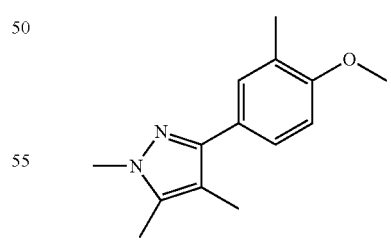

¹H-NMR (CDCl₃) δ: 7.43 (1H, s), 7.40 (1H, dd, J=8.2, 2.2 Hz), 6.86 (1H, d, J=8.5 Hz), 3.85 (3H, s), 3.80 (3H, s), 2.25 (3H, s), 2.21 (3H, s), 2.11 (3H, s).

Reference Preparation Example 131

A mixture of 3-(4-methoxy-3-methyl-phenyl)-1,4,5-trimethyl-1H-pyrazole (described in Reference Preparation example 130) 0.6 g, 47% hydrobromic acid 5 ml and acetic acid 5 ml was stirred with heating under reflux for thirteen hours. The solvent was distilled off and to the resulting residue was added ethyl acetate 30 ml, and the resulting mixture was stirred at room temperature for one hour. The precipitates were filtered and were washed with hexane, and were dried under reduced pressure to give 4-(1,4,5-trimethyl-1H-pyrazol-3-yl)-2-methyl-phenol 0.5 g.

4-(1,4,5-trimethyl-1H-pyrazol-3-yl)-2-methyl-phenol

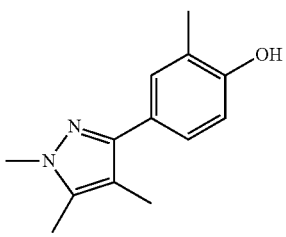 [SMILES: Cc1cc(-c2nn(C)c(C)c2C)ccc1O]

$^1$H-NMR (DMSO-D$_6$) δ: 7.33 (1H, d, J=2.2 Hz), 7.26 (1H, dd, J=8.2, 2.2 Hz), 6.88 (1H, d, J=8.2 Hz), 3.82 (3H, s), 2.26 (3H, s), 2.17 (3H, s), 2.08 (3H, s).

Reference Preparation Example 132

A similar reaction to Reference Preparation example 65 using 3-cyclopropyl-1H-pyrazole instead of 3,4,5-trimethyl-1H-pyrazole gave 1-(4-methoxy-3-methyl-phenyl)-3-cyclopropyl-1H-pyrazole and 1-(4-methoxy-3-methyl-phenyl)-5-cyclopropyl-1H-pyrazole.

1-(4-methoxy-3-methyl-phenyl)-3-cyclopropyl-1H-pyrazole

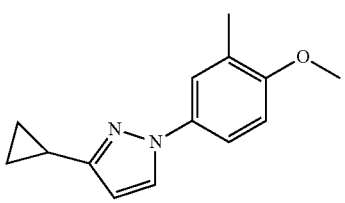 [SMILES: COc1ccc(-n2ccc(C3CC3)n2)cc1C]

$^1$H-NMR (CDCl$_3$) δ: 7.67 (1H, d, J=2.4 Hz), 7.43 (1H, d, J=2.9 Hz), 7.37 (1H, dd, J=8.7, 2.7 Hz), 6.83 (1H, d, J=8.7 Hz), 6.05 (1H, d, J=2.4 Hz), 3.85 (3H, s), 2.26 (3H, s), 2.07-2.00 (1H, m), 0.98-0.93 (2H, m), 0.80-0.76 (2H, m).

1-(4-methoxy-3-methyl-phenyl)-5-cyclopropyl-1H-pyrazole

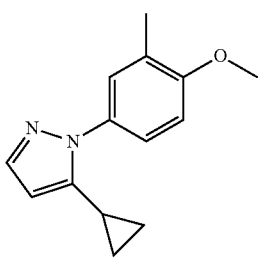 [SMILES: COc1ccc(-n2nccc2C2CC2)cc1C]

$^1$H-NMR (CDCl$_3$) δ: 7.51 (1H, d, J=1.9 Hz), 7.37-7.35 (2H, m), 6.89-6.87 (1H, m), 5.91 (1H, d, J=1.9 Hz), 3.88 (3H, s), 2.27 (3H, s), 1.81-1.74 (1H, m), 0.97-0.93 (2H, m), 0.76-0.72 (2H, m).

Reference Preparation Example 133

A similar reaction to Reference Preparation example 28 using 1-(4-methoxy-3-methyl-phenyl)-5-cyclopropyl-1H-pyrazole (described in Reference Preparation example 132) instead of 1-(4-methoxy-3-methyl-phenyl)-3,4,5-trimethyl-1H-pyrazole gave 2-methyl-(4-methoxy-3-cyclopropyl-1H-pyrazol-3-yl)-phenol.

2-methyl-(4-methoxy-3-cyclopropyl-1H-pyrazol-3-yl)-phenol

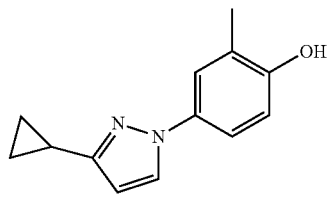 [SMILES: Cc1cc(-n2ccc(C3CC3)n2)ccc1O]

$^1$H-NMR (DMSO-D$_6$) δ: 8.10 (1H, d, J=1.4 Hz), 7.45 (1H, d, J=2.2 Hz), 7.35-7.32 (1H, m), 6.81 (1H, d, J=8.2 Hz), 6.15-6.14 (1H, m), 2.16 (3H, s), 1.97-1.90 (1H, m), 0.91-0.87 (2H, m), 0.71-0.67 (2H, m).

Reference Preparation Example 134

A similar reaction to Reference Preparation example 60 using 5-(4-methoxy-3-methyl-phenyl)-1-methyl-1H-pyrazole (described in Reference Preparation example 95) instead of 3-(4-methoxy-3-methyl-phenyl)-1-methyl-1H-pyrazole gave 2-methyl-(1,3-dimethyl-1H-pyrazol-5-yl)-phenol.

2-methyl-(1,3-dimethyl-1H-pyrazol-5-yl)-phenol

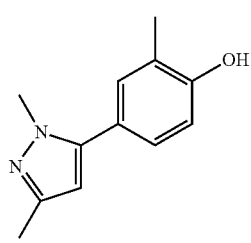

$^1$H-NMR (DMSO-D$_6$) δ: 7.22 (1H, s), 7.15 (1H, dd, J=8.2, 1.9 Hz), 6.89 (1H, d, J=8.2 Hz), 6.20 (1H, s), 3.77 (3H, s), 2.21 (3H, s), 2.16 (3H, s).

Reference Preparation Example 135

At room temperature, to a mixture of 4-methoxy-3-methyl-benzoic acid 5.0 g and tetrahydrofuran 100 ml was added oxalyl chloride 4.0 g and dimethylformamide 0.2 ml. The resulting mixture was stirred for two and a half hours and then was concentrated under reduced pressure. To the resulting mixture was further added chloroform 150 ml, N,O-dimethyl-hydroxyamine hydrochloride salt 3.5 g and N,N-diidopropyl-ethylamine 9.3 g at room temperature, and the resulting mixture was stirred for four hours. Thereto was added water and the resulting mixture was extracted with chloroform. The organic layer was washed with water and was dried over anhydrous magnesium sulfate, and was then concentrated under reduced pressure. The resulting residue was subjected to a silica gel column chromatography to give 4-methoxy-N-methoxy-3-methyl-N-methylbenzamide 6.1 g.

4-methoxy-N-methoxy-3-methyl-N-methylbenzamide

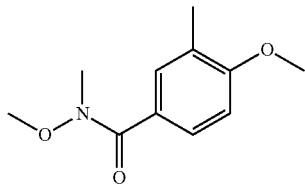

$^1$H-NMR (CDCl$_3$) δ: 7.61-7.58 (1H, m), 7.54 (1H, dd, J=2.1, 0.6 Hz), 6.81 (1H, d, J=8.5 Hz), 3.87 (3H, s), 3.57 (3H, s), 3.35 (3H, s), 2.23 (3H, s).

Reference Preparation Example 136

A mixture of 4-methoxy-N-methoxy-3-methyl-N-methyl-benzamide (described in Reference Preparation example 135) 5.7 g, tetrahydrofuran 100 ml and 0.95 mol/L solution of ethylmagnesium bromide in tetrahydrofuran 43 ml was stirred with heating under reflux for six hours. Thereto was added saturated ammonium chloride solution at room temperature, and the resulting mixture was extracted with ethyl acetate. The organic layer was washed with water and was dried over anhydrous magnesium sulfate, and was then concentrated under reduced pressure. The resulting residue was subjected to a silica gel column chromatography to give 1-(4-methoxy-3-methyl-phenyl)-propane-1-one 4.6 g.

1-(4-methoxy-3-methyl-phenyl)-propane-1-one

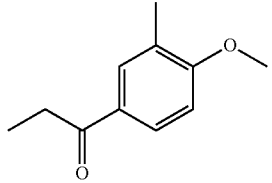

$^1$H-NMR (CDCl$_3$) δ: 7.83 (1H, dd, J=8.6, 2.3 Hz), 7.79-7.78 (1H, m), 6.84 (1H, d, J=8.7 Hz), 3.89 (3H, s), 2.95 (2H, q, J=7.2 Hz), 2.25 (3H, s), 1.21 (3H, t, J=7.2 Hz).

Reference Preparation Example 137

A mixture of 1-(4-methoxy-3-methyl-phenyl)-propane-1-one (described in Reference preparation example 136) 5.2 g, tetrahydrofuran 100 ml, potassium tert-butoxide 4.1 g and diethyl carbonate 3.6 g was stirred with heating under reflux for five and a half hours. Thereto was added 6N aqueous hydrochloric acid solution 20 ml at room temperature, and the resulting mixture was extracted with ethyl acetate. The organic layer was washed with water and was dried over anhydrous magnesium sulfate, and was then concentrated under reduced pressure. The resulting residue was subjected to a silica gel column chromatography to give 3-(4-methoxy-3-methyl-phenyl)-2-methyl-3-oxo-propionic acid ethyl ester 3.5 g.

3-(4-methoxy-3-methyl-phenyl)-2-methyl-3-oxo-propionic acid ethyl ester

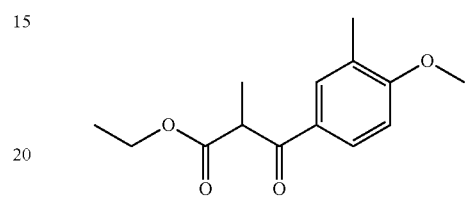

$^1$H-NMR (CDCl$_3$) δ: 7.86 (1H, dd, J=8.6, 2.3 Hz), 7.80 (1H, d, J=2.2 Hz), 6.86 (1H, d, J=8.7 Hz), 4.19-4.10 (3H, m), 3.90 (3H, s), 2.25 (3H, s), 1.47 (3H, d, J=7.2 Hz), 1.19 (3H, t, J=7.1 Hz).

Reference Preparation Example 138

A mixture of 3-(4-methoxy-3-methyl-phenyl)-2-methyl-3-oxo-propionic acid ethyl ester (described in Reference Preparation example 137) 3.5 g, toluene 100 ml and methyl hydrazine 7.4 g was stirred with heating under reflux for eighteen hours. The toluene distilled off and to the resulting residue was added aqueous 3N hydrochloric acid solution, and the precipitates were filtered and were washed with hexane to give 3-(4-methoxy-3-methyl-phenyl)-1,4-dimethyl-5-hydroxy-1H-pyrazole 1.4 g.

3-(4-methoxy-3-methyl-phenyl)-1,4-dimethyl-5-hydroxy-1H-pyrazole

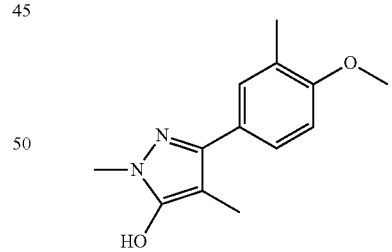

$^1$H-NMR (DMSO-D$_6$) δ: 7.47-7.44 (2H, m), 7.07 (1H, d, J=8.2 Hz), 3.84 (3H, s), 3.66 (3H, s), 2.20 (3H, s), 2.05 (3H, s).

Reference Preparation Example 139

A mixture of 3-(4-methoxy-3-methyl-phenyl)-1,4-dimethyl-5-hydroxy-1H-pyrazole (described in Reference Preparation example 138) 1.4 g and phosphorus oxychloride 31.8 g was stirred at 100° C. for eleven hours. The reaction mixture was concentrated under reduced pressure and was extracted with ethyl acetate. The organic layer was washed with water and was dried over anhydrous magnesium sulfate, and was then concentrated under reduced pressure. The resulting residue was subjected to a silica gel column chromatography to give 5-chloro-3-(4-methoxy-3-methyl-phenyl)-1,4-dimethyl-1H-pyrazole 0.4 g.

5-chloro-3-(4-methoxy-3-methyl-phenyl)-1,4-dimethyl-1H-pyrazole

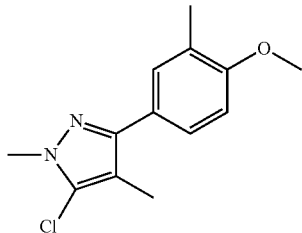

$^1$H-NMR (DMSO-D$_6$) δ: 7.42-7.40 (2H, m), 6.98 (1H, d, J=9.2 Hz), 3.81 (3H, s), 3.80 (3H, s), 2.19 (3H, s), 2.11 (3H, s).

Reference Preparation Example 140

A mixture of 5-chloro-3-(4-methoxy-3-methyl-phenyl)-1,4-dimethyl-1H-pyrazole (described in Reference Preparation examples 139 and 168) 0.4 g, 47% hydrobromic acid 3 ml and acetic acid 3 ml was stirred with heating under reflux for fifteen hours. The solvent was distilled off and to the resulting residue was added ethyl acetate 20 ml, and the resulting mixture was stirred at room temperature for one hour. The precipitates were filtered and were washed with hexane, and were dried under reduced pressure to give 4-(5-chloro-1,4-dimethyl-1H-pyrazol-3-yl)-2-methyl-phenol 0.3 g.

4-(5-chloro-1,4-dimethyl-1H-pyrazol-3-yl)-2-methyl-phenol

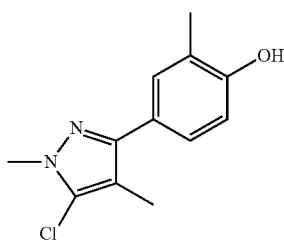 [SMILES: Cc1cc(-c2nn(C)c(Cl)c2C)ccc1O]

$^1$H-NMR (DMSO-D$_6$) δ: 7.33 (1H, s), 7.24 (1H, d, J=8.2 Hz), 6.83 (1H, d, J=8.2 Hz), 3.78 (3H, s), 2.15 (3H, s), 2.09 (3H, s).

Reference Preparation Example 141

At 0° C., to a mixture of 2,5-dimethylphenol 20 g and chloroform 150 ml was added acetyl chloride 15 g and trietylamine 49 g. The resulting mixture was raised to room temperature and was stirred for four hours. Then, the reaction mixture was extracted with chloroform. The organic layer was washed with water and was dried over anhydrous magnesium sulfate, and was then concentrated under reduced pressure. The resulting residue was subjected to a silica gel column chromatography to give acetic acid 2,5-dimethylphenyl ester 24 g.

acetic acid 2,5-dimethylphenyl ester

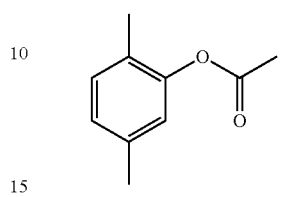

$^1$H-NMR (CDCl$_3$) δ: 7.10 (1H, d, J=7.7 Hz), 6.95 (1H, d, J=7.2 Hz), 6.82 (1H, s), 2.31 (6H, s), 2.13 (3H, s).

Reference Preparation Example 142

A similar reaction to Reference Preparation example 141 using 2-bromophenol instead of 2,5-dimethylphenol gave acetic acid 2-bromophenyl ester.

Acetic acid 2-bromophenyl ester

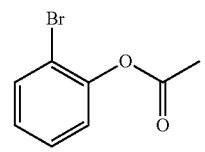

$^1$H-NMR (CDCl$_3$) δ: 7.61 (1H, d, J=7.3 Hz), 7.34 (1H, t, J=7.3 Hz), 7.16-7.10 (2H, m), 2.36 (3H, s).

Reference Preparation Example 143

A similar reaction to Reference Preparation example 113 using cyclopropanecarbonyl chloride instead of propionyl chloride gave cyclopropane carboxylic acid 2-methylphenyl ester.

Cyclopropane carboxylic acid 2-methylphenyl ester

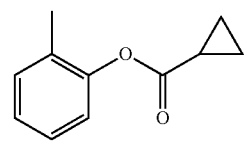

$^1$H-NMR (CDCl$_3$) δ: 7.24-7.17 (2H, m), 7.13 (1H, td, J=7.38, 1.26 Hz), 7.01 (1H, dd, J=7.67, 1.26 Hz), 2.19 (3H, s), 1.88 (1H, tt, J=8.01, 3.78 Hz), 1.21-1.16 (2H, m), 1.06-1.00 (2H, m).

Reference Preparation Example 144

A similar reaction to Reference Preparation example 113 using 3,3-dimethylbutanoyl chloride instead of propionyl chloride gave 3,3-dimethylbutanoic acid 2-methylphenyl ester.

3,3-dimethylbutanoic acid 2-methylphenyl ester

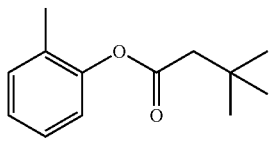

¹H-NMR (CDCl₃) δ: 7.24-7.18 (2H, m), 7.13 (1H, td, J=7.33, 1.37 Hz), 7.00 (1H, d, J=7.33 Hz), 2.48 (2H, s), 2.20 (3H, s), 1.15 (9H, s).

Reference Preparation Example 145

A similar reaction to Reference Preparation example 113 using 2-methylpropionyl chloride instead of propionyl chloride gave 2-methylpropionic acid 2-methylphenyl ester.

2-methylpropionic acid 2-methylphenyl ester

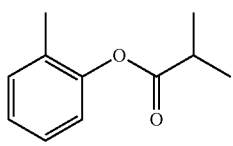

¹H-NMR (CDCl₃) δ: 7.24-7.17 (2H, m), 7.13 (1H, t, J=7.10 Hz), 6.98 (1H, d, J=7.79 Hz), 2.89-2.80 (1H, m), 2.17 (3H, s), 1.34 (6H, d, J=6.87 Hz).

Reference Preparation Example 146

A similar reaction to Reference Preparation example 113 using cyclohexanecarbonyl chloride instead of propionyl chloride gave cyclohexane carboxylic acid 2-methylphenyl ester.

Cyclohexane carboxylic acid 2-methylphenyl ester

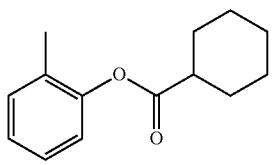 [SMILES: Cc1ccccc1OC(=O)C1CCCCC1]

¹H-NMR (CDCl₃) δ: 7.24-7.17 (2H, m), 7.12 (1H, t, J=7.33 Hz), 6.97 (1H, d, J=8.01 Hz), 2.63-2.55 (1H, m), 2.16 (3H, s), 2.11-2.07 (2H, m), 1.88-1.80 (2H, m), 1.70-1.59 (2H, m), 1.43-1.28 (4H, m).

Reference Preparation Example 147

A similar reaction to Reference Preparation example 113 using pentanoyl chloride instead of propionyl chloride gave pentanoic acid 2-methylphenyl ester.

Pentanoic acid 2-methylphenyl ester

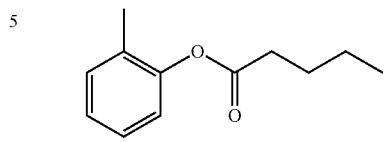

¹H-NMR (CDCl₃) δ: 7.22-7.19 (2H, m), 7.13 (1H, td, J=7.37, 1.09 Hz), 6.99 (1H, dd, J=7.61, 1.09 Hz), 2.58 (2H, t, J=7.61 Hz), 2.18 (3H, s), 1.80-1.73 (2H, m), 1.50-1.42 (2H, m), 0.98 (3H, t, J=7.37 Hz).

Reference Preparation Example 148

At room temperature, to a mixture of acetic acid 2,5-dimethylphenyl ester (described in Reference Preparation example 141) 24 g and nitromethane 200 ml was added aluminum trichloride 49 g, and the resulting mixture was heated to 50° C. The resulting mixture was stirred for eight and a half hours and thereto was added ice water 300 ml. The resulting mixture was extracted with chloroform. The organic layer was washed with water and was dried over anhydrous magnesium sulfate, and was then concentrated under reduced pressure. The resulting residue was subjected to a silica gel column chromatography to give 1-(2,5-dimetyl-4-hydroxy-phenyl)-ethanone 21 g.

1-(2,5-dimetyl-4-hydroxy-phenyl)-ethanone

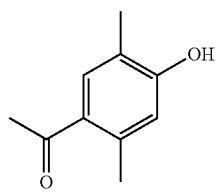

¹H-NMR (CDCl₃) δ: 7.59 (1H, s), 6.64 (1H, s), 5.56 (1H, s), 2.55 (3H, s), 2.50 (3H, s), 2.26 (3H, s).

Reference Preparation Example 149

A similar reaction to Reference Preparation example 114 using acetic acid 2-bromophenyl ester (described in Reference Preparation example 142) instead of propionic acid o-tolyl ester gave 1-(3-bromo-4-hydroxy-phenyl)-ethanone.

1-(3-bromo-4-hydroxy-phenyl)-ethanone

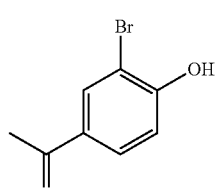

$^1$H-NMR (CDCl$_3$) δ: 7.08 (1H, d, J=8.01 Hz), 6.68-6.60 (2H, m), 5.31 (1H, br s), 2.30 (3H, s).

Reference Preparation Example 150

A similar reaction to Reference Preparation example 114 using cyclopropane carboxylic acid 2-methylphenyl ester (described in Reference Preparation example 143) instead of propionic acid o-tolyl ester gave cyclopropyl-(4-hydroxy-3-methyl-phenyl)-methanone.

Cyclopropyl-(4-hydroxy-3-methyl-phenyl)-methanone

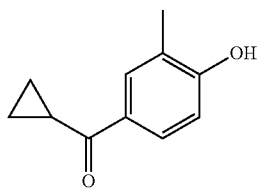

$^1$H-NMR (CDCl$_3$) δ: 7.85 (1H, d, J=2.17 Hz), 7.80 (1H, dd, J=8.45, 2.17 Hz), 6.84 (1H, d, J=8.45 Hz), 6.15 (1H, br s), 2.68-2.61 (1H, m), 2.30 (3H, s), 1.25-1.20 (2H, m), 1.04-0.98 (2H, m).

Reference Preparation Example 151

A similar reaction to Reference Preparation example 114 using 3,3-dimethylbutanoic acid 2-methylphenyl ester (described in Reference Preparation example 144) instead of propionic acid o-tolyl ester gave 1-(4-hydroxy-3-methyl-phenyl)-3,3-dimethylbutane-1-one.

1-(4-hydroxy-3-methyl-phenyl)-3,3-dimethylbutane-1-one

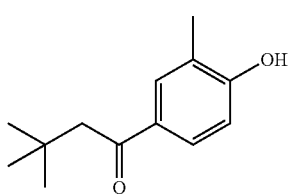

$^1$H-NMR (CDCl$_3$) δ: 7.79-7.77 (1H, m), 7.72 (1H, dd, J=8.47, 2.29 Hz), 6.83 (1H, d, J=8.47 Hz), 6.23 (1H, s), 2.80 (2H, s), 2.29 (3H, s), 1.05 (9H, s).

Reference Preparation Example 152

A similar reaction to Reference Preparation example 114 using 2-methylpropionic acid 2-methylphenyl ester (described in Reference Preparation example 145) instead of propionic acid o-tolyl ester gave 1-(4-hydroxy-3-methyl-phenyl)-2-methyl-propane-1-one.

1-(4-hydroxy-3-methyl-phenyl)-2-methyl-propane-1-one

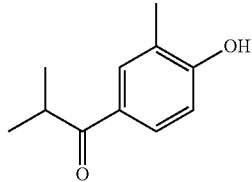

$^1$H-NMR (CDCl$_3$) δ: 7.80 (1H, d, J=2.18 Hz), 7.74 (1H, dd, J=8.24, 2.18 Hz), 6.84 (1H, d, J=8.24 Hz), 6.08 (1H, br s), 3.57-3.49 (1H, m), 2.30 (3H, s), 1.20 (6H, d, J=6.75 Hz).

Reference Preparation Example 153

A similar reaction to Reference Preparation example 114 using cyclohexanoic acid 2-methylphenyl ester (described in Reference Preparation example 146) instead of propionic acid o-tolyl ester gave cyclohexyl-(4-hydroxy-3-methyl-phenyl)-methanone.

Cyclohexyl-(4-hydroxy-3-methyl-phenyl)-methanone

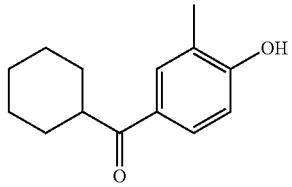 [SMILES: Cc1cc(C(=O)C2CCCCC2)ccc1O]

$^1$H-NMR (CDCl$_3$) δ: 7.77 (1H, d, J=2.17 Hz), 7.73 (1H, dd, J=8.45, 2.17 Hz), 6.82 (1H, d, J=8.45 Hz), 3.25-3.19 (1H, m), 2.29 (3H, s), 1.87-1.83 (4H, m), 1.76-1.25 (6H, m).

Reference Preparation Example 154

A similar reaction to Reference Preparation example 114 using pentanoic acid 2-methylphenyl ester (described in Reference Preparation example 147) instead of propionic acid o-tolyl ester gave 1-(4-hydroxy-3-methyl-phenyl)-pentane-1-one.

1-(4-hydroxy-3-methyl-phenyl)-pentane-1-one

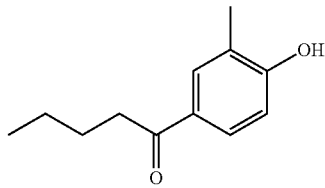

$^1$H-NMR (CDCl$_3$) δ: 7.80 (1H, d, J=2.17 Hz), 7.74 (1H, dd, J=8.45, 2.17 Hz), 6.85 (1H, d, J=8.45 Hz), 6.28 (1H, br s), 2.92 (2H, t, J=7.49 Hz), 2.31 (3H, t, J=5.31 Hz), 1.75-1.67 (2H, m), 1.44-1.36 (2H, m), 0.95 (3H, t, J=7.31 Hz).

Reference Preparation Example 155

At room temperature, to a mixture of 1-(4-methoxy-3-methyl)-ethanone (described in Reference Preparation example 102) 6.9 g and tetrahydrofuran 200 ml was added trifluoroacetic acid ethyl ester 11.9 g and 20% solution of sodium ethoxide in ethanol 28.5 g. The resulting mixture was stirred with heating under reflux for six hours. To the reaction mixture was added water, and the resulting mixture was acidified with 6N aqueous hydrochloric acid solution. The resulting mixture was extracted with ethyl acetate. The organic layer was washed with water and was dried over anhydrous magnesium sulfate, and was then concentrated under reduced pressure. The resulting residue was subjected to a silica gel column chromatography to give 4,4,4-trifluoro-1-(4-methoxy-3-methyl-phenyl)-butane-1,3-dione 10 g.

4,4,4-trifluoro-1-(4-methoxy-3-methyl-phenyl)-butane-1,3-dione

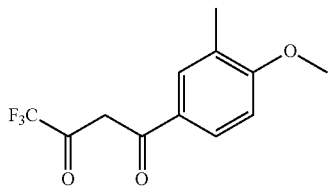 [SMILES: COc1ccc(C(=O)CC(=O)C(F)(F)F)cc1C]

$^1$H-NMR (CDCl$_3$: 23° C.) δ: 7.84 (1H, dd, J=8.7, 2.4 Hz), 7.75 (1H, dd, J=1.7, 0.7 Hz), 6.90 (1H, d, J=8.7 Hz), 6.51 (1H, s), 3.93 (3H, s), 2.27 (3H, s).

Reference Preparation Example 156

At 0° C., to a mixture of 4,4,4-trifluoro-1-(4-methoxy-3-methyl-phenyl)-butane-1,3-dione (described in Reference Preparation example 155) 6.8 g and ethanol 100 ml was added methyl hydrazine 1.7 g. The resulting mixture was raised to room temperature and was stirred for one hour. The reaction mixture was concentrated under reduced pressure and the resulting residue was subjected to a silica gel column chromatography to give 5-(4-methoxy-3-methyl-phenyl)-2-methyl-3-trifluoromethyl-3,4-dihydro-2H-pyrazol-3-ol 3.2 g and 5-(4-methoxy-3-methyl-phenyl)-1-methyl-3-trifluoromethyl-1H-pyrazole 2 g.

5-(4-methoxy-3-methyl-phenyl)-2-methyl-3-trifluoromethyl-3,4-dihydro-2H-pyrazol-3-ol

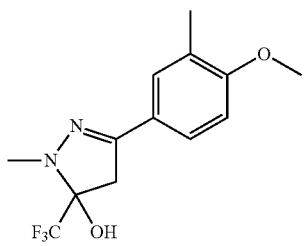

$^1$H-NMR (CDCl$_3$) δ: 7.44-7.44 (1H, m), 7.33 (1H, dd, J=8.5, 2.4 Hz), 6.79 (1H, d, J=8.5 Hz), 3.85 (3H, s), 3.50 (1H, d, J=17.6 Hz), 3.24 (1H, d, J=17.6 Hz), 3.06 (3H, s), 2.87 (1H, s), 2.22 (3H, s).

5-(4-methoxy-3-methyl-phenyl)-1-methyl-3-trifluoromethyl-1H-pyrazole

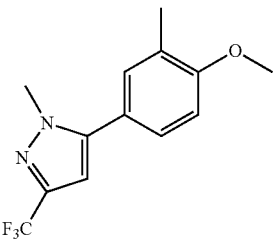 [SMILES: COc1ccc(-c2cc(C(F)(F)F)nn2C)cc1C]

$^1$H-NMR (CDCl$_3$) δ: 7.22-7.17 (2H, m), 6.91 (1H, d, J=8.5 Hz), 6.48 (1H, s), 3.90 (3H, s), 3.89 (3H, s), 2.27 (3H, s).

Reference Preparation Example 157

A mixture of 5-(4-methoxy-3-methyl-phenyl)-2-methyl-3-trifluoromethyl-3,4-dihydro-2H-pyrazol-3-ol (described in Reference preparation example 156) 2.3 g, 6N aqueous hydrochloric acid solution 4 ml and tetrahydrofuran 30 ml was stirred with heating under reflux for two hours. The reaction mixture was extracted with ethyl acetate. The organic layer was washed with saturated aqueous sodium carbonate solution and saturated saline. The organic layer was dried over anhydrous magnesium sulfate, and was then concentrated under reduced pressure. The resulting residue was subjected to a silica gel column chromatography to give 3-(4-methoxy-3-methyl-phenyl)-1-methyl-5-trifluoromethyl-1H-pyrazole 2.2 g.

3-(4-methoxy-3-methyl-phenyl)-1-methyl-5-trifluoromethyl-1H-pyrazole

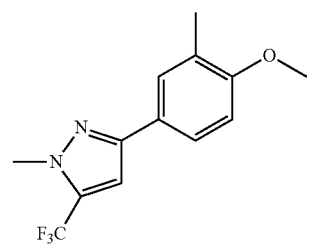

$^1$H-NMR (CDCl$_3$) δ: 7.56-7.53 (2H, m), 6.85 (1H, d, J=8.2 Hz), 6.81 (1H, s), 4.01 (3H, s), 3.86 (3H, s), 2.26 (3H, s).

Reference Preparation Example 158

A mixture of 3-(4-methoxy-3-methyl-phenyl)-1-methyl-5-trifluoromethyl-1H-pyrazole (described in Reference Preparation example 157) 0.4 g, 47% hydrobromic acid 24 ml and acetic acid 24 ml was stirred with heating under reflux for twelve hours. The solvent was distilled off and to the resulting residue was added ice water 70 ml. The precipitates were filtered and were washed with ice water 70 ml, and then were dried under reduced pressure to give 2-methyl-4-(1-methyl-5-trifluoromethyl-1H-pyrazol-3-yl)-phenol 2 g.

2-methyl-4-(1-methyl-5-trifluoromethyl-1H-pyrazol-3-yl)-phenol

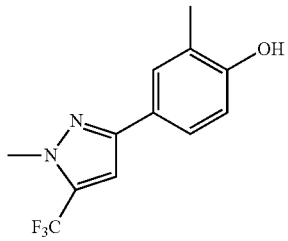 [SMILES: Cc1cc(-c2cc(C(F)(F)F)n(C)n2)ccc1O]

$^1$H-NMR (DMSO-D$_6$) δ: 9.52 (1H, s), 7.57 (1H, s), 7.47 (1H, d, J=8.2 Hz), 7.22 (1H, s), 6.80 (1H, d, J=8.5 Hz), 3.96 (3H, s), 2.15 (3H, s).

Reference Preparation Example 159

A mixture of 1-(2,5-dimethyl-4-hydroxy-phenyl)-ethanone (described in Reference Preparation example 148) 14.6 g, methyl iodide 16.6 g, potassium carbonate 26.8 g and acetone 200 ml was stirred with heating under reflux for eight hours. The reaction mixture was cooled to room temperature and was filtered, and was then concentrated under reduced pressure. The resulting residue was subjected to a silica gel column chromatography to give 1-(4-methoxy-2,5-dimethyl)-ethanone 15.1 g.

1-(4-methoxy-2,5-dimethyl)-ethanone

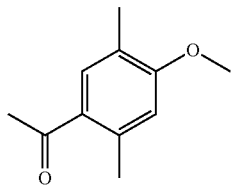

$^1$H-NMR (CDCl$_3$) δ: 7.56 (1H, s), 6.65 (1H, s), 3.87 (3H, s), 2.56 (3H, s), 2.54 (3H, s), 2.21 (3H, s).

Reference Preparation Example 160

At room temperature, to a mixture of 1-(4-methoxy-2,5-dimethyl)-ethanone (described in Reference Preparation example 159) 6.9 g and tetrahydrofuran 200 ml was added trifluoroacetic acid ethyl ester 7.9 g and 20% sodium ethoxide solution in ethanol 19 g. The resulting mixture was stirred with heating under reflux for seven hours, and then to the reaction mixture was added water 70 ml, and the resulting mixture was acidified with 6N aqueous hydrochloric acid solution. The resulting mixture was extracted with ethyl acetate. The organic layer was washed with water and was dried over anhydrous magnesium sulfate, and was then concentrated under reduced pressure. The resulting residue was subjected to a silica gel column chromatography to give 4,4,4-trifluoro-1-(4-methoxy-2,5-dimethyl-phenyl)-butane-1,3-dione 6.8 g.

4,4,4-trifluoro-1-(4-methoxy-2,5-dimethyl-phenyl)-butane-1,3-dione

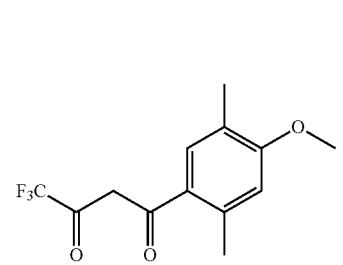 [SMILES: COc1cc(C)c(C(=O)CC(=O)C(F)(F)F)cc1C]

$^1$H-NMR (CDCl$_3$: 23° C.) δ: 7.44 (1H, s), 6.69 (1H, s), 6.35 (1H, s), 3.89 (3H, s), 2.57 (3H, s), 2.21 (3H, s).

Reference Preparation Example 161

At 0° C., to a mixture of 4,4,4-trifluoro-1-(4-methoxy-2,5-dimethyl-phenyl)-butane-1,3-dione (described in Reference Preparation example 160) 6.8 g and ethanol 100 ml was added methyl hydrazine 1.7 g. The resulting mixture was raised to room temperature and was stirred for one hour. The reaction mixture was concentrated under reduced pressure and the resulting residue was subjected to a silica gel column chromatography to give 5-(4-methoxy-2,5-dimethyl-phenyl)-2-methyl-3-trifluoromethyl-3,4-dihydro-2H-pyrazole-3-ol 3.2 g and 5-(4-methoxy-2,5-dimethyl-phenyl)-1-methyl-3-trifluoromethyl-1H-pyrazole 3 g.

5-(4-methoxy-2,5-dimethyl-phenyl)-2-methyl-3-trifluoromethyl-3,4-dihydro-2H-pyrazole-3-ol

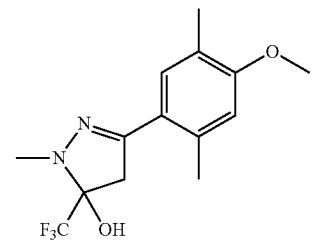

$^1$H-NMR (CDCl$_3$) δ: 7.06 (1H, s), 6.67 (1H, s), 3.84 (3H, s), 3.59 (1H, d, J=17.4 Hz), 3.27 (1H, d, J=17.4 Hz), 3.06 (3H, s), 2.78 (1H, s), 2.53 (3H, s), 2.18 (3H, s).

5-(4-methoxy-2,5-dimethyl-phenyl)-1-methyl-3-trifluoromethyl-1H-pyrazole

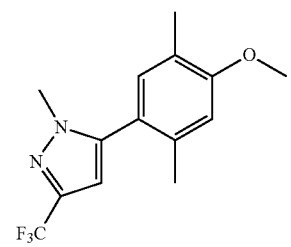 [SMILES: COc1cc(C)c(-c2cc(C(F)(F)F)nn2C)cc1C]

¹H-NMR (CDCl₃) δ: 6.96 (1H, s), 6.75 (1H, s), 6.41 (1H, s), 3.87 (3H, s), 3.69 (3H, s), 2.20 (3H, s), 2.14 (3H, s).

Reference Preparation Example 162

A mixture of 5-(4-methoxy-2,5-dimethyl-phenyl)-2-methyl-3-trifluoromethyl-3,4-dihydro-2H-pyrazole-3-ol (described in Reference preparation example 161) 3.2 g, 6N aqueous hydrochloric acid solution 5.3 ml and tetrahydrofuran 50 ml was stirred with heating under reflux for one hour. The reaction mixture was extracted with ethyl acetate. The organic layer was washed with saturated aqueous sodium carbonate solution and saturated saline. The organic layer was dried over anhydrous magnesium sulfate, and was then concentrated under reduced pressure. The resulting residue was subjected to a silica gel column chromatography to give 3-(4-methoxy-2,5-dimethyl-phenyl)-1-methyl-5-trifluoromethyl-1H-pyrazole 3 g.

3-(4-methoxy-2,5-dimethyl-phenyl)-1-methyl-5-trifluoromethyl-1H-pyrazole

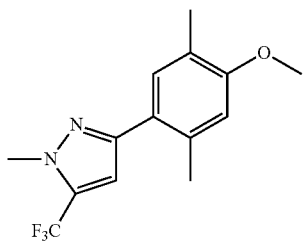

¹H-NMR (CDCl₃) δ: 7.30 (1H, s), 6.70 (1H, s), 6.69 (1H, s), 4.03 (3H, s), 3.85 (3H, s), 2.43 (3H, s), 2.21 (3H, s).

Reference Preparation Example 163

A mixture of 3-(4-methoxy-2,5-dimethyl-phenyl)-1-methyl-5-trifluoromethyl-1H-pyrazole (described in Reference Preparation example 162) 3 g, 47% hydrobromic acid 29 ml and acetic acid 29 ml was stirred with heating under reflux for twenty one hours. The solvent was distilled off and to the resulting residue was added ice water 90 ml. The precipitates was filtered and was washed with ice water 90 ml and hexane 100 ml, and then was concentrated under reduced pressure to give 2,5-dimethyl-4-(1-methyl-5-trifluoromethyl-1H-pyrazol-3-yl)-phenol 2.9 g.

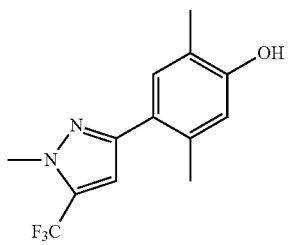 [SMILES: Cc1cc(-c2cc(C(F)(F)F)n(C)n2)c(C)cc1O]

¹H-NMR (DMSO-D₆) δ: 9.37 (1H, s), 7.26 (1H, s), 7.02 (1H, s), 6.66 (1H, s), 3.98 (3H, s), 2.32 (3H, s), 2.10 (3H, s).

Reference Preparation Example 164

A similar reaction to Reference Preparation example 158 using 5-(4-methoxy-3-methyl-phenyl)-1-methyl-3-trifluoromethyl-1H-pyrazole (described in Reference Preparation example 156) instead of 3-(4-methoxy-3-methyl-phenyl)-1-methyl-5-trifluoromethyl-1H-pyrazole gave 2-methyl-4-(1-methyl-3-trifluoromethyl-1H-pyrazol-5-yl)-phenol.

2-methyl-4-(1-methyl-3-trifluoromethyl-1H-pyrazol-5-yl)-phenol

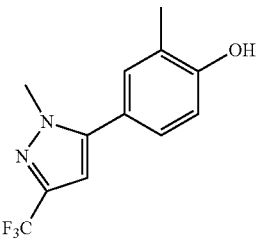 [SMILES: Cc1cc(-c2cc(C(F)(F)F)nn2C)ccc1O]

¹H-NMR (DMSO-D₆) δ: 7.29 (1H, s), 7.22 (1H, dd, J=8.2, 2.2 Hz), 6.90 (1H, d, J=8.2 Hz), 6.74 (1H, s), 3.88 (3H, s), 2.17 (3H, s).

Reference Preparation Example 165

At room temperature, to a mixture of 1-(4-methoxy-3-methyl)-ethanone (described in Reference Preparation example 102) and tetrahydrofuran 200 ml was added diethyl carbonate 16.1 g, 55% sodium hydride 6.2 g, dibenzo-18-crown-6 0.05 g and ethanol 3 mL, and the resulting mixture was stirred with heating under reflux for eight hours. To the reaction mixture was added water, and the resulting mixture was acidified with 10% aqueous hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 3-(4-methoxy-3-methyl-phenyl)-3-oxo-propionic acid ethyl ester 14.8 g.

3-(4-methoxy-3-methyl-phenyl)-3-oxo-propionic acid ethyl ester

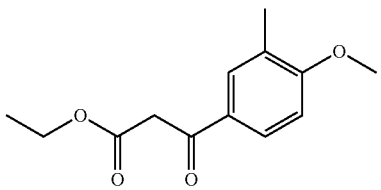 [SMILES: CCOC(=O)CC(=O)c1ccc(OC)c(C)c1]

¹H-NMR (CDCl₃) δ: 7.81 (1H, dd, J=8.5, 2.4 Hz), 7.76-7.76 (1H, m), 6.86 (1H, d, J=8.5 Hz), 4.21 (2H, q, J=7.1 Hz), 3.93 (2H, s), 3.90 (3H, s), 2.24 (3H, s), 1.26 (3H, t, J=7.1 Hz).

Reference Preparation Example 166

At room temperature, to a mixture of 3-(4-methoxy-3-methyl-phenyl)-3-oxo-propionic acid ethyl ester (described in Reference Preparation example 165) 14.8 g and toluene 100 ml was added N-methyl hydrazine 29 g, and the resulting mixture was stirred for twelve hours. The toluene was distilled off. At room temperature, to the reaction mixture was added water 100 ml and the resulting mixture was acidified with 10% aqueous hydrochloric acid solution and was stirred for three hours. The precipitates were filtered and were washed with water 400 ml and ethyl acetate 500 ml, and then were dried under reduced pressure to give 5-hydroxy-3-(4-methoxy-3-methyl-phenyl)-1-methyl-1H-pyrazole 9.3 g.

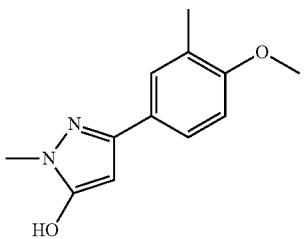

$^1$H-NMR (DMSO-D$_6$) δ: 7.58-7.56 (2H, m), 6.97 (1H, d, J=8.9 Hz), 5.90 (1H, s), 3.81 (3H, s), 3.60 (3H, s), 2.18 (3H, s).

Reference Preparation Example 167

At 0° C., to phosphorus oxychloride 56 g was added N,N-dimethylformamide 4.0 g and the resulting mixture was stirred for a half hour. Thereto was added 5-hydroxy-3-(4-methoxy-3-methyl-phenyl)-1-methyl-1H-pyrazole (described in Reference preparation example 166) 9.3 g. The resulting mixture was stirred for seven hours and the reaction solvent was distilled off under reduced pressure. To the reaction mixture was added ice water 100 ml and the resulting mixture was extracted with ethyl acetate. The organic layer was washed with water and was dried over anhydrous magnesium sulfate, and was then concentrated under reduced pressure. The resulting residue was subjected to a silica gel column chromatography to give 5-chloro-4-formyl-3-(4-methoxy-3-methyl-phenyl)-1-methyl-1H-pyrazole 6.3 g.

5-chloro-4-formyl-3-(4-methoxy-3-methyl-phenyl)-1-methyl-1H-pyrazole

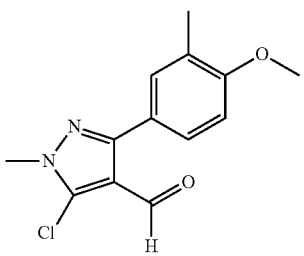

$^1$H-NMR (CDCl$_3$) δ: 9.93 (1H, s), 7.55 (1H, dd, J=8.5, 2.2 Hz), 7.51 (1H, s), 6.90 (1H, d, J=8.5 Hz), 3.92 (3H, s), 3.88 (3H, s), 2.27 (3H, s).

Reference Preparation Example 168

At 0° C., a mixture of 5-chloro-4-formyl-3-(4-methoxy-3-methyl-phenyl)-1-methyl-1H-pyrazole (described in Reference Preparation example 167) 0.3 g and trifluoroacetic acid 10 ml was added triethylsilane 0.27 g. The resulting mixture was stirred at room temperature for three hours, and thereto was added water 5 ml. The resulting mixture was extracted with ethyl acetate. The organic layer was washed with water and was dried over anhydrous magnesium sulfate, and was then concentrated under reduced pressure. The resulting residue was subjected to a silica gel column chromatography to give 5-chloro-3-(4-methoxy-3-methyl-phenyl)-1,4-dimethyl-1H-pyrazole 0.28 g.

5-chloro-3-(4-methoxy-3-methyl-phenyl)-1,4-dimethyl-1H-pyrazole

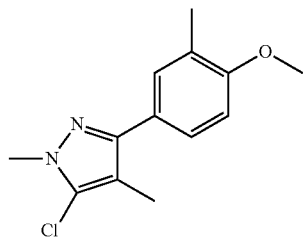

$^1$H-NMR (DMSO-D$_6$) δ: 7.42-7.40 (2H, m), 6.98 (1H, d, J=9.2 Hz), 3.81 (3H, s), 3.80 (3H, s), 2.19 (3H, s), 2.11 (3H, s).

Reference Preparation Example 169

A mixture of 1-(4-hydroxy-3-methyl-phenyl)-ethanone 10 g, isopropyl iodide 13.6 g, potassium carbonate 18.4 g and acetone 250 ml was stirred with heating under reflux for twelve hours. The reaction mixture was filtered and the resulting filtrate was concentrated under reduced pressure, and the resulting residue was subjected to a silica gel column chromatography to give 1-(4-isopropoxy-3-methyl-phenyl)-ethanone 9.5 g.

1-(4-isopropoxy-3-methyl-phenyl)-ethanone

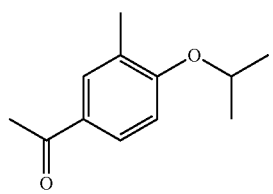

$^1$H-NMR (CDCl$_3$) δ: 7.80-7.78 (2H, m), 6.84 (1H, d, J=8.2 Hz), 4.69-4.60 (1H, m), 2.54 (3H, s), 2.23 (3H, s), 1.37 (6H, d, J=6.0 Hz).

Reference Preparation Example 170

At room temperature, to a mixture of 1-(4-isopropoxy-3-methyl-phenyl)-ethanone (described in Reference Preparation example 169) 9.4 g and tetrahydrofuran 150 ml was added diethyl carbonate 11.6 g, 55% sodium hydride 4.5 g, dibenzo-18-crown-6 0.04 g and ethanol 3 mL, and the resulting mixture was stirred with heating under reflux for nine hours. To the reaction mixture was added water, and the resulting mixture was acidified with 10% aqueous hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 3-(4-isopropoxy-3-methyl-phenyl)-3-oxo-propionic acid ethyl ester 12.1 g.

3-(4-isopropoxy-3-methyl-phenyl)-3-oxo-propionic acid ethyl ester

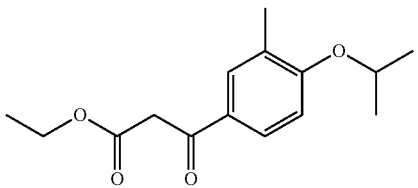 [SMILES: CCOC(=O)CC(=O)c1ccc(OC(C)C)c(C)c1]

$^1$H-NMR (CDCl$_3$) δ: 7.79-7.76 (2H, m), 6.85-6.83 (1H, m), 4.68-4.62 (1H, m), 4.21 (2H, q, J=7.2 Hz), 3.93 (2H, s), 2.22 (3H, s), 1.37 (6H, d, J=6.0 Hz), 1.26 (3H, t, J=7.1 Hz).

Reference Preparation Example 171

At room temperature, to a mixture of 3-(4-isopropoxy-3-methyl-phenyl)-3-oxo-propionic acid ethyl ester (described in Reference Preparation example 170) 12.1 g and toluene 100 ml was added N-methyl hydrazine 21 g, and the resulting mixture was stirred for twelve hours. The toluene was distilled off under reduced pressure. At room temperature, to the reaction mixture was added water 100 ml and the resulting mixture was acidified with 10% aqueous hydrochloric acid solution and was stirred for three hours. The precipitates were filtered and were washed with water 400 ml and ethyl acetate 500 ml, and then were dried under reduced pressure to give 5-hydroxy-3-(4-isopropoxy-3-methyl-phenyl)-1-methyl-1H-pyrazole 9.5 g.

5-hydroxy-3-(4-isopropoxy-3-methyl-phenyl)-1-methyl-1H-pyrazole

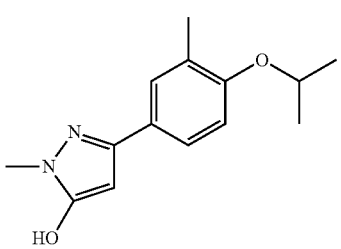 [SMILES: Cc1cc(-c2cc(O)n(C)n2)ccc1OC(C)C]

$^1$H-NMR (DMSO-D$_6$) δ: 7.58-7.54 (2H, m), 7.01-6.98 (1H, m), 5.95 (1H, s), 4.66-4.60 (1H, m), 3.62 (3H, s), 2.16 (3H, s), 1.28 (6H, d, J=5.1 Hz).

Reference Preparation Example 172

At 0° C., to phosphorus oxychloride 150 g was added N,N-dimethylformamide 10.9 g and the resulting mixture was stirred for a half hour. Thereto was added 5-hydroxy-3-(4-isopropoxy-3-methyl-phenyl)-1-methyl-1H-pyrazole (described in Reference preparation example 171) 28 g. The resulting mixture was stirred at 100° C. for ten hours and the reaction solvent was distilled off under reduced pressure. To the reaction mixture was added ice water 100 ml and the resulting mixture was extracted with ethyl acetate. The organic layer was washed with water and was dried over anhydrous magnesium sulfate, and was then concentrated under reduced pressure. The resulting residue was subjected to a silica gel column chromatography to give 5-chloro-4-formyl-3-(4-isopropoxy-3-methyl-phenyl)-1-methyl-1H-pyrazole 21 g, 2-methyl-4-(5-chloro-4-formyl-1-methyl-1H-pyrazol-3-yl)-phenol 1 g and 4-formyl-5-hydroxy-3-(4-isopropoxy-3-methyl-phenyl)-1-methyl-1H-pyrazole 1 g.

5-chloro-4-formyl-3-(4-isopropoxy-3-methyl-phenyl)-1-methyl-1H-pyrazole

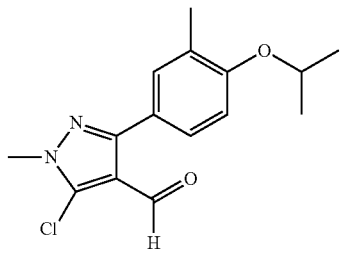 [SMILES: Cc1cc(-c2nn(C)c(Cl)c2C=O)ccc1OC(C)C]

$^1$H-NMR (CDCl$_3$) δ: 9.93 (1H, s), 7.52-7.50 (2H, m), 6.91-6.89 (1H, m), 4.63-4.54 (1H, m), 3.92 (3H, s), 2.25 (3H, s), 1.36 (6H, d, J=6.0 Hz).

2-methyl-4-(5-chloro-4-formyl-1-methyl-1H-pyrazol-3-yl)-phenol

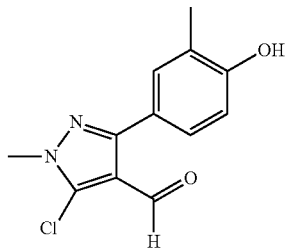 [SMILES: Cc1cc(-c2nn(C)c(Cl)c2C=O)ccc1O]

$^1$H-NMR (CDCl$_3$) δ: 9.92 (1H, s), 7.52-7.51 (1H, m), 7.47 (1H, dd, J=8.2, 2.3 Hz), 6.85 (1H, d, J=8.2 Hz), 4.95 (1H, s), 3.93 (3H, s), 2.30 (3H, s).

4-formyl-5-hydroxy-3-(4-isopropoxy-3-methyl-phenyl)-1-methyl-1H-pyrazole

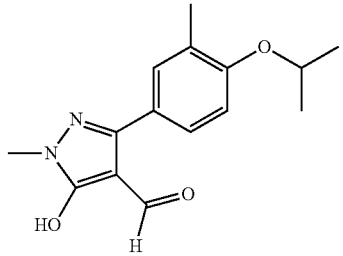 [SMILES: Cc1cc(-c2nn(C)c(O)c2C=O)ccc1OC(C)C]

$^1$H-NMR (DMSO-D$_6$) δ: 10.79 (1H, s), 9.45 (1H, s), 7.31-7.29 (2H, m), 7.08 (1H, d, J=8.8 Hz), 4.74-4.65 (1H, m), 3.55 (3H, s), 2.18 (3H, s), 1.32 (6H, d, J=5.9 Hz)

Reference Preparation Example 173

At room temperature, to a mixture of 5-chloro-4-formyl-3-(4-isopropoxy-3-methyl-phenyl)-1-methyl-1H-pyrazole (described in Reference Preparation example 172) 4.8 g and tetrahydrofuran 100 ml was added methanol 0.6 g and 55% sodium hydride 0.8 g, and the resulting mixture was stirred for three hours. To the reaction mixture was added water 50 ml, and the resulting mixture was extracted with ethyl acetate. The organic layer was washed with water and was dried over anhydrous magnesium sulfate, and was then concentrated under reduced pressure. The resulting residue was subjected to a silica gel column chromatography to give 4-formyl-3-(4-isopropoxy-3-methyl-phenyl)-5-methoxy-1-methyl-1H-pyrazole 4.5 g.

4-formyl-3-(4-isopropoxy-3-methyl-phenyl)-5-methoxy-1-methyl-1H-pyrazole

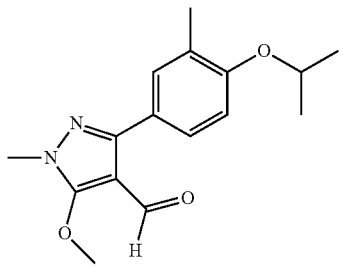 [SMILES: COc1c(C=O)c(-c2ccc(OC(C)C)c(C)c2)nn1C]

$^1$H-NMR (CDCl$_3$) δ: 9.75 (1H, s), 7.39 (1H, d, J=1.9 Hz), 7.35 (1H, dd, J=8.3, 2.3 Hz), 6.90 (1H, d, J=8.5 Hz), 4.63-4.54 (1H, m), 4.30 (3H, s), 3.71 (3H, s), 2.24 (3H, s), 1.36 (6H, d, J=6.0 Hz).

Reference Preparation Example 174

At 0° C., a mixture of 4-formyl-3-(4-isopropoxy-3-methyl-phenyl)-5-methoxy-1-methyl-1H-pyrazole (described in Reference Preparation example 173) 4.2 g and trifluoroacetic acid 20 ml was added triethylsilane 4.2 g. The resulting mixture was stirred at room temperature for six hours, and the solvent was distilled off under reduced pressure, and thereto was added water 10 ml. The resulting mixture was extracted with ethyl acetate. The organic layer was washed with water and was dried over anhydrous magnesium sulfate, and was then concentrated under reduced pressure. The resulting residue was subjected to a silica gel column chromatography to give 1,4-dimethyl-3-(4-isopropoxy-3-methyl-phenyl)-5-methoxy-1H-pyrazole 3.8 g.

1,4-dimethyl-3-(4-isopropoxy-3-methyl-phenyl)-5-methoxy-1H-pyrazole

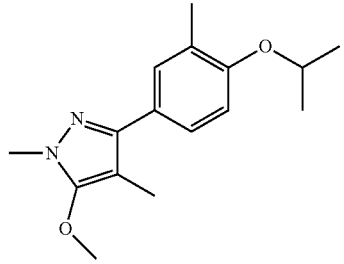 [SMILES: COc1c(C)c(-c2ccc(OC(C)C)c(C)c2)nn1C]

$^1$H-NMR (CDCl$_3$) δ: 7.43 (1H, dd, J=2.1, 0.7 Hz), 7.37-7.34 (1H, m), 6.86 (1H, d, J=8.5 Hz), 4.57-4.51 (1H, m), 3.93 (3H, s), 3.71 (3H, s), 2.24 (3H, s), 2.14 (3H, s), 1.35 (6H, d, J=6.0 Hz).

Reference Preparation Example 175

A mixture of 1,4-dimethyl-3-(4-isopropoxy-3-methyl-phenyl)-5-methoxy-1H-pyrazole (described in Reference Preparation example 174) 7.4 g and 30% aqueous sulfurinc acid solution 100 ml was stirred with heating under reflux for fifteen hours. Next, the following work-up treatments were carried out. The reaction mixture was cooled to 0° C., and the resulting precipitates were filtered and were washed with cool water to give solid. Again, the filtrate was concentrated under reduced pressure to about a half volume and was cooled to 0° C., and the resulting precipitates were filtered and were washed with cool water to give solid. These work-up treatments were carried out four times and the resulting all solids were dried under reduced pressure to give 4-(1,4-dimethyl-5-methoxy-1H-pyrazol-3-yl)-2-methyl-phenol 6.4 g.

4-(1,4-dimethyl-5-methoxy-1H-pyrazol-3-yl)-2-methyl-phenol

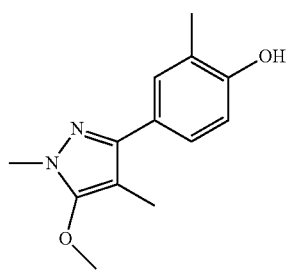 [SMILES: COc1c(C)c(-c2ccc(O)c(C)c2)nn1C]

$^1$H-NMR (DMSO-D$_6$) δ: 9.33 (1H, s), 7.29 (1H, s), 7.20 (1H, d, J=8.2 Hz), 6.79 (1H, d, J=8.2 Hz), 3.87 (3H, s), 3.60 (3H, s), 2.14 (3H, s), 2.04 (3H, s).

Reference Preparation Example 176

A similar reaction to Reference Preparation example 173 using ethanol instead of methanol gave 5-ethoxy-4-formyl-3-(4-isopropoxy-3-methyl-phenyl)-1-methyl-1H-pyrazole.

5-ethoxy-4-formyl-3-(4-isopropoxy-3-methyl-phenyl)-1-methyl-1H-pyrazole

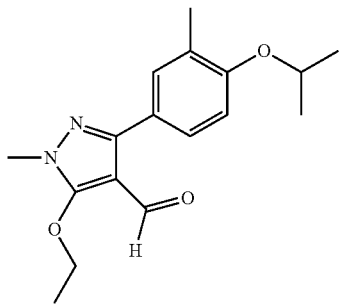 [SMILES: CCOc1c(C=O)c(-c2ccc(OC(C)C)c(C)c2)nn1C]

$^1$H-NMR (CDCl$_3$) δ: 9.74 (1H, s), 7.39 (1H, d, J=1.8 Hz), 7.35 (1H, dd, J=8.2, 2.3 Hz), 6.89 (1H, d, J=8.5 Hz), 4.63 (2H, q, J=7.1 Hz), 4.61-4.55 (1H, m), 3.72 (3H, s), 2.24 (3H, s), 1.44 (3H, t, J=7.1 Hz), 1.36 (6H, d, J=6.0 Hz).

Reference Preparation Example 177

A similar reaction to Reference Preparation example 174 using 5-ethoxy-4-formyl-3-(4-isopropoxy-3-methyl-phenyl)-1-methyl-1H-pyrazole (described in Reference Preparation example 176) instead of 4-formyl-3-(4-isopropoxy-3-methyl-phenyl)-5-methoxy-1-methyl-1H-pyrazole gave 1,4-dimethyl-5-ethoxy-3-(4-isopropoxy-3-methyl-phenyl)-1H-pyrazole.

1,4-dimethyl-5-ethoxy-3-(4-isopropoxy-3-methyl-phenyl)-1H-pyrazole

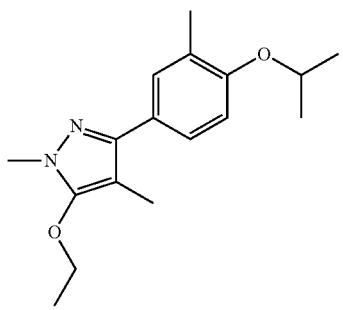 [SMILES: CCOc1c(C)c(-c2ccc(OC(C)C)c(C)c2)nn1C]

$^1$H-NMR (CDCl$_3$) δ: 7.43 (1H, d, J=1.6 Hz), 7.38-7.35 (1H, m), 6.86 (1H, d, J=8.5 Hz), 4.57-4.51 (1H, m), 4.14 (2H, q, J=7.0 Hz), 3.71 (3H, s), 2.24 (3H, s), 2.12 (3H, s), 1.41 (3H, t, J=7.0 Hz), 1.35 (6H, d, J=6.0 Hz).

Reference Preparation Example 178

A similar reaction to Reference Preparation example 175 using 1,4-dimethyl-5-ethoxy-3-(4-isopropoxy-3-methyl-phenyl)-1H-pyrazole (described in Reference Preparation example 0.177) instead of 1,4-dimethyl-3-(4-isopropoxy-3-methyl-phenyl)-5-methoxy-1H-pyrazole gave 4-(1,4-dimethyl-5-ethoxy-1H-pyrazol-3-yl)-2-methyl-phenol.

4-(1,4-dimethyl-5-ethoxy-1H-pyrazol-3-yl)-2-methyl-phenol

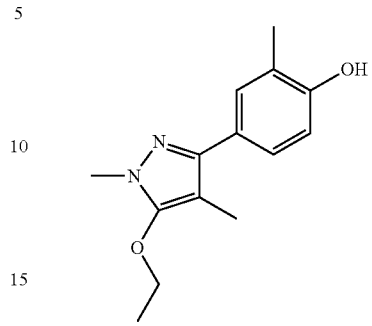

$^1$H-NMR (DMSO-D$_6$) δ: 7.32 (1H, d, J=1.4 Hz), 7.23 (1H, dd, J=8.2, 2.3 Hz), 6.84 (1H, d, J=8.2 Hz), 4.18 (2H, q, J=7.0 Hz), 3.65 (3H, s), 2.15 (3H, s), 2.06 (3H, s), 1.34 (3H, t, J=7.0 Hz).

Reference Preparation Example 179

At room temperature, to a mixture of 5-chloro-4-formyl-3-(4-isopropoxy-3-methyl-phenyl)-1-methyl-1H-pyrazole (described in Reference Preparation example 172) 10 g and tetrahydrofuran 100 ml was added sodium thiomethoxide 2.9 g and the resulting mixture was stirred for eight hours. To the reaction mixture was added water 50 mL and the resulting mixture was extracted with ethyl acetate. The organic layer was washed with water and was dried over anhydrous magnesium sulfate, and was then concentrated under reduced pressure. The resulting residue was subjected to a silica gel column chromatography to give 4-formyl-3-(4-isopropoxy-3-methyl-phenyl)-5-methylthio-1H-pyrazole 10.4 g.

4-formyl-3-(4-isopropoxy-3-methyl-phenyl)-5-methylthio-1H-pyrazole

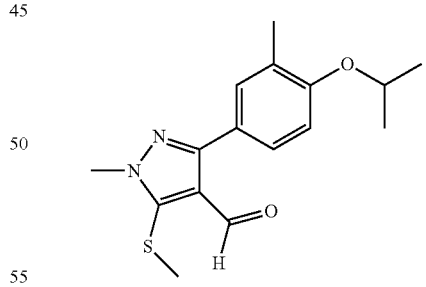

$^1$H-NMR (CDCl$_3$) δ: 10.02 (1H, s), 7.50-7.48 (2H, m), 6.91-6.89 (1H, m), 4.62-4.56 (1H, m), 4.02 (3H, s), 2.54 (3H, s), 2.25 (3H, s), 1.36 (6H, d, J=6.0 Hz).

Reference Preparation Example 180

A similar reaction to Reference Preparation example 174 using 4-formyl-3-(4-isopropoxy-3-methyl-phenyl)-5-methylthio-1H-pyrazole (described in Reference Preparation example 179) instead of 4-formyl-3-(4-isopropoxy-3- methyl-phenyl)-5-methoxy-1-methyl-1H-pyrazole gave 1,4-dimethyl-3-(4-isopropoxy-3-methyl-phenyl)-5-methylthio-1H-pyrazole.

1,4-dimethyl-3-(4-isopropoxy-3-methyl-phenyl)-5-methylthio-1H-pyrazole

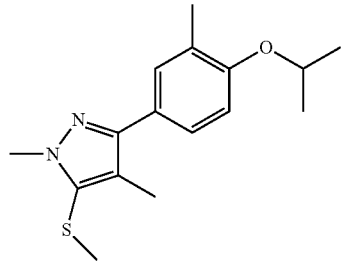

¹H-NMR (CDCl₃) δ: 7.45 (1H, dd, J=2.2, 0.6 Hz), 7.39 (1H, dd, J=8.5, 2.3 Hz), 6.87 (1H, d, J=8.5 Hz), 4.58-4.52 (1H, m), 3.99 (3H, s), 2.27 (3H, s), 2.26 (3H, s), 2.24 (3H, s), 1.35 (6H, d, J=6.2 Hz).

Reference Preparation Example 181

A mixture of 1,4-dimethyl-3-(4-isopropoxy-3-methyl-phenyl)-5-methylthio-1H-pyrazole (described in Reference Preparation example 180) 8.9 g and 30% aqueous sulfuric acid solution 120 ml was stirred with heating under reflux for twenty hours. The reaction mixture was cooled to 0° C. and thereto was added ice water 50 ml. The resulting precipitates were filtered and were washed with cool water and hexane, and were dried under reduced pressure to give 4-(1,4-dimethyl-5-methylthio-1H-pyrazol-3-yl)-2-methyl-phenol 7.3 g.

4-(1,4-dimethyl-5-methylthio-1H-pyrazol-3-yl)-2-methyl-phenol

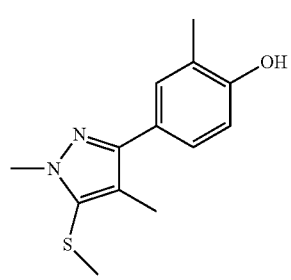 [SMILES: CSc1c(C)c(-c2ccc(O)c(C)c2)nn1C]

¹H-NMR (CDCl₃) δ: 7.44 (1H, d, J=1.6 Hz), 7.33 (1H, dd, J=8.3, 2.2 Hz), 6.80 (1H, d, J=8.2 Hz), 3.99 (3H, s), 2.28 (3H, s), 2.27 (3H, s), 2.26 (3H, s).

Reference Preparation Example 182

A similar reaction to Reference Preparation example 169 using 1-(3-chloro-4-hydroxy-phenyl)-ethanone instead of 1-(4-hydroxy-3-methyl-phenyl)-ethanone gave 1-(3-chloro-4-isopropoxy-phenyl)-ethanone.

1-(3-chloro-4-isopropoxy-phenyl)-ethanone

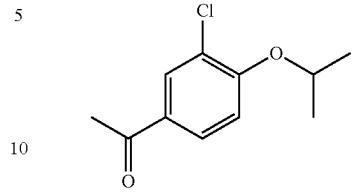

¹H-NMR (CDCl₃) δ: 7.99 (1H, d, J=2.2 Hz), 7.83 (1H, dd, J=8.7, 2.2 Hz), 6.96 (1H, d, J=8.7 Hz), 4.73-4.64 (1H, m), 2.55 (3H, s), 1.42 (6H, d, J=6.3 Hz).

Reference Preparation Example 183

A similar reaction to Reference Preparation example 170 using 1-(3-chloro-4-isopropoxy-phenyl)-ethanone (described in Reference Preparation example 182) instead of 1-(4-isopropoxy-3-methyl-phenyl)-ethanone gave 3-(3-chloro-4-isopropoxy-phenyl)-3-oxo-propionic acid ethyl ester.

3-(3-chloro-4-isopropoxy-phenyl)-3-oxo-propionic acid ethyl ester

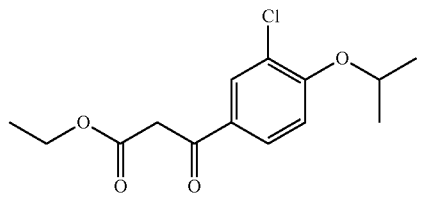 [SMILES: CCOC(=O)CC(=O)c1ccc(OC(C)C)c(Cl)c1]

¹H-NMR (CDCl₃) δ: 7.98 (1H, d, J=2.4 Hz), 7.83 (1H, dd, J=8.7, 2.2 Hz), 6.96 (1H, d, J=8.7 Hz), 4.72-4.62 (1H, m), 4.22 (2H, q, J=7.1 Hz), 3.92 (2H, s), 1.42 (6H, d, J=6.0 Hz), 1.27 (3H, t, J=7.1 Hz).

Reference Preparation Example 184

A similar reaction to Reference Preparation example 171 using 3-(3-chloro-4-isopropoxy-phenyl)-3-oxo-propionic acid ethyl ester (described in Reference Preparation example 183) instead of 3-(4-isopropoxy-3-methyl-phenyl)-3-oxo-propionic acid ethyl ester gave 5-hydroxy-3-(3-chloro-4-isopropoxy-phenyl)-1-methyl-1H-pyrazole.

5-hydroxy-3-(3-chloro-4-isopropoxy-phenyl)-1-methyl-1H-pyrazole

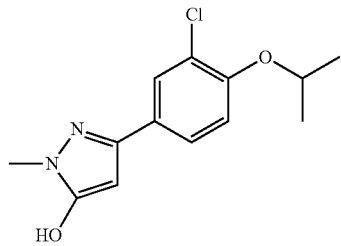 [SMILES: CC(C)Oc1ccc(-c2cc(O)n(C)n2)cc1Cl]

¹H-NMR (DMSO-D₆) δ: 7.77 (1H, d, J=1.9 Hz), 7.65-7.62 (1H, m), 7.18 (1H, d, J=8.7 Hz), 5.90 (1H, s), 4.72-4.66 (1H, m), 3.58 (3H, s), 1.30 (6H, d, J=6.0 Hz).

Reference Preparation Example 185

A similar reaction to Reference Preparation example 172 using 5-hydroxy-3-(3-chloro-4-isopropoxy-phenyl)-1-methyl-1H-pyrazole (described in Reference Preparation example 184) instead of 5-hydroxy-3-(4-isopropoxy-3-methyl-phenyl)-1-methyl-1H-pyrazole gave 5-chloro-4-formyl-3-(3-chloro-4-isopropoxy-phenyl)-1-methyl-1H-pyrazole.

5-chloro-4-formyl-3-(3-chloro-4-isopropoxy-phenyl)-1-methyl-1H-pyrazole

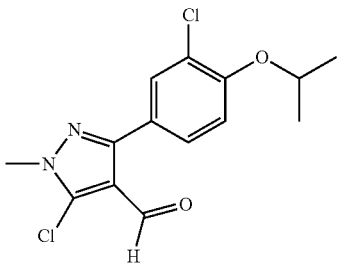 [SMILES: CC(C)Oc1ccc(-c2nn(C)c(Cl)c2C=O)cc1Cl]

¹H-NMR (CDCl₃) δ: 9.93 (1H, s), 7.84-7.83 (1H, m), 7.69-7.66 (1H, m), 7.00 (1H, d, J=8.7 Hz), 4.66-4.60 (1H, m), 3.93 (3H, s), 1.41 (6H, d, J=6.2 Hz).

Reference Preparation Example 186

A similar reaction to Reference Preparation example 173 using 5-chloro-4-formyl-3-(3-chloro-4-isopropoxy-phenyl)-1-methyl-1H-pyrazole (described in Reference Preparation example 185) instead of 5-chloro-4-formyl-3-(4-isopropoxy-3-methyl-phenyl)-1-methyl-1H-pyrazole gave 4-formyl-3-(3-chloro-4-isopropoxy-phenyl)-5-methoxy-1-methyl-1H-pyrazole.

4-formyl-3-(3-chloro-4-isopropoxy-phenyl)-5-methoxy-1-methyl-1H-pyrazole

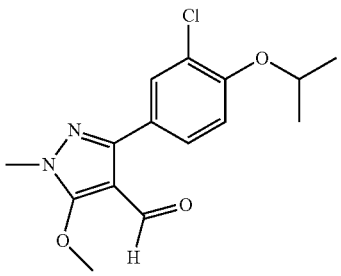 [SMILES: COc1c(C=O)c(-c2ccc(OC(C)C)c(Cl)c2)nn1C]

¹H-NMR (CDCl₃) δ: 9.75 (1H, s), 7.65 (1H, d, J=2.2 Hz), 7.44 (1H, dd, J=8.5, 2.2 Hz), 7.01 (1H, d, J=8.7 Hz), 4.65-4.59 (1H, m), 4.30 (3H, s), 3.72 (3H, s), 1.42-1.39 (6H, m).

Reference Preparation Example 187

A similar reaction to Reference Preparation example 174 using 4-formyl-3-(3-chloro-4-isopropoxy-phenyl)-5-methoxy-1-methyl-1H-pyrazole (described in Reference Preparation example 186) instead of 4-formyl-3-(4-isopropoxy-3-methyl-phenyl)-5-methoxy-1-methyl-1H-pyrazole gave 1,4-dimethyl-3-(3-chloro-4-isopropoxy-phenyl)-5-methoxy-1H-pyrazole.

1,4-dimethyl-3-(3-chloro-4-isopropoxy-phenyl)-5-methoxy-1H-pyrazole

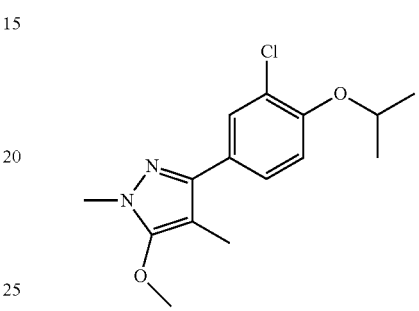

¹H-NMR (CDCl₃) δ: 7.60 (1H, d, J=2.2 Hz), 7.44 (1H, dd, J=8.5, 2.2 Hz), 6.99 (1H, d, J=8.7 Hz), 4.62-4.56 (1H, m), 3.99 (3H, s), 3.75 (3H, s), 2.15 (3H, s), 1.40 (6H, d, J=6.0 Hz).

Reference Preparation Example 188

A similar reaction to Reference Preparation example 175 using 1,4-dimethyl-3-(3-chloro-4-isopropoxy-phenyl)-5-methoxy-1H-pyrazole (described in Reference Preparation example 187) instead of 1,4-dimethyl-3-(4-isopropoxy-3-methyl-phenyl)-5-methoxy-1H-pyrazole gave 2-chloro-4-(1,4-dimethyl-5-methoxy-1H-pyrazol 3-yl)-phenol.

2-chloro-4-(1,4-dimethyl-5-methoxy-1H-pyrazol 3-yl)-phenol

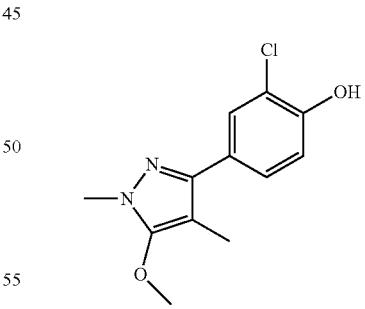

¹H-NMR (DMSO-D₆) δ: 7.50 (1H, d, J=1.9 Hz), 7.37 (1H, dd, J=8.5, 2.2 Hz), 7.00 (1H, d, J=8.5 Hz), 3.89 (3H, s), 3.62 (3H, s), 2.06 (3H, s).

Reference Preparation Example 189

To a mixture of 3-(4-isopropoxy-3-methyl-phenyl)-3-oxo-propionic acid ethyl ester (described in Reference preparation example 170) 8.6 g and ethanol 80 ml was added hydrazine one hydrate 3.5 g, and the resulting mixture was stirred with heating under reflux for two hours. The reaction mixture was cooled to room temperature, and the resulting precipitates were then filtered and were washed with ethanol and hexane, and were dried under reduced pressure to give 5-hydroxy-3-(4-isopropoxy-3-methyl-phenyl)-1H-pyrazole 4 g.

5-hydroxy-3-(4-isopropoxy-3-methyl-phenyl)-1H-pyrazole

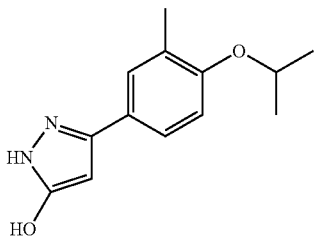 [SMILES: Cc1cc(-c2cc(O)[nH]n2)ccc1OC(C)C]

$^1$H-NMR (DMSO-D$_6$) δ: 7.44-7.41 (2H, m), 6.96 (1H, d, J=8.5 Hz), 5.75 (1H, s), 4.64-4.58 (1H, m), 2.14 (3H, s), 1.28 (6H, d, J=6.0 Hz).

Reference Preparation Example 190

A mixture of 5-hydroxy-3-(4-isopropoxy-3-methyl-phenyl)-1H-pyrazole (described in Reference Preparation example 189) 2.7 g, 1,2-dibromoethane 4.3 g, potassium carbonate 3.5 g and acetonitrile 80 ml was stirred with heating under reflux for twelve hours. The reaction mixture was cooled to room temperature and was filtered and the filtrate was concentrated. The resulting residue was subjected to a silica gel column chromatography to give 6-(4-isopropoxy-3-methyl-phenyl)-2,3-dihydro-pyrazolo[5,1-b]oxazole 1.2 g.

6-(4-isopropoxy-3-methyl-phenyl)-2,3-dihydro-pyrazolo[5,1-b]oxazole

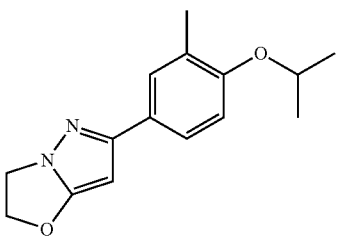 [SMILES: Cc1cc(-c2cc3n(n2)CCO3)ccc1OC(C)C]

$^1$H-NMR (CDCl$_3$) δ: 7.55-7.54 (1H, m), 7.48 (1H, dd, J=8.5, 2.4 Hz), 6.84 (1H, d, J=8.5 Hz), 5.62 (1H, s), 5.04 (2H, t, J=7.8 Hz), 4.57-4.51 (1H, m), 4.32 (2H, t, J=8.0 Hz), 2.23 (3H, s), 1.35 (6H, d, J=6.0 Hz).

Reference Preparation Example 191

A mixture of 6-(4-isopropoxy-3-methyl-phenyl)-2,3-dihydro-pyrazolo[5,1-b]oxazole (described in Reference Preparation example 190) 3.3 g and 30% aqueous sulfuric acid solution 25 ml was stirred with heating under reflux for eleven hours. The reaction mixture was cooled to 0° C. and the resulting precipitates were filtered. The resulting solid was washed with cool water and hexane and was dried under reduced pressure to give 4-(2,3-dihydro-pyrazolo[5,1-b]oxazol-6-yl)-2-methyl-phenol 0.5 g.

4-(2,3-dihydro-pyrazolo[5,1-b]oxazol-6-yl)-2-methyl-phenol

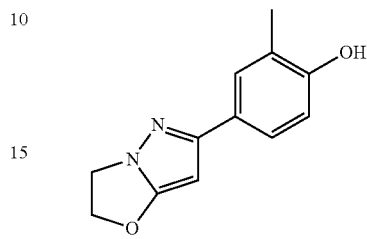

$^1$H-NMR (DMSO-D$_6$) δ: 7.44-7.43 (1H, m), 7.35 (1H, dd, J=8.2, 2.2 Hz), 6.76 (1H, d, J=8.2 Hz), 5.76 (1H, s), 5.08-5.03 (2H, m), 4.25 (2H, t, J=7.8 Hz), 2.13 (3H, s).

Reference Preparation Example 192

A mixture of 3-(isopropoxy-3-methyl-phenyl)-3-oxo-propionic acid ethyl ester (described in Reference Preparation example 170) 8 g, methyl iodide 5.1 g, potassium carbonate 5 g and acetone 150 ml was stirred with heating under reflux for three hours. The reaction mixture was cooled to room temperature and filtrated. The filtrate was concentrated. The resulting residue was subjected to a silica gel column chromatography to give 3-(4-isopropoxy-3-methyl-phenyl)-2-methyl-3-oxo-propionic acid ethyl ester 6.4 g.

3-(4-isopropoxy-3-methyl-phenyl)-2-methyl-3-oxo-propionic acid ethyl ester

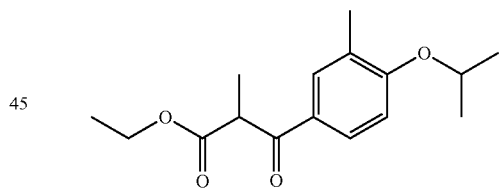

$^1$H-NMR (CDCl$_3$) δ: 7.83-7.76 (2H, m), 6.84 (1H, d, J=8.2 Hz), 4.68-4.61 (1H, m), 4.34 (1H, q, J=7.1 Hz), 4.17-4.12 (2H, m), 2.22 (3H, s), 1.47 (3H, d, J=7.2 Hz), 1.37 (6H, d, J=6.0 Hz), 1.19 (3H, t, J=7.1 Hz).

Reference Preparation Example 193

To a mixture of 3-(4-isopropoxy-3-methyl-phenyl)-2-methyl-3-oxo-propionic acid ethyl ester (described in Reference preparation example 192) 6.4 g and ethanol 80 ml was added hydrazine one hydrate 2.5 g, and the resulting mixture was stirred with heating under reflux for six hours. The reaction mixture was cooled to room temperature, and the resulting precipitates were then filtered and were washed with ethanol and hexane, and were dried under reduced pressure to give 5-hydroxy-3-(4-isopropoxy-3-methyl-phenyl)-4-methyl-1H-pyrazole 2.8 g.

5-hydroxy-3-(4-isopropoxy-3-methyl-phenyl)-4-methyl-1H-pyrazole

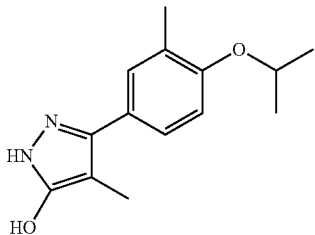 [SMILES: Cc1cc(-c2n[nH]c(O)c2C)ccc1OC(C)C]

¹H-NMR (DMSO-D₆) δ: 7.30-7.27 (2H, m), 7.01 (1H, d, J=8.2 Hz), 4.65-4.59 (1H, m), 2.16 (3H, s), 1.95 (3H, s), 1.29 (6H, d, J=6.0 Hz).

Reference Preparation Example 194

A mixture of 5-hydroxy-3-(4-isopropoxy-3-methyl-phenyl)-4-methyl-1H-pyrazole (described in Reference Preparation example 193) 2.1 g, 1,2-dibromoethane 3.2 g, potassium carbonate 2.6 g and acetonitrile 80 ml was stirred with heating under reflux for thirteen hours. The reaction mixture was cooled to room temperature and was filtered and the filtrate was concentrated. The resulting residue was subjected to a silica gel column chromatography to give 6-(4-isopropoxy-3-methyl-phenyl)-7-methyl-2,3-dihydro-pyrazolo[5,1-b]oxazole 1.2 g.

6-(4-isopropoxy-3-methyl-phenyl)-7-methyl-2,3-dihydro-pyrazolo[5,1-b]oxazole

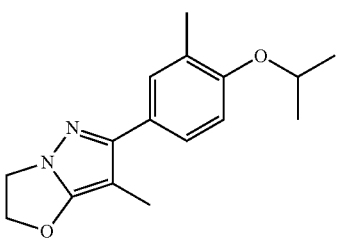 [SMILES: Cc1cc(-c2nn3c(c2C)OCC3)ccc1OC(C)C]

¹H-NMR (CDCl₃) δ: 7.46 (1H, d, J=2.2 Hz), 7.39 (1H, dd, J=8.5, 2.2 Hz), 6.86 (1H, d, J=8.5 Hz), 5.01 (2H, t, J=7.8 Hz), 4.58-4.52 (1H, m), 4.30 (2H, t, J=7.8 Hz), 2.24 (3H, s), 2.07 (3H, s), 1.35 (6H, d, J=5.9 Hz).

Reference Preparation Example 195

A mixture of 6-(4-isopropoxy-3-methyl-phenyl)-7-methyl-2,3-dihydro-pyrazolo[5,1-b]oxazole (described in Reference Preparation example 194) 2.0 g and 30% aqueous sulfuric acid solution 14 ml was stirred with heating under reflux for fourteen hours. The reaction mixture was cooled to 0° C. and thereto was added ice water 10 mL, and the resulting precipitates were filtered. The resulting solid was washed with cool water and hexane and was dried under reduced pressure to give 4-(7-methyl-2,3-dihydro-pyrazolo[5,1-b]oxazol-6-yl)-2-methyl-phenol 0.5 g.

4-(7-methyl-2,3-dihydro-pyrazolo[5,1-b]oxazol-6-yl)-2-methyl-phenol

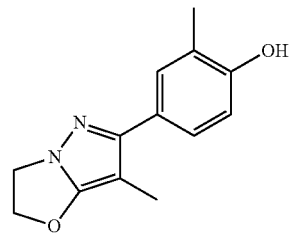 [SMILES: Cc1cc(-c2nn3c(c2C)OCC3)ccc1O]

¹H-NMR (DMSO-D₆) δ: 7.31-7.31 (1H, m), 7.23-7.21 (1H, m), 6.81 (1H, d, J=8.2 Hz), 5.04 (2H, t, J=7.8 Hz), 4.25 (2H, t, J=7.8 Hz), 2.14 (3H, s), 1.97 (3H, s).

Reference Preparation Example 196

A similar reaction to Reference Preparation example 194 using 1,3-dibromopropane instead of 1,2-dibromoethane gave 2-(4-isopropoxy-3-methyl-phenyl)-3-methyl-6,7-dihydro-5H-pyrazolo[5,1-b]oxazine.

2-(4-isopropoxy-3-methyl-phenyl)-3-methyl-6,7-dihydro-5H-pyrazolo[5,1-b]oxazine

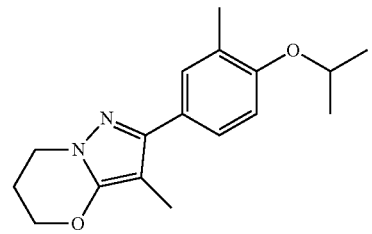 [SMILES: Cc1cc(-c2nn3c(c2C)OCCC3)ccc1OC(C)C]

¹H-NMR (CDCl₃) δ: 7.46 (1H, d, J=2.2 Hz), 7.39 (1H, dd, J=8.3, 2.3 Hz), 6.86 (1H, d, J=8.5 Hz), 4.57-4.51 (1H, m), 4.30 (2H, t, J=5.1 Hz), 4.19 (2H, t, J=6.3 Hz), 2.29-2.23 (5H, m), 2.03 (3H, s), 1.35 (6H, d, J=5.9 Hz).

Reference Preparation Example 197

A similar reaction to Reference Preparation example 191 using 2-(4-isopropoxy-3-methyl-phenyl)-3-methyl-6,7-dihydro-5H-pyrazolo[5,1-b]oxazine (described in Reference Preparation example 196) instead of 6-(4-isopropoxy-3-methyl-phenyl)-2,3-dihydro-pyrazolo[5,1-b]oxazole gave 2-methyl-4-(3-methyl-6,7-dihydro-5H-pyrazolo[5,1-b][1,3]oxazin-2-yl)-phenol.

2-methyl-4-(3-methyl-6,7-dihydro-5H-pyrazolo[5,1-b][1,3]oxazin-2-yl)-phenol

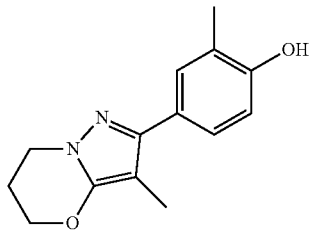 [SMILES: Cc1cc(-c2nn3c(c2C)OCCC3)ccc1O]

¹H-NMR (DMSO-D₆) δ: 9.39 (1H, br s), 7.32-7.31 (1H, m), 7.23-7.21 (1H, m), 6.79 (1H, d, J=8.2 Hz), 4.29 (2H, t, J=5.1 Hz), 4.06 (2H, t, J=6.2 Hz), 2.21-2.16 (2H, m), 2.14 (3H, s), 1.93 (3H, s).

Reference Preparation Example 198

At room temperature, to a mixture of 1-(4-methoxy-3-methyl)-ethanone (described in Reference Preparation example 102) and tetrahydrofuran 100 ml was added ethyl difluoroacetate 11.5 g, 20% sodium ethoxide-ethanol solution 31.4 g and dibenzo-18-crown-6 0.03 g, and the resulting mixture was stirred with heating under reflux for twelve hours. The reaction mixture was cooled to room temperature, and to the reaction mixture was added water, and the resulting mixture was acidified with 10% aqueous hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 4,4-difluoro-1-(4-methoxy-3-methyl-phenyl)-butane-1,3-dione 9.5 g.

4,4-difluoro-1-(4-methoxy-3-methyl-phenyl)-butane-1,3-dione

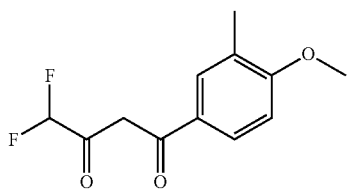 [SMILES: COc1ccc(C(=O)CC(=O)C(F)F)cc1C]

¹H-NMR (CDCl₃: 23° C.) δ: 7.83 (1H, dd, J=8.6, 2.4 Hz), 7.76 (1H, dd, J=2.3, 0.7 Hz), 6.89 (1H, d, J=8.5 Hz), 6.50 (1H, s), 6.01 (1H, t, J=53.8 Hz), 3.92 (3H, s), 2.26 (3H, s).

Reference Preparation Example 199

At room temperature, to a mixture of 4,4-difluoro-1-(4-methoxy-3-methyl-phenyl)-butane-1,3-dione (described in Reference Preparation example 198) 5.2 g and ethanol 50 ml was added hydrazine one hydrate 3.2 g and the resulting mixture was stirred for fifteen hours. The reaction mixture was subjected to a silica gel column chromatography to give 3-difluoromethyl-5-(4-methoxy-3-methyl-phenyl)-2H-pyrazole 4.9 g.

3-difluoromethyl-5-(4-methoxy-3-methyl-phenyl)-2H-pyrazole

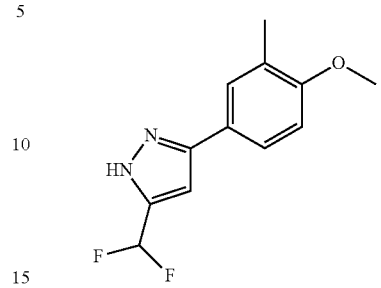

¹H-NMR (CDCl₃) δ: 7.39-7.34 (2H, m), 6.89 (1H, d, J=8.5 Hz), 6.72 (1H, t, J=55.0 Hz), 6.66 (1H, s), 3.88 (3H, s), 2.27 (3H, s), 1.66 (1H, br s).

Reference Preparation Example 200

At 0° C., to a mixture of 3-difluoromethyl-5-(4-methoxy-3-methyl-phenyl)-2H-pyrazole (described in Reference Preparation example 199) 4.9 g and N,N-dimethylformamide 80 ml was added 55% sodium hydride 1 g. The resulting mixture was stirred for one hour and thereto was added methyl iodide 4.3 g. The reaction mixture was raised to room temperature and was stirred for twelve hours. To the reaction mixture was added water 5 ml, and the resulting mixture was extracted with ethyl acetate. The organic layer was washed with water, and was dried over anhydrous magnesium sulfate and was then concentrated under reduced pressure. The resulting solid was filtered and washed with hexane, and was dried under reduced pressure to give 5-difluoromethyl-3-(4-methoxy-3-methyl-phenyl)-1-methyl-1H-pyrazole 0.9 g.

5-difluoromethyl-3-(4-methoxy-3-methyl-phenyl)-1-methyl-1H-pyrazole

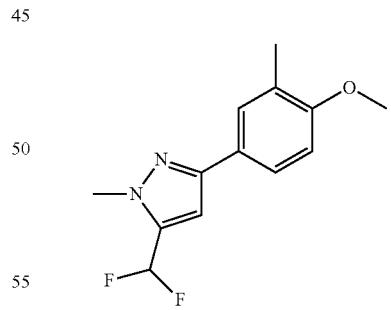

¹H-NMR (CDCl₃) δ: 7.57-7.57 (1H, m), 7.54 (1H, dd, J=8.5, 2.2 Hz), 6.85 (1H, d, J=8.2 Hz), 6.74 (1H, t, J=54.2 Hz), 6.68-6.67 (1H, m), 4.00 (3H, s), 3.86 (3H, s), 2.26 (3H, s).

Reference Preparation Example 201

A similar reaction to Reference Preparation example 60 using 5-difluoromethyl-3-(4-methoxy-3-methyl-phenyl)-1- methyl-1H-pyrazole (described in Reference Preparation example 200) instead of 3-(4-methoxy-3-methyl-phenyl)-1-methyl-1H-pyrazole gave 4-(5-difluoromethyl-1-methyl-1H-pyrazol-3-yl)-2-methyl-phenol.

4-(5-difluoromethyl-1-methyl-1H-pyrazol-3-yl)-2-methyl-phenol

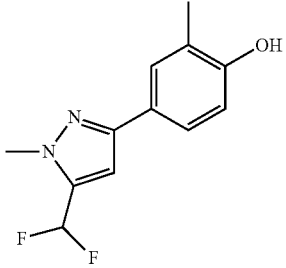 [SMILES: Cc1cc(-c2cc(C(F)F)n(C)n2)ccc1O]

$^1$H-NMR (DMSO-D$_6$) δ: 7.52-7.52 (1H, m), 7.44-7.41 (1H, m), 7.30 (1H, t, J=53.8 Hz), 6.88 (1H, s), 6.79 (1H, d, J=8.2 Hz), 3.90 (3H, s), 2.15 (3H, s).

Reference Preparation Example 202

At room temperature, to a mixture of 3-butyl-pentane-2,4-dione 7 g and ethanol 70 ml was added hydrazine one hydrate 3.3 g and the resulting mixture was stirred for twelve hours. The reaction mixture was subjected to a silica gel column chromatography to give 4-butyl-3,5-dimethyl-1H-pyrazole 7 g.

4-butyl-3,5-dimethyl-1H-pyrazole

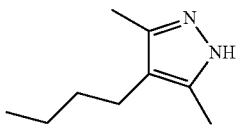

$^1$H-NMR (CDCl$_3$) δ: 2.33 (2H, t, J=7.5 Hz), 2.20 (3H, s), 2.20 (3H, s), 1.46-1.37 (2H, m), 1.36-1.27 (2H, m), 0.91 (3H, t, J=7.2 Hz).

Reference Preparation Example 203

A similar reaction to Reference Preparation example 65 using 4-butyl-3,5-dimethyl-1H-pyrazole (described in Reference Preparation example 202) instead of 3,4,5-trimethyl-1H-pyrazole gave 4-butyl-1-(4-methoxy-3-methyl-phenyl)-3,5-dimethyl-1H-pyrazole.

4-butyl-1-(4-methoxy-3-methyl-phenyl)-3,5-dimethyl-1H-pyrazole

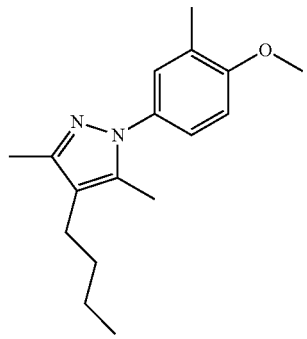

$^1$H-NMR (CDCl$_3$) δ: 7.19 (1H, d, J=2.4 Hz), 7.15 (1H, dd, J=8.7, 2.7 Hz), 6.84 (1H, d, J=8.7 Hz), 3.86 (3H, s), 2.38 (2H, t, J=7.5 Hz), 2.25 (3H, s), 2.24 (3H, s), 2.16 (3H, s), 1.50-1.43 (2H, m), 1.36 (2H, td, J=14.6, 7.3 Hz), 0.94 (3H, t, J=7.1 Hz).

Reference Preparation Example 204

A similar reaction to Reference Preparation example 60 using 4-butyl-1-(4-methoxy-3-methyl-phenyl)-3,5-dimethyl-1H-pyrazole (described in Reference Preparation example 203) instead of 3-(4-methoxy-3-methyl-phenyl)-1-methyl-1H-pyrazole gave 4-(4-butyl-3,5-dimethyl-pyrazol-1-yl)-2-methyl-phenol.

4-(4-butyl-3,5-dimethyl-pyrazol-1-yl)-2-methyl-phenol

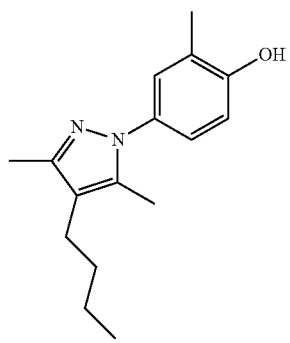 [SMILES: CCCCc1c(C)nn(-c2ccc(O)c(C)c2)c1C]

$^1$H-NMR (DMSO-D$_6$) δ: 7.18 (1H, d, J=2.7 Hz), 7.09 (1H, dd, J=8.7, 2.7 Hz), 6.86 (1H, d, J=8.5 Hz), 2.37 (2H, t, J=7.2 Hz), 2.17 (3H, s), 2.16 (3H, s), 2.14 (3H, s), 1.45-1.37 (2H, m), 1.36-1.27 (2H, m), 0.91 (3H, t, J=7.2 Hz).

Reference Preparation Example 205

To a mixture of sodium sulfate 136.2 g, water 480 mL and Chloral hydrate 8.6 g was added a mixture of 2-fluoro-5-methyl-aniline 6.1 g, concentrated hydrochloric acid 4.2 mL and water 24 ml under stirring, followed by further addition of a mixture of hydroxylamine hydrochloride salt 10.6 g and water 30 ml. The resulting mixture was stirred with heating under reflux for one and a half hours, and then the precipitated solid was filtered to give N-(2-fluoro-5-methyl-phenyl)-2-hydroxyiminoacetamide.

To a mixture of concentrated sulfuric acid 19.5 ml and water 4 ml was added N-(2-fluoro-5-dimethylphenyl)-2-hydroxyiminoacetamide, and the resulting mixture was stirred at 80° C. for one hour. After cooling, the reaction solution was added to ice water. The precipitated solids were filtered to give 4-methyl-7-fluoroisatin.

To a mixture of 4-methyl-7-fluoroisatin, sodium hydroxide 9.0 g and water 40 ml was added 30% hydrogen peroxide solution 3 ml. To the reaction mixture was added dropwise acetic acid while the reaction temperature was being kept around 70° C., so that the pH of the reaction solution was adjusted around 4. The precipitated solid was filtered to give 2 amino-3-fluoro-6-methyl benzoic acid 2.3 g.

2 amino-3-fluoro-6-methyl benzoic acid

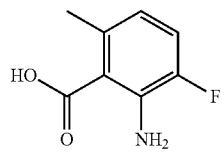

$^1$H-NMR (DMSO-D$_6$) δ(ppm): 7.03 (1H, dd, J=11.3, 8.2 Hz), 6.39 (1H, dd, J=8.2, 5.1 Hz), 2.32 (3H, s).

Reference Preparation Example 206

To a mixture of 2-amino-3-fluoro-6-methyl benzoic acid (described in Reference preparation example 205) 2.3 g, ethyl acetate 70 ml and ethanol 70 ml was added a 2.0 M solution of trimethylsilyl diazomethane in diethyl ether 13.7 ml under ice-cooling. The resulting mixture was stirred at room temperature for one and a half hours and the reaction solution was then concentrated under reduced pressure. To the resulting residue was added water and the mixture was extracted with methyl tert-butyl ether. The organic layer was washed with water and saturated saline, and was dried over anhydrous magnesium sulfate and was then concentrated under reduced pressure. The resulting residue was subjected to a silica gel column chromatography to give 2-amino-3-fluoro-6-methyl-benzoic acid methyl ester 0.81 g.

2-amino-3-fluoro-6-methyl-benzoic acid methyl ester

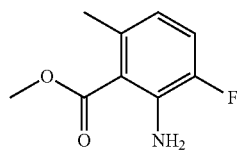

$^1$H-NMR (CDCl$_3$) δ(ppm): 6.94 (1H, dd, J=10.9, 8.2 Hz), 6.45-6.41 (1H, m), 5.26 (2H, br s), 3.91 (3H, s), 2.41 (3H, s).

Reference Preparation Example 207

To a mixture of 2-amino-3-fluoro-6-methyl-benzoic acid methyl ester (described in Reference Preparation example 206) 0.81 g and toluene 15 ml was added triphosgene 2.0 g at room temperature, and the resulting mixture was stirred with heating in reflux for three hours. The reaction mixture was concentrated under reduced pressure to give 2-isocyanato-3-fluoro-6-methyl benzoic acid methyl ester 0.92 g.

2-isocyanato-3-fluoro-6-methyl benzoic acid methyl ester

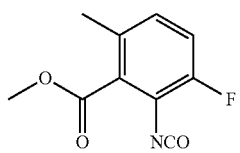

$^1$H-NMR (CDCl$_3$) δ(ppm): 7.09 (1H, t, J=8.7 Hz), 7.02-6.98 (1H, m), 3.96 (3H, s), 2.30 (3H, s).

Reference Preparation Example 208

Anhydrous aluminium trichloride 0.65 g was added to N,N-dimethylformamide 10 ml under ice-cooling, and the mixture was stirred for twenty minutes. Thereto was added sodium azide 0.32 g and the resulting mixture was stirred for fifteen minutes. Thereto was then added 2-isocyanato-3-fluoro-6-methyl benzoic acid methyl ester (described in Reference Preparation example 207) 0.92 g and the resulting mixture was heated at 80° C. with stirring for four hours. After cooling, the reaction solution was added to a mixture of sodium nitrite 1.0 g and ice water 200 ml with stirring. The reaction mixture was acidified with 10% hydrochloric acid and was extracted with ethyl acetate. The organic layer was washed with water and saturated saline and then was dried over anhydrous magnesium sulfate and was then concentrated under reduced pressure to give 3-fluoro-6-methyl-2-(5-oxo-4,5-dihydrotetrazol-1-yl)-benzoic acid methyl ester 1.4 g.

3-fluoro-6-methyl-2-(5-oxo-4,5-dihydrotetrazol-1-yl)-benzoic acid methyl ester

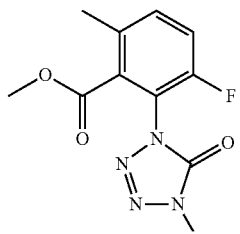

$^1$H-NMR (DMSO-D$_6$) δ(ppm): 7.65-7.62 (1H, m), 7.59-7.56 (1H, m), 3.71 (3H, s), 2.38 (3H, s).

Reference Preparation Example 209

To a mixture of 3-fluoro-6-methyl-2-(5-oxo-4,5-dihydrotetrazol-1-yl)-benzoic acid methyl ester (described in Reference Preparation example 208) 1.4 g and N,N-dimethylformamide 20 ml was added potassium carbonate 1.2 g and methyl iodide 1.3 g at room temperature, and the resulting mixture was stirred for four hours. To the reaction solution was added water and the reaction mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 3-fluoro-6-methyl-2-(4-methyl-5-oxo-4,5-dihydrotetrazol-1-yl)-benzoic acid methyl ester 0.65 g.

3-fluoro-6-methyl-2-(4-methyl-5-oxo-4,5-dihydro-tetrazol-1-yl)-benzoic acid methyl ester

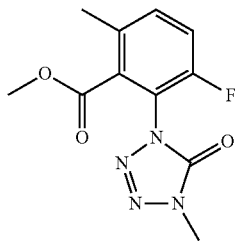 [SMILES: COC(=O)c1c(C)ccc(F)c1-n1nnn(C)c1=O]

$^1$H-NMR (CDCl$_3$) δ(ppm): 7.38 (1H, dd, J=8.6, 5.0 Hz), 7.28 (1H, t, J=8.6 Hz), 3.80 (3H, s), 3.71 (3H, s), 2.45 (3H, s).

Reference Preparation Example 210

Under ice-cooling, to a mixture of 3-fluoro-6-methyl-2-(4-methyl-5-oxo-4,5-dihydrotetrazol-1-yl)-benzoic acid methyl ester (described in Reference Preparation example 209) 0.65 g and tetrahydrofuran 11 ml was added a 1.0 M solution of lithium triethylborohydride in tetrahydrofuran 5.4 ml and the mixture was stirred at room temperature for one hour. To the reaction solution was added water, and the reaction mixture was acidified with 10% hydrochloric acid and was extracted with ethyl acetate. The organic layer was washed with water and saturated saline and was dried over anhydrous magnesium sulfate, and was then concentrated under reduced pressure to give 1-(2-hydroxymethyl-3-methyl-6-fluorophenyl)-4-methyl-1,4-dihydrotetrazole-5-one 0.58 g.

1-(2-hydroxymethyl-3-methyl-6-fluorophenyl)-4-methyl-1,4-dihydrotetrazole-5-one

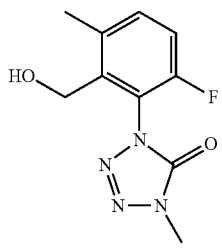 [SMILES: Cc1ccc(F)c(-n2nnn(C)c2=O)c1CO]

$^1$H-NMR (CDCl$_3$) δ(ppm): 7.37 (1H, dd, J=8.6, 5.4 Hz), 7.15 (1H, t, J=8.6 Hz), 4.54-4.36 (2H, m), 3.76 (3H, s), 3.28-3.24 (1H, m), 2.50 (3H, s).

Reference Preparation Example 211

To a mixture of 1-(2-hydroxymethyl-3-methyl-6-fluorophenyl)-4-methyl-1,4-dihydrotetrazole-5-one (described in Reference Preparation example 211) 0.58 g and chloroform 8 ml was added phosphorus tribromide 1.32 g and the resulting mixture was stirred at room temperature for twenty hours. To the reaction solution was added ice water and the reaction mixture was extracted with ethyl acetate. The organic layer was washed with water and saturated saline and was dried over anhydrous magnesium sulfate, and was then concentrated under reduced pressure. The resulting residue was subjected to a silica gel column chromatography to give 1-(2-bromomethyl-3-methyl-6-fluorophenyl)-4-methyl-1,4-dihydrotetrazole-5-one 0.66 g.

1-(2-bromomethyl-3-methyl-6-fluorophenyl)-4-methyl-1,4-dihydrotetrazole-5-one

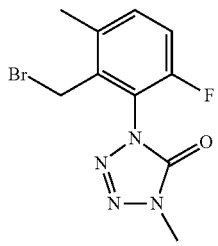 [SMILES: Cc1ccc(F)c(-n2nnn(C)c2=O)c1CBr]

$^1$H-NMR (CDCl$_3$) δ(ppm): 7.36 (1H, dd, J=8.7, 5.6 Hz), 7.16 (1H, t, J=8.7 Hz), 4.43 (1H, d, J=10.6 Hz), 4.32 (1H, d, J=10.6 Hz), 3.76 (3H, s), 2.46 (3H, s).

Reference Preparation Example 212

To a mixture of sodium sulfate 272.4 g, water 960 ml and Chloral hydrate 17.2 g was added a mixture of 4-fluoro-3-methylaniline 12.2 g, concentrated hydrochloric acid 8.4 ml and water 48 ml under stirring, followed by further addition of a mixture of hydroxylamine hydrochloride salt 21.1 g and water 60 ml. After the resulting mixture was stirred with heating under reflux for forty minutes, the precipitated solid was filtered off to give N-(4-fluoro-3-methylphenyl)-2-hydroxyiminoacetamide 25.4 g.

To a mixture of concentrated sulfuric acid 78 ml and water 16 ml was added N-(4-fluoro-3-methylphenyl)-2-hydroxyiminoacetamide 25.4 g. The mixture was stirred at 80° C. for one hour and the reaction solution was added to ice water 500 ml. The precipitated solid was filtered off to give a mixture of 4-methyl-5-fluoroisatin and 6-methyl-5-fluoroisatin.

To a mixture containing a mixture of 4-methyl-5-fluoroisatin and 6-methyl-5-fluoroisatin, sodium hydroxide 18.0 g and water 80 ml was added 30% hydrogen peroxide solution 6 ml. To the reaction mixture was added dropwise acetic acid while the reaction temperature was being kept around 70° C., so that the pH of the reaction solution was adjusted around 4. The precipitated solid was filtered to give a mixture of 6-amino-3-fluoro-2-methyl benzoic acid and 2-amino-5-fluoro-4-methyl benzoic acid 11.5 g.

To a mixture containing a mixture of 6-amino-3-fluoro-2-methyl benzoic acid and 2-amino-5-fluoro-4-methyl benzoic acid 11.5 g, ethyl acetate 340 ml and ethanol 340 ml was added a 2.0 M solution of trimethylsilyl diazomethane in diethyl ether 68 ml under ice-cooling. The mixture was stirred at room temperature for one and a half hours and was concentrated under reduced pressure. The resulting residue was subjected to a silica gel column chromatography to give 6-amino-3-fluoro-2-methyl-benzoic acid methyl ester 3.0 g.

6-amino-3-fluoro-2-methyl-benzoic acid methyl ester

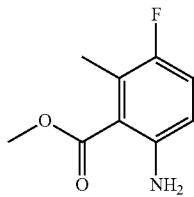

$^1$H-NMR (CDCl$_3$) δ(ppm): 6.93 (1H, t, J=9.0 Hz), 6.48 (1H, dd, J=9.0, 4.5 Hz), 4.82 (2H, br s), 3.91 (3H, s), 2.31 (3H, d, J=2.7 Hz).

Reference Preparation Example 213

To a mixture of 6-amino-3-fluoro-2-methyl-benzoic acid methyl ester (described in Reference Preparation example 212) 3.0 g and toluene 60 ml was added triphosgene 7.6 g at room temperature, and the resulting mixture was stirred with heating in reflux for three hours. The reaction mixture was concentrated under reduced pressure to give 6-isocyanato-3-fluoro-2-methyl benzoic acid methyl ester 3.6 g.

6-isocyanato-3-fluoro-2-methyl benzoic acid methyl ester

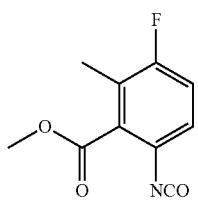

$^1$H-NMR (CDCl$_3$) δ(ppm): 7.04 (1H, t, J=8.8 Hz), 6.94 (1H, dd, J=8.8, 4.6 Hz), 3.98 (3H, s), 2.26 (3H, d, J=2.5 Hz).

Reference Preparation Example 214

Anhydrous aluminium trichloride 2.5 g was added to N,N-dimethylformamide 30 ml under ice-cooling, and the resulting mixture was stirred for twenty minutes. Thereto was added sodium azide 1.2 g and the resulting mixture was stirred for fifteen minutes. Thereto was then added 6-isocyanato-3-fluoro-2-methyl benzoic acid methyl ester (described in Reference Preparation example 213) 3.6 g and the resulting mixture was heated at 80° C. with stirring for four hours. After cooling, the reaction solution was added to a mixture of sodium nitrite 4.0 g and ice water 500 ml with stirring. The reaction mixture was acidified with 10% hydrochloric acid and was extracted with ethyl acetate. The organic layer was washed with water and saturated saline and then was dried over anhydrous magnesium sulfate and was then concentrated under reduced pressure to give 2-methyl-3-fluoro-6-(5-oxo-4,5-dihydrotetrazol-1-yl)-benzoic acid methyl ester 6.0 g.

2-methyl-3-fluoro-6-(5-oxo-4,5-dihydrotetrazol-1-yl)-benzoic acid methyl ester

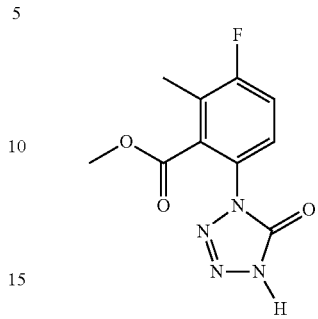

$^1$H-NMR (DMSO-D$_6$) δ(ppm): 7.62-7.56 (2H, m), 5.29 (1H, br s), 3.73 (3H, s), 2.29 (3H, d, J=2.3 Hz).

Reference Preparation Example 215

To a mixture of 2-methyl-3-fluoro-6-(5-oxo-4,5-dihydrotetrazol-1-yl)-benzoic acid methyl ester (described in Reference Preparation example 214) 6.0 g and N,N-dimethylformamide 85 ml was added potassium carbonate 4.7 g and methyl iodide 4.9 g at room temperature, and the resulting mixture was stirred for six hours. To the reaction solution was added water and the reaction mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 2-methyl-3-fluoro-6-(4-methyl-5-oxo-4,5-dihydrotetrazol-1-yl)-benzoic acid methyl ester 2.8 g.

2-methyl-3-fluoro-6-(4-methyl-5-oxo-4,5-dihydrotetrazol-1-yl)-benzoic acid methyl ester

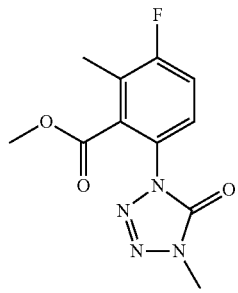 [SMILES: COC(=O)c1c(-n2nnn(C)c2=O)ccc(F)c1C]

$^1$H-NMR (CDCl$_3$) δ(ppm): 7.47 (1H, dd, J=8.9, 4.6 Hz), 7.25 (1H, t, J=8.9 Hz), 3.84 (3H, s), 3.69 (3H, s), 2.36 (3H, d, J=2.4 Hz).

Reference Preparation Example 216

Under ice-cooling, to a mixture of 2-methyl-3-fluoro-6-(4-methyl-5-oxo-4,5-dihydrotetrazol-1-yl)-benzoic acid methyl ester (described in Reference Preparation example 215) 2.8 g and tetrahydrofuran 46 ml was added a 1.0 M solution of lithium triethylborohydride in tetrahydrofuran 22.9 ml and the resulting mixture was stirred at room temperature for one hour. To the reaction solution was added water, and the reaction mixture was acidified with 10% hydrochloric acid and was extracted with ethyl acetate. The organic layer was washed with water and saturated saline and was dried over anhydrous magnesium sulfate, and was then concentrated under reduced pressure to give 1-(2-hydroxymethyl-3-methyl-4-fluorophenyl)-4-methyl-1,4-dihydrotetrazole-5-one 2.4 g.

1-(2-hydroxymethyl-3-methyl-4-fluorophenyl)-4-methyl-1,4-dihydrotetrazole-5-one

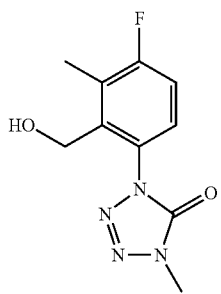 [SMILES: Cc1c(F)ccc(-n2nnn(C)c2=O)c1CO]

$^1$H-NMR (CDCl$_3$) δ(ppm): 7.21 (1H, dd, J=8.7, 5.1 Hz), 7.15 (1H, t, J=8.7 Hz), 4.47 (2H, dd, J=7.2, 1.0 Hz), 3.75 (3H, s), 2.45 (3H, d, J=2.4 Hz).

Reference Preparation Example 217

To a mixture of 1-(2-hydroxymethyl-3-methyl-4-fluorophenyl)-4-methyl-1,4-dihydrotetrazole-5-one (described in Reference Preparation example 215) 2.4 g and chloroform 34 ml was added phosphorus tribromide 5.5 g and the resulting mixture was stirred at room temperature for twenty hours. To the reaction solution was added ice water and the mixture was extracted with ethyl acetate. The organic layer was washed with water and saturated saline and was dried over anhydrous magnesium sulfate, and was then concentrated under reduced pressure. The resulting residue was subjected to a silica gel column chromatography to give 1-(2-bromomethyl-3-methyl-4-fluorophenyl)-4-methyl-1,4-dihydrotetrazole-5-one 2.5 g.

1-(2-bromomethyl-3-methyl-4-fluorophenyl)-4-methyl-1,4-dihydrotetrazole-5-one

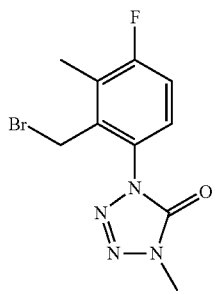 [SMILES: Cc1c(F)ccc(-n2nnn(C)c2=O)c1CBr]

$^1$H-NMR (CDCl$_3$) δ(ppm): 7.22 (1H, dd, J=8.7, 5.1 Hz), 7.16 (1H, t, J=8.7 Hz), 4.46 (2H, s), 3.75 (3H, s), 2.39 (3H, d, J=2.4 Hz).

Reference Preparation Example 218

At room temperature, to a mixture of sodium tetrahydroborate 15.6 g and tetrahydrofuran 200 ml was added 2-methyl-6-nitrobenzoic acid 50 g. At 0° C., to the reaction mixture was added dimethyl sulfate 34 ml, and the resulting mixture was stirred at room temperature for twenty hours. At 0° C., thereto was added 5% aqueous hydrochloric acid solution 300 ml and the resulting mixture was stirred for one hour. The reaction mixture was extracted with ethyl acetate, and the organic layer was washed with water, and was dried over anhydrous magnesium sulfate, and was then concentrated under reduced pressure to give 2-methyl-6-nitrobenzyl alcohol 30.5 g.

2-methyl-6-nitrobenzyl alcohol

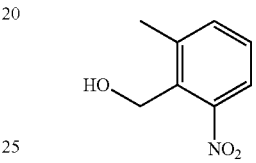

$^1$H-NMR (CDCl$_3$) δ: 7.71 (1H, d, J=7.7 Hz), 7.49 (1H, d, J=7.5 Hz), 7.36 (1H, t, J 7.9 Hz), 4.71 (2H, d, J=7.2 Hz), 2.62 (1H, t, J=7.4 Hz), 2.56 (3H, s).

Reference Preparation Example 219

At room temperature, to a mixture of 2-methyl-6-nitrobenzyl alcohol 30.5 g and chloroform 100 ml was added phosphorus tribromide 74.1 g and the resulting mixture was stirred at room temperature for ten hours. To the reaction solution was added ice water 200 ml and the reaction mixture was extracted with chloroform. The organic layer was washed with water and was dried over anhydrous magnesium sulfate, and was then concentrated under reduced pressure to give 2-methyl-6-nitrobenzyl bromide 35 g.

2-methyl-6-nitrobenzyl bromide

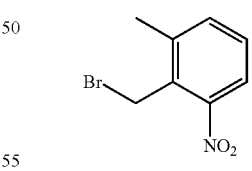

$^1$H-NMR (CDCl$_3$) δ: 7.75 (1H, d, J=8.2 Hz), 7.46 (1H, d, J=7.7 Hz), 7.36 (1H, t, J 7.8 Hz), 4.72 (2H, s), 2.54 (3H, s).

Reference Preparation Example 220

A similar reaction to Reference Preparation example 99 using 1-(4-methoxy-2,5-dimethyl)-ethanone (described in Reference Preparation example 159) instead of 1-(4-methoxy-3-methyl)-ethanone gave 3-dimethylamino-1-(4-methoxy-2,5-dimethyl-phenyl)-propenone.

3-dimethylamino-1-(4-methoxy-2,5-dimethyl-phenyl)-propenone

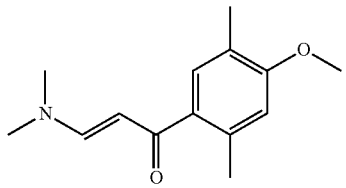

$^1$H-NMR (CDCl$_3$) δ: 7.44 (1H, d, J=12.3 Hz), 7.19 (1H, s), 6.63 (1H, s), 5.37 (1H, d, J=12.8 Hz), 3.83 (3H, s), 3.04 (3H, br s), 2.88 (3H, br s), 2.42 (3H, s), 2.18 (3H, s).

Reference Preparation Example 221

A similar reaction to Reference Preparation example 96 using 3-dimethylamino-1-(4-methoxy-2,5-dimethyl-phenyl)-propenone (described in Reference Preparation example 220) instead of 3-dimethylamino-1-(4-methoxy-3-methyl)-propenone gave 3-(2,5-dimethyl-4-methoxy-phenyl)-1H-pyrazole.

Next, a similar reaction to Reference Preparation example 91 using the above-prepared 3-(2,5-dimethyl-4-methoxy-phenyl)-1H-pyrazole instead of 3-(4-methoxy-3-methyl-phenyl)-1H-pyrazole gave 3-(2,5-dimethyl-4-methoxy-phenyl)-1-methyl-1H-pyrazole. A mixture of the obtained 3-(2,5-dimethyl-4-methoxy-phenyl)-1-methyl-1H-pyrazole 1.5 g, hydrobromic acid 18 ml and acetic acid 18 ml was stirred at 100° C. for forty eight hours. The solvent was distilled off under reduced pressure and the resulting residue was washed with water 100 ml, ethyl acetate 100 ml and hexane 100 ml, and was dried under reduced pressure to give 2,5-dimethyl-4-(1-methyl-1H-pyrazol-3-yl)-phenol 1.4 g.

2,5-dimethyl-4-(1-methyl-1H-pyrazol-3-yl)-phenol

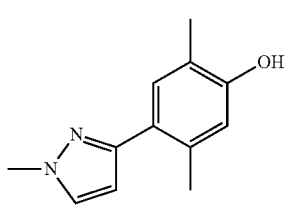

$^1$H-NMR (DMSO-D$_6$) δ: 7.70 (1H, d, J=2.3 Hz), 7.22 (1H, s), 6.64 (1H, s), 6.36 (1H, d, J=2.3 Hz), 3.86 (3H, s), 2.30 (3H, s), 2.09 (3H, s).

Reference Preparation Example 222

At 0° C., to a mixture of 4-formyl-5-hydroxy-3-(4-isopropoxy-3-methyl-phenyl)-1-methyl-1H-pyrazole (described in Reference Preparation example 172) 3 g, acetonitrile 30 ml, water 30 ml and potassium hydroxide 6.1 g was added bromo-difluoromethyl-dimethyl phosphonate 6.1 g and the resulting mixture was stirred for fifteen hours. The reaction mixture was extracted with ethyl acetate. The organic layer was washed with water and was dried over anhydrous magnesium sulfate, and was then concentrated under reduced pressure. The resulting residue was subjected to a silica gel column chromatography to give 4-formyl-5-difluoromethoxy-3-(4-isopropoxy-3-methyl-phenyl)-1-methyl-1H-pyrazole 1 g.

4-formyl-5-difluoromethoxy-3-(4-isopropoxy-3-methyl-phenyl)-1-methyl-1H-pyrazole

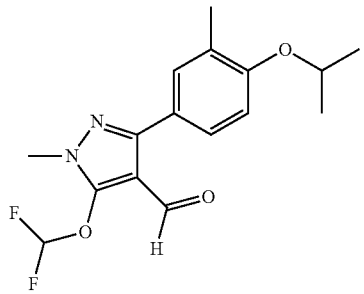 [SMILES: Cc1cc(-c2nn(C)c(OC(F)F)c2C=O)ccc1OC(C)C]

$^1$H-NMR (CDCl$_3$) δ: 9.60 (1H, s), 7.20-7.17 (2H, m), 7.13 (1H, t, J=72.8 Hz), 6.94 (1H, d, J=8.4 Hz), 4.67-4.58 (1H, m), 3.69 (3H, s), 2.25 (3H, s), 1.40 (6H, d, J=6.1 Hz).

Reference Preparation Example 223

At room temperature, a mixture of 4-formyl-5-difluoromethoxy-3-(4-isopropoxy-3-methyl-phenyl)-1-methyl-1H-pyrazole (described in Reference Preparation example 222) 1 g and trifluoroacetic acid 7 ml was added triethylsilane 0.9 g. The resulting mixture was stirred at room temperature for fifteen hours. The solvent was distilled off under reduced pressure, and the resulting mixture was extracted with ethyl acetate. The organic layer was washed with water and was dried over anhydrous magnesium sulfate, and was then concentrated under reduced pressure. The resulting residue was subjected to a silica gel column chromatography to give 5-difluoromethoxy-1,4-dimethyl-3-(4-isopropoxy-3-methyl-phenyl)-1H-pyrazole 0.9 g.

5-difluoromethoxy-1,4-dimethyl-3-(4-isopropoxy-3-methyl-phenyl)-1H-pyrazole

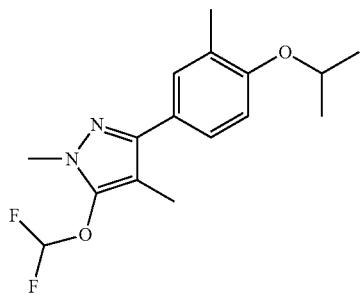 [SMILES: Cc1cc(-c2nn(C)c(OC(F)F)c2C)ccc1OC(C)C]

$^1$H-NMR (CDCl$_3$) δ: 6.56-6.54 (2H, m), 6.41-6.38 (1H, m), 6.39 (1H, t, J=74.0 Hz), 4.13-4.04 (1H, m), 3.14 (3H, s), 1.74 (3H, s), 1.39 (3H, s), 0.88 (6H, d, J=5.9 Hz).

Reference Preparation Example 224

A mixture of 5-difluoromethoxy-1,4-dimethyl-3-(4-isopropoxy-3-methyl-phenyl)-1H-pyrazole (described in Reference Preparation example 223) 0.9 g and 30% aqueous sulfuric acid solution 15 ml was stirred at 100° C. for thirty one hours. The reaction mixture was extracted with ethyl acetate. The organic layer was washed with water and saturated saline and was dried over anhydrous magnesium sulfate to give 4-(5-difluoromethoxy-1,4-dimethyl-1H-pyrazol-3-yl)-2-methyl-phenol 0.5 g.

4-(5-difluoromethoxy-1,4-dimethyl-1H-pyrazol-3-yl)-2-methyl-phenol

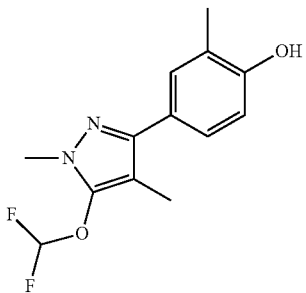 [SMILES: Cc1cc(-c2nn(C)c(OC(F)F)c2C)ccc1O]

$^1$H-NMR (CDCl$_3$) δ: 7.06 (1H, s), 7.03-6.98 (1H, m), 6.92-6.86 (1H, m), 6.89 (1H, t, J=74.8 Hz), 3.64 (3H, s), 2.30 (3H, s), 1.89 (3H, s).

Reference Preparation Example 225

At room temperature, to a mixture of 1-[2-(2-methyl-4-propionyl-phenoxymethyl]-3-methyl-phenyl)-4-methyl-1,4-dihydrotetrazole-5-one (described in Preparation example 179) (Present compound 179) 6.1 g, diethyl oxalate 4.8 g and N,N-dimethylformamide 100 ml was added potassium tert-butoxide 3.7 g. The resulting mixture was stirred for twelve hours. Thereto was added water 70 ml and the resulting mixture was acidified with 10% aqueous hydrochloric acid solution and was extracted with ethyl acetate. The organic layer was washed with water and was dried over anhydrous magnesium sulfate, and was concentrated under reduced pressure. The resulting residue was subjected to a silica gel column chromatography to give 3-methyl-4-{3-methyl-4-[2-methyl-6-(4-methyl-5-oxo-4,5-dihydro-tetrazol-1yl)-benzyloxy]-phenyl}-2,4-dioxo-butyric acid ethyl ester 3.8 g.

3-methyl-4-{3-methyl-4-[2-methyl-6-(4-methyl-5-oxo-4,5-dihydro-tetrazol-1yl)-benzyloxy]-phenyl}-2,4-dioxo-butyric acid ethyl ester

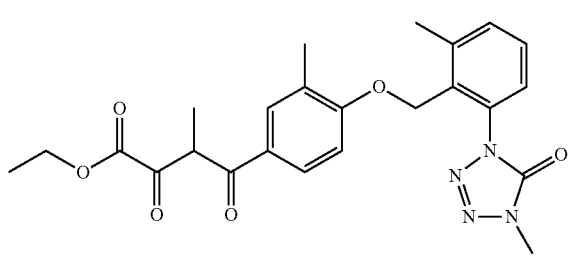 [SMILES: CCOC(=O)C(=O)C(C)C(=O)c1ccc(OCc2c(C)cccc2-n2nnn(C)c2=O)c(C)c1]

$^1$H-NMR (CDCl$_3$) δ: 7.84 (1H, dd, J=8.4, 2.3 Hz), 7.77 (1H, d, J=1.6 Hz), 7.48-7.41 (2H, m), 7.30 (1H, dd, J=7.2, 1.8 Hz), 6.92 (1H, d, J=8.6 Hz), 5.13 (2H, s), 5.01 (1H, q, J=7.1 Hz), 4.27 (2H, q, J=7.2 Hz), 3.65 (3H, s), 2.51 (3H, s), 2.14 (3H, s), 1.44 (3H, d, J=7.2 Hz), 1.30 (3H, t, J=7.1 Hz).

Reference Preparation Example 226

At room temperature, to a mixture of 1-{3-methyl-2-[2-methyl-4-(5-ethoxycarbonyl-1,4-dimethyl-1H-pyrazol-3-yl)-phenoxymethyl]-phenyl}-4-methyl-1,4-dihydrotetrazole-5-one (described in Preparation example 253) (Present compound 253) 2.1 g, tetrahydrofuran 30 ml, methanol 10 ml and water 5 ml was added lithium hydroxide 0.3 g. The resulting mixture was stirred for twelve hours, and the solvent was distilled off. The reaction mixture was acidified with 10% aqueous hydrochloric acid solution 30 ml and the precipitates were filtered and were washed with water and hexane, and were concentrated under reduced pressure to give 2,4-dimethyl-5-{3-methyl-4-[2-methyl-6-(4-methyl-5-oxo-4,5-dihydro-tetrazol-1-yl)-benzyloxy]-phenyl}-2H-pyrazole-3-carboxylic acid 1.6 g.

2,4-dimethyl-5-{3-methyl-4-[2-methyl-6-(4-methyl-5-oxo-4,5-dihydro-tetrazol-1-yl)-benzyloxy]-phenyl}-2H-pyrazole-3-carboxylic acid

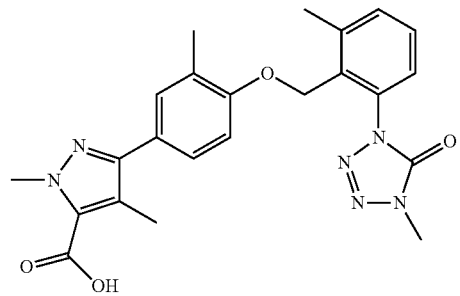 [SMILES: Cc1cc(-c2nn(C)c(C(=O)O)c2C)ccc1OCc1c(C)cccc1-n1nnn(C)c1=O]

$^1$H-NMR (DMSO-D$_6$) δ: 7.54-7.51 (2H, m), 7.39-7.36 (1H, m), 7.34-7.32 (2H, m), 7.03 (1H, d, J=9.2 Hz), 5.05 (2H, s), 4.05 (3H, s), 3.55 (3H, s), 2.50 (3H, s), 2.31 (3H, s), 2.05 (3H, s).

Reference Preparation Example 227

At room temperature, to a mixture of 2,4-dimethyl-5-{3-methyl-4-[2-methyl-6-(4-methyl-5-oxo-4,5-dihydro-tetrazol-1-yl)-benzyloxy]-phenyl}-2H-pyrazole-3-carboxylic acid (described in Reference Preparation example 226) 2.1 g and tetrahydrofuran 25 ml was added oxalyl dichloride 0.89 g and N,N-dimethylformamide 0.1 ml. The resulting mixture was stirred for three hours and the solvent was distilled off to give 2,4-dimethyl-5-{3-methyl-4-[2-methyl-6-(4-methyl-5-oxo-4,5-dihydro-tetrazol-1-yl)-benzyloxy]-phenyl}-2H-pyrazole-3-carbonyl chloride 2.1 g.

497

2,4-dimethyl-5-{3-methyl-4-[2-methyl-6-(4-methyl-5-oxo-4,5-dihydro-tetrazol-1-yl)-benzyloxy]-phenyl}-2H-pyrazole-3-carbonyl chloride

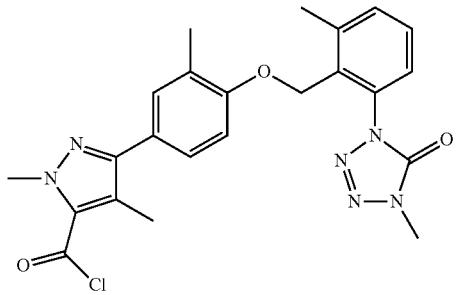 [SMILES: Cc1cc(-c2nn(C)c(C(=O)Cl)c2C)ccc1OCc1c(C)cccc1-n1nnn(C)c1=O]

$^1$H-NMR (CDCl$_3$) δ: 7.46-7.41 (2H, m), 7.31-7.28 (3H, m), 6.92 (1H, d, J=9.1 Hz), 5.08 (2H, s), 4.16 (3H, s), 3.64 (3H, s), 2.52 (3H, s), 2.48 (3H, s), 2.14 (3H, s).

Reference Preparation Example 228

A similar reaction to Reference Preparation example 104 using 1-[2-(4-acetyl-2-methyl-phenoxymethyl]-3-methyl-phenyl)-4-methyl-1,4-dihydrotetrazole-5-one (described in Preparation example 178) instead of 1-[2-(4-acetyl-2-methyl-phenoxymethyl]-3-methoxy-phenyl)-4-methyl-,4-dihydrotetrazole-5-one gave 1-{2-[4-(3-dimethylamino-acryloyl)-2-methyl-phenoxymethyl]-3-methoxy-phenyl}-4-methyl-1,4-dihydrotetrazole-5-one.

1-{2-[4-(3-dimethylamino-acryloyl)-2-methyl-phenoxymethyl]-3-methoxy-phenyl}-4-methyl-1,4-dihydrotetrazole-5-one

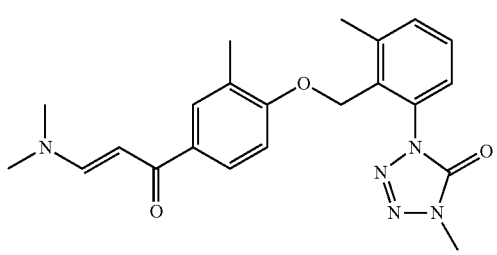 [SMILES: Cc1cc(C(=O)/C=C/N(C)C)ccc1OCc1c(C)cccc1-n1nnn(C)c1=O]

$^1$H-NMR (CDCl$_3$) δ: 7.78 (1H, d, J=12.4 Hz), 7.76-7.72 (2H, m), 7.45-7.40 (2H, m), 7.29-7.27 (1H, m), 6.85 (1H, d, J=8.5 Hz), 5.70 (1H, d, J=12.4 Hz), 5.09 (2H, s), 3.61 (3H, s), 3.12 (3H, br s), 2.94 (3H, br s), 2.50 (3H, s), 2.12 (3H, s).

Reference Preparation Example 229

A similar reaction to Reference Preparation example 225 using 1-[2-(2-methyl-4-propionyl-phenoxymethyl]-2-ethyl-phenyl}-4-methyl-1,4-dihydrotetrazole-5-one (Present compound 268) instead of 1-[2-(2-methyl-4-propionyl-phenoxymethyl]-3-methyl-phenyl)-4-methyl-1,4-dihydrotetrazole-5-one (Present compound 179) gave 3-methyl-4-{3-methyl-4-[2-ethyl-6-(4-methyl-5-oxo-4,5-dihydro-tetrazol-1-yl)-benzyloxy]-phenyl}-2,4-dioxo-butyric acid ethyl ester.

498

3-methyl-4-{3-methyl-4-[2-ethyl-6-(4-methyl-5-oxo-4,5-dihydro-tetrazol-1-yl)-benzyloxy]-phenyl}-2,4-dioxo-butyric acid ethyl ester

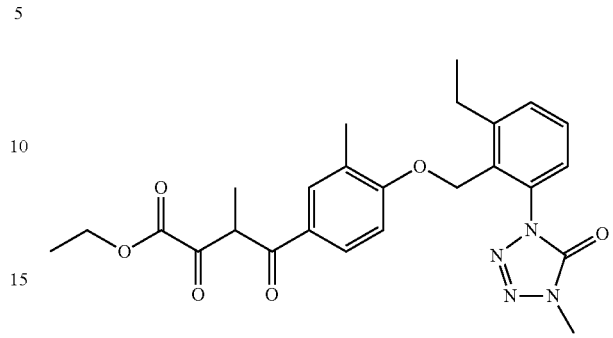

$^1$H-NMR (CDCl$_3$) δ: 7.84 (1H, dd, J=8.5, 2.3 Hz), 7.77-7.77 (1H, m), 7.53-7.46 (2H, m), 7.30 (1H, dd, J=7.3, 1.8 Hz), 6.94 (1H, d, J=8.7 Hz), 5.15 (2H, s), 5.01 (1H, q, J=7.1 Hz), 4.27 (2H, q, J=7.1 Hz), 3.61 (3H, s), 2.84 (2H, q, J=7.6 Hz), 2.12 (3H, s), 1.44 (3H, d, J=7.1 Hz), 1.31 (3H, t, J=7.6 Hz), 1.29 (3H, t, J=7.6 Hz).

Reference Preparation Example 230

A similar reaction to Reference Preparation example 226 using 1-{3-ethyl-2-[2-methyl-4-(5-ethoxycarbonyl-1,4-dimethyl-1H-pyrazol-3-yl)-phenoxymethyl]-phenyl}-4-methyl-1,4-dihydrotetrazole-5-one (Present compound 271) instead of 1-{3-methyl-2-[2-methyl-4-(5-ethoxycarbonyl-1,4-dimethyl-1H-pyrazol-3-yl)-phenoxymethyl]-phenyl}-4-methyl-1,4-dihydrotetrazole-5-one (Present compound 253) gave 2,4-dimethyl-5-{3-methyl-4-[2-ethyl-6-(4-methyl-5-oxo-4,5-dihydro-tetrazol-1-yl)-benzyloxy]-phenyl}-2H-pyrazole-3-carboxylic acid.

2,4-dimethyl-5-{3-methyl-4-[2-ethyl-6-(4-methyl-5-oxo-4,5-dihydro-tetrazol-1-yl)-benzyloxy]-phenyl}-2H-pyrazole-3-carboxylic acid

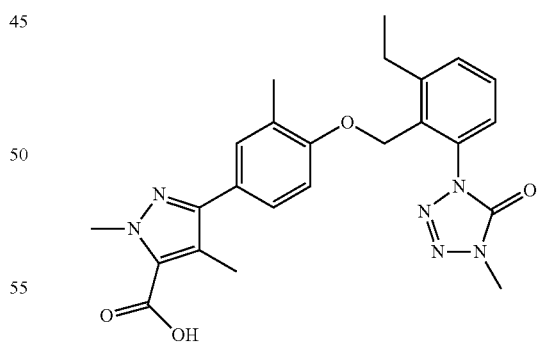

$^1$H-NMR (CDCl$_3$) δ: 7.50-7.45 (2H, m), 7.36-7.33 (2H, m), 7.29 (1H, dd, J=7.1, 2.3 Hz), 6.92 (1H, d, J=8.0 Hz), 5.09 (2H, s), 4.21 (3H, s), 3.61 (3H, s), 2.86 (2H, q, J=7.6 Hz), 2.42 (3H, s), 2.13 (3H, s), 1.29 (3H, t, J=7.6 Hz).

Reference Preparation Example 231

A similar reaction to Reference Preparation example 227 using 2,4-dimethyl-5-{3-methyl-4-[2-ethyl-6-(4-methyl-5- oxo-4,5-dihydro-tetrazol-1-yl)-benzyloxy]-phenyl}-2H-pyrazole-3-carboxylic acid (described in Reference Preparation example 230) instead of 2,4-dimethyl-5-{3-methyl-4-[2-methyl-6-(4-methyl-5-oxo-4,5-dihydro-tetrazol-1-yl)-benzyloxy]-phenyl}-2H-pyrazole-3-carboxylic acid gave 2,4-dimethyl-5-{3-methyl-4-[2-ethyl-6-(4-methyl-5-oxo-4,5-dihydro-tetrazol-1-yl)-benzyloxy]-phenyl}-2H-pyrazole-3-carbonyl chloride.

2,4-dimethyl-5-{3-methyl-4-[2-ethyl-6-(4-methyl-5-oxo-4,5-dihydro-tetrazol-1-yl)-benzyloxy]-phenyl}-2H-pyrazole-3-carbonyl chloride

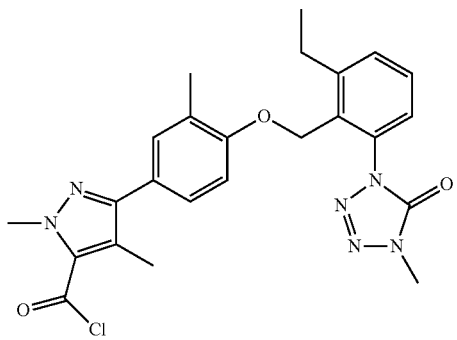 [SMILES: CCc1cccc(-n2nnn(C)c2=O)c1COc1ccc(-c2nn(C)c(C(=O)Cl)c2C)cc1C]

$^1$H-NMR (CDCl$_3$) δ: 7.53-7.42 (3H, m), 7.30-7.27 (2H, m), 6.94-6.92 (1H, m), 5.09 (2H, s), 4.15 (3H, s), 3.62 (3H, s), 2.89-2.83 (2H, m), 2.48 (3H, s), 2.13 (3H, s), 1.29 (3H, t, J=7.6 Hz).

Reference Preparation Example 232

A similar reaction to Reference Preparation example 225 using 1-[2-(2-methyl-4-propionyl-phenoxymethyl]-3-chloro-phenyl)-4-methyl-1,4-dihydrotetrazole-5-one (Present compound 278) instead of 1-[2-(2-methyl-4-propionyl-phenoxymethyl]-3-methyl-phenyl)-4-methyl-1,4-dihydrotetrazole-5-one (Present compound 179) gave 3-methyl-4-{3-methyl-4-[2-chloro-6-(4-methyl-5-oxo-4,5-dihydro-tetrazol-1-yl)-benzyloxy]-phenyl}-2,4-dioxo-butyric acid ethyl ester.

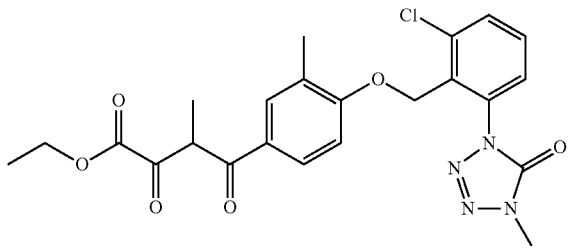 [SMILES: CCOC(=O)C(=O)C(C)C(=O)c1ccc(OCc2c(Cl)cccc2-n2nnn(C)c2=O)c(C)c1]

$^1$H-NMR (CDCl$_3$) δ: 7.82 (1H, dd, J=8.6, 2.2 Hz), 7.76-7.75 (1H, m), 7.64 (1H, d, J=8.2 Hz), 7.50 (1H, t, J=7.9 Hz), 7.42 (1H, d, J=7.8 Hz), 6.93 (1H, d, J=8.5 Hz), 5.40 (2H, s), 5.00 (1H, q, J=7.1 Hz), 4.27 (2H, q, J=7.2 Hz), 3.62 (3H, s), 2.07 (3H, s), 1.44 (3H, d, J=7.1 Hz), 1.30 (3H, t, J=7.2 Hz).

Reference Preparation Example 233

A similar reaction to Reference Preparation example 226 using 1-{3-chloro-2-[2-methyl-4-(5-ethoxycarbonyl-1,4-dimethyl-1H-pyrazol-3-yl)-phenoxymethyl]-phenyl}-4-methyl-1,4-dihydrotetrazole-5-one (Present compound 280) instead of 1-{3-methyl-2-[2-methyl-4-(5-ethoxycarbonyl-1,4-dimethyl-1H-pyrazol-3-yl)-phenoxymethyl]-phenyl}-4-methyl-1,4-dihydrotetrazole-5-one (Present compound 253) gave 2,4-dimethyl-5-{3-methyl-4-[2-chloro-6-(4-methyl-5-oxo-4,5-dihydro-tetrazol-1-yl)-benzyloxy]-phenyl}-2H-pyrazole-2-carboxylic acid.

2,4-dimethyl-5-{3-methyl-4-[2-chloro-6-(4-methyl-5-oxo-4,5-dihydro-tetrazol-1-yl)-benzyloxy]-phenyl}-2H-pyrazole-2-carboxylic acid

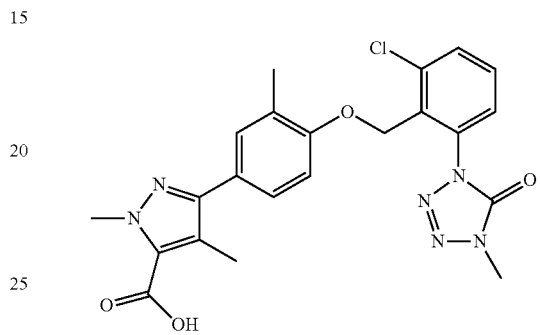

$^1$H-NMR (CDCl$_3$) δ: 7.61 (1H, dd, J=7.9, 1.1 Hz), 7.47 (1H, t, J=7.9 Hz), 7.41 (1H, dd, J=7.9, 1.1 Hz), 7.35-7.33 (2H, m), 6.91 (1H, d, J=8.4 Hz), 5.35 (2H, s), 4.22 (3H, s), 3.62 (3H, s), 2.40 (3H, s), 2.08 (3H, s).

Reference Preparation Example 234

A similar reaction to Reference Preparation example 227 using 2,4-dimethyl-5-{3-methyl-4-[2-chloro-6-(4-methyl-5-oxo-4,5-dihydro-tetrazol-1-yl)-benzyloxy]-phenyl}-2H-pyrazole-2-carboxylic acid. (described in Reference Preparation example 233) instead of 2,4-dimethyl-5-{3-methyl-4-[2-methyl-6-(4-methyl-5-oxo-4,5-dihydro-tetrazol-1-yl)-benzyloxy]-phenyl}-2H-pyrazole-3-carboxylic acid gave 2,4-dimethyl-5-{3-methyl-4-[2-chloro-6-(4-methyl-5-oxo-4,5-dihydro-tetrazol-1-yl)-benzyloxy]-phenyl}-2H-pyrazole-3-carbonyl chloride.

2,4-dimethyl-5-{3-methyl-4-[2-chloro-6-(4-methyl-5-oxo-4,5-dihydro-tetrazol-1-yl)-benzyloxy]-phenyl}-2H-pyrazole-3-carbonyl chloride

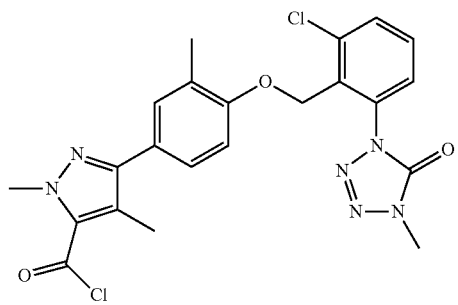 [SMILES: Cc1cc(-c2nn(C)c(C(=O)Cl)c2C)ccc1OCc1c(Cl)cccc1-n1nnn(C)c1=O]

$^1$H-NMR (DMSO-D$_6$) δ: 7.79 (1H, dd, J=8.2, 1.1 Hz), 7.67-7.63 (1H, m), 7.56 (1H, dd, J=7.9, 1.1 Hz), 7.31-7.28

(2H, m), 6.99 (1H, d, J=9.1 Hz), 5.18 (2H, s), 4.02 (3H, s), 3.52 (3H, s), 2.27 (3H, s), 1.99 (3H, s).

Reference Preparation Example 235

At room temperature, 1-{3-methyl-2-[2-methyl-4-(3,5-dimethyl-4-formyl-pyrazol-1-yl)-phenoxymethyl]-phenyl}-4-methyl-1,4-dihydrotetrazole-5-one (Present compound 283) 3.3 g, hydroxylamine hydrochloride salt 0.8 g, pyridine 1.5 g and chloroform 70 ml was stirred for 15 hours. The resulting mixture was concentrated under reduced pressure and was added 10%-hydrochloric acid solution. The precipitates were filtereted and were washed with water and hexane, and were concentrated under reduced pressure to give 3,5-Dimethyl-1-{3-methyl-4-[2-methyl-6-(4-methyl-5-oxo-4,5-dihydro-tetrazol-1-yl)-benzyloxy]-phenyl}-1H-pyrazole-4-carbaldehyde oxime 3,5-Dimethyl-1-{3-methyl-4-[2-methyl-6-(4-methyl-5-oxo-4,5-dihydro-tetrazol-1-yl)-benzyloxy]-phenyl}-1H-pyrazole-4-carbaldehyde oxime

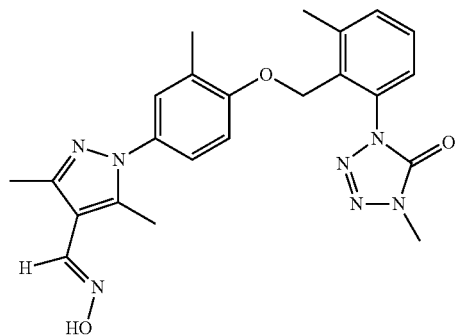 [SMILES: Cc1cc(-n2nc(C)c(/C=N/O)c2C)ccc1OCc1c(C)cccc1-n1nnn(C)c1=O]

$^1$H-NMR (CDCl$_3$) δ: 8.14 (1H, s), 7.77 (1H, s), 7.46-7.40 (2H, m), 7.29 (1H, dd, J=7.1, 2.1 Hz), 7.16 (1H, d, J=2.5 Hz), 7.12 (1H, dd, J=8.6, 2.6 Hz), 6.88 (1H, d, J=8.7 Hz), 5.07 (2H, s), 3.65 (3H, s), 2.51 (3H, s), 2.38 (3H, s), 2.34 (3H, s), 2.12 (3H, s).

Reference Preparation Example 236

Propionic acid 2-chloro-phenyl ester was obtained by reference to Reference Preparation example 113.

Propionic acid 2-chloro-phenyl ester

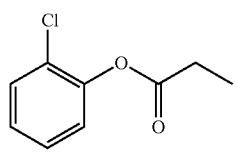

$^1$H-NMR (CDCl$_3$) δ: 7.45-7.43 (1H, m), 7.28 (1H, td, J=7.9, 1.8 Hz), 7.21-7.17 (1H, m), 7.14-7.12 (1H, m), 2.66 (2H, q, J=7.7 Hz), 1.30 (3H, t, J=7.7 Hz).

Reference Preparation Example 237

1-(3-Chloro-4-hydroxy-phenyl)-propan-1-one was obtained by reference to Reference Preparation example 114.

1-(3-Chloro-4-hydroxy-phenyl)-propan-1-one

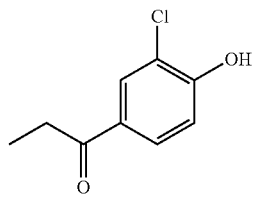

$^1$H-NMR (CDCl$_3$) δ: 8.00 (1H, d, J=2.0 Hz), 7.83 (1H, dd, J=8.4, 2.0 Hz), 7.08 (1H, d, J=8.4 Hz), 6.19 (1H, br s), 2.94 (2H, q, J=7.2 Hz), 1.22 (3H, t, J=7.2 Hz).

Reference Preparation Example 238

3,5-Dimethyl-1-{3-methyl-4-[2-chloro-6-(4-methyl-5-oxo-4,5-dihydro-tetrazol-1-yl)-benzyloxy]-phenyl}-1H-pyrazole-4-carbaldehyde oxime was obtained by reference to Reference Preparation example 235.

3,5-Dimethyl-1-{3-methyl-4-[2-chloro-6-(4-methyl-5-oxo-4,5-dihydro-tetrazol-1-yl)-benzyloxy]-phenyl}-1H-pyrazole-4-carbaldehyde oxime

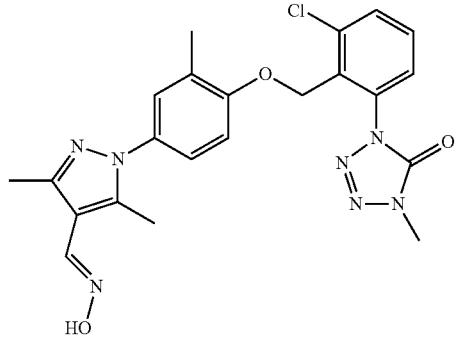 [SMILES: Cc1cc(-n2nc(C)c(/C=N/O)c2C)ccc1OCc1c(Cl)cccc1-n1nnn(C)c1=O]

$^1$H-NMR (CDCl$_3$) δ: 8.13 (1H, s), 7.96 (1H, br s), 7.62 (1H, dd, J=8.0, 1.2 Hz), 7.48 (1H, t, J=8.0 Hz), 7.41 (1H, dd, J=8.0, 1.2 Hz), 7.14-7.13 (1H, m), 7.12-7.09 (1H, m), 6.89 (1H, d, J=8.6 Hz), 5.33 (2H, s), 3.63 (3H, s), 2.37 (3H, s), 2.32 (3H, s), 2.05 (3H, s).

Reference Preparation Example 239

3,5-Dimethyl-1-{3-methyl-4-[2-ethyl-6-(4-methyl-5-oxo-4,5-dihydro-tetrazol-1-yl)-benzyloxy]-phenyl}-1H-pyrazole-4-carbaldehyde oxime was obtained by reference to Reference Preparation example 235.

503

3,5-Dimethyl-{3-methyl-4-[2-ethyl-6-(4-methyl-5-oxo-4,5-dihydro-tetrazol-1-yl)-benzyloxy]-phenyl}-1H-pyrazole-4-carbaldehyde oxime

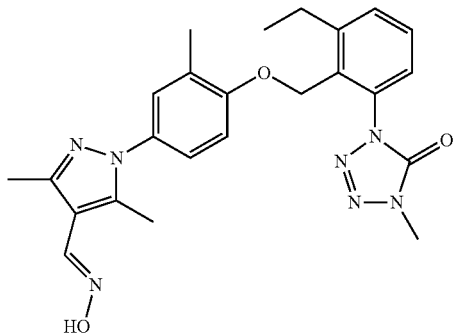 [SMILES: CCc1cccc(-n2nnn(C)c2=O)c1COc1ccc(-n2nc(C)c(/C=N/O)c2C)cc1C]

$^1$H-NMR (CDCl$_3$) δ: 8.15 (1H, s), 7.99 (1H, s), 7.51-7.45 (2H, m), 7.30 (1H, dd, J=7.2, 1.8 Hz), 7.16-7.12 (2H, m), 6.90 (1H, d, J=8.6 Hz), 5.09 (2H, s), 3.63 (3H, s), 2.85 (2H, q, J=7.6 Hz), 2.39 (3H, s), 2.34 (3H, s), 2.11 (3H, s), 1.29 (3H, t, J=7.6 Hz).

Reference Preparation Example 240

2-ethyl-4-methyl-5-{3-methyl-2-[2-methyl-6-(4-methyl-5-oxo-4,5-dihydro-tetrazol-1-yl)-benzyloxy]-phenyl}-2H-pyrazole-3-carboxylic acid was obtained by reference to Reference Preparation example 226.

2-ethyl-4-methyl-5-{3-methyl-2-[2-methyl-6-(4-methyl-5-oxo-4,5-dihydro-tetrazol-1-yl)-benzyloxy]-phenyl}-2H-pyrazole-3-carboxylic acid

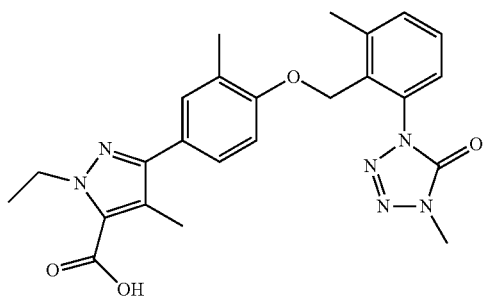 [SMILES: CCn1nc(-c2ccc(OCc3c(C)cccc3-n3nnn(C)c3=O)c(C)c2)c(C)c1C(=O)O]

$^1$H-NMR (CDCl$_3$) δ: 7.43-7.38 (2H, m), 7.34 (1H, s), 7.30 (1H, s), 7.28-7.25 (2H, m), 6.87 (1H, d, J=8.4 Hz), 5.05 (2H, s), 4.56 (2H, q, J=7.1 Hz), 3.62 (3H, s), 2.49 (3H, s), 2.35 (3H, s), 2.11 (3H, s), 1.40 (3H, t, J=7.1 Hz).

Reference Preparation Example 241

2-ethyl-4-methyl-5-{3-methyl-4-[2-methyl-6-(4-methyl-5-oxo-4,5-dihydro-tetrazol-1-yl)-benzyloxy]-phenyl}-2H-pyrazole-3-carbonyl chloride was obtained by reference to Reference Preparation example 227.

504

2-ethyl-4-methyl-5-{3-methyl-4-[2-methyl-6-(4-methyl-5-oxo-4,5-dihydro-tetrazol-1-yl)-benzyloxy]-phenyl}-2H-pyrazole-3-carbonyl chloride

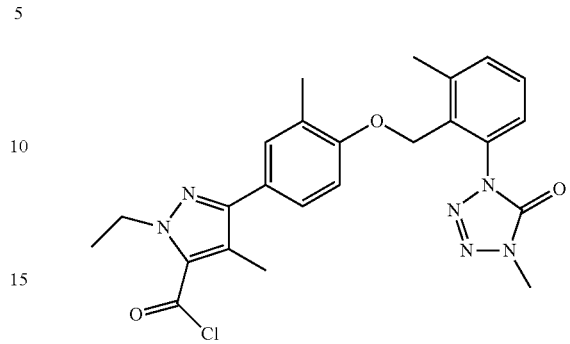

$^1$H-NMR (CDCl$_3$) δ: 7.46-7.40 (2H, m), 7.30-7.27 (3H, m), 6.91 (1H, d, J=8.0 Hz), 5.08 (2H, s), 4.52 (2H, q, J=7.2 Hz), 3.64 (3H, s), 2.52 (3H, s), 2.47 (3H, s), 2.14 (3H, s), 1.44 (3H, t, J=7.2 Hz).

Reference Preparation Example 242

At room temperature, to mixture of 5-hydroxy-3-(4-isopropoxy-3-methyl-phenyl)-1-methyl-1H-pyrazole (described in Reference Preparation example 171) 9.5 g, and N,N-dimethylformamide 70 ml was added 55%-sodium hydride 2.5 g and was stirred for one hour, and thereto was then added dimethyl sulfate 9.7 g and stirred at 100° C. for 12 hours. Thereto was added water 50 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 3-(4-isopropoxy-3-methyl-phenyl)-5-methoxy-1-methyl-1H-pyrazole 5.8 g.

3-(4-isopropoxy-3-methyl-phenyl)-5-methoxy-1-methyl-1H-pyrazole

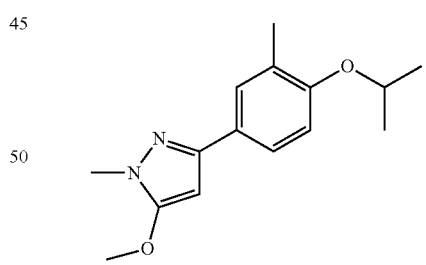

$^1$H-NMR (CDCl$_3$) δ: 7.55 (1H, dd, J=2.3, 0.7 Hz), 7.49-7.47 (1H, m), 6.84 (1H, d, J=8.5 Hz), 5.75 (1H, s), 4.56-4.50 (1H, m), 3.92 (3H, s), 3.66 (3H, s), 2.23 (3H, s), 1.35 (3H, s), 1.33 (3H, s).

Reference Preparation Example 243

At room temperature, a mixture of 3-(4-isopropoxy-3-methyl-phenyl)-5-methoxy-1-methyl-1H-pyrazole (described in Reference Preparation example 242) 5.8 g, N-chlorosuccinimide 3.3 g and chloroform 70 ml was stirred for 14 hour. Thereto was added water 50 ml and the resulting mixture was extracted with chloroform. The organic layer was washed with water, and was dried over anhydrous magnesium sulfate and was then concentrated under reduced pressure. The resulting residue was subjected to a silica gel column chromatography to give 4-Chloro-3-(4-isopropoxy-3-methyl-phenyl)-5-methoxy-1-methyl-1H-pyrazole 5.6 g.

4-Chloro-3-(4-isopropoxy-3-methyl-phenyl)-5-methoxy-1-methyl-1H-pyrazole

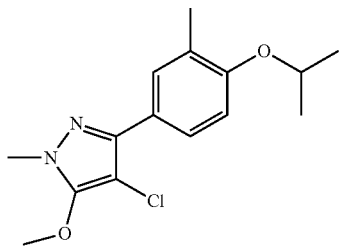 [SMILES: COc1c(Cl)c(-c2ccc(OC(C)C)c(C)c2)nn1C]

$^1$H-NMR (CDCl$_3$) δ: 7.62-7.59 (2H, m), 6.87 (1H, d, J=9.1 Hz), 4.59-4.53 (1H, m), 4.11 (3H, s), 3.70 (3H, s), 2.24 (3H, s), 1.36 (3H, s), 1.34 (3H, s).

Reference Preparation Example 244

A mixture of 4-Chloro-3-(4-isopropoxy-3-methyl-phenyl)-5-methoxy-1-methyl-1H-pyrazole (described in Reference Preparation example 243) 5.6 g and 30% aqueous sulfuirnc acid solution 60 ml was stirred with heating under reflux for 24 hours. Thereto was added ice water 10 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 4-(4-Chloro-5-methoxy-1-methyl-1H-pyrazol-3-yl)-2-methyl-phenol 1.2 g.

4-(4-Chloro-5-methoxy-1-methyl-1H-pyrazol-3-yl)-2-methyl-phenol

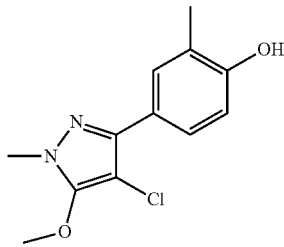 [SMILES: COc1c(Cl)c(-c2ccc(O)c(C)c2)nn1C]

$^1$H-NMR (CDCl$_3$) δ: 7.59 (1H, d, J=2.0 Hz), 7.55 (1H, dd, J=8.4, 2.0 Hz), 6.80 (1H, d, J=8.5 Hz), 5.06 (1H, s), 4.11 (3H, s), 3.70 (3H, s), 2.28 (3H, s).

Reference Preparation Example 245

At room temperature, 1-{3-methyl-2-[2-methyl-4-(4-formyl-5-methoxy-1-methyl-1H-pyrazol-3-yl)-phenoxymethyl]-phenyl}-4-methyl-1,4-dihydrotetrazole-5-one (Present compound 266) 1.6 g, hydroxylamine hydrochloride salt 0.8 g, pyridine 1.4 g and chloroform 20 ml was stirred for 15 hours. The resulting mixture was concentrated under reduced pressure and was added 10%-hydrochloric acid solution. The precipitates were filtereted and were washed with water and hexane, and were concentrated under reduced pressure to give 5-methoxy-1-methyl-3-{3-methyl-4-[2-methyl-6-(4-methyl-5-oxo-4,5-dihydro-tetrazol-1-yl)-benzyloxy]-phenyl}-1H-pyrazole-4-carbaldehyde oxime.

5-methoxy-1-methyl-3-{3-methyl-4-[2-methyl-6-(4-methyl-5-oxo-4,5-dihydro-tetrazol-1-yl)-benzyloxy]-phenyl}-1H-pyrazole-4-carbaldehyde oxime

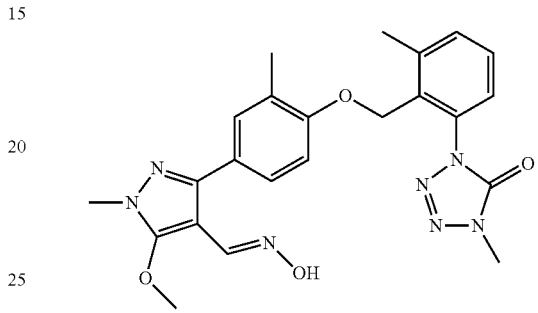

$^1$H-NMR (CDCl$_3$) δ: 8.09 (1H, s), 7.43-7.40 (2H, m), 7.32-7.27 (3H, m), 6.88 (1H, d, J=8.2 Hz), 5.07 (2H, s), 4.04 (3H, s), 3.75 (3H, s), 3.64 (3H, s), 2.51 (3H, s), 2.12 (3H, s).

Reference Preparation Example 246

1-{2-[4-(3-dimethylamino-acryloyl)-2-methyl-phenoxymethyl]-3-ethyl-phenyl}-4-methyl-1,4-dihydrotetrazole-5-one was obtained by reference to Reference Preparation example 104.

1-{2-[4-(3-dimethylamino-acryloyl)-2-methyl-phenoxymethyl]-3-ethyl-phenyl}-4-methyl-1,4-dihydrotetrazole-5-one

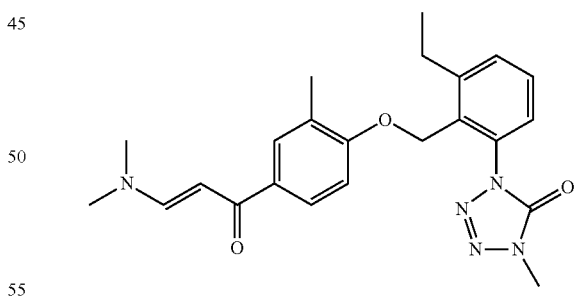

$^1$H-NMR (CDCl$_3$) δ: 7.83-7.77 (2H, m), 7.75-7.74 (1H, m), 7.54-7.47 (2H, m), 7.32 (1H, dd, J=7.2, 2.0 Hz), 6.90 (1H, d, J=8.6 Hz), 5.73 (1H, d, J=12.5 Hz), 5.14 (2H, s), 3.61 (3H, s), 3.17-2.97 (6H, m), 2.88 (2H, q, J=7.2 Hz), 2.14 (3H, s), 1.31 (3H, t, J=7.2 Hz).

Reference Preparation Example 247

1-[2-(4-acetyl-2-methyl-phenoxymethyl]-3-methyl-phenyl)-4-methyl-1,4-dihydrotetrazole-5-one (Present compound 178) 6.3 g and tetrahydrofuran 100 ml was added diethyl carbonate 4.2 g, 55% sodium hydride 1.6 g, dibenzo-18-crown-6 0.01 g and ethanol 0.8 g, and the resulting mixture was stirred with heating under reflux for ten hours. To the reaction mixture was added water, and the resulting mixture was acidified with 10% aqueous hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 3-{3-Methyl-4-[2-methyl-6-(4-methyl-5-oxo-4,5-dihydro-tetrazol-1-yl)-benzyloxy]-phenyl}-3-oxo-propionic acid ethyl ester 3.7 g.

3-{3-Methyl-4-[2-methyl-6-(4-methyl-5-oxo-4,5-dihydro-tetrazol-1-yl)-benzyloxy]-phenyl}-3-oxo-propionic acid ethyl ester

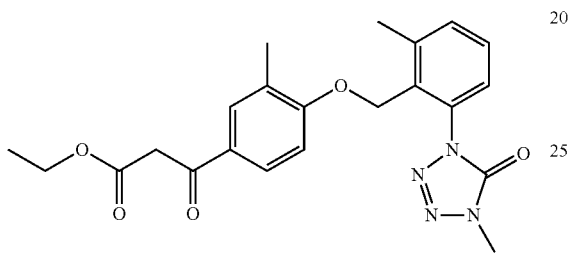

$^1$H-NMR (CDCl$_3$) δ: 7.78 (1H, dd, J=8.5, 2.3 Hz), 7.74-7.73 (1H, m), 7.47-7.40 (2H, m), 7.29 (1H, dd, J=7.3, 1.8 Hz), 6.88 (1H, d, J=8.5 Hz), 5.12 (2H, s), 4.21 (2H, q, J=7.2 Hz), 3.93 (2H, s), 3.62 (3H, s), 2.50 (3H, s), 2.12 (3H, s), 1.27 (3H, t, J=7.2 Hz).

According to the above-mentioned processes, the following compounds can be prepared:
Compounds EP1A-001~EP1A-1023, EP1B-001~EP1B-1023, EP1C-001~EP1C-1023, EP1D-001~EP1D-1023, EP1E-001~EP1E-1023, EP1F-001~EP1F-1023, EP1G-001~EP1G-1023, EP1H-001~EP1H-1023, EP1I-001~EP1I-1023, EP1J-001~EP1J-1023, EP2A-001~EP2A-1023, EP2B-001~EP2B-1023, EP2C-001~EP2C-1023, EP2D-001~EP2D-1023, EP2E-001~EP2E-1023, EP2F-001~EP2F-1023, EP2G-001~EP2G-1023, EP2H-001~EP2H-1023, EP2I-001~EP2I-1023, EP2J-001~EP2J-1023, EP3A-001~EP3A-1023, EP3B-001~EP3B-1023, EP3C-00~EP3C-1023, EP3D-001~EP3D-1023, EP3E-001~EP3E-1023, EP3F-001~EP3F-1023, EP3G-001~EP3G-1023, EP3H-001~EP3H-1023, EP3I-001~EP3I-1023, EP3J-001~EP3J-1023, EP4A-001~EP4A-1023, EP4B-001~EP4B-1023, EP4C-001~EP4C-1023, EP4D-001~EP4D-1023, EP4E-001~EP4E-1023, EP4F-001~EP4F-1023, EP4G-001~EP4G-1023, EP4H-001~EP4H-1023, EP4I-001~EP4I-1023, EP4J-001~EP4J-1023, EP5A-001~EP5A-1023, EP5B-001~EP5B-1023, EP5C-001~EP5C-1023, EP5D-001~EP5D-1023, EP5E-001~EP5E-1023, EP5F-001~EP5F-1023, EP5G-001~EP5G-1023, EP5H-001~EP5H-1023, EP5I-001~EP5I-1023, EP5J-001~EP5J-1023, EP6A-001~EP6A-1023, EP6B-001~EP6B-1023, EP6C-001~EP6C-1023, EP6D-001~EP6D-1023, EP6E-001~EP6E-1023, EP6F-001~EP6F-1023, EP6G-001~EP6G-1023, EP6H-001~EP6H-1023, EP6I-001~EP6I-1023, EP6J-001~EP6J-1023, EP7A-001~EP7A-1023, EP7B-001~EP7B-1023, EP7C-001~EP7C-1023, EP7D-001~EP7D-1023, EP7E-001~EP7E-1023, EP7F-001~EP7F-1023, EP7G-001~EP7G-1023, EP7H-001~EP7H-1023, EP7I-001~EP7I-1023, EP7J-001~EP7J-1023, EP8A-001~EP8A-1023, EP8B-001~EP8B-1023, EP8C-001~EP8C-1023, EP8D-001~EP8D-1023, EP8E-001~EP8E-1023, EP8F-001~EP8F-1023, EP8G-001~EP8G-1023, EP8H-001~EP8H-1023, EP8I-001~EP8I-1023, EP8J-001~EP8J-1023, EP9A-001~EP9A-1023, EP9B-001~EP9B-1023, EP9C-001~EP9C-1023, EP9D-001~EP9D-1023, EP9E-001~EP9E-1023, EP9F-001~EP9F-1023, EP9G-001~EP9G-1023, EP9H-001~EP9H-1023, EP9I-001~EP9I-1023 and EP9J-001~EP9J-1023.

Compounds EP1A-001~EP1A-1023 represent compounds

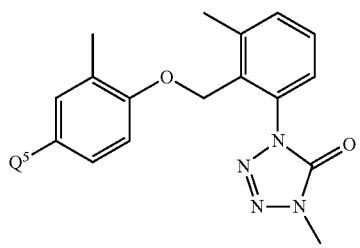
(EP1A)

[in the formula (EP1A), Q$^5$ represents a substituent corresponding to each of substituents Nos. 1 to 1023 indicated in Table 1 to Table 54 as below-mentioned];

Compounds EP1B-001~EP1B-1023 represent compounds represented by a formula:

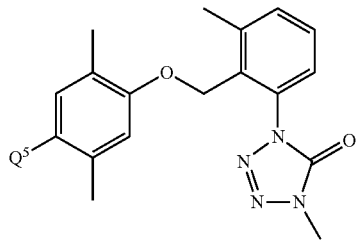
(EP1B)

[in the formula (EP1B), Q$^5$ represents a substituent corresponding to each of substituents Nos. 1 to 1023 indicated in Table 1 to Table 54 as below-mentioned];

Compounds EP1C-001~EP1C-1023 represent compounds represented by a formula:

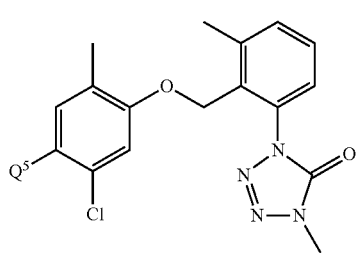
(EP1C)

[in the formula (EP1C), Q$^5$ represents a substituent corresponding to each of substituents Nos. 1 to 1023 indicated in Table 1 to Table 54 as below-mentioned];

Compounds EP1D-001~EP1D-1023 represent compounds represented by a formula:

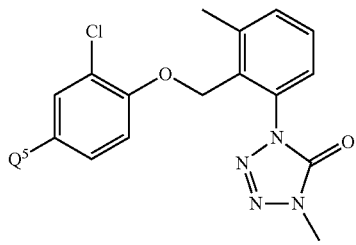
(EP1D)

[in the formula (EP1D), $Q^5$ represents a substituent corresponding to each of substituents Nos. 1 to 1023 indicated in Table 1 to Table 54 as below-mentioned];

Compounds EP1E-001~EP1E-1023 represent compounds represented by a formula:

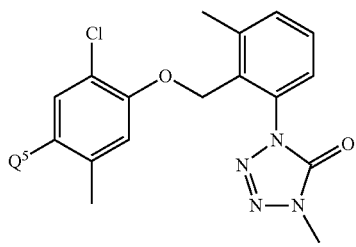
(EP1E)

[in the formula (EP1E), $Q^5$ represents a substituent corresponding to each of substituents Nos. 1 to 1023 indicated in Table 1 to Table 54 as below-mentioned];

Compounds EP1F-001~EP1F-1023 represent compounds represented by a formula:

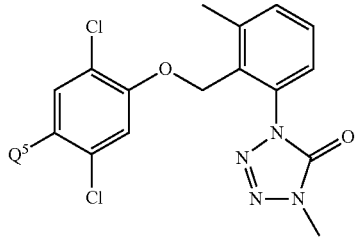
(EP1F)

[in the formula (EP1F), $Q^5$ represents a substituent corresponding to each of substituents Nos. 1 to 1023 indicated in Table 1 to Table 54 as below-mentioned];

Compounds EP1G-001~EP1G-1023 represent compounds represented by a formula:

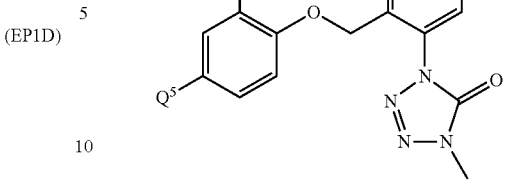
(EP1G)

[in the formula (EP1G), $Q^5$ represents a substituent corresponding to each of substituents Nos. 1 to 1023 indicated in Table 1 to Table 54 as below-mentioned];

Compounds EP1H-001~EP1H-1023 represent compounds represented by a formula:

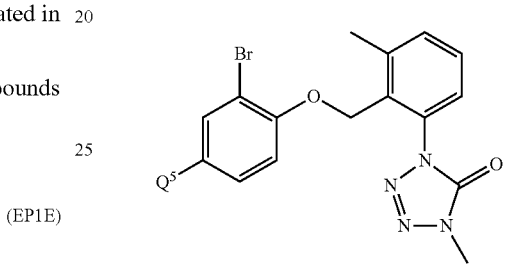
(EP1H)

[in the formula (EP1H), $Q^5$ represents a substituent corresponding to each of substituents Nos. 1 to 1023 indicated in Table 1 to Table 54 as below-mentioned];

Compounds EP1I-001~EP1I-1023 represent compounds represented by a formula:

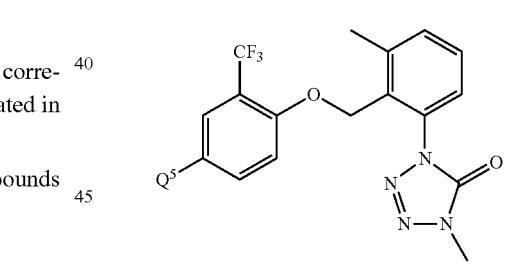
(EP1I)

[in the formula (EP1I), $Q^5$ represents a substituent corresponding to each of substituents Nos. 1 to 1023 indicated in Table 1 to Table 54 as below-mentioned];

Compounds EP1J-001~EP1J-1023 represent compounds represented by a formula:

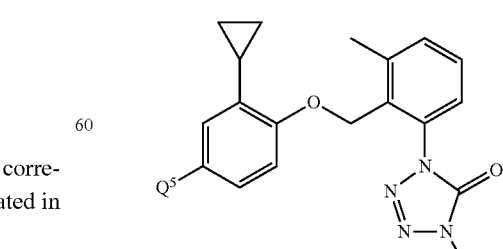
(EP1J)

[in the formula (EP1J), $Q^5$ represents a substituent corresponding to each of substituents Nos. 1 to 1023 indicated in Table 1 to Table 54 as below-mentioned];

Compounds EP2A-001~EP2A-1023 represent compounds represented by a formula:

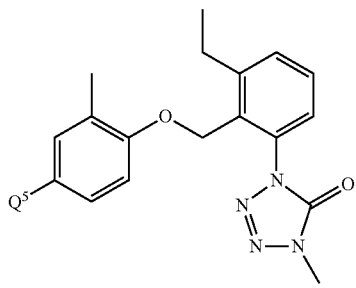

(EP2A)

[in the formula (EP2A), $Q^5$ represents a substituent corresponding to each of substituents Nos. 1 to 1023 indicated in Table 1 to Table 54 as below-mentioned];

Compounds EP2B-001~EP2B-1023 represent compounds represented by a formula:

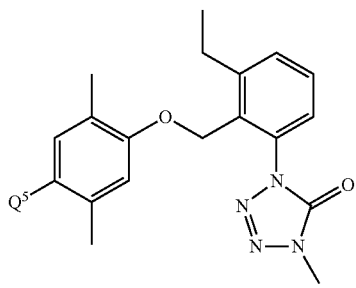

(EP2B)

[in the formula (EP2B), $Q^5$ represents a substituent corresponding to each of substituents Nos. 1 to 1023 indicated in Table 1 to Table 54 as below-mentioned];

Compounds EP2C-001~EP2C-1023 represent compounds represented by a formula:

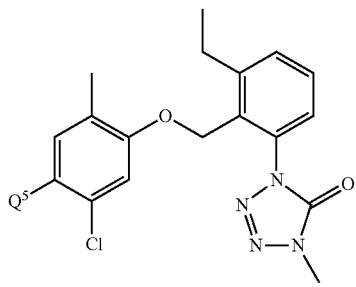

(EP2C)

[in the formula (EP2C), $Q^5$ represents a substituent corresponding to each of substituents Nos. 1 to 1023 indicated in Table 1 to Table 54 as below-mentioned];

Compounds EP2D-001~EP2D-1023 represent compounds represented by a formula:

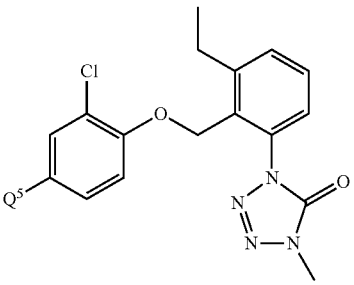

(EP2D)

[in the formula (EP2D), $Q^5$ represents a substituent corresponding to each of substituents Nos. 1 to 1023 indicated in Table 1 to Table 54 as below-mentioned];

Compounds EP2E-001~EP2E-1023 represent compounds represented by a formula:

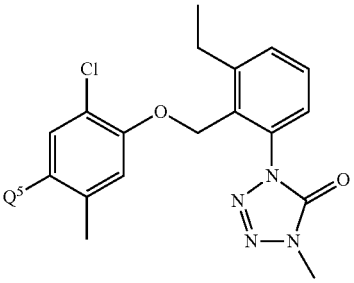

(EP2E)

[in the formula (EP2E), $Q^5$ represents a substituent corresponding to each of substituents Nos. 1 to 1023 indicated in Table 1 to Table 54 as below-mentioned];

Compounds EP2F-001~EP2F-1023 represent compounds represented by a formula:

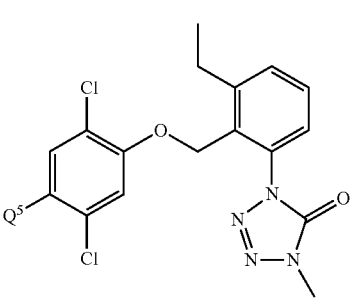

(EP2F)

[in the formula (EP2F), $Q^5$ represents a substituent corresponding to each of substituents Nos. 1 to 1023 indicated in Table 1 to Table 54 as below-mentioned];

Compounds EP2G-001~EP2G-1023 represent compounds represented by a formula:

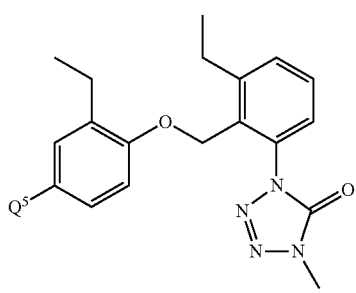
(EP2G)

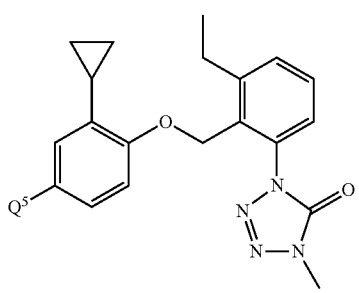
(EP2J)

[in the formula (EP2G), $Q^5$ represents a substituent corresponding to each of substituents Nos. 1 to 1023 indicated in Table 1 to Table 54 as below-mentioned];

Compounds EP2H-001~EP2H-1023 represent compounds represented by a formula:

[in the formula (EP2J), $Q^5$ represents a substituent corresponding to each of substituents Nos. 1 to 1023 indicated in Table 1 to Table 54 as below-mentioned];

Compounds EP3A-001~EP3A-1023 represent compounds represented by a formula:

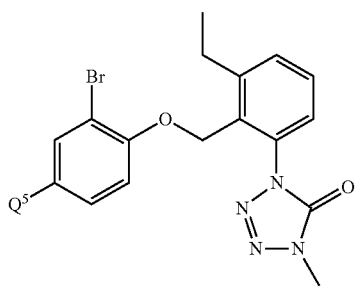
(EP2H)

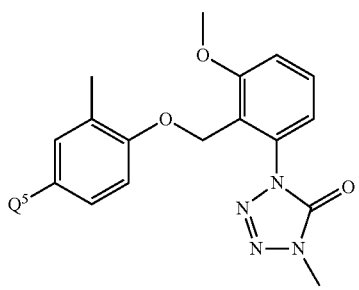
(EP3A)

[in the formula (EP2H), $Q^5$ represents a substituent corresponding to each of substituents Nos. 1 to 1023 indicated in Table 1 to Table 54 as below-mentioned];

Compounds EP2I-001~EP2I-1023 represent compounds represented by a formula:

[in the formula (EP3A), $Q^5$ represents a substituent corresponding to each of substituents Nos. 1 to 1023 indicated in Table 1 to Table 54 as below-mentioned];

Compounds EP3B-001~EP3B-1023 represent compounds represented by a formula:

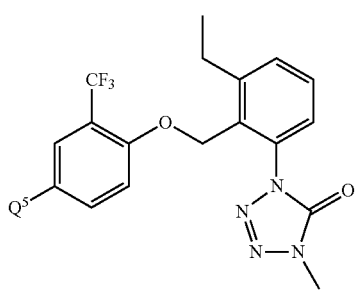
(EP2I)

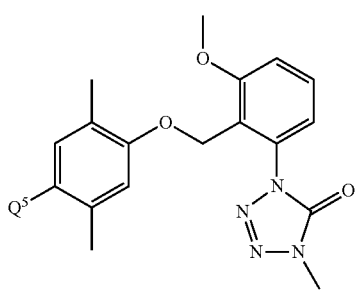
(EP3B)

[in the formula (EP2I), $Q^5$ represents a substituent corresponding to each of substituents Nos. 1 to 1023 indicated in Table 1 to Table 54 as below-mentioned];

Compounds EP2J-001~EP2J-1023 represent compounds represented by a formula:

[in the formula (EP3B), $Q^5$ represents a substituent corresponding to each of substituents Nos. 1 to 1023 indicated in Table 1 to Table 54 as below-mentioned];

Compounds EP3C-001~EP3C-1023 represent compounds represented by a formula:

(EP3C)

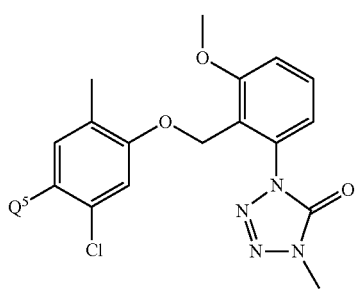

[in the formula (EP3C), $Q^5$ represents a substituent corresponding to each of substituents Nos. 1 to 1023 indicated in Table 1 to Table 54 as below-mentioned];

Compounds EP3D-001~EP3D-1023 represent compounds represented by a formula:

(EP3D)

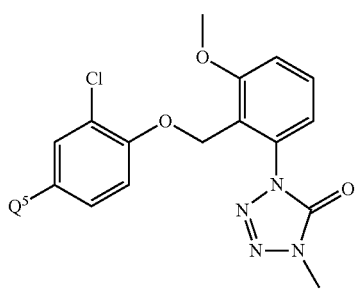

[in the formula (EP3D), $Q^5$ represents a substituent corresponding to each of substituents Nos. 1 to 1023 indicated in Table 1 to Table 54 as below-mentioned];

Compounds EP3E-001~EP3E-1023 represent compounds represented by a formula:

(EP3E)

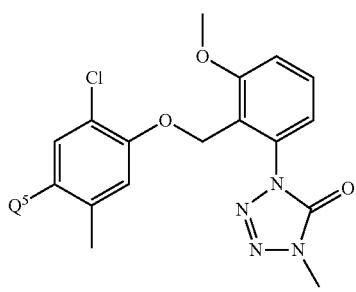

[in the formula (EP3E), $Q^5$ represents a substituent corresponding to each of substituents Nos. 1 to 1023 indicated in Table 1 to Table 54 as below-mentioned];

Compounds EP3F-001~EP3F-1023 represent compounds represented by a formula:

(EP3F)

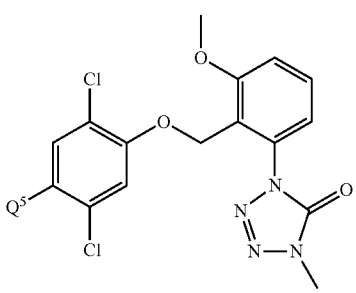

[in the formula (EP3F), $Q^5$ represents a substituent corresponding to each of substituents Nos. 1 to 1023 indicated in Table 1 to Table 54 as below-mentioned];

Compounds EP3G-001~EP3G-1023 represent compounds represented by a formula:

(EP3G)

[in the formula (EP3G), $Q^5$ represents a substituent corresponding to each of substituents Nos. 1 to 1023 indicated in Table 1 to Table 54 as below-mentioned];

Compounds EP3H-001~EP3H-1023 represent compounds represented by a formula:

(EP3H)

[in the formula (EP3H), $Q^5$ represents a substituent corresponding to each of substituents Nos. 1 to 1023 indicated in Table 1 to Table 54 as below-mentioned];

Compounds EP3I-001~EP3I-1023 represent compounds represented by a formula:

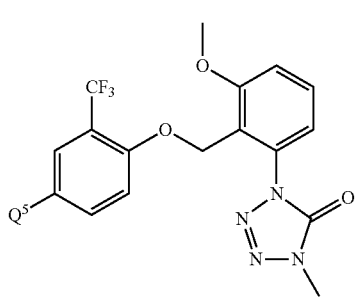
(EP3I)

[in the formula (EP3I), Q$^5$ represents a substituent corresponding to each of substituents Nos. 1 to 1023 indicated in Table 1 to Table 54 as below-mentioned];

Compounds EP3J-001~EP3J-1023 represent compounds represented by a formula:

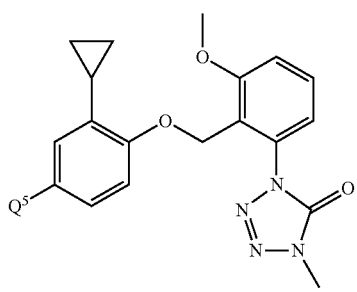
(EP3J)

[in the formula (EP3J), Q$^5$ represents a substituent corresponding to each of substituents Nos. 1 to 1023 indicated in Table 1 to Table 54 as below-mentioned];

Compounds EP4A-001~EP4A-1023 represent compounds represented by a formula:

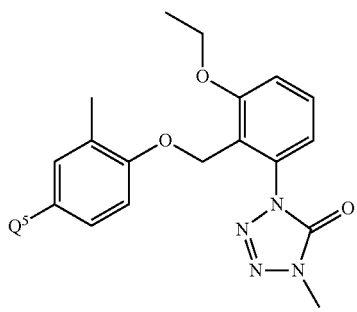
(EP4A)

[in the formula (EP4A), Q$^5$ represents a substituent corresponding to each of substituents Nos. 1 to 1023 indicated in Table 1 to Table 54 as below-mentioned];

Compounds EP4B-001~EP4B-1023 represent compounds represented by a formula:

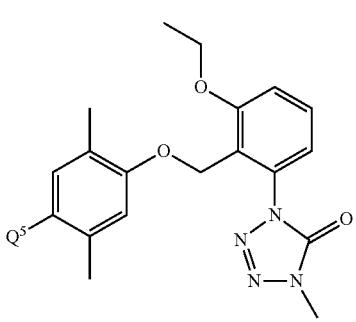
(EP4B)

[in the formula (EP4B), Q$^5$ represents a substituent corresponding to each of substituents Nos. 1 to 1023 indicated in Table 1 to Table 54 as below-mentioned];

Compounds EP4C-001~EP4C-1023 represent compounds represented by a formula:

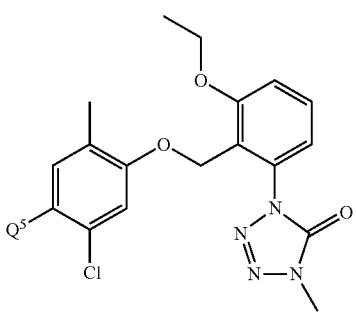
(EP4C)

[in the formula (EP4C), Q$^5$ represents a substituent corresponding to each of substituents Nos. 1 to 1023 indicated in Table 1 to Table 54 as below-mentioned];

Compounds EP4D-001~EP4D-1023 represent compounds represented by a formula:

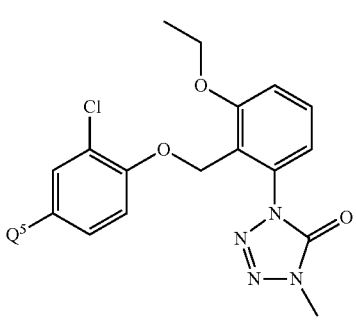
(EP4D)

[in the formula (EP4D), Q$^5$ represents a substituent corresponding to each of substituents Nos. 1 to 1023 indicated in Table 1 to Table 54 as below-mentioned];

Compounds EP4E-001~EP4E-1023 represent compounds represented by a formula:

(EP4E)

[in the formula (EP4E), $Q^5$ represents a substituent corresponding to each of substituents Nos. 1 to 1023 indicated in Table 1 to Table 54 as below-mentioned];

Compounds EP4F-001~EP4F-1023 represent compounds represented by a formula:

(EP4F)

[in the formula (EP4F), $Q^5$ represents a substituent corresponding to each of substituents Nos. 1 to 1023 indicated in Table 1 to Table 54 as below-mentioned];

Compounds EP4G-001~EP4G-1023 represent compounds represented by a formula:

(EP4G)

[in the formula (EP4G), $Q^5$ represents a substituent corresponding to each of substituents Nos. 1 to 1023 indicated in Table 1 to Table 54 as below-mentioned];

Compounds EP4H-001~EP4H-1023 represent compounds represented by a formula:

(EP4H)

[in the formula (EP4H), $Q^5$ represents a substituent corresponding to each of substituents Nos. 1 to 1023 indicated in Table 1 to Table 54 as below-mentioned];

Compounds EP4I-001~EP4I-1023 represent compounds represented by a formula:

(EP4I)

[in the formula (EP4I), $Q^5$ represents a substituent corresponding to each of substituents Nos. 1 to 1023 indicated in Table 1 to Table 54 as below-mentioned];

Compounds EP4J-001~EP4J-1023 represent compounds represented by a formula:

(EP4J)

[in the formula (EP4J), $Q^5$ represents a substituent corresponding to each of substituents Nos. 1 to 1023 indicated in Table 1 to Table 54 as below-mentioned];

Compounds EP5A-001~EP5A-1023 represent compounds represented by a formula:

(EP5A)

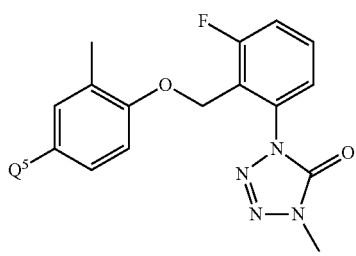

[in the formula (EP5A), Q$^5$ represents a substituent corresponding to each of substituents Nos. 1 to 1023 indicated in Table 1 to Table 54 as below-mentioned];

Compounds EP5B-001~EP5B-1023 represent compounds represented by a formula:

(EP5B)

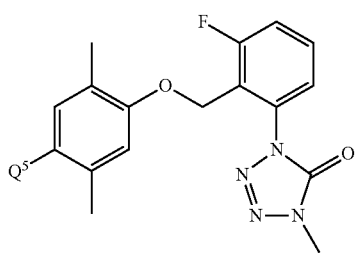

[in the formula (EP5B), Q$^5$ represents a substituent corresponding to each of substituents Nos. 1 to 1023 indicated in Table 1 to Table 54 as below-mentioned];

Compounds EP5C-001~EP5C-1023 represent compounds represented by a formula:

(EP5C)

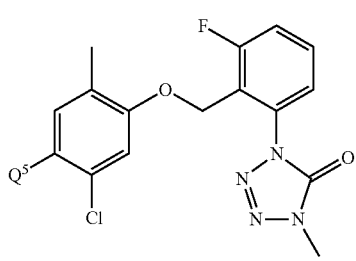

[in the formula (EP5C), Q$^5$ represents a substituent corresponding to each of substituents Nos. 1 to 1023 indicated in Table 1 to Table 54 as below-mentioned];

Compounds EP5D-001~EP5D-1023 represent compounds represented by a formula:

(EP5D)

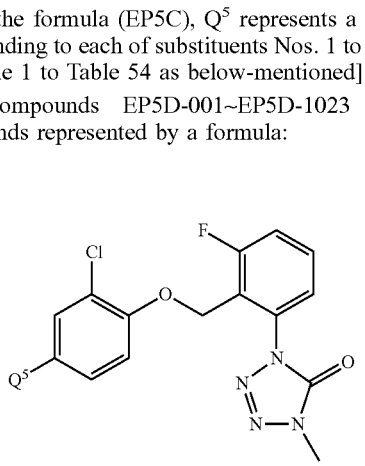

[in the formula (EP5D), Q$^5$ represents a substituent corresponding to each of substituents Nos. 1 to 1023 indicated in Table 1 to Table 54 as below-mentioned];

Compounds EP5E-001~EP5E-1023 represent compounds represented by a formula:

(EP5E)

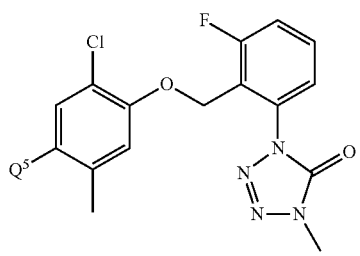

[in the formula (EP5E), Q$^5$ represents a substituent corresponding to each of substituents Nos. 1 to 1023 indicated in Table 1 to Table 54 as below-mentioned];

Compounds EP5F-001~EP5F-1023 represent compounds represented by a formula:

(EP5F)

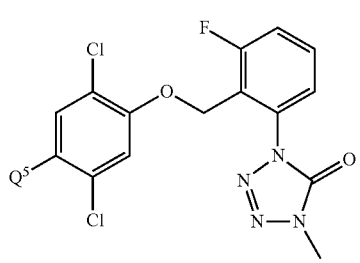

[in the formula (EP5F), Q$^5$ represents a substituent corresponding to each of substituents Nos. 1 to 1023 indicated in Table 1 to Table 54 as below-mentioned];

Compounds EP5G-001~EP5G-1023 represent compounds represented by a formula:

(EP5G)

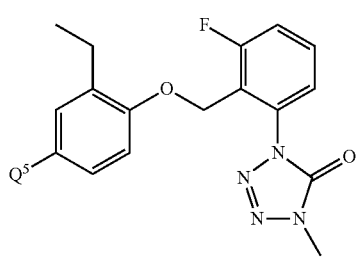

[in the formula (EP5G), Q$^5$ represents a substituent corresponding to each of substituents Nos. 1 to 1023 indicated in Table 1 to Table 54 as below-mentioned];

Compounds EP5H-001~EP5H-1023 represent compounds represented by a formula:

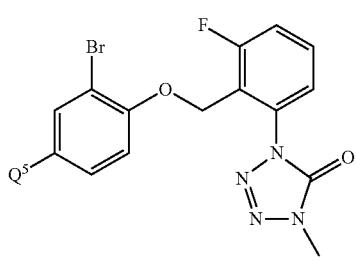

(EP5H)

[in the formula (EP5H), $Q^5$ represents a substituent corresponding to each of substituents Nos. 1 to 1023 indicated in Table 1 to Table 54 as below-mentioned];

Compounds EP5I-001~EP5I-1023 represent compounds represented by a formula:

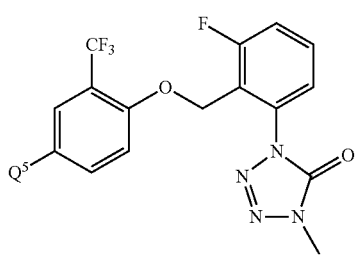

(EP5I)

[in the formula (EP5I), $Q^5$ represents a substituent corresponding to each of substituents Nos. 1 to 1023 indicated in Table 1 to Table 54 as below-mentioned];

Compounds EP5J-001~EP5J-1023 represent compounds represented by a formula:

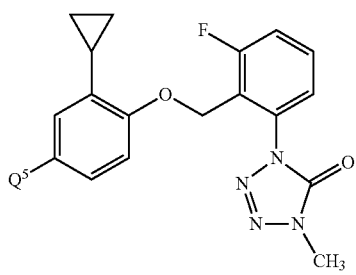

(EP5J)

[in the formula (EP5J), $Q^5$ represents a substituent corresponding to each of substituents Nos. 1 to 1023 indicated in Table 1 to Table 54 as below-mentioned];

Compounds EP6A-001~EP6A-1023 represent compounds represented by a formula:

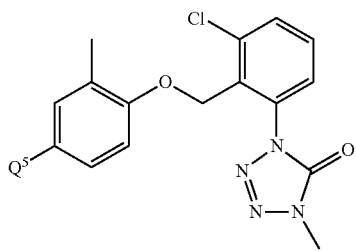

(EP6A)

[in the formula (EP6A), $Q^5$ represents a substituent corresponding to each of substituents Nos. 1 to 1023 indicated in Table 1 to Table 54 as below-mentioned];

Compounds EP6B-001~EP6B-1023 represent compounds represented by a formula:

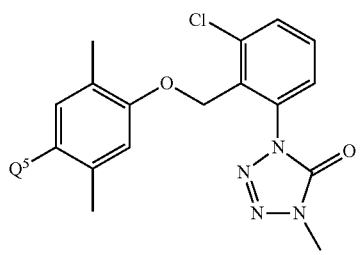

(EP6B)

[in the formula (EP6B), $Q^5$ represents a substituent corresponding to each of substituents Nos. 1 to 1023 indicated in Table 1 to Table 54 as below-mentioned];

Compounds EP6C-001~EP6C-1023 represent compounds represented by a formula:

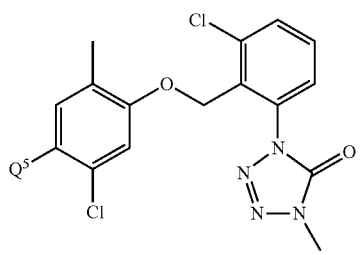

(EP6C)

[in the formula (EP6C), $Q^5$ represents a substituent corresponding to each of substituents Nos. 1 to 1023 indicated in Table 1 to Table 54 as below-mentioned];

Compounds EP6D-001~EP6D-1023 represent compounds represented by a formula:

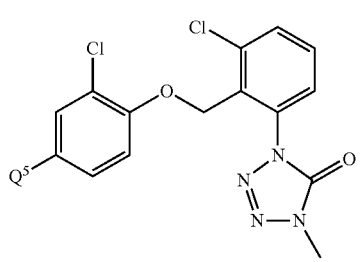

(EP6D)

[in the formula (EP6D), $Q^5$ represents a substituent corresponding to each of substituents Nos. 1 to 1023 indicated in Table 1 to Table 54 as below-mentioned];

Compounds EP6E-001~EP6E-1023 represent compounds represented by a formula:

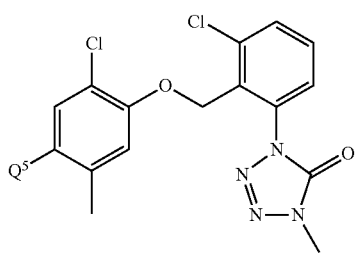
(EP6E)

[in the formula (EP6E), $Q^5$ represents a substituent corresponding to each of substituents Nos. 1 to 1023 indicated in Table 1 to Table 54 as below-mentioned];

Compounds EP6F-001~EP6F-1023 represent compounds represented by a formula:

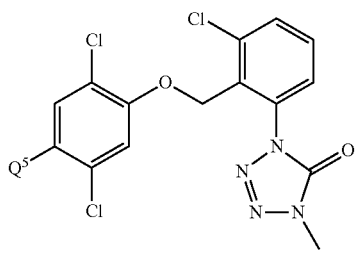
(EP6F)

[in the formula (EP6F), $Q^5$ represents a substituent corresponding to each of substituents Nos. 1 to 1023 indicated in Table 1 to Table 54 as below-mentioned];

Compounds EP6G-001~EP6G-1023 represent compounds represented by a formula:

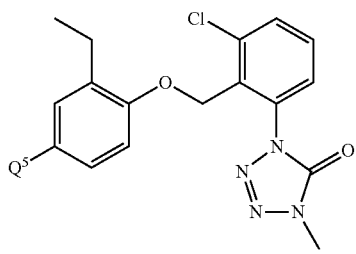
(EP6G)

[in the formula (EP6G), $Q^5$ represents a substituent corresponding to each of substituents Nos. 1 to 1023 indicated in Table 1 to Table 54 as below-mentioned];

Compounds EP6H-001~EP6H-1023 represent compounds represented by a formula:

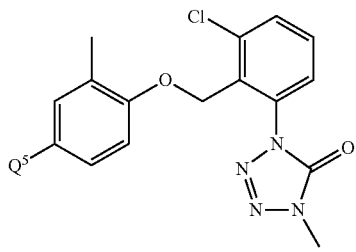
(EP6H)

[in the formula (EP6H), $Q^5$ represents a substituent corresponding to each of substituents Nos. 1 to 1023 indicated in Table 1 to Table 54 as below-mentioned];

Compounds EP6I-001~EP6I-1023 represent compounds represented by a formula:

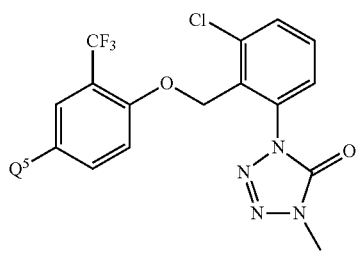
(EP6I)

[in the formula (EP6I), $Q^5$ represents a substituent corresponding to each of substituents Nos. 1 to 1023 indicated in Table 1 to Table 54 as below-mentioned];

Compounds EP6J-001~EP6J-1023 represent compounds represented by a formula:

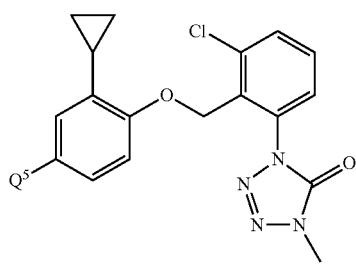
(EP6J)

[in the formula (EP6J), $Q^5$ represents a substituent corresponding to each of substituents Nos. 1 to 1023 indicated in Table 1 to Table 54 as below-mentioned];

Compounds EP7A-001~EP7A-1023 represent compounds represented by a formula:

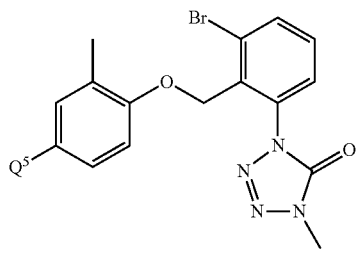
(EP7A)

[in the formula (EP7A), $Q^5$ represents a substituent corresponding to each of substituents Nos. 1 to 1023 indicated in Table 1 to Table 54 as below-mentioned];

Compounds EP7B-001~EP7B-1023 represent compounds represented by a formula:

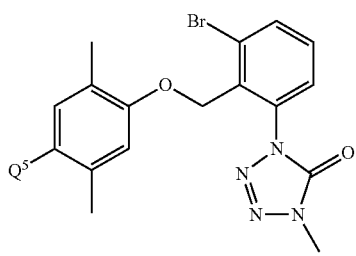
(EP7B)

[in the formula (EP7B), $Q^5$ represents a substituent corresponding to each of substituents Nos. 1 to 1023 indicated in Table 1 to Table 54 as below-mentioned];

Compounds EP7C-001~EP7C-1023 represent compounds represented by a formula:

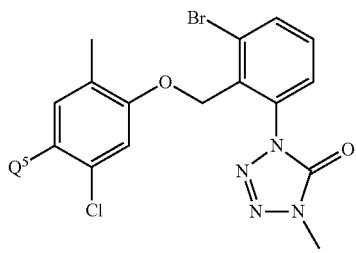
(EP7C)

[in the formula (EP7C), $Q^5$ represents a substituent corresponding to each of substituents Nos. 1 to 1023 indicated in Table 1 to Table 54 as below-mentioned];

Compounds EP7D-001~EP7D-1023 represent compounds

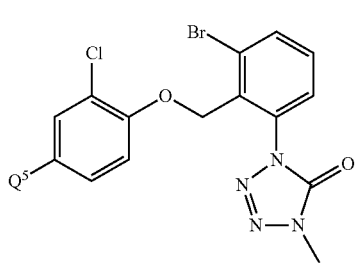
(EP7D)

[in the formula (EP7D), $Q^5$ represents a substituent corresponding to each of substituents Nos. 1 to 1023 indicated in Table 1 to Table 54 as below-mentioned];

Compounds EP7E-001~EP7E-1023 represent compounds represented by a formula:

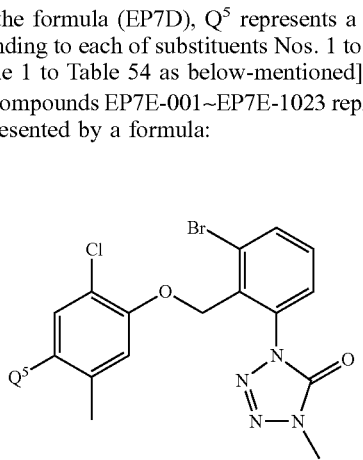
(EP7E)

[in the formula (EP7E), $Q^5$ represents a substituent corresponding to each of substituents Nos. 1 to 1023 indicated in Table 1 to Table 54 as below-mentioned];

Compounds EP7F-001~EP7E-1023 represent compounds represented by a formula:

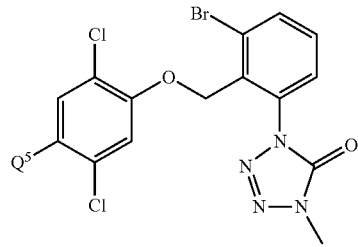
(EP7F)

[in the formula (EP7F), $Q^5$ represents a substituent corresponding to each of substituents Nos. 1 to 1023 indicated in Table 1 to Table 54 as below-mentioned];

Compounds EP7G-001~EP7G-1023 represent compounds represented by a formula:

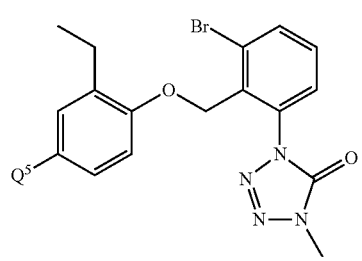
(EP7G)

[in the formula (EP7G), $Q^5$ represents a substituent corresponding to each of substituents Nos. 1 to 1023 indicated in Table 1 to Table 54 as below-mentioned];

Compounds EP7H-001~EP7H-1023 represent compounds represented by a formula:

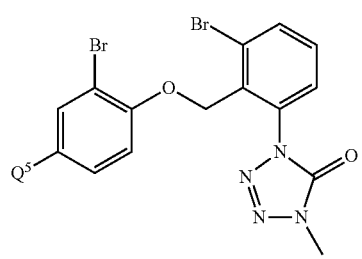
(EP7H)

[in the formula (EP7H), $Q^5$ represents a substituent corresponding to each of substituents Nos. 1 to 1023 indicated in Table 1 to Table 54 as below-mentioned];

Compounds EP7I-001~EP7I-1023 represent compounds represented by a formula:

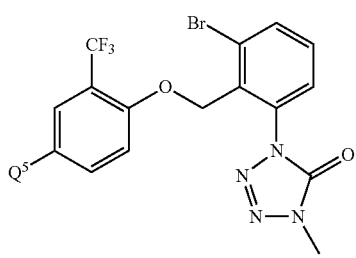

(EP7I)

[in the formula (EP7I), Q⁵ represents a substituent corresponding to each of substituents Nos. 1 to 1023 indicated in Table 1 to Table 54 as below-mentioned];
Compounds EP7J-001~EP7J-1023 represent compounds represented by a formula:

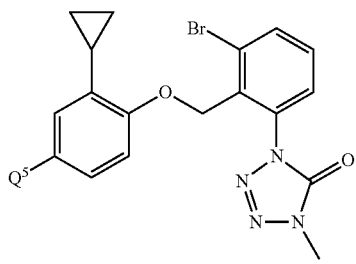

(EP7J)

[in the formula (EP7J), Q⁵ represents a substituent corresponding to each of substituents Nos. 1 to 1023 indicated in Table 1 to Table 54 as below-mentioned];
Compounds EP8A-001~EP8A-1023 represent compounds represented by a formula:

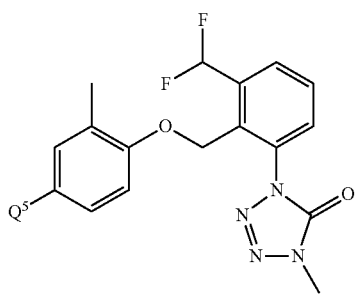

(EP8A)

[in the formula (EP8A), Q⁵ represents a substituent corresponding to each of substituents Nos. 1 to 1023 indicated in Table 1 to Table 54 as below-mentioned];
Compounds EP8B-001~EP8B-1023 represent compounds represented by a formula:

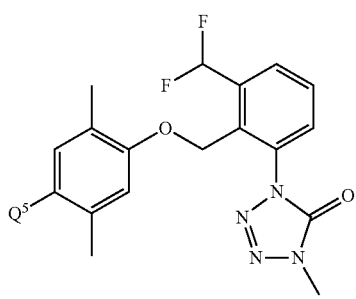

(EP8B)

[in the formula (EP8B), Q⁵ represents a substituent corresponding to each of substituents Nos. 1 to 1023 indicated in Table 1 to Table 54 as below-mentioned];
Compounds EP8C-001~EP8C-1023 represent compounds represented by a formula:

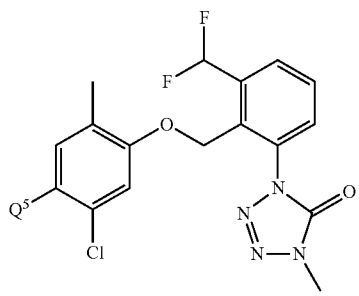

(EP8C)

[in the formula (EP8C), Q⁵ represents a substituent corresponding to each of substituents Nos. 1 to 1023 indicated in Table 1 to Table 54 as below-mentioned];
Compounds EP8D-001~EP8D-1023 represent compounds represented by a formula:

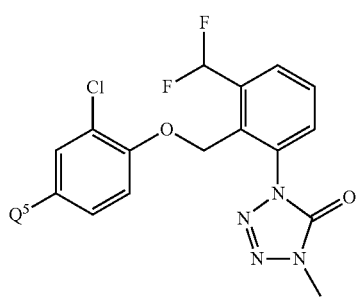

(EP8D)

[in the formula (EP8D), Q⁵ represents a substituent corresponding to each of substituents Nos. 1 to 1023 indicated in Table 1 to Table 54 as below-mentioned];
Compounds EP8E-001~EP8E-1023 represent compounds represented by a formula:

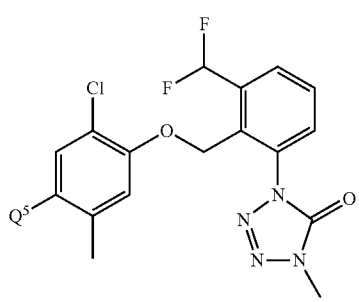

(EP8E)

[in the formula (EP8E), Q⁵ represents a substituent corresponding to each of substituents Nos. 1 to 1023 indicated in Table 1 to Table 54 as below-mentioned];
Compounds EP8F-001~EP8F-1023 represent compounds represented by a formula:

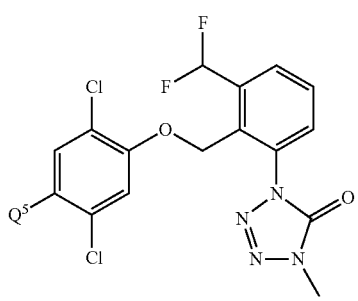
(EP8F)

[in the formula (EP8F), $Q^5$ represents a substituent corresponding to each of substituents Nos. 1 to 1023 indicated in Table 1 to Table 54 as below-mentioned];

Compounds EP8G-001~EP8G-1023 represent compounds represented by a formula:

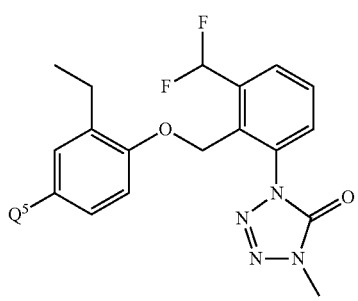
(EP8G)

[in the formula (EP8G), $Q^5$ represents a substituent corresponding to each of substituents Nos. 1 to 1023 indicated in Table 1 to Table 54 as below-mentioned];

Compounds EP8H-001~EP8H-1023 represent compounds represented by a formula:

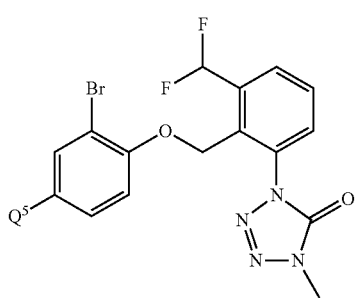
(EP8H)

[in the formula (EP8H), $Q^5$ represents a substituent corresponding to each of substituents Nos. 1 to 1023 indicated in Table 1 to Table 54 as below-mentioned];

Compounds EP8I-001~EP8I-1023 represent compounds represented by a formula:

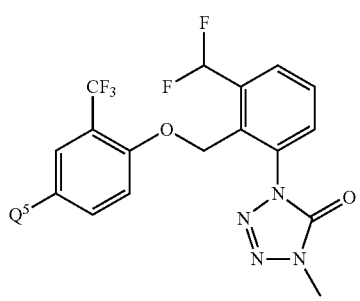
(EP8I)

[in the formula (EP8I), $Q^5$ represents a substituent corresponding to each of substituents Nos. 1 to 1023 indicated in Table 1 to Table 54 as below-mentioned];

Compounds EP8J-001~EP8J-1023 represent compounds represented by a formula:

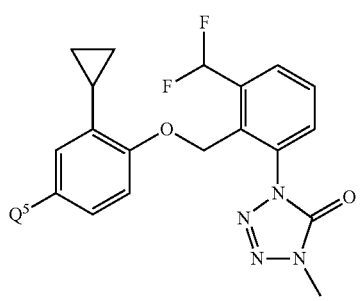
(EP8J)

[in the formula (EP8J), $Q^5$ represents a substituent corresponding to each of substituents Nos. 1 to 1023 indicated in Table 1 to Table 54 as below-mentioned];

Compounds EP9A-001~EP9A-1023 represent compounds represented by a formula:

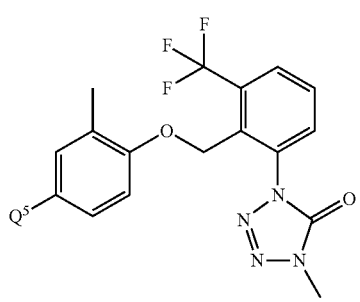
(EP9A)

[in the formula (EP9A), $Q^5$ represents a substituent corresponding to each of substituents Nos. 1 to 1023 indicated in Table 1 to Table 54 as below-mentioned];

Compounds EP9B-001~EP9B-1023 represent compounds represented by a formula:

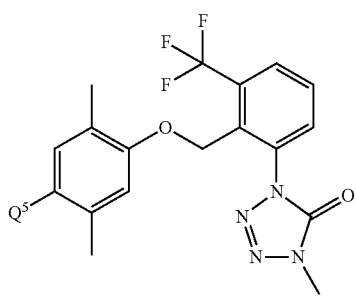

(EP9B)

[in the formula (EP9B), $Q^5$ represents a substituent corresponding to each of substituents Nos. 1 to 1023 indicated in Table 1 to Table 54 as below-mentioned];

Compounds EP9C-001~EP9C-1023 represent compounds

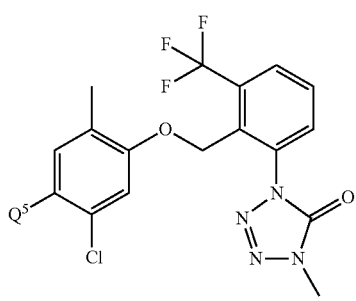

(EP9C)

[in the formula (EP9C), $Q^5$ represents a substituent corresponding to each of substituents Nos. 1 to 1023 indicated in Table 1 to Table 54 as below-mentioned];

Compounds EP9D-001~EP9D-1023 represent compounds represented by a formula:

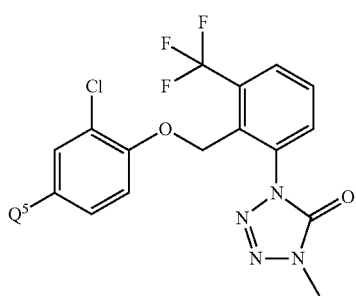

(EP9D)

[in the formula (EP9D), $Q^5$ represents a substituent corresponding to each of substituents Nos. 1 to 1023 indicated in Table 1 to Table 54 as below-mentioned];

Compounds EP9E-001~EP9E-1023 represent compounds represented by a formula:

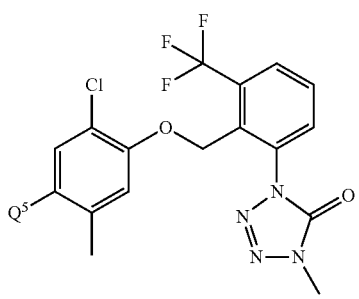

(EP9E)

[in the formula (EP9E), $Q^5$ represents a substituent corresponding to each of substituents Nos. 1 to 1023 indicated in Table 1 to Table 54 as below-mentioned];

Compounds EP9F-001~EP9F-1023 represent compounds represented by a formula:

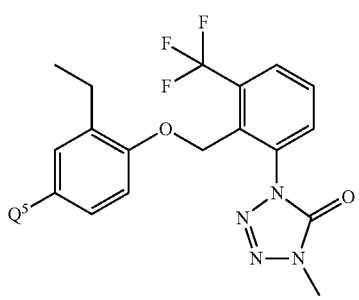

(EP9F)

[in the formula (EP9F), $Q^5$ represents a substituent corresponding to each of substituents Nos. 1 to 1023 indicated in Table 1 to Table 54 as below-mentioned];

Compounds EP9G-001~EP9G-1023 represent compounds represented by a formula:

(EP9G)

[in the formula (EP9G), $Q^5$ represents a substituent corresponding to each of substituents Nos. 1 to 1023 indicated in Table 1 to Table 54 as below-mentioned];

Compounds EP9H-001~EP9H-1023 represent compounds represented by a formula:

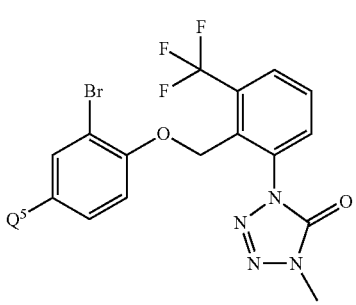

[in the formula (EP9H), $Q^5$ represents a substituent corresponding to each of substituents Nos. 1 to 1023 indicated in Table 1 to Table 54 as below-mentioned];

Compounds EP9I-001~EP9I-1023 represent compounds represented by a formula:

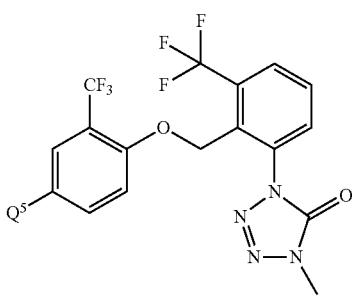

[in the formula (EP9I), $Q^5$ represents a substituent corresponding to each of substituents Nos. 1 to 1023 indicated in Table 1 to Table 54 as below-mentioned]; and Compounds EP9J-001~EP9J-1023 represent compounds represented by a formula:

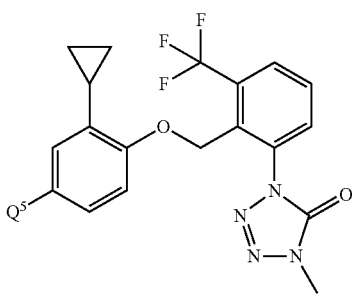

[in the formula (EP9J), $Q^5$ represents a substituent corresponding to each of substituents Nos. 1 to 1023 indicated in Table 1 to Table 54 as below-mentioned].

TABLE 1

| substituents Nos. | $Q^5$ |
|---|---|
| 1 | pyrazol-1-yl group |
| 2 | 4-fluoro-pyrazol-1-yl group |
| 3 | 4-chloro-pyrazol-1-yl group |
| 4 | 4-bromo-pyrazol-1-yl group |

TABLE 1-continued

| substituents Nos. | $Q^5$ |
|---|---|
| 5 | 4-methyl-pyrazol-1-yl group |
| 6 | 4-ethyl-pyrazol-1-yl group |
| 7 | 4-propyl-pyrazol-1-yl group |
| 8 | 4-isopropyl-pyrazol-1-yl group |
| 9 | 4-cyclopropyl-pyrazol-1-yl group |
| 10 | 4-difluoromethyl-pyrazol-1-yl group |
| 11 | 4-cyano-pyrazol-1-yl group |
| 12 | 4-ethynyl-pyrazol-1-yl group |
| 13 | 4-propynyl-pyrazol-1-yl group |
| 14 | 5-methyl-pyrazol-1-yl group |
| 15 | 4-fluoro-5-methyl-pyrazol-1-yl group |
| 16 | 4-chloro-5-methyl-pyrazol-1-yl group |
| 17 | 4-bromo-5-methyl-pyrazol-1-yl group |
| 18 | 4,5-dimethylpyrazol-1-yl group |
| 19 | 4-ethyl-5-methyl-pyrazol-1-yl group |
| 20 | 5-methyl-4-propyl-pyrazol-1-yl group |
| 21 | 4-isopropyl-5-methyl-pyrazol-1-yl group |
| 22 | 4-cyclopropyl-5-methyl-pyrazol-1-yl group |
| 23 | 4-difluoromethyl-5-methyl-pyrazol-1-yl group |
| 24 | 4-cyano-5-methyl-pyrazol-1-yl group |
| 25 | 4-ethynyl-5-methyl-pyrazol-1-yl group |
| 26 | 5-methyl-4-propynyl-pyrazol-1-yl group |
| 27 | 5-ethylpyrazol-1-yl group |
| 28 | 4-fluoro-5-ethylpyrazol-1-yl group |
| 29 | 4-chloro-5-ethylpyrazol-1-yl group |

TABLE 2

| substituents Nos. | $Q^5$ |
|---|---|
| 30 | 4-bromo-5-ethyl-pyrazol-1-yl group |
| 31 | 5-ethyl-4-methyl-pyrazol-1-yl group |
| 32 | 4,5-diethyl-pyrazol-1-yl group |
| 33 | 4,5,6,7-tetrahydro-indazol-1-yl group |
| 34 | 3-methyl-4,5,6,7-tetrahydro-indazol-1-yl group |
| 35 | 4,5,6,7-tetrahydro-indazol-2-yl group |
| 36 | 3-methyl-4,5,6,7-tetrahydro-indazol-2-yl group |
| 37 | 1,4,5,6-tetrahydro-cyclopentapyrazol-1-yl group |
| 38 | 3-methyl-4,5,6,7-tetrahydro-indazol-2-yl group |
| 39 | 3-methyl-pyrazol-1-yl group |
| 40 | 4-fluoro-3-methyl-pyrazol-1-yl group |
| 41 | 4-chloro-3-methyl-pyrazol-1-yl group |
| 42 | 4-bromo-3-methyl-pyrazol-1-yl group |
| 43 | 3,4-dimethyl-pyrazol-1-yl group |
| 44 | 4-ethyl-3-methyl-pyrazol-1-yl group |
| 45 | 4-propyl-3-methyl-pyrazol-1-yl group |
| 46 | 4-isopropyl-3-methyl-pyrazol-1-yl group |
| 47 | 4-cyclopropyl-3-methyl-pyrazol-1-yl group |
| 48 | 4-difluoromethyl-3-methyl-pyrazol-1-yl group |
| 49 | 3-methyl-4-trifluoromethyl-pyrazol-1-yl group |
| 50 | 4-cyano-3-methyl-pyrazol-1-yl group |
| 51 | 4-ethynyl-3-methylpyrazol-1-yl group |
| 52 | 3-methyl-4-propynyl-pyrazol-1-yl group |
| 53 | 3,5-dimethyl-pyrazol-1-yl group |
| 54 | 4-fluoro-3,5-dimethyl-pyrazol-1-yl group |
| 55 | 4-chloro-3,5-dimethyl-pyrazol-1-yl group |
| 56 | 4-bromo-3,5-dimethyl-pyrazol-1-yl group |
| 57 | 3,4,5-trimethyl-pyrazol-1-yl group |
| 58 | 4-ethyl-3,5-dimethyl-pyrazol-1-yl group |

TABLE 3

| substituents Nos. | $Q^5$ |
|---|---|
| 59 | 3,5-dimethyl-4-propyl-pyrazol-1-yl group |
| 60 | 3,5-dimethyl-4-isopropyl-pyrazol-1-yl group |
| 61 | 3,5-dimethyl-4-cyclopropyl-pyrazol-1-yl group |
| 62 | 4-difluoromethyl-3,5-dimethyl-pyrazol-1-yl group |
| 63 | 4-cyano-3,5-dimethyl-pyrazol-1-yl group |
| 64 | 4-ethynyl-3,5-dimethyl-pyrazol-1-yl group |

TABLE 3-continued

| substituents Nos. | Q⁵ |
|---|---|
| 65 | 3,5-dimethyl-4-propynyl-pyrazol-1-yl group |
| 66 | 5-ethyl-3-methyl-pyrazol-1-yl group |
| 67 | 5-ethyl-4-fluoro-3-methyl-pyrazol-1-yl group |
| 68 | 4-chloro-5-ethyl-3-methyl-pyrazol-1-yl group |
| 69 | 4-bromo-5-ethyl-3-methyl-pyrazol-1-yl group |
| 70 | 3,4-dimethyl-5-ethyl-pyrazol-1-yl group |
| 71 | 4,5-diethyl-3-methyl-pyrazol-1-yl group |
| 72 | 5-ethyl-4-propyl-3-methyl-pyrazol-1-yl group |
| 73 | 5-ethyl-4-isopropyl-3-methyl-pyrazol-1-yl group |
| 74 | 5-ethyl-4-cyclopropyl-3-methyl-pyrazol-1-yl group |
| 75 | 5-ethyl-4-difluoromethyl-3-methyl-pyrazol-1-yl group |
| 76 | 4-cyano-5-ethyl-3-methyl-pyrazol-1-yl group |
| 77 | 5-ethyl-4-ethynyl-3-methyl-pyrazol-1-yl group |
| 78 | 5-ethyl-3-methyl-4-propynyl-pyrazol-1-yl group |
| 79 | 3,5-dimethyl-4-methoxy-pyrazol-1-yl group |
| 80 | 4-ethoxy-3,5-dimethyl-pyrazol-1-yl group |
| 81 | 3,5-dimethyl-4-(2-propynyloxy)-pyrazol-1-yl group |
| 82 | 3,5-dimethyl-4-trifluoromethyl-pyrazol-1-yl group |
| 83 | 3-ethyl-pyrazol-1-yl group |
| 84 | 4-fluoro-3-ethyl-pyrazol-1-yl group |
| 85 | 4-chloro-3-ethyl-pyrazol-1-yl group |
| 86 | 4-bromo-3-ethyl-pyrazol-1-yl group |
| 87 | 3-ethyl-4-methyl-pyrazol-1-yl group |

TABLE 4

| substituents Nos. | Q⁵ |
|---|---|
| 88 | 3,4-diethylpyrazol-1-yl group |
| 89 | 3-ethyl-4-propyl-pyrazol-1-yl group |
| 90 | 3-ethyl-4-isopropyl-pyrazol-1-yl group |
| 91 | 4-cyclopropyl-3-ethylpyrazol-1-yl group |
| 92 | 3-ethyl-4-difluoromethyl-pyrazol-1-yl group |
| 93 | 4-cyano-3-ethylpyrazol-1-yl group |
| 94 | 3-ethyl-4-ethynyl-pyrazol-1-yl group |
| 95 | 3-ethyl-4-propynyl-pyrazol-1-yl group |
| 96 | 3-ethyl-5-methyl-pyrazol-1-yl group |
| 97 | 3-ethyl-4-fluoro-5-methyl-pyrazol-1-yl group |
| 98 | 4-chloro-3-ethyl-5-methyl-pyrazol-1-yl group |
| 99 | 4-bromo-3-ethyl-5-methyl-pyrazol-1-yl group |
| 100 | 3-ethyl-4,5-dimethyl-pyrazol-1-yl group |
| 101 | 3,4-diethyl-5-methyl-pyrazol-1-yl group |
| 102 | 3-ethyl-5-methyl-4-propyl-pyrazol-1-yl group |
| 103 | 3-ethyl-4-isopropyl-5-methyl-pyrazol-1-yl group |

TABLE 5

| substituents Nos. | Q⁵ |
|---|---|
| 104 | 4-difluoromethyl-3-ethyl-5-methyl-pyrazol-1-yl group |
| 105 | 3-ethyl-5-methyl-4-trifluoromethyl-pyrazol-1-yl group |
| 106 | 3-ethyl-4-ethynyl-5-methyl-pyrazol-1-yl group |
| 107 | 3-ethyl-5-methyl-4-propynyl-pyrazol-1-yl group |
| 108 | 3-cyclopropyl-pyrazol-1-yl group |
| 109 | 3-cyclopropyl-4-fluoro-pyrazol-1-yl group |
| 110 | 4-chloro-3-cyclopropyl-pyrazol-1-yl group |
| 111 | 4-bromo-3-cyclopropyl-pyrazol-1-yl group |
| 112 | 3-cyclopropyl-4-methyl-pyrazol-1-yl group |
| 113 | 3-cyclopropyl-4-ethyl-pyrazol-1-yl group |
| 114 | 3-cyclopropyl-4-propyl-pyrazol-1-yl group |
| 115 | 3,5-dimethyl-4-(2-propynyloxy)-1-yl group |
| 116 | 3,5-dimethyl-4-(2-butynyloxy)-1-yl group |

TABLE 6

| substituents Nos. | Q⁵ |
|---|---|
| 117 | 3-cyclopropyl-4-isopropyl-pyrazol-1-yl group |
| 118 | 3,5-dicyclopropyl-pyrazol-1-yl group |
| 119 | 3-cyclopropyl-4-difluoromethyl-pyrazol-1-yl group |
| 120 | 3-cyclopropyl-4-trifluoromethyl-pyrazol-1-yl group |
| 121 | 3-cyclopropyl-4-ethynyl-pyrazol-1-yl group |
| 122 | 3-cyclopropyl-4-propynyl-pyrazol-1-yl group |
| 123 | 3-cyclopropyl-5-methyl-pyrazol-1-yl group |
| 124 | 3-cyclopropyl-4-fluoro-5-methyl-pyrazol-1-yl group |
| 125 | 4-chloro-3-cyclopropyl-5-methyl-pyrazol-1-yl group |
| 126 | 4-bromo-3-cyclopropyl-5-methyl-pyrazol-1-yl group |
| 127 | 3-cyclopropyl-4,5-dimethylpyrazol-1-yl group |
| 128 | 3-cyclopropyl-4-ethyl-5-methyl-pyrazol-1-yl group |
| 129 | 3-cyclopropyl-4-propyl-5-methyl-pyrazol-1-yl group |
| 130 | 3-cyclopropyl-4-isopropyl-5-methyl-pyrazol-1-yl group |
| 131 | 3,5-dicyclopropyl-4-methyl-pyrazol-1-yl |

TABLE 7

| substituents Nos. | Q⁵ |
|---|---|
| 132 | 3-cyclopropyl-4-difluoromethyl-5-methyl-pyrazol-1-yl group |
| 133 | 3-cyclopropyl-4-trifluoromethyl5-methyl-pyrazol-1-yl group |
| 134 | 3-cyclopropyl-4-ethynyl-5-methyl-pyrazol-1-yl group |
| 135 | 3-cyclopropyl-4-propynyl-5-methyl-pyrazol-1-yl group |
| 136 | 3-difluoromethyl-pyrazol-1-yl group |
| 137 | 3-difluoromethyl-4-methyl-pyrazol-1-yl group |
| 138 | 3-difluoromethyl-4-ethyl-pyrazol-1-yl group |
| 139 | 3-difluoromethyl-4-propyl-pyrazol-1-yl group |
| 140 | 3-difluoromethyl-4-isopropyl-pyrazol-1-yl group |
| 141 | 3-difluoromethyl-4-cyclopropyl-pyrazol-1-yl group |
| 142 | 3-difluoromethyl-4-ethynyl-pyrazol-1-yl group |
| 143 | 3-difluoromethyl-4-propynyl-pyrazol-1-yl group |
| 144 | 3-difluoromethyl-4-isopropyl-pyrazol-1-yl group |
| 145 | 3-difluoromethyl-4-fluoro-pyrazol-1-yl group |

TABLE 8

| substituents Nos. | Q⁵ |
|---|---|
| 146 | 4-chloro-3-difluoromethyl-pyrazol-1-yl group |
| 147 | 4-bromo-3-difluoromethyl-pyrazol-1-yl group |
| 148 | 3-trifluoromethyl-pyrazol-1-yl group |
| 149 | 4-fluoro-3-trifluoromethyl-pyrazol-1-yl group |
| 150 | 4-chloro-3-trifluoromethyl-pyrazol-1-yl group |
| 151 | 4-bromo-3-trifluoromethyl-pyrazol-1-yl group |
| 152 | 4-methyl-3-trifluoromethyl-pyrazol-1-yl group |
| 153 | 4-ethyl-3-trifluoromethyl-pyrazol-1-yl group |
| 154 | 4-propyl-3-trifluoromethyl-pyrazol-1-yl group |
| 155 | 4-isopropyl-3-trifluoromethyl-pyrazol-1-yl group |
| 156 | 4-cyclopropyl-3-trifluoromethyl-pyrazol-1-yl group |
| 157 | 4-difluoromethyl-3-trifluoromethyl-pyrazol-1-yl group |
| 158 | 3,4-bistrifluoromethyl-pyrazol-1-yl group |
| 159 | 4-ethynyl-3-trifluoromethyl-pyrazol-1-yl group |

TABLE 9

| substituents Nos. | $Q^5$ |
|---|---|
| 160 | 4-propynyl-3-trifluoromethyl-pyrazol-1-yl group |
| 161 | 3,5-dimethyl-4-trifluoromethyl-pyrazol-1-yl group |
| 162 | 3-propyl-pyrazol-1-yl group |
| 163 | 3-propyl-4-methyl-pyrazol-1-yl group |
| 164 | 3-propyl-4,5-dimethyl-pyrazol-1-yl group |
| 165 | 3-isopropyl-pyrazol-1-yl group |
| 166 | 3-isopropyl-4-methyl-pyrazol-1-yl group |
| 167 | 3-isopropyl-4,5-dimethyl-pyrazol-1-yl group |
| 168 | 3-tert-butyl-pyrazol-1-yl group |
| 169 | 4-methyl-3-tert-butyl-pyrazol-1-yl group |
| 170 | 4,5-dimethyl-3-tert-butyl-pyrazol-1-yl group |
| 171 | 5-methyl-3-propyl-pyrazol-1-yl group |
| 172 | 3-isopropyl-5-methyl-pyrazol-1-yl group |
| 173 | 5-methyl-3-tert-butyl-pyrazol-1-yl group |
| 174 | 3-ethyl-4-methoxy-5-methyl-pyrazol-1-yl group |

TABLE 10

| substituents Nos. | $Q^5$ |
|---|---|
| 175 | 1-methyl-1H-pyrazol-3-yl group |
| 176 | 1-ethyl-1H-pyrazol-3-yl group |
| 177 | 1-isopropyl-1H-pyrazol-3-yl group |
| 178 | 1-difluoroethyl-1H-pyrazol-3-yl group |
| 179 | 1-(2-propyny)-1H-pyrazol-3-yl group |
| 180 | 1-(2-butynyl)-1H-pyrazol-3-yl group |
| 181 | 1-cyclopropylmethyl-1H-pyrazol-3-yl group |
| 182 | 1-trifluoroethyl-1H-pyrazol-3-yl group |
| 183 | 1-propyl-1H-pyrazol-3-yl group |
| 184 | 1-butyl-1H-pyrazol-3-yl group |
| 185 | 1-isobutyl-1H-pyrazol-3-yl group |
| 186 | 1-(3-methylbutyl)-1H-pyrazol-3-yl group |
| 187 | 1-(4-methyl-pentyl)-1H-pyrazol-3-yl group |
| 188 | 1,4-dimethyl-1H-pyrazol-3-yl group |
| 189 | 1-ethyl-4-methyl-1H-pyrazol-3-yl group |

TABLE 11

| substituents Nos. | $Q^5$ |
|---|---|
| 190 | 1-isopropyl-4-methyl-1H-pyrazol-3-yl group |
| 191 | 1-(2,2-difluoroethyl)-4-methyl-1H-pyrazol-3-yl group |
| 192 | 1-(2-propynyl)-4-methyl-1H-pyrazol-3-yl group |
| 193 | 1-(2-butynyl)-4-methyl-1H-pyrazol-3-yl group |
| 194 | 1-cyclopropylmethyl-4-methyl-1H-pyrazol-3-yl group |
| 195 | 1-(2,2,2-trifluoroethyl)-4-methyl-1H-pyrazol-3-yl group |
| 196 | 4-methyl-1-propyl-1H-pyrazol-3-yl group |
| 197 | 1-butyl-4-methyl-1H-pyrazol-3-yl group |
| 198 | 1-isobutyl-4-methyl-1H-pyrazol-3-yl group |
| 199 | 1-(3-methylbutyl)-4-methyl-1H-pyrazol-3-yl group |
| 200 | 1-(4-methyl-pentyl)-4-methyl-1H-pyrazol-3-yl group |
| 201 | 5-ethyl-1-methyl-1H-pyrazol-3-yl group |
| 202 | 4-ethyl-1-isopropyl-1H-pyrazol-3-yl group |
| 203 | 4-ethyl-1-(2,2-difluoroethyl)-1H-pyrazol-3-yl group |

TABLE 12

| substituents Nos. | $Q^5$ |
|---|---|
| 204 | 4-ethyl-1-(2-propynyl)-1H-pyrazol-3-yl group |
| 205 | 1-(2-butynyl)-4-ethyl-1H-pyrazol-3-yl group |
| 206 | 4-ethyl-1-(2,2,2-trifluoroethyl)-1H-pyrazol-3-yl group |
| 207 | 4-ethyl-1-(2,2-difluoroethyl)-1H-pyrazol-3-yl group |
| 208 | 4-ethyl-1-propyl-1H-pyrazol-3-yl group |
| 209 | 1-butyl-4-ethyl-1H-pyrazol-3-yl group |
| 210 | 4-ethyl-1-isobutyl1H-pyrazol-3-yl group |
| 211 | 4-ethyl-1-(3-methylbutyl)-1H-pyrazol-3-yl group |
| 212 | 4-ethyl-1-(4-methyl-pentyl)-1H-pyrazol-3-yl group |
| 213 | 4-fluoro-1-methyl-1H-pyrazol-3-yl group |
| 214 | 1-ethyl-4-fluoro-1H-pyrazol-3-yl group |
| 215 | 4-fluoro-1-isopropyl-1H-pyrazol-3-yl group |
| 216 | 4-fluoro-1-(2,2-difluoroethyl)-1H-pyrazol-3-yl group |
| 217 | 4-fluoro-1-(2-propynyl)-1H-pyrazol-3-yl group |
| 218 | 1-(2-butynyl)-4-fluoro-1H-pyrazol-3-yl group |

TABLE 13

| substituents Nos. | $Q^5$ |
|---|---|
| 219 | 1-cyclopropylmethyl-4-fluoro-1H-pyrazol-3-yl group |
| 220 | 4-fluoro-1-(2,2,2-trifluoroethyl)-1H-pyrazol-3-yl group |
| 221 | 4-fluoro-1-propyl-1H-pyrazol-3-yl group |
| 222 | 1-butyl-4-fluoro-1H-pyrazol-3-yl group |
| 223 | 4-fluoro-1-isobutyl-1H-pyrazol-3-yl group |
| 224 | 4-fluoro-1-(3-methylbutyl)-1H-pyrazol-3-yl group |
| 225 | 4-fluoro-1-(4-methyl-pentyl)-1H-pyrazol-3-yl group |
| 226 | 4-chloro-1-methyl-1H-pyrazol-3-yl group |
| 227 | 4-chloro-1-ethyl-1H-pyrazol-3-yl group |
| 228 | 4-chloro-1-isopropyl-1H-pyrazol-3-yl group |
| 229 | 4-chloro-1-cyclopropylmethyl-1H-pyrazol-3-yl group |
| 230 | 4-chloro-1-(2,2,2-trifluoroethyl)-1H-pyrazol-3-yl group |
| 231 | 4-chloro-1-propyl-1H-pyrazol-3-yl group |
| 232 | 1-butyl-4-chloro-1H-pyrazol-3-yl group |

TABLE 14

| substituents Nos. | $Q^5$ |
|---|---|
| 233 | 4-chloro-1-isobutyl-1H-pyrazol-3-yl group |
| 234 | 4-chloro-1-(3-methylbutyl)-1H-pyrazol-3-yl group |
| 235 | 4-chloro-1-(4-methyl-pentyl)-1H-pyrazol-3-yl group |
| 236 | 1,4-diethyl-1H-pyrazol-3-yl |
| 237 | 4-bromo-1-methyl-1H-pyrazol-3-yl group |
| 238 | 4-bromo-1-ethyl-1H-pyrazol-3-yl group |
| 239 | 4-bromo-1-isopropyl-1H-pyrazol-3-yl group |
| 240 | 4-bromo-1-(2,2-difluoroethyl)-1H-pyrazol-3-yl group |
| 241 | 4-bromo-1-(2-propynyl)-1H-pyrazol-3-yl group |
| 242 | 4-bromo-1-(2-butynyl)-1H-pyrazol-3-yl group |
| 243 | 4-bromo-1-cyclopropylmethyl-1H-pyrazol-3-yl group |
| 244 | 4-bromo-1-(2,2,2-trifluoroethyl)-1H-pyrazol-3-yl group |

TABLE 14-continued

| substituents Nos. | Q⁵ |
|---|---|
| 245 | 4-bromo-1-propyl-1H-pyrazol-3-yl group |
| 246 | 4-bromo-1-butyl-1H-pyrazol-3-yl group |
| 247 | 4-bromo-1-isobutyl-1H-pyrazol-3-yl group |

TABLE 15

| substituents Nos. | Q⁵ |
|---|---|
| 248 | 4-bromo-1-(3-methylbutyl)-1H-pyrazol-3-yl group |
| 249 | 4-bromo-1-(4-methyl-pentyl)-1H-pyrazol-3-yl group |
| 250 | 1,5-dimethyl-1H-pyrazol-3-yl group |
| 251 | 1-ethyl-5-methyl-1H-pyrazol-3-yl group |
| 252 | 1-isopropyl-5-methyl-1H-pyrazol-3-yl group |
| 253 | 1-(2,2-difluoroethyl)-5-methyl-1H-pyrazol-3-yl group |
| 254 | 5-methyl-1-(2-propynyl)-1H-pyrazol-3-yl group |
| 255 | 1-(2-butynyl)-5-methyl-1H-pyrazol-3-yl group |
| 256 | 1-cyclopropylmethyl-5-methyl-1H-pyrazol-3-yl group |
| 257 | 5-methyl-1-(2,2,2-trifluoroethyl)-1H-pyrazol-3-yl group |
| 258 | 5-methyl-1-propyl-1H-pyrazol-3-yl-group |
| 259 | 1-butyl-5-methyl-1H-pyrazol-3-yl group |
| 260 | 1-isobutyl-5-methyl-1H-pyrazol-3-yl group |
| 261 | 1-(3-methylbutyl)-5-methyl-1H-pyrazol-3-yl group |

TABLE 16

| substituents Nos. | Q⁵ |
|---|---|
| 262 | 1-(4-methyl-pentyl)-5-methyl-1H-pyrazol-3-yl group |
| 263 | 1,4,5-trimethyl-1H-pyrazol-3-yl group |
| 264 | 1-ethyl-4,5-dimethyl-1H-pyrazol-3-yl group |
| 265 | 4,5-dimethyl-1-isopropyl-1H-pyrazol-3-yl group |
| 266 | 1-(2,2-difluoroethyl)-4,5-dimethyl-1H-pyrazol-3-yl group |
| 267 | 4,5-dimethyl-1-(2-propynyl)-1H-pyrazol-3-yl group |
| 268 | 1-(2-butynyl)-4,5-dimethyl-1H-pyrazol-3-yl group |
| 269 | 1-cyclopropylmethyl-4,5-dimethyl-1H-pyrazol-3-yl group |
| 270 | 4,5-dimethyl-1-(2,2,2-trifluoroethyl)-1H-pyrazol-3-yl group |
| 271 | 4,5-dimethyl-1-propyl-1H-pyrazol-3-yl group |
| 272 | 1-butyl-4,5-dimethyl-1H-pyrazol-3-yl group |
| 273 | 4,5-dimethyl-1-isobutyl-1H-pyrazol-3-yl group |
| 274 | 4,5-dimethyl-1-(3-methylbutyl)-1H-pyrazol-3-yl group |
| 275 | 4,5-dimethyl-1-(4-methyl-pentyl)-1H-pyrazol-3-yl group |
| 276 | 4-ethyl-1,5-dimethyl-1H-pyrazol-3-yl group |

TABLE 17

| substituents Nos. | Q⁵ |
|---|---|
| 277 | 1,4-diethyl-5-methyl-1H-pyrazol-3-yl group |
| 278 | 1-isopropyl-4-ethyl-5-methyl-1H-pyrazol-3-yl group |
| 279 | 4-ethyl-1-(2,2-difluoroethyl)-5-methyl-1H-pyrazol-3-yl group |
| 280 | 4-ethyl-5-methyl-1-(2-propynyl)-1H-pyrazol-3-yl group |
| 281 | 1-(2-butynyl)-4-ethyl-5-methyl-1H-pyrazol-3-yl group |
| 282 | 1-cyclopropylmethyl-4-ethyl-5-methyl-1H-pyrazol-3-yl group |
| 283 | 4-ethyl-1-(2,2,2-trifluoroethyl)-5-methyl-1H-pyrazol-3-yl group |
| 284 | 4-ethyl-1-propyl-5-methyl-1H-pyrazol-3-yl group |
| 285 | 1-butyl-4-ethyl-5-methyl-1H-pyrazol-3-yl group |
| 286 | 4-ethyl-1-isobutyl-5-methyl-1H-pyrazol-3-yl group |
| 287 | 4-ethyl-1-(3-methylbutyl)-5-methyl-1H-pyrazol-3-yl group |
| 288 | 4-ethyl-1-(4-methyl-pentyl)-5-methyl-1H-pyrazol-3-yl group |
| 289 | 4-fluoro-1,5-dimethyl-1H-pyrazol-3-yl group |
| 290 | 1-ethyl-4-fluoro-5-methyl-1H-pyrazol-3-yl group |

TABLE 18

| substituents Nos. | Q⁵ |
|---|---|
| 291 | 4-fluoro-1-isopropyl-5-methyl-1H-pyrazol-3-yl group |
| 292 | 1-(2,2-difluoroethyl)-4-fluoro5-methyl-1H-pyrazol-3-yl group |
| 293 | 4-fluoro-5-methyl-1-(2-propynyl)-1H-pyrazol-3-yl group |
| 294 | 1-(2-butynyl)-4-fluoro-5-methyl-1H-pyrazol-3-yl group |
| 295 | 1-cyclopropylmethyl-4-fluoro-5-methyl-1H-pyrazol-3-yl group |
| 296 | 1-(2,2,2-trifluoroethyl)-4-fluoro5-methyl-1H-pyrazol-3-yl group |
| 297 | 1-propyl-4-fluoro-5-methyl-1H-pyrazol-3-yl group |
| 298 | 1-butyl-4-fluoro-5-methyl-1H-pyrazol-3-yl group |
| 299 | 1-isobutyl-4-fluoro-5-methyl-1H-pyrazol-3-yl group |
| 300 | 4-fluoro-1-(3-methylbutyl)-5-methyl-1H-pyrazol-3-yl group |
| 301 | 4-fluoro-1-(4-methyl-pentyl)-5-methyl-1H-pyrazol-3-yl group |
| 302 | 4-chloro-1,5-dimethyl-1H-pyrazol-3-yl group |
| 303 | 4-chloro-1-ethyl-5-methyl-1H-pyrazol-3-yl group |
| 304 | 4-chloro-1-isopropyl-5-methyl-1H-pyrazol-3-yl group |
| 305 | 4-chloro-1-(2,2-difluoroethyl)-5-methyl-1H-pyrazol-3-yl group |

TABLE 19

| substituents Nos. | Q⁵ |
|---|---|
| 306 | 4-chloro-5-methyl-1-(2-propynyl)-1H-pyrazol-3-yl group |
| 307 | 1-(2-butynyl)-4-chloro-5-methyl-1H-pyrazol-3-yl group |
| 308 | 4-chloro-1-cyclopropylmethyl-5-methyl-1H-pyrazol-3-yl group |
| 309 | 4-chloro-1-(2,2,2-trifluoroethyl)-5-methyl-1H-pyrazol-3-yl group |
| 310 | 4-chloro-5-methyl-1-propyl-1H-pyrazol-3-yl group |
| 311 | 1-butyl-4-chloro-5-methyl-1H-pyrazol-3-yl group |
| 312 | 4-chloro-1-isobutyl-5-methyl-1H-pyrazol-3-yl group |
| 313 | 4-chloro-1-(3-methylbutyl)-5-methyl-1H-pyrazol-3-yl group |
| 314 | 4-chloro-1-(4-methyl-pentyl)-5-methyl-1H-pyrazol-3-yl group |
| 315 | 4-bromo-1,5-dimethyl-1H-pyrazol-3-yl group |
| 316 | 4-bromo-1-ethyl-5-methyl-1H-pyrazol-3-yl group |

TABLE 19-continued

| substituents Nos. | Q⁵ |
|---|---|
| 317 | 4-bromo-1-isopropyl-5-methyl-1H-pyrazol-3-yl group |
| 318 | 4-bromo-1-(2,2-difluoroethyl)-5-methyl-1H-pyrazol-3-yl group |
| 319 | 4-bromo-5-methyl-1-(2-propynyl)-1H-pyrazol-3-yl group |

TABLE 20

| substituents Nos. | Q⁵ |
|---|---|
| 320 | 4-bromo-1-(2-butynyl)-5-methyl-1H-pyrazol-3-yl group |
| 321 | 4-bromo-1-cyclopropylmethyl-5-methyl-1H-pyrazol-3-yl group |
| 322 | 4-bromo-5-methyl-1-(2,2,2-trifluoroethyl)-1H-pyrazol-3-yl group |
| 323 | 4-bromo-5-methyl-1-propyl-1H-pyrazol-3-yl group |
| 324 | 4-bromo-1-butyl-5-methyl-1H-pyrazol-3-yl group |
| 325 | 4-bromo-1-isobutyl-5-methyl-1H-pyrazol-3-yl group |
| 326 | 4-bromo-1-(3-methylbutyl)-5-methyl-1H-pyrazol-3-yl group |
| 327 | 4-bromo-1-(4-methyl-pentyl)-5-methyl-1H-pyrazol-3-yl group |
| 328 | 5-ethyl-1-methyl-1H-pyrazol-3-yl group |
| 329 | 1,5-diethyl-1H-pyrazol-3-yl group |
| 330 | 5-ethyl-1-isopropyl-1H-pyrazol-3-yl group |
| 331 | 5-ethyl-1-(2,2-difluoroethyl)-1H-pyrazol-3-yl group |
| 332 | 5-ethyl-1-(2-propynyl)-1H-pyrazol-3-yl group |
| 333 | 1-(2-butynyl)-5-ethyl-1H-pyrazol-3-yl group |
| 334 | 1-cyclopropylmethyl-5-ethyl-1H-pyrazol-3-yl group |
| 335 | 1-(2,2,2-trifluoroethyl)-5-ethyl-1H-pyrazol-3-yl group |

TABLE 21

| substituents Nos. | Q⁵ |
|---|---|
| 336 | 5-ethyl-1-propyl-1H-pyrazol-3-yl group |
| 337 | 1-butyl-5-ethyl-1H-pyrazol-3-yl group |
| 338 | 5-ethyl-1-isobutyl-1H-pyrazol-3-yl group |
| 339 | 5-ethyl-1-(3-methylbutyl)-1H-pyrazol-3-yl group |
| 340 | 5-ethyl-1-(4-methyl-pentyl)-1H-pyrazol-3-yl group |
| 341 | 5-ethyl-1,4-dimethyl-1H-pyrazol-3-yl group |
| 342 | 1,5-diethyl-4-methyl-1H-pyrazol-3-yl group |
| 343 | 5-ethyl-1-isopropyl-4-methyl-1H-pyrazol-3-yl group |
| 344 | 5-ethyl-1-(2,2-difluoroethyl)-4-methyl-1H-pyrazol-3-yl group |
| 345 | 5-ethyl-1-(2-propynyl)-4-methyl-1H-pyrazol-3-yl group |
| 346 | 1-(2-butynyl)-5-ethyl4-methyl-1H-pyrazol-3-yl group |
| 347 | 1-cyclopropylmethyl-5-ethyl-4-methyl-1H-pyrazol-3-yl group |
| 348 | 5-ethyl-4-methyl-1-(2,2,2-trifluoroethyl)-1H-pyrazol-3-yl group |

TABLE 22

| substituents Nos. | Q⁵ |
|---|---|
| 349 | 5-ethyl4-methyl-1-propyl-1H-pyrazol-3-yl group |
| 350 | 1-butyl-5-ethyl4-methyl-1H-pyrazol-3-yl group |
| 351 | 5-ethyl-1-isobutyl-4-methyl-1H-pyrazol-3-yl group |
| 352 | 5-ethyl-1-(3-methylbutyl)-4-methyl-1H-pyrazol-3-yl group |
| 353 | 5-ethyl-1-(4-methyl-pentyl)-4-methyl-1H-pyrazol-3-yl group |
| 354 | 4,5-diethyl-1-methyl-1H-pyrazol-3-yl group |
| 355 | 1,4,5-triethyl-1H-pyrazol-3-yl group |
| 356 | 4,5-diethyl-1-isopropyl-1H-pyrazol-3-yl group |
| 357 | 4,5-diethyl-1-(2,2-difluoroethyl)-1H-pyrazol-3-yl group |
| 358 | 4,5-diethyl-1-(2-propynyl)-1H-pyrazol-3-yl group |
| 359 | 1-(2-butynyl)-4,5-diethyl-1H-pyrazol-3-yl group |
| 360 | 1-cyclopropylmethyl-4,5-diethyl-1H-pyrazol-3-yl group |
| 361 | 4,5-diethyl-1-(2,2,2-trifluoroethyl)-1H-pyrazol-3-yl group |
| 362 | 4,5-diethyl-1-propyl-1H-pyrazol-3-yl group |
| 363 | 1-butyl-4,5-diethyl-1H-pyrazol-3-yl group |

TABLE 23

| substituents Nos. | Q⁵ |
|---|---|
| 364 | 4,5-diethyl-1-pentyl-1H-pyrazol-3-yl group |
| 365 | 4,5-diethyl-1-isobutyl-1H-pyrazol-3-yl group |
| 366 | 4,5-diethyl-1-(3-methylbutyl)-1H-pyrazol-3-yl group |
| 367 | 4,5-diethyl-1-(4-methyl-pentyl)-1H-pyrazol-3-yl group |
| 368 | 5-ethyl-4-fluoro-1-methyl-1H-pyrazol-3-yl group |
| 369 | 1,5-diethyl-4-fluoro-1H-pyrazol-3-yl group |
| 370 | 5-ethyl-4-fluoro-1-isopropyl-1H-pyrazol-3-yl group |
| 371 | 1-(2,2-difluoroethyl)-5-ethyl-4-fluoro-1H-pyrazol-3-yl group |
| 372 | 5-ethyl-4-fluoro-1-(2-propynyl)-1H-pyrazol-3-yl group |
| 373 | 1-(2-butynyl)-5-ethyl-4-fluoro-1H-pyrazol-3-yl group |
| 374 | 1-cyclopropylmethyl-5-ethyl-4-fluoro-1H-pyrazol-3-yl group |
| 375 | 5-ethyl-4-fluoro-1-(2,2,2-trifluoroethyl)-1H-pyrazol-3-yl group |
| 376 | 5-ethyl-4-fluoro-1-propyl-1H-pyrazol-3-yl group |
| 377 | 1-butyl-5-ethyl-4-fluoro-1H-pyrazol-3-yl group |

TABLE 24

| substituents Nos. | Q⁵ |
|---|---|
| 378 | 5-ethyl-4-fluoro-1-pentyl-1H-pyrazol-3-yl group |
| 379 | 5-ethyl-4-fluoro-1-isobutyl-1H-pyrazol-3-yl group |
| 380 | 5-ethyl-4-fluoro-(3-methylbutyl(-1H-pyrazol-3-yl group |
| 381 | 5-ethyl-4-fluoro(4-methyl-penty)-1H-pyrazol-3-yl group |
| 382 | 4-bromo-5-ethyl-1-methyl-1H-pyrazol-3-yl group |

TABLE 24-continued

| substituents Nos. | Q⁵ |
|---|---|
| 383 | 4-bromo-5-ethyl-1-ethyl-1H-pyrazol-3-yl group |
| 384 | 4-bromo-5-ethyl-1-isopropyl-1H-pyrazol-3-yl group |
| 385 | 4-bromo-1-(2,2-difluoroethyl)-5-ethyl-1H-pyrazol-3-yl group |
| 386 | 4-bromo-5-ethyl-1-(2-propynyl)-1H-pyrazol-3-yl group |
| 387 | 4-bromo-1-(2-butynyl)-5-ethyl-1H-pyrazol-3-yl group |
| 388 | 4-bromo-1-cyclopropylmethyl-5-ethyl-1H-pyrazol-3-yl group |
| 389 | 4-bromo-1-5-ethyl-(2,2,2-trifluoroethyl)-1H-pyrazol-3-yl group |
| 390 | 4-bromo-5-ethyl-1-propyl-1H-pyrazol-3-yl group |
| 391 | 4-bromo-1-butyl-5-ethyl-1H-pyrazol-3-yl group |
| 392 | 4-bromo-5-ethyl-1-pentyl-1H-pyrazol-3-yl group |

TABLE 25

| substituents Nos. | Q⁵ |
|---|---|
| 393 | 4-bromo-5-ethyl-1-isobutyl-1H-pyrazol-3-yl group |
| 394 | 4-bromo-5-ethyl-(3-methylbutyl)-1H-pyrazol-3-yl group |
| 395 | 4-bromo-5-ethyl-(4-methyl-pentyl)-1H-pyrazol-3-yl group |
| 396 | 5-cyclopropyl-1-methyl-1H-pyrazol-3-yl group |
| 397 | 5-cyclopropyl-1-ethyl-1H-pyrazol-3-yl group |
| 398 | 5-cyclopropyl-1-isopropyl-1H-pyrazol-3-yl group |
| 399 | 5-cyclopropyl-1-(2,2-difluoroethyl)-1H-pyrazol-3-yl group |
| 400 | 5-cyclopropyl-1-(2-propynyl)-1H-pyrazol-3-yl group |
| 401 | 1-(2-butynyl)-5-cyclopropyl-1H-pyrazol-3-yl group |
| 402 | 1-cyclopropylmethyl-5-cyclopropyl-1H-pyrazol-3-yl group |
| 403 | 5-cyclopropyl-1-(2,2,2-trifluoroethyl)-1H-pyrazol-3-yl group |
| 404 | 5-cyclopropyl-1-propyl-1H-pyrazol-3-yl group |
| 405 | 1-butyl-5-cyclopropyl-1H-pyrazol-3-yl group |
| 406 | 5-cyclopropyl-1-pentyl-1H-pyrazol-3-yl group |

TABLE 26

| substituents Nos. | Q⁵ |
|---|---|
| 407 | 5-cyclopropyl-1-isobutyl-1H-pyrazol-3-yl group |
| 408 | 5-cyclopropyl-1-(3-methylbutyl)-1H-pyrazol-3-yl group |
| 409 | 5-cyclopropyl-1-(4-methyl-pentyl)-1H-pyrazol-3-yl group |
| 410 | 5-cyclopropyl-1,4-dimethyl-1H-pyrazol-3-yl group |
| 411 | 5-cyclopropyl-1-ethyl-4-methyl-1H-pyrazol-3-yl group |
| 412 | 5-cyclopropyl-1-isopropyl-4-methyl-1H-pyrazol-3-yl group |
| 413 | 5-cyclopropyl-1-(2,2-difluoroethyl)-4-methyl-1H-pyrazol-3-yl group |
| 414 | 5-cyclopropyl-4-methyl-1-(2-propynyl)-1H-pyrazol-3-yl group |
| 415 | 1-(2-butynyl)-5-cyclopropyl-4-methyl-1H-pyrazol-3-yl group |

TABLE 26-continued

| substituents Nos. | Q⁵ |
|---|---|
| 416 | 1-cyclopropylmethyl-5-cyclopropyl-4-methyl-1H-pyrazol-3-yl group |
| 417 | 5-cyclopropyl-1-(2,2,2-trifluoroethyl)-4-methyl-1H-pyrazol-3-yl group |
| 418 | 5-cyclopropyl-4-methyl-1-propyl-1H-pyrazol-3-yl group |
| 419 | 1-butyl-5-cyclopropyl-4-methyl-1H-pyrazol-3-yl group |
| 420 | 5-cyclopropyl-4-methyl-1-pentyl-1H-pyrazol-3-yl group |
| 421 | 5-cyclopropyl-1-isobutyl-4-methyl-1H-pyrazol-3-yl group |

TABLE 27

| substituents Nos. | Q⁵ |
|---|---|
| 422 | 5-cyclopropyl-4-methyl-1-(3-methylbutyl)-1H-pyrazol-3-yl group |
| 423 | 5-cyclopropyl-4-methyl-1-(4-methyl-pentyl)-1H-pyrazol-3-yl group |
| 424 | 5-cyclopropyl-4-fluoro-1-methyl-1H-pyrazol-3-yl group |
| 425 | 5-cyclopropyl-4-fluoro-1-ethyl-1H-pyrazol-3-yl group |
| 426 | 5-cyclopropyl-4-fluoro-1-isopropyl-1H-pyrazol-3-yl group |
| 427 | 5-cyclopropyl-4-fluoro-1-(2,2-difluoroethyl)-1H-pyrazol-3-yl group |
| 428 | 5-cyclopropyl-4-fluoro-1-(2-propynyl)-1H-pyrazol-3-yl group |
| 429 | 1-(2-butynyl)-5-cyclopropyl-4-fluoro-1H-pyrazol-3-yl group |
| 430 | 5-cyclopropyl-1-cyclopropylmethyl-4-fluoro-1H-pyrazol-3-yl group |
| 431 | 5-cyclopropyl-4-fluoro-1-(2,2,2-trifluoroethyl)-1H-pyrazol-3-yl group |
| 432 | 5-cyclopropyl-4-fluoro-1-propyl-1H-pyrazol-3-yl group |
| 433 | 1-butyl-5-cyclopropyl-4-fluoro-1H-pyrazol-3-yl group |
| 434 | 5-cyclopropyl-4-fluoro-1-pentyl-1H-pyrazol-3-yl group |
| 435 | 5-cyclopropyl-4-fluoro-1-isobutyl-1H-pyrazol-3-yl group |

TABLE 28

| substituents Nos. | Q⁵ |
|---|---|
| 436 | 5-cyclopropyl-4-fluoro-1-(3-methylbutyl)-1H-pyrazol-3-yl group |
| 437 | 5-cyclopropyl-4-fluoro-1-(4-methyl-pentyl)-1H-pyrazol-3-yl group |
| 438 | 4-chloro-5-cyclopropyl-1-methyl-1H-pyrazol-3-yl group |
| 439 | 4-chloro-5-cyclopropyl-1-ethyl-1H-pyrazol-3-yl group |
| 440 | 4-chloro-5-cyclopropyl-1-isopropyl-1H-pyrazol-3-yl group |
| 441 | 4-chloro-5-cyclopropyl-1-(2,2-difluoroethyl)-1H-pyrazol-3-yl group |
| 442 | 4-chloro-5-cyclopropyl-1-(2-propynyl)-1H-pyrazol-3-yl group |
| 443 | 1-(2-butynyl)-4-chloro-5-cyclopropyl-1H-pyrazol-3-yl group |
| 444 | 4-chloro-1-cyclopropylmethyl-5-cyclopropyl-1H-pyrazol-3-yl group |
| 445 | 4-chloro-5-cyclopropyl-1-(2,2,2-trifluoroethyl)-1H-pyrazol-3-yl group |

TABLE 28-continued

| substituents Nos. | $Q^5$ |
|---|---|
| 446 | 4-chloro-5-cyclopropyl-1-propyl-1H-pyrazol-3-yl group |
| 447 | 4-chloro-5-cyclopropyl-1-butyl-1H-pyrazol-3-yl group |
| 448 | 4-chloro-5-cyclopropyl-1-pentyl-1H-pyrazol-3-yl group |
| 449 | 4-chloro-5-cyclopropyl-1-isobutyl-1H-pyrazol-3-yl group |

TABLE 29

| substituents Nos. | $Q^5$ |
|---|---|
| 450 | 4-bromo-5-cyclopropyl-1-methyl-1H-pyrazol-3-yl group |
| 451 | 4-bromo-5-cyclopropyl-1-ethyl-1H-pyrazol-3-yl group |
| 452 | 4-bromo-5-cyclopropyl-1-isopropyl-1H-pyrazol-3-yl group |
| 453 | 4-bromo-5-cyclopropyl-1-(2,2-difluoroethyl)-1H-pyrazol-3-yl group |
| 454 | 4-bromo-5-cyclopropyl-1-(2-propynyl)-1H-pyrazol-3-yl group |
| 455 | 4-bromo-1-(2-butynyl)-5-cyclopropyl-1H-pyrazol-3-yl group |
| 456 | 4-bromo-1-cyclopropyl-methyl-5-cyclopropyl-1H-pyrazol-3-yl group |
| 457 | 4-bromo-5-cyclopropyl-1-(2,2,2-trifluoroethyl)-1H-pyrazol-3-yl group |
| 458 | 4-bromo-5-cyclopropyl-1-propyl-1H-pyrazol-3-yl group |
| 459 | 4-bromo-1-butyl-5-cyclopropyl-1H-pyrazol-3-yl group |
| 460 | 4-bromo-5-cyclopropyl-1-pentyl-1H-pyrazol-3-yl group |
| 461 | 4-bromo-5-cyclopropyl-1-isobutyl-1H-pyrazol-3-yl group |
| 462 | 5-isopropyl-1-methyl-1H-pyrazol-3-yl group |
| 463 | 1-ethyl-5-isopropyl-1H-pyrazol-3-yl group |
| 464 | 1,5-diisopropyl-1H-pyrazol-3-yl group |

TABLE 30

| substituents Nos. | $Q^5$ |
|---|---|
| 465 | 1-(2,2-difluoroethyl)-5-isopropyl-1H-pyrazol-3-yl group |
| 466 | 5-isopropyl-1-(2-propynyl)-1H-pyrazol-3-yl group |
| 467 | 1-(2-butynyl)-5-isopropyl-1H-pyrazol-3-yl group |
| 468 | 1-cyclopropylmethyl-5-isopropyl-1H-pyrazol-3-yl group |
| 469 | 5-isopropyl-1-(2,2,2-trifluoroethyl)-1H-pyrazol-3-yl group |
| 470 | 5-isopropyl-1-propyl-1H-pyrazol-3-yl group |
| 471 | 1-butyl-5-isopropyl-1H-pyrazol-3-yl group |
| 472 | 5-isopropyl-1-pentyl-1H-pyrazol-3-yl group |
| 473 | 1-isobutyl-5-isopropyl-1H-pyrazol-3-yl group |
| 474 | 5-isopropyl-1-(3-methylbutyl)-1H-pyrazol-3-yl group |
| 475 | 5-isopropyl-1-(4-methyl-pentyl)-1H-pyrazol-3-yl group |
| 476 | 1,4-dimethyl-5-isopropyl-1H-pyrazol-3-yl group |
| 477 | 1-ethyl-5-isopropyl-4-methyl-1H-pyrazol-3-yl group |

TABLE 30-continued

| substituents Nos. | $Q^5$ |
|---|---|
| 478 | 1,5-diisopropyl-4-methyl-1H-pyrazol-3-yl group |
| 479 | 1-(2,2-difluoroethy)-5-isopropyl4-methyl-1H-pyrazol-3-yl group |

TABLE 31

| substituents Nos. | $Q^5$ |
|---|---|
| 480 | 5-isopropyl-4-methyl-1-(2-propynyl)-1H-pyrazol-3-yl group |
| 481 | 1-(2-butynyl)-5-isopropyl-4-methyl-1H-pyrazol-3-yl group |
| 482 | 1-cyclopropylmethyl-5-isopropyl-4-methyl-1H-pyrazol-3-yl group |
| 483 | 5-isopropyl-4-methyl-1-(2,2,2-trifluoroethyl)-1H-pyrazol-3-yl group |
| 484 | 5-isopropyl-1-propyl-4-methyl-1H-pyrazol-3-yl group |
| 485 | 1-butyl-5-isopropyl-4-methyl-1H-pyrazol-3-yl group |
| 486 | 5-isopropyl-4-methyl-1-pentyl-1H-pyrazol-3-yl group |
| 487 | 5-isopropyl-4-methyl-1-isobutyl-1H-pyrazol-3-yl group |
| 488 | 5-isopropyl-1-(3-methylbutyl)-4-methy-1H-pyrazol-3-yl group |
| 489 | 5-isopropyl-4-methyl-1-(4-methyl-pentyl)-1H-pyrazol-3-yl group |
| 490 | 4-fluoro-5-isopropyl-1-methyl-1H-pyrazol-3-yl group |
| 491 | 4-fluoro-5-isopropyl-1-ethyl-1H-pyrazol-3-yl group |
| 492 | 4-fluoro-1,5-diisopropyl-1H-pyrazol-3-yl group |
| 493 | 4-fluoro-5-isopropyl-1-(2,2-difluoroethyl)-1H-pyrazol-3-yl group |

TABLE 32

| substituents Nos. | $Q^5$ |
|---|---|
| 494 | 4-fluoro-5-isopropyl-1-(2-propynyl)-1H-pyrazol-3-yl group |
| 495 | 4-fluoro-5-isopropyl-1-(2-butynyl)-1H-pyrazol-3-yl group |
| 496 | 4-fluoro-5-isopropyl-1-cyclopropylmethyl-1H-pyrazol-3-yl group |
| 497 | 4-fluoro-5-isopropyl-1-(2,2,2-trifluoroethyl)-1H-pyrazol-3-yl group |
| 498 | 4-fluoro-5-isopropyl-1-propyl-1H-pyrazol-3-yl group |
| 499 | 4-fluoro-5-isopropyl-1-butyl-1H-pyrazol-3-yl group |
| 500 | 4-fluoro-5-isopropyl-1-pentyl-1H-pyrazol-3-yl group |
| 501 | 4-fluoro-5-isopropyl-1-isobutyl-1H-pyrazol-3-yl group |
| 502 | 4-fluoro-5-isopropyl-1-(3-methylbutyl)-1H-pyrazol-3-yl group |
| 503 | 4-fluoro-5-isopropyl-1-(4-methyl-pentyl)-1H-pyrazol-3-yl group |
| 504 | 4-chloro-5-isopropyl-1-methyl-1H-pyrazol-3-yl group |
| 505 | 4-chloro-5-isopropyl-1-ethyl-1H-pyrazol-3-yl group |
| 506 | 4-chloro-1,5-diisopropyl-1H-pyrazol-3-yl group |

TABLE 32-continued

| substituents Nos. | Q⁵ |
|---|---|
| 507 | 4-chloro-1-(2,2-difluoroethyl)-5-isopropyl-1H-pyrazol-3-yl group |
| 508 | 4-chloro-5-isopropyl-1-(2-propynyl)-1H-pyrazol-3-yl group |

TABLE 33

| substituents Nos. | Q⁵ |
|---|---|
| 509 | 1-(2-butynyl)-4-chloro-5-isopropyl-1H-pyrazol-3-yl group |
| 510 | 4-chloro-5-isopropyl-1-cyclopropylmethyl-1H-pyrazol-3-yl group |
| 511 | 4-chloro-5-isopropyl-1-(2,2,2-trifluoroethyl)-1H-pyrazol-3-yl group |
| 512 | 4-chloro-5-isopropyl-1-propyl-1H-pyrazol-3-yl group |
| 513 | 4-chloro-5-isopropyl-1-butyl-1H-pyrazol-3-yl group |
| 514 | 4-chloro-5-isopropyl-1-pentyl-1H-pyrazol-3-yl group |
| 515 | 4-chloro-5-isopropyl-1-isobutyl-1H-pyrazol-3-yl group |
| 516 | 4-chloro-5-isopropyl-1-(3-methylbutyl)-1H-pyrazol-3-yl group |
| 517 | 4-chloro-5-isopropyl-1-(4-methyl-pentyl)-1H-pyrazol-3-yl group |
| 518 | 4-bromo-5-isopropyl-1-methyl-1H-pyrazol-3-yl group |
| 519 | 4-bromo-1-ethyl-5-isopropyl-1H-pyrazol-3-yl group |
| 520 | 4-bromo-1,5-diisopropyl-1H-pyrazol-3-yl group |
| 521 | 4-bromo-1-(2,2-difluoroethyl)-5-isopropyl-1H-pyrazol-3-yl group |
| 522 | 4-bromo-5-isopropyl-1-(2-propynyl)-1H-pyrazol-3-yl group |

TABLE 34

| substituents Nos. | Q⁵ |
|---|---|
| 523 | 4-bromo-1-(2-butynyl)-5-isopropyl-1H-pyrazol-3-yl group |
| 524 | 4-bromo-1-cyclopropylmethyl-5-isopropyl-1H-pyrazol-3-yl group |
| 525 | 4-bromo-5-isopropyl-1-(2,2,2-trifluoroethyl)-1H-pyrazol-3-yl group |
| 526 | 4-bromo-5-isopropyl-1-propyl-1H-pyrazol-3-yl group |
| 527 | 4-bromo-1-butyl-5-isopropyl-1H-pyrazol-3-yl group |
| 528 | 4-bromo-5-isopropyl-1-pentyl-1H-pyrazol-3-yl group |
| 529 | 4-bromo-5-isopropyl-1-isobutyl-1H-pyrazol-3-yl group |
| 530 | 4-bromo-5-isopropyl-1-(3-methylbutyl)-1H-pyrazol-3-yl group |
| 531 | 4-bromo-5-isopropyl-1-(4-methyl-pentyl)-1H-pyrazol-3-yl group |
| 532 | 5-methoxy-1-methyl-1H-pyrazol-3-yl group |
| 533 | 1-ethyl-5-methoxy-1H-pyrazol-3-yl group |
| 534 | 5-methoxy-1-isopropyl-1H-pyrazol-3-yl group |
| 535 | 1-(2,2-difluoroethyl)-5-methoxy-1H-pyrazol-3-yl group |
| 536 | 5-methoxy-1-(2-propynyl)-1H-pyrazol-3-yl group |
| 537 | 1-(2-butynyl)-5-methoxy-1H-pyrazol-3-yl group |

TABLE 35

| substituents Nos. | Q⁵ |
|---|---|
| 538 | 1-cyclopropylmethyl-5-methoxy-1H-pyrazol-3-yl group |
| 539 | 1,4-dimethyl-5-methoxy-1H-pyrazol-3-yl group |
| 540 | 1-ethyl-5-methoxy-4-methyl-1H-pyrazol-3-yl group |
| 541 | 5-methoxy-1-isopropyl-4-methyl-1H-pyrazol-3-yl group |
| 542 | 1-(2,2-difluoroethyl)-5-methoxy4-methyl-1H-pyrazol-3-yl group |
| 543 | 5-methoxy-1-(2-propynyl)-4-methyl-1H-pyrazol-3-yl group |
| 544 | 1-(2-2-butynyl)-5-methoxy-4-methyl-1H-pyrazol-3-yl group |
| 545 | 1-cyclopropylmethyl-5-methoxy-4-methyl-1H-pyrazol-3-yl group |
| 546 | 4-fluoro-5-methoxy-1-methyl-1H-pyrazol-3-yl group |
| 547 | 4-fluoro-5-methoxy-1-ethyl-1H-pyrazol-3-yl group |
| 548 | 4-fluoro-5-methoxy-1-isopropyl-1H-pyrazol-3-yl group |
| 549 | 1-(2,2-difluoroethyl)-4-fluoro-5-methoxy-1H-pyrazol-3-yl group |
| 550 | 4-fluoro-5-methoxy-1-(2-propynyl)-1H-pyrazol-3-yl group |
| 551 | 1-(2-butynyl)-4-fluoro-5-methoxy-1H-pyrazol-3-yl group |

TABLE 36

| substituents Nos. | Q⁵ |
|---|---|
| 552 | 1-cyclopropylmethyl-4-fluoro-5-methoxy-1H-pyrazol-3-yl group |
| 553 | 4-chloro-5-methoxy-1-methyl-1H-pyrazol-3-yl group |
| 554 | 4-chloro-5-methoxy-1-ethyl-1H-pyrazol-3-yl group |
| 555 | 4,5-dichloro-1-ethyl-1H-pyrazol-3-yl group |
| 556 | 4-chloro-1-ethyl-5-trifluoromethyl-1H-pyrazol-3-yl group |
| 557 | 1-ethyl-5-trifluoromethyl-1H-pyrazol-3yl group |
| 558 | 1-ethyl-4-methyl-5-trifluoromethyl-1H-pyrazol-3-yl group |
| 559 | 5-chloro-1-ethyl-1H-pyrazol-3-yl group |
| 560 | 5-chloro-1-ethyl4-methyl-1H-pyrazol-3-yl group |
| 561 | 4,5-dichloro-1-methyl-1H-pyrazol-3-yl group |
| 562 | 4-chloro-1-methyl-5-trifluoromethyl-1H-pyrazol-3-yl group |
| 563 | 1-methyl-5-trifluoromethyl-1H-pyrazol-3-yl group |
| 564 | 1,4-dimethyl-5-trifluoromethyl-1H-pyrazol-3-yl group |

TABLE 37

| substituents Nos. | Q⁵ |
|---|---|
| 565 | 5-chloro-1-methyl-1H-pyrazol-3-yl group |
| 566 | 5-chloro-1,4-dimethyl-1H-pyrazol-3-yl group |
| 567 | 5,6-dihydro-4H-pyrolo[1,2-b]pyrazol-2-yl group |
| 568 | 4,5,6,7-tetrahydro-pyrazolo[1,2-a]pyridin-2-yl group |
| 569 | 5,6-dihydro-3-methyl-4H-pyrolo[1,2-b]pyrazol-2-yl group |
| 570 | 4,5,6,7-3-methyl-tetrahydro-pyrazolo[1,2-a]pyridin-2-yl group |

TABLE 37-continued

| substituents Nos. | Q⁵ |
|---|---|
| 571 | 1-methyl-1H-pyrazol-4-yl group |
| 572 | 1,5-dimethyl-1H-pyrazol-4-yl group |
| 573 | 1-ethyl-1H-pyrazol-4-yl group |
| 574 | 1-ethyl-5-methyl-1H-pyrazol-4-yl group |
| 575 | 1,3-dimethyl-1H-pyrazol-4-yl group |
| 576 | 1,3,5-trimethyl-1H-pyrazol-4-yl group |
| 577 | 1-ethyl-3-methyl-1H-pyrazol-4-yl group |
| 578 | 3,5-dimethyl-1-ethyl-1H-pyrazol-4-yl group |
| 579 | 1-(2-propynyl)-1H-pyrazol-4-yl group |
| 580 | 5-methyl-1-(2-propynyl)-1H-pyrazol-4-yl group |

TABLE 38

| substituents Nos. | Q⁵ |
|---|---|
| 581 | 3-methyl-1-(2-propynyl)-1H-pyrazol-4-yl group |
| 582 | 3,5-dimethyl-1-(2-propynyl)-1H-pyrazol-4-yl group |
| 583 | 1-cyclopropylmethyl-1H-pyrazol-4-yl group |
| 584 | 1-cyclopropylmethyl-3-methyl-1H-pyrazol-4-yl group |
| 585 | 1-cyclopropylmethyl-5-methyl-1H-pyrazol-4-yl group |
| 586 | 1-cyclopropylmethyl-3,5-dimethyl-1H-pyrazol-4-yl group |
| 587 | 1-(2,2-difluoroethyl)-1H-pyrazol-4-yl group |
| 588 | 1-(2,2-difluoroethyl)-3-methyl-1H-pyrazol-4-yl group |
| 589 | 1-(2,2-difluoroethyl)-5-methyl-1H-pyrazol-4-yl group |
| 590 | 1-(2,2-difluoroethyl)-3,5-dimethyl-1H-pyrazol-4-yl group |
| 591 | 1-methyl-1H-pyrazol-5-yl group |
| 592 | 1,4-dimethyl-1H-pyrazol-5-yl group |
| 593 | 4-fluoro-1-methyl-1H-pyrazol-5-yl group |
| 594 | 4-chloro-1-methyl-1H-pyrazol-5-yl group |
| 595 | 4-bromo-1-methyl-1H-pyrazol-5-yl group |
| 596 | 1-ethyl-1H-pyrazol-5-yl group |
| 597 | 1-ethyl-4-methyl-1H-pyrazol-5-yl group |
| 598 | 1-ethyl-4-fluoro-1H-pyrazol-5-yl group |
| 599 | 4-chloro-1-ethyl-1H-pyrazol-5-yl group |
| 600 | 4-bromo-1-ethyl-1H-pyrazol-5-yl group |
| 601 | 1-propyl-1H-pyrazol-5-yl group |
| 602 | 4-methyl-1-propyl-1H-pyrazol-5-yl group |
| 603 | 4-fluoro-1-propyl-1H-pyrazol-5-yl group |
| 604 | 4-chloro-1-propyl-1H-pyrazol-5-yl group |
| 605 | 4-bromo-1-propyl-1H-pyrazol-5-yl group |
| 606 | 1-butyl-1H-pyrazol-5-yl group |
| 607 | 1-butyl-4-methyl-1H-pyrazol-5-yl group |
| 608 | 1-butyl-4-fluoro-1H-pyrazol-5-yl group |
| 609 | 1-butyl4-chloro-1H-pyrazol-5-yl group |

TABLE 39

| substituents Nos. | Q⁵ |
|---|---|
| 610 | 1-butyl-4-bromo-1H-pyrazol-5-yl group |
| 611 | 1,3-dimethyl-1H-pyrazol-5-yl group |
| 612 | 1,3,4-trimethyl-1H-pyrazol-5-yl group |
| 613 | 1,3-dimethyl-4-fluoro-1H-pyrazol-5-yl group |
| 614 | 4-chloro-1,3-dimethyl-1H-pyrazol-5-yl group |
| 615 | 4-bromo-1,3-dimethyl-1H-pyrazol-5-yl group |
| 616 | 1-ethyl-3-methyl-1H-pyrazol-5-yl group |
| 617 | 3,4-dimethyl-1-ethyl-1H-pyrazol-5-yl group |
| 618 | 1-ethyl-4-fluoro-3-methyl-1H-pyrazol-5-yl group |
| 619 | 4-chloro-1-ethyl-3-methyl-1H-pyrazol-5-yl group |
| 620 | 4-bromo-1-ethyl-3-methyl-1H-pyrazol-5-yl group |

TABLE 39-continued

| substituents Nos. | Q⁵ |
|---|---|
| 621 | 3-methyl-1-propyl-1H-pyrazol-5-yl group |
| 622 | 3,4-dimethyl-1-propyl-1H-pyrazol-5-yl group |
| 623 | 3-methyl-4-fluoro-1-propyl-1H-pyrazol-5-yl group |
| 624 | 4-chloro-3-methyl-1-propyl-1H-pyrazol-5-yl group |

TABLE 40

| substituents Nos. | Q⁵ |
|---|---|
| 625 | 4-bromo-3-methyl-1-propyl-1H-pyrazol-5-yl group |
| 626 | 1-butyl-3-methyl-1H-pyrazol-5-yl group |
| 627 | 1-butyl-3,4-dimethyl-1H-pyrazol-5-yl group |
| 628 | 1-butyl-4-fluoro3-methyl-1H-pyrazol-5-yl group |
| 629 | 1-butyl-4-chloro-3-methyl-1H-pyrazol-5-yl group |
| 630 | 1-butyl-4-bromo-3-methyl-1H-pyrazol-5-yl group |
| 631 | 3-ethyl-1-methyl-1H-pyrazol-5-yl group |
| 632 | 1,4-dimethyl-3-ethyl-1H-pyrazol-5-yl group |
| 633 | 3-ethyl-4-fluoro-1-methyl-1H-pyrazol-5-yl group |
| 634 | 4-chloro-3-ethyl-1-methyl-1H-pyrazol-5-yl group |
| 635 | 4-bromo-3-ethyl-1-methyl-1H-pyrazol-5-yl group |
| 636 | 1,3-diethyl-1H-pyrazol-5-yl group |
| 637 | 1,3-diethyl-4-methyl-1H-pyrazol-5-yl group |
| 638 | 1,3-diethyl-4-fluoro-1H-pyrazol-5-yl group |

TABLE 41

| substituents Nos. | Q⁵ |
|---|---|
| 639 | 4-chloro-1,3-diethyl-1H-pyrazol-5-yl group |
| 640 | 4-bromo-1,3-diethyl-1H-pyrazol-5-yl group |
| 641 | 4-fluoro-1,3-diethyl-1H-pyrazol-5-yl group |
| 642 | 3-ethyl-1-propyl-1H-pyrazol-5-yl group |
| 643 | 3-ethyl-4-methyl-1-propyl-1H-pyrazol-5-yl group |
| 644 | 4-fluoro-3-ethyl-1-propyl-1H-pyrazol-5-yl group |
| 645 | 4-chloro-3-ethyl-1-propyl-1H-pyrazol-5-yl group |
| 646 | 4-bromo-3-ethyl-1-propyl-1H-pyrazol-5-yl group |
| 647 | 1-butyl-3-ethyl-1H-pyrazol-5-yl group |
| 648 | 1-butyl-3-ethyl-4-methyl-1H-pyrazol-5-yl group |
| 649 | 1-butyl-3-ethyl-4-fluoro-1H-pyrazol-5-yl group |
| 650 | 1-butyl-4-chloro-3-ethyl-1H-pyrazol-5-yl group |
| 651 | 4-bromo-1-butyl-3-ethyl-1H-pyrazol-5-yl group |
| 652 | 1-(2-propynyl)-1H-pyrazol-5-yl group |
| 653 | 4-methyl-1-(2-propynyl)-1H-pyrazol-5-yl group |
| 654 | 3-methyl-1-(2-propynyl)-1H-pyrazol-5-yl group |
| 655 | 3,4-dimethyl-1-(2-propynyl)-1H-pyrazol-5-yl group |
| 656 | 1-cyclopropylmethyl-1H-pyrazol-5-yl group |
| 657 | 1-cyclopropylmethyl-4-methyl-1H-pyrazol-5-yl group |
| 658 | 1-cyclopropylmethyl-3-methyl-1H-pyrazol-5-yl group |

TABLE 41-continued

| substituents Nos. | $Q^5$ |
|---|---|
| 659 | 1-cyclopropylmethyl-3,4-dimethyl-1H-pyrazol-5-yl group |
| 660 | 1-(2-butynyl)-1H-pyrazol-5-yl group |

TABLE 42

| substituents Nos. | $Q^5$ |
|---|---|
| 661 | 1,5-dimethyl-4-iodo-1H-pyrazol-3-yl group |
| 662 | 4-cyano-1,5-dimethyl-1H-pyrazol-3-yl group |
| 663 | 5-ethyl-1-methyl-4-iodo-1H-pyrazol-3-yl group |
| 664 | 4-cyano-5-ethyl-1-methyl-1H-pyrazol-3-yl group |
| 665 | 1,5-diethyl-4-iodo-1H-pyrazol-3-yl group |
| 666 | 4-cyano-1,5-diethyl-1H-pyrazol-3-yl group |
| 667 | 1,4-dimethyl-5-ethoxy-1H-pyrazol-3-yl group |
| 668 | 4-ethyl-1-methyl-5-ethoxy-1H-pyrazol-3-yl group |
| 669 | 1-ethyl-4-methyl-5-ethoxy-1H-pyrazol-3-yl group |
| 670 | 1,4-dimethyl-5-methylthio-1H-pyrazol-3-yl group |
| 671 | 1,4-dimethyl-5-ethylthio-1H-pyrazol-3-yl group |
| 672 | 1,4-diethyl-5-methylthio-1H-pyrazol-3-yl group |
| 673 | 5-cyano-1,4-dimethyl-1H-pyrazol-3-yl group |
| 674 | 5-cyano-1,4-diethyl-1H-pyrazol-3-yl group |
| 675 | 5-cyano-4-ethyl-1-methyl-1H-pyrazol-3-yl group |
| 676 | 5-cyano-1-ethyl-4-methyl-1H-pyrazol-3-yl group |
| 677 | 5-difluoromethoxy-1,4-dimethyl-1H-pyrazol-3-yl group |
| 678 | 1,4-dimethyl-5-trifluoromethoxy-1H-pyrazol-3-yl group |
| 679 | 1,4-dimethyl-5-(2-propynyloxy)-1H-pyrazol-3-yl group |
| 680 | 1,4-dimethyl-5-(2-butynyloxy)-1H-pyrazol-3-yl group |

TABLE 43

| substituents Nos. | $Q^5$ |
|---|---|
| 681 | 5-fluoro-1-methyl-1H-pyrazol-3-yl group |
| 682 | 5-bromo-1-methyl-1H-pyrazol-3-yl group |
| 683 | 5-ethoxy-1-methyl-1H-pyrazol-3-yl group |
| 684 | 5-cyano-1-methyl-1H-pyrazol-3-yl group |
| 685 | 5-difluoromethyl-1-methyl-1H-pyrazol-3-yl group |
| 686 | 4,5-difluoro-1-methyl-1H-pyrazol-3-yl group |
| 687 | 5-chloro-4-fluoro-1-methyl-1H-pyrazol-3-yl group |
| 688 | 5-bromo-4-fluoro-1-methyl-1H-pyrazol-3-yl group |
| 689 | 5-ethoxy-4-fluoro-1-methyl-1H-pyrazol-3-yl group |
| 690 | 5-cyano-4-fluoro-1-methyl-1H-pyrazol-3-yl group |
| 691 | 5-difluoromethyl-4-fluoro-1-methyl-1H-pyrazol-3-yl group |
| 692 | 5-trifluoromethyl-4-fluoro-1-methyl-1H-pyrazol-3-yl group |
| 693 | 4-chloro-5-fluoro-1-methyl-1H-pyrazol-3-yl group |
| 694 | 5-bromo-4-chloro-1-methyl-1H-pyrazol-3-yl group |
| 695 | 4-chloro-5-ethyl-1-methyl-1H-pyrazol-3-yl group |

TABLE 43-continued

| substituents Nos. | $Q^5$ |
|---|---|
| 696 | 4-chloro-5-ethoxy-1-methyl-1H-pyrazol-3-yl group |
| 697 | 4-chloro-5-cyano-1-methyl-1H-pyrazol-3-yl group |
| 698 | 4-chloro-5-difluoromethyl-1-methyl-1H-pyrazol-3-yl group |
| 699 | 4-bromo-5-fluoro-1-methyl-1H-pyrazol-3-yl group |
| 700 | 4-bromo-5-chloro-1-methyl-1H-pyrazol-3-yl group |
| 701 | 4,5-dibromo-1-methyl-1H-pyrazol-3-yl group |
| 702 | 4-bromo-5-methoxy-1-methyl-1H-pyrazol-3-yl group |
| 703 | 4-bromo-5-ethoxy-1-methyl-1H-pyrazol-3-yl group |
| 704 | 4-bromo-5-cyano-1-methyl-1H-pyrazol-3-yl group |
| 705 | 4-bromo-5-difluoromethyl-1-methyl-1H-pyrazol-3-yl group |
| 706 | 4-bromo-5-trifluoromethyl-1-methyl-1H-pyrazol-3-yl group |
| 707 | 5-fluoro-1,4-dimethyl-1H-pyrazol-3-yl group |
| 708 | 5-bromo-1,4-dimethyl-1H-pyrazol-3-yl group |
| 709 | 5-ethoxy-1,4-dimethyl-1H-pyrazol-3-yl group |

TABLE 44

| substituents Nos. | $Q^5$ |
|---|---|
| 710 | 5-cyclopropyl-1,4-dimethyl-1H-pyrazol-3-yl group |
| 711 | 5-difluoromethyl-1,4-dimethyl-1H-pyrazol-3-yl group |
| 712 | 4-ethyl-5-fluoro-1-methyl-1H-pyrazol-3-yl group |
| 713 | 4-ethyl-5-chloro-1-methyl-1H-pyrazol-3-yl group |
| 714 | 5-bromo-4-ethyl-1-methyl-1H-pyrazol-3-yl group |
| 715 | 4-ethyl-5-methoxy-1-methyl-1H-pyrazol-3-yl group |
| 716 | 5-cyclopropyl-4-ethyl-1-methyl-1H-pyrazol-3-yl group |
| 717 | 4-ethyl-5-difluoromethyl-1-methyl-1H-pyrazol-3-yl group |
| 718 | 4-ethyl-5-trifluoromethyl-1-methyl-1H-pyrazol-3-yl group |
| 719 | 4-methoxy-1-methyl-1H-pyrazol-3-yl group |
| 720 | 5-fluoro-4-methoxy-1-methyl-1H-pyrazol-3-yl group |
| 721 | 5-chloro-4-methoxy-1-methyl-1H-pyrazol-3-yl group |
| 722 | 5-bromo-4-methoxy-1-methyl-1H-pyrazol-3-yl group |
| 723 | 4-methoxy-1,5-dimethyl-1H-pyrazol-3-yl group |
| 724 | 5-ethyl-4-methoxy-1-methyl-1H-pyrazol-3-yl group |
| 725 | 4,5-dimethoxy-1-methyl-1H-pyrazol-3-yl group |
| 726 | 5-ethoxy-4-methoxy-1-methyr-1H-pyrazol-3-yl group |
| 727 | 5-cyano-4-methoxy-1-methyl-1H-pyrazol-3-yl group |
| 728 | 5-cyclopropyl-4-methoxy-1-methyl-1H-pyrazol-3-yl group |
| 729 | 5-difluoromethyl-4-methoxy-1-methyl-1H-pyrazol-3-yl group |
| 730 | 5-trifluoromethyl-4-methoxy-1-methyl-1H-pyrazol-3-yl group |
| 731 | 4-ethoxy-1-methyl-1H-pyrazol-3-yl group |
| 732 | 5-fluoro-4-ethoxy-1-methyl-1H-pyrazol-3-yl group |
| 733 | 5-chloro-4-ethoxy-1-methyl-1H-pyrazol-3-yl group |
| 734 | 5-bromo-4-ethoxy-1-methyl-1H-pyrazol-3-yl group |
| 735 | 4-ethoxy-1,5-dimethyl-1H-pyrazol-3-yl group |
| 736 | 5-ethyl-4-ethoxy-1-methyl-1H-pyrazol-3-yl group |
| 737 | 4-ethoxy-5-methoxy-1-methyl-1H-pyrazol-3-yl group |
| 738 | 4,5-diethoxy-1-methyl-1H-pyrazol-3-yl group |

TABLE 45

| substituents Nos. | $Q^5$ |
|---|---|
| 739 | 5-cyano-4-ethoxy-1-methyl-1H-pyrazol-3-yl group |
| 740 | 5-cyclopropyl-4-ethoxy-1-methyl-1H-pyrazol-3-yl group |
| 741 | 5-difluoromethyl-4-ethoxy-1-methyl-1H-pyrazol-3-yl group |
| 742 | 5-trifluoromethyl-4-ethoxy-1-methyl-1H-pyrazol-3-yl group |
| 743 | 4-cyano-1-methyl-1H-pyrazol-3-yl group |
| 744 | 4-cyano-5-fluoro-1-methyl-1H-pyrazol-3-yl group |
| 745 | 4-cyano-5-chloro-1-methyl-1H-pyrazol-3-yl group |
| 746 | 5-bromo-4-cyano-1-methyl-1H-pyrazol-3-yl group |
| 747 | 4-cyano-5-methoxy-1-methyl-1H-pyrazol-3-yl group |
| 748 | 4-cyano-5-ethoxy-1-methyl-1H-pyrazol-3-yl group |
| 749 | 4,5-dicyano-1-methyl-1H-pyrazol-3-yl group |
| 750 | 4-cyano-5-cyclopropyl-1-methyl-1H-pyrazol-3-yl group |
| 751 | 4-cyano-5-difluoromethyl-1-methyl-1H-pyrazol-3-yl group |
| 752 | 4-cyano-1-methyl-5-trifluoromethyl-1H-pyrazol-3-yl group |
| 753 | 4-difluoromethyl-1 methyl-1H-pyrazol-3-yl group |
| 754 | 5-fluoro-4-difluoromethyl-1-methyl-1H-pyrazol-3-yl group |
| 755 | 5-chloro-4-difluoromethyl-1-methyl-1H-pyrazol-3-yl group |
| 756 | 5-bromo-4-difluoromethyl-1-methyl-1H-pyrazol-3-yl group |
| 757 | 4-difluoromethyl-1,5-dimethyl-1H-pyrazol-3-yl group |
| 758 | 5-ethyl-4-difluoromethyl-1-methyl-1H-pyrazol-3-yl group |
| 759 | 4-difluoromethyl-5-methoxy-1-methyl-1H-pyrazol-3-yl group |
| 760 | 5-ethoxy-4-difluoromethyl-1-methyl-1H-pyrazol-3-yl group |
| 761 | 5-cyano-4-difluoromethyl-1-methyl-1H-pyrazol-3-yl group |
| 762 | 5-cyclopropyl-4-difluoromethyl-1-methyl-1H-pyrazol-3-yl group |
| 763 | 4,5-bis(difluoromethyl)-1-methyl-1H-pyrazol-3-yl group |
| 764 | 4-difluoromethyl-1-methyl-5-trifluoromethyl-1H-pyrazol-3-yl group |
| 765 | 1-methyl-4-trifluoromethyl-1H-pyrazol-3-yl group |
| 766 | 5-fluoro-1-methyl-4-trifluoromethyl-1H-pyrazol-3-yl group |
| 767 | 5-chloro-1-methyl-4-trifluoromethyl-1H-pyrazol-3-yl group |

TABLE 46

| substituents Nos. | $Q^5$ |
|---|---|
| 768 | 5-bromo-1-methyl-4-trifluoromethyl-1H-pyrazol-3-yl group |
| 769 | 1,5-dimethyl-4-trifluoromethyl-1H-pyrazol-3-yl group |
| 770 | 5-ethyl-1-methyl-4-trifluoromethyl-1H-pyrazol-3-yl group |
| 771 | 5-methoxy-1-methyl-4-trifluoromethyl-1H-pyrazol-3-yl group |
| 772 | 5-ethoxy-1-methyl-4-trifluoromethyl-1H-pyrazol-3-yl group |
| 773 | 5-cyano-1-methyl-4-trifluoromethyl-1H-pyrazol-3-yl group |
| 774 | 5-cyclopropyl-1-methyl-4-trifluoromethyl-1H-pyrazol-3-yl group |
| 775 | 5-difluoromethyl-1-methyl-4-trifluoromethyl-1H-pyrazol-3-yl group |
| 776 | 1-methyl-4,5-bis(trifluoromethyl)-1H-pyrazol-3-yl group |
| 777 | 1-ethyl-5-fluoro-1H-pyrazol-3-yl group |
| 778 | 5-bromo-1-ethyl-1H-pyrazol-3-yl group |

TABLE 46-continued

| substituents Nos. | $Q^5$ |
|---|---|
| 779 | 5-cyano-1-ethyl-1H-pyrazol-3-yl group |
| 780 | 1-ethyl-5-difluoromethyl-1H-pyrazol-3-yl group |
| 781 | 1-ethyl-4,5-difluoro-1H-pyrazol-3-yl group |
| 782 | 1-ethyl-4-chloro-1H-pyrazol-3-yl group |
| 783 | 1-ethyl-5-bromo-4-fluoro-1H-pyrazol-3-yl group |
| 784 | 1-ethyl-5-cyano-4-fluoro-1H-pyrazol-3-yl group |
| 785 | 1-ethyl-5-difluoromethyl-4-fluoro-1H-pyrazol-3-yl group |
| 786 | 1-ethyl-5-trifluoromethyle-4-fluoro-1H-pyrazol-3-yl group |
| 787 | 4-chloro-1-ethyl-5-fluoro-1H-pyrazol-3-yl group |
| 788 | 5-bromo-4-chloro-1-ethyl-1H-pyrazol-3-yl group |
| 789 | 4-chloro-1,5-diethyl-1H-pyrazol-3-yl group |
| 790 | 1-ethyl-5-cyano-4-chloro-1H-pyrazol-3-yl group |
| 791 | 1-ethyl-4-chloro-5-difluoro-1H-pyrazol-3-yl group |
| 792 | 4-bromo-1-ethyl-5-fluoro-1H-pyrazol-3-yl group |
| 793 | 4-bromo-1-ethyl-5-chloro-1H-pyrazol-3-yl group |
| 794 | 4-bromo-1-ethyl-5-methoxy-1H-pyrazol-3-yl group |
| 795 | 4-bromo-5-cyano-1-ethyl-1H-pyrazol-3-yl group |
| 796 | 5-fluoro-1-ethyl-4-methyl-1H-pyrazol-3-yl group |

TABLE 47

| substituents Nos. | $Q^5$ |
|---|---|
| 797 | 5-bromo-1-ethyl-4-methyl-1H-pyrazol-3-yl group |
| 798 | 5-cyclopropyl-1-ethyl-4-methyl-1H-pyrazol-3-yl group |
| 799 | 1-ethyl-5-difluoromethyl-4-methyl-1H-pyrazol-3-yl group |
| 800 | 1,4-diethyl-1H-pyrazol-3-yl group |
| 801 | 1,4-diethyl-5-fluoro-1H-pyrazol-3-yl group |
| 802 | 1,4-diethyl-5-chloro-1H-pyrazol-3-yl group |
| 803 | 1,4-diethyl-5-methoxy-1-methyl-1H-pyrazol-3-yl group |
| 804 | 4-methoxy-1-ethyl-1H-pyrazol-3-yl group |
| 805 | 5-fluoro-1-ethyl-4-methoxy-1H-pyrazol-3-yl group |
| 806 | 5-chloro-1-ethyl-4-methoxy-1H-pyrazol-3-yl group |
| 807 | 5-bromo-1-ethyl-4-methoxy-1H-pyrazol-3-yl group |
| 808 | 1-ethyl-5-methoxy-4-methyl-1H-pyrazol-3-yl group |
| 809 | 1,5-diethyl-4-methoxy-1H-pyrazol-3-yl group |
| 810 | 1-ethyl-4,5-dimethoxy-1H-pyrazol-3-yl group |
| 811 | 1-ethyl-5-cyano-4-methoxy-1H-pyrazol-3-yl group |
| 812 | 5-cyclopropyl-1-ethyl-4-methoxy-1H-pyrazol-3-yl group |
| 813 | 1-ethyl-5-difluoromethyl-4-methoxy-1H-pyrazol-3-yl group |
| 814 | 1-ethyl-4-methoxy-5-trifluoromethyl-1H-pyrazol-3-yl group |
| 815 | 4-cyano-1-ethyl-1H-pyrazol-3-yl group |
| 816 | 4-cyano-5-fluoro-1-ethyl-1H-pyrazol-3-yl group |
| 817 | 4-cyano-5 chloro-1-ethyl-1H-pyrazol-3-yl group |
| 818 | 5-bromo-4-cyano-1-ethyl-1H-pyrazol-3-yl group |
| 819 | 4-cyano-1-ethyl-5-methoxy-1H-pyrazol-3-yl group |
| 820 | 4,5-dicyano-1-ethyl-1H-pyrazol-3-yl group |
| 821 | 4-cyano-5-cyclopropyl-1-ethyl-1H-pyrazol-3-yl group |
| 822 | 4-cyano-5-difluoromethyl-1-ethyl-1H-pyrazol-3-yl group |
| 823 | 4-cyano-1-ethylpyrazole-5-trifluoromethyl-1H-pyrazol-3-yl group |
| 824 | 4-difluoromethyl-1-ethyl-1H-pyrazol-3-yl group |
| 825 | 5-fluoro-4-difluoromethyl-1-ethyl-1H-pyrazol-3-yl group |

TABLE 48

| substituents Nos. | Q⁵ |
|---|---|
| 826 | 5-chloro-4-difluoromethyl-1-ethyl-1H-pyrazol-3-yl group |
| 827 | 4-difluoromethyl-1-ethyl-4-methyl-1H-pyrazol-3-yl group |
| 828 | 4-difluoromethyl-1-ethyl-5-methoxy-1H-pyrazol-3-yl group |
| 829 | 5-cyano-4-difluoromethyl-1-ethyl-1H-pyrazol-3-yl group |
| 830 | 1-ethyl-4-trifluoromethyl-1H-pyrazol-3-yl group |
| 831 | 5-fluoro-1-ethyl-4-trifluoromethyl-1H-pyrazol-3-yl group |
| 832 | 5-chloro-1-ethyl-4-trifluoromethyl-1H-pyrazol-3-yl group |
| 833 | 1-ethyl-4-trifluoromethyl-5-methyl-1H-pyrazol-3-yl group |
| 834 | 1-ethyl-4-trifluoromethyl-5-methoxy-1H-pyrazol-3-yl group |
| 835 | 5-cyano-1-ethyl-4-trifluoromethyl-1H-pyrazol-3-yl group |
| 836 | 4-methoxy-5-methylpyrazol-1-yl group |
| 837 | 4-ethoxy-5-methylpyrazol-1-yl group |
| 838 | 4-cyclopropyl-5-methylpyrazol-1-yl group |
| 839 | 4-trifluoromethyl-5-methylpyrazol-1-yl group |
| 840 | 4-bromo-3-methylpyrazol-1-yl group |
| 841 | 4-ethyl-3-methylpyrazol-1-yl group |
| 842 | 4-methoxy-3-methylpyrazol-1-yl group |
| 843 | 4-ethoxy-3-methylpyrazol-1-yl group |
| 844 | 4-cyclopropyl-3-methylpyrazol-1-yl group |
| 845 | 5-fluoro-3-methylpyrazol-1-yl group |
| 846 | 4,5-difluoro-3-methylpyrazol-1-yl group |
| 847 | 4-chloro-5-fluoro-3-methylpyrazol-1-yl group |
| 848 | 4-bromo-5-fluoro-3-methylpyrazol-1-yl group |
| 849 | 5-fluoro-3,4-dimethylpyrazol-1-yl group |
| 850 | 4-ethyl-5-fluoro-3-methylpyrazol-1-yl group |
| 851 | 5-fluoro-4-methoxy-3-methylpyrazol-1-yl group |
| 852 | 4-ethoxy-5-fluoro-3-methylpyrazol-1-yl group |
| 853 | 4-cyano-5-fluoro-3-methylpyrazol-1-yl group |
| 854 | 4-cyclopropyl-5-fluoro-3-methylpyrazol-1-yl group |

TABLE 49

| substituents Nos. | Q⁵ |
|---|---|
| 855 | 4-difluoromethyl-5-fluoro-3-methylpyrazol-1-yl group |
| 856 | 4-trifluoromethyl-5-fluoro-3-methylpyrazol-1-yl group |
| 857 | 5-chloro-3-methylpyrazol-1-yl group |
| 858 | 5-chloro-4-fluoro-3-methylpyrazol-1-yl group |
| 859 | 4,5-dichloro-3-methylpyrazol-1-yl group |
| 860 | 4-bromo-5-chloro-3-methylpyrazol-1-yl group |
| 861 | 5-chloro-3,4-dimethylpyrazol-1-yl group |
| 862 | 5-chloro-4-ethyl-3-methylpyrazol-1-yl group |
| 863 | 5-chloro-4-methoxy-3-methylpyrazol-1-yl group |
| 864 | 5-chloro-4-ethoxy-3-methylpyrazol-1-yl group |
| 865 | 5-chloro-4-cyano-3-methylpyrazol-1-yl group |
| 866 | 5-chloro-4-cyclopropyl-3-methylpyrazol-1-yl group |
| 867 | 5-chloro-4-difluoromethyl-3-methylpyrazol-1-yl group |
| 868 | 5-chloro-4-trifluoromethyl-3-methylpyrazol-1-yl group |
| 869 | 5-bromo-3-methylpyrazol-1-yl group |
| 870 | 5-bromo-4-fluoro-3-methylpyrazol-1-yl group |
| 871 | 5-bromo-4-chloro-3-methylpyrazol-1-yl group |
| 872 | 4,5-dibromo-3-methylpyrazol-1-yl-group |
| 873 | 5-bromo-3,4-dimethylpyrazol-1-yl group |
| 874 | 5-bromo-4-ethyl-3-methylpyrazol-1-yl group |
| 875 | 5-bromo-4-methoxy-3-methylpyrazol-1-yl group |
| 876 | 5-bromo-4-ethoxy-3-methylpyrazol-1-yl group |
| 877 | 5-bromo-4-cyano-3-methylpyrazol-1-yl group |
| 878 | 5-bromo-4-cyclopropyl-3-methylpyrazol-1-yl group |
| 879 | 5-bromo-4-difluoromethyl-3-methylpyrazol-1-yl group |

TABLE 49-continued

| substituents Nos. | Q⁵ |
|---|---|
| 880 | 5-bromo-4-trifluoromethyl-3-methylpyrazol-1-yl group |
| 881 | 3,5-dimethylpyrazol-1-yl group |
| 882 | 5-ethyl-4-fluoro-3-methylpyrazol-1-yl group |
| 883 | 5-ethyl-4-methoxy-3-methylpyrazol-1-yl group |

TABLE 50

| substituents Nos. | Q⁵ |
|---|---|
| 884 | 4-ethoxy-5-ethyl-3-methylpyrazol-1-yl group |
| 885 | 5-trifluoromethyl-4-methoxy-3-methylpyrazol-1-yl group |
| 886 | 5 methoxy-3-methylpyrazol-1-yl group |
| 887 | 4-fluoro-5-methoxy-3-methylpyrazol-1-yl group |
| 888 | 4-chloro-5-methoxy-3-methylpyrazol-1-yl group |
| 889 | 4-bromo-5-methoxy-3-methylpyrazol-1-yl group |
| 890 | 4-ethyl-5-methoxy-3-methylpyrazol-1-yl group |
| 891 | 4,5-dimethoxy-3-methylpyrazol-1-yl group |
| 892 | 4-ethyle-5-methoxy-3-methylpyrazol-1-yl group |
| 893 | 4-ethoxy-5-methoxy-3-methylpyrazol-1-yl group |
| 894 | 4-cyano-5-methoxy-3-methylpyrazol-1-yl group |
| 895 | 4-cyclopropyl-5-methoxy-3-methylpyrazol-1-yl group |
| 896 | 4-difluoromethy-5-methoxy-3-methylpyrazol-1-yl group |
| 897 | 5-methoxy-3-methyl-4-trifluoromethypyrazol-1-yl group |
| 898 | 5-ethoxy-3-methylpyrazol-1-yl group |
| 899 | 5-ethoxy-4-fluoro-3-methylpyrazol-1-yl group |
| 900 | 5-ethoxy-4-chloro-3-methylpyrazol-1-yl group |
| 901 | 5 ethoxy-4-bromo3-methylpyrazol-1-yl group |
| 902 | 5-ethoxy-3,4-dimethylpyrazol-1-yl group |
| 903 | 5-ethoxy-4-ethyl-3-methylpyrazol-1-yl group |
| 904 | 5-ethoxy-4-methoxy-3-methylpyrazol-1-yl group |
| 905 | 4,5-diethoxy-3-methylpyrazol-1-yl group |
| 906 | 4-cyano-5-ethoxy-3-methylpyrazol-1-yl group |
| 907 | 4-cyclopropyl-5-ethoxy-3-methylpyrazol-1-yl group |
| 908 | 4-difluoromethyl-5-ethoxy-3-methylpyrazol-1-yl group |
| 909 | 5-ethoxy-4-trifluoromethyl-3-methylpyrazol-1-yl group |
| 910 | 5-cyano-3-methylpyrazol-1-yl group |
| 911 | 5-cyano-4-fluoro-3-methylpyrazol-1-yl group |
| 912 | 5-cyano-4-chloro-3-methylpyrazol-1-yl group |

TABLE 51

| substituents Nos. | Q⁵ |
|---|---|
| 913 | 5-cyano-4-bromo-3-methylpyrazol-1-yl group |
| 914 | 5-cyano-3,4-dimethylpyrazol-1-yl group |
| 915 | 5-cyano-4-ethyl-3-methylpyrazol-1-yl group |
| 916 | 5-cyano-4-methoxy-3-methylpyrazol-1-yl group |
| 917 | 5-cyano-4-ethoxy-3-methylpyrazol-1-yl group |
| 918 | 4,5-dicyano-3-methylpyrazol-1-yl group |
| 919 | 5-cyano-4-cyclopropyl-3-methylpyrazol-1-yl group |
| 920 | 5-cyano-4-difluoromethyl-3-methylpyrazol-1-yl group |
| 921 | 5-cyano-4-trifluoromethyl-3-methylpyrazol-1-yl group |
| 922 | 5-difluoromethyl-3-methylpyrazol-1-yl group |
| 923 | 5-difluoromethyl-4-fluoro-3-methylpyrazol-1-yl group |
| 924 | 4-chloro-5-difluoromethyl-3-methylpyrazol-1-yl group |

TABLE 51-continued

| substituents Nos. | Q⁵ |
|---|---|
| 925 | 4-bromo-5-difluoromethyl-3-methylpyrazol-1-yl group |
| 926 | 5-difluoromethyl-3,4-dimethylpyrazol-1-yl group |
| 927 | 4-ethyl-5-difluoromethyl-3-methylpyrazol-1-yl group |
| 928 | 5-difluoromethyl-4-methoxy-3-methylpyrazol-1-yl group |
| 929 | 4-ethoxy-5-difluoromethyl-3-methylpyrazol-1-yl group |
| 930 | 4-cyano-5-difluoromethyl-3-methylpyrazol-1-yl group |
| 931 | 4-cyclopropyl-5-difluoromethyl-3-methylpyrazol-1-yl group |
| 932 | 4,5-bis(difluoromethyl)-3-methylpyrazol-1-yl group |
| 933 | 5-difluoromethyl-3-methyl-4-trifluoromethylpyrazol-1-yl group |
| 934 | 3-methyl-5-trifluoromethylpyrazol-1-yl group |
| 935 | 4-fluoro-3-methyl-5-trifluoromethypyrazol-1-yl group |
| 936 | 4-chloro-3-methyl-5-trifluoromethypyrazol-1-yl group |
| 937 | 4-bromo-3-methyl-5-trifluoromethylpyrazol-1-yl group |
| 938 | 3,4-dimethyl-5-trifluoromethylpyrazol-1-yl group |
| 939 | 4-ethyl-3-methyl-5-trifluoromethylpyrazol-1-yl group |
| 940 | 4-methoxy-3-methyl-5-trifluoromethylpyrazol-1-yl group |
| 941 | 4-ethoxy-3-methyl-5-trifluoromethylpyrazol-1-yl group |

TABLE 52

| substituents Nos. | Q⁵ |
|---|---|
| 942 | 4-cyano-3-methyl-5-trifluoromethylpyrazole-1-yl group |
| 943 | 4-cyclopropyl-3-methyl-5-trifluoromethylpyrazol-1-yl group |
| 944 | 4-difluoromethyl-3-methyl-5-trifluoromethylpyrazole-1-yl group |
| 945 | 4,5-bis(trifluoromethyl)-3-methylpyrazol-1-yl group |
| 946 | 3-ethyl-4-ethoxy-5-methylpyrazole-1-yl group |
| 947 | 3-ethyl-4-cyano-5-methylpyrazole-1-yl group |
| 948 | 3-ethyl-4-cyclopropyl-5-methylpyrazol-1-yl group |
| 949 | 3-fluoro-5-methylpyrazol-1-yl group |
| 950 | 3,4-difluoro-5-methylpyrazol-1-yl group |
| 951 | 4-chloro-3-fluoro-5-methylpyrazol-1-yl group |
| 952 | 4-bromo-3-fluoro-5-methylpyrazol-1-yl group |
| 953 | 3-fluoro-4,5-dimethylpyrazol-1-yl group |
| 954 | 4-ethyl-3-fluoro-5-methylpyrazol-1-yl group |
| 955 | 3-fluoro-4-methoxy-5-methylpyrazol-1-yl group |
| 956 | 4-ethoxy-3-fluoro-5-methylpyrazol-1-yl group |
| 957 | 4-cyano-3-fluoro-5-methylpyrazol-1-yl group |
| 958 | 4-cyclopropyl-3-fluoro-5-methylpyrazol-1-yl group |
| 959 | 4-difluoromethyl-3-fluoro-5-methylpyrazol-1-yl group |
| 960 | 3-fluoro-5-methyl-4-trifluoromethyl-1-yl group |
| 961 | 3-chloro-5-methylpyrazol-1-yl group |
| 962 | 3-chloro-4-fluoro-5-methylpyrazol-1-yl group |
| 963 | 3,4-dichloro-5-methylpyrazol-1-yl group |
| 964 | 4-bromo-3-chloro-5-methylpyrazol-1-yl group |
| 965 | 3-chloro-4,5-dimethylpyrazol-1-yl group |
| 966 | 3-chloro-4-ethyl-5-methylpyrazol-1-yl group |
| 967 | 3-chloro-4-methoxy-5-methylpyrazol-1-yl group |
| 968 | 3-chloro-4-ethoxy-5-methylpyrazol-1-yl group |
| 969 | 3-chloro-4-cyano-5-methylpyrazol-1-yl group |
| 970 | 3-chloro-4-cyclopropyl-5-methylpyrazol-1-yl group |

TABLE 53

| substituents Nos. | Q⁵ |
|---|---|
| 971 | 3-chloro-4-difluoromethyl-5-methylpyrazol-1-yl group |
| 972 | 3-chloro-5-methyl-4-trifluoromethylpyrazol-1-yl group |
| 973 | 3-methoxy-5-methylpyrazol-1-yl group |
| 974 | 4-fluoro-3-methoxy-5-methylpyrazol-1-yl group |
| 975 | 4-chloro-3-methoxy-5-methylpyrazol-1-yl group |
| 976 | 4-bromo-3-methoxy-5-methylpyrazol-1-yl group |
| 977 | 3-methoxy-4,5-dimethylpyrazol-1-yl group |
| 978 | 4-ethyl-3-methoxy-5-methylpyrazol-1-yl group |
| 979 | 3,4-dimethoxy-5-methylpyrazol-1-yl group |
| 980 | 4-ethoxy-3-methoxy-5-methylpyrazol-1-yl group |
| 981 | 4-cyano-3 methoxy-5-methylpyrazol-1-yl group |
| 982 | 4-cyclopropyl-3-methoxy-5-methylpyrazol-1-yl group |
| 983 | 4-difluoromethyl-3-methoxy-5-methylpyrazol-1-yl group |
| 984 | 5-methyl-3-methoxy-4-trifluoromethylpyrazol-1-yl group |
| 985 | 3-cyano-5-methylpyrazol-1-yl group |
| 986 | 3-cyano-4-fluoro-5-methylpyrazol-1-yl group |
| 987 | 4-chloro-3-cyano-5-methylpyrazol-1-yl group |
| 988 | 4-bromo-3-cyano-5-methylpyrazol-1-yl group |
| 989 | 3-cyano-4,5-dimethylpyrazol-1-yl group |
| 990 | 3-cyano-4-ethyl-5-methylpyrazol-1-yl group |
| 991 | 3-cyano-4-methoxy-5-methylpyrazol-1-yl group |
| 992 | 3-cyano-4-ethoxy-5-methylpyrazol-1-yl group |
| 993 | 3,4-dicyano-5-methylpyrazol-1-yl group |
| 994 | 3-cyano-4-cyclopropyl-5-methylpyrazol-1-yl group |
| 995 | 3-cyano-4-difluoromethyl-5-methylpyrazol-1-yl group |
| 996 | 3-cyano-5-methyl-4-trifluoromethylpyrazol-1-yl group |
| 997 | 3-cyclopropyl-4-methoxy-5-methylpyrazol-1-yl group |
| 998 | 3-cyclopropyl-4-ethoxy-5-methylpyrazol-1-yl group |
| 999 | 3-cyclopropyl-4-cyano-5-methylpyrazol-1-yl group |

TABLE 54

| substituents Nos. | Q⁵ |
|---|---|
| 1000 | 3-difluoromethyl-5-methylpyrazol-1-yl group |
| 1001 | 4-fluoromethyl-3-difluoro-5-methylpyrazol-1-yl group |
| 1002 | 4-chloro-3-difluoromethyl-5-methylpyrazol-1-yl group |
| 1003 | 4-bromo-3-difluoromethyl-5-methylpyrazol-1-yl group |
| 1004 | 3-difluoromethyl-4,5-dimethylpyrazol-1-yl group |
| 1005 | 3-difluoromethyl-4-ethyl-5-methylpyrazol-1-yl group |
| 1006 | 3-difluoromethyl-4-methoxy-5-methylpyrazol-1-yl group |
| 1007 | 3-difluoromethyl-4-ethoxy-5-methylpyrazol-1-yl group |
| 1008 | 3-difluoromethyl-4-cyano-5-methylpyrazol-1-yl group |
| 1009 | 3-difluoromethyl-4-cyclopropyl-5-methylpyrazol-1-yl group |
| 1010 | 4-difuruoromethyl-5-methylpyrazol-1-yl group |
| 1011 | 5-methyl-4-trifluoromethylpyrazol-1-yl group |
| 1012 | 5-methyl-3-trifluoromethylpyrazol-1-yl group |
| 1013 | 4-fluoro-5-methyl-3-trifluoromethylpyrazol-1-yl group |
| 1014 | 4-chloro-5-methyl-3-trifluoromethylpyrazol-1-yl group |
| 1015 | 4-bromo-5-methyl-3trifluoromethylpyrazol-1-yl group |

TABLE 54-continued

| substituents Nos. | $Q^5$ |
|---|---|
| 1016 | 4,5-dimethyl-3-trifluoromethylpyrazol-1-yl group |
| 1017 | 4-ethyl-5-methyl-3-trifluoromethylpyrazol-1-yl group |
| 1018 | 4-methoxy-5-methyl-3-trifluoromethylpyrazol-1-yl group |
| 1019 | 4-ethoxy-5-methyl-3-trifluoromethylpyrazol-1-yl group |
| 1020 | 4-cyano-5-methyl-3-trifluoromethylpyrazol-1-yl group |
| 1021 | 4-cyclopropyl-5-methyl-3-trifluoromethylpyrazol-1-yl group |
| 1022 | 4-difluoro-5-methyl-3-trifluoromethylpyrazol-1-yl group |
| 1023 | 5-methyl-3,4-bis(trifluoromethyl)pyrazol-1-yl group |

According to the above-mentioned processes, the following compounds can be prepared:

Compounds EB1A-001~EB1A-20, EB1B-001~EB1B-20, EB1C-001~EB1C-20, EB1D-001~EB1D-20, EB1E-001~EB1E-20, EB2A-001~EB2A-20, EB2B-001~EB2B-20, EB2C-001~EB2C-20, EB3A-001~EB3A-20, EB3B-001~EB3B-20, EB3C-001~EB3C-20, EB4A-001~EB4A-20, EB4B-001~EB4B-20, EB5A-001~EB5A-20, EB5B-001~EB5B-20, EB5C-001~EB5C-20, EB6A-001~EB6A-20 and EB6B-001~EB6B-20.

Compounds EB1A-001~EB1A-20 represent Compounds represented by a formula:

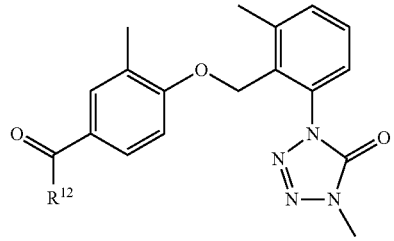

(EB1A)

[in the formula (EB1A), $R^{12}$ represents a substituent corresponding to each of substituents Nos. 1 to 20 indicated in Table 55 as below-mentioned];

Compounds EB1B-001~EB1B-20 represent Compounds represented by a formula:

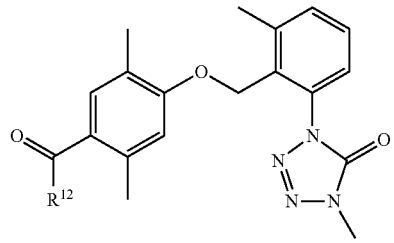

(EB1B)

[in the formula (EB1B), $R^{12}$ represents a substituent corresponding to each of substituents Nos. 1 to 20 indicated in Table 55 as below-mentioned];

Compounds EB1C-001~EB1C-20 represent Compounds represented by a formula:

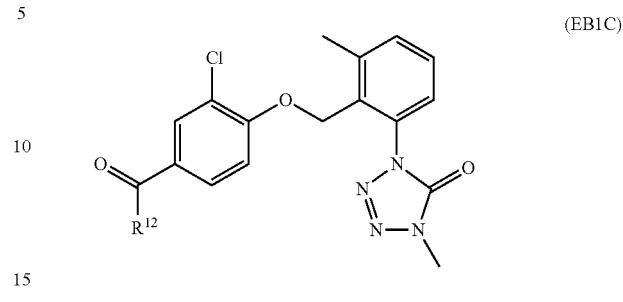

(EB1C)

[in the formula (EB1C), $R^{12}$ represents a substituent corresponding to each of substituents Nos. 1 to 20 indicated in Table 55 as below-mentioned];

Compounds EB1D-001~EB1D-20 represent Compounds represented by a formula:

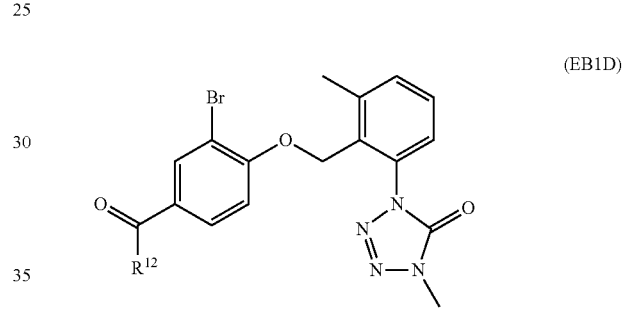

(EB1D)

[in the formula (EB1D), $R^{12}$ represents a substituent corresponding to each of substituents Nos. 1 to 20 indicated in Table 55 as below-mentioned];

Compounds EB1E-001~EB1E-20 represent Compounds represented by a formula:

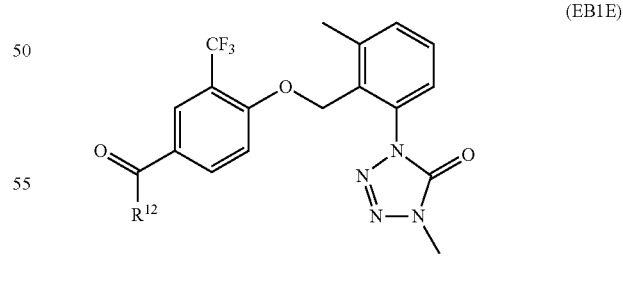

(EB1E)

[in the formula (EB1E), $R^{12}$ represents a substituent corresponding to each of substituents Nos. 1 to 20 indicated in Table 55 as below-mentioned];

Compounds EB2A-001~EB2A-20 represent Compounds represented by a formula:

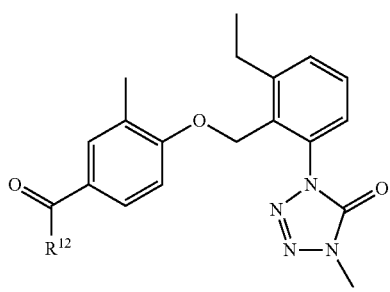
(EB2A)

[in the formula (EB2A), $R^{12}$ represents a substituent corresponding to each of substituents Nos. 1 to 20 indicated in Table 55 as below-mentioned];

Compounds EB2B-001~EB2B-20 represent Compounds represented by a formula:

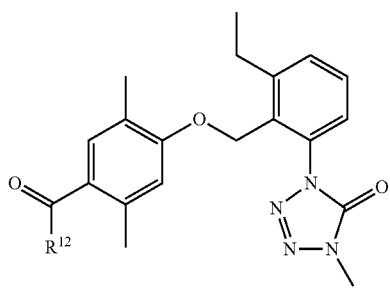
(EB2B)

[in the formula (EB2B), $R^{12}$ represents a substituent corresponding to each of substituents Nos. 1 to 20 indicated in Table 55 as below-mentioned];

Compounds EB2C-001~EB2C-20 represent Compounds represented by a formula:

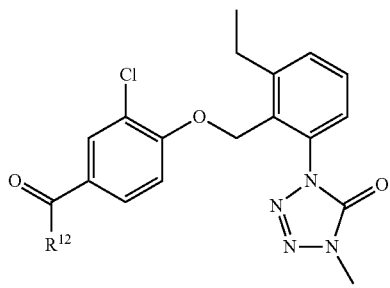
(EB2C)

[in the formula (EB2C), $R^{12}$ represents a substituent corresponding to each of substituents Nos. 1 to 20 indicated in Table 55 as below-mentioned];

Compounds EB3A-001~EB3A-20 represent Compounds represented by a formula:

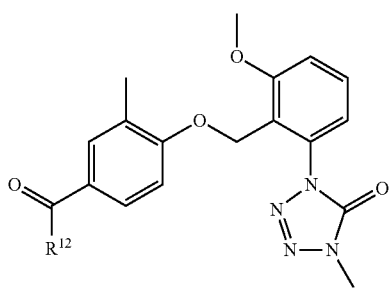
(EB3A)

[in the formula (EB3A), $R^{12}$ represents a substituent corresponding to each of substituents Nos. 1 to 20 indicated in Table 55 as below-mentioned];

Compounds EB3B-001~EB3B-20 represent Compounds represented by a formula:

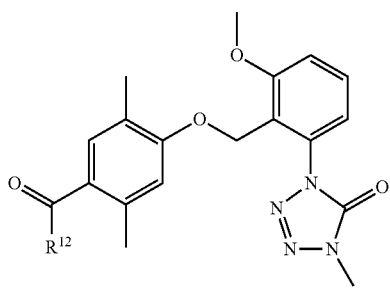
(EB3B)

[in the formula (EB3B), $R^{12}$ represents a substituent corresponding to each of substituents Nos. 1 to 20 indicated in Table 55 as below-mentioned];

Compounds EB3C-001~EB3C-20 represent Compounds represented by a formula:

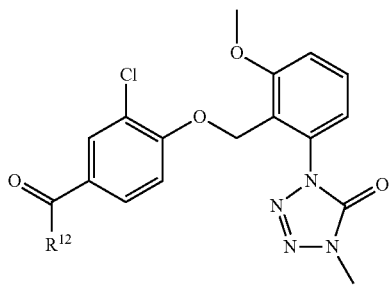
(EB3C)

[in the formula (EB3C), $R^{12}$ represents a substituent corresponding to each of substituents Nos. 1 to 20 indicated in Table 55 as below-mentioned];

Compounds EB4A-001~EB4A-20 represent Compounds represented by a formula:

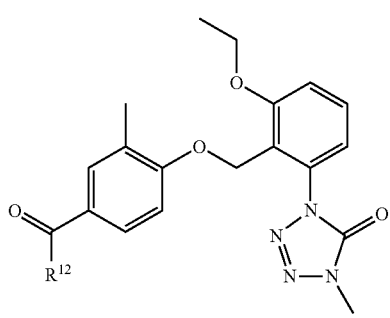

(EB4A)

[in the formula (EB4A), R$^{12}$ represents a substituent corresponding to each of substituents Nos. 1 to 20 indicated in Table 55 as below-mentioned];

Compounds EB4B-001~EB4B-20 represent Compounds represented by a formula:

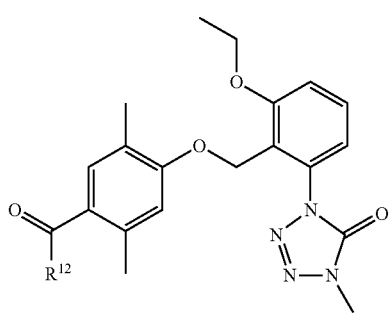

(EB4B)

[in the formula (EB4B), R$^{12}$ represents a substituent corresponding to each of substituents Nos. 1 to 20 indicated in Table 55 as below-mentioned];

Compounds EB5A-001~EB5A-20 represent Compounds represented by a formula:

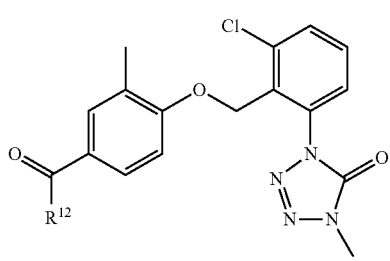

(EB5A)

[in the formula (EB5A), R$^{12}$ represents a substituent corresponding to each of substituents Nos. 1 to 20 indicated in Table 55 as below-mentioned];

Compounds EB5B-001~EB5B-20 represent Compounds represented by a formula:

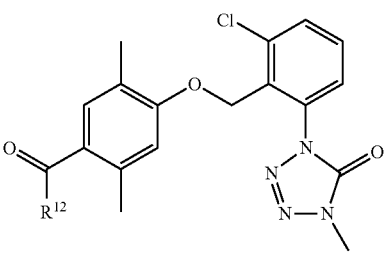

(EB5B)

[in the formula (EB5B), R$^{12}$ represents a substituent corresponding to each of substituents Nos. 1 to 20 indicated in Table 55 as below-mentioned];

Compounds EB5C-001~EB5C-20 represent Compounds represented by a formula:

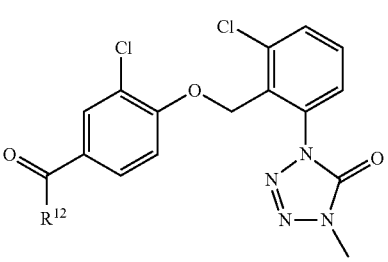

(EB5C)

[in the formula (EB5C), R$^{12}$ represents a substituent corresponding to each of substituents Nos. 1 to 20 indicated in Table 55 as below-mentioned];

Compounds EB6A-001~EB6A-20 represent Compounds represented by a formula:

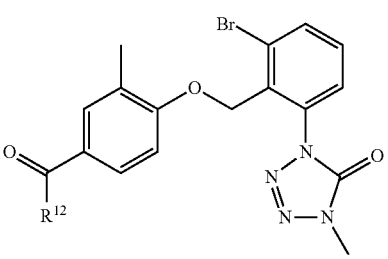

(EB6A)

[in the formula (EB6A), R$^{12}$ represents a substituent corresponding to each of substituents Nos. 1 to 20 indicated in Table 55 as below-mentioned]; and Compounds EB6B-001~EB6B-20 represent Compounds represented by a formula:

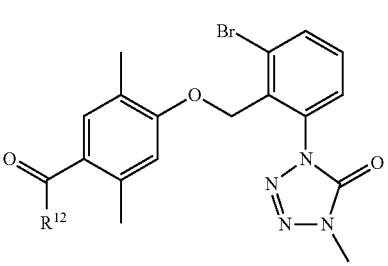

(EB6B)

[in the formula (EB6B), $R^{12}$ represents a substituent corresponding to each of substituents Nos. 1 to 20 indicated in Table 55 as below-mentioned].

TABLE 55

| substituents Nos. | $R^{12}$ |
|---|---|
| 1 | methyl group |
| 2 | ethyl group |
| 3 | propyl group |
| 4 | butyl group |
| 5 | pentyl group |
| 6 | hexyl group |
| 7 | isopropyl group |
| 8 | tert-butyl group |
| 9 | isobutyl group |
| 10 | trifluoromethyl group |
| 11 | trichloromethyl group |
| 12 | 2.2-difluoroethyl group |
| 13 | cyclopropyl group |
| 14 | cyclobutyl group |
| 15 | cyclohexyl group |
| 16 | 1-fluoro-cyclopropyl group |
| 17 | 1-chloro-cyclopropyl group |
| 18 | 2,2-difluoro-cyclopropyl group |
| 19 | 2,2,3,3-tetrafluoro-cyclopropyl group |
| 20 | 1,2,2,3,3-pentafluoro-cyclopropyl group |

According to the above-mentioned processes, the following compounds can be prepared:
Compounds EC1A-001~EC1A-103, EC1B-001~EC1B-103, EC1C-001~EC1C-103, EC1D-001~EC1D-103, EC1E-001~EC1E-103, EC2A-001~EC2A-103, EC2B-001~EC2B-103, EC2C-001~EC2C-103, EC3A-001~EC3A-103, EC3B-001~EC3B-103, EC3C-001~EC3C-103, EC4A-001~EC4A-103, EC4B-001~EC4B-103, EC5A-001~EC5A-103, EC5B-001~EC5B-103, EC5C-001~EC5C-103, EC6A-001~EC6A-103 and EC6B-001~EC6B-103.

Compounds EC1A-001~EC1A-103 represent Compounds represented by a formula:

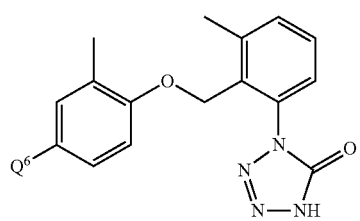

(EC1A)

[in the formula (EC1A), $Q^6$ represents a substituent corresponding to each of substituents Nos. 1 to 103 indicated in Table 56 to Table 60 as below-mentioned];
Compounds EC1B-001~EC1B-103 represent Compounds represented by a formula:

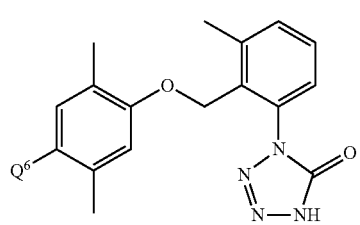

(EC1B)

[in the formula (EC1B), $Q^6$ represents a substituent corresponding to each of substituents Nos. 1 to 103 indicated in Table 56 to Table 60 as below-mentioned];
Compounds EC1C-001~EC1C-103 represent Compounds represented by a formula:

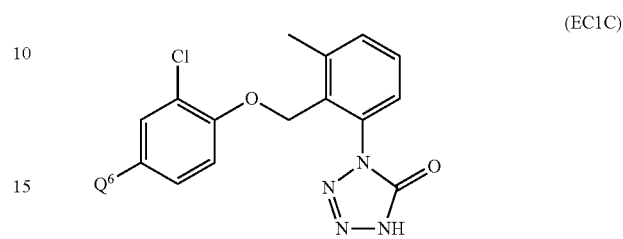

(EC1C)

[in the formula (EC1C), $Q^6$ represents a substituent corresponding to each of substituents Nos. 1 to 103 indicated in Table 56 to Table 60 as below-mentioned];
Compounds EC1D-001~EC1D-103 represent Compounds represented by a formula:

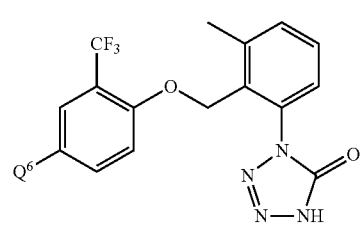

(EC1D)

[in the formula (EC1D), $Q^6$ represents a substituent corresponding to each of substituents Nos. 1 to 103 indicated in Table 56 to Table 60 as below-mentioned];
Compounds EC1E-001~EC1E-103 represent Compounds represented by a formula:

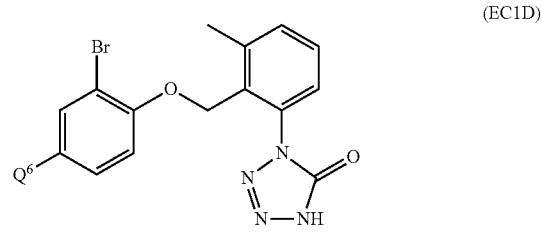

(EC1E)

[in the formula (EC1E), $Q^6$ represents a substituent corresponding to each of substituents Nos. 1 to 103 indicated in Table 56 to Table 60 as below-mentioned];
Compounds EC2A-001~EC2A-103 represent Compounds represented by a formula:

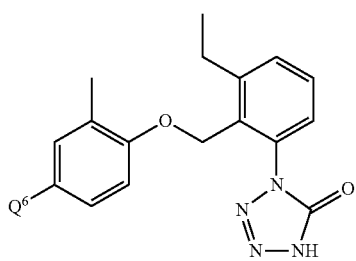

(EC2A)

[in the formula (EC2A), $Q^6$ represents a substituent corresponding to each of substituents Nos. 1 to 103 indicated in Table 56 to Table 60 as below-mentioned];

Compounds EC2B-001~EC2B-103 represent Compounds represented by a formula:

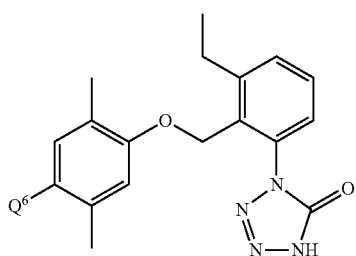

(EC2B)

[in the formula (EC2B), $Q^6$ represents a substituent corresponding to each of substituents Nos. 1 to 103 indicated in Table 56 to Table 60 as below-mentioned];

Compounds EC2C-001~EC2C-103 represent Compounds represented by a formula:

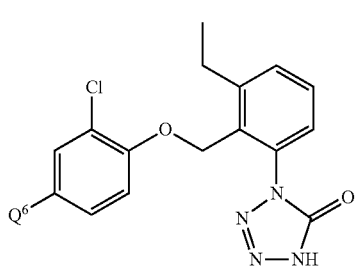

(EC2C)

[in the formula (EC2C), $Q^6$ represents a substituent corresponding to each of substituents Nos. 1 to 103 indicated in Table 56 to Table 60 as below-mentioned];

Compounds EC3A-001~EC3A-103 represent Compounds represented by a formula:

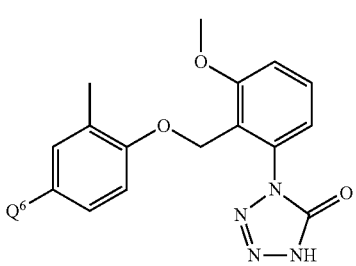

(EC3A)

[in the formula (EC3A), $Q^6$ represents a substituent corresponding to each of substituents Nos. 1 to 103 indicated in Table 56 to Table 60 as below-mentioned];

Compounds EC3B-001~EC3B-103 represent Compounds represented by a formula:

(EC3B)

[in the formula (EC3B), $Q^6$ represents a substituent corresponding to each of substituents Nos. 1 to 103 indicated in Table 56 to Table 60 as below-mentioned];

Compounds EC3C-001~EC3C-103 represent Compounds represented by a formula:

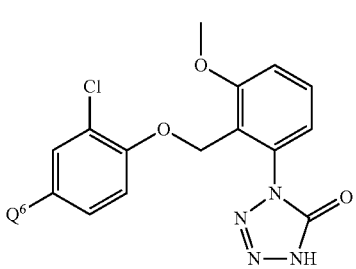

(EC3C)

[in the formula (EC3C), $Q^6$ represents a substituent corresponding to each of substituents Nos. 1 to 103 indicated in Table 56 to Table 60 as below-mentioned];

Compounds EC4A-001~EC4A-103 represent Compounds represented by a formula:

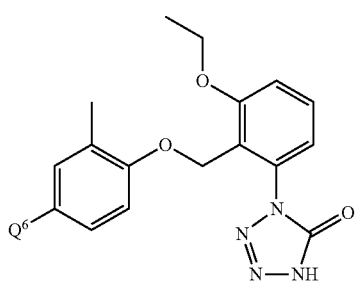
(EC4A)

[in the formula (EC4A), Q⁶ represents a substituent corresponding to each of substituents Nos. 1 to 103 indicated in Table 56 to Table 60 as below-mentioned];

Compounds EC4B-001~EC4B-103 represent Compounds represented by a formula:

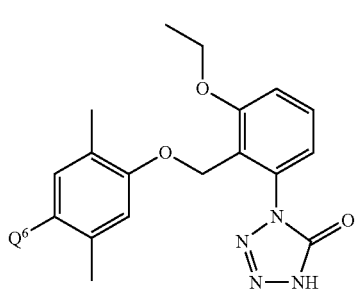
(EC4B)

[in the formula (EC4B), Q⁶ represents a substituent corresponding to each of substituents Nos. 1 to 103 indicated in Table 56 to Table 60 as below-mentioned];

Compounds EC5A-001~EC5A-103 represent Compounds represented by a formula:

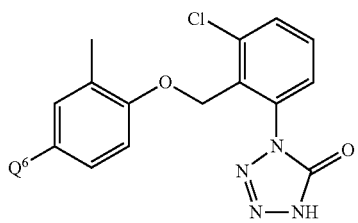
(EC5A)

[in the formula (EC5A), Q⁶ represents a substituent corresponding to each of substituents Nos. 1 to 103 indicated in Table 56 to Table 60 as below-mentioned];

Compounds EC5B-001~EC5B-103 represent Compounds represented by a formula:

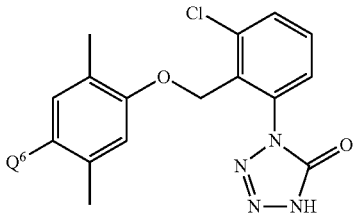
(EC5B)

[in the formula (EC5B), Q⁶ represents a substituent corresponding to each of substituents Nos. 1 to 103 indicated in Table 56 to Table 60 as below-mentioned];

Compounds EC5C-001~EC5C-103 represent Compounds represented by a formula:

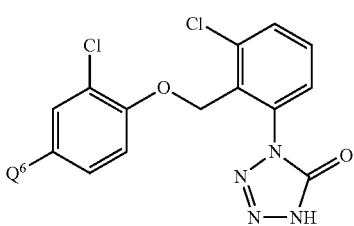
(EC5C)

[in the formula (EC5C), Q⁶ represents a substituent corresponding to each of substituents Nos. 1 to 103 indicated in Table 56 to Table 60 as below-mentioned];

Compounds EC6A-001~EC6A-103 represent Compounds represented by a formula:

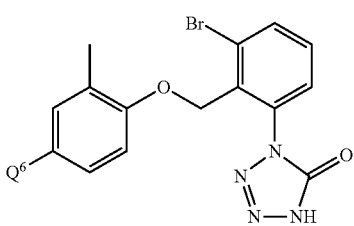
(EC6A)

[in the formula (EC6A), Q⁶ represents a substituent corresponding to each of substituents Nos. 1 to 103 indicated in Table 56 to Table 60 as below-mentioned]; and Compounds EC6B-001~EC6B-103 represent Compounds represented by a formula:

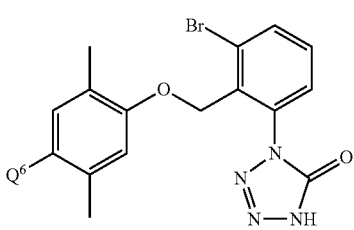
(EC6B)

[in the formula (EC6B), Q⁶ represents a substituent corresponding to each of substituents Nos. 1 to 103 indicated in Table 56 to Table 60 as below-mentioned].

TABLE 56

| substituents Nos. | $Q^6$ |
|---|---|
| 1 | 1,4,5-trimethyl-1H-pyrazol-3-yl group |
| 2 | 1,5-dimethyl-4-ethyl-1H-pyrazol-3-yl group |
| 3 | 1,5-dimethyl-4-fluoro-1H-pyrazol-3-yl group |
| 4 | 1,5-dimethyl-4-chloro-1H-pyrazol-3-yl group |
| 5 | 1,5-dimethyl-4-bromo-1H-pyrazol-3-yl group |
| 6 | 1,5-dimethyl-4-iodo-1H-pyrazol-3-yl group |
| 7 | 1,5-dimethyl-4-cyano-1H-pyrazol-3-yl group |
| 8 | 1-methyl-4,5-diethyl-1H-pyrazol-3-yl group |
| 9 | 1-methyl-5-ethyl-4-fluoro-1H-pyrazol-3-yl group |
| 10 | 1-methyl-5-ethyl-4-chloro-1H-pyrazol-3-yl group |
| 11 | 1-methyl-5-ethyl-4-bromo-1H-pyrazol-3-yl group |
| 12 | 1-methyl-5-ethyl-4-iodo-1H-pyrazol-3-yl group |
| 13 | 1-methyl-5-ethyl-4-cyano-1H-pyrazol-3-yl group |
| 14 | 1,4-dimethy-5-propyl-1H-pyrazol-3-yl group |
| 15 | 1-methyl-5-propyl-4-ethyl-1H-pyrazol-3-yl group |
| 16 | 1-methyl-5-propyl-4-fluoro-1H-pyrazol-3-yl group |
| 17 | 1-methyl-5-propyl-4-chloro-1H-pyrazol-3-yl group |
| 18 | 1-methyl-5-propyl-4-bromo-1H-pyrazol-3-yl group |
| 19 | 1-methyl-5-propyl-4-iodo-1H-pyrazol-3-yl group |
| 20 | 1-methyl-5-propyl-4-cyano-1H-pyrazol-3-yl group |
| 21 | 1,4-dimethyl-5-methoxy-1H-pyrazol-3-yl group |
| 22 | 1-methyl-5-methoxy-4-ethyl-1H-pyrazol-3-yl group |

TABLE 57

| substituents Nos. | $Q^6$ |
|---|---|
| 23 | 1-methyl-5-methoxy-4-fluoro-1H-pyrazol-3-yl group |
| 24 | 1-methyl-5-methoxy-4-chloro-1H-pyrazol-3-yl group |
| 25 | 1-methyl-5-methoxy-4-bromo-1H-pyrazol-3-yl group |
| 26 | 1-methyl-5-methoxy-4-iodo-1H-pyrazol-3-yl group |
| 27 | 1-methyl-5-methoxy-4-cyano-1H-pyrazol-3-yl group |
| 28 | 1,4-dimethyl-5-ethoxy-1H-pyrazol-3-yl group |
| 29 | 1-methyl-5-ethoxy-4-ethyl-1H-pyrazol-3-yl group |
| 30 | 1-methyl-5-ethoxy-4-fluoro-1H-pyrazol-3-yl group |
| 31 | 1-methyl-5-ethoxy-4-chloro-1H-pyrazol-3-yl group |
| 32 | 1-methyl-5-ethoxy-4-bromo-1H-pyrazol-3-yl group |
| 33 | 1-methyl-5-ethoxy-4-iodo-1H-pyrazol-3-yl group |
| 34 | 1-methyl-5-ethoxy-4-cyano-1H-pyrazol-3-yl group |
| 35 | 1,4-dimethyl-5-methylthio-1H-pyrazol-3-yl group |
| 36 | 1-methyl-5-methylthio-4-ethyl-1H-pyrazol-3-yl group |
| 37 | 1-methyl-5-methylthio-4-fluoro-1H-pyrazol-3-yl group |
| 38 | 1-methyl-5-methylthio-4-chloro-1H-pyrazol-3-yl group |
| 39 | 1-methyl-5-methylthio-4-bromo-1H-pyrazol-3-yl group |
| 40 | 1-methyl-5-methylthio-4-iodo-1H-pyrazol-3-yl group |

TABLE 57-continued

| substituents Nos. | $Q^6$ |
|---|---|
| 41 | 1-methyl-5-methylthio-4-cyano-1H-pyrazol-3-yl group |
| 42 | 1,4-dimethyl-5-fluoro-1H-pyrazol-3-yl group |
| 43 | 1-methyl-4-ethyl-5-fluoro-1H-pyrazol-3-yl group |
| 44 | 1,4-dimethyl-5-chloro-1H-pyrazol-3-yl group |

TABLE 58

| substituents Nos. | $Q^6$ |
|---|---|
| 45 | 1-methyl-4-ethyl-5-chloro-1H-pyrazol-3-yl group |
| 46 | 1,4-dimethyl-5-bromo-1H-pyrazol-3-yl group |
| 47 | 1-methyl-4-ethyl-5-bromo-1H-pyrazol-3-yl group |
| 48 | 1,4-dimethyl-5-iodo-1H-pyrazol-3-yl group |
| 49 | 1-methyl-4-ethyl-5-iodo-1H-pyrazol-3-yl group |
| 50 | 1,4-dimethyl-5-cyano-1H-pyrazol-3-yl group |
| 51 | 1-methyl-4-ethyl-5-cyano-1H-pyrazol-3-yl group |
| 52 | 1-ethyl-4,5-dimethyl-1H-pyrazol-3-yl group |
| 53 | 1,4-diethyl-5-methyl-1H-pyrazol-3-yl group |
| 54 | 1-ethyl-5-methyl-4-fluoro-1H-pyrazol-3-yl group |
| 55 | 1-ethyl-5-methyl-4-chloro-1H-pyrazol-3-yl group |
| 56 | 1-ethyl-5-methyl-4-bromo-1H-pyrazol-3-yl group |
| 57 | 1-ethyl-5-methyl-4-iodo-1H-pyrazol-3-yl group |
| 58 | 1-ethyl-5-methyl-4-cyano-1H-pyrazol-3-yl group |
| 59 | 1,5-diethyl-4-methyl-1H-pyrazol-3-yl group |
| 60 | 1,4,5-triethyl-1H-pyrazol-3-yl group |
| 61 | 1,5-diethyl-4-fluoro-1H-pyrazol-3-yl group |
| 62 | 1,5-diethyl-4-chloro-1H-pyrazol-3-yl group |
| 63 | 1,5-diethyl-4-bromo-1H-pyrazol-3-yl group |
| 64 | 1,5-diethyl-4-iodo-1H-pyrazol-3-yl group |
| 65 | 1,5-diethyl-4-cyano-1H-pyrazol-3-yl group |
| 66 | 1-ethyl-5-propyl-4-methyl-1H-pyrazol-3-yl group |

TABLE 59

| substituents Nos. | $Q^6$ |
|---|---|
| 67 | 1,4-diethyl-5-propyl-1H-pyrazol-3-yl group |
| 68 | 1-ethyl-5-propyl-4-fluoro-1H-pyrazol-3-yl group |
| 69 | 1-ethyl-5-propyl-4-chloro-1H-pyrazol-3-yl group |
| 70 | 1-ethyl-5-propyl-4-bromo-1H-pyrazol-3-yl group |
| 71 | 1-ethyl-5-propyl-4-iodo-1H-pyrazol-3-yl group |
| 72 | 1-ethyl-5-propyl-4-cyano-1H-pyrazol-3-yl group |
| 73 | 1-ethyl-5-methoxy-4-methyl-1H-pyrazol-3-yl group |
| 74 | 1,4-diethyl-5-methoxy-1H-pyrazol-3-yl group |
| 75 | 1-ethyl-5-methoxy-4-fluoro-1H-pyrazol-3-yl group |
| 76 | 1-ethyl-5-methoxy-4-chloro-1H-pyrazol-3-yl group |
| 77 | 1-ethyl-5-methoxy-4-bromo-1H-pyrazol-3-yl group |
| 78 | 1-ethyl-5-methoxy-4-iodo-1H-pyrazol-3-yl group |
| 79 | 1-ethyl-5-methoxy-4-cyano-1H-pyrazol-3-yl group |

TABLE 59-continued

| substituents Nos. | $Q^6$ |
|---|---|
| 80 | 1-ethyl-5-ethoxy-4-methyl-1H-pyrazol-3-yl group |
| 81 | 1,4-diethyl-5-ethoxy-1H-pyrazol-3-yl group |
| 82 | 1-ethyl-5-ethoxy-4-fluoro-1H-pyrazol-3-yl group |
| 83 | 1-ethyl-5-ethoxy-4-chloro-1H-pyrazol-3-yl group |
| 84 | 1-ethyl-5-ethoxy-4-bromo-1H-pyrazol-3-yl group |
| 85 | 1-ethyl-5-ethoxy-4-iodo-1H-pyrazol-3-yl group |
| 86 | 1-ethyl-5-ethoxy-4-cyano-1H-pyrazol-3-yl group |
| 87 | 1-ethyl-5-methylthio-4-methyl-1H-pyrazol-3-yl group |
| 88 | 1,4-diethyl-5-methylthio-1H-pyrazol-3-yl group |

TABLE 60

| substituents Nos. | $Q^6$ |
|---|---|
| 89 | 1-ethyl-5-methylthio-4-fluoro-1H-pyrazol-3-yl group |
| 90 | 1-ethyl-5-methylthio-4-chloro-1H-pyrazol-3-yl group |
| 91 | 1-ethyl-5-methylthio-4-bromo-1H-pyrazol-3-yl group |
| 92 | 1-ethyl-5-methylthio-4-iodo-1H-pyrazol-3-yl group |
| 93 | 1-ethyl-5-methylthio-4-cyano-1H-pyrazol-3-yl group |
| 94 | 1-ethyl-5-fluoro-4-methyl-1H-pyrazol-3-yl group |
| 95 | 1,4-diethyl-5-fluoro-1H-pyrazol-3-yl group |
| 96 | 1-ethyl-5-chloro-4-methyl-1H-pyrazol-3-yl group |
| 97 | 1,4-diethyl-5-chloro-1H-pyrazol-3-yl group |
| 98 | 1-ethyl-5-bromo-4-methyl-1H-pyrazol-3-yl group |
| 99 | 1,4-diethyl-5-bromo-1H-pyrazol-3-yl group |
| 100 | 1-ethyl-5-iodo-4-methyl-1H-pyrazol-3-yl group |
| 101 | 1,4-diethyl-5-iodo-1H-pyrazol-3-yl group |
| 102 | 1-ethyl-5-cyano-4-methyl-1H-pyrazol-3-yl group |
| 103 | 1,4-diethyl-5-cyano-1H-pyrazol-3-yl group |

According to the above-mentioned processes, the following compounds can be prepared:

Compounds ED1A-001~ED1A-103, ED1B-001~ED1B-103, ED1C-001~ED1C-103, ED1D-001~ED1D-103, ED1E-001~ED1E-103, ED2A-001~ED2A-103, ED2B-001~ED2B-103, ED2C-001~ED2C-103, ED3A-001~ED3A-103, ED3B-001~ED3B-103, ED4A-001~ED4A-103, ED4B-001~ED4B-103, ED5A-001~ED5A-103, ED5B-001~ED5B-103, ED5C-001~ED5C-103, ED6A-001~ED6A-103 and ED6B-001~ED6B-103.

Compounds ED1A-001~ED1A-103 represent Compounds represented by a formula:

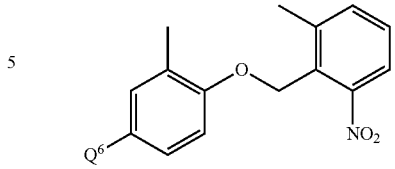
(ED1A)

[in the formula (ED1A), $Q^6$ represents a substituent corresponding to each of substituents Nos. 1 to 103 indicated in Table 56 to Table 60 as above-mentioned];

Compounds ED1B-001~ED1B-103 represent Compounds represented by a formula:

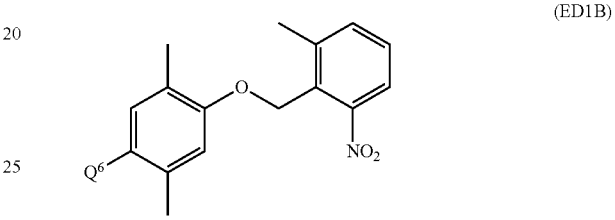
(ED1B)

[in the formula (ED1B), $Q^6$ represents a substituent corresponding to each of substituents Nos. 1 to 103 indicated in Table 56 to Table 60 as above-mentioned];

Compounds ED1C-001~ED1C-103 represent Compounds represented by a formula:

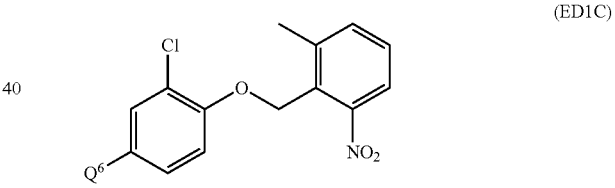
(ED1C)

[in the formula (ED1C), $Q^6$ represents a substituent corresponding to each of substituents Nos. 1 to 103 indicated in Table 56 to Table 60 as above-mentioned];

Compounds ED1D-001~ED1D-103 represent Compounds represented by a formula:

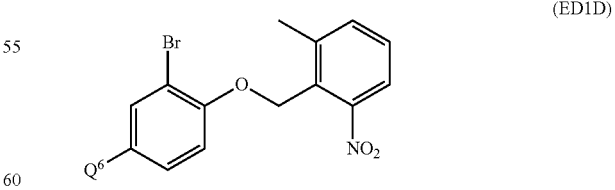
(ED1D)

[in the formula (ED1D), $Q^6$ represents a substituent corresponding to each of substituents Nos. 1 to 103 indicated in Table 56 to Table 60 as above-mentioned];

Compounds ED1E-001~ED1E-103 represent Compounds represented by a formula:

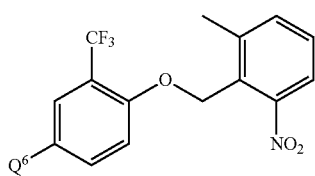

(ED1E)

[in the formula (ED1E), $Q^6$ represents a substituent corresponding to each of substituents Nos. 1 to 103 indicated in Table 56 to Table 60 as above-mentioned];

Compounds ED2A-001~ED2A-103 represent Compounds represented by a formula:

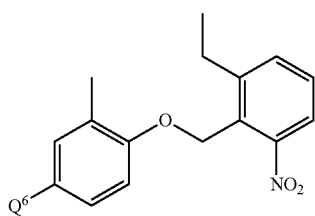

(ED2A)

[in the formula (ED2A), $Q^6$ represents a substituent corresponding to each of substituents Nos. 1 to 103 indicated in Table 56 to Table 60 as above-mentioned];

Compounds ED2B-001~ED2B-103 represent Compounds represented by a formula:

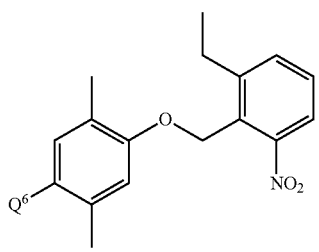

(ED2B)

[in the formula (ED2B), $Q^6$ represents a substituent corresponding to each of substituents Nos. 1 to 103 indicated in Table 56 to Table 60 as above-mentioned];

Compounds ED2C-001~ED2C-103 represent Compounds represented by a formula:

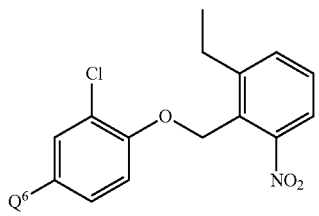

(ED2C)

[in the formula (ED2C), $Q^6$ represents a substituent corresponding to each of substituents Nos. 1 to 103 indicated in Table 56 to Table 60 as above-mentioned];

Compounds ED3A-001~ED3A-103 represent Compounds represented by a formula:

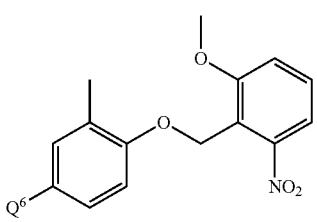

(ED3A)

[in the formula (ED3A), $Q^6$ represents a substituent corresponding to each of substituents Nos. 1 to 103 indicated in Table 56 to Table 60 as above-mentioned];

Compounds ED3B-001~ED3B-103 represent Compounds represented by a formula:

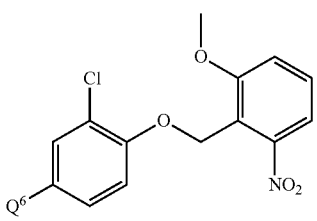

(ED3B)

[in the formula (ED3B), $Q^6$ represents a substituent corresponding to each of substituents Nos. 1 to 103 indicated in Table 56 to Table 60 as above-mentioned];

Compounds ED4A-001~ED4A-103 represent Compounds represented by a formula:

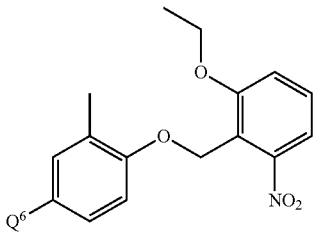

(ED4A)

[in the formula (ED4A), $Q^6$ represents a substituent corresponding to each of substituents Nos. 1 to 103 indicated in Table 56 to Table 60 as above-mentioned];

Compounds ED4B-001~ED4B-103 represent Compounds represented by a formula:

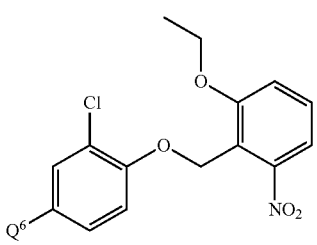

(ED4B)

[in the formula (ED4B), $Q^6$ represents a substituent corresponding to each of substituents Nos. 1 to 103 indicated in Table 56 to Table 60 as above-mentioned];

Compounds ED5A-001~ED5A-103 represent Compounds represented by a formula:

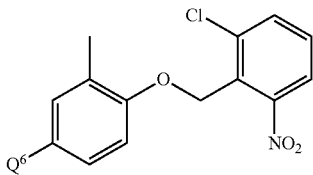
(ED5A)

[in the formula (ED5A), Q⁶ represents a substituent corresponding to each of substituents Nos. 1 to 103 indicated in Table 56 to Table 60 as above-mentioned];

Compounds ED5B-001~ED5B-103 represent Compounds represented by a formula:

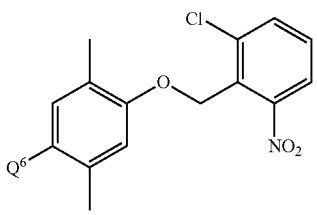
(ED5B)

[in the formula (ED5B), Q⁶ represents a substituent corresponding to each of substituents Nos. 1 to 103 indicated in Table 56 to Table 60 as above-mentioned];

Compounds ED5C-001~ED5C-103 represent Compounds represented by a formula:

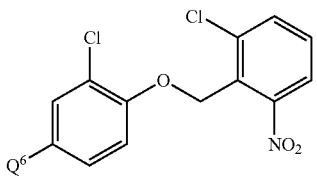
(ED5C)

[in the formula (ED5C), Q⁶ represents a substituent corresponding to each of substituents Nos. 1 to 103 indicated in Table 56 to Table 60 as above-mentioned];

Compounds ED6A-001~ED6A-103 represent Compounds represented by a formula:

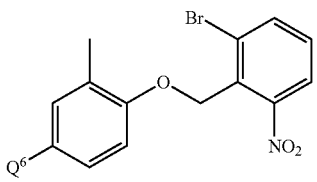
(ED6A)

[in the formula (ED6A), Q⁶ represents a substituent corresponding to each of substituents Nos. 1 to 103 indicated in Table 56 to Table 60 as above-mentioned]; and Compounds ED6B-001~ED6B-103 represent Compounds represented by a formula:

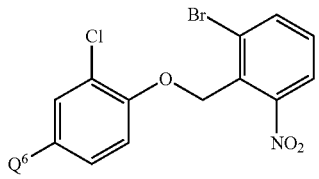
(ED6B)

[in the formula (ED6B), Q⁶ represents a substituent corresponding to each of substituents Nos. 1 to 103 indicated in Table 56 to Table 60 as above-mentioned].

According to the above-mentioned processes, the following compounds can be prepared:

Compounds EE1A-001~EE1A-103, EE1B-001~EE1B-103, EE1C-001~EE1C-103, EE1D-001~EE1D-103, EE1E-001~EE1E-103, EE2A-001~EE2A-103, EE2B-001~EE2B-103, EE2C-001~EE2C-103, EE3A-001~EE3A-103, EE3B-001~EE3B-103, EE4A-001~EE4A-103, EE4B-001~EE4B-103, EE5A-001~EE5A-103, EE5B-001~EE5B-103, EE5C-001~EE5C-103, EE6A-001~EE6A-103 and EE6B-001~EE6B-103.

Compounds EE1A-001~EE1A-103 represent Compounds represented by a formula:

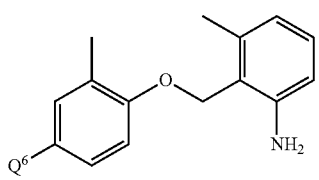
(EE1A)

[in the formula (EE1A), Q⁶ represents a substituent corresponding to each of substituents Nos. 1 to 103 indicated in Table 56 to Table 60 as above-mentioned];

Compounds EE1B-001~EE1B-103 represent Compounds represented by a formula:

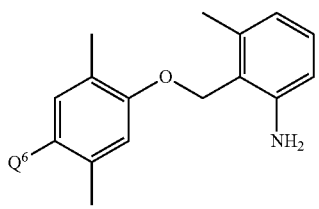
(EE1B)

[in the formula (EE1B), Q⁶ represents a substituent corresponding to each of substituents Nos. 1 to 103 indicated in Table 56 to Table 60 as above-mentioned];

Compounds EE1C-001~EE1C-103 represent Compounds represented by a formula:

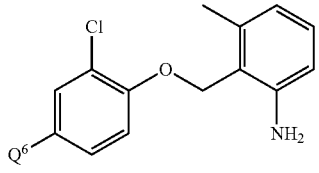
(EE1C)

[in the formula (EE1C), $Q^6$ represents a substituent corresponding to each of substituents Nos. 1 to 103 indicated in Table 56 to Table 60 as above-mentioned];

Compounds EE1D-001~EE1D-103 represent Compounds represented by a formula:

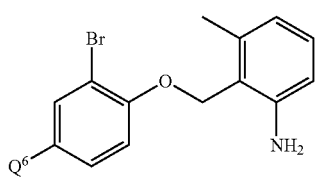

(EE1D)

[in the formula (EE1D), $Q^6$ represents a substituent corresponding to each of substituents Nos. 1 to 103 indicated in Table 56 to Table 60 as above-mentioned];

Compounds EE1E-001~EE1E-103 represent Compounds represented by a formula:

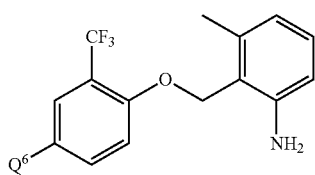

(EE1E)

[in the formula (EE1E), $Q^6$ represents a substituent corresponding to each of substituents Nos. 1 to 103 indicated in Table 56 to Table 60 as above-mentioned];

Compounds EE2A-001~EE2A-103 represent Compounds represented by a formula:

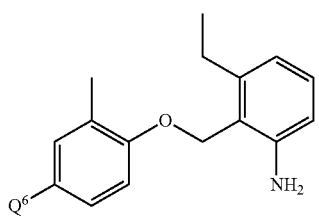

(EE2A)

[in the formula (EE2A), $Q^6$ represents a substituent corresponding to each of substituents Nos. 1 to 103 indicated in Table 56 to Table 60 as above-mentioned];

Compounds EE2B-001~EE2B-103 represent Compounds represented by a formula:

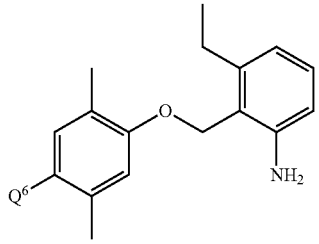

(EE2B)

[in the formula (EE2B), $Q^6$ represents a substituent corresponding to each of substituents Nos. 1 to 103 indicated in Table 56 to Table 60 as above-mentioned];

Compounds EE2C-001~EE2C-103 represent Compounds represented by a formula:

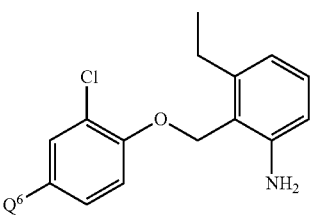

(EE2C)

[in the formula (EE2C), $Q^6$ represents a substituent corresponding to each of substituents Nos. 1 to 103 indicated in Table 56 to Table 60 as above-mentioned];

Compounds EE3A-001~EE3A-103 represent Compounds represented by a formula:

(EE3A)

[in the formula (EE3A), $Q^6$ represents a substituent corresponding to each of substituents Nos. 1 to 103 indicated in Table 56 to Table 60 as above-mentioned];

Compounds EE3B-001~EE3B-103 represent Compounds represented by a formula:

(EE3B)

[in the formula (EE3B), $Q^6$ represents a substituent corresponding to each of substituents Nos. 1 to 103 indicated in Table 56 to Table 60 as above-mentioned];

Compounds EE4A-001~EE4A-103 represent Compounds represented by a formula:

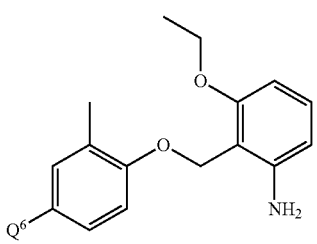

(EE4A)

[in the formula (EE4A), $Q^6$ represents a substituent corresponding to each of substituents Nos. 1 to 103 indicated in Table 56 to Table 60 as above-mentioned];
Compounds EE4B-001~EE4B-103 represent Compounds represented by a formula:

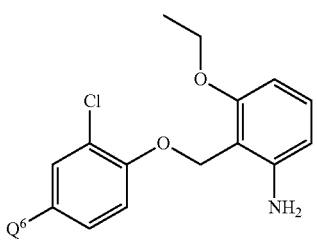

(EE4B)

[in the formula (EE4B), $Q^6$ represents a substituent corresponding to each of substituents Nos. 1 to 103 indicated in Table 56 to Table 60 as above-mentioned];
Compounds EE5A-001~EE5A-103 represent Compounds represented by a formula:

(EE5A)

[in the formula (EE5A), $Q^6$ represents a substituent corresponding to each of substituents Nos. 1 to 103 indicated in Table 56 to Table 60 as above-mentioned];
Compounds EE5B-001~EE5B-103 represent Compounds represented by a formula:

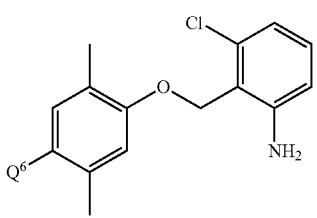

(EE5B)

[in the formula (EE5B), $Q^6$ represents a substituent corresponding to each of substituents Nos. 1 to 103 indicated in Table 56 to Table 60 as above-mentioned];
Compounds EE5C-001~EE5C-103 represent Compounds represented by a formula:

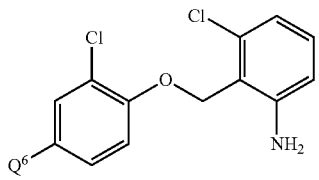

(EE5C)

[in the formula (EE5C), $Q^6$ represents a substituent corresponding to each of substituents Nos. 1 to 103 indicated in Table 56 to Table 60 as above-mentioned];
Compounds EE6A-001~EE6A-103 represent Compounds represented by a formula:

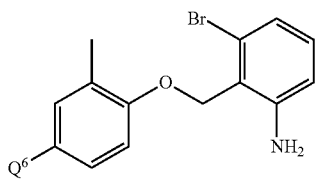

(EE6A)

[in the formula (EE6A), $Q^6$ represents a substituent corresponding to each of substituents Nos. 1 to 103 indicated in Table 56 to Table 60 as above-mentioned]; and
Compounds EE6B-001~EE6B-103 represent Compounds represented by a formula:

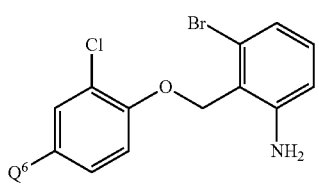

(EE6B)

[in the formula (EE6B), $Q^6$ represents a substituent corresponding to each of substituents Nos. 1 to 103 indicated in Table 56 to Table 60 as above-mentioned].

According to the above-mentioned processes, the following compounds can be prepared:
Compounds EF1A-001~EF1A-103, EF1B-001~EF1B-103, EF1C-001~EF1C-103, EF1D-001~EF1D-103, EF1E-001~EF1E-103, EF2A-001~EF2A-103, EF2B-001~EF2B-103, EF2C-001~EF2C-103, EF3A-001~EF3A-103, EF3B-001~EF3B-103, EF4A-001~EF4A-103, EF4B-001~EF4B-103, EF5A-001~EF5A-103, EF5B-001~EF5B-103, EF5C-001~EF5C-103, EF6A-001~EF6A-103 and EF6B-001~EF6B-103.

Compounds EF1A-001~EF1A-103 represent Compounds represented by a formula:

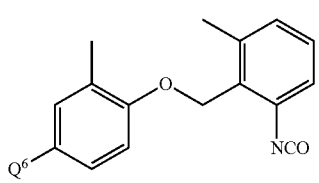

(EF1A)

[in the formula (EF1A), $Q^6$ represents a substituent corresponding to each of substituents Nos. 1 to 103 indicated in Table 56 to Table 60 as above-mentioned];

Compounds EF1B-001~EF1B-103 represent Compounds represented by a formula:

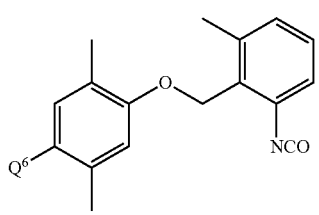
(EF1B)

[in the formula (EF1B), $Q^6$ represents a substituent corresponding to each of substituents Nos. 1 to 103 indicated in Table 56 to Table 60 as above-mentioned];

Compounds EF1C-001~EF1C-103 represent Compounds represented by a formula:

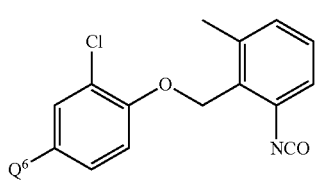
(EF1C)

[in the formula (EF1C), $Q^6$ represents a substituent corresponding to each of substituents Nos. 1 to 103 indicated in Table 56 to Table 60 as above-mentioned];

Compounds EF1D-001~EF1D-103 represent Compounds represented by a formula:

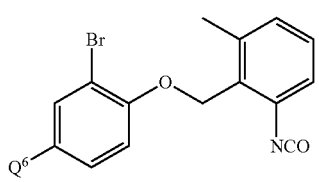
(EF1D)

[in the formula (EF1D), $Q^6$ represents a substituent corresponding to each of substituents Nos. 1 to 103 indicated in Table 56 to Table 60 as above-mentioned];

Compounds EF1E-001~EF1E-103 represent Compounds represented by a formula:

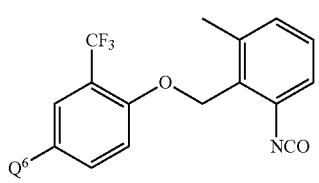
(EF1E)

[in the formula (EF1E), $Q^6$ represents a substituent corresponding to each of substituents Nos. 1 to 103 indicated in Table 56 to Table 60 as above-mentioned];

Compounds EF2A-001~EF2A-103 represent Compounds represented by a formula:

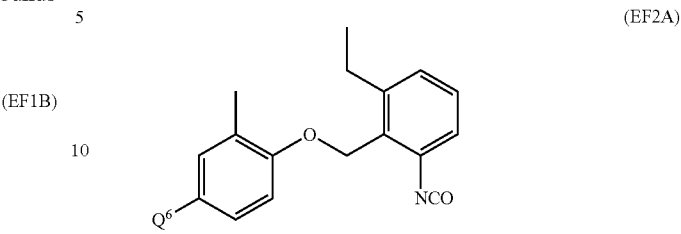
(EF2A)

[in the formula (EF2A), $Q^6$ represents a substituent corresponding to each of substituents Nos. 1 to 103 indicated in Table 56 to Table 60 as above-mentioned];

Compounds EF2B-001~EF2B-103 represent Compounds represented by a formula:

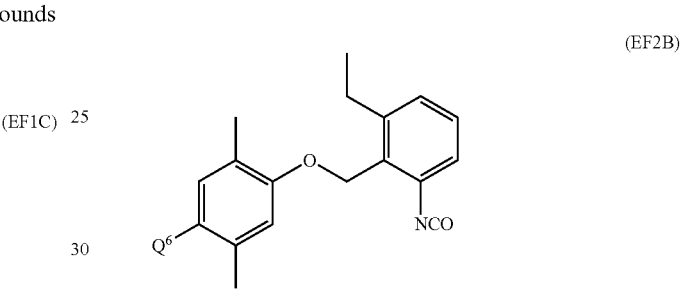
(EF2B)

[in the formula (EF2B), $Q^6$ represents a substituent corresponding to each of substituents Nos. 1 to 103 indicated in Table 56 to Table 60 as above-mentioned];

Compounds EF2C-001~EF2C-103 represent Compounds represented by a formula:

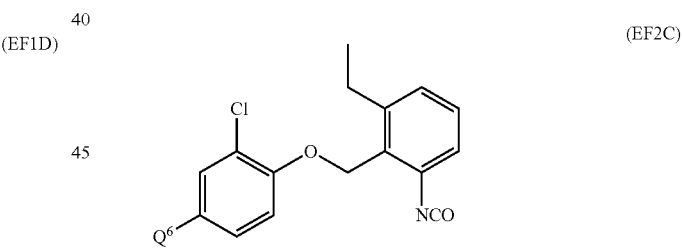
(EF2C)

[in the formula (EF2C), $Q^6$ represents a substituent corresponding to each of substituents Nos. 1 to 103 indicated in Table 56 to Table 60 as above-mentioned];

Compounds EF3A-001~EF3A-103 represent Compounds represented by a formula:

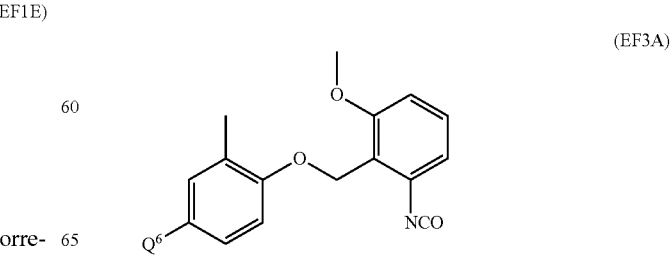
(EF3A)

[in the formula (EF3A), $Q^6$ represents a substituent corresponding to each of substituents Nos. 1 to 103 indicated in Table 56 to Table 60 as above-mentioned];

Compounds EF3B-001~EF3B-103 represent Compounds represented by a formula:

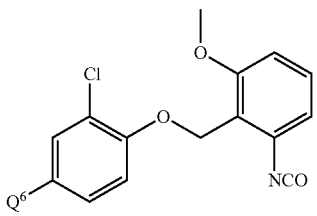

(EF3B)

[in the formula (EF3B), $Q^6$ represents a substituent corresponding to each of substituents Nos. 1 to 103 indicated in Table 56 to Table 60 as above-mentioned];

Compounds EF4A-001~EF4A-103 represent Compounds represented by a formula:

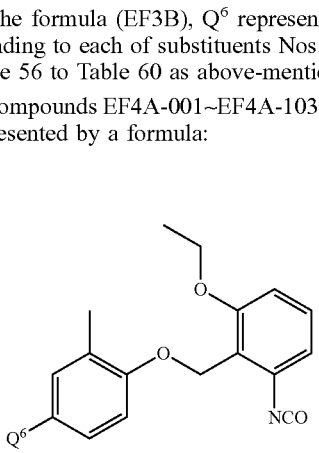

(EF4A)

[in the formula (EF4A), $Q^6$ represents a substituent corresponding to each of substituents Nos. 1 to 103 indicated in Table 56 to Table 60 as above-mentioned];

Compounds EF4B-001~EF4B-103 represent Compounds represented by a formula:

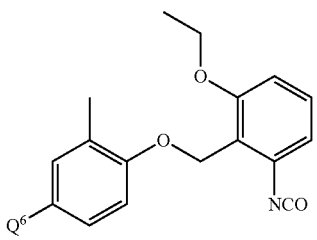

(EF4B)

[in the formula (EF4B), $Q^6$ represents a substituent corresponding to each of substituents Nos. 1 to 103 indicated in Table 56 to Table 60 as above-mentioned];

Compounds EF5A-001~EF5A-103 represent Compounds represented by a formula:

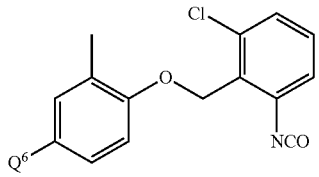

(EF5A)

[in the formula (EF5A), $Q^6$ represents a substituent corresponding to each of substituents Nos. 1 to 103 indicated in Table 56 to Table 60 as above-mentioned];

Compounds EF5B-001~EF5B-103 represent Compounds represented by a formula:

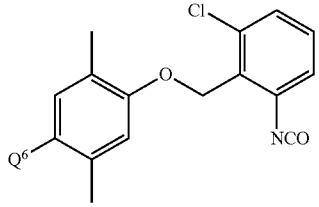

(EF5B)

[in the formula (EF5B), $Q^6$ represents a substituent corresponding to each of substituents Nos. 1 to 103 indicated in Table 56 to Table 60 as above-mentioned];

Compounds EF5c-001~EF5c-103 represent Compounds represented by a formula:

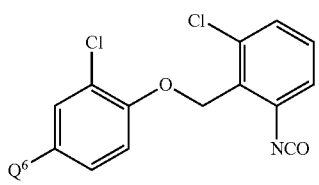

(EF5C)

[in the formula (EF5c), $Q^6$ represents a substituent corresponding to each of substituents Nos. 1 to 103 indicated in Table 56 to Table 60 as above-mentioned];

Compounds EF6A-001~EF6A-103 represent Compounds represented by a formula:

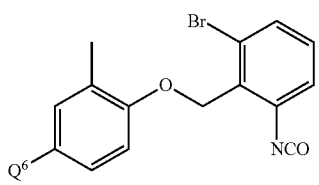

(EF6A)

[in the formula (EF6A), $Q^6$ represents a substituent corresponding to each of substituents Nos. 1 to 103 indicated in Table 56 to Table 60 as above-mentioned]; and Compounds EF6B-001~EF6B-103 represent Compounds represented by a formula:

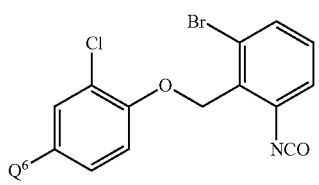

(EF6B)

[in the formula (EF6B), $Q^6$ represents a substituent corresponding to each of substituents Nos. 1 to 103 indicated in Table 56 to Table 60 as above-mentioned].

According to the above-mentioned processes, the following compounds can be prepared:

Compounds EG1A-001~EG1A-103, EG1B-001~EG1B-103, EG1C-001~EG1C-103, EG1D-001~EG1D-103, EG1E-001~EG1E-103, EG2A-001~EG2A-103, EG2B-001~EG2B-103, EG2C-001~EG2C-103, EG3A-001~EG3A-103, EG3B-001~EG3B-103, EG4A-001~EG4A-103, EG4B-001~EG4B-103, EG5A-001~EG5A-103, EG5B-001~EG5B-103, EG5C-001~EG5C-103, EG6A-001~EG6A-103 and EG6B-001~EG6B-103.

Compounds EG1A-001~EG1A-103 represent Compounds represented by a formula:

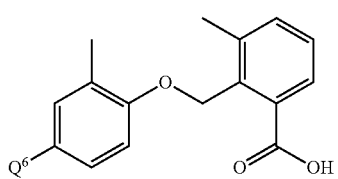

(EG1A)

[in the formula (EG1A), $Q^6$ represents a substituent corresponding to each of substituents Nos. 1 to 103 indicated in Table 56 to Table 60 as above-mentioned];

Compounds EG1B-001~EG1B-103 represent Compounds represented by a formula:

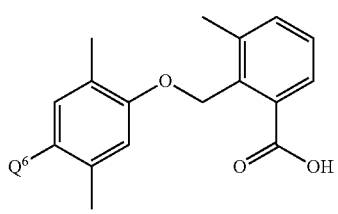

(EG1B)

[in the formula (EG1B), $Q^6$ represents a substituent corresponding to each of substituents Nos. 1 to 103 indicated in Table 56 to Table 60 as above-mentioned];

Compounds EG1C-001~EG1C-103 represent Compounds represented by a formula:

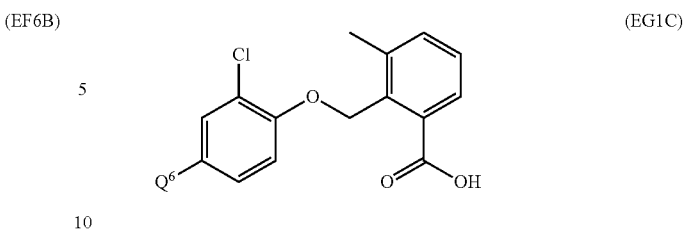

(EG1C)

[in the formula (EG1C), $Q^6$ represents a substituent corresponding to each of substituents Nos. 1 to 103 indicated in Table 56 to Table 60 as above-mentioned];

Compounds EG1D-001~EG1D-103 represent Compounds represented by a formula:

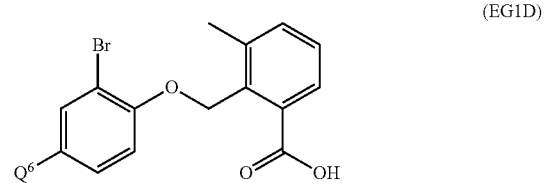

(EG1D)

[in the formula (EG1D), $Q^6$ represents a substituent corresponding to each of substituents Nos. 1 to 103 indicated in Table 56 to Table 60 as above-mentioned];

Compounds EG1E-001~EG1E-103 represent Compounds represented by a formula:

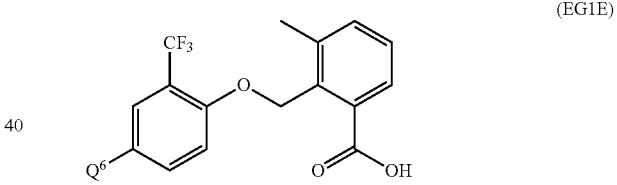

(EG1E)

[in the formula (EG1E), $Q^6$ represents a substituent corresponding to each of substituents Nos. 1 to 103 indicated in Table 56 to Table 60 as above-mentioned];

Compounds EG2A-001~EG2A-103 represent Compounds represented by a formula:

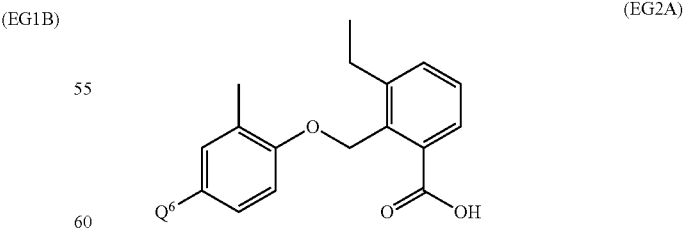

(EG2A)

[in the formula (EG2A), $Q^6$ represents a substituent corresponding to each of substituents Nos. 1 to 103 indicated in Table 56 to Table 60 as above-mentioned];

Compounds EG2B-001~EG2B-103 represent Compounds represented by a formula:

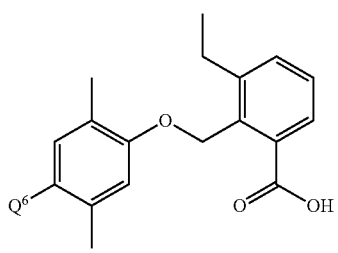

(EG2B)

[in the formula (EG2B), $Q^6$ represents a substituent corresponding to each of substituents Nos. 1 to 103 indicated in Table 56 to Table 60 as above-mentioned];

Compounds EG2C-001~EG2C-103 represent Compounds represented by a formula:

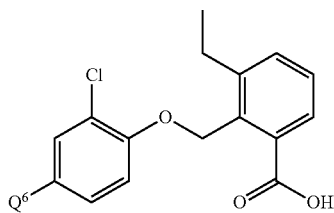

(EG2C)

[in the formula (EG2C), $Q^6$ represents a substituent corresponding to each of substituents Nos. 1 to 103 indicated in Table 56 to Table 60 as above-mentioned];

Compounds EG3A-001~EG3A-103 represent Compounds represented by a formula:

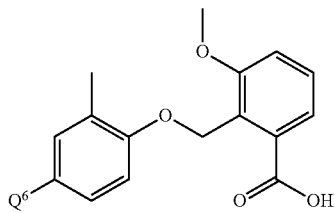

(EG3A)

[in the formula (EG3A), $Q^6$ represents a substituent corresponding to each of substituents Nos. 1 to 103 indicated in Table 56 to Table 60 as above-mentioned];

Compounds EG3B-001~EG3B-103 represent Compounds represented by a formula:

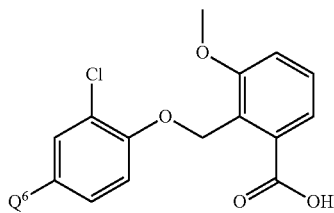

(EG3B)

[in the formula (EG3B), $Q^6$ represents a substituent corresponding to each of substituents Nos. 1, to 103 indicated in Table 56 to Table 60 as above-mentioned];

Compounds EG4A-001~EG4A-103 represent Compounds represented by a formula:

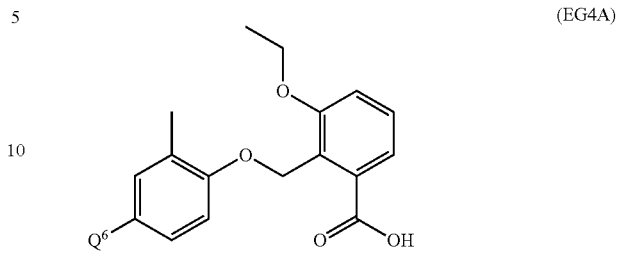

(EG4A)

[in the formula (EG4A), $Q^6$ represents a substituent corresponding to each of substituents Nos. 1 to 103 indicated in Table 56 to Table 60 as above-mentioned];

Compounds EG4B-001~EG4B-103 represent Compounds represented by a formula:

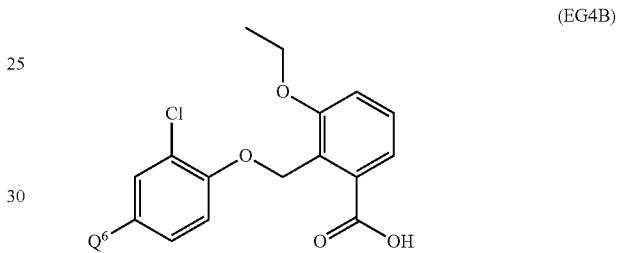

(EG4B)

[in the formula (EG4B), $Q^6$ represents a substituent corresponding to each of substituents Nos. 1 to 103 indicated in Table 56 to Table 60 as above-mentioned];

Compounds EG5A-001~EG5A-103 represent Compounds represented by a formula:

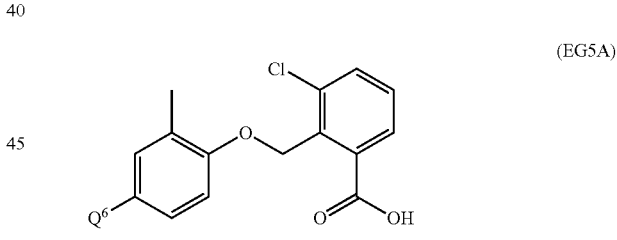

(EG5A)

[in the formula (EG5A), $Q^6$ represents a substituent corresponding to each of substituents Nos. 1 to 103 indicated in Table 56 to Table 60 as above-mentioned];

Compounds EG5B-001~EG5B-103 represent Compounds represented by a formula:

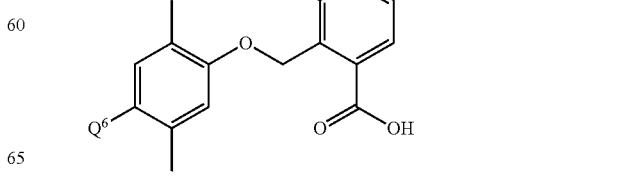

(EG5B)

[in the formula (EG5B), $Q^6$ represents a substituent corresponding to each of substituents Nos. 1 to 103 indicated in Table 56 to Table 60 as above-mentioned];

Compounds EG5C-001~EG5C-103 represent Compounds represented by a formula:

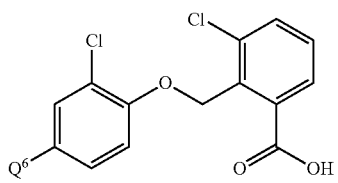

(EG5C)

[in the formula (EG5C), $Q^6$ represents a substituent corresponding to each of substituents Nos. 1 to 103 indicated in Table 56 to Table 60 as above-mentioned];

Compounds EG6A-001~EG6A-103 represent Compounds represented by a formula:

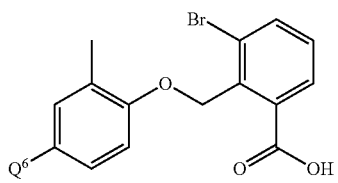

(EG6A)

[in the formula (EG6A), $Q^6$ represents a substituent corresponding to each of substituents Nos. 1 to 103 indicated in Table 56 to Table 60 as above-mentioned]; and Compounds EG6B-001~EG6B-103 represent Compounds represented by a formula:

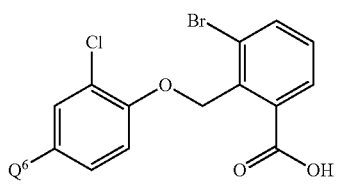

(EG6B)

[in the formula (EG6B), $Q^6$ represents a substituent corresponding to each of substituents Nos. 1 to 103 indicated in Table 56 to Table 60 as above-mentioned].

According to the above-mentioned processes, the following compounds can be prepared:

Compounds EH1A-001~EH1A-103, EH1B-001~EH1B-103, EH1C-001~EH1C-103, EH1D-001~EH1D-103, EH1E-001~EH1E-103, EH1A-001~EH2A-103, EH2B-001~EH2B-103, EH2C-001~EH2C-103, EH3A-001~EH3A-103, EH3B-001~EH3B-103, EH4A-001~EH4A-103, EH4B-001~EH4B-103, EH5A-001~EH5A-103, EH5B-001~EH5B-103, EH5C-001~EH5C-103, EH6A-001~EH6A-103 and EH6B-001~EH6B-103.

Compounds EH1A-001~EH1A-103 represent Compounds represented by a formula:

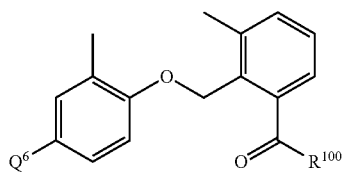

(EH1A)

[in the formula (EH1A), $R^{100}$ are the same as described above, and $Q^6$ represents a substituent corresponding to each of substituents Nos. 1 to 103 indicated in Table 56 to Table 60 as above-mentioned];

Compounds EH1B-001~EH1B-103 represent Compounds represented by a formula:

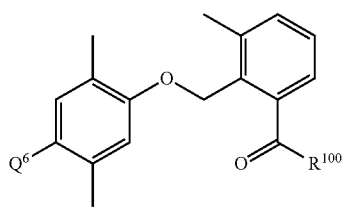

(EH1B)

[in the formula (EH1B), $R^{100}$ are the same as described above, and $Q^6$ represents a substituent corresponding to each of substituents Nos. 1 to 103 indicated in Table 56 to Table 60 as above-mentioned];

Compounds EH1C-001~EH1C-103 represent Compounds represented by a formula:

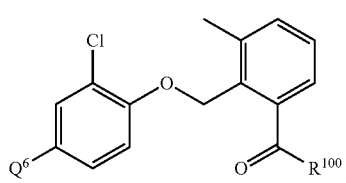

(EH1C)

[in the formula (EH1C), $R^{100}$ are the same as described above, and $Q^6$ represents a substituent corresponding to each of substituents Nos. 1 to 103 indicated in Table 56 to Table 60 as above-mentioned];

Compounds EH1D-001~EH1D-103 represent Compounds represented by a formula:

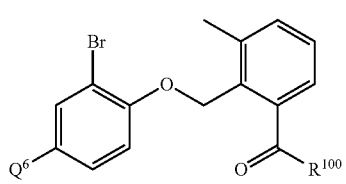

(EH1D)

[in the formula (EH1D), $R^{100}$ are the same as described above, and $Q^6$ represents a substituent corresponding to each of substituents Nos. 1 to 103 indicated in Table 56 to Table 60 as above-mentioned];

Compounds EH1E-001~EH1E-103 represent Compounds represented by a formula:

(EH1E)

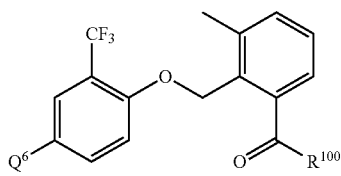

[in the formula (EH1E), $R^{100}$ are the same as described above, and $Q^6$ represents a substituent corresponding to each of substituents Nos. 1 to 103 indicated in Table 56 to Table 60 as above-mentioned];

Compounds EH2A-001~EH2A-103 represent Compounds represented by a formula:

(EH2A)

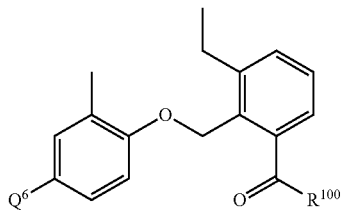

[in the formula (EH2A), $R^{100}$ are the same as described above, and $Q^6$ represents a substituent corresponding to each of substituents Nos. 1 to 103 indicated in Table 56 to Table 60 as above-mentioned];

Compounds EH2B-001~EH2B-103 represent Compounds represented by a formula:

(EH2B)

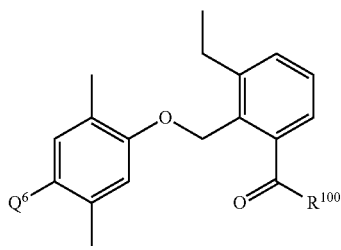

[in the formula (EH2B), $R^{100}$ are the same as described above, and $Q^6$ represents a substituent corresponding to each of substituents Nos. 1 to 103 indicated in Table 56 to Table 60 as above-mentioned];

Compounds EH2C-001~EH2C-103 represent Compounds represented by a formula:

(EH2C)

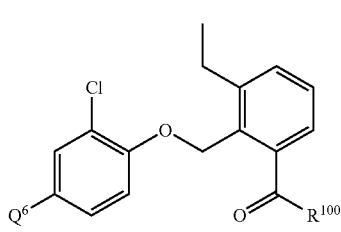

[in the formula (EH2C), $R^{100}$ are the same as described above, and $Q^6$ represents a substituent corresponding to each of substituents Nos. 1 to 103 indicated in Table 56 to Table 60 as above-mentioned];

Compounds EH3A-001~EH3A-103 represent Compounds represented by a formula:

(EH3A)

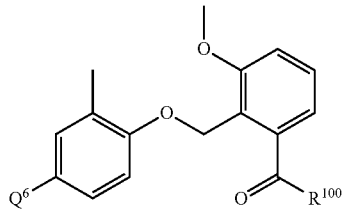

[in the formula (EH3A), $R^{100}$ are the same as described above, and $Q^6$ represents a substituent corresponding to each of substituents Nos. 1 to 103 indicated in Table 56 to Table 60 as above-mentioned];

Compounds EH3B-001~EH3B-103 represent Compounds represented by a formula:

(EH3B)

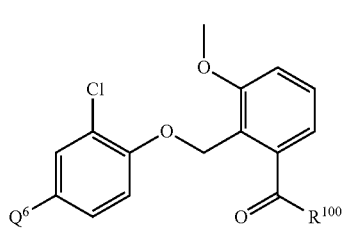

[in the formula (EH3B), $R^{100}$ are the same as described above, and $Q^6$ represents a substituent corresponding to each of substituents Nos. 1 to 103 indicated in Table 56 to Table 60 as above-mentioned];

Compounds EH4A-001~EH4A-103 represent Compounds represented by a formula:

(EH4A)

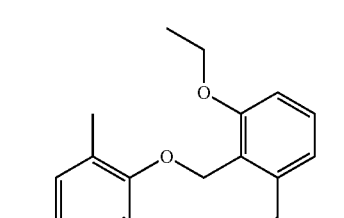

[in the formula (EH4A), $R^{100}$ are the same as described above, and $Q^6$ represents a substituent corresponding to each of substituents Nos. 1 to 103 indicated in Table 56 to Table 60 as above-mentioned];

Compounds EH4B-001~EH4B-103 represent Compounds represented by a formula:

(EH4B)

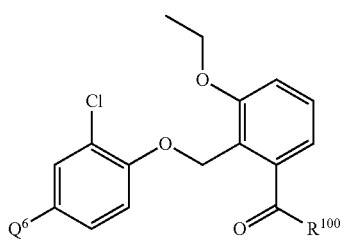

[in the formula (EH4B), $R^{100}$ are the same as described above, and $Q^6$ represents a substituent corresponding to each of substituents Nos. 1 to 103 indicated in Table 56 to Table 60 as above-mentioned];

Compounds EH5A-001~EH5A-103 represent Compounds represented by a formula:

(EH5A)

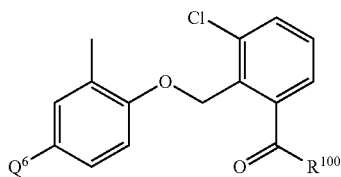

[in the formula (EH5A), $R^{100}$ are the same as described above, and $Q^6$ represents a substituent corresponding to each of substituents Nos. 1 to 103 indicated in Table 56 to Table 60 as above-mentioned];

Compounds EH5B-001~EH5B-103 represent Compounds represented by a formula:

(EH5B)

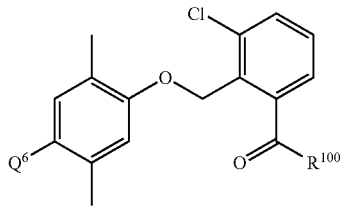

[in the formula (EH5B), $R^{100}$ are the same as described above, and $Q^6$ represents a substituent corresponding to each of substituents Nos. 1 to 103 indicated in Table 56 to Table 60 as above-mentioned];

Compounds EH5C-001~EH5C-103 represent Compounds represented by a formula:

(EH5C)

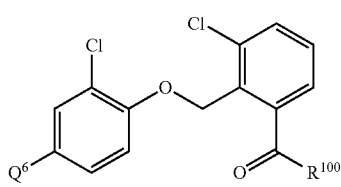

[in the formula (EH5C), $R^{100}$ are the same as described above, and $Q^6$ represents a substituent corresponding to each of substituents Nos. 1 to 103 indicated in Table 56 to Table 60 as above-mentioned];

Compounds EH6A-001~EH6A-103 represent Compounds represented by a formula:

(EH6A)

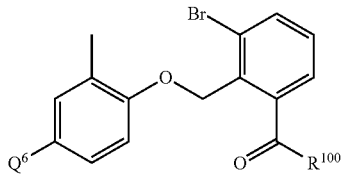

[in the formula (EH6A), $R^{100}$ are the same as described above, and $Q^6$ represents a substituent corresponding to each of substituents Nos. 1 to 103 indicated in Table 56 to Table 60 as above-mentioned]; and Compounds EH6B-001~EH6B-103 represent Compounds represented by a formula:

(EH6B)

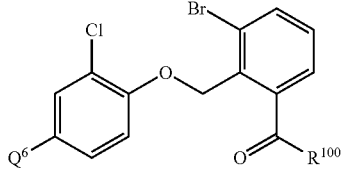

[in the formula (EH6B), $R^{100}$ are the same as described above, and $Q^6$ represents a substituent corresponding to each of substituents Nos. 1 to 103 indicated in Table 56 to Table 60 as above-mentioned].

According to the above-mentioned processes, the following compounds can be prepared:

Compounds EI1A-001~EI1A-103, EI1B-001~EI1B-103, EI1C-001~EI1C-103, EI1D-001~EI1D-103, EI1E-001~EI1E-103, EI1A-001~EI2A-103, EI2B-001~EI2B-103, EI2C-001~EI2C-103, EI3A-001~EI3A-103, EI3B-001~EI3B-103, EI4A-001~EI4A-103, EI4B-001~EI4B-103, EI5A-001~EI5A-103, EI5B-001~EI5B-103, EI5C-001~EI5C-103, EI6A-001~EI6A-103 and EI6B-001~EI6B-103.

Compounds EI1A-001~EI1A-103 represent Compounds represented by a formula:

(EI1A)

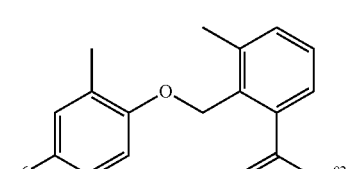

[in the formula (EI1A), $R^{92}$ are the same as described above, and $Q^6$ represents a substituent corresponding to each of substituents Nos. 1 to 103 indicated in Table 56 to Table 60 as above-mentioned];

Compounds EI1B-001~EI1B-103 represent Compounds represented by a formula:

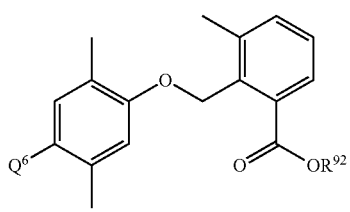

(EI1B)

[in the formula (EI1B), $R^{92}$ are the same as described above, and $Q^6$ represents a substituent corresponding to each of substituents Nos. 1 to 103 indicated in Table 56 to Table 60 as above-mentioned];

Compounds EI1C-001~EI1C-103 represent Compounds represented by a formula:

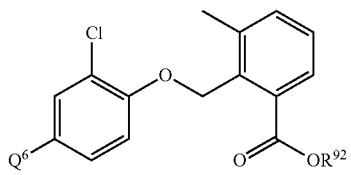

(EI1C)

[in the formula (EI1C), $R^{92}$ are the same as described above, and $Q^6$ represents a substituent corresponding to each of substituents Nos. 1 to 103 indicated in Table 56 to Table 60 as above-mentioned];

Compounds EI1D-001~EI1D-103 represent Compounds represented by a formula:

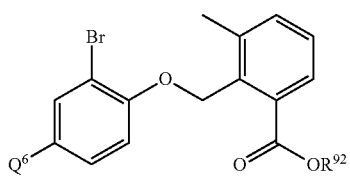

(EI1D)

[in the formula (EI1D), $R^{92}$ are the same as described above, and $Q^6$ represents a substituent corresponding to each of substituents Nos. 1 to 103 indicated in Table 56 to Table 60 as above-mentioned];

Compounds EI1E-001~EI1E-103 represent Compounds represented by a formula:

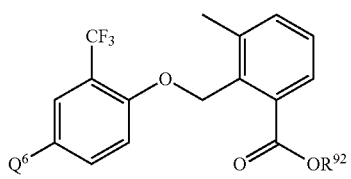

(EI1E)

[in the formula (EI1E), $R^{92}$ are the same as described above, and $Q^6$ represents a substituent corresponding to each of substituents Nos. 1 to 103 indicated in Table 56 to Table 60 as above-mentioned];

Compounds EI2A-001~EI2A-103 represent Compounds represented by a formula:

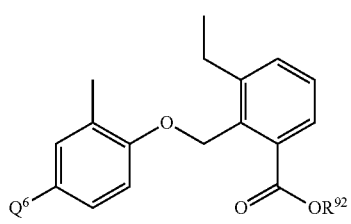

(EI2A)

[in the formula (EI2A), $R^{92}$ are the same as described above, and $Q^6$ represents a substituent corresponding to each of substituents Nos. 1 to 103 indicated in Table 56 to Table 60 as above-mentioned];

Compounds EI2B-001~EI2B-103 represent Compounds represented by a formula:

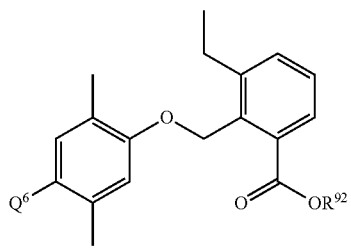

(EI2B)

[in the formula (EI2B), $R^{92}$ are the same as described above, and $Q^6$ represents a substituent corresponding to each of substituents Nos. 1 to 103 indicated in Table 56 to Table 60 as above-mentioned];

Compounds EI2C-001~EI2C-103 represent Compounds represented by a formula:

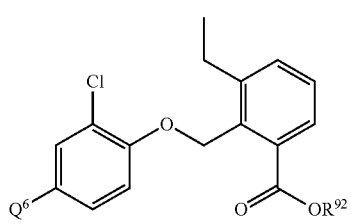

(EI2C)

[in the formula (EI2C), $R^{92}$ are the same as described above, and $Q^6$ represents a substituent corresponding to each of substituents Nos. 1 to 103 indicated in Table 56 to Table 60 as above-mentioned];

Compounds EI3A-001~EI3A-103 represent Compounds represented by a formula:

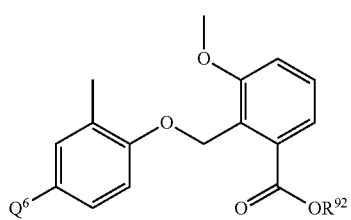

(EI3A)

[in the formula (EI3A), $R^{92}$ are the same as described above, and $Q^6$ represents a substituent corresponding to each of substituents Nos. 1 to 103 indicated in Table 56 to Table 60 as above-mentioned];

Compounds EI3B-001~EI3B-103 represent Compounds represented by a formula:

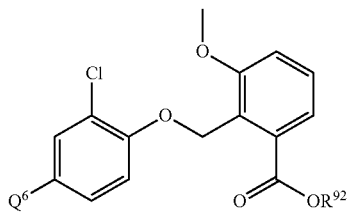
(EI3B)

[in the formula (EI3B), $R^{92}$ are the same as described above, and $Q^6$ represents a substituent corresponding to each of substituents Nos. 1 to 103 indicated in Table 56 to Table 60 as above-mentioned];

Compounds EI4A-001~EI4A-103 represent Compounds represented by a formula:

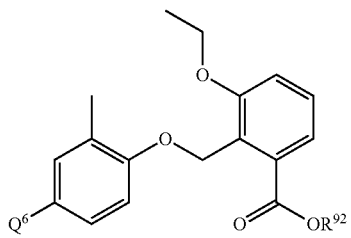
(EI4A)

[in the formula (EI4A), $R^{92}$ are the same as described above, and $Q^6$ represents a substituent corresponding to each of substituents Nos. 1 to 103 indicated in Table 56 to Table 60 as above-mentioned];

Compounds EI4B-001~EI4B-103 represent Compounds represented by a formula:

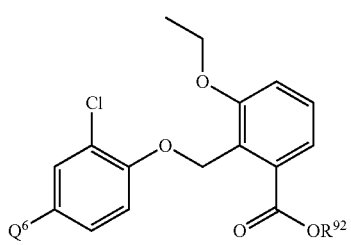
(EI4B)

[in the formula (EI4B), $R^{92}$ are the same as described above, and $Q^6$ represents a substituent corresponding to each of substituents Nos. 1 to 103 indicated in Table 56 to Table 60 as above-mentioned];

Compounds EI5A-001~EI5A-103 represent Compounds represented by a formula:

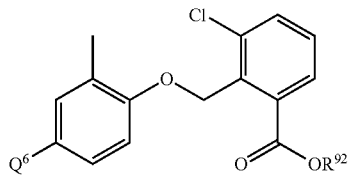
(EI5A)

[in the formula (EI5A), $R^{92}$ are the same as described above, and $Q^6$ represents a substituent corresponding to each of substituents Nos. 1 to 103 indicated in Table 56 to Table 60 as above-mentioned];

Compounds EI5B-001~EI5B-103 represent Compounds represented by a formula:

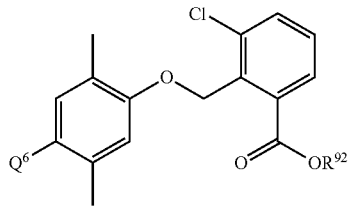
(EI5B)

[in the formula (EI5B), $R^{92}$ are the same as described above, and $Q^6$ represents a substituent corresponding to each of substituents Nos. 1 to 103 indicated in Table 56 to Table 60 as above-mentioned];

Compounds EI5C-001~EI5C-103 represent Compounds represented by a formula:

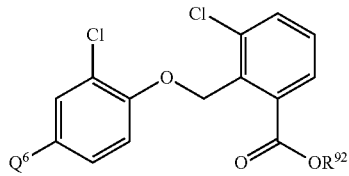
(EI5C)

[in the formula (EI5C), $R^{92}$ are the same as described above, and $Q^6$ represents a substituent corresponding to each of substituents Nos. 1 to 103 indicated in Table 56 to Table 60 as above-mentioned];

Compounds EI6A-001~EI6A-103 represent Compounds represented by a formula:

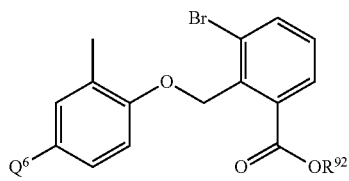
(EI6A)

[in the formula (EI6A), $R^{92}$ are the same as described above, and $Q^6$ represents a substituent corresponding to each of substituents Nos. 1 to 103 indicated in Table 56 to Table 60 as above-mentioned]; and Compounds EI6B-001~EI6B-103 represent Compounds represented by a formula:

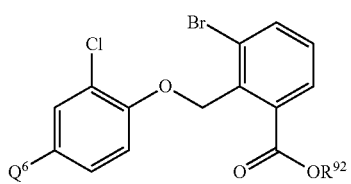

(EI6B)

[in the formula (EI6B), $R^{92}$ are the same as described above, and $Q^6$ represents a substituent corresponding to each of substituents Nos. 1 to 103 indicated in Table 56 to Table 60 as above-mentioned].

According to the above-mentioned processes, the following compounds can be prepared:

Compounds EJ1A-001~EJ1A-103, EJ1B-001~EJ1B-103 and EJ1C-001~EJ1C-103.

Compounds EJ1A-001~EJ1A-103 represent Compounds represented by a formula:

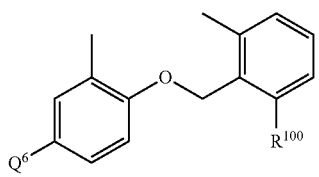

(EJ1A)

[in the formula (EJ1A), $R^{100}$ are the same as described above, and $Q^6$ represents a substituent corresponding to each of substituents Nos. 1 to 103 indicated in Table 56 to Table 60 as above-mentioned];

Compounds EJ1B-001~EJ1B-103 represent Compounds represented by a formula:

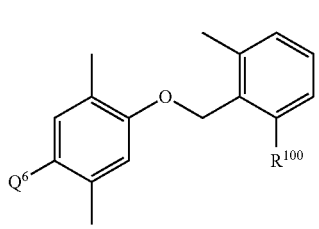

(EJ1B)

[in the formula (EJ1B), $R^{100}$ are the same as described above, and $Q^6$ represents a substituent corresponding to each of substituents Nos. 1 to 103 indicated in Table 56 to Table 60 as above-mentioned]; and Compounds EJ1C-001~EJ1C-103 represent Compounds represented by a formula:

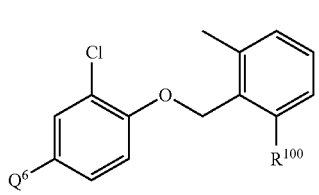

(EJ1C)

[in the formula (EJ1C), $R^{100}$ are the same as described above, and $Q^6$ represents a substituent corresponding to each of substituents Nos. 1 to 103 indicated in Table 56 to Table 60 as above-mentioned].

According to the above-mentioned processes, the following compounds can be prepared:

Compounds EK1A-001~EK1A-103, EK1B-001~EK1B-103 and EK1C-001~EK1C-103.

Compounds EK1A-001~EK1A-103 represent Compounds represented by a formula:

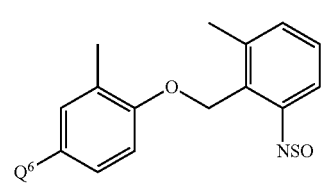

(EK1A)

[in the formula (EK1A), $Q^6$ represents a substituent corresponding to each of substituents Nos. 1 to 103 indicated in Table 56 to Table 60 as above-mentioned];

Compounds EK1B-001~EK1B-103 represent Compounds represented by a formula:

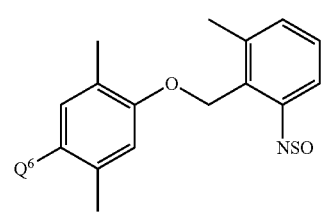

(EK1B)

[in the formula (EK1B), $Q^6$ represents a substituent corresponding to each of substituents Nos. 1 to 103 indicated in Table 56 to Table 60 as above-mentioned]; and Compounds EK1C-001~EK1C-103 represent Compounds represented by a formula:

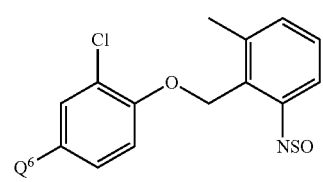

(EK1C)

[in the formula (EK1C), $Q^6$ represents a substituent corresponding to each of substituents Nos. 1 to 103 indicated in Table 56 to Table 60 as above-mentioned].

According to the above-mentioned processes, the following compounds can be prepared:

Compounds EL1A-001~EL1A-103, EL1B-001~EL1B-103 and EL1C-001~EL1C-103.

Compounds EL1A-001~EL1A-103 represent Compounds represented by a formula:

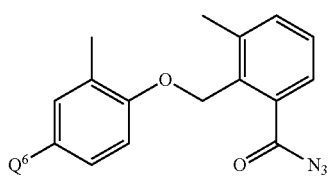
(EL1A)

[in the formula (EL1A), $Q^6$ represents a substituent corresponding to each of substituents Nos. 1 to 103 indicated in Table 56 to Table 60 as above-mentioned];
Compounds EL1B-001~EL1B-103 represent Compounds represented by a formula:

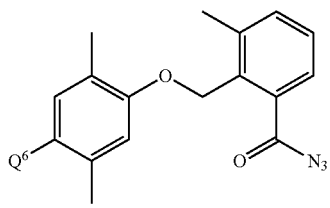
(EL1B)

[in the formula (EL1B), $Q^6$ represents a substituent corresponding to each of substituents Nos. 1 to 103 indicated in Table 56 to Table 60 as above-mentioned]; and
Compounds EL1C-001~EL1C-103 represent Compounds represented by a formula:

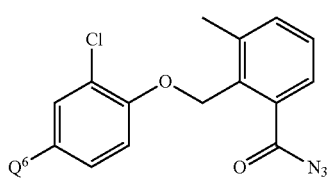
(EL1C)

[in the formula (EL1C), $Q^6$ represents a substituent corresponding to each of substituents Nos. 1 to 103 indicated in Table 56 to Table 60 as above-mentioned].
According to the above-mentioned processes, the following compounds can be prepared:
Compounds EM1A-001~EM1A-103, EM1B-001~EM1B-103 and EM1C-001~EM1C-103.
Compounds EM1A-001~EM1A-103 represent Compounds represented by a formula:

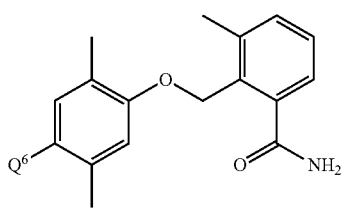
(EM1A)

[in the formula (EM1A), $Q^6$ represents a substituent corresponding to each of substituents Nos. 1 to 103 indicated in Table 56 to Table 60 as above-mentioned];
Compounds EM1B-001~EM1B-103 represent Compounds represented by a formula:

(EM1B)

[in the formula (EM1B), $Q^6$ represents a substituent corresponding to each of substituents Nos. 1 to 103 indicated in Table 56 to Table 60 as above-mentioned]; and
Compounds EM1C-001~EM1C-103 represent Compounds represented by a formula:

(EM1C)

[in the formula (EM1C), $Q^6$ represents a substituent corresponding to each of substituents Nos. 1 to 103 indicated in Table 56 to Table 60 as above-mentioned].
According to the above-mentioned processes, the following compounds can be prepared:
Compounds EN1A-001~EN1A-103, EN1B-001~EN1B-103 and EN1C-001~EN1C-103.
Compounds EN1A-001~EN1A-103 represent Compounds represented by a formula:

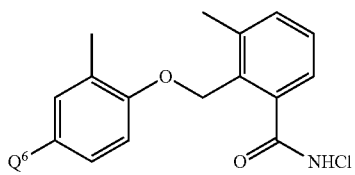
(EN1A)

[in the formula (EN1A), $Q^6$ represents a substituent corresponding to each of substituents Nos. 1 to 103 indicated in Table 56 to Table 60 as above-mentioned];
Compounds EN1B-001~EN1B-103 represent Compounds represented by a formula:

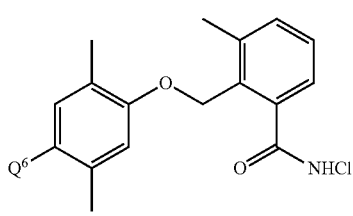
(EN1B)

[in the formula (EN1B), $Q^6$ represents a substituent corresponding to each of substituents Nos. 1 to 103 indicated in Table 56 to Table 60 as above-mentioned]; and
Compounds EN1C-001~EN1C-103 represent Compounds represented by a formula:

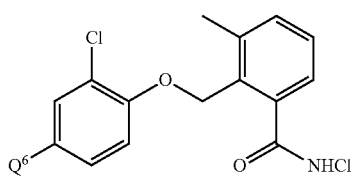

(EN1C)

[in the formula (EN1C), $Q^6$ represents a substituent corresponding to each of substituents Nos. 1 to 103 indicated in Table 56 to Table 60 as above-mentioned].

According to the above-mentioned processes, the following compounds can be prepared:

Compounds EO1A-001~EO1A-103, EO1B-001~EO1B-103 and EO1C-001~EO1C-103.

Compounds EO1A-001~EO1A-103 represent Compounds represented by a formula:

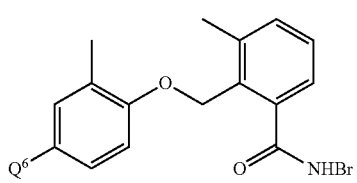

(EO1A)

[in the formula (EO1A), $Q^6$ represents a substituent corresponding to each of substituents Nos. 1 to 103 indicated in Table 56 to Table 60 as above-mentioned];

Compounds EO1B-001~EO1B-103 represent Compounds represented by a formula:

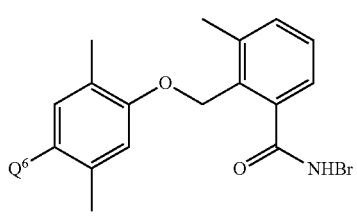

(EO1B)

[in the formula (EO1B), $Q^6$ represents a substituent corresponding to each of substituents Nos. 1 to 103 indicated in Table 56 to Table 60 as above-mentioned]; and Compounds EO1C-001~EO1C-103 represent Compounds represented by a formula:

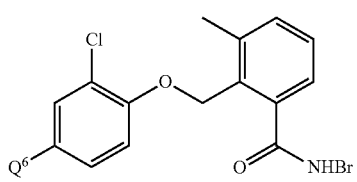

(EO1C)

[in the formula (EO1C), $Q^6$ represents a substituent corresponding to each of substituents Nos. 1 to 103 indicated in Table 56 to Table 60 as above-mentioned].

According to the above-mentioned processes, the following compounds can be prepared:

Compounds EQ1A-001~EQ1A-103, EQ1B-001~EQ1B-103 and EQ1C-001~EQ1C-103.

Compounds EQ1A-001~EQ1A-103 represent Compounds represented by a formula:

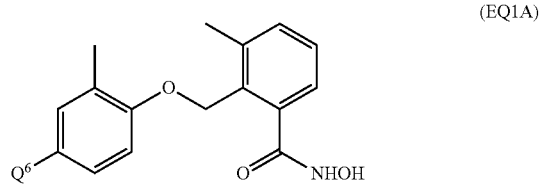

(EQ1A)

[in the formula (EQ1A), $Q^6$ represents a substituent corresponding to each of substituents Nos. 1 to 103 indicated in Table 56 to Table 60 as above-mentioned];

Compounds EQ1B-001~EQ1B-103 represent Compounds represented by a formula:

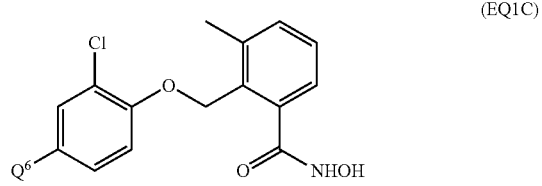

(EQ1B)

[in the formula (EQ1B), $Q^6$ represents a substituent corresponding to each of substituents Nos. 1 to 103 indicated in Table 56 to Table 60 as above-mentioned]; and Compounds EQ1C-001~EQ1C-103 represent Compounds represented by a formula:

(EQ1C)

[in the formula (EQ1C), $Q^6$ represents a substituent corresponding to each of substituents Nos. 1 to 103 indicated in Table 56 to Table 60 as above-mentioned].

Next, the Formulation examples are shown below. In the Examples, the term "part(s)" means part(s) by weight unless otherwise specified.

Formulation Example 1

Fifty (50) parts of any one of the present Compounds 1 to 306, 3 parts of calcium lignosulfonate, 2 parts of magnesium lauryl sulfate and 45 parts of synthetic hydrated silicon dioxide are well mixed while grinding to obtain a formulation.

Formulation Example 2

Twenty (20) parts of any one of the present Compounds 1 to 306, 1.5 parts of sorbitan trioleate are mixed with 28.5 parts of an aqueous solutions containing 2 parts of polyvinyl alcohol, and the mixture is then finely-ground by a wet grinding method. To this mixture is then added 40 parts of an aqueous solutions containing 0.05 parts of xanthane gum and 0.1 parts of magnesium aluminium, silicate, and 10 parts of propylene glycol is further added thereto. The mixture is stirred to obtain a formulation.

Formulation Example 3

Two (2) parts of any one of the present Compounds 1 to 306, 88 parts of kaolin clay and 10 parts of talc are mixed-grinding to obtain a formulation.

Formulation Example 4

Five (5) parts of any one of the present Compounds 1 to 306, 14 parts of polyoxyethylene styryl phenyl ether, 6 parts of calcium dodecylbenzene sulfonate and 75 parts of xylene are mixed-grinding to obtain a formulation.

Formulation Example 5

Two (2) parts of any one of the present Compounds 1 to 306, one part of synthetic hydrated silicon dioxide, 2 parts of calcium lignosulfonate, 30 parts of bentonite and 65 parts of kaolin clay are mixed-grinding and thereto is added water and the mixture is well kneaded and is then granulated and dried to obtain a formulation.

Formulation Example 6

Ten (10) parts of any one of the present Compounds 1 to 306, 35 parts of white carbon containing 50 parts of ammonium polyoxyethylene alkyl ether sulfate, and 55 parts of water are mixed, and the mixture is then finely-ground by a wet grinding method to obtain a formulation.

Next, Test examples are used to show an efficacy of the present Compounds on controlling plant diseases.

Here the controlling effects were evaluated by visually observing a lesion area on the tested plants and followed by comparing the lesion area of the plants treated with the present Compounds with a lesion area of the untreated plants.

Test Example 1

A plastic pot was filled with soil and thereto rice (cv; Nipponbare) seeds were sown and the plants were grown in a greenhouse for twenty days. Thereafter, each of the present Compounds 2, 3, 4, 5, 6, 7, 13, 15, 17, 30, 34, 36, 40, 41, 44, 47, 48, 50, 53, 54, 55, 56, 57, 58, 59, 60, 62, 63, 64, 65, 66, 72, 75, 76, 78, 84, 85, 86, 87, 89, 90, 91, 104, 105, 106, 107, 108, 117, 118, 119, 121, 122, 124, 129, 130, 141, 143, 146, 148, 150, 156, 157, 159, 160, 181, 224, 225, 292, 295, 298, 299 and 300 was made to a formulation according to the above-mentioned Formulation examples and was then diluted with water so as to make a predetermined concentration (500 ppm). The dilutions were sprayed to foliar parts so as to adhere adequately on the leaves of the above-mentioned rice. After spraying the dilutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*), and a lesion area was observed. As a result, every of the lesion areas in plants treated with the present Compounds, 3, 4, 5, 6, 7, 13, 15, 17, 30, 34, 36, 40, 41, 44, 47, 48, 50, 53, 54, 55, 56, 57, 58, 59, 60, 62, 63, 64, 65, 66, 72, 75, 76, 78, 84, 85, 86, 87, 89, 90, 91, 104, 105, 106, 107, 108, 117, 118, 119, 121, 122, 124, 129, 130, 141, 143, 146, 148, 150, 156, 157, 159, 160, 181, 224, 225, 292, 295, 298, 299 and 300 showed 30% or less compared to the lesion area in an untreated plants.

Test Example 2

A plastic pot was filled with soil and thereto wheat (cv; Shirogane) seeds were sown and the plants were grown in a greenhouse for 9 days. Thereafter, each of the present Compounds 4, 5, 6, 7, 13, 15, 22, 30, 39, 41, 44, 46, 47, 48, 50, 51, 52, 53, 54, 55, 56, 57, 58, 59, 62, 63, 72, 84, 85, 86, 87, 88, 89, 94, 127, 130, 131, 140, 142, 143, 144, 145, 146, 152, 156, 157, 158, 159, 160, 163, 164, 165, 166, 167, 168, 169, 170, 171, 172, 173, 174, 190, 191, 192, 194 and 292 was made to a formulation according to the above-mentioned Formulation examples and was then diluted with water so as to make a predetermined concentration (500 ppm). The dilutions were sprayed to foliar parts so as to adhere adequately on the leaves of the above-mentioned wheat. After spraying dilutions, the plants were air-dried and were placed at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compounds 4, 5, 6, 7, 13, 15, 22, 30, 39, 41, 44, 46, 47, 48, 50, 51, 52, 53, 54, 55, 56, 57, 58, 59, 62, 63, 72, 84, 85, 86, 87, 88, 89, 94, 127, 130, 131, 140, 142, 143, 144, 145, 146, 152, 156, 157, 158, 159, 160, 163, 164, 165, 166, 167, 168, 169, 170, 171, 172, 173, 174, 190, 191, 192, 194 and 292 showed 30% or less compared to the lesion area in an untreated plants.

Test Example 3

A plastic pot was filled with soil and thereto barley (cv; Mikamo Golden) seeds were sown and the plants were grown in a greenhouse for 7 days. Thereafter, each of the present Compounds 1, 4, 5, 6, 7, 8, 9, 10, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 90, 91, 92, 93, 94, 104, 105, 106, 107, 108, 109, 110, 111, 112, 113, 114, 115, 116, 117, 124, 125, 126, 128, 129, 130, 131, 132, 133, 140, 141, 142, 143, 144, 145, 146, 147, 148, 158, 163, 164, 165, 166, 167, 168, 169, 170, 171, 172, 173, 174, 175, 178, 179, 181, 182, 185, 190, 191, 192, 194, 223, 224, 225, 226, 227, 292, 293, 295, 297, 299 and 300 was made to a formulation according to the above-mentioned Formulation examples and was then diluted with water so as to make a predetermined concentration (500 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds 1, 4, 5, 6, 7, 8, 9, 10, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 90, 91, 92, 93, 94, 104, 105, 106, 107, 108, 109, 110, 111, 112, 113, 114, 115, 116, 117, 124, 125, 126, 128, 129, 130, 131, 132, 133, 140, 141, 142, 143, 144, 145, 146, 147, 148, 158, 163, 164, 165, 166, 167, 168, 169, 170, 171, 172, 173, 174, 175, 178, 179, 181, 182, 185, 190, 191, 192, 194, 223, 224, 225, 226, 227, 292, 293, 295, 297, 299 and 300 showed 30% or less compared to the lesion area in an untreated plants.

Test Example 4

A plastic pot was filled with soil and thereto Kidney bean (cv; Nagauzurasaitou) seeds were sown and the plants were grown in a greenhouse for 8 days. Either of the present Compounds 1, 2, 3, 4, 5, 6, 7, 8, 9, 10, 12, 13, 14, 15, 17, 18, 19, 20, 21, 22, 23, 24, 25, 26, 27, 28, 29, 30, 31, 32, 33, 34, 35, 37, 38, 39, 40, 41, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 100, 102, 109, 110, 111, 116, 117, 120, 122, 123, 124, 125, 126, 127, 128, 129, 132, 140, 141, 142, 143, 144, 145, 146, 147, 148, 149, 150, 175, 178, 179, 181, 182, 203, 204, 205, 206, 207, 208, 209, 210, 211, 212, 213, 214, 215, 216, 217, 218, 220, 221, 222, 223, 224, 225, 226, 227, 292, 295, 297, 298, 299 and 300 was made to a formulation according to the above-mentioned Formulation examples and was then diluted with water so as to make a predetermined concentration (500 ppm). The dilutions were sprayed to foliar parts so as to adhere adequately on the leaves of the above-mentioned kidney bean. After spraying the dilutions, the plants were air-dried and a PDA medium containing hyphae of kidney bean sclerotinia rot fungi (Sclerotinia sclerotiorum) was placed on the leaves of the kidney bean. After inoculation, all kidney beans were placed under a high humidity during only night and after four days, and a lesion area was observed. As a result, every of the lesion areas in plants treated with either the present Compounds 1, 2, 3, 4, 5, 6, 7, 8, 9, 10, 12, 13, 14, 15, 17, 18, 19, 20, 21, 22, 23, 24, 25, 26, 27, 28, 29, 30, 31, 32, 33, 34, 35, 37, 38, 39, 40, 41, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 100, 102, 109, 110, 111, 116, 117, 120, 122, 123, 124, 125, 126, 127, 128, 129, 132, 140, 141, 142, 143, 144, 145, 146, 147, 148, 149, 150, 175, 178, 179, 181, 182, 203, 204, 205, 206, 207, 208, 209, 210, 211, 212, 213, 214, 215, 216, 217, 218, 220, 221, 222, 223, 224, 225, 226, 227, 292, 295, 297, 298, 299 and 300 showed 30% or less compared to the lesion area in an untreated plants.

Test Example 5

A plastic pot was filled with soil and thereto wheat (cv; Apogee) seeds were sown and the plants were grown in a greenhouse for 10 days. Each of the present Compounds 1, 4, 5, 6, 7, 8, 9, 10, 12, 13, 14, 15, 17, 19, 20, 21, 22, 23, 24, 26, 27, 28, 29, 30, 32, 33, 34, 35, 36, 37, 38, 39, 40, 41, 44, 46, 47, 48, 49, 50, 51, 52, 53, 54, 55, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 104, 115, 116, 117, 118, 119, 120, 121, 122, 123, 124, 125, 126, 127, 128, 129, 140, 142, 143, 144, 145, 146, 153, 154, 155, 156, 157, 163, 164, 165, 166, 167, 168, 169, 170, 171, 172, 173, 174, 179, 181, 182, 190, 191, 192, 194, 292, 293, 299 and 300 was made to a formulation according to the above-mentioned Formulation examples and was then diluted with water so as to make a predetermined concentration (500 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (Septoria tritici) was spraying-inoculated. After inoculation, the plants were placed at 18° C. under a high humidity for 3 days and then under lighting for 14 to 18 days, and a lesion area was observed. As a result, every of the lesion areas in plants treated with the present Compounds 1, 4, 5, 6, 7, 8, 9, 10, 12, 13, 14, 15, 17, 19, 20, 21, 22, 23, 24, 26, 27, 28, 29, 30, 32, 33, 34, 35, 36, 37, 38, 39, 40, 41, 44, 46, 47, 48, 49, 50, 51, 52, 53, 54, 55, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 104, 115, 116, 117, 118, 119, 120, 121, 122, 123, 124, 125, 126, 127, 128, 129, 140, 142, 143, 144, 145, 146, 153, 154, 155, 156, 157, 163, 164, 165, 166, 167, 168, 169, 170, 171, 172, 173, 174, 179, 181, 182, 190, 191, 192, 194, 292, 293, 299 and 300 showed 30% or less compared to the lesion area in an untreated plants.

Test Example 6

A plastic pot was filled with soil and thereto cucumber (cv; Sagamihanjiro) seeds were sown and the plants were grown in a greenhouse for 12 days. Each of the present Compounds 1, 4, 5, 6, 7, 9, 12, 13, 14, 15, 16, 17, 19, 20, 22, 23, 24, 26, 27, 28, 29, 30, 31, 32, 33, 34, 35, 37, 38, 39, 40, 41, 42, 43, 44, 45, 46, 47, 48, 49, 50, 51, 52, 53, 54, 55, 57, 58, 59, 60, 61, 62, 63, 64, 65, 66, 68, 69, 70, 71, 72, 73, 74, 75, 76, 77, 78, 80, 81, 82, 83, 84, 85, 86, 87, 88, 89, 90, 91, 92, 94, 126, 182, 219, 292, 295, 297, 298, 299 and 300 was made to a formulation according to the above-mentioned Formulation examples and was then diluted with water so as to make a predetermined concentration (500 ppm). The dilutions were sprayed to foliar parts so as to adhere adequately on the leaves of the above-mentioned cucumber. After spraying the dilutions, the plants were air-dried and the spores of powdery mildew fungi (Sphaerotheca fuliginea) were sprinkling-inoculated. The plants were placed in a greenhouse of 24° C. during daytime and 20° C. during nighttime for 8 days, and a lesion area was observed. As a result, every of the lesion areas in plants treated with the present Compounds 1, 4, 5, 6, 7, 9, 12, 13, 14, 15, 16, 17, 19, 20, 22, 23, 24, 26, 27, 28, 29, 30, 31, 32, 33, 34, 35, 37, 38, 39, 40, 41, 42, 43, 44, 45, 46, 47, 48, 49, 50, 51, 52, 53, 54, 55, 57, 58, 59, 60, 61, 62, 63, 64, 65, 66, 68, 69, 70, 71, 72, 73, 74, 75, 76, 77, 78, 80, 81, 82, 83, 84, 85, 86, 87, 88, 89, 90, 91, 92, 94, 126, 182, 219, 292, 295, 297, 298, 299 and 300 showed 30% or less compared to the lesion area in an untreated plants.

Test Example 7

A plastic pot was filled with soil and thereto rice (cv; Nipponbare) seeds were sown and the plants were grown in a greenhouse for twenty days. Thereafter, each of the present Compounds 2, 3, 9, 10, 11, 14, 18, 24, 27, 37, 46, 49, 54, 74, 88, 92, 94, 95, 96, 97, 98, 99, 100, 101, 102, 103, 109, 110, 115, 118, 119, 120, 121, 123, 124, 128, 131, 142, 144, 145, 149, 152, 153, 154, 155, 169, 182, 190, 191, 192, 193, 194, 195, 196, 204, 205, 206, 207, 208, 209, 210, 211, 212, 213, 214, 215, 216, 218, 220, 221, 222, 223, 224, 230, 231, 232, 233, 234, 235, 236, 238, 244, 246, 247, 256, 257, 258, 259, 260, 263, 265, 267, 272, 274, 275, 276, 277, 281, 284 and 285 was made to a formulation according to the above-mentioned Formulation examples and was then diluted with water so as to make a predetermined concentration (200 ppm). The dilutions were sprayed to foliar parts so as to adhere adequately on the leaves of the above-mentioned rice. After spraying the dilutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*), and a lesion area was observed. As a result, every of the lesion areas in plants treated with the present Compounds 2, 3, 9, 10, 11, 14, 18, 24, 27, 37, 46, 49, 54, 74, 88, 92, 94, 95, 96, 97, 98, 99, 100, 101, 102, 103, 109, 110, 115, 118, 119, 120, 121, 123, 124, 128, 131, 142, 144, 145, 149, 152, 153, 154, 155, 169, 182, 190, 191, 192, 193, 194, 195, 196, 204, 205, 206, 207, 208, 209, 210, 211, 212, 213, 214, 215, 216, 218, 220, 221, 222, 223, 224, 230, 231, 232, 233, 234, 235, 236, 238, 244, 246, 247, 256, 257, 258, 259, 260, 263, 265, 267, 272, 274, 275, 276, 277, 281, 284 and 285 showed 30% or less compared to the lesion area in an untreated plants.

Test Example 8

A plastic pot was filled with soil and thereto wheat (cv; Shirogane) seeds were sown and the plants were grown in a greenhouse for 9 days. Thereafter, each of the present Compounds 1, 2, 3, 8, 17, 19, 24, 29, 35, 37, 38, 40, 43, 49, 60, 61, 65, 66, 70, 71, 73, 74, 75, 76, 80, 81, 82, 83, 84, 85, 87, 90, 91, 92, 95, 96, 98, 99, 101, 102, 103, 105, 106, 107, 108, 109, 110, 114, 115, 118, 119, 120, 121, 122, 123, 124, 128, 129, 132, 141, 147, 148, 149, 150, 153, 154, 155, 163, 164, 165, 166, 167, 168, 169, 170, 171, 172, 173, 174, 179, 181, 182, 190, 191, 192, 194, 195, 196, 204, 205, 206, 207, 208, 209, 210, 211, 212, 213, 214, 215, 216, 217, 218, 219, 220, 221, 222, 223, 224, 227, 230, 231, 232, 233, 235, 236, 238, 241, 242, 243, 244, 245, 246, 247, 250, 256, 257, 258, 259, 260, 263, 265, 267, 272, 274, 275, 276, 277, 281, 284 and 285 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and were placed at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compounds 1, 2, 3, 8, 17, 19, 24, 29, 35, 37, 38, 40, 43, 49, 60, 61, 65, 66, 70, 71, 73, 74, 75, 76, 80, 81, 82, 83, 84, 85, 87, 90, 91, 92, 95, 96, 98, 99, 101, 102, 103, 105, 106, 107, 108, 109, 110, 114, 115, 118, 119, 120, 121, 122, 123, 124, 128, 129, 132, 141, 147, 148, 149, 150, 153, 154, 155, 163, 164, 165, 166, 167, 168, 169, 170, 171, 172, 173, 174, 179, 181, 182, 190, 191, 192, 194, 195, 196, 204, 205, 206, 0.207, 208, 209, 210, 211, 212, 213, 214, 215, 216, 217, 218, 219, 220, 221, 222, 223, 224, 227, 230, 231, 232, 233, 235, 236, 238, 241, 242, 243, 244, 245, 246, 247, 250, 256, 257, 258, 259, 260, 263, 265, 267, 272, 274, 275, 276, 277, 281, 284 and 285 showed 30% or less compared to the lesion area in an untreated plants.

Test Example 9

A plastic pot was filled with soil and thereto barley (cv; Mikamo Golden) seeds were sown and the plants were grown in a greenhouse for 7 days. Thereafter, each of the present Compounds 2, 3, 18, 30, 31, 89, 95, 96, 97, 98, 99, 100, 101, 102, 103, 112, 118, 119, 120, 121, 149, 150, 152, 153, 154, 155, 156, 157, 159, 160, 163, 164, 165, 166, 167, 168, 169, 170, 171, 172, 173, 174, 190, 191, 192, 194, 195, 196, 203, 204, 205, 206, 207, 208, 209, 210, 211, 212, 213, 214, 215, 216, 217, 218, 219, 220, 221, 222, 223, 224, 227, 230, 231, 232, 233, 235, 236, 238, 241, 242, 243, 244, 245, 246, 247, 250, 256, 257, 258, 259, 260, 263, 265, 267, 272, 274, 275, 276, 277, 281, 284 and 285 was made to a formulation according to the above-mentioned Formulation examples and was then diluted with water so as to make a predetermined concentration (200 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds 2, 3, 18, 30, 31, 89, 95, 96, 97, 98, 99, 100, 101, 102, 103, 112, 118, 119, 120, 121, 149, 150, 152, 153, 154, 155, 156, 157, 159, 160, 163, 164, 165, 166, 167, 168, 169, 170, 171, 172, 173, 174, 190, 191, 192, 194, 195, 196, 203, 204, 205, 206, 207, 208, 209, 210, 211, 212, 213, 214, 215, 216, 217, 218, 219, 220, 221, 222, 223, 224, 227, 230, 231, 232, 233, 235, 236, 238, 241, 242, 243, 244, 245, 246, 247, 250, 256, 257, 258, 259, 260, 263, 265, 267, 272, 274, 275, 276, 277, 281, 284 and 285 showed 30% or less compared to the lesion area in an untreated plants.

Test Example 10

A plastic pot was filled with soil and thereto Kidney bean (cv; Nagauzurasaitou) seeds were sown and the plants were grown in a greenhouse for 8 days. Either of the present Compounds 12, 13, 21, 22, 26, 27, 28, 29, 30, 31, 32, 33, 34, 35, 37, 38, 40, 41, 43, 47, 48, 49, 50, 51, 52, 57, 58, 59, 60, 61, 62, 63, 65, 66, 67, 69, 71, 72, 73, 79, 80, 81, 82, 85, 104, 105, 106, 107, 108, 112, 113, 114, 115, 118, 119, 121, 122, 123, 124, 125, 126, 127, 128, 129, 130, 131, 152, 153, 154, 155, 156, 157, 158, 159, 160, 221, 223, 228, 229, 231, 244, 245, 246, 247, 248, 250, 255, 256, 259, 260, 263, 265, 267, 274, 275, 276, 277 and 285 was made to a formulation according to the above-mentioned Formulation examples and was then diluted with water so as to make a predetermined concentration (200 ppm). The dilutions were sprayed to foliar parts so as to adhere adequately on the leaves of the above-mentioned kidney bean. After spraying the dilutions, the plants were air-dried and a PDA medium containing hyphae of kidney bean *sclerotinia* rot fungi (*Sclerotinia sclerotiorum*) was placed on the leaves of the kidney bean. After inoculation, all kidney beans were placed under a high humidity during only night and after four days, and a lesion area was observed. As a result, every of the lesion areas in plants treated with either the present Compounds 12, 13, 21, 22, 26, 27, 28, 29, 30, 31, 32, 33, 34, 35, 37, 38, 40, 41, 43, 47, 48, 49, 50, 51, 52, 57, 58, 59, 60, 61, 62, 63, 65, 66, 67, 69, 71, 72, 73, 79, 80, 81, 82, 85, 104, 105, 106, 107, 108, 112, 113, 114, 115, 118, 119, 121, 122, 123, 124, 125, 126, 127, 128, 129, 130, 131, 152, 153, 154, 155, 156, 157, 158, 159, 160, 221, 223, 228, 229, 231, 244, 245, 246, 247, 248, 250, 255, 256, 259, 260, 263, 265, 267, 274, 275, 276, 277 and 285 showed 30% or less compared to the lesion area in an untreated plants.

Test Example 11

A plastic pot was filled with soil and thereto wheat (cv; Apogee) seeds were sown and the plants were grown in a greenhouse for 10 days. Each of the present Compounds 2, 3, 20, 31, 41, 43, 57, 56, 58, 66, 68, 69, 79, 80, 81, 95, 96, 97, 98, 99, 100, 101, 102, 103, 105, 106, 107, 108, 109, 110, 111, 112, 113, 114, 118, 119, 120, 121, 122, 123, 124, 125, 126, 127, 128, 129, 130, 131, 132, 141, 147, 148, 149, 150, 152, 158, 159, 160, 163, 164, 165, 166, 167, 168, 169, 170, 171, 172, 173, 174, 175, 178, 179, 181, 182, 190, 191, 192, 194, 195, 196, 204, 205, 206, 207, 208, 209, 210, 211, 212, 213, 214, 215, 216, 217, 218, 220, 221, 222, 223, 224, 227, 230, 231, 232, 233, 234, 235, 236, 238, 241, 244, 245, 246, 247, 250, 253, 254, 256, 263, 265, 267, 272, 274, 275, 276, 277, 281, 284 and 285 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present Compounds 2, 3, 20, 31, 41, 43, 57, 56, 58, 66, 68, 69, 79, 80, 81, 95, 96, 97, 98, 99, 100, 101, 102, 103, 105, 106, 107, 108, 109, 110, 111, 112, 113, 114, 118, 119, 120, 121, 122, 123, 124, 125, 126, 127, 128, 129, 130, 131, 132, 141, 147, 148, 149, 150, 152, 158, 159, 160, 163, 164, 165, 166, 167, 168, 169, 170, 171, 172, 173, 174, 175, 178, 179, 181, 182, 190, 191, 192, 194, 195, 196, 204, 205, 206, 207, 208, 209, 210, 211, 212, 213, 214, 215, 216, 217, 218, 220, 221, 222, 223, 224, 227, 230, 231, 232, 233, 234, 235, 236, 238, 241, 244, 245, 246, 247, 250, 253, 254, 256, 263, 265, 267, 272, 274, 275, 276, 277, 281, 284 and 285 showed 30% or less compared to the lesion area in an untreated plants.

Test Example 12

A plastic pot was filled with soil and thereto cucumber (cv; Sagamihanjiro) seeds were sown and the plants were grown in a greenhouse for 12 days. Each of the present Compounds 2, 3, 56, 79, 80, 86, 87, 95, 96, 97, 98, 100, 102, 104, 105, 106, 107, 108, 109, 110, 112, 113, 114, 115, 118, 119, 120, 121, 122, 123, 124, 129, 130, 131, 132, 141, 142, 143, 144, 145, 146, 147, 149, 150, 152, 154, 155, 156, 157, 158, 159, 160, 181, 186, 188, 189, 190, 191, 192, 193, 194, 195, 196, 204, 205, 206, 208, 209, 210, 211, 212, 213, 214, 215, 216, 217, 218, 220, 221, 222, 223, 224, 225, 227, 231, 232, 233, 234, 235, 236, 238, 244, 245, 246, 247, 250, 255, 256, 258, 259, 260, 261, 263, 264, 265, 267, 272, 274, 275, 276, 281, 284 and 285 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and the spores of powdery mildew fungi (*Sphaerotheca fuliginea*) were sprinkling-inoculated. The plants were placed in a greenhouse of 24° C. during daytime and 20° C. during nighttime for 8 days, and a lesion area was observed. As a result, every of the lesion areas in plants treated with the present Compounds 2, 3, 56, 79, 80, 86, 87, 95, 96, 97, 98, 100, 102, 104, 105, 106, 107, 108, 109, 110, 112, 113, 114, 115, 118, 119, 120, 121, 122, 123, 124, 129, 130, 131, 132, 141, 142, 143, 144, 145, 146, 147, 149, 150, 152, 154, 155, 156, 157, 158, 159, 160, 181, 186, 188, 189, 190, 191, 192, 193, 194, 195, 196, 204, 205, 206, 208, 209, 210, 211, 212, 213, 214, 215, 216, 217, 218, 220, 221, 222, 223, 224, 225, 227, 231, 232, 233, 234, 235, 236, 238, 244, 245, 246, 247, 250, 255, 256, 258, 259, 260, 261, 263, 264, 265, 267, 272, 274, 275, 276, 281, 284 and 285 showed 30% or less compared to the lesion area in an untreated plants.

Test Example 13

A plastic pot was filled with soil and thereto soybean (cv: Kurosengoku) seeds were sown and the plants were grown in a greenhouse for 13 days. Each of the present Compounds 2, 4, 5, 7, 13, 17, 20, 22, 24, 26, 29, 30, 35, 39, 40, 41, 44, 46, 47, 48, 49, 50, 51, 52, 53, 54, 55, 56, 57, 58, 59, 60, 62, 63, 64, 65, 66, 70, 71, 72, 73, 75, 76, 80, 81, 82, 84, 85, 86, 87, 89, 90, 91, 92, 94, 96, 98, 99, 100, 101, 102, 105, 106, 107, 108, 109, 110, 114, 115, 118, 119, 122, 123, 124, 127, 130, 131, 141, 143, 147, 148, 150, 153, 154, 160, 181, 188, 190, 191, 192, 193, 194, 196, 204, 205, 206, 207, 208, 210, 211, 212, 213, 214, 215, 216, 218, 219, 220, 222, 223, 225, 229, 230, 231, 232, 233, 236, 238, 244, 245, 250, 263, 272, 275, 276 and 284 was made to a formulation according to the above-mentioned Formulation examples and was then diluted with water so as to make a predetermined concentration (200 ppm). The dilutions were sprayed to foliar parts so as to adhere adequately on the leaves of the above-mentioned soybean. After spraying the dilutions, the plants were air-dried and after 2 days, an aqueous suspension of the spores of soybean rust fungi (*phakopsora pachyrhizi*) was spraying-inoculated. After inoculation, the plants were placed in a greenhouse of 23° C. during daytime and 20° C. during nighttime under a high humidity for 3 days and were then cultivated in the greenhouse for 14 days, and a lesion area was observed. As a result, every of the lesion areas in plants treated with the present Compounds 2, 4, 5, 7, 13, 17, 20, 22, 24, 26, 29, 30, 35, 39, 40, 41, 44, 46, 47, 48, 49, 50, 51, 52, 53, 54, 55, 56, 57, 58, 59, 60, 62, 63, 64, 65, 66, 70, 71, 72, 73, 75, 76, 80, 81, 82, 84, 85, 86, 87, 89, 90, 91, 92, 94, 96, 98, 99, 100, 101, 102, 105, 106, 107, 108, 109, 110, 114, 115, 118, 119, 122, 123, 124, 127, 130, 131, 141, 143, 147, 148, 150, 153, 154, 160, 181, 188, 190, 191, 192, 193, 194, 196, 204, 205, 206, 207, 208, 210, 211, 212, 213, 214, 215, 216, 218, 219, 220, 222, 223, 225, 229, 230, 231, 232, 233, 236, 238, 244, 245, 250, 263, 272, 275, 276 and 284 showed 30% or less compared to the lesion area in an untreated plants.

Test Example 14

A plastic pot was filled with soil and thereto barley (cv; Mikamo Golden) seeds were sown and the plants were grown in a greenhouse for 7 days. Each of the present Compounds 1, 2, 3, 6, 7, 8, 9, 11, 13, 14, 15, 17, 18, 20, 22, 23, 24, 25, 26, 27, 28, 29, 30, 31, 32, 33, 35, 36, 38, 39, 40, 43, 44, 45, 46, 47, 49, 52, 53, 54, 56, 57, 59, 61, 64, 66, 67, 68, 69, 70, 72, 74, 76, 77, 78, 79, 80, 81, 82, 83, 87, 88, 90, 92, 95, 96, 97, 98, 99, 100, 101, 102, 103, 105, 106, 107, 108, 109, 110, 111, 112, 113, 114, 115, 116, 117, 118, 119, 120, 121, 124, 125, 129, 130, 131, 132, 141, 142, 143, 144, 145, 146, 147, 148, 149, 150, 152, 153, 154, 155, 156, 157, 159, 160, 163, 164, 165, 166, 167, 168, 169, 170, 171, 172, 173, 174, 175, 178, 179, 181, 181, 190, 191, 192, 194, 195, 196, 203, 204, 205, 206, 207, 208, 209, 210, 211, 212, 213, 214, 215, 216, 217, 218, 219, 220, 221, 222, 223, 224, 227, 230, 231, 232, 233, 234, 235, 238, 244, 245, 246, 248, 250, 253, 256, 257, 258, 259, 260, 261, 263, 264, 265, 267, 272, 275, 276, 277, 281, 284 and 285 was made to a formulation according to the above-mentioned Formulation examples and was then diluted with water so as to make a predetermined concentration (200 ppm). The dilutions were sprayed to foliar parts so as to adhere adequately on the leaves of the above-mentioned barley. After spraying the dilutions, the plants were air-dried and after 2 days, an aqueous suspension of the spores of barley leaf blotch fungi (*Rhynchosporium secalis*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, every of the lesion areas in plants treated with the present Compounds 1, 2, 3, 6, 7, 8, 9, 11, 13, 14, 15, 17, 18, 20, 22, 23, 24, 25, 26, 27, 28, 29, 30, 31, 32, 33, 35, 36, 38, 39, 40, 43, 44, 45, 46, 47, 49, 52, 53, 54, 56, 57, 59, 61, 64, 66, 67, 68, 69, 70, 72, 74, 76, 77, 78, 79, 80, 81, 82, 83, 87, 88, 90, 92, 95, 96, 97, 98, 99, 100, 101, 102, 103, 105, 106, 107, 108, 109, 110, 111, 112, 113, 114, 115, 116, 117, 118, 119, 120, 121, 124, 125, 129, 130, 131, 132, 141, 142, 143, 144, 145, 146, 147, 148, 149, 150, 152, 153, 154, 155, 156, 157, 159, 160, 163, 164, 165, 166, 167, 168, 169, 170, 171, 172, 173, 174, 175, 178, 179, 181, 181, 190, 191, 192, 194, 195, 196, 203, 204, 205, 206, 207, 208, 209, 210, 211, 212, 213, 214, 215, 216, 217, 218, 219, 220, 221, 222, 223, 224, 227, 230, 231, 232, 233, 234, 235, 238, 244, 245, 246, 248, 250, 253, 256, 257, 258, 259, 260, 261, 263, 264, 265, 267, 272, 275, 276, 277, 281, 284 and 285 showed 30% or less compared to the lesion area in an untreated plants.

Test Example 15

A plastic pot was filled with soil and thereto tomato (cv; Patio) seeds were sown and the plants were grown in a greenhouse for 20 days. The present compounds 24, 44, 47, 48, 52, 53, 57, 59, 65, 84, 85, 87, 90, 93 and 100 was made to a formulation according to the above-mentioned Formulation examples and was then diluted with water so as to make a predetermined concentration (500 ppm). The dilutions were sprayed to foliar parts so as to adhere adequately on the leaves of the above-mentioned tomato. After the plants were air-dried to such an extent that the dilutions were dried, an aqueous suspension of the spores of tomato late blight fungi (*Phytophthora infestans*) was spraying-inoculated. After inoculation, the plants were at first placed at 23° C. under a high humidity for 1 day and were then cultivated in the greenhouse for 4 days, and a lesion area was observed. As a result, every of the lesion areas in plants treated with the present compounds 24, 44, 47, 48, 52, 53, 57, 59, 65, 84, 85, 87, 90, 93 and 100 showed 30% or less compared to the lesion area in untreated plants.

Test Example 16

A plastic pot was filled with soil and thereto cucumber (cv; Sagamihanjiro) seeds were sown and the plants were grown in a greenhouse for 19 days. Each of the present Compounds 2, 3, 6, 47, 48, 54, 56 to 59, 90, 91, 93 to 96, 98, 100, 102, 104 to 110, 112 to 115, 118 to 121, 123, 130 to 132, 141 to 152, 154 to 174, 188 to 196, 204 to 208, 210 to 221, 223, 225, 227, 228, 229, 231, 232, 233, 235, 236, 261, 263, 295, 297, 298, 299 and 300 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber target spot fungi (*Corynespora cassiicola*) was spaying-inoculated. After an inoculation, the plants were placed at 24° C. during daytime and 20° C. during nighttime under a high humidity for 7 days, and a lesion area was observed. As a result, every of the lesion areas in plants treated with the present Compounds 2, 3, 6, 47, 48, 54, 56 to 59, 90, 91, 93 to 96, 98, 100, 102, 104 to 110, 112 to 115, 118 to 121, 123, 130 to 132, 141 to 152, 154 to 174, 188 to 196, 204 to 208, 210 to 221, 223, 225, 227, 228, 229, 231, 232, 233, 235, 236, 261, 263, 295, 297, 298, 299 and 300 showed 30% or less compared to the lesion area in an untreated plants.

Test Example 17

A plastic pot was filled with soil and thereto cucumber (cv; Sagamihanjiro) seeds were sown and the plants were grown in a greenhouse for 19 days. Each of the present Compounds 2, 3, 47, 48, 56 to 59, 90, 91, 93 to 96, 98, 100, 102, 104 to 110, 112 to 115, 118 to 121, 130, 131, 142 to 146, 148 to 152, 154 to 157, 159, 160, 162 to 174, 188 to 196, 204 to 206, 208 to 218, 220, 221, 223 to 225, 227 to 229, 231, 232, 233, 234, 235, 236, 238, 241, 244, 245, 246, 247, 248, 250, 255, 256, 259, 260, 261, 263, 264, 265, 267, 272, 274, 275, 276, 277, 281, 284 and 285 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber anthracnose fungi (*Colletotrichum lagenarium*) was spraying-inoculated. After an inoculation, the plants were placed firstly at 23° C. under a high humidity for 1 day and were then cultivated in a greenhouse of 24° C. during daytime and 20° C. during nighttime for 6 days, and a lesion area was observed. As a result, every of the lesion areas in plants treated with the present Compounds 2, 3, 47, 48, 56 to 59, 90, 91, 93 to 96, 98, 100, 102, 104 to 110, 112 to 115, 118 to 121, 130, 131, 142 to 146, 148 to 152, 154 to 157, 159, 160, 162 to 174, 188 to 196, 204 to 206, 208 to 218, 220, 221, 223 to 225, 227 to 229, 231, 232, 233, 234, 235, 236, 238, 241, 244, 245, 246, 247, 248, 250, 255, 256, 259, 260, 261, 263, 264, 265, 267, 272, 274, 275, 276, 277, 281, 284 and 285 showed 30% or less compared to the lesion area in an untreated plants.

Test Example 18

The testing drug dilutions to be used in this Test example were prepared as follows: each of the present Compounds 9, 11, 22, 50, 53, 59, 68, 77, 87, 112, 129, 154, 206, 209 and 210 was made to a formulation according to the above-mentioned Formulation examples and the formulations were diluted with an ion-exchange water so that the active ingredient concentration was set to 500 ppm.

Cucumber (cv; Sagami-hanjiro-fushinari) was grown in a polyethylene cup until the first true leaf was developed. Thirty (30) heads of cotton aphid (*Aphis gossypii*) (including the adults and the larvae) was released onto the leaves of the cabbage and next day, the above-mentioned testing drug dilutions 20 mL were sprayed. After 6 days, the number of the surviving insects was counted and the control value was calculated by the following equation.

Control value (%)={1−($Cb$×$Tai$)/($Cai$×$Tb$)}×100 wherein the symbols in the formula represent the following descriptions.

Cb: Number of the insects before treatment in untreated area;

Cai: Number of the insects at the time of the observation in untreated area;

Tb: Number of the insects before treatment in treated area;

Tai: Number of the insects at the time of the observation in treated area;

As a result, the present Compounds 9, 11, 22, 50, 53, 59, 68, 77, 87, 112, 129, 154, 206, 209 and 210 showed 90% or more as the control value.

Test Example 19

The testing drug dilutions to be used in this Test example were prepared as follows: each of the present Compounds 9, 146 and 209 was made to a formulation according to the above-mentioned Formulation examples and the formulations were diluted with an ion-exchange water so that the active ingredient concentration was set to 500 ppm. The above-mentioned drug solutions 0.7 mL were added to an ion-exchange water 100 mL so that the active ingredient concentration was set to 3.5 ppm. Twenty (20) last instar larvae of common house mosquito (*Culex pipiens pallens*) were released into the dilutions and after 8 day, the number of the dead insects was counted.

The mortality of insects was calculated by the following equation.

Mortality of insects (%)=(Number of dead insects/Number of tested insects)×100

As a result, the present Compounds 9, 146 and 209 showed 100% as the mortality of insects.

Test Example 20

The testing drug dilutions to be used in this Test example were prepared as follows: each of the present Compounds 9, 13, 16, 31, 44, 50, 90, 143 and 210 was made to a formulation according to the above-mentioned Formulation examples and the formulations were diluted with an ion-exchange water so that the active ingredient concentration was set to 500 ppm. Cabbage (green ball) was planted in a polyethylene cup and was grown until the third true leaf or the fourth true leaf was developed. To the cabbage was spread the above-mentioned testing dilutions in a ratio of 20 mL/cup. After the drug dilutions were dried, to a polyethylene cup (diameter 5.5 cm) covered with a filter paper on the bottom, the cabbage cut out from the root was installed and five heads of cabbage moth (*Plutella xylostella*) at the three instar larval stages were released into the cup and the cup was covered with the lid. The cup was held at 25° C. and after 5 days, the number of the surviving insects was counted and the mortality of insects was calculated by the following equation.

Mortality of insects (%)=(Number of dead insects/Number of tested insects)×100

As a result, the experiments treated with the present compounds 9, 13, 16, 31, 44, 50, 90, 143 and 210 showed 80% as the mortality of insects.

Comparative Test Example

A plastic pot was filled with soil and thereto wheat (cv; Shirogane) seeds were sown and the plants were grown in a greenhouse for 9 days. A control compound, 1-{2-[2-chloro-4-(3,5-dimethyl-pyrazol-1-yl)-phenoxymethyl]-phenyl}-4-methyl-1,4-dihydrotetrazole-5-one was made to a formulation according to the above-mentioned Formulation examples and was then diluted with water so as to make a predetermined concentration (500 ppm). The dilutions were sprayed to foliar parts so as to adhere adequately on the leaves of the above-mentioned wheat. After spraying the dilutions, the plants were air-dried and were then cultivated at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, the lesion area in plants treated with the control compound, 1-{2-[2-chloro-4-(3,5-dimethyl-pyrazol-1-yl)-phenoxymethyl]-phenyl}-4-methyl-1,4-dihydrotetrazole-5-one showed 70% or more compared to the lesion area in an untreated plants.

The invention claimed is:

1. A tetrazolinone compound of formula (1):

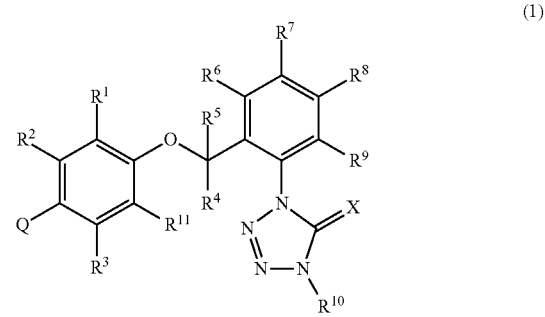

(1)

wherein

Q represents a group selected from the following group: Q1 or Q2:

Q;

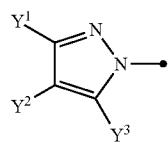

Q1

-continued

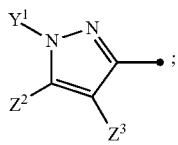

Q2

$R^1$, $R^2$, $R^3$ and $R^{11}$ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group $P^1$ or an C3-C6 cycloalkyl group optionally having one or more groups selected from Group $P^1$;

$R^4$ and $R^5$ represent independently of each other a hydrogen atom, a halogen atom or an C1-C3 alkyl group;

$R^6$ represents an C1-C4 alkyl group, a halogen atom, an C1-C4 alkoxy group or a C1-C4 haloalkyl group;

$R^7$, $R^8$ and $R^9$ represent independently of each other a hydrogen atom, a halogen atom, an C1-C3 alkyl group, a C1-C3 haloalkyl group, an C2-C3 alkenyl group, a C2-C3 haloalkenyl group or an C1-C3 alkoxy group;

$R^{10}$ represents an C1-C3 alkyl group, a C1-C3 haloalkyl group, an C2-C3 alkenyl group, a C2-C3 haloalkenyl group, an C2-C3 alkynyl group, a C2-C3 haloalkynyl group, a C3-C5 cycloalkyl group or a C3-C5 halocycloalkyl group;

X represents an oxygen atom or a sulfur atom;

$Z^1$ represents a hydrogen atom, an amino group, an C3-C6 alkenyl group, a C3-C6 haloalkenyl group, an C3-C6 alkynyl group, a C3-C6 haloalkynyl group, an C1-C6 alkylsulfinyl group, a C1-C6 haloalkylsulfinyl group, an C1-C6 alkylsulfonyl group, a C1-C6 haloalkylsulfonyl group, a C3-C6 cycloalkylsulfonyl group, a C3-C6 halocycloalkylsulfonyl group, an C2-C8 alkylaminosulfonyl group, a C2-C8 haloalkylaminosulfonyl group, a C3-C9 trialkylsilyl group, an C2-C6 alkylcarbonyl group, an C2-C6 alkoxycarbonyl group, an C2-C8 alkylaminocarbonyl group, a C4-C7 cycloalkylmethyl group, an C1-C6 alkyl group optionally having one or more groups selected from Group $P^1$ or a C3-C6 cycloalkyl group optionally having one or more groups selected from Group $P^1$;

$Y^1$, $Y^2$, $Y^3$, $Z^2$ and $Z^3$ represent independently of each other a hydrogen atom, a halogen atom, a cyano group, a nitro group, an amino group, a hydroxy group, a thiol group, an aldehyde group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C3-C6 alkenyloxy group, a C3-C6 haloalkenyloxy group, an C3-C6 alkynyloxy group, a C3-C6 haloalkynyloxy group, an C3-C6 alkenylthio group, a C3-C6 alkynylthio group, a C3-C6 haloalkenylthio group, a C3-C6 haloalkynylthio group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloakylsulfonyl group, an C1-C8 alkylaminosulfonyl group, a pentaflurosulfanyl group, a C3-C9 trialkylsilyl group, an C2-C6 alkylcarbonyl group, an C2-C6 alkoxycarbonyl group, an C2-C8 alkylaminocarbonyl group, an aminocarbonyl group, an C1-C6 alkyl group optionally having one or more groups selected from Group $P^1$ or a C3-C6 cycloalkyl group optionally having one or more groups selected from Group $P^1$; or $Y^1$ and $Y^2$ may combine each other together with the carbon atom to which they are attached to form a five-, six- or seven-membered saturated ring with the proviso that the saturated ring may optionally contain one or more oxygen atoms or sulfur atoms as the ring-constituent atom, and the saturated ring may optionally have one or more substituents selected from Group $P^1$; or $Y^2$ and $Y^3$ may combine each other together with the carbon atom to which they are attached to form a five-, six- or seven-membered saturated ring with the proviso that the saturated ring may optionally contain one or more oxygen atoms or sulfur atoms as the ring-constituent atom, and the saturated ring may optionally have one or more substituents selected from Group $P^1$; or $Z^1$ and $Z^2$ may combine each other together with the carbon atom or nitrogen atom to which they are attached to form a five-, six- or seven-membered saturated ring with the proviso that the saturated ring may optionally contain one or more oxygen atoms, nitrogen atoms or sulfur atoms as the ring-constituent atom, and the saturated ring may optionally have one or more substituents selected from Group $P^1$; or $Z^2$ and $Z^3$ may combine each other together with the carbon atom to which they are attached to form a five-, six- or seven-membered saturated ring with the proviso that the saturated ring may optionally contain one or more oxygen atoms, nitrogen atoms or sulfur atoms as the ring-constituent atom, and the saturated ring may optionally have one or more substituents selected from Group $P^1$; and Group $P^1$: a group consisting of a halogen atom, a cyano group, a C3-C6 cycloalkyl group, a C3-C6 halocycloalkyl group, an C1-C4 alkoxy group, a C1-C4 haloalkoxy group, an C1-C4 alkylthio group or a C1-C4 haloalkylthio group.

2. The tetrazolinone compound according to claim 1, wherein $R^1$ represents an C1-C3 alkyl group, a halogen atom, a C1-C3 haloalkyl group, an C2-C3 alkynyl group, a C2-C3 haloalkynyl group, a C3-C5 cycloalkyl group, a C3-C5 halocycloalkyl group, an C1-C3 alkoxy group or a C1-C3 haloalkoxy group;

$R^2$, $R^4$, $R^5$, $R^7$, $R^8$, $R^9$ and $R^{11}$ represent a hydrogen atom;

$R^3$ represents a hydrogen atom, a halogen atom, an C1-C3 alkyl group or a C1-C3 haloalkyl group;

$R^6$ represents an C1-C4 alkyl group, a halogen atom, an C1-C4 alkoxy group or a C1-C4 haloalkyl group;

$R^{10}$ represents a methyl group; and

X represents an oxygen atom.

3. The tetrazolinone compound according to claim 1, wherein
$Y^1$ and $Y^2$ may combine each other together with the carbon atom to which they are attached to form a five- or six-membered saturated ring;
$Y^2$ and $Y^3$ may combine each other together with the carbon atom to which they are attached to form a five- or six-membered saturated ring;
when each of $Y^1$, $Y^2$ and $Y^3$ does not form the five- or six-membered saturated ring,
$Y^1$ represents a hydrogen atom, an C1-C6 alkyl group, a C1-C6 haloalkyl group, a C3-C6 cycloalkyl group or a C3-C6 halocycloalkyl group;
$Y^2$ represents a hydrogen atom, a halogen atom, an C1-C6 alkyl group, a C1-C6 haloalkyl group, an C2-C6 alkynyl group, an C1-C6 alkoxy group, a C1-C6 haloalkoxy group, a C3-C6 cycloalkyl group or a C3-C6 halocycloalkyl group;
$Y^3$ represents a hydrogen atom, an C1-C4 alkyl group or a C1-C4 haloalkyl group.

4. The tetrazolinone compound according to claim 1, wherein
$Z^1$ represents an C1-C6 alkyl group, a C1-C6 haloalkyl group, an C3-C6 alkynyl group, a C3-C6 haloalkynyl group, a C3-C6 cycloalkyl group, a C3-C6 halocycloalkyl group or a C4-C7 cycloalkylmethyl group;
$Z^2$ represents a hydrogen atom, a halogen atom, an C1-C6 alkyl group, a C1-C6 haloalkyl group, an C1-C6 alkoxy group, a C1-C6 haloalkoxy group, a C3-C6 cycloalkyl group or a C3-C6 halocycloalkyl group; alternatively, $Z^1$ and $Z^2$ may combine each other together with the carbon atom or the nitrogen atom to which they are attached to form a five- or six-membered saturated ring; and
$Z^3$ represents a hydrogen atom, a halogen atom, an C1-C4 alkyl group or a C1-C4 haloalkyl group.

5. The tetrazolinone compound according to claim 1, wherein
$Y^1$ and $Y^2$ connect to each other to represent —CH$_2$—CH$_2$—CH$_2$— or —CH$_2$—CH$_2$—CH$_2$—CH$_2$—, which combines together with the carbon atoms to which $Y^1$ and $Y^2$ are attached to form a five-membered or six-membered ring;
$Y^2$ and $Y^3$ connect to each other to represent —CH$_2$—CH$_2$—CH$_2$— or —CH$_2$—CH$_2$—CH$_2$—CH$_2$—, which combines together with the carbon atoms to which $Y^2$ and $Y^3$ are attached to form a five-membered or six-membered ring;
when each of $Y^1$, $Y^2$ and $Y^3$ does not form the five- or six-membered saturated ring,
$Y^1$ represents a hydrogen atom, an C1-C3 alkyl group, a C1-C3 haloalkyl group or a cyclopropyl group;
$Y^2$ represents a hydrogen atom, an C1-C3 alkyl group, a C1-C3 haloalkyl group or an C1-C3 alkoxy group; and
$Y^3$ represents a hydrogen atom or a methyl group.

6. The tetrazolinone compound according to claim 1, wherein
$Z^1$ represents an C1-C6 alkyl group, a C1-C6 haloalkyl group, an C3-C6 alkynyl group or a C4-C7 cycloalkylmethyl group;
$Z^2$ represents a hydrogen atom, a halogen atom, a cyano group, an C1-C6 alkyl group, a C1-C6 haloalkyl group, an C1-C6 alkoxy group, an C3-C6 alkynyloxy group, an C1-C6 alkylthio group or a C1-C6 haloalkoxy group; and
$Z^3$ represents a hydrogen atom, a halogen atom, a cyano group, an C1-C4 alkyl group or a C1-C4 haloalkyl group.

7. The tetrazolinone compound according to claim 1, wherein
$Z^1$ represents an C1-C6 alkyl group or a C1-C6 haloalkyl group;
$Z^2$ represents a hydrogen atom, a chlorine atom, a cyano group, a methoxy group, an ethoxy group, a 2-propynyloxy group, a methylthio group, a difluoromethyl group, a trifluoromethyl group or an C1-C3 alkyl group; and
$Z^3$ represents a hydrogen atom, a halogen atom, a cyano group or a methyl group.

8. The tetrazolinone compound according to claim 1, wherein
$Z^1$ represents an C1-C6 alkyl group or a C1-C6 haloalkyl group;
$Z^2$ represents a hydrogen atom, a chlorine atom, a trifluoromethyl group or an C1-C3 alkyl group; and
$Z^3$ represents a hydrogen atom, a chlorine atom or a methyl group.

9. The tetrazolinone compound according to claim 1, wherein
$Y^1$ and $Y^2$ connect to each other to represent —CH$_2$—CH$_2$—CH$_2$—CH$_2$—, which combines together with the carbon atoms to which they are attached to form a six-membered ring;
$Y^2$ and $Y^3$ connect to each other to represent —CH$_2$—CH$_2$—CH$_2$—CH$_2$—, which combines together with the carbon atoms to which they are attached to form a six-membered ring;
when each of $Y^1$, $Y^2$ and $Y^3$ does not form the six-membered saturated ring,
$Y^1$ represents a hydrogen atom or an C1-C3 alkyl group;
$Y^2$ represents a hydrogen atom, a halogen atom, a cyano group, an C1-C3 alkyl group, a C1-C3 haloalkyl group or an C1-C3 alkoxy group; and
$Y^3$ represents a hydrogen atom or a methyl group.

10. The tetrazolinone compound according to claim 1, wherein
$R^1$ represents a methyl group, an ethyl group, a chlorine atom, a bromine atom or a trifluoromethyl group;
$R^3$ represents a hydrogen atom or a methyl group; and
$R^6$ represents a methyl group, an ethyl group, a chlorine atom, a bromine atom, a methoxy group or an ethoxy group.

11. A tetrazolinone compound represented by formula (3):

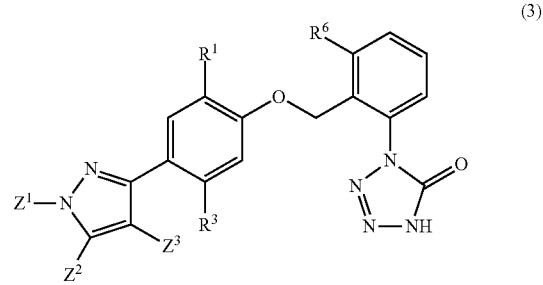

wherein
$R^1$ represents a methyl group, an ethyl group, a chlorine atom, a bromine atom or a trifluoromethyl group;
$R^3$ represents a hydrogen atom or a methyl group;

R⁶ represents an C1-C3 alkyl group, a halogen atom or an C1-C2 alkoxy group;

Z¹ represents an C1-C3 alkyl group;

Z² represents a hydrogen atom, an C1-C2 alkoxy group, an C1-C3 alkyl group, an C1-C2 alkylthio group, a halogen atom or a cyano group; and Z³ represents a hydrogen atom, an C1-C3 alkyl group, a halogen atom or a cyano group.

12. The tetrazolinone compound according to claim 11, wherein

R¹ represents a methyl group;

R³ represents a hydrogen atom;

R⁶ represents an C1-C2 alkyl group;

Z¹ represents an C1-C3 alkyl group;

Z² represents a C1-C2 alkoxy group or a halogen atom;

Z³ represents an C1-C3 alkyl group.

13. An agent for controlling pests comprising the tetrazolinone compound according to claim 1.

14. A method for controlling pests comprising applying an effective amount of the tetrazolinone compound according to claim 1 to plant or soil.

15. A tetrazolinone compound of formula (2):

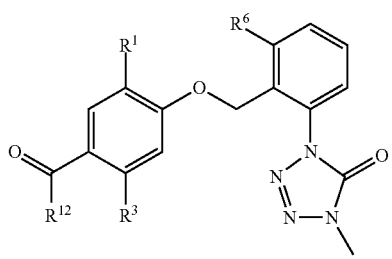

(2)

wherein

R¹ represents a methyl group, an ethyl group, a chlorine atom, a bromine atom, a trifluoromethyl group or a cyclopropyl group;

R³ represents a hydrogen atom or a methyl group;

R⁶ represents a methyl group, an ethyl group, a chlorine atom, a bromine atom, a methoxy group or an ethoxy group; and R¹² represents an C1-C6 alkyl group, a C1-C6 haloalkyl group, a C3-C6 cycloalkyl group or a C3-C6 halocycloalkyl group.

16. The tetrazolinone compound according to claim 15, wherein

R¹ represents a methyl group, an ethyl group, a chlorine atom or a bromine atom;

R³ represents a hydrogen atom or a methyl group;

R⁶ represents a methyl group, an ethyl group, a chlorine atom, a bromine atom or a methoxy group; and R¹² represents a methyl group, an ethyl group or a cyclopropyl group.

17. A pyrazole compound represented by formula (4):

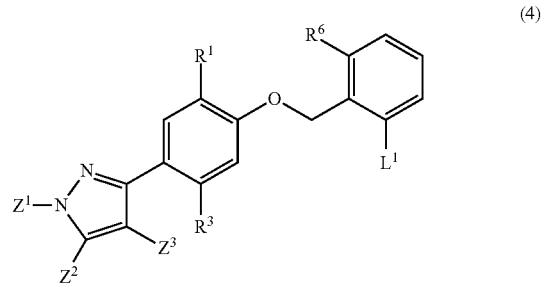

(4)

wherein

R¹ represents a methyl group, an ethyl group, a chlorine atom, a bromine atom or a trifluoromethyl group;

R³ represents a hydrogen atom or a methyl group;

R⁶ represents an C1-C3 alkyl group, a halogen atom or an C1-C2 alkoxy group;

Z¹ represents an C1-C3 alkyl group;

Z² represents a hydrogen atom, an C1-C2 alkoxy group, an C1-C3 alkyl group, an C1-C2 alkylthio group, a halogen atom or a cyano group;

Z³ represents a hydrogen atom, an C1-C3 alkyl group, a halogen atom or a cyano group; and L¹ represents a nitro group, an amino group, an isocyanate group, a carboxyl group, an C2-C6 alkoxycarbonyl group, a halogen atom, a halocarbonyl group, NSO, C(O)N₃, C(O)NH₂, C(O)NHCl, C(O)NHBr or C(O)NHOH.

18. The pyrazole compound according to claim 17, wherein

R¹ represents a methyl group;

R³ represents a hydrogen atom;

R⁶ represents an C1-C2 alkyl group;

Z¹ represents an C1-C3 alkyl group;

Z² represents an C1-C2 alkoxy group or a halogen atom;

Z³ represents an C1-C3 alkyl group; and

L¹ represents a nitro group, an amino group or an isocyanate group.

* * * * *